US012637662B2

(12) United States Patent
Yoshihara et al.

(10) Patent No.: US 12,637,662 B2
(45) Date of Patent: May 26, 2026

(54) CELLS, ISLETS, AND ORGANOIDS THAT EVADE IMMUNE DETECTION AND AUTOIMMUNITY, METHODS OF PRODUCTION AND USE THEREOF

(71) Applicant: SALK INSTITUTE FOR BIOLOGICAL STUDIES, La Jolla, CA (US)

(72) Inventors: Eiji Yoshihara, La Jolla, CA (US); Ruth Yu, La Jolla, CA (US); Michael Downes, La Jolla, CA (US); Ronald Evans, La Jolla, CA (US); Annette Atkins, La Jolla, CA (US)

(73) Assignee: SALK INSTITUTE FOR BIOLOGICAL STUDIES, La Jolla, CA (US)

( * ) Notice: Subject to any disclaimer, the term of this patent is extended or adjusted under 35 U.S.C. 154(b) by 794 days.

(21) Appl. No.: 17/284,355

(22) PCT Filed: Oct. 11, 2019

(86) PCT No.: PCT/US2019/055827
§ 371 (c)(1),
(2) Date: Apr. 9, 2021

(87) PCT Pub. No.: WO2020/077204
PCT Pub. Date: Apr. 16, 2020

(65) Prior Publication Data
US 2021/0363490 A1 Nov. 25, 2021

Related U.S. Application Data

(60) Provisional application No. 62/795,284, filed on Jan. 22, 2019, provisional application No. 62/745,086, filed on Oct. 12, 2018.

(51) Int. Cl.
*A61K 35/39* (2015.01)
*C12N 5/071* (2010.01)

(52) U.S. Cl.
CPC ............ *C12N 5/0677* (2013.01); *A61K 35/39* (2013.01); *C12N 2501/415* (2013.01); *C12N 2502/1382* (2013.01); *C12N 2502/28* (2013.01); *C12N 2506/45* (2013.01); *C12N 2510/00* (2013.01); *C12N 2533/70* (2013.01); *C12N 2533/90* (2013.01)

(58) Field of Classification Search
None
See application file for complete search history.

(56) References Cited

U.S. PATENT DOCUMENTS

| | | |
|---|---|---|
| 4,683,202 A | 7/1987 | Mullis |
| 5,399,346 A | 3/1995 | Anderson et al. |
| 5,854,033 A | 12/1998 | Lizardi |
| 5,942,435 A | 8/1999 | Wheeler |
| 9,102,920 B2 | 8/2015 | Feng et al. |
| 9,546,379 B2 | 1/2017 | Evans et al. |
| 10,520,494 B2 | 12/2019 | Lickert et al. |
| 10,912,800 B2 | 2/2021 | Evans et al. |
| 10,920,199 B2 | 2/2021 | Evans et al. |
| 11,685,901 B2 | 6/2023 | Evans et al. |
| 11,760,977 B2 | 9/2023 | Evans et al. |
| 2009/0281191 A1 | 11/2009 | Rangwala et al. |
| 2010/0145470 A1 | 6/2010 | Cohen et al. |
| 2011/0028401 A1 | 2/2011 | Minchiotti et al. |
| 2011/0165570 A1 | 7/2011 | Feng et al. |
| 2012/0039919 A1 | 2/2012 | Yang et al. |
| 2012/0302491 A1 | 11/2012 | Narkar et al. |
| 2013/0195811 A1 | 8/2013 | Wang et al. |
| 2014/0289877 A1 | 9/2014 | Taniguchi et al. |
| 2015/0203818 A1 | 7/2015 | Mountford et al. |
| 2015/0368667 A1 | 12/2015 | Evans et al. |
| 2016/0083693 A1 | 3/2016 | Xu et al. |
| 2017/0087189 A1 | 3/2017 | Evans et al. |
| 2018/0044642 A1 | 2/2018 | Evans et al. |
| 2019/0211310 A1 | 7/2019 | Evans et al. |

(Continued)

FOREIGN PATENT DOCUMENTS

| | | |
|---|---|---|
| CA | 2937882 A1 | 9/2015 |
| CN | 101878298 A | 11/2010 |

(Continued)

OTHER PUBLICATIONS

Ma et al (Transplantation Proceedings, 47, 165e170 (2015), http://dx.doi.org/10.1016/j.transproceed.2014.10.043) (Year: 2015).*
Cardozo et al (Diabetologia (2003) 46:255-266, DOI 10.1007/s00125-002-1017-0) (Year: 2003).*
Shen et al (The Journal of Immunology, 2007, 179: 3672-3679. https://doi.org/10.4049/jimmunol.179.6.3672). (Year: 2007).*
Sivanathan et al (Stem Cell Rev and Rep (2014) 10:351-375, DOI 10.1007/s12015-014-9495-2) (Year: 2014).*
Raikwar et al (PLoS ONE 10(1): e0116582. doi:10.1371/journal.pone.0116582, Jan. 28, 2015). (Year: 2015).*
Wang et al (BioMed Research International vol. 2017, Article ID 2501578, 13 pages https://doi.org/10.1155/2017/2501578). (Year: 2017).*

(Continued)

*Primary Examiner* — Peter Paras, Jr.
*Assistant Examiner* — Khoa Nhat Tran
(74) *Attorney, Agent, or Firm* — Greenberg Traurig, LLP; Melissa Hunter-Ensor; Leslie Serunian

(57) ABSTRACT

The invention features cells, islet-like cells, pancreatic islets and organoids (e.g., human islet-like organoids or HILOs), as well as cell cultures and methods that are useful for the rapid and reliable generation of cells and organoids, such as pancreatic islets and organoids, that are sustainable in vivo and that evade immune detection, rejection and autoimmunity. The invention also features methods of treating pancreatic diseases, such as type 2 diabetes, and pancreatic cancer, using the cells, islet-like cells, pancreatic islets and organoids (e.g., HILOs) that are designed to modulate the activity of immune cells that would otherwise react against them.

11 Claims, 67 Drawing Sheets

Specification includes a Sequence Listing.

(56) References Cited

U.S. PATENT DOCUMENTS

| | | | | |
|---|---|---|---|---|
| 2020/0095321 A1* | 3/2020 | Zeng | | C07K 16/2812 |
| 2021/0283187 A1 | 9/2021 | Evans et al. | | |
| 2022/0220446 A1 | 7/2022 | Evans et al. | | |
| 2022/0315901 A1 | 10/2022 | Evans et al. | | |
| 2024/0101962 A1 | 3/2024 | Evans et al. | | |

FOREIGN PATENT DOCUMENTS

| | | | | |
|---|---|---|---|---|
| EP | 2878664 A1 | 6/2015 | | |
| EP | 2940127 A1 | 11/2015 | | |
| JP | 2009533017 A | 9/2009 | | |
| JP | 2011522520 A | 8/2011 | | |
| JP | 2016514481 A | 5/2016 | | |
| WO | 2001015755 A2 | 3/2001 | | |
| WO | 2006063733 A1 | 6/2006 | | |
| WO | 2006063734 A2 | 6/2006 | | |
| WO | 2006063735 A1 | 6/2006 | | |
| WO | 2006063736 A1 | 6/2006 | | |
| WO | 2006119886 A1 | 11/2006 | | |
| WO | 2006119887 A1 | 11/2006 | | |
| WO | 2006119888 A2 | 11/2006 | | |
| WO | 2009070592 A2 | 6/2009 | | |
| WO | 2009136867 A1 | 11/2009 | | |
| WO | 2011160066 A1 | 12/2011 | | |
| WO | 2012044486 A1 | 4/2012 | | |
| WO | 2013159103 A1 | 10/2013 | | |
| WO | 2014017513 A1 | 1/2014 | | |
| WO | 2014104364 A1 | 7/2014 | | |
| WO | 2014145625 A1 | 9/2014 | | |
| WO | 2015144861 A1 | 10/2015 | | |
| WO | 2015148832 A1 | 10/2015 | | |
| WO | 2016015158 A1 | 2/2016 | | |
| WO | 2016100898 A1 | 6/2016 | | |
| WO | 2016100909 A1 | 6/2016 | | |
| WO | 2016100921 A1 | 6/2016 | | |
| WO | 2016100925 A1 | 6/2016 | | |
| WO | 2016100930 A1 | 6/2016 | | |
| WO | 2016123117 A1 | 8/2016 | | |
| WO | 2017205511 A1 | 11/2017 | | |
| WO | WO-2018094107 A1 * | 5/2018 | | A61K 35/39 |
| WO | 2018156955 A1 | 8/2018 | | |

OTHER PUBLICATIONS

Yoshihara et al (Cell Metabolism 23, 622-634, Apr. 12, 2016, http://dx.doi.org/10.1016/j.cmet.2016.03.005). (Year: 2016).*

Osum et al (Scientific Reports | (2018) 8:8295 | DOI:10.1038/s41598-018-26471-9, Published online: May 29, 2018) (Year: 2018).*

Marwaha et al (Clinical Immunology (2014) 154, 84-89, DOI: 10.1016/j.clim.2014.06.006) (Year: 2014).*

Chen et al (Blood. 2015;126(24):2621-2631, DOI 10.1182/blood-2015-06-652453) (Year: 2015).*

Yang et al (Annals of Clinical & Laboratory Science, vol. 45, No. 3, 2015). (Year: 2015).*

Office Action dated Sep. 25, 2023 in corresponding Japanese Patent Application No. 2021-519749 (7 pages).

English translation of Office Action dated Sep. 25, 2023 in corresponding Japanese Patent Application No. 2021-519749 (7 pages).

Office Action dated Dec. 29, 2023 in corresponding Chinese Patent Application No. 201980082516.6 (10 pages).

English translation of Office Action dated Dec. 29, 2023 in corresponding Chinese Patent Application No. 201980082516.6 (5 pages).

Gui et al., "Wnt3a Regulates Proliferation, Apoptosis and Function of Pancreatic NIT-1 Beta Cells Via Activation of IRS2/PI3K Signaling," Journal of Cellular Biochemistry, 2013, vol. 114, No. 7, pp. 1488-1497.

Rulifson et al., "Wnt signaling regulates pancreatic β cell proliferation," Proceedings of the National Academy of Sciences of the United States of America, Apr. 10, 2007, vol. 104, No. 15, pp. 6247-6252.

Cardozo et al., "IL-1β and IFN-γ induce the expression of diverse chemokines and IL-15 in human and rat pancreatic islet cells, and in islets from pre-diabetic NOD mice," Diabetologica, 2003, vol. 46, pp. 255-266.

Li et al., PD-1/PD-L1 Costimulatory Pathway-induced Mouse Islet Transplantation Immune Tolerance, Transplantation Proceedings, 2015, vol. 47, pp. 165-170.

Shen et al., "The Function of Donor versus Receipient Programmed Death-Ligand 1 in Corneal Allograft Survival," The Journal of Immunology, 2007, vol. 179, No. 6, pp. 3672-3679.

Brouwer et al., "Choices for Induction of Pluripotency: Recent Developments in Human Induced Pluripotent Stem Cell Reprogramming Strategies," Stem Cell Reviews and Reports, 2016, vol. 12, pp. 54-72.

Buganim et al., "Single-Cell Expression Analyses during Cellular Reprogramming Reveal an Early Stochastic and a Late Hierarchic Phase," Cell, Sep. 14, 2012, vol. 150, pp. 1209-1222.

Carey et al., "Single-gene transgenic mouse strains for reprogramming adult somatic cells," Nature Methods, Jan. 2010, vol. 7, No. 1, pp. 56-59.

Chen et al., "Integration of External Signaling Pathways with the Core Transcriptional Network in Embryonic Stem Cells," Cell, Jun. 13, 2008, vol. 133, pp. 1106-1117.

Deng et al., "Non-Viral Methods For Generating Integration-Free, Induced Pluripotent Stem Cells," Current Stem Cell Research & Therapy, 2015, vol. 10, pp. 153-158.

Feng et al., "Reprogramming of fibroblasts into induced pluripotent stem cells with orphan nuclear receptor Esrrb," Nature Cell Biology, Feb. 2009, vol. 11, No. 2, pp. 197-203.

Festuccia et al., "Esrrb Is a Direct Nanog Target Gene that Can Substitute for Nanog Function in Pluripotent Cells," Cell Stem Cell, Oct. 5, 2012, vol. 11, pp. 477-490.

Folmes et al., "Somatic Oxidative Bioenergetics Transitions into Pluripotency-Dependent Glycolysis to Facilitate Nuclear Reprogramming," Cell Metabolism, Aug. 3, 2011, vol. 14, pp. 264-271.

Holmes et al., "Concise Review: Stem Cell Antigen-1: Expression, Function, and Enigmat," Stem Cells, 2007, vol. 25, pp. 1339-1347.

Hsiao et al., "Endogenous Cardiac Stem Cell Therapy for Ischemic Heart Failure," Journal of Clinical & Experimental Cardiology, 2013, vol. S11, pp. 1-5.

Ishibashi et al., "ESAM is a novel human hematopoietic stem cell marker associated with a subset of human leukemias," Experimental Hematology, 2016, vol. 44, pp. 269-281.

Jiao et al., "Research Progress on Organoid Culture under Three-Dimensional Conditions," Guangxi Medicine, 2017, vol. 39, No. 5, pp. 700-707.

Kawamura et al., "Linking the p53 tumour suppressor pathway to somatic cell reprogramming," Nature, Aug. 27, 2009, vol. 460, No. 7259, pp. 1140-1144.

Kemp et al., "Transplantation of Isolated Pancreatic Islets into the Portal Vein of Diabetic Rats," Nature, 1973, vol. 244, p. 447.

Kim et al., "Technical note: Induction of pluripotent stem cell-like cells from chicken feather follicle cells," Journal of Animal Science, 2017, vol. 95, pp. 3479-3486.

Mangelsdorf et al., "The Nuclear Receptor Superfamily: The Second Decade," Cell, Dec. 15, 1995, vol. 83, No. 6, pp. 835-839.

Mao et al., "Automated genome annotation and pathway identification using the KEGG Orthology (KO) as a controlled vocabulary," Bioinformatics, 2005, vol. 21, No. 19, pp. 3787-3793.

Martello et al., "Esrrb Is a Pivotal Target of the Gsk3/Tcf3 Axis Regulating Embryonic Stem Cell Self-Renewal," Cell Stem Cell, Oct. 5, 2012, vol. 11, pp. 491-504.

Mathieu et al., "Investigating the real role of HIF-1 and HIF-2 in iron recycling by macrophages," Haematologica, 2014, vol. 99, pp. e112-e114.

Narkar et al., "Exercise and PGC-1a-Independent Synchronization of Type I Muscle Metabolism and Vasculature by ERRy," Cell Metabolism, Mar. 2, 2011, vol. 13, pp. 283-293.

Panopoulos et al., "The metabolome of induced pluripotent stem cells reveals metabolic changes occurring in somatic cell reprogramming," Cell Research, 2012, vol. 22, pp. 168-177.

Proksch et al., "Does the Human Skeletal Muscle Harbor the Murine Equivalents of Cardiac Precursor Cells?," Molecular Therapy, Apr. 2009, vol. 17, No. 4, pp. 733-741.

(56) References Cited

OTHER PUBLICATIONS

Rossello et al., "Mammalian genes induce partially reprogrammed pluripotent stem cells in non-mammalian vertebrate and invertebrate species," elife, 2013, vol. 2, No. e00036, pp. 1-24.

Seo et al., "Cellular Reprogramming Using Protein and Cell-Penetrating Peptides," International Journal of Molecular Sciences, 2017, vol. 18, p. 552.

Shyh-Chang et al., "Influence of Threonine Metabolism on S-Adenosylmethionine and Histone Methylation," Science, Jan. 11, 2013, vol. 339, No. 6116, pp. 222-226.

Si-Tayeb et al., "Generation of human induced pluripotent stem cells by simple transient transfection of plasmid DNA encoding reprogramming factors," BMC Developmental Biology, 2010, vol. 10, No. 81, pp. 1-10.

Sugii et al., "Human and mouse adipose-derived cells support feeder-independent induction of pluripotent stem cells," PNAS, Feb. 23, 2010, vol. 107, No. 8, pp. 3558-3563.

Taha et al., "Upregulation of Pluripotency Markers in Adipose Tissue-Derived Stem Cells by miR-302 and Leukemia Inhibitory Factor," BioMed Research International, 2014, vol. 2014, No. 941486, pp. 1-10.

Takahashi et al., "Induction of Pluripotent Stem Cells from Mouse Embryonic and Adult Fibroblast Cultures by Defined Factors," Cell, Aug. 25, 2006, vol. 126, pp. 663-676.

Tsonkova et al., "The EndoC-13H1 cell line is a valid model of human beta cells and applicable for screenings to identify novel drug target candidates," Molecular Metabolism, 2018, vol. 8, pp. 144-157.

Vethe et al., "The Effect of Wnt Pathway Modulators on Human iPSC-Derived Pancreatic Beta Cell Maturation," Frontiers in Endocrinology, May 2019, vol. 10, No. 293, pp. 1-13.

Wei et al., "Klf4 Interacts Directly with Oct4 and Sox2 to Promote Reprogramming," Stem Cells, 2009, vol. 27, No. 12, pp. 2969-2978.

Wei et al., "Klf4 Organizes Long-Range Chromosomal Interactions with the Oct4 Locus in Reprogramming and Pluripotency," Cell Stem Cell, Jul. 3, 2013, vol. 13, pp. 36-47.

Yang et al., "Nuclear Receptor Expression Links the Circadian Clock to Metabolism," Cell, Aug. 25, 2006, vol. 126, pp. 801-810.

Yu et al., "Induced Pluripotent Stem Cell Lines Derived from Human Somatic Cells," Science, 2007, vol. 318, pp. 1917-1920.

Zhang et al., "Cardiac progenitor/stem cells on myocardial infarction or ischemic heart disease: what we have known from current research," Heart Failure Reviews, 2014, vol. 19, pp. 247-258.

Zhang et al., "Esrrb Activates Oct4 Transcription and Sustains Self-renewal and Pluripotency in Embryonic Stem Cells," Journal of Biological Chemistry, Dec. 19, 2008, vol. 283, No. 51, pp. 35825-35833.

Zhang et al., "Metabolic Regulation in Pluripotent Stem Cells during Reprogramming and Self-Renewal," Cell Stem Cell, Nov. 2, 2012, vol. 11, pp. 589-595.

Office Action dated Apr. 24, 2023 in corresponding Eurasian Patent Application No. 202190994 (4 pages).

English translation of the Office Action dated Apr. 24, 2023 in corresponding Eurasian Patent Application No. 202190994 (5 pages).

International Search Report and Written Opinion in International Patent Application No. PCT/US2019/055827, mailed Jan. 17, 2020 (22 pages).

Osum et al., "Interferon-gamma drives programmed death-ligand 1 expression on islet β cells to limit T cell function during autoimmune diabetes," Sci Rep. May 29, 2018; 8(1):8295. doi: 10.1038/s41598-018-26471-9.

Bar-Ephraim et al., "Modelling cancer immunomodulation using epithelial organoid cultures," bioRxiv; Aug. 7, 2018. DOI: 10.1101/377655.

Subudhi et al., "Local expression of B7-H1 promotes organ-specific autoimmunity and transplant rejection," J Clin Invest. Mar. 2004; 113(5): 694-700. doi: 10.1172/JCI19210.

Vaithilingam et al., "Co-encapsulation and co-transplantation of mesenchymal stem cells reduces pericapsular fibrosis and improves encapsulated islet survival and function when allografted," Scl Rep 7, 10059 (Aug. 30, 2017). DOI: 10.1038/s41598-017-10359-1.

Akinci et al., "Reprogramming of Various Cell Types to a Beta-Like State by Pdx1, Ngn3 and MafA," PLoS One, Nov. 2013, vol. 8, No. 11, e82424, pp. 1-11.

Alaynick et al., "ERRγ Directs and Maintains the Transition to Oxidative Metabolism in the Postnatal Heart," Cell Metabolism, Jul. 2007, vol. 6, No. 1, pp. 13-24.

Anderson, W. French, "Prospects for Human Gene Therapy," Science, Oct. 26, 1984, vol. 226, No. 4673, pp. 401-409.

Anello et al., "Functional and morphological alterations of mitochondria in pancreatic beta cells from type 2 diabetic patients," Diabetologia, 2005, vol. 48, pp. 282-289.

Ansari et al., "The Programmed Death-1 (PD-1) Pathway Regulates Autoimmune Diabetes in Nonobese Diabetic (NOD) Mice," The Journal of Experimental Medicine, Jul. 7, 2003, vol. 198, pp. 63-69.

Bader et al., "Identification of proliferative and mature β-cells in the islets of Langerhans," Nature, Jul. 21, 2016, vol. 535, pp. 430-434.

Baidal et al., "Bioengineering of an Intraabdominal Endocrine Pancreas," The New England Journal of Medicine, May 11, 2017, No. 376, No. 19, pp. 1887-1889.

Barany, Francis, "Genetic disease detection and DNA amplification using cloned thermostable ligase," Proceedings of the National Academy of Sciences of the United States of America, Jan. 1991, vol. 88, pp. 189-193.

Blomer et al., "Highly efficient and sustained gene transfer in adult neurons with a lentivirus vector," Journal of Virology, Sep. 1997, vol. 71, No. 9, pp. 6641-6649.

Brevini et al., "No shortcuts to pig embryonic stem cells," Theriogenology, 2010, vol. 74, No. 4, pp. 544-550.

Buenrostro et al., "ATAC-seq: A Method for Assaying Chromatin Accessibility Genome-Wide," Current Protocols In Molecular Biology, Jan. 5, 2015, vol. 109, p. 21.29.1-21.29.9.

Burns et al., "High-Throughput Luminescent Reporter of Insulin Secretion for Discovering Regulators of Pancreatic Beta-Cell Function," Cell Metabolism, Jan. 6, 2015, vol. 21, pp. 126-137.

Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy, Mar. 1997, vol. 8, No. 4, pp. 423-430.

Chen et al., "PDGF signalling controls age-dependent proliferation in pancreatic β-cells," Nature, 2011, vol. 478, pp. 349-355.

Colli et al., "PDL1 is expressed in the islets of people with type 1 diabetes and is up-regulated by interferons-α and-γ via IRF1 induction," EBioMedicine, 2018, vol. 36, pp. 367-375.

Conrad et al., "Revealing transcription factors during human pancreatic β cell development," Trends in Endocrinology & Metabolism, Aug. 2014, vol. 25, No. 8, pp. 407-414.

Crunkhorn, Sarah, "Human iPSC-derived β-like cells rescue diabetic mice," Nature Reviews Drug Discovery, 2016, vol. 15, Article No. 383, 1 page.

D'Amour et al., "Production of pancreatic hormone-expressing endocrine cells from human embryonic stem cells," Nature Biotechnology, 2006, vol. 24, No. 11, pp. 1392-1401.

Ding et al., "Activation of CD4+ T cells by delivery of the B7 costimulatory signal on bystander antigen-presenting cells (transcostimulation)," European Journal of Immunology, Apr. 1994, vol. 24, No. 4, pp. 859-866.

Dobin et al., "STAR: ultrafast universal RNA-seq aligner," Bioinformatics, Jan. 2013, vol. 29, No. 1, pp. 15-21.

Dor et al., "Adult pancreatic β-cells are formed by self-duplication rather than stem-cell differentiation," Nature, May 6, 2004, vol. 429, pp. 41-46.

Dufour et al., "Genome-wide Orchestration of Cardiac Functions by the Orphan Nuclear Receptors ERRα and γ," Cell Metabolism, May 2007, vol. 5, No. 5, pp. 345-356.

Felgner et al., "Lipofection: a highly efficient, lipid-mediated DNA-transfection procedure," Proceeding of the National Academy of Sciences of the United States of America, Nov. 1987, vol. 84, No. 21, pp. 7413-7417.

Foks et al., "Immune checkpoint proteins: exploring their therapeutic potential to regulate atherosclerosis," British Journal of Pharmacology, 2017, vol. 174, pp. 3940-3955.

(56)          References Cited

OTHER PUBLICATIONS

Friedmann, Theodore, "Progress Toward Human Gene Therapy," Science, Jun. 16, 1989, vol. 244, No. 4910, pp. 1275-1281.

Guatelli et al., "Isothermal, in vitro amplification of nucleic acids by a multienzyme reaction modeled after retroviral replication," Proceedings of the National Academy of Sciences of the United States of America, Mar. 1990, vol. 87, No. 5, pp. 1874-1878.

Hackenbrock, Charles R., "Ultrastructural Bases for Metabolically Linked Mechanical Activity in Mitochondria : I. Reversible Ultrastructural Changes with Change in Metabolic Steady State in Isolated Liver Mitochondria," Journal of Cell Biology, 1966, vol. 30, No. 2, pp. 262-297.

Hart et al., "Attenuation of FGF signalling in mouse β-cells leads to diabetes," Nature, Dec. 14, 2000, vol. 408, pp. 864-868.

Heinz et al., "Simple Combinations of Lineage-Determining Transcription Factors Prime cis-Regulatory Elements Required for Macrophage and B Cell Identities," Molecular Cell, May 28, 2010, vol. 38, No. 4, pp. 576-589.

Hickey et al., "Generation of islet-like cells from mouse gall bladder by direct ex vivo reprogramming," Stem Cell Research, Jul. 2013, vol. 11, No. 1, pp. 503-515.

Hrvatin et al., "Differentiated human stem cells resemble fetal, not adult, β cells," Proceedings of the National Academy of Sciences of the United States of America, Feb. 25, 2014, vol. 111, No. 8, pp. 3038-3043.

Huang et al., "Systematic and integrative analysis of large gene lists using DAVID bioinformatics resources," Nature Protocols, 2009, vol. 4, pp. 44-57.

Johnson, Larry G., "Gene Therapy for Cystic Fibrosis," Chest, Feb. 1995, vol. 107, No. 2, pp. 77S-83S.

Kapturczak et al., "Transduction of Human and Mouse Pancreatic Islet Cells Using a Bicistronic Recombinant Adeno-associated Viral Vector," Molecular Therapy, Feb. 2002, vol. 5, No. 2, pp. 154-160.

Kroon et al., "Pancreatic endoderm derived from human embryonic stem cells generates glucose-responsive insulin-secreting cells in vivo," Nature Biotechnology, 2008, vol. 26, pp. 443-452.

Kwoh et al., "Transcription-based amplification system and detection of amplified human immunodeficiency virus type 1 with a bead-based sandwich hybridization format," Proceedings of the National Academy of Sciences of the United States of America, Feb. 1989, vol. 86, No. 4, pp. 1173-1177.

Le Gal La Salle et al., "An Adenovirus Vector for Gene Transfer into Neurons and Glia in the Brain," Science, Feb. 12, 1993, vol. 259, No. 5097, pp. 988-990.

Li et al., "Small Molecules Facilitate the Reprogramming of Mouse Fibroblasts into Pancreatic Lineages," Cell Stem Cell, Feb. 6, 2014, vol. 14, No. 2, pp. 228-236.

Liu et al., "Cells that present both specific ligand and costimulatory activity are the most efficient inducers of clonal expansion of normal CD4 T cells," Proceedings of the National Academy of Sciences of the United States of America, May 1992, vol. 89, No. 9, pp. 3845-3849.

Ludwig et al., "Feeder-independent culture of human embryonic stem cells," Nature Methods, Aug. 2006, vol. 3, No. 8, pp. 637-646.

Ludwig et al., "Transplantation of human islets without immunosuppression," Proceedings of the National Academy of Sciences of the United States of America, Nov. 19, 2013, vol. 110, No. 47, pp. 19054-19058.

Mandel et al., "SERKAL Syndrome: An Autosomal-Recessive Disorder Caused by a Loss-of-Function Mutation in WNT4," The American Journal of Human Genetics, Jan. 2008, vol. 82, No. 1, pp. 39-47.

Mao et al., "Lentiviral Vectors Mediate Long-Term and High Efficiency Transgene Expression in HEK 293T cells," International Journal of Medical Sciences, 2015, vol. 12, No. 5, pp. 407-415.

Miller et al., "Improved Retroviral Vectors for Gene Transfer and Expression," Biotechniques, Oct. 1989, vol. 7, No. 9, pp. 980-990.

Miller, Dusty A., "Retrovirus Packaging Cells," Human Gene Therapy, Apr. 1990, vol. 1, No. 1, pp. 5-14.

Miyoshi et al., "Stable and efficient gene transfer into the retina using an HIV-based lentiviral vector," Proceedings of the National Academy of Sciences of the United States of America, Sep. 16, 1997, vol. 94, No. 19, pp. 10319-10323.

Morizane et al., "MHC matching improves engraftment of iPSC-derived neurons in non-human primates," Nature Communications, 2017, vol. 8, No. 385, pp. 1-12.

Munoz et al., "Conventional pluripotency markers are unspecific for bovine embryonic-derived cell-lines," Theriogenology, Jun. 2008, vol. 69, No. 9, pp. 1159-1164.

Naldini et al., "In Vivo Gene Delivery and Stable Transduction of Nondividing Cells by a Lentiviral Vector," Science, Apr. 12, 1996, vol. 272, No. 5259, pp. 263-267.

Nasr et al., "PD-L1 genetic overexpression or pharmacological restoration in hematopoietic stem and progenitor cells reverses autoimmune diabetes," Science Translational Medicine, Nov. 15, 2017, vol. 9, No. 416, pp. 1-14.

Al-Chaqmaqchi et al., "The Role of Programmed Cell Death Ligand-1 (PD-L1/CD274) in the Development of Graft versus Host Disease," PLoS One, Apr. 2013, vol. 8, No. 4, e60367, pp. 1-7.

Bosnak et al., "Somatostatin Therapy in the Management of Resistant Diabetic Ketoacidosis," Diabetes Care, Mar. 2002, vol. 25, No. 3, pp. 629-630.

Jaramillo et al., "Potential for Pancreatic Maturation of Differentiating Human Embryonic Stem Cells Is Sensitive to the Specific Pathway of Definitive Endoderm Commitment," PLoS One, Apr. 2014, vol. 9, No. 4, e94307, pp. 1-14.

Liu et al., "All mixed up: defining roles for β-cell subtypes in mature islets," Genes & Development, 2017, vol. 31, pp. 228-240.

Yoshihara et al., "Immune evasive human islet-like organoids ameliorate diabetes," Nature, Oct. 2020, vol. 586, No. 7830, pp. 606-611.

Extended European Search Report dated Jun. 14, 2022 in corresponding European Patent Application No. 19871339.8 (8 pages).

Nichols et al., "Adult tissue sources for new β cells," Translational Research, Apr. 2014, vol. 163, No. 4, pp. 418-431.

Ono et al., "Plasmid DNAs directly injected into mouse brain with lipofectin can be incorporated and expressed by brain cells," Neuroscince Letters, Sep. 18, 1990, vol. 117, No. 3, pp. 259-263.

Pagliuca et al., "Generation of Functional Human Pancreatic β Cells In Vitro," Cell, Oct. 9, 2014, vol. 159, No. 2, pp. 428-439.

Pagliuca et al., "How to make a functional β-cell," Development, Jun. 15, 2013, vol. 140, No. 12, pp. 2472-2483.

Paris et al., "Equine embryos and embryonic stem cells: Defining reliable markers of pluripotency," Theriogenology, Sep. 2010, vol. 74, No. 4, pp. 516-524.

Raikwar et al., "Human iPS Cell-Derived Insulin Producing Cells Form Vascularized Organoids under the Kidney Capsules of Diabetic Mice," PLoS One, Jan. 28, 2015, vol. 10, No. 1, pp. e0116582.

Ravassard et al., "A genetically engineered human pancreatic β cell line exhibiting glucose-inducible insulin secretion," The Journal of Clinical Investigation, Sep. 2011, vol. 121, No. 9, pp. 3589-3597.

Rezania et al., "Reversal of diabetes with insulin-producing cells derived in vitro from human pluripotent stem cells," Nature Biotechnology, Nov. 2014, vol. 32, No. 11, pp. 1121-1133.

Roberts et al., "Identification of novel transcripts in annotated genomes using RNA-Seq," Bioinformatics, Sep. 2011, vol. 27, No. 17, pp. 2325-2329.

Rosenberg et al., "Gene Transfer into Humans—Immunotherapy of Patients with Advanced Melanoma, Using Tumor-Infiltrating Lymphocytes Modified by Retroviral Gene Transduction," The New England Journal of Medicine, Aug. 30, 1990, vol. 323, No. 9, pp. 570-578.

Roska et al., "Dissection of the functions of antigen-presenting cells in the induction of T cell activation." The Journal of Immunology, Nov. 1985, vol. 135, No. 5, pp. 2953-2961.

Russ et al., "Controlled induction of human pancreatic progenitors produces functional beta-like cells in vitro," The EMBO Journal, 2015, vol. 34, No. 13, pp. 1759-1772.

Said et al., "Programmed death-1-induced interleukin-10 production by monocytes impairs CD4+ T cell activation during HIV infection," Nature Medicine, Mar. 7, 2020, vol. 16, pp. 452-459.

(56) References Cited

OTHER PUBLICATIONS

Saito et al., "Generation of Glucose-Responsive Functional Islets with a Three-Dimensional Structure from Mouse Fetal Pancreatic Cells and iPS Cells In Vitro," PLoS One, Dec. 2011, vol. 6, No. 12, pp. e28209.

Schulz et al., "A Scalable System for Production of Functional Pancreatic Progenitors from Human Embryonic Stem Cells," PLoS One, May 2012, vol. 7, No. 5, 37004, pp. 1-17.

Sneddon et al., "Self-renewal of embryonic-stem-cell-derived progenitors by organ-matched mesenchyme," Nature, Nov. 29, 2012, vol. 491, No. 7426, pp. 765-768.

Soltanian et al., "Morphogenesis of Human Pluripotent Stem Cell Aggregates toward Pancreatic Progenitors in Suspension Culture," Cell Journal (Yakhteh), 2015, vol. 17, Suppl. 1, Ps-86, p. 59.

Sutton et al., "Isolation of Rat Pancreatic Islets By Ductal Injection of Collagenase," Transplantation, Dec. 1986, vol. 42, No. 6, pp. 689-690.

Takebe et al., "Vascularized and functional human liver from an iPSC-derived organ bud transplant," Nature, 2013, vol. 499, pp. 481-484.

Tang et al., "Desnutrin/ATGL Activates PPARδ to Promote Mitochondrial Function for Insulin Secretion in Islet B Cells," Cell Metabolism, Dec. 3, 2013, vol. 18, No. 6, pp. 883-895.

Teta et al., "Very Slow Turnover of β-Cells in Aged Adult Mice," Diabetes , Sep. 2005, vol. 54, No. 9, pp. 2557-2567.

Tolstoshev et al., "Gene expression using retroviral vectors," Current Opinion in Biotechnology, Oct. 1990, vol. 1, No. 1, pp. 55-61.

Trapnell et al., "Differential analysis of gene regulation at transcript resolution with RNA-seq," Nature Biotechnology, 2013, vol. 31, pp. 46-53.

Vegas et al., "Combinatorial hydrogel library enables identification of materials that mitigate the foreign body response in primates," Nature Biotechnology, Mar. 2016, vol. 34, No. 3, pp. 345-352.

Vegas et al., "Long-term glycemic control using polymer-encapsulated human stem cell-derived beta cells in immune-competent mice," Nature Medicine, Mar. 2016, vol. 22, No. 3, pp. 306-311.

Wendeln et al., "Innate immune memory in the brain shapes neurological disease hallmarks," Nature, Apr. 19, 2018, vol. 556, pp. 332-338.

Willert et al., "Wnt Proteins," Cold Spring Harbor Perspectives in Biology, 2012, vol. 4, No. a007864, pp. 1-14.

Wolff et al., "Direct Gene Transfer into Mouse Muscle in Vivo," Science, Mar. 23, 1990, vol. 247, No. 4949, pp. 1465-1468.

Wu et al., "Receptor-mediated gene delivery and expression in vivo," Journal of Biological Chemistry, Oct. 15, 1988, vol. 263, No. 29, pp. 14621-14624.

Wu et al., "Targeting Genes: Delivery and Persistent Expression of a Foreign Gene Driven by Mammalian Regulatory Elements in Vivo," Journal of Biological Chemistry, Oct. 15, 1989, vol. 264, No. 29, pp. 16985-16987.

Wulfing et al., "A Receptor/Cytoskeletal Movement Triggered by Costimulation During T Cell Activation," Science, Dec. 18, 1998, vol. 282, No. 5397, pp. 2266-2269.

Xu et al., "The role of pyruvate carboxylase in insulin secretion and proliferation in rat pancreatic beta cells," Diabetologia, 2008, vol. 51, pp. 2022-2030.

Yoshihara et al., "Disruption of TBP-2 ameliorates insulin sensitivity and secretion without affecting obesity," Nature Communications, 2010, vol. 1, No. 127, pp. 1-12.

Yoshihara et al., "ERRγ Is Required for the Metabolic Maturation of Therapeutically Functional Glucose-Responsive 3 Cells," Cell Metabolism, Apr. 12, 2016, vol. 23, No. 4, pp. 622-634.

Yu et al., "Human Induced Pluripotent Stem Cells Free of Vector and Transgene Sequences," Science, May 8, 2009, vol. 324, No. 5928, pp. 797-801.

Zhao et al., "Overexpression of lactate dehydrogenase A attenuates glucose-induced insulin secretion in stable MIN-6 3-cell lines," FEBS Letters, Jul. 29, 1998, vol. 430, No. 3, pp. 213-216.

Zuckermann et al., "Discovery of Nanomolar Ligands for 7-Transmembrane G-Protein-Coupled Receptors from a Diverse N-(Substituted)glycine Peptoid Library," Journal of Medicinal Chemistry, 1994, vol. 37, No. 17, pp. 2678-2685.

Sheng et al., "A critical role of IFNγ in priming MSC-mediated suppression of T cell proliferation through up-regulation of B7-H1", Cell Research, 2008, vol. 18, pp. 846-857.

Polchert et al., "IFN-γ activation of mesenchymal stem cells for treatment and prevention of graft versus host disease", Eur. J. Immunol. 2008, vol. 38, pp. 1745-1755.

Krampera et al., "Role for Interferon-γ in the immunomodulatory activity of human bone marrow mesenchymal stem cells", Stem Cells, 2006, vol. 24, pp. 386-398.

Keir et al., "Tissue expression of PD-L1 mediates peripheral T cell tolerance." The Journal of Experimental Medicine, Apr. 17, 2006, vol. 203, No. 4, pp. 883-895.

Office Action in corresponding Chinese Patent Application No. 201980082516.6 (6 pages).

Office Action in corresponding Korean Application No. 10-2021-7013863 (5 pages).

English translation of Office Action in corresponding Korean Applicatiot No. 10-2021-7013863 (3 pages).

Office Action in corresponding Mexican Application No. MX/a/2021/004140 (11 pages).

Foreign associate summary in English of the Office Action in corresponding Mexican Application No. MX/a/2021/004140 (4 pages).

Office Action dated Jul. 10, 2025, in corresponding Canadian Patent Application No. 3115118 (3 pages).

Office Action dated Dec. 24, 2025, in corresponding Korean Patent Application No. 10-2021-7013863 (6 pages).

English Translation of the Office Action dated Dec. 24, 2025, in corresponding Korean Patent Application No. 10-2021-7013863 (4 pages).

* cited by examiner

1mm     self-organization of hADSC

Day 15-19          >Day 20-24

Gellan-Gum based 3D Culture

Insulin granule     Lipid droplet

ERRγ     NDUFA1     COX7A2

*FIG. 2B*
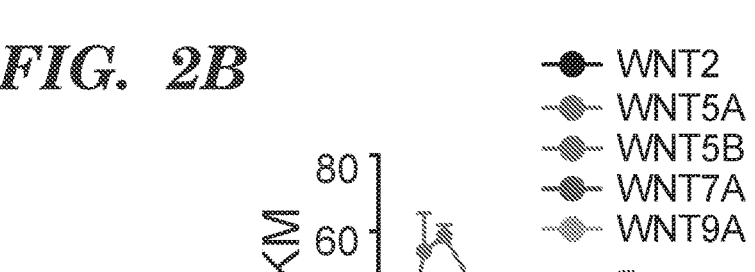
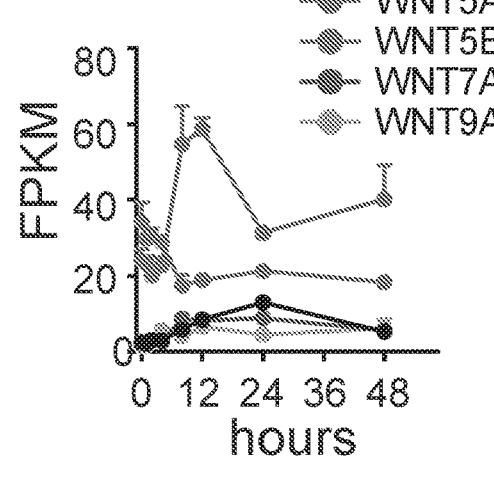
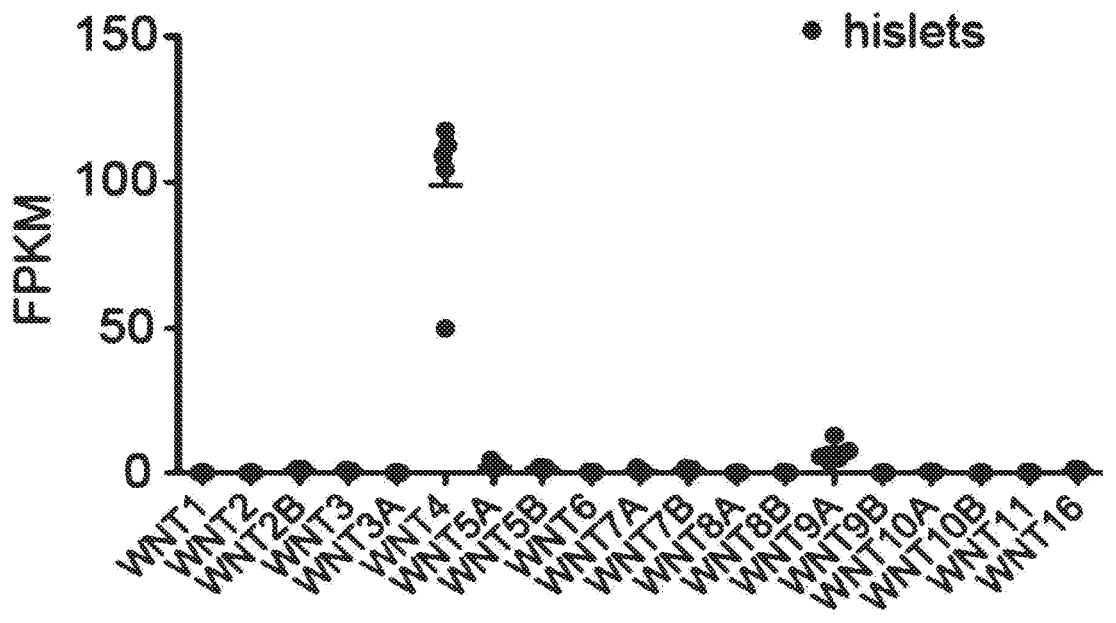
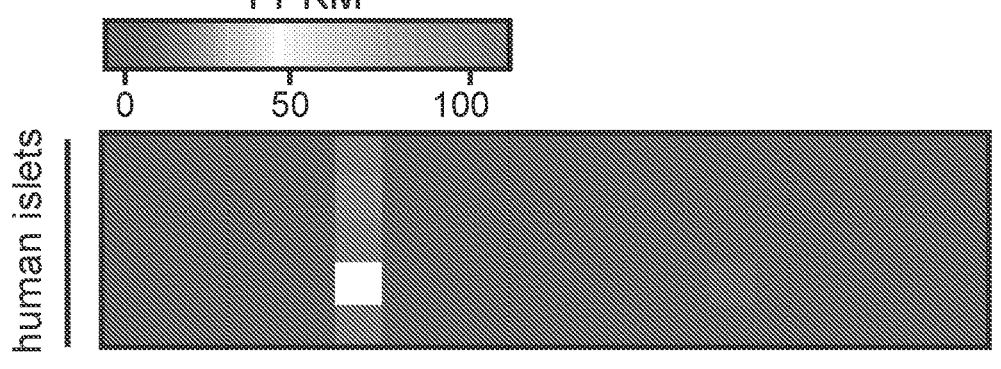
*FIG. 2C*

Commercial
hiPSC-Beta like cells

2D Culture

>5 days

3D Gellan Gum Culture
+rhWnt4

*Pseudoislet*

*FIG.  6A*
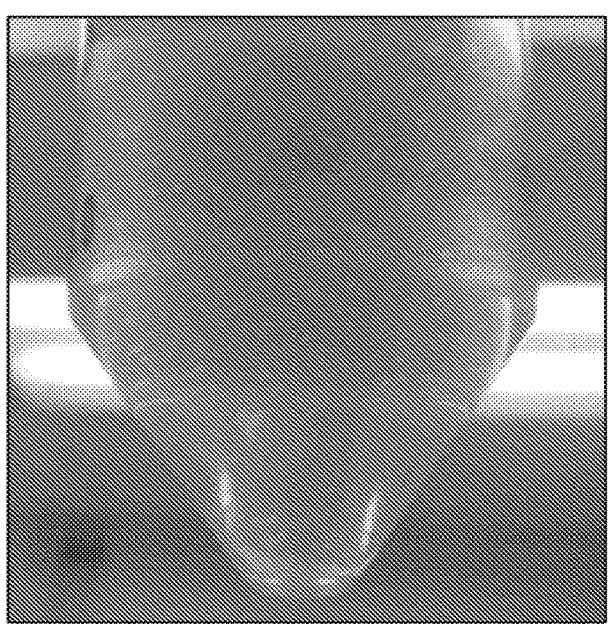
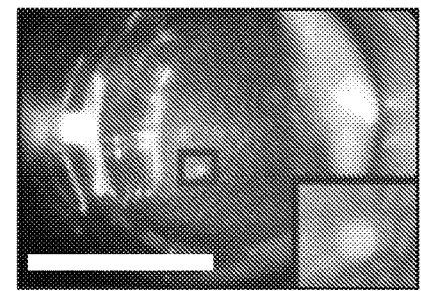
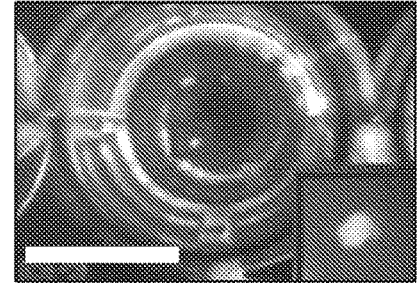
MCS                    hislets
hInsulin-GFP        EC-mCherry        Merge
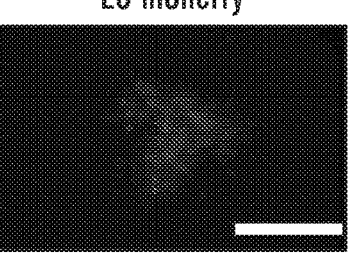
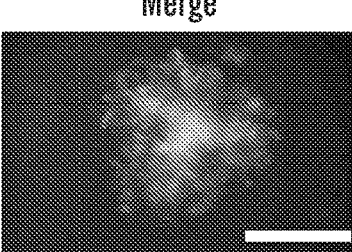
*FIG.  6B*
*in vitro* vascularization
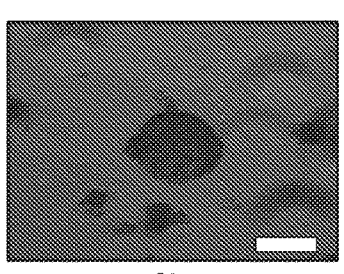
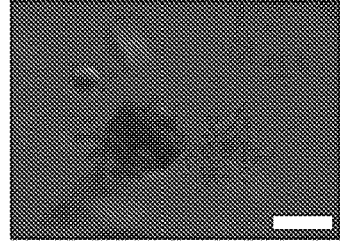
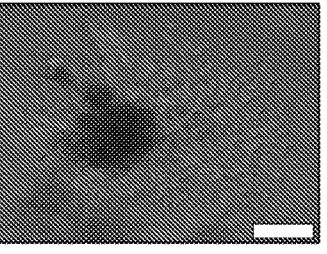
0hr                    24hr                    48hr
*FIG.  6C* scRNA-seq analysis single suspention cells

Drop-seq

Seurat, Monocle, GO analysis

CRISPR-Cas9

Chromosome  Insulin promoter

Edited
Chromosome

Insulin promoter GFP

DIC          Insulin GFP   Ucn3 RFP

*FIG. 7D-2*

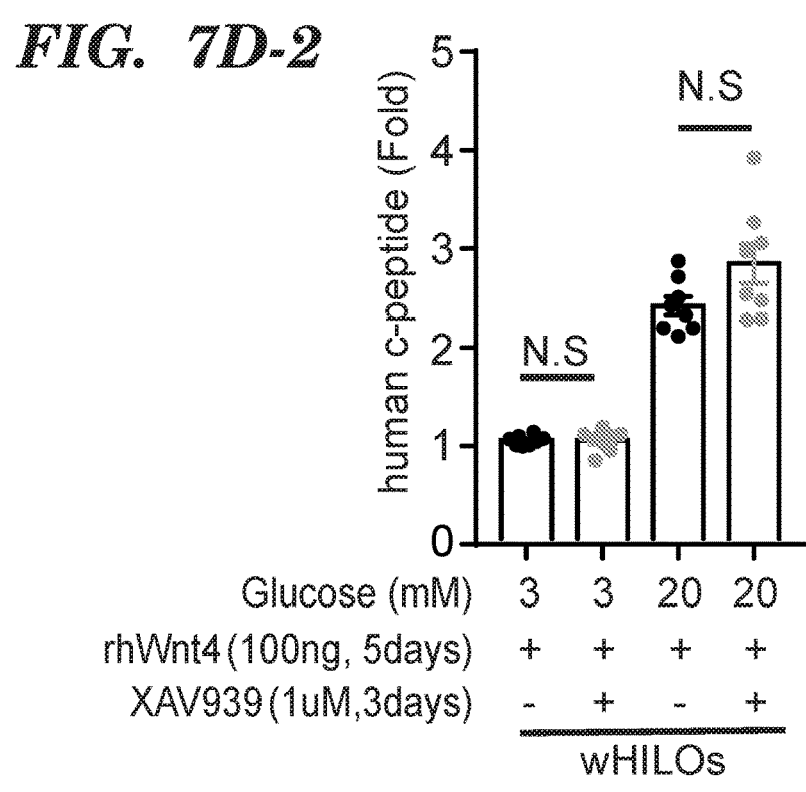

| Glucose (mM) | 3 | 3 | 20 | 20 |
| rhWnt4 (100ng, 5days) | + | + | + | + |
| XAV939 (1uM, 3days) | - | + | - | + | wHILOs

| Motif | Transcription Factor | Function | p-Value |
|---|---|---|---|
| | Foxa2 | β-cell Diff | 1e-148 |
| | Foxo1 | β-cell De-Diff | 1e-57 |
| | Pdx1 | Pancreas Diff | 1e-34 |
| | Rfx6 | β-cell Diff | 1e-27 |
| | MafA | β-cell Diff/maturation | 1e-23 |
| | Nkx6-1 | β-cell Diff | 1e-23 |
| | Isl1 | β-cell Diff | 1e-23 |
| | Esrr | β-cell Metab/maturation | 1e-22 |
| | Coup-TFII | β-cell Function | 1e-19 |
| | THRb | β-cell Maturation | 1e-17 |
| | HNF1β | Pancreas Diff | 1e-16 |
| | MafB | β-cell Diff/maturation | 1e-16 |
| | Ptf1a | Pancreas Diff | 1e-16 |

*FIG. 7E*

TP day3

Sham
wHILO
hislets

ATAC-seq
4841

123

RNA-seq
1458

| Enriched Pathways | P-value |
| --- | --- |
| Ribosome | 7.3E-03 |
| Metabolic Pathway | 9.7E-03 |
| Oxidative phosphorylation | 2.0E-02 |
| Cysteine & methionine metabolism | 3.6E-02 |
| Glycine, serine and threonine metabolism | 3.7E-02 |
| Pyruvate metabolism | 3.9E-02 |

β cell enriched Factors

Veh

Wnt4

Analyzed

Safety Switch

*iCaspase9

Immune Evasion

*Immune checkpoint
*Transcriptional memory PD-L1

Differentiation
*Endoderm (Sox17)
*Pancreatic progenitor (Pdx1, Nkx6-1)
*Endocrine progenitor (Ngn3)
*Immature β-cells (Insulin)

Functional Maturation

*HILOs Technology
*Non-Canonical Wnt
*Ucn3, MafA/B
*Mitochondria OxPhos/ERRs
*3 dimentional culture

CELLS, ISLETS, AND ORGANOIDS THAT EVADE IMMUNE DETECTION AND AUTOIMMUNITY, METHODS OF PRODUCTION AND USE THEREOF

CROSS-REFERENCE TO RELATED APPLICATIONS

This application is the U.S. national phase application, pursuant to 35 U.S.C. § 371, of PCT International Application No. PCT/US2019/055827, filed on Oct. 11, 2019, designating the United States and published in English, which claims priority to and benefit of U.S. Provisional Application No. 62/795,284, filed on Jan. 22, 2019, and U.S. Provisional Application No. 62/745,086, filed on Oct. 12, 2018, the entire contents of each of which are incorporated by reference herein in their entireties.

STATEMENT OF RIGHTS TO INVENTIONS MADE UNDER FEDERALLY SPONSORED RESEARCH

This invention was made with government support under Grant Nos. DK057978, DK090962, HL088093, HL105278 and ES010337 awarded by the National Institutes of Health, and Grant No. P30 014195 awarded by the National Institutes of Health and the National Cancer Institute. The government has certain rights in the invention.

BACKGROUND

For the treatment of insulin dependent diabetes, such as type 1 diabetes and late-stage type 2 diabetes, the shortage of human islets limits the number of patients who can benefit from this therapy. Despite progress in the field of in vitro differentiation of human induced pluripotent stem cells (hiPSCs) into β-like cells, the β-like cells generated in this manner typically exhibit impairments in glucose-stimulated insulin secretion (GSIS) and mitochondrial metabolic function, as well as detection and destruction by a recipient's immune system following administration. Thus, further improvements to the maturation process are required to fully capture pancreatic islet physiology and the generation of functional and lasting organoids.

Needed in the art are methods for generating functional human organs that survive transplant for the treatment of diseases, as well as new platforms for drug-screening and disease modeling to provide new treatment strategies and therapeutics for patients with organ failure.

SUMMARY OF THE DESCRIBED EMBODIMENTS

Provided are compositions and methods for generating an immunoprotected cell, islet, organoid, or islet-like organoid, including, but not limited to, a human pancreatic islet organoid or a pancreatic organoid, in particular, a human islet-like organoid (abbreviated as "HILO" herein), that survives and evades detection by the immune system (autoimmunity) following administration to or transplant or implant in a subject. In an embodiment, the cell, islet, organoid, islet-like organoid (and cells therein) expresses interferon gamma (IFNγ)-receptors. In an embodiment, the cell, islet, organoid, or islet-like organoid (and cells therein) is human.

In an aspect, a method of increasing survival or reducing cell death of a transplanted donor cell is provided in which the method comprises contacting the donor cell with multiple intermittent exposures to interferon gamma (IFNγ) over a given time period, e.g., a time period of at least 24 hours, thereby increasing survival of the transplanted donor cell. In an embodiment, the the transplanted donor cell is an organoid cell, an islet cell, an islet-like organoid cell, or a β-like islet cell. In an embodiment, the transplanted donor cell is syngeneic to the subject who receives the transplant. In an embodiment, the transplanted donor cell is autologous to the subject who receives the transplant. In an embodiment, the transplanted donor cell is allogeneic or xenogeneic to the subject who receives the transplant. In an embodiment, the transplanted donor cell is an interferon gamma (IFNγ) receptor-expressing cell. In an embodiment, the transplanted donor cell is a human cell.

In another aspect, a method of generating an immunoprotected cell, islet, or organoid that survives detection by immune system cells, e.g., T cells or B cell, is provided in which the method comprises subjecting an interferon gamma (IFNγ) receptor-expressing cell, islet, or organoid, or cells thereof, to multiple intermittent exposure to IFNγ over a given time period, e.g., a time period of at least 24 hours, thereby inducing expression of an immune checkpoint protein by the cell, islet, or organoid and allowing said cell, islet, or organoid to survive immune detection or autoimmunity.

In an aspect, the human islet-like organoid (HILO) and the cells comprising the HILO, namely, beta (β)-like cells, express or are induced to express following exposure to IFNγ one or more molecules involved in modulating the immune response or autoimmunity, such as an immune checkpoint protein, to overcome immune rejection or autoimmunity of "non-self" cells or HILOs introduced into, e.g., transplanted or implanted, into a subject. In an embodiment, the immune checkpoint protein is PD-L1. In an embodiment, the subject into whom HILOs are introduced, transplanted, or implanted has diabetes. In an embodiment, the subject into whom HILOs are introduced, transplanted, or implanted has type 1, type 2 diabetes, or late stage type 2 diabetes. In an embodiment, the subject into whom HILOs are introduced, transplanted, or implanted has type 1 diabetes. In an embodiment, the subject into whom HILOs are introduced, transplanted, or implanted is a human subject or patient. In an embodiment, the one or more immune checkpoint protein is recombinantly expressed in the introduced, transplanted, or implanted cells or HILOs. The terms "transplant" and "implant" may be used interchangeably herein to refer to cells, islets, or organoids (and cells therein) that are introduced or transferred into a subject by procedures practiced in the medical arts to effect or provide a function therein, especially a therapeutic function to treat a disease, disorder or pathology.

In one aspect, a method of generating a pancreatic islet organoid is provided in which induced pluripotent stem cell (iPSC)-derived beta (β)-like cells are cultured in a 3-dimensional matrix containing gellan gum, thereby generating a pancreatic islet organoid in which the organoid cells express one or more checkpoint proteins. Also provided is a cell culture including an iPSC-derived beta-like cell, which expresses one or more immune checkpoint proteins, in a three-dimensional matrix containing gellan gum. In an embodiment, the one or more immune checkpoint proteins is PD-L1.

In an aspect, a cell culture including a human iPSC-derived beta-like cell, a human adipose-derived stem cell (hADSC), and a human umbilical vein endothelial cell (HUVEC) in a three-dimensional matrix containing gellan gum is provided, in which the cells of the culture express one or more immune checkpoint proteins.

In various embodiments of any aspect delineated herein, the cell culture includes an adipose-derived stem cell and/or an endothelial cell.

In an aspect, a pancreatic islet-like organoid containing an iPSC-derived beta-like cell which expresses one or more immune checkpoint proteins is provided, wherein the organoid is vascularized and exhibits glucose-stimulated insulin secretion (GSIS) and wherein the cells of the organoid and the organoid express one or more immune checkpoint proteins. In an embodiment, the pancreatic islet-like organoid is a human pancreatic islet-like organoid. In an embodiment the one or more immune checkpoint proteins is PD-L1.

In an aspect, a pancreatic islet organoid containing an iPSC-derived beta (ß)-like cell, an iPSC-derived alpha (α) cell, an iPSC-derived delta (δ) cell, an iPSC-derived duct cell, an adipose-derived stem cell (hADSC), and an endothelial cell. wherein the iPSC cell expresses one or more immune checkpoint proteins, the organoid is vascularized and exhibits glucose-stimulated insulin secretion (GSIS), KCl-stimulated insulin secretion, GLP-1 stimulated insulin secretion, somatostatin secretion, and glucagon secretion is provided.

In a related aspect, a non-human organism transplanted or implanted with the organoid of any aspect delineated herein is provided.

In an aspect, a method of treating a pancreatic disease in a subject is provided, in which a pancreatic islet organoid, or HILO, is introduced or transplanted or implanted into the subject, wherein the pancreatic islet organoid, or HILO, contains iPSC-derived beta-like cells, which express one or more immune checkpoint proteins to evade immune detection; wherein the pancreatic islet organoid, or HILO, is vascularized and exhibits glucose-stimulated insulin secretion (GSIS). In an embodiment, the one or more immune checkpoint proteins is PD-L1. In an embodiment, the subject is human and the pancreatic islet organoid, or HILO, is generated from human tissue or cells.

In an aspect, a method of treating type 1 diabetes in a subject is provided, in which a pancreatic islet organoid, or HILO, is introduced, transplanted, or implanted into the subject, wherein the pancreatic islet organoid, or HILO, contains iPSC-derived beta-like cells, which express one or more immune checkpoint proteins to evade immune detection; wherein the pancreatic islet organoid, or HILO, is vascularized and exhibits glucose-stimulated insulin secretion (GSIS). In an embodiment, the pancreatic islet organoid, or HILO, expresses a checkpoint protein to evade immune detection. In an embodiment, the one or more immune checkpoint proteins is PD-L1. In an embodiment, the subject is human and the pancreatic islet organoid, or HILO, is generated from human tissue or cells.

In an aspect, a pancreatic islet organoid or HILO is provided, in which the pancreatic islet organoid or HILO is generated by culturing an induced pluripotent stem cell (iPSC)-derived beta-like cell in a 3-dimensional matrix containing gellan gum. In an embodiment, the pancreatic islet organoid, or HILO, expresses one or more immune checkpoint proteins to evade immune detection. In an embodiment, the subject is human and the pancreatic islet organoid, or HILO, is generated from human tissue or cells. In an embodiment, the one or more immune checkpoint proteins is PD-L1.

Provided in another aspect is a pancreatic organoid or HILO generated by culturing an induced pluripotent stem cell (iPSC)-derived beta-like cell and an iPSC-derived exocrine component cell in a 3-dimensional matrix containing gellan gum. In an embodiment, the pancreatic islet organoid, or HILO, expresses one or more immune checkpoint proteins to evade immune detection. In an embodiment, the one or more immune checkpoint proteins is PD-L1. In an embodiment, the subject is human and the pancreatic islet organoid, or HILO, is generated from human tissue or cells.

Provided in another aspect is a pancreatic organoid or HILO generated by culturing an induced pluripotent stem cell (iPSC)-derived beta-like cell and an iPSC-derived exocrine component cell in a culture medium, such as a 3-dimensional matrix containing gellan gum and an agent that stimulates expression and production of a checkpoint protein in the cells of the pancreatic organoid (β-cells) or HILO. Without wishing to be bound by theory, the PD-L1 is produced in the β-cells or HILO through the mechanism of transcriptional memory. In an embodiment, the culture medium or matrix comprises interferon gamma (IFNγ). In an embodiment, the pancreatic islet organoid, or HILO, expresses one or more immune checkpoint proteins to evade immune detection. In an embodiment, the one or more immune checkpoint proteins is PD-L1. In an embodiment, the subject is human and the pancreatic islet organoid, or HILO, is generated from human tissue or cells.

In another aspect, the invention provides a liver organoid generated by culturing an induced pluripotent stem cell (iPSC)-derived hepatocyte in a 3-dimensional matrix containing gellan gum; wherein the iPSC-derived hepatocyte expresses one or more immune checkpoint proteins such that the liver organoid evades immune detection. In an embodiment, the one or more immune checkpoint proteins is PD-L1.

In another aspect, the invention provides a heart organoid generated by culturing an induced pluripotent stem cell (iPSC)-derived cardiomyocyte in a 3-dimensional matrix containing gellan gum wherein the iPSC-derived cardiomyocyte expresses one or more immune checkpoint proteins such that the heart organoid evades immune detection. In an embodiment, the one or more immune checkpoint proteins is PD-L1.

In another aspect, the invention provides an intestinal organoid generated by culturing an induced pluripotent stem cell (iPSC)-derived intestinal cell in a 3-dimensional matrix containing gellan gum, wherein the iPSC-derived intestinal cell expresses one or more immune checkpoint proteins such that the intestinal organoid evades immune detection. In an embodiment, the one or more immune checkpoint proteins is PD-L1.

In various embodiments of any aspect delineated herein, the method involves culturing the iPSC-derived beta-like cell, which expresses one or more immune checkpoint proteins, with an adipose-derived stem cell and/or an endothelial cell. In an embodiment, the one or more immune checkpoint proteins is PD-L1. In various embodiments of any aspect delineated herein, the method involves culturing the iPSC-derived beta-like cell, which expresses one or more immune checkpoint proteins, with an iPSC-derived alpha-like cell, an iPSC-derived delta-like cell, and/or an iPSC-derived duct-like cell.

In various embodiments of any aspect delineated herein, the pancreatic islet organoid contains an iPSC-derived alpha-like cell, an iPSC-derived delta-like cell, and/or an iPSC-derived duct-like cell. In various embodiments of any aspect delineated herein, the pancreatic islet organoid includes an adipose-derived stem cell and/or an endothelial cell. In various embodiments of any aspect delineated herein, the pancreatic islet organoid exhibits KCl-stimulated insulin secretion, GLP-1 stimulated insulin secretion, somatostatin secretion, c-peptide expression, and/or glucagon secretion. In various embodiments of any aspect delineated herein, the pancreatic islet organoid expresses one or more of the beta cell transcription factors Pdx1, MafA, Pax4, Pax6, NeuroD1, Nkx6-1, Gata6, and Foxa2. In certain embodiments, the pancreatic islet organoid contains an iPSC-derived beta-like cell, which expresses one or more immune checkpoint proteins, an iPSC-derived alpha cell, an iPSC-derived delta cell, an iPSC-derived duct cell, an adipose-derived stem cell (hADSC), and an endothelial cell, where the organoid is vascularized and exhibits glucose-stimulated insulin secretion (GSIS), KCl-stimulated insulin secretion, GLP-1 stimulated insulin secretion, somatostatin secretion, and glucagon secretion. In an embodiment, the one or more immune checkpoint proteins is PD-L1. In various embodiments of any aspect delineated herein, the pancreatic islet organoid is surrounded by an iPSC-derived exocrine component. In various embodiments, the iPSC-derived exocrine component expresses one or more of the markers PDX1, Nkx6-1, and Ptf1.

In various embodiments of any aspect delineated herein, the liver organoid expresses one or more of the markers AFP, ALB, and Cyp3a7. In various embodiments of any aspect delineated herein, the liver organoid exhibits insulin signaling, insulin resistance by palmitic acids, and lipid accumulation.

In various embodiments of any aspect delineated herein, the heart organoid expresses one or more of the markers hMlc2a, hNkx2-5, alphaMHC and KCNQ1. In various embodiments of any aspect delineated herein, the heart organoid exhibits cardiac beating.

In various embodiments of any aspect delineated herein, the intestinal organoid expresses one or more of the markers CDX2, Muc2, and Lgr5. In various embodiments of any aspect delineated herein, the intestinal organoid exhibits budding in response to R-spondin.

In various embodiments of any aspect delineated herein, the iPSC-derived beta-like cell, iPSC-derived alpha-like cell, iPSC-derived delta-like cell, and/or iPSC-derived duct-like cell is human. In various embodiments of any aspect delineated herein, the iPSC-derived beta-like cell, iPSC-derived exocrine component cell, iPSC-derived hepatocyte, iPSC-derived cardiomyocyte, or iPSC-derived intestinal cell is human. In various embodiments, the adipose-derived stem cell is a human adipose-derived stem cell (hADSC). In various embodiments of any aspect delineated herein, the endothelial cell is a human umbilical vein endothelial cell (HUVEC). In various embodiments, the organoids are generated from human cells.

In various embodiments of any aspect delineated herein, the pancreatic islet organoid, pancreatic organoid, liver organoid, heart organoid, or intestinal organoid, contains an adipose-derived stem cell and/or an endothelial cell. In various embodiments of any aspect delineated herein, the pancreatic islet organoid, pancreatic organoid, liver organoid, heart organoid, or intestinal organoid is vascularized.

In another aspect, the invention provides a method of generating a pancreatic islet organoid of HILO, the method comprising culturing an induced pluripotent stem cell (iPSC)-derived beta-like cell, which expresses one or more immune checkpoint proteins, in a medium comprising Wnt4 or Wnt5a protein. In an embodiment, the one or more immune checkpoint proteins is PD-L1. In an embodiment, the induced pluripotent stem cell (iPSC)-derived beta-like cell is cultured in a 3-dimensional matrix. In an embodiment of the foregoing aspect, the Wnt4 or Wnt5a protein is a recombinant human Wnt4 or Wnt5a protein. In a particular embodiment, the medium comprises recombinant human Wnt4 protein. In another particular embodiment, the medium comprises recombinant human Wnt5a protein. In a particular embodiment, a Wnt4- or Wnt5-induced human islet organoid or HILO is a mature islet or a mature HILO.

In another aspect the invention provides a cell culture comprising a human iPSC-derived beta-like cell, which expresses one or more immune checkpoint proteins, and Wnt4 or Wnt5a protein. In an embodiment, the one or more immune checkpoint proteins is PD-L1. In an embodiment, the human iPSC-derived beta-like cell is in a three-dimensional matrix comprising gellan gum. In an embodiment, the Wnt4 or Wnt5a protein is a recombinant human Wnt4 or Wnt5a protein. In a particular embodiment, the medium comprises recombinant human Wnt4 protein. In another particular embodiment, the medium comprises recombinant human Wnt5a protein. In a particular embodiment, a Wnt4- or Wnt5-induced human islet organoid or HILO is a mature islet or a mature HILO.

In another aspect, the invention provides a pancreatic islet organoid comprising an iPSC-derived beta-like cell, which expresses one or more immune checkpoint proteins, cultured in medium comprising Wnt4 or Wnt5a protein, wherein the organoid is vascularized and exhibits glucose-stimulated insulin secretion (GSIS). In an embodiment, the one or more immune checkpoint proteins is PD-L1. In an embodiment, the organoid further exhibits KCl-stimulated insulin secretion or glucose stimulated insulin secretion. In an embodiment, the pancreatic islet organoid expresses Fltp and Esrrg genes. In an embodiment, the Wnt4 or Wnt5a protein is a recombinant human Wnt4 or Wnt5a protein. In a particular embodiment, the medium comprises recombinant human Wnt4 protein. In another particular embodiment, the medium comprises recombinant human Wnt5a protein. In a particular embodiment, a Wnt4- or Wnt5-induced human islet organoid or HILO is a mature islet or a mature HILO.

In another aspect, the invention provides a non-human organism transplanted or implanted with the organoid defined in the above described aspects.

In another aspect, the invention provides a method of enhancing self organization of adipose-derived stem cells (ADSCs) for generating an induced pluripotent stem cell (iPSC)-derived organoid, which evades immune surveillance and rejection, the method comprising culturing the ADSCs in a 3-dimensional (3-D) culture matrix medium comprising a Wnt5a protein. In an embodiment, the one or more immune checkpoint proteins is PD-L1. In an embodiment of the method, the ADSCs are cultured in a 3-D culture matrix comprising gellan gum. In an embodiment, the ADSCs are cultured in the 3-D culture matrix medium comprising a Wnt5 protein and an iPSC-derived cell selected from an iPSC-derived beta-like cell, an iPSC-derived exocrine component cell, an iPSC-derived hepatocyte, an iPSC-derived cardiomyocyte, or an iPSC-derived intestinal cell. which expresses one or more immune checkpoint proteins. In an embodiment, the one or more immune checkpoint proteins is PD-L1. In an embodiment of the method, the iPSC-derived organoid is selected from a pancreatic islet organoid, pancreatic organoid, a liver organoid, a heart organoid, or an intestinal organoid. In an embodiment of the method, the induced pluripotent stem cell (iPSC)-derived organoid is a human induced pluripotent stem cell (hiPSC)-derived organoid. In an embodiment of the method, the Wnt5a protein is a recombinant human Wnt5a protein. In an embodiment of the method, the pancreatic islet organoid, pancreatic organoid, liver organoid, heart organoid, or intestinal organoid is derived from an iPSC-derived cell selected from an iPSC-derived beta-like cell, an iPSC-derived exocrine component cell, an iPSC-derived hepatocyte, an iPSC-derived cardiomyocyte, or an iPSC-derived intestinal cell, respectively. In an embodiment, of any of the above, the iPSC-derived cell is human.

In another aspect, the invention provides a method of enhancing self organization of adipose-derived stem cells (ADSCs) for generating a pancreatic islet or pancreatic organoid that evades immune rejection or autoimmunity, comprising culturing ADSCs, which express one or more immune checkpoint proteins, in medium comprising Wnt5a protein. In an embodiment, the one or more immune checkpoint proteins is PD-L1. In an embodiment, the ADSCs are cultured in a 3-dimensional matrix comprising gellan gum. In another embodiment, the Wnt5a protein a recombinant human Wnt5a protein.

In another aspect, the invention provides a pancreatic islet organoid, pancreatic organoid, a liver organoid, a heart organoid, or intestinal organoid produced by any of the above-delineated methods and embodiments thereof.

In various aspects of any of the foregoing embodiments, the immune checkpoint protein, or the one or more immune checkpoint proteins, or a fragment or portion of the immune checkpoint protein that binds to cognate ligand, is recombinantly expressed in or molecularly introduced into the cells of an organoid, (e.g., β-like cells that constitute HILOs) which express the one or more checkpoint proteins as membrane surface proteins that bind to a cognate ligand on an immune cell, e.g., a T cell, that is involved in autoimmunity, or that reacts against a foreign or 'non-self' cell, so as to suppress or block the T cell response (an allogeneic immune response or autoimmune response) and thus evade immune system surveillance and rejection in a recipient.

In embodiments, the cells of an organoid, (e.g., β-like cells that constitute HILOs) express one or more checkpoint proteins or molecules that bind to cognate ligands on the surface of an immune cell to suppress allogeneic immune activity or autoimmunity against the cells and the organoid. In a particular embodiment, the cells of an organoid, (e.g., a β-like cell) and the organoid (e.g., HILO) express the immune checkpoint protein PD-L1, programmed cell-death ligand 1, which binds to PD-1, programmed cell-death protein 1, which is expressed, for example, on T cells. PD-L2, programmed cell-death ligand 2, also binds to PD-1, but with a different Kd. In other embodiments, the cells of an organoid, (e.g., a β-like cell) and the organoid (e.g., HILO) are molecularly engineered to express a molecule that binds a checkpoint protein expressed on the surface of an immune cell, such as a T cell (e.g., an effector T cell), wherein the checkpoint protein expressed on the surface of an immune cell is CTLA-4 (cytotoxic T-lymphocyte protein 4, also called CD152); LAG-3, lymphocyte activation gene 3 protein; KIR, killer cell immunoglobulin-like receptor; IDO1, indoleamine 2,3-dioxygenase 1; 4-1BB, a tumor necrosis factor receptor superfamily member 9, (also known as CD137); GITR, "glucocorticoid-induced TNFR family related gene; TIM-3, "T-cell immunoglobulin domain and mucin domain;" OX40, tumor necrosis factor receptor superfamily member 4, (also known as CD134); A2AR, adenosine A2A receptor; B7-H3 (also called CD276); B7-H4 (also called VTCN1); B7-1/B7-2; BTLA (also called CD272); VISTA, "V-domain Ig suppressor of T cell activation;" or a combination of any of the foregoing.

In an aspect of any of the foregoing embodiments, the immune checkpoint protein comprises all, or a portion, e.g., the extracellular domain, of the checkpoint protein (also called a "checkpoint molecule" herein). In a particular embodiment, the immune checkpoint protein is PD-L1 or a binding portion thereof. In an embodiment, the checkpoint protein is the extracellular domain of the PD-L1 protein.

Another aspect provides a human induced pluripotent stem cell (hiPSC), human beta (β)-cell, or human islet-like organoid (HILO) generated therefrom, molecularly engineered to express one or more immune checkpoint proteins that bind to a cognate ligand on an immune cell, such as a T cell. In an embodiment, the one or more immune checkpoint proteins expressed by a hiPSC, human beta (β)-cell, or human islet-like organoid (HILO) binds to an immune cell-expressed cognate ligand selected from programmed cell-death protein 1 (PD-1); cytotoxic T-lymphocyte protein 4 (CTLA-4); lymphocyte activation gene 3 protein (LAG-3); killer cell immunoglobulin-like receptor (KIR); indoleamine 2,3-dioxygenase 1 (IDO1); tumor necrosis factor receptor superfamily member 9 (4-1BB); glucocorticoid-induced TNFR family related gene (GITR); T-cell immunoglobulin domain and mucin domain (TIM-3); tumor necrosis factor receptor superfamily member 4, (OX40); adenosine A2A receptor (A2AR); B7-H3; B7-H4; B7-1/B7-2; BTLA; V-domain Ig suppressor of T cell activation (VISTA); or a combination of any of the foregoing. In a particular embodiment, the hiPSC, human beta (β)-cell, or HILO expresses the immune checkpoint protein, programmed cell-death protein-ligand 1 (PD-L1), which binds to PD-1.

In another aspect, a method of generating cells, islets, organoids that survive and have reduced cell death following transplantation, implantation, or transfer is provided in which the method comprises: (a) contacting interferon gamma (IFNγ)-receptor expressing cells, islets, or organoids with interferon gamma (IFNγ) for at least 0.5 hour or at least one hour at a predetermined time point; and (b) repeating step (a) at least about two times during a time period of about or equal to 72-hours; wherein the cells, islets, or organoids are maintained in the absence of IFNγ between times of contact with IFNγ; and wherein steps (a) and (b) induce sustained expression of PD-L1 in the cells, islets, or organoids. In an embodiment of the method, the cells, islets, organoids or cells are contacted with IFNγ for a time period selected from about or equal to at least 0.5 hour, at least 1 hour, at least 2 hours, or more than 2 hours in step (a). In another embodiment of the method, the cells, islets, or organoids are contacted with IFNγ for a time period selected from about or equal to 0.5 hour, or about or equal to 1 hour, or about or equal to 2 hours. or about or equal to 12 hours in step (a). In another embodiment of the method, step (a) is repeated at least three times for at least about 0.5 hour each time, or for at least about 1 hour each time, or for at least about 2 hours each time in the about or equal to 72-hour time period of step (b). In another embodiment of the method, the cells, islets, or organoids are washed to remove the presence of IFNγ between step (a) and step (b). In another embodiment of the method, IFNγ is used in an amount of 1-25 ng/ml. In another embodiment of the method, IFNγ is used in an amount of 10 ng/ml. In another embodiment of the method, PD-L1 expression in the cells, islets, or organoids is maintained following step (b) for greater than about or equal to 7 days. In an embodiment, sustained expression of PD-L1 comprises about or equal to 3 days, 4 days, 5 days, 6 days, 7 days, 8 days, 9 days, 10 days, 11 days, 12 days, 13 days, 14 days, or longer, of PD-L1 expression in a cell.

In another aspect, a method of generating islets, or organoids and the cells thereof that survive and have reduced cell death following transplant, implant or transfer is provided, in which the method comprises: (a) contacting interferon gamma (IFNγ)-receptor expressing islets or organoids and the cells thereof with interferon gamma (IFNγ) in an amount of about 1 ng/ml to 25 ng/ml for greater than 1 hour at a first time point during a given time period, e.g., a time period of about or equal to 24-hours; and (b) contacting the islets or organoids and the cells thereof with IFNγ in an amount of about 1 ng/ml to 25 ng/ml for greater about 0.5-1 hour or longer at two or more additional time points during a following time period, e.g., a 48-hour time period, following step (a); wherein said islets or organoids are washed and rested in medium in the absence of IFNγ between being contacted with IFNγ; and wherein steps (a) and (b) induce sustained expression of PD-L1 in said islets or organoids. In an embodiment of the method, the islets or organoids are contacted with IFNγ in an amount of 10 ng/ml for at least 2 hours in step (a) and step (b). In another embodiment of the method, the islets or organoids are contacted with IFNγ for at least about 2 hours at 3 timepoints during the 72-hour time period.

In an embodiment of any of the above-denoted methods, the cells, islets, or organoids are human cells, islets, or organoids. In another embodiment of the above methods, the organoids are HILOs or human HILOs. In another embodiment of the above methods, the islets are human cadaveric islets which are protected from destruction or clearance by the immune system.

In another aspect, a method of generating human cells, islets, or human islet like organoids (HILOs) that evade immune detection or autoimmunity is provided in which the method involves (a) contacting the human cells, islets or HILOs with interferon gamma (IFNγ) for greater than one hour at predetermined time point; repeating step (a) at least two times during a given time period, e.g., a 72-hour time period; wherein the human cells, islets, or HILOs are maintained in the absence of IFNγ between times of contact with IFNγ; and wherein steps (a) and (b) induce sustained expression of PD-L1 in the human islets or HILOs. In an embodiment of the method, the human cells, islets, or HILOs are contacted with IFNγ for 2 hours or more in step (a). In another embodiment of the method, the human cells, islets, or HILOs are contacted with IFNγ for 2 hours or 12 hours in step (a). In another embodiment of the method, step (a) is repeated three times for at least 2 hours each time in the given time period, i.e., a 72-hour time period. In another embodiment of the method, the human cells, islets, or HILOs are washed to remove IFNγ between step (a) and step (b). In another embodiment of the method, IFNγ is used in an amount of 1-25 ng/ml. In another embodiment of the method, IFNγ is used in an amount of 10 ng/ml. In another embodiment of the method, PD-L1 expression in the islets or HILOs is maintained or sustained following step (b) for greater than 7 days.

In another aspect, a method of generating human cells, islets or human islet like organoids (HILOs) that evade immune detection or autoimmunity is provided in which the method involves (a) contacting the human cells, islets or HILOs with interferon gamma (IFNγ) in an amount of about 1 ng/ml to 25 ng/ml for greater than 1 hour at a first time point during a given time period, e.g., a 24-hour time period; and (b) contacting the human cells, islets or HILOs with IFNγ in an amount of about 1 ng/ml to 25 ng/ml for greater than 1 hour at at least two additional time points during a next given time period, e.g., a 48-hour time period, following step (a); wherein the human cells, islets, or HILOs are washed and rested in medium in the absence of IFNγ between being contacted with IFNγ; and wherein steps (a) and (b) induce sustained expression of PD-L1 in the human islets or HILOs. In an embodiment of the method, the human islets or HILOs are contacted with interferon gamma (IFNγ) in an amount of 10 ng/ml for at least 2 hours in step (a) and step (b). In another embodiment of the method, the human islets or HILOs are contacted with interferon gamma (IFNγ) for at least 2 hours at 3 different intervals (time points) during a given time period, such as a 72-hour time period. In an embodiment of the method of the foregoing aspects, the human islets or HILOs are mature human islets or HILOs. In an embodiment, sustained expression of PD-L1 comprises about or equal to 3 days, 4 days, 5 days, 6 days, 7 days, 8 days, 9 days, 10 days, 11 days, 12 days, 13 days, 14 days, or longer, of PD-L1 expression in a cell. In embodiments of the method, the cells comprise cardiac cells, colon cells, kidney cells, bladder cells, liver cells (hepatocytes), esophageal cells, gastrointestinal cells, gastric (stomach) cells, lung cells, ovarian cells, cervical cells, uterine cells, testicular cells, pancreatic cells, pancreatic β cells, retinal cells, corneal cells, brain cells, muscle cells, hematopoietic cells, immune cells (B cells, T cells), chimeric antigen receptor-T cells (CAR-T cells), bone marrow cells, mononuclear cells, neurons, neuronal cells, insulin-producing pancreatic β cells derived from human skin cells, umbilical cord blood (UCB) cells, adipose derived mesenchymal stromal (stem) cells, cardiac stem cells, colon stem cells, kidney stem cells, liver (hepatocyte) stem cells, gastrointestinal stem cells, gastric stem cells, lung stem cells, pancreatic stem cells, pancreatic μ stem cells, muscle stem cells, hematopoietic stem cells, immune cell (T cell or B cell) stem cells, bone marrow stem cells, CD133+ stem cells, CD34+ hematopoietic cells, CD34+ hematopoietic stem cells, mesenchymal stem cells, umbilical cord mesenchymal stem cells, retinal stem cells, neuronal stem cells, ectoderm-derived neuronal cells, immortalized dopaminergic neuronal precursor cells and organoids generated from or containing said cells. In an embodiment of the method, the organoids comprise cardiac organoids, intestinal/gastrointestinal organoids, colonic organoids, hepatic organoids, kidney organoids, bladder organoids, ovarian organoids, cervical organoids, neural organoids, or pulmonary (lung) organoids.

In an embodiment of the methods of any of the above-delineated aspects, the interferon gamma (IFNγ)-receptor expressing cells, islets, or organoids are contacted with IFNγ in culture medium or a physiologically acceptable solution, or in a three-dimensional matrix. In an embodiment, the the interferon gamma (IFNγ)-receptor expressing cells, islets, or organoids are contacted with IFNγ in a three-dimensional (3D) matrix, e.g., gellan gum, as described herein.

In another aspect, a method of generating an islet-like organoid that evades immune detection or autoimmunity is provided, in which the method comprises culturing endocrine progenitor cells in a three-dimensional matrix comprising Wnt4 or Wnt5a protein for a time sufficient to generate a multicellular islet-like organoid comprising two or more cell types selected from beta (β) cells, alpha (α) cells, delta (δ) cells, epsilon (ε) cells and duct-like cells; wherein the islet-like organoid secretes insulin in response to glucose; and subjecting the islet-like organoid to multiple intermittent exposure to interferon gamma (IFNγ) over a given time period, e.g., a time period of at least 24 hours; thereby inducing sustained expression of an immune checkpoint protein by the islet-like organoid and allowing the islet-like organoid to evade immune detection or autoimmunity. In an embodiment of the method, the islet-like organoid is exposed to IFNγ at least two times over at least a two-day time period. In another embodiment of the method, the islet-like organoid is exposed to IFNγ at least three times over a three-day time period. In another embodiment of the method, the islet-like organoid is exposed to IFNγ for greater than one hour at least two times over a two-day time period. In another embodiment of the method, the islet-like organoid is exposed to IFNγ for greater than one hour at least three times over a three-day time period. In another embodiment of the method, the islet-like organoid is exposed to IFNγ for two hours at least two times over a two-day time period. In another embodiment of the method, the islet-like organoid is exposed to IFNγ for two hours at least three times over a three-day time period. In embodiments of the method, the the islet-like organoid is intermittently exposed to IFNγ over a time period of 1, 2, 3, 4, 5, 6, 7, 8, 9, or 10 days, or longer.

In another aspect, a method of generating an islet-like organoid that evades immune detection or autoimmunity is provided, in which the method comprises culturing endocrine progenitor cells which recombinantly express an immune checkpoint protein in a three-dimensional matrix comprising Wnt4 or Wnt5a protein for a time sufficient to generate a multicellular islet-like organoid comprising two or more cell types selected from beta (β) cells, alpha (α) cells, delta (δ) cells, epsilon (ε) cells and duct-like cells; wherein the islet-like organoid secretes insulin in response to glucose and wherein the islet-like organoid evades immune detection and autoimmunity. In an embodiment, recombinant expression of the immune checkpoint protein results from transduction of islet-like organoid cells with a vector containing a polynucleotide encoding the immune checkpoint protein.

In an embodiment of the methods of the foregoing aspects, the three-dimensional matrix comprises a human Wnt4 protein, a recombinant human Wnt4 protein, a human Wnt5 protein, or a recombinant human Wnt5a protein. In a particular embodiment, the three-dimensional matrix comprises a recombinant human Wnt4 protein.

In an embodiment of the foregoing methods of generating an islet-like organoid that evades immune detection or autoimmunity, the three-dimensional matrix comprises gellan gum. In an embodiment, the three-dimensional matrix comprises recombinant human Wnt4 protein. In embodiments of the foregoing methods, the immune checkpoint protein binds to an immune cell-expressed cognate ligand selected from programmed cell-death protein 1 (PD-1); cytotoxic T-lymphocyte protein 4 (CTLA-4); lymphocyte activation gene 3 protein (LAG-3); killer cell immunoglobulin-like receptor (KIR); indoleamine 2,3-dioxygenase 1 (IDO1); tumor necrosis factor receptor superfamily member 9 (4-1BB); glucocorticoid-induced TNFR family related gene (GITR); T-cell immunoglobulin domain and mucin domain (TIM-3); tumor necrosis factor receptor superfamily member 4, (OX40); adenosine A2A receptor (A2AR); B7-H3; B7-H4; B7-1/B7-2; BTLA; V-domain Ig suppressor of T cell activation (VISTA); or a combination of any of the foregoing. In a particular embodiment, the immune checkpoint protein is programmed death ligand-1 (PD-L1).

In an embodiment of the methods of the foregoing aspects, the endocrine progenitor cells are selected from induced pluripotent stem cells (iPSCs), embryonic pluripotent stem cells (ePSCs), and/or pancreatic progenitor cells.

In an embodiment of the methods of the foregoing aspects, the the endocrine progenitor cells express at least one of neurogenin 3, neurod1, Nkx2.2 and Pax4 biomarkers.

In an embodiment of the methods of the foregoing aspects, the islet-like organoid is a human islet-like organoid (HILO). In a particular embodiment, the islet-like organoid is vascularized. In a particular embodiment, the islet-like organoid further comprises an adipose-derived stem cell and/or an endothelial cell. In an embodiment, the adipose-derived stem cell is a human adipose-derived stem cell (hADSC) and/or the endothelial cell is a human umbilical vein endothelial cell (HUVEC).

In an embodiment of the methods of the foregoing aspects, the islet-like organoid further exhibits at least one of KCl-stimulated insulin secretion, GLP-1 stimulated insulin secretion, somatostatin secretion, glucagon secretion.

In an embodiment of the methods of the foregoing aspects, the islet-like organoid expresses a beta cell lineage marker selected from the group consisting of NKX2-2, NEUROD1, RFX6, GCK, INS, NKX6-1, UCN3, MAFB and SYT4 and an ARX alpha cell lineage marker.

In an embodiment of the methods of the foregoing aspects, the islet-like organoid exhibits increased expression of Estrogen Related Receptor gamma (ERRγ).

In another embodiment of the methods of the foregoing aspects, the islet-like organoid exhibits increased oxidative metabolism characterized by increased oxygen consumption rate (OCR) and decreased cellular acidification rate (ECAR).

In an embodiment of the methods of the foregoing aspects, the islet-like organoid is a pancreatic islet organoid, a pancreatic organoid, a liver organoid, a heart organoid, or intestinal organoid. In a particular embodiment of the methods, the islet-like organoid is a human pancreatic islet organoid.

In another aspect, a method of generating a human islet like organoid (HILO) that evades immune detection or autoimmunity is provided, in which the method comprises (a) culturing endocrine progenitor cells in culture medium or a three-dimensional matrix comprising Wnt4 or Wnt5a protein for a time sufficient to generate a multicellular human islet-like organoid comprising two or more cell types selected from beta (β) cells, alpha (α) cells, delta (δ) cells, epsilon (ε) cells and duct-like cells; wherein the human islet-like organoid secretes insulin in response to glucose; (b) contacting the HILO of step (a) with interferon gamma (IFNγ) two or three times for greater than one hour each time over a total time period of at least 48-72 hours; wherein the human islets or HILOs are maintained in the absence of IFNγ between times of contact with IFNγ; and wherein steps (a) and (b) induce sustained expression of immune checkpoint protein programmed death ligand-1 (PD-L1) in the HILO. In an embodiment of the method, the HILO is contacted with IFNγ for 2 hours in step (b). In another embodiment of the method, the HILO is contacted with IFNγ two times for two hours each time, over at least 48 hours. In another embodiment of the method, the HILO is contacted with IFNγ three times for two hours each time, over at least 72 hours. In another embodiment of the method, the endocrine progenitor cells are selected from induced pluripotent stem cells (iPSCs), embryonic pluripotent stem cells (ePSCs), and/or pancreatic progenitor cells. In another embodiment of the method, the endocrine progenitor cells express at least one of neurogenin 3, neurod1, Nkx2.2 and Pax4 biomarkers. In another embodiment of the method, the HILO is vascularized and exhibits increased oxidative metabolism characterized by increased oxygen consumption rate (OCR) and decreased cellular acidification rate (ECAR).

In an embodiment of the methods of the foregoing aspects, IFNγ is used in an amount of 1-25 ng/ml. In an embodiment of the methods of the foregoing aspects, IFNγ is used in an amount of 10 ng/ml. In an embodiment of the methods of the foregoing aspects, PD-L1 expression in the islet-like organoid or HILO is maintained for greater than 7 days.

In an aspect, a human islet-like organoid or pancreatic islet organoid having sustained expression of an immune checkpoint protein is produced by the method as described in the above-delineated aspects. In an embodiment, the human islet-like organoid or pancreatic islet organoid exhibits sustained expression of the immune checkpoint protein PD-L1.

In another aspect is provided a human islet-like organoid (HILO) derived from endocrine progenitor cells cultured in culture medium or a three-dimensional matrix comprising Wnt4 or Wnt5 protein and comprising multi-lineage cells comprising at least two of beta (β) cells, alpha (α) cells, delta (δ) cells, epsilon (ε) cells and duct-like cells, wherein the HILO is vascularized, exhibits glucose-stimulated insulin secretion (GSIS) and exhibits sustained expression of an immune checkpoint protein. In an embodiment, the human islet-like organoid (HILO) is a pancreatic islet-like organoid or a pancreatic organoid. In an embodiment, the human islet-like organoid (HILO) further exhibits KCl-stimulated insulin secretion or glucose stimulated insulin secretion. In another embodiment, the three-dimensional matrix for culturing the human islet-like organoid (HILO) comprises gellan gum. In another embodiment, the three-dimensional matrix for culturing the human islet-like organoid (HILO) comprises recombinant human Wnt4 protein. In an embodiment, the human islet-like organoid (HILO) is derived from endocrine progenitor cells which are selected from induced pluripotent stem cells (iPSCs), embryonic pluripotent stem cells (ePSCs), and/or pancreatic progenitor cells. In an embodiment, the endocrine progenitor cells express at least one of neurogenin 3, neurod1, Nkx2.2 and Pax4 biomarkers. In an embodiment, the human islet-like organoid (HILO) expresses FLTP and ESRR gamma genes. In an embodiment, the human islet-like organoid (HILO) further comprises an adipose-derived stem cell and/or an endothelial cell. In a particular embodiment, the adipose-derived stem cell is a human adipose-derived stem cell (hADSC) and/or the endothelial cell is a human umbilical vein endothelial cell (HUVEC). In another embodiment, the human islet-like organoid (HILO) further exhibits KCl-stimulated insulin secretion, GLP-1 stimulated insulin secretion, somatostatin secretion, or glucagon secretion. In another embodiment, the human islet-like organoid (HILO) expresses a beta cell lineage marker selected from the group consisting of NKX2-2, NEUROD1, RFX6, GCK, INS, NKX6-1, UCN3, MAFB and SYT4 and an ARX alpha cell lineage marker. In another embodiment, the human islet-like organoid (HILO) is a pancreatic HILO that expresses a beta cell transcription factor selected from the group consisting of Pdx1, MafA, Pax4, Pax6, NeuroD1, Nkx6-1, Gata6, and Foxa2. In embodiments, the human islet-like organoid (HILO) exhibit sustained expression of an immune checkpoint protein which binds to an immune cell-expressed cognate ligand selected from programmed cell-death protein 1 (PD-1); cytotoxic T-lymphocyte protein 4 (CTLA-4); lymphocyte activation gene 3 protein (LAG-3); killer cell immunoglobulin-like receptor (KIR); indoleamine 2,3-dioxygenase 1 (IDO1); tumor necrosis factor receptor superfamily member 9 (4-1BB); glucocorticoid-induced TNFR family related gene (GITR); T-cell immunoglobulin domain and mucin domain (TIM-3); tumor necrosis factor receptor superfamily member 4, (OX40); adenosine A2A receptor (A2AR); B7-H3; B7-H4; B7-1/B7-2; BTLA; V-domain Ig suppressor of T cell activation (VISTA); or a combination of any of the foregoing. In an embodiment, the human islet-like organoid (HILO) exhibits sustained expression of an immune checkpoint protein which binds to an immune cell-express cognate ligand, wherein the immune checkpoint protein is programmed death ligand-1 (PD-L1).

In another aspect is provided a non-human organism transplanted or implanted with the human islet-like organoid, pancreatic islet organoid, or HILO as described in the foregoing aspects delineated above. In an embodiment, the non-human organism is a mammal. In an embodiment, the non-human organism is a mouse.

In another aspect, a method of treating a pancreatic disease in a subject is provided, in which the method comprises transplanting or implanting an islet-like organoid or a pancreatic islet organoid into the subject, wherein the islet-like organoid or a pancreatic islet organoid comprises endocrine progenitor cell-derived, multi-lineage cells including beta, alpha, delta, epsilon cells, duct-like cells, or a combination thereof, is vascularized, exhibits glucose-stimulated insulin secretion (GSIS) and exhibits sustained expression of an immune checkpoint protein to evade immune detection or autoimmunity.

In another aspect, a method of treating type 1 diabetes in a subject is provided, in which the method comprises transplanting or implanting an islet-like organoid or a pancreatic islet organoid into the subject, wherein the islet-like organoid or a pancreatic islet organoid comprises endocrine progenitor cell-derived multi-lineage cells including beta, alpha, delta, epsilon cells, duct-like cells, or a combination thereof, is vascularized, exhibits glucose-stimulated insulin secretion (GSIS) and exhibits sustained expression of an immune checkpoint protein to evade immune detection or autoimmunity.

In an embodiment of the methods delineated in the above-described aspects, the islet-like organoid or pancreatic islet organoid further exhibits KCl-stimulated insulin secretion, GLP-1 stimulated insulin secretion, somatostatin secretion, or glucagon secretion. In an embodiment of the methods delineated in the above-described aspects, the islet-like organoid or pancreatic islet organoid expresses a beta cell lineage marker selected from the group consisting of NKX2-2, NEUROD1, RFX6, GCK, INS, NKX6-1, UCN3, MAFB and SYT4 and an ARX alpha cell lineage marker. In an embodiment of the methods delineated in the above-described aspects, the endocrine progenitor cells are selected from induced pluripotent stem cells (iPSCs), embryonic pluripotent stem cells (ePSCs), and/or pancreatic progenitor cells. In an embodiment, the endocrine progenitor cells express at least one of neurogenin 3, neurod1, Nkx2.2 and Pax4 biomarkers. In an embodiment of the methods delineated in the above-described aspects, the islet-like organoid or pancreatic islet organoid expresses a beta cell transcription factor selected from the group consisting of Pdx1, MafA, Pax4, Pax6, NeuroD1, Nkx6-1, Gata6, and Foxa2. In an embodiment of the treatment methods as described in the above-delineated aspects, the immune checkpoint protein binds to an immune cell-expressed cognate ligand selected from programmed cell-death protein 1 (PD-1); cytotoxic T-lymphocyte protein 4 (CTLA-4); lymphocyte activation gene 3 protein (LAG-3); killer cell immunoglobulin-like receptor (KIR); indoleamine 2,3-dioxygenase 1 (IDO1); tumor necrosis factor receptor superfamily member 9 (4-1BB); glucocorticoid-induced TNFR family related gene (GITR); T-cell immunoglobulin domain and mucin domain (TIM-3); tumor necrosis factor receptor superfamily member 4, (OX40); adenosine A2A receptor (A2AR); B7-H3; B7-H4; B7-1/B7-2; BTLA; V-domain Ig suppressor of T cell activation (VISTA); or a combination of any of the foregoing. In a particular embodiment, the immune checkpoint protein is programmed death ligand-1 (PD-L1). In an embodiment of the treatment methods as described in the above-delineated aspects, the islet-like organoid or pancreatic islet organoid is produced by a method described in the aspects hereinabove. In an embodiment of the treatment methods as described in the above-delineated aspects, the islet-like organoid or pancreatic islet organoid is the organoid as described in the above-delineated aspects. In an embodiment of the treatment methods as described in the above-delineated aspects, an immunosuppressive agent is administered to the subject. In an embodiment of the treatment methods as described in the above-delineated aspects, the subject is human. In an embodiment of the treatment methods as described in the above-delineated aspects, the pancreatic disease is type 1 diabetes or type 2 diabetes.

In another aspect, a method of cell transplantation is provided, in which the method comprises administering to a subject in need thereof an immunoprotected cell, human islet-like organoid or pancreatic islet organoid as described in the above-delineated aspects. In an embodiment, the immunoprotected cell, human islet-like organoid or pancreatic islet organoid is syngeneic, autologous, allogeneic or xenogeneic to the subject receiving the transplant.

In another aspect, a kit containing an immunoprotected cell, human islet-like organoid or pancreatic islet organoid as described in the above-delineated aspects, or a pharmaceutically acceptable composition comprising the immunoprotected cell, human islet-like organoid or pancreatic islet organoid is provided. In an embodiment, the kit contains an immunoprotected cell, human islet-like organoid or pancreatic islet organoid that is syngeneic, autologous, allogeneic, or xenogeneic.

Other features and advantages will be apparent from the detailed description of the embodiments and from the claims.

Definitions

Unless defined otherwise, all technical and scientific terms used herein have the meaning commonly understood by a person skilled in the art to which this invention pertains. The following references provide one of skill in the pertinent art with a general definition of many of the terms used in this invention: Singleton et al., Dictionary of Microbiology and MolecularBiology (2nd ed. 1994); The Cambridge Dictionary of Science and Technology (Walker ed., 1988); The Glossary of Genetics, 5th Ed., R. Rieger et. al.. (eds.), Springer Verlag (1991); and Hale & Marham, The Harper Collins Dictionary of Biology (1991). As used herein, the following terms have the meanings ascribed to them below, unless specified otherwise.

By "AFP polypeptide" or "alpha-fetoprotein" is meant a protein or fragment thereof having at least 85% amino acid sequence identity to the sequence provided at NCBI Accession No. NP_001125.1 and having a biological activity of an AFP polypeptide. Exemplary biological activities of an AFP polypeptide include binding to copper, nickel, fatty acids, and bilirubin. The amino acid sequence provided at NCBI Accession No. NP_001125.1 is shown below:

```
  1    MKWVESIFLI  FLLNFTESRT  LHRNEYGIAS  ILDSYQCTAE  ISLADLATIF  FAQFVQEATY

61    KEVSKMVKDA  LTAIEKPTGD  EQSSGCLENQ  LPAFLEELCH  EKEILEKYGH  SDCCSQSEEG

121    RHNCFLAHKK  PTPASIPLFQ  VPEPVTSCEA  YEEDRETFMN  KFIYEIARRH  PFLYAPTILL

181    WAARYDKIIP  SCCKAENAVE  CFQTKAATVT  KELRESSLLN  QHACAVMKNF  GTRTFQAITV

241    TKLSQKFTKV  NFTEIQKLVL  DVAHVHEHCC  RGDVLDCLQD  GEKIMSYICS  QQDTLSNKIT

301    ECCKLTTLER  GQCIIHAEND  EKPEGLSPNL  NRFLGDRDFN  QFSSGEKNIF  LASFVHEYSR

361    RHPQLAVSVI  LRVAKGYQEL  LEKCFQTENP  LECQDKGEEE  LQKYIQESQA  LAKRSCGLFQ

421    KLGEYYLQNA  FLVAYTKKAP  QLTSSELMAI  TRKMAATAAT  CCQLSEDKLL  ACGEGAADII

481    IGHLCIRHEM  TPVNPGVGQC  CTSSYANRRP  CFSSLVVDET  YVPPAFSDDK  FIFHKDLCQA

541    QGVALQTMKQ  EFLINLVKQK  PQITEEQLEA  VIADFSGLLE  KCCQGQEQEV  CFAEEGQKLI

601    SKTRAALGV
```

By "AFP polynucleotide" is meant a polynucleotide encoding a AFP polypeptide or fragment thereof. An exemplary AFP polynucleotide sequence is provided at NCBI Ref: NM_001134.2. The sequence provided at NCBI Ref: NM_001134.2 is reproduced below:

```
  1    atattgtgct  tccaccactg  ccaataacaa  aataactagc  aaccatgaag  tgggtggaat 61    caattttttt  aattttccta  ctaaatttta  ctgaatccag  aacactgcat  agaaatgaat 121    atggaatagc  ttccatattg  gattcttacc  aatgtactgc  agagataagt  ttagctgacc 181    tggctaccat  attttttgcc  cagtttgttc  aagaagccac  ttacaaggaa  gtaagcaaaa 241    tggtgaaaga  tgcattgact  gcaattgaga  aacccactgg  agatgaacag  tcttcagggt 301    gtttagaaaa  ccagctacct  gcctttctgg  aagaactttg  ccatgagaaa  gaaattttgg
```

-continued

```
 361   agaagtacgg acattcagac tgctgcagcc aaagtgaaga gggaagacat aactgttttc 421   ttgcacacaa aaagcccact ccagcatcga tcccactttt ccaagttcca gaacctgtca 481   caagctgtga agcatatgaa gaagacaggg agacattcat gaacaaattc atttatgaga 541   tagcaagaag gcatcccttc ctgtatgcac ctacaattct tctttgggct gctcgctatg 601   acaaaataat tccatcttgc tgcaaagctg aaaatgcagt tgaatgcttc caaacaaagg 661   cagcaacagt tacaaaagaa ttaagagaaa gcagcttgtt aaatcaacat gcatgtgcag 721   taatgaaaaa ttttgggacc cgaactttcc aagccataac tgttactaaa ctgagtcaga 781   agtttaccaa agttaatttt actgaaatcc agaaactagt cctggatgtg gcccatgtac 841   atgagcactg ttgcagagga gatgtgctgg attgtctgca ggatggggaa aaaatcatgt 901   cctacatatg ttctcaacaa gacactctgt caaacaaaat aacagaatgc tgcaaactga 961   ccacgctgga acgtggtcaa tgtataattc atgcagaaaa tgatgaaaaa cctgaaggtc 1021   tatctccaaa tctaaacagg tttttaggag atagagattt taaccaattt tcttcagggg 1081   aaaaaaatat cttcttggca agttttgttc atgaatattc aagaagacat cctcagcttg 1141   ctgtctcagt aattctaaga gttgctaaag gataccagga gttattggag aagtgtttcc 1201   agactgaaaa ccctcttgaa tgccaagata aggagaaga agaattacag aaatacatcc 1261   aggagagcca agcattggca aagcgaagct gcggcctctt ccagaaacta ggagaatatt 1321   acttacaaaa tgcgtttctc gttgcttaca caaagaaagc cccccagctg acctcgtcgg 1381   agctgatggc catcaccaga aaaatggcag ccacagcagc cacttgttgc caactcagtg 1441   aggacaaact attggcctgt ggcgagggag cggctgacat tattatcgga cacttatgta 1501   tcagacatga aatgactcca gtaaaccctg tgttggcca gtgctgcact tcttcatatg 1561   ccaacaggag gccatgcttc agcagcttgg tggtggatga aacatatgtc cctcctgcat 1621   tctctgatga caagttcatt ttccataagg atctgtgcca agctcaggggt gtagcgctgc 1681   aaacgatgaa gcaagagttt ctcattaacc ttgtgaagca aaagccacaa ataacagagg 1741   aacaacttga ggctgtcatt gcagatttct caggcctgtt ggagaaatgc tgccaaggcc 1801   aggaacagga gtctgctttt gctgaagagg acaaaaaact gatttcaaaa actcgtgctg 1861   ctttgggagt ttaaattact tcaggggaag agaagacaaa acgagtcttt cattcggtgt 1921   gaactttct ctttaatttt aactgattta acacttttg tgaattaatg aaatgataaa 1981   gactttatg tgagatttcc ttatcacaga aataaaatat ctccaaatgt ttccttttca 2041   aaaaaaaaa aaaaaaa
```

By "ALB polypeptide" or "albumin" is meant a protein or fragment thereof having at least 85% amino acid sequence identity to the sequence provided at NCBI Accession No. NP_000468.1 and having a biological activity of ALB polypeptide. Exemplary biological activities of ALB polypeptide include binding to fatty acids, calcium ions, sodium ions, potassium ions, hormones, and bilirubin; stabilization of extracellular fluid volume; and, transport of plasma zinc. The amino acid sequence provided at NCBI Accession No. NP_000468.1 is shown below:

```
  1   MKWVTFISLL FLFSSAYSRG VFRRDAHKSE VAHRFKDLGE ENFKALVLIA FAQYLQQCPF

61   EDHVKLVNEV TEFAKTCVAD ESAENCDKSL HTLFGDKLCT VATLRETYGE MADCCAKQEP

121   ERNECFLQHK DDNPNLPRLV RPEVDVMCTA FHDNEETFLK KYLYEIARRH PYFYAPELLF

181   FAKRYKAAFT ECCQAADKAA CLLPKLDELR DEGKASSAKQ RLKCASLQKF GERAFKAWAV

241   ARLSQRFPKA EFAEVSKLVT DLTKVHTECC HGDLLECADD RADLAKYICE NQDSISSKLK

301   ECCEKPLLEK SHCIAEVEND EMPADLPSLA ADFVESKDVC KNYAEAKDVF LGMFLYEYAR

361   RHPDYSVVLL LRLAKTYETT LEKCCAAADP HECYAKVFDE FKPLVEEPQN LIKQNCELFE
```

-continued

```
421   QLGEYKFQNA LLVRYTKKVP QVSTPTLVEV SRNLGKVGSK CCKHPEAKRM PCAEDYLSVV

481   LNQLCVLHEK TPVSDRVTKC CTESLVNRRP CFSALEVDET YVPKEFNAET FTFHADICTL

541   SEKERQIKKQ TALVELVKHK PKATKEQLKA VMDDFAAFVE KCCKADDKET CFAEEGKKLV

601   AASQAALGL
```

By "ALB polynucleotide" is meant a polynucleotide encoding a ALB polypeptide or fragment thereof. An exemplary AFP polynucleotide sequence is provided at NCBI Ref: NM_000477.5. The sequence provided at NCBI Ref: NM_000477.5 is reproduced below:

```
   1   agtatattag tgctaatttc cctccgtttg tcctagcttt tctcttctgt caaccccaca 61   cgcctttggc acaatgaagt gggtaacctt tatttccctt cttttttctct ttagctcggc 121   ttattccagg ggtgtgtttc gtcgagatgc acacaagagt gaggttgctc atcggtttaa 181   agatttggga gaagaaaatt tcaaagcctt ggtgttgatt gcctttgctc agtatcttca 241   gcagtgtcca tttgaagatc atgtaaaatt agtgaatgaa gtaactgaat ttgcaaaaac 301   atgtgttgct gatgagtcag ctgaaaattg tgacaaatca cttcataccc tttttggaga 361   caaattatgc acagttgcaa ctcttcgtga aacctatggt gaaatggctg actgctgtgc 421   aaaacaagaa cctgagagaa atgaatgctt cttgcaacac aaagatgaca acccaaacct 481   cccccgattg gtgagaccag aggttgatgt gatgtgcact gctttcatg acaatgaaga 541   gacatttttg aaaaaatact tatatgaaat tgccagaaga catccttact tttatgcccc 601   ggaactcctt ttctttgcta aaaggtataa agctgctttt acagaatgtt gccaagctgc 661   tgataaagct gcctgcctgt tgccaaagct cgatgaactt cgggatgaag ggaaggcttc 721   gtctgccaaa cagagactca agtgtgccag tctccaaaaa tttggagaaa gagctttcaa 781   agcatgggca gtagctcgcc tgagccagag atttcccaaa gctgagtttg cagaagtttc 841   caagttagtg acagatctta ccaaagtcca cacggaatgc tgccatggag atctgcttga 901   atgtgctgat gacagggcgg accttgccaa gtatatctgt gaaaatcaag attcgatctc 961   cagtaaactg aaggaatgct gtgaaaaacc tctgttggaa aaatcccact gcattgccga 1021   agtggaaaat gatgagatgc ctgctgactt gccttcatta gctgctgatt ttgttgaaag 1081   taaggatgtt tgcaaaaact atgctgaggc aaaggatgtc ttcctgggca tgttttttgta 1141   tgaatatgca agaaggcatc ctgattactc tgtcgtgctg ctgctgagac ttgccaagac 1201   atatgaaacc actctagaga agtgctgtgc cgctgcagat cctcatgaat gctatgccaa 1261   agtgttcgat gaatttaaac ctcttgtgga agagcctcag aatttaatca aacaaaattg 1321   tgagcttttt gagcagcttg gagagtacaa attccagaat gcgctattag ttcgttacac 1381   caagaaagta ccccaagtgt caactccaac tcttgtagag gtctcaagaa acctaggaaa 1441   agtgggcagc aaatgttgta acatcctga agcaaaaga atgccctgtg cagaagacta 1501   tctatccgtg tcctgaacc agttatgtgt gttgcatgag aaaacgccag taagtgacag 1561   agtcaccaaa tgctgcacag aatccttggt gaacaggcga ccatgctttt cagctctgga 1621   agtcgatgaa acatacgttc ccaaagagtt taatgctgaa acattcacct tccatgcaga 1681   tatatgcaca ctttctgaga aggagagaca aatcaagaaa caaactgcac ttgttgagct 1741   cgtgaaacac aagcccaagg caacaaaaga gcaactgaaa gctgttatgg atgatttcgc 1801   agctttttgta gagaagtgct gcaaggctga cgataaggag acctgctttg ccgaggaggg 1861   taaaaaactt gttgctgcaa gtcaagctgc cttaggctta taacatcaca tttaaaagca
```

-continued

```
1921   tctcagccta ccatgagaat aagagaaaga aaatgaagat caaaagctta ttcatctgtt 1981   tttctttttc gttggtgtaa agccaacacc ctgtctaaaa aacataaatt tctttaatca 2041   ttttgcctct tttctctgtg cttcaattaa taaaaaatgg aaagaatcta atagagtggt 2101   acagcactgt tatttttcaa agatgtgttg ctatcctgaa aattctgtag gttctgtgga 2161   agttccagtg ttctctctta ttccacttcg gtagaggatt tctagtttct tgtgggctaa 2221   ttaaataaat cattaatact cttctaaaaa aaaaaaaaaa aaaa
```

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "altered" is meant an increase or decrease. An increase is any positive change, e.g., by at least about 5%, 10%, or 20%; by at least about 25%, 50%, 75%, or even by 100%, 200%, 300% or more. A decrease is a negative change, e.g., a decrease by at least about 5%, 10%, or 20%; by at least about 25%, 50%, 75%; or even an increase by 100%, 200%, 300% or more.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "CDX2 polypeptide" is meant a protein or fragment thereof having at least 85% amino acid sequence identity to the sequence provided at NCBI Accession No. NP_001256.3 and having transcription factor activity. The amino acid sequence provided at NCBI Accession No. NP_001256.3 is shown below:

```
  1   MYVSYLLDKD VSMYPSSVRH SGGLNLAPQN FVSPPQYPDY GGYHVAAAAA AAANLDSAQS

61   PGPSWPAAYG APLREDWNGY APGGAAAAAN AVAHGLNGGS PAAAMGYSSP ADYHPHHHPH

121   HHPHHPAAAP SCASGLLQTL NPGPPGPAAT AAAEQLSPGG QRRNLCEWMR KPAQQSLGSQ

181   VKTRTKDKYR VVYTDHQRLE LEKEFHYSRY ITIRRKAELA ATLGLSERQV KIWFQNRRAK

241   ERKINKKKLQ QQQQQQPPQP PPPPPQPPQP QPGPLRSVPE PLSPVSSLQA SVSGSVPGVL

301   GPTGGVLNPT VTQ
```

By "CDX2 polynucleotide" is meant a polynucleotide encoding a CDX2 polypeptide or fragment thereof. An exemplary CDX2 polynucleotide sequence is provided at NCBI Ref: NM_001265.4. The sequence provided at NCBI Ref: NM_001265.4 is reproduced below:

```
  1   ctccaaccat tggtgtctgt gtcattacta atagagtctt gtaaacactc gttaatcacg 61   gaaggccgcc ggcctggggc tccgcacgcc agcctgtggc gggtcttccc cgcctctgca 121   gcctagtggg aaggaggtgg gaggaaagaa ggaagaaagg gagggaggga ggaggcaggc 181   cagaggagg gaccgcctcg gaggcagaag agccgcgagg agccagcgga gcaccgcggg 241   ctggggcgca gccacccgcc gctcctcgag tccctcgcc cctttccctt cgtgccccc 301   ggcagcctcc agcgtcggtc cccaggcagc atggtgaggt ctgctcccgg accctcgcca 361   ccatgtacgt gagctacctc ctggacaag acgtgagcat gtaccctagc tccgtgcgcc 421   actctggcgg cctcaacctg gcgccgcaga acttcgtcag cccccgcag tacccggact 481   acggcggtta ccacgtggcg gccgcagctg cagcggcagc gaacttggac agcgcgcagt 541   cccgggggcc atcctggccg gcagcgtatg gcgccccact ccgggaggac tggaatggct 601   acgcgcccgg aggcgccgcg gccgccgcca acgccgtggc tcacggcctc aacggtggct 661   ccccggccgc agccatgggc tacagcagcc ccgcagacta ccatccgcac caccacccgc 721   atcaccaccc gcaccacccg gccgccgcgc cttcctgcgc ttctgggctg ctgcaaacgc
```

-continued

```
 781  tcaacccggg ccctcctggg cccgccgcca ccgctgccgc cgagcagctg tctcccggcg 841  gccagcggcg gaacctgtgc gagtggatgc ggaagccggc gcagcagtcc ctcggcagcc 901  aagtgaaaac caggacgaaa gacaaatatc gagtggtgta cacggaccac cagcggctgg 961  agctggagaa ggagtttcac tacagtcgct acatcaccat ccggaggaaa gccgagctag 1021  ccgccacgct ggggctctct gagaggcagg ttaaaatctg gtttcagaac cgcagagcaa 1081  aggagaggaa aatcaacaag aagaagttgc agcagcaaca gcagcagcag ccaccacagc 1141  cgcctccgcc gccaccacag cctccccagc ctcagccagg tcctctgaga agtgtcccag 1201  agcccttgag tccggtgtct tccctgcaag cctcagtgtc tggctctgtc cctggggttc 1261  tggggccaac tggggggggtg ctaaacccca ccgtcaccca gtgacccacc gggttctgca 1321  gcggcagagc aattccaggc tgagccatga ggagcgtgga ctctgctaga ctcctcagga 1381  gagacccctc ccctcccacc cacagccata gacctacaga cctggctctc agaggaaaaa 1441  tgggagccag gagtaagaca agtgggattt ggggcctcaa gaaatatact ctcccagatt 1501  tttacttttt cccatctggc ttttttctgcc actgaggaga cagaaagcct ccgctgggct 1561  tcattccgga ctggcagaag cattgcctgg actgaccaca ccaaccaggc cttcatcctc 1621  ctccccagct cttctcttcc tagatctgca ggctgcacct ctggctagag ccgaggggag 1681  agagggactc aagggaaagg caagcttgag gccaagatgg ctgctgcctg ctcatggccc 1741  tcggaggtcc agctgggcct cctgcctccg ggcaggcaag gtttacactg cggaagccaa 1801  aggcagctaa gatagaaagc tggactgacc aaagactgca gaaccccccag gtggcctgcg 1861  tcttttttct cttcccttcc cagaccagga aaggcttggc tggtgtatgc acagggtgtg 1921  gtatgagggg gtggttattg gactccaggc ctgaccaggg ggcccgaaca gggacttgtt 1981  tagagagcct gtcaccagag cttctctggg ctgaatgtat gtcagtgcta taaatgccag 2041  agccaacctg gacttcctgt cattttcaca atcttggggc tgatgaagaa gggggtgggg 2101  ggagtttgtg ttgttgttgc tgctgtttgg gttgttggtc tgtgtaacat ccaagccaga 2161  gtttttaaag ccttctggat ccatggggggg agaagtgata tggtgaaggg aagtggggag 2221  tatttgaaca cagttgaatt ttttctaaaa agaaaaagag ataaatgagc tttccagatt 2281  tcagattctg tatttatctt cagattttgt ctgcaactat tttttatttt ttaaagaaat 2341  gaaatatctt caaaaaaaaa aaaaaaaaa
```

By "CYP3A7 polypeptide" or "cytochrome P450" is meant a protein or fragment thereof having at least 85% amino acid sequence identity to the sequence provided at NCBI Accession No. NP_000756.3 and having monooxygenase activity. The amino acid sequence provided at NCBI Accession No. NP_000756.3 is shown below:

```
  1  MDLIPNLAVE TWLLLAVSLI LLYLYGTRTH GLFKKLGIPG PTPLPFLGNA LSFRKGYWTF

61  DMECYKKYRK VWGIYDCQQP MLAITDPDMI KTVLVKECYS VFTNRRPFGP VGFMKNAISI

121  AEDEEWKRIR SLLSPTFTSG KLKEMVPIIA QYGDVLVRNL RREAETGKPV TLKHVFGAYS

181  MDVITSTSFG VSIDSLNNPQ DPFVENTKKL LRFNPLDPFV LSIKVFPFLT PILEALNITV

241  FPRKVISFLT KSVKQIKEGR LKETQKHRVD FLQLMIDSQN SKDSETHKAL SDLELMAQSI

301  IFIFAGYETT SSVLSFIIYE LATHPDVQQK VQKEIDTVLP NKAPPTYDTV LQLEYLDMVV

361  NETLRLFPVA MRLERVCKKD VEINGMFIPK GVVVMIPSYV LHHDPKYWTE PEKFLPERFS

421  KKNKDNIDPY IYTPFGSGPR NCIGMRFALV NMKLALVRVL QNFSFKPCKE TQIPLKLRFG

481  GLLLTEKPIV LKAESRDETV SGA
```

By "CYP3A7 polynucleotide" is meant a polynucleotide encoding a CYP3A7 polypeptide or fragment thereof. An exemplary AFP polynucleotide sequence is provided at NCBI Ref: NM_000765.4. The sequence provided at NCBI Ref: NM_000765.4 is reproduced below:

subject, or patient. By way of example, autologous transplants (e.g., donor cells, tissues, organs, islets, organoids, or islet-like organoids) involve one individual, subject, or patient as both donor and recipient. "Syngeneic" refers to cells, tissues, organs, islets, organoids, islet-like organoids,

```
   1   aatcactgct gtgcagggca ggaaagctcc acacacacag cccagcaaac agcagcacgc 61   tgctgaaaaa aagactcaga ggagagagat aaggaaggaa agtagtgatg gatctcatcc 121   caaacttggc cgtggaaacc tggcttctcc tggctgtcag cctgatactc ctctatctat 181   atggaacccg tacacatgga cttttttaaga agcttggaat tccagggccc acacctctgc 241   ctttttgggg aaatgctttg tccttccgta agggctattg gacgtttgac atggaatgtt 301   ataaaaagta tagaaaagtc tggggtattt atgactgtca acagcctatg ctggctatca 361   cagatcccga catgatcaaa acagtgctag tgaaagaatg ttattctgtc ttcacaaacc 421   ggaggccttt cgggccagtg ggatttatga aaaatgccat ctctatagct gaggatgaag 481   aatggaagag aatacgatca ttgctgtctc caacattcac cagcggaaaa ctcaaggaga 541   tggtccctat cattgcccag tatggagatg tgttggtgag aaatctgagg cgggaagcag 601   agacaggcaa gcctgtcacc ttgaaacacg tctttggggc ctacagcatg gatgtgatca 661   ctagcacatc atttggagtg agcatcgact ctctcaacaa tccacaagac ccctttgtgg 721   aaaacaccaa gaagctttta agatttaatc cattagatcc attcgttctc tcaataaaag 781   tctttccatt ccttaccccca attcttgaag cattaaatat cactgtgttt ccaagaaaag 841   ttataagttt tctaacaaaa tctgtaaaac agataaaaga aggtcgcctc aaagagacac 901   aaaagcaccg agtggatttc cttcagctga tgattgactc tcagaattca aaagactctg 961   agacccacaa agctctgtct gatctggagc tcatggccca atcaattatc tttatttttg 1021   ctggctatga aaccacgagc agtgttctct ccttcattat atatgaactg gccactcacc 1081   ctgatgtcca gcagaaagtg cagaaggaaa ttgatacagt tttacccaat aaggcaccac 1141   ccacctatga tactgtgcta cagttggagt atcttgacat ggtggtgaat gaaacactca 1201   gattattccc agttgctatg agacttgaga gggtctgcaa aaaagatgtt gaaatcaatg 1261   ggatgtttat tcccaaaggg gtggtggtga tgattccaag ctatgttctt catcatgacc 1321   caaagtactg gacagagcct gagaagttcc tccctgaaag gttcagtaaa aagaacaagg 1381   acaacataga tccttacata tacacaccct ttggaagtgg acccagaaac tgcattggca 1441   tgaggtttgc tctcgtgaac atgaaacttg ctctagtcag agtccttcag aacttctcct 1501   tcaaaccttg taaagaaaca cagatccccc tgaaattacg ctttggagga cttcttctaa 1561   cagaaaaacc cattgttcta aaggctgagt caagggatga daccgtaagt ggagcctgat 1621   ttccctaagg acttctggtt tgctctttaa gaaagctgtg ccccagaaca ccagagacct 1681   caaattactt tacaaataga accctgaaat gaagacgggc ttcatccaat gtgctgcata 1741   aataatcagg gattctgtac gtgcattgtg ctctctcatg gtctgtatag agtgttatac 1801   ttggtaatat agaggagatg accaaatcag tgctggggaa gtagatttgg cttctctgct 1861   tctcatagga ctatctccac cacccccagt tagcaccatt aactcctcct gagctctgat 1921   aacataatta acatttctca ataatttcaa ccacaatcat taataaaaat aggaattatt 1981   ttgatggctc taacagtgac atttatatca tgtgttatat ctgtagtatt ctatagtaag 2041   ctttatatta agcaaatcaa taaaaacctc tttacaaaag taaaaaaaaa aaaaaaaa
```

"Autologous" refers to biological material, e.g., autologous cells, tissues, islets, organoids, or islet-like organoids, that are obtained or derived from the same individual, or organisms (or other biological material) that are genetically similar or identical, (and of the same species) and thus, are immunologically compatible. Syngeneic donor biological material is typically so closely related that transplantation does not provoke an immune response in the recipient. "Allogeneic" refers to biological material, e.g., donor allogeneic cells, tissues, organs, islets, organoids, or islet-like organoids, that is genetically dissimilar to the recipient. Allogeneic biological material is typically obtained or derived from individuals of the same species. In addition, allogeneic biological material may be from an unrelated donor or from a donor matched as to MHC or HLA histocompatibility antigen type(s) with that of the recipient. "Xenogeneic" refers to biological material (e.g., cells, tissues, organs, islets, organoids, or islet-like organoids) that are derived or obtained from individuals of a different species. By way of example, autologous, syngeneic, allogeneic, or xenogeneic cells, tissues, organs, islets, organoids, or islet-like organoids may be used for transplant or implant, particularly, those generated by the methods involving IFNγ treatment (e.g., MPS IFNγ treatment) as described herein to yield long-term, immune evasive, transplanted or implanted biological material. In an embodiment, such biological material is obtained or generated from a living donor (individual, subject, or organism). In an embodiment, such biological material is obtained or generated from a nonliving donor, e.g., cadaveric human islets or donor-matched cadaveric human islets.

As used herein, the term "carrier" refers to a physiologically acceptable diluent, excipient, buffer, or vehicle with which a composition (e.g., a physiologically acceptable or pharmaceutical composition), e.g., comprising a cell, islet, islet-like organoid, or organoid, may be administered to a subject or in which it may be stored. Pharmaceutical and pharmaceutically acceptable carriers include sterile liquids, such as medium, saline, buffers, and the like. In embodiments, the physiologically acceptable carriers are used in pharmaceutical compositions that are administered to or transplanted into a subject, including, but not limited to, a human subject or patient. In some embodiments, water or aqueous saline solutions and aqueous dextrose and glycerol solutions may be employed as carriers, particularly for injectable solutions. Suitable pharmaceutical carriers (and pharmaceutical compositions) are known and used by practitioners in the art and are described in Remington: The Science and Practice of Pharmacy (20th ed.), ed. A. R. Gennaro, Lippincott Williams & Wilkins, 2000, and later editions thereof.

By "fragment" is meant a portion of a polypeptide or nucleic acid molecule. This portion contains at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

As used herein, the term "immune response" refers to a subject's immune system response or reaction to one or more antigens, (e.g., an immunogenic protein or peptide), and/or the epitopes of the antigens, recognized by the immune system as foreign, allogeneic, or heterologous. Immune responses include both cell-mediated immune responses (i.e., responses mediated by effector T cells, such as antigen-specific or non-specific T-cells, such as CD8+ T-cells, Th1 cells, Th2 cells, and Th17 cells) as well as humoral immune responses (i.e., responses characterized by B-cell activation and the production of antigen-specific antibodies). The term "immune response" encompasses both the innate immune responses to an antigen or immunogen, as well as memory responses that are a result of acquired immunity and can involve either B cells or T cells, or both.

By "immune checkpoint protein" or "immune checkpoint molecule," or simply, "checkpoint protein or molecule" is meant a protein or molecule that can either induce or hinder activation of T cells, or a particular process in a cellular or immune system pathway, e.g., to prevent errors or an abnormal or pathological activity or condition. In an immune response, the crucial interaction between antigen presenting cells (APCs) and T-cells is tightly regulated by a 'three signal model': (1) display of a surface complex consisting of an antigen bound on a major histocompatibility complex (MHC) protein class I or II (MHC I or II) molecule to a T-cell receptor (TCR) on a T-cell (CD8+ or CD4+); (2) costimulation by immune checkpoint proteins and (β) cytokines. Immune checkpoint proteins comprise costimulatory and inhibitory proteins that can either induce or inhibit activation of T-cells. Naive T-cells that only receive signal 1 without costimulatory signal 2 become anergic or die through apoptosis. The engagement of costimulatory ligand/receptor pairs triggers an accumulation of receptors and protein complexes at the center of the immunological synapse, which then amplifies and enhances the duration of TCR signaling (Wulfing, C. and Davis, M. M., 1998, *Science,* 282:2266-2269). The cytokine environment, signal 3, then induces naïve CD4+ T-cells to differentiate into various T-cell subsets, such as T helper (Th)1 cells, Th2 cells, Th17 cells and regulatory T-cells (Tregs), each of which produce and release a distinct set of cytokines upon activation. (Foks, A. C. and Kuiper, J., 2017, *Br. J. Pharmacol.,* 174:3940-3955).

The immune system provides a large variety of stimulatory and inhibitory immune checkpoint proteins (signal 2), and each pathway has its own unique effect on the fate of individual immune cells. Signaling through stimulatory immune checkpoint proteins can promote cell survival, cell cycle progression and differentiation to effector and memory cells, while inhibitory immune checkpoint protein signaling can terminate these processes directly or indirectly by the induction of Tregs. Costimulation can be provided in cis, i.e., both signals 1 and 2 are provided by the same APC, or in trans, i.e., signal 2 is provided by a different or 'bystander' APC than signal 1 (Roska, A. K. and Lipsky, P. E., 1985, *J. Immunol.,* 135:2953-2961; Liu, Y. and Janeway, C. A., Jr., 1992, *Proc. Natl. Acad. Sci. USA,* 89:3845-3849; Ding, L. and Shevach, E. M., 1994, *Eur. J. Immunol.,* 24:859-866).

Checkpoint proteins are regulators of the immune system and frequently are bound by or interact with ligands (cognate ligands), which may cause a given effect, e.g., cell stimulation, anergy, or apoptosis. In an embodiment, the immune checkpoint protein is one which binds a cognate ligand (e.g., a receptor ligand) on an immune cell surface, e.g., a T cell surface receptor. In a specific embodiment, the immune checkpoint protein is PD-L1 or a binding portion thereof, where the cognate ligand of PD-L1 is PD-1 expressed on the surface of T cells. In an embodiment, the checkpoint protein is the extracellular domain of the checkpoint protein.

The term "cognate ligand" refers to the specific binding partner, binding member, or ligand with which an immune checkpoint protein specifically interacts or with which it specifically binds. For example, a specific ligand to which a receptor protein binds or with which it interacts is a "cognate ligand" for that receptor protein. Similarly, the receptor protein is a cognate ligand for a specific ligand molecule or protein.

By "constitutive expression" is meant expression of a gene that is transcribed continually compared to a facultative gene which is only transcribed as needed. Genes that are constitutively expressed are transcribed in an ongoing manner, with control limited to that which is directly associated with the metabolic state of a cell, tissue, or organism. The level of expression of a constitutively expressed gene may be modified, e.g., via post-transcriptional or post-translational modification. In an embodiment, the gene is PD-L1 that encodes the PD-L1 polypeptide.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

"Differentiation" refers to the developmental process of lineage commitment. Differentiation can be assayed by measuring an increase in one or more cell specific markers relative to their expression in a corresponding undifferentiated control cell. A "lineage" refers to a pathway of cellular development, in which precursor or "progenitor" cells undergo progressive physiological changes to become a specified cell type having a characteristic function. In some embodiments, the cell type is a beta cell. In some embodiments, the cell type is an alpha cell, delta cell, or duct cell. In some other embodiments, the cell type is a hepatocyte. In still other embodiments, the cell type is a cardiomyocyte. In some embodiments, the cell type is an intestinal cell. Differentiation occurs in stages, whereby cells gradually become more specified until they reach full maturity, which is also referred to as "terminal differentiation." A "terminally differentiated cell" is a cell that has committed to a specific lineage, and has reached the end stage of differentiation (i.e., a cell that has fully matured). In some embodiments, an induced pluripotent stem cell (iPSC) is differentiated into a beta-like cell, an alpha-like cell, a delta-like cell, or a duct-like cell. In some other embodiments, an induced pluripotent stem cell (iPSC) is differentiated into a hepatocyte, cardiomyocyte, or intestinal cell.

A "de-differentiated cell" is a cell in which the process of differentiation has been, at least to some degree, reversed. De-differentiation can be assayed, for example, by identifying a reduction in the expression of one or more cell specific markers relative to their expression in a corresponding control cell. Alternatively, de-differentiation can be assayed by measuring an increase in one or more markers typically expressed in an embryonic stem cell, a pluripotent or multi-potent cell type, or expressed at an earlier stage of development. In some embodiments, the de-differentiated cell is an induced pluripotent stem cell (iPSC). In certain embodiments, the de-differentiated cell is a human induced pluripotent stem cell (iPSC).

By "disease" is meant any condition or disorder that adversely affects, damages or interferes with the normal function of a cell, tissue, or organ, or a part of the body, such as autoimmunity or autoimmune disease. Examples of diseases include type 1 diabetes, type 2 diabetes, and pancreatic cancer. An autoimmune disease is one in which the body produces immune cells (e.g., effector T cells or NK cells) and/or antibodies produced by B cells that immunologically react against (attack) its own tissues or organs (or tissue or organ transplants or implants), leading to the deterioration, and, in some cases, to the destruction of the tissue or organ (or tissue or organ transplant or implant).

By "effective amount" is meant the amount of a therapeutic agent or organoid required to ameliorate the symptoms of a disease in a subject relative to an untreated subject. The effective amount of a therapeutic used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount. In some embodiments, the therapeutic organoid is a pancreatic islet organoid. In some other embodiments, an effective amount of a pancreatic islet organoid is administered to a subject having type 1 or type 2 diabetes.

By "ESRRG polypeptide" is meant a protein or fragment thereof having at least 85% amino acid sequence identity to the sequence provided at NCBI Accession No. NP_001230448.1 and having nuclear hormone receptor activity. The amino acid sequence provided at NCBI Accession No. NP 001230448.1 is shown below:

```
  1   MSNKDRHIDS SCSSFIKTEP SSPASLTDSV NHHSPGGSSD ASGSYSSTMN GHQNGLDSPP

61   LYPSAPILGG SGPVRKLYDD CSSTIVEDPQ TKCEYMLNSM PKRLCLVCGD IASGYHYGVA

121   SCEACKAFFK RTIQGNIEYS CPATNECEIT KRRRKSCQAC RFMKCLKVGM LKEGVRLDRV

181   RGGRQKYKRR IDAENSPYLN PQLVQPAKKP YNKIVSHLLV AEPEKIYAMP DPTVPDSDIK

241   ALTTLCDLAD RELVVIIGWA KHIPGFSTLS LADQMSLLQS AWMEILILGV VYRSLSFEDE

301   LVYADDYIMD EDQSKLAGLL DLNNAILQLV KKYKSMKLEK EEFVTLKAIA LANSDSMHIE

361   DVEAVQKLQD VLHEALQDYE AGQHMEDPRR AGKMLMTLPL LRQTSTKAVQ HFYNIKLEGK

421   VPMHKLFLEM LEAKV
```

By "ESRRG polynucleotide" is meant a polynucleotide encoding a ESRRG polypeptide or fragment thereof. An exemplary ESRRG polynucleotide sequence is provided at NCBI Ref: NM_001243519.1. The sequence provided at NCBI Ref: NM_001243519.1 is reproduced below:

```
   1  aagctccaat cggggcttta agtccttgat taggagagtg tgagagcttt ggtcccaact
  61  ggctgtgcct ataggcttgt cactaggaga acatttgtgt taattgcact gtgctctgtc
 121  aaggaaactt tgatttatag ctggggtgca caaataatgg ttgccggtcg cacatggatt
 181  cggtagaact ttgccttcct gaatcttttt ccctgcacta cgaggaagag tagacttgaa
 241  tgagacctgc ctcatcagtc atgggatcat agtgtcacag atggaaaagc aactatcagc
 301  tgaattgtac tgaactacac acttggctaa ttcatcttat tgctctacac atctaaagga
 361  aggctcattc tgttcttgga gtctagacag catcaggagt tgggctcagt gaacaaaact
 421  ttaatgtcta gagcatttat gagggtttta atgattggaa aatctatcct gagaatgtgg
 481  tcaccatatg tgacagcctt gctttctatc ttgtcttcag tttctggggc ttctctgcag
 541  aatgtcaaac aaagatcgac acattgattc cagctgttcg tccttcatca agacggaacc
 601  ttccagccca gcctccctga cggacagcgt caaccaccac agccctggtg gctcttcaga
 661  cgccagtggg agctacagtt caaccatgaa tggccatcag aacggacttg actcgccacc
 721  tctctaccct tctgctccta tcctgggagg tagtgggcct gtcaggaaac tgtatgatga
 781  ctgctccagc accattgttg aagatcccca gaccaagtgt gaatacatgc tcaactcgat
 841  gcccaagaga ctgtgtttag tgtgtggtca tcgcttct gggtaccact atggggtagc
 901  atcatgtgaa gcctgcaagg cattcttcaa gaggacaatt caaggcaata tagaatacag
 961  ctgccctgcc acgaatgaat gtgaaatcac aaagcgcaga cgtaaatcct gccaggcttg
1021  ccgcttcatg aagtgtttaa aagtgggcat gctgaaagaa ggggtgcgtc ttgacagagt
1081  acgtggaggt cggcagaagt acaagcgcag gatagatgcg gagaacagcc catacctgaa
1141  ccctcagctg gttcagccag ccaaaaagcc atataacaag attgtctcac atttgttggt
1201  ggctgaaccg gagaagatct atgccatgcc tgaccctact gtccccgaca gtgacatcaa
1261  agccctcact acactgtgtg acttggccga ccgagagttg gtggttatca ttggatgggc
1321  gaagcatatt ccaggcttct ccacgctgtc cctggcggac cagatgagcc ttctgcagag
1381  tgcttggatg gaaattttga tccttggtgt cgtataccgg tctctttcgt ttgaggatga
1441  acttgtctat gcagacgatt atataatgga cgaagaccag tccaaattag caggccttct
1501  tgatctaaat aatgctatcc tgcagctggt aaagaaatac aagagcatga agctggaaaa
1561  agaagaattt gtcaccctca aagctatagc tcttgctaat tcagactcca tgcacataga
1621  agatgttgaa gccgttcaga agcttcagga tgtcttacat gaagcgctgc aggattatga
1681  agctggccag cacatggaag accctcgtcg agctggcaag atgctgatga cactgccact
1741  cctgaggcag acctctacca aggccgtgca gcatttctac aacatcaaac tagaaggcaa
1801  agtcccaatg cacaaacttt ttttggaaat gttggaggcc aaggtctgac taaaagctcc
1861  ctgggccttc ccatccttca tgttgaaaaa gggaaaataa acccaagagt gatgtcgaag
1921  aaacttagag tttagttaac aacatcaaaa atcaacagac tgcactgata atttagcagc
1981  aagactatga agcagctttc agattcctcc ataggttcct gatgagtttc tttctacttt
2041  ctccatcatc ttctttcctc tttcttccca catttctctt tctctttatt ttttctcctt
2101  ttcttctttc acctccctta tttctttgct tctttcattc ctagttccca ttctccttta
2161  ttttcttccc gtctgcctgc cttctttctt ttctttacct actctcattc ctctctttc
2221  tcatccttcc ccttttttct aaatttgaaa tagctttagt ttaaaaaaaa atcctccctt
```

-continued

```
2281  cccccttttcc tttcccttttc tttcctttttt ccctttcctt ttccctttcc tttccttttcc 2341  tcttgacctt ctttccatct ttcttttttct tccttctgct gctgaacttt taaaagaggt 2401  ctctaactga agagagatgg aagccagccc tgccaaagga tggagatcca taatatggat 2461  gccagtgaac ttattgtgaa ccatactgtc cccaatgact aaggaatcaa agagagagaa 2521  ccaacgttcc taaaagtaca gtgcaacata tacaaattga ctgagtgcag tattagattt 2581  catgggagca gcctctaatt agacaactta agcaacgttg catcggctgc ttcttatcat 2641  tgctttttcca tctagatcag ttacagccat ttgattcctt aattgttttt tcaagtcttc 2701  caggtatttg ttagtttagc tactatgtaa cttttttcagg gaatagttta agctttattc 2761  attcatgcaa tactaaagag aaataagaat actgcaattt tgtgctggct ttgaacaatt 2821  acgaacaata atgaaggaca aatgaatcct gaaggaagat ttttaaaaat gttttgtttc 2881  ttcttacaaa tggagatttt tttgtaccag ctttaccact tttcagccat ttattaatat 2941  gggaatttaa cttactcaag caatagttga agggaaggtg catattatca cggatgcaat 3001  ttatgttgtg tgccagtctg gtcccaaaca tcaatttctt aacatgagcc ccagtttacc 3061  taaatgttca ctgacacaaa ggatgagatt acacctacag tgactctgag tagtcacata 3121  tataagcact gcacatgaga tatagatccg tagaattgtc aggagtgcac ctctctactt 3181  gggaggtaca attgccatat gatttctagc tgccatggtg gttaggaatg tgatactgcc 3241  tgtttgcaaa gtcacagacc ttgcctcaga aggagctgtg agccagtatt catttaagag 3301  gcaataaggc aaatgccaga attaaaaaaa aaaatcatca aagacagaaa atgcctgacc 3361  aaattctaaa acctaatcca tataagttta ttcatttagg aatgttcgtt taaattaatc 3421  tgcagttttt accaagagct aagccaatat atgtgctttt caaccagtat tgtcacagca 3481  tgaaagtcaa gtcaggttcc agactgttaa gaggtgtaat ctaatgaaga aatcaattag 3541  atgccccgaa atctacagtc gctgaataac caataaacag taacctccat caaatgctat 3601  accaatggac cagtgttagt agctgctccc tgtattatgt gaacagtctt attctatgta 3661  cacagatgta attaaaattg taatcctaac aaacaaaga aatgtagttc agcttttcaa 3721  tgtttcatgt ttgctgtgct tttctgaatt ttatgttgca ttcaaagact gttgtcttgt 3781  tcttgtggtg tttggattct tgtggtgtgt gcttttagac acagggtaga attagagaca 3841  atattggatg tacaattcct caggagacta cagtagtata ttctattcct taccagtaat 3901  aaggttcttc ctaataataa ttaagagatt gaaactccaa acaagtattc attatgaaca 3961  gatacacatc aaaatcataa taatattttc aaaacaagga ataatttctc taatggttta 4021  ttatagaata ccaatgtata gcttagaaat aaaactttga atatttcaag aatatagata 4081  agtctaattt ttaaatgctg tatatatggc tttcactcaa tcatctctca gatgttgtta 4141  ttaactcgct ctgtgttgtt gcaaaacttt ttggtgcaga ttcgtttcca aaactattgc 4201  tactttgtgt gctttaaaca aaataccttg ggttgatgaa acatcaaccc agtgctagga 4261  atactgtgta tctatcatta gctatatggg actatattgt agattgtggt ttctcagtag 4321  agaagtgact gtagtgtgat tctagataaa tcatcattag caattcattc agatggtcaa 4381  taacttgaaa tttatagctg tgataggagt tcagaaattg gcacatccct ttaaaaataa 4441  caacagaaaa tacaactcct gggaaaaaag gtgctgattc tataagatta tttatatatg 4501  taagtgttta aaaagattat tttccagaaa gtttgtgcag ggtttaagtt gctactattc 4561  aactacacta tatataaata aaatatatac aatatataca ttgtttttcac tgtatcacat 4621  taaagtactt gggcttcaga agtaagagcc aaccaactga aaacctgaga tggagatatg 4681  ttcaaagaat gagatacaat tttttagttt tcagtttaag taactctcag cattacaaaa
```

-continued

```
4741  gagtaagtat ctcacaaata ggaaataaaa ctaaaacgtg gatttaaaaa gaactgcacg 4801  ggctttaggg taaatgctca tcttaaacct cactagaggg aagtcttctc aagtttcaag 4861  caagaccatt tacttaatgt gaagtttggg aaagttataa aggtgtatgt tttagccata 4921  tgattttaat tttaattttg cttctttag  gttcgttctt atttaaagca atatgattgt 4981  gtgactcctt gtagttacac ttgtgtttca atcagatcag attgttgtat ttattccact 5041  attttgcatt taaatgataa cataaaagat ataaaaaatt taaaactgct atttttctta 5101  tagaagagaa aatgggtgtt ggtgattgta ttttaattat ttaagcgtct ctgtttacct 5161  gcctaggaaa acattttatg gcagtcttat gtgcaaagat cgtaaaagga caaaaaattt 5221  aaactgctta taataatcca ggagttgcat tatagccagt agtaaaaata ataataataa 5281  taataaaacc atgtctatag ctgtagatgg gcttcacatc tgtaaagcaa tcaattgtat 5341  atttttgtga tgtgtaccat actgtgtgct ccagcaaatg tccatttgtg taaatgtatt 5401  tattttatat tgtatatatt gttaaatgca aaaaggagat atgattctgt aactccaatc 5461  agttcagatg tgtaactcaa attattatgc ctttcaggat gatggtagag caatattaaa 5521  caagcttcca cttttgactg ctaaaaaaaa aaaaaaaaa
```

As used herein, "endocrine" refers to secretion of an agent (e.g., a hormone) into a bloodstream. "Exocrine" refers to secretion of an agent into an epithelial surface by way of a duct.

By "fragment" is meant a portion of a polypeptide or nucleic acid molecule. This portion contains at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "FOXA2 polypeptide" is meant a protein or fragment thereof having at least 85% amino acid sequence identity to the sequence provided at NCBI Accession No. NP_068556.2 and having transcription factor activity. The amino acid sequence provided at NCBI Accession No. NP_068556.2 is shown below:

```
  1   MHSASSMLGA VKMEGHEPSD WSSYYAEPEG YSSVSNMNAG LGMNGMNTYM SMSAAAMGSG

61   SGNMSAGSMN MSSYVGAGMS PSLAGMSPGA GAMAGMGGSA GAAGVAGMGP HLSPSLSPLG

121   GQAAGAMGGL APYANMNSMS PMYGQAGLSR ARDPKTYRRS YTHAKPPYSY ISLITMAIQQ

181   SPNKMLTLSE IYQWIMDLFP FYRQNQQRWQ NSIRHSLSFN DCFLKVPRSP DKPGKGSFWT

241   LHPDSGNMFE NGCYLRRQKR FKCEKQLALK EAAGAAGSGK KAAAGAQASQ AQLGEAAGPA

301   SETPAGTESP HSSASPCQEH KRGGLGELKG TPAAALSPPE PAPSPGQQQQ AAAHLLGPPH

361   HPGLPPEAHL KPEHHYAFNH PFSINNLMSS EQQHHHSHHH HQPHKMDLKA YEQVMHYPGY

421   GSPMPGSLAM GPVTNKTGLD ASPLAADTSY YQGVYSRPIM NSS
```

By "FOXA2 polynucleotide" is meant a polynucleotide encoding a FOXA2 polypeptide or fragment thereof. An exemplary FOXA2 polynucleotide sequence is provided at NCBI Ref: NM_021784.4. The sequence provided at NCBI Ref: NM_021784.4 is reproduced below:

```
  1   cccgcccact tccaactacc gcctccggcc tgcccaggga gagagaggga gtggagccca 61   gggagaggga gcgcgagaga gggagggagg aggggacggt gctttggctg acttttttt 121   aaaagagggt gggggtgggg ggtgattgct ggtcgtttgt tgtggctgtt aaattttaaa 181   ctgccatgca ctcggcttcc agtatgctgg gagcggtgaa gatggaaggg cacgagccgt 241   ccgactggag cagctactat gcagagcccg agggctactc ctccgtgagc aacatgaacg 301   ccggcctggg gatgaacggc atgaacacgt acatgagcat gtcggcggcc gccatgggca
```

-continued

```
 361    gcggctcggg caacatgagc gcgggctcca tgaacatgtc gtcgtacgtg ggcgcctggca 421    tgagcccgtc cctggcgggg atgtccccg gcgcgggcgc catggcgggc atgggcggct 481    cggccggggc ggccggcgtg gcgggcatgg ggccgcactt gagtcccagc ctgagcccgc 541    tcggggggca ggcggccggg gccatgggcg gcctggcccc ctacgccaac atgaactcca 601    tgagccccat gtacgggcag gcgggcctga gccgcgcccg cgaccccaag acctacaggc 661    gcagctacac gcacgcaaag ccgccctact cgtacatctc gctcatcacc atggccatcc 721    agcagagccc caacaagatg ctgacgctga gcgagatcta ccagtggatc atggacctct 781    tccccttcta ccggcagaac cagcagcgct ggcagaactc catccgccac tcgctctcct 841    tcaacgactg tttcctgaag gtgccccgct cgcccgacaa gcccggcaag ggctccttct 901    ggacccctgca ccctgactcg ggcaacatgt tcgagaacgg ctgctacctg cgccgccaga 961    agcgcttcaa gtgcgagaag cagctggcgc tgaaggaggc cgcaggcgcc gccggcagcg 1021    gcaagaaggc ggccgccgga gcccaggcct cacaggctca actcggggag gccgccgggc 1081    cggcctccga gactccggcg ggcaccgagt cgcctcactc gagcgcctcc ccgtgccagg 1141    agcacaagcg aggggccctg ggagagctga aggggacgcc ggctgcggcg ctgagcccccc 1201    cagagccggc gccctctccc gggcagcagc agcaggccgc ggcccacctg ctgggcccgc 1261    cccaccaccc gggcctgccg cctgaggccc acctgaagcc ggaacaccac tacgccttca 1321    accaccgtt ctccatcaac aacctcatgt cctcggagca gcagcaccac cacagccacc 1381    accaccacca accccacaaa atggacctca aggcctacga acaggtgatg cactaccccg 1441    gctacggttc ccccatgcct ggcagcttgg ccatgggccc ggtcacgaac aaaacgggcc 1501    tggacgcctc gccctggcc gcagatacct cctactacca gggggtgtac tcccggccca 1561    ttatgaactc ctcttaagaa gacgacggct tcaggcccgg ctaactctgg caccccggat 1621    cgaggacaag tgagagagca agtggggggtc gagactttgg ggagacggtg ttgcagagac 1681    gcaagggaga agaaatccat aacacccca ccccaacacc cccaagacag cagtcttctt 1741    caccgctgc agccgttccg tcccaaacag agggccacac agataccca cgttctatat 1801    aaggaggaaa acgggaaaga atataaagtt aaaaaaaagc ctccggtttc cactactgtg 1861    tagactcctg cttcttcaag cacctgcaga ttctgatttt tttgttgttg ttgttctcct 1921    ccattgctgt tgttgcaggg aagtcttact taaaaaaaaa aaaaaatttt gtgagtgact 1981    cggtgtaaaa ccatgtagtt ttaacagaac cagagggttg tactattgtt taaaaacagg 2041    aaaaaaaata atgtaagggt ctgttgtaaa tgaccaagaa aaagaaaaaa aaagcattcc 2101    caatcttgac acggtgaaat ccaggtctcg ggtccgatta atttatggtt tctgcgtgct 2161    ttatttatgg cttataaatg tgtattctgg ctgcaagggc cagagttcca caaatctata 2221    ttaaagtgtt atacccggtt ttatcccttg aatctttttct tccagatttt tcttttcttt 2281    acttggctta caaaatatac aggcttggaa attatttcaa gaaggaggga gggataccct 2341    gtctggttgc aggttgtatt ttattttggc ccagggagtg ttgctgtttt cccaacattt 2401    tattaataaa attttcagac ataaaaaa
```

By "GATA6 polypeptide" is meant a protein or fragment thereof having at least 85% amino acid sequence identity to the sequence provided at NCBI Accession No. NP_005248.2 and having transcription factor activity. The amino acid sequence provided at NCBI Accession No. NP_005248.2 is shown below:

```
  1 MALTDGGWCL PKRFGAAGAD ASDSRAFPAR EPSTPPSPIS
    SSSSSCSRGG ERGPGGASNC
 61 GTPQLDTEAA AGPPARSLLL SSYASHPFGA PHGPSAPGVA
    GPGGNLSSWE DLLLFTDLDQ
121 AATASKLLWS SRGAKLSPFA PEQPEEMYQT LAALSSQGPA
    AYDGAPGGFV HSAAAAAAAA
181 AAASSPVYVP TTRVGSMLPG LPYHLQGSGS GPANHAGGAG
    AHPGWPQASA DSPPYGSGGG
241 AAGGGAAGPG GAGSAAAHVS ARFPYSPSPP MANGAAREPG
    GYAAAGSGGA GGVSGGGSSL
301 AAMGGREPQY SSLSAARPLN GTYHHHHHHH HHHPSPYSPY
    VGAPLTPAWP AGPFETPVLH
361 SLQSRAGAPL PVPRGPSADL LEDLSESREC VNCGSIQTPL
    WRRDGTGHYL CNACGLYSKM
421 NGLSRPLIKP QKRVPSSRRL GLSCANCHTT TTTLWRRNAE
    GEPVCNACGL YMKLHGVPRP
481 LAMKKEGIQT RKRKPKNINK SKTCSGNSNN SIPMTPTSTS
    SNSDDCSKNT SPTTQPTASG
541 AGAPVMTGAG ESTNPENSEL KYSGQDGLYI GVSLASPAEV
    TSSVRPDSWC ALALA
```

By "GATA6 polynucleotide" is meant a polynucleotide encoding a GATA6 polypeptide or fragment thereof. An exemplary KCNK3 polynucleotide sequence is provided at NCBI Ref: NM_005257.5. The sequence provided at NCBI Ref: NM_005257.5 is reproduced below:

```
   1 agttccgacc cacagcctgg cacccttcgg cgagcgctgt
     ttgtttaggg ctcggtgagt
  61 ccaatcagga gcccaggctg cagttttccg gcagagcagt
     aagaggcgcc tcctctctcc
 121 tttttattca ccagcagcgc ggcgcagacc ccggactcgc
     gctcgcccgc tggcgccctc
 181 ggcttctctc cgcgcctggg agcaccctcc gccgcggccg
     ttctccatgc gcagcgcccg
 241 cccgaggagc tagacgtcag cttggagcgg cgccggaccg
     tggatggcct tgactgacgg
 301 cggctggtgc ttgccgaagc gcttcggggc cgcgggtgcg
     gacgccagcg actccagagc
```

-continued
```
 361 ctttccagcg cgggagccct ccacgccgcc ttcccccatc
     tcttcctcgt cctcctcctg
 421 ctcccggggc ggagagcggg gccccggcgg cgccagcaac
     tgcgggacgc ctcagctcga
 481 cacggaggcg gcggccggac ccccggcccg ctcgctgctg
     ctcagttcct acgcttcgca
 541 tcccttcggg gctccccacg gaccttcggc gcctggggtc
     gcgggccccg ggggcaacct
 601 gtcgagctgg gaggacttgc tgctgttcac tgacctcgac
     caagccgcga ccgccagcaa
 661 gctgctgtgg tccagccgcg gcgccaagct gagccccttc
     gcacccgagc agccggagga
 721 gatgtaccag accctcgccg ctctctccag ccagggtccg
     gccgcctacg acggcgcgcc
 781 cggcggcttc gtgcactctg cggccgcggc ggcagcagcc
     gcggcggcgg ccagctcccc
 841 ggtctacgtg cccaccaccc gcgtgggttc catgctgccc
     ggcctaccgt accacctgca
 901 ggggtcgggc agtgggccag ccaaccacgc gggcggcgcg
     ggcgcgcacc ccggctggcc
 961 tcaggcctcg gccgacagcc ctccatacgg cagcggaggc
     ggcgcggctg gcggcggggc
1021 cgcgggggcct ggcgcgctg gctcagccgc ggcgcacgtc
     tcggcgcgct tcccctactc
1081 tcccagcccg cccatggcca acggcgccgc gcgggagccg
     ggaggctacg cggcggcggg
1141 cagtgggggc gcgggaggcg tgagcggcgg cggcagtagc
     ctggcggcca tgggcggccg
1201 cgagccccag tacagctcgc tgtcggccgc gcggccgctg
     aacgggacgt accaccacca
1261 ccaccaccac caccaccacc atccgagccc ctactcgccc
     tacgtggggg cgccactgac
1321 gcctgcctgg cccgccggac ccttcgagac cccggtgctg
     cacagcctgc agagccgcgc
1381 cggagccccg ctcccggtgc cccggggtcc cagtgcagac
     ctgctggagg acctgtccga
1441 gagccgcgag tgcgtgaact gcggctccat ccagacgccg
     ctgtggcggc gggacggcac
1501 cggccactac ctgtgcaacg cctgcgggct ctacagcaag
     atgaacgccc tcagccggcc
```

-continued

```
1561  cctcatcaag  ccgcagaagc  gcgtgccttc  atcacggcgg cttggattgt  cctgtgccaa 1621  ctgtcacacc  acaactacca  ccttatggcg  cagaaacgcc gagggtgaac  ccgtgtgcaa 1681  tgcttgtgga  ctctacatga  aactccatgg  ggtgcccaga ccacttgcta  tgaaaaaga 1741  gggaattcaa  accaggaaac  gaaaacctaa  gaacataaat aaatcaaaga  cttgctctgg 1801  taatagcaat  aattccattc  ccatgactcc  aacttccacc tcttctaact  cagatgattg 1861  cagcaaaaat  acttccccca  caacacaacc  tacagcctca ggggcgggtg  ccccggtgat 1921  gactggtgcg  ggagagagca  ccaatcccga  gaacagcgag ctcaagtatt  cgggtcaaga 1981  tgggctctac  ataggcgtca  gtctcgcctc  gccggccgaa gtcacgtcct  ccgtgcgacc 2041  ggattcctgg  tgcgccctgg  ccctggcctg  agcccacgcc gccaggaggc  agggagggct 2101  ccgccgcggg  cctcactcca  ctcgtgtctg  cttttgtgca gcggtccaga  cagtggcgac 2161  tgcgctgaca  gaacgtgatt  ctcgtgcctt  tattttgaaa gagatgtttt  tcccaagagg 2221  cttgctgaaa  gagtgagaga  agatggaagg  gaagggccag tgcaactggg  cgcttgggcc 2281  actccagcca  gcccgcctcc  ggggcggacc  ctgctccact tccagaagcc  aggactagga 2341  cctgggcctt  gcctgctatg  gaatattgag  agagattttt taaaaaagat  tttgcatttt 2401  gtccaaaatc  atgtgcttct  tctgatcaat  tttggttgtt ccagaatttc  ttcatacctt 2461  ttccacatcc  agatttcatg  tgcgttcatg  gagaagatca cttgaggcca  tttggtacac 2521  atctctggag  gctgagtcgg  ttcatgaggt  ctcttatcaa aaatattact  cagtttgcaa 2581  gactgcattg  taactttaac  atacactgtg  actgacgttt ctcaaagttc  atattgtgtg 2641  gctgatctga  agtcagtcgg  aatttgtaaa  cagggtagca aacaagatat  ttttcttcca 2701  tgtatacaat  aatttttttta  aaaagtgcaa  tttgcgttgc agcaatcagt  gttaaatcat
```

-continued

```
2761  ttgcataaga  tttaacagca  ttttttataa  tgaatgtaaa cattttaact  taatggtact 2821  taaaataatt  taaaagaaaa  atgttaactt  agacattctt atgcttcttt  tacaactaca 2881  tcccatttta  tatttccaat  tgttaaagaa  aaatatttca agaacaaatc  ttctctcagg 2941  aaaattgcct  ttctctattt  gttaagaatt  tttatacaag aacaccaata  taccccctttt 3001  attttactgt  ggaatatgtg  ctggaaaaat  tgcaacaaca ctttactacc  taacggatag 3061  catttgtaaa  tactctaggt  atctgtaaac  actctgatga agtctgtata  gtgtgactaa 3121  cccacaggca  ggttggttta  cattaatttt  tttttttgaa tgggatgtcc  tatggaaacc 3181  tatttcacca  gagtttttaaa  aataaaaagg  gtattgtttt gtcttctgta  cagtgagttc 3241  cttcccttttt  caaagctttc  tttttatgct  gtatgtgact atagatattc  atataaaaca 3301  agtgcacgtg  aagtttgcaa  aatgctttaa  ggccttcctt tcaaagcata  gtcctttttgg 3361  agccgttttg  tacctttttat  accttggctt  atttgaagtt gacacatggg  gttagttact 3421  actctccatg  tgcattgggg  acagtttttta  taagtgggaa ggactcagta  ttattatatt 3481  tgagatgata  agcattttgt  ttgggaacaa  tgcttaaaaa tattccagaa  agttcagatt 3541  tttttttcttt  gtgaatgaaa  tatattctgg  cccacgaaca gggcgatttc  ctttcagttt 3601  tttccttttg  caacgtgcct  tgaagtctca  aagctcacct gaggttgcag  acgttacccc 3661  caacagaaga  taggtagaaa  tgattccagt  ggcctctttg tattttcttc  attgttgagt 3721  agatttcagg  aaatcaggag  gtgtttcaca  atacagaatg atggccttta  actgtgaaaa 3781  aaaaa
```

By "gellan gum" is meant a polysaccharide having a straight chain with a repeating unit that has any one of the following molecular structures:

Gellan gum-high acyl form

Gellan gum-low acyl form

In the foregoing structures, "Ac" refers to an acetate group and "Gly" refers to a glycerate group and "M+" is a monovalent cation. In some embodiments, the gellan gum is KELCOGEL® gellan gum.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "immunosuppressive agent" or "immunosuppressant" is meant an agent that inhibits or prevents an immune reaction, such as rejection, of a transplanted or implanted organ, islet, or organoid in a subject. Examples of immunosuppressants include, but are not limited to, basilizimab, antithymocyte globulin, alemtuzumab, prednisone, azathioprine, mycophenolate, cyclosporine, sirolimus, methotrexate, interferon, and tacrolimus.

By "induced pluripotent stem cell" or "iPSC" is meant a differentiated somatic cell that acquires pluripotency by the exogenous expression of one or more transcription factors in the cell. An "iPSC-derived cell" is a cell derived from an induced pluripotent stem cell. An "iPSC-derived beta-like cell," "iPSC-derived alpha-like cell," "iPSC-derived delta-like cell," or "iPSC-derived duct-like cell" is a cell derived from an induced pluripotent stem cell and has characteristics of a beta cell, alpha cell, delta cell, or duct cell, respectively.

"Interferon gamma (IFNγ) receptor-expressing" cells (e.g., donor cells), islets, organoids (and the cells therein) refer to cells, islets, organoids (and the cells therein) that express IFNγ receptor on their surface in an amount or level sufficient to respond to IFNγ following contact or exposure to IFNγ, e.g., MPS IFNγ exposure according to the methods described herein, and, in turn, to express or upregulate expression of a checkpoint protein-encoding gene or a checkpoint protein, e.g. PD-L1 (PD-L1 marker protein). In an embodiment, PD-L1 protein is expressed on the surface of the cells (cell membrane expression). In an embodiment, the expression or upregulation of the checkpoint protein, e.g., PD-L1 is sustained, e.g. for greater than or equal to 1, 2, 3, 4, 5, 6, or 7 days or longer. In an embodiment, the expression or upregulation of the checkpoint protein, e.g., PD-L1 is sustained, e.g. for greater than or equal to 7 days or longer. (e.g., more than 1, 2, 3, 4, 5, 6 weeks, or longer). The expression of PD-L1 or the level of expression of PD-L1 in or on cells, for example, may be detected or determined by any assay that is routinely known or used by those skilled in the art to detect or determine levels of proteins or polynucleotides, e.g., without limitation, enzymatic, fluorescent, chemiluminescent or electrochemiluminescent immunoassay, flow cytometry, spectrometry (mass spectrometry); PCR, or RNA or DNA detection methods.

Intermittent exposure as used herein refers to repeated exposure, e.g., short repeated exposure, of cells, islets, organoids (islet-like organoids, e.g., human islet-like organoids, and the cells therein), especially of interferon-gamma (IFNγ) receptor-expressing cells, islets, organoids (islet-like organoids and the cells therein), to multiple pulses, e.g., short repeated pulses, called multiple pulse stimulation (MPS), of IFNγ, as used in the described protocols to generate immunoprotected cells, islets, or organoids that survive and have reduced cell death, e.g., evade immune detection, following transplantation, implantation, or transfer, as described herein. The duration of each of the repeated pulses of IFNγ exposure is typically a short time period, such as minutes or a few hours, rather than a prolonged period of time. By way of example, the exposure to IFNγ may comprise a time period of 0.5 hour, 1 hour, 2 hours, or 3 hours, and the like, multiple times over a given or overall time period, e.g., hours (e.g., 2, 4, 6, 12, 24, 36, 48, 72, 144, or more hours, or intervals therebetween), days (1, 2, 3, 4, 5, 6, 7, 8, 9, 10, 11, 12, 13, 14, or more days), or weeks (1, 2, 3, 4, 5, 6, 7, 8, or more weeks), as described herein.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. The preparation can be at least 75%, at least 90%, and at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "KCNK3 polypeptide" is meant a protein or fragment thereof having at least 85%, at least 90%, at least 95%, at least 98%, or at least 99% amino acid sequence identity to the sequence provided at NCBI Accession No. NP_002237.1 and having potassium channel activity. The amino acid sequence provided at NCBI Accession No. NP_002237.1 is shown below:

```
  1 MKRQNVRTLA LIVCTFTYLL VGAAVFDALE SEPELIERQR

LELRQQELRA RYNLSQGGYE

61 ELERVVLRLK PHKAGVQWRF AGSFYFAITV ITTIGYGHAA

PSTDGGKVFC MFYALLGIPL

121 TLVMFQSLGE RINTLVRYLL HRAKKGLGMR RADVSMANMV

LIGFFSCIST LCIGAAAFSH

181 YEHWTFFQAY YYCFITLTTI GFGDYVALQK DQALQTQPQY

VAFSFVYILT GLTVIGAFLN

241 LVVLRFMTMN AEDEKRDAEH RALLTRNGQA GGGGGGGSAH

TTDTASSTAA AGGGGFRNVY

301 AEVLHFQSMC SCLWYKSREK LQYSIPMIIP RDLSTSDTCV

EQSHSSPGGG GRYSDTPSRR

361 CLCSGAPRSA ISSVSTGLHS LSTFRGLMKR RSSV
```

By "KCNK3 polynucleotide" is meant a polynucleotide encoding a KCNK3 polypeptide or fragment thereof. An exemplary KCNK3 polynucleotide sequence is provided at NCBI Ref: NM_002246.2. The sequence provided at NCBI Ref: NM_002246.2 is reproduced below:

```
   1 ggcggcggcg gcggcggcgg ccccgggcgc tgagcgggtg cccggcgcgg agagcggcga 61 gcgcagccat gccccaggcc gcctccgggg cagcagcagc ggcggccggg gccgaggcgc 121 gggccggggg cgccgggggg ccggcggcgg cccgggcggg acgatgaagc ggcagaacgt 181 gcgcacgctg gcgctcatcg tgtgcacctt cacctacctg ctggtgggcg ccgcggtctt 241 cgacgcgctg gagtcggagc ccgagctgat cgagcggcag cggctggagc tgcggcagca 301 ggagctgcgg gcgcgctaca acctcagcca gggcggctac gaggagctgg agcgcgtcgt
```

```
 361 gctgcgcctc aagccgcaca aggccggcgt gcagtggcgc ttcgccggct ccttctactt 421 cgccatcacc gtcatcacca ccatcggcta cgggcacgcg gcacccagca cggatggcgg 481 caaggtgttc tgcatgttct acgcgctgct gggcatcccg ctcacgctcg tcatgttcca 541 gagcctgggc gagcgcatca acaccttggt gaggtacctg ctgcaccgcg ccaagaaggg 601 gctgggcatg cggcgcgccg acgtgtccat ggccaacatg gtgctcatcg gcttcttctc 661 gtgcatcagc acgctgtgca tcggcgccgc cgccttctcc cactacgagc actggacctt 721 cttccaggcc tactactact gcttcatcac cctcaccacc atcggcttcg gcgactacgt 781 ggcgctgcag aaggaccagg ccctgcagac gcagccgcag tacgtggcct tcagcttcgt 841 ctacatcctt acgggcctca cggtcatcgg cgccttcctc aacctcgtgg tgctgcgctt 901 catgaccatg aacgccgagg acgagaagcg cgacgccgag caccgcgcgc tgctcacgcg 961 caacgggcag gcgggcggcg gcggaggggg tggcagcgcg cacactacgg acaccgcctc 1021 atccacgcg gcagcgggcg gcggcggctt ccgcaacgtc tacgcggagg tgctgcactt 1081 ccagtccatg tgctcgtgcc tgtggtacaa gagccgcgag aagctgcagt actccatccc 1141 catgatcatc ccgcggacc tctccacgtc cgacacgtgc gtggagcaga gccactcgtc 1201 gccgggaggg ggcggccgct acagcgacac gccctcgcga cgctgcctgt gcagcggggc 1261 gccacgctcc gccatcagct cggtgtccac gggtctgcac agcctgtcca ccttccgcgg 1321 cctcatgaag cgcaggagct ccgtgtgact gccccgaggg gcctggagca cctgggggcg 1381 cgggcggggg accctgctg ggaggccagg agactgcccc tgctgccttc tgcccagtgg 1441 gaccccgcac aacatccctc accactctcc cccagcaccc ccatctccga ctgtgcctgc 1501 ttgcaccagc cggcaggagg ccgggctctg aggaccctg gggcccccat cggagccctg
```

-continued

-continued

```
1561 caaattccga gaaatgtgaa acttggtggg gtcagggagg
     aaaggcagaa gctgggagcc 1621 tcccttccct ttgaaaatct aagaagctcc cagtcctcag
     agaccctgct ggtacccaga 1681 cccccacctt cggaggggac ttcatgttcc gtgtacgttt
     gcatctctat ttatacctct 1741 gtcctgctag gtctcccacc ttcccttggt tccaaaagcc
     agggtgtcta tgtccaagtc 1801 acccctactc agccccactc cccttcctca tccccagctg
     tgtctcccaa cctcccttcg 1861 tgttgttttg catggctttg cagttatgga gaaagtggaa
     acccagcagt ccctaaagct 1921 ggtccccaga aagcaggaca gaaagaagga gggacaggca
     ggcagcagga ggggcgagct 1981 gggaggcagg aggcagcggc ctgtcagtct gcagaatggt
     cgcactggag gttcaagcta 2041 actggcctcc agccacattc tcatagcagg taggacttca
     gccttccaga cactgccctt 2101 agaatctgga acagaagact tcagactcac cataattgct
     gataattacc cactcttaaa 2161 tttgtcgagt gattttttagc ctctgaaaac tctatgctgg
     ccactgattc ctttgagtct 2221 cacaaaaccc tacttaggtc atcagggcag gagttctcac
     tcccatttta cagatgagaa 2281 tactgaggcc tggacaggtg aagtgaccag agagcaaaag
     gcaaaggggt gggggctggg 2341 tgcagtggct cacacctgta ttcccaacac ttttggaggc
     tgaggttgga ggattgcttg 2401 agcccaggaa tttgagacca gcctaggtga catagtgaga
     ccccatctct acaaaaaata 2461 aaaaattaac caggtgtggt ggcacgtgcc tgggagtccc
     agcgacttgg gaggctgagg 2521 tgggaggatt gtttgagcct gggaggtcga ggctgtagtg
     agccctgatt gcaccactgt 2581 actccagcct gggtgacagg gcaagaccct gtctcaaaaa
     aaaaaaaaaa aatggcaaag 2641 ggagacaaga gcccagcctg cttgttgcta gccaaagtgt
     tctttccttc cagcttggcc 2701 tgctcttaaa agcaaagctc ctgcagtgta catcctggca
     ttgtgtggct acctgggttt
```

```
2761 taaaccagaa tcagaagtcc cggatcagag ggcactgctg
     aggttcagcc tcttctcttc 2821 ttggccagga ggcagcagct ctgaatgggc ccctgaggct
     gcacaggggc ctttgtcact 2881 ggggcgcatg cttacaaaca gtgcagttct tgggaccgag
     gtaagcaggg ctgggtctca 2941 tggcagaaag gccaggatct ggggctctag gaatttggga
     attgggcaga gtggccaaga 3001 aagctggcag gcatatccta tgggacatca cacctggcac
     cattgtcatt gttggtgcct 3061 gtgtcccaag tagctagtga taagctgagg ctgcagcaag
     aaacaccctt cccaggtggg 3121 ggagtttgga ccagaggtgc cctctgccca ccacacctgc
     aacccagaag cccagatgga 3181 acgcagctga cgaaggtgat gcttgaggct cacttttggg
     gccccacagc tggagccggt 3241 ataatgactg ggacaacatc aagggtggga tgaggggcct
     ctcctcccgc aacactgcct 3301 tcccatgctg ttcccctgcc agctccttaa cactgccgac
     caaggccagc cctggcattc 3361 agggaaattg gagggcagca cccgtagggt ggccagcctc
     aggccccacc ccagctgtgt 3421 cctctagtct ctggggaccc ctgggggggaa gaagtctacc
     ctgcttgtga gtcccgtctc 3481 agtgtggagg aactggctgc acgtgggacc tgaaggtgcc
     ctctgtgttt atgttggggg 3541 tggggggggca gtgctggctg cctctgtcct gtgtgtgacc
     ctgccctcga agggtcctgt 3601 cctgtcagtc ccgagggagc cacaaccaaa gctgcggaga
     gaaggtgggg aagggtgcag 3661 aatggccgtg gggcacagcg tggcagactg ttcagtctct
     gctgggtctt tcctagggac 3721 ctggaaggcc agtgttgctt ccccctcact ccctttcact
     gcaggcagcc tctctgcttc 3781 cccaatgcct tatgcctggg cacactgcca cagaatatgc
     aatatgtgtg ggtgaccatg 3841 ccctcacgac cacaccccca ccccgggcag cccccggact
     ccaaaggtcg tggctgccac
```

-continued

```
3901 agcctccctc agctcttcct gcctatctgt cttcacactg agaatggcgc ccaataaatg 3961 ctatccacgg agaccagg
```

By "KCNQ1 polypeptide" is meant a protein or fragment thereof having at least 85%, at least 90%, at least 95%, at least 98%, or at least 99% amino acid sequence identity to the sequence provided at NCBI Accession No. NP_000209.2 (isoform 1) or NP_861463.1 (isoform 2) and having potassium channel activity. The amino acid sequence provided at NCBI Accession No. NP_000209.2 is shown below:

```
  1 MAAASSPPRA ERKRWGWGRL PGARRGSAGL AKKCPFSLEL

AEGGPAGGAL YAPIAPGAPG

61 PAPPASPAAP AAPPVASDLG PRPPVSLDPR VSIYSTRRPV

LARTHVQGRV YNFLERPTGW

121 KCFVYHFAVF LIVLVCLIFS VLSTIEQYAA LATGTLFWME

IVLVVFFGTE YVVRLWSAGC

181 RSKYVGLWGR LRFARKPISI IDLIVVVASM VVLCVGSKGQ

VFATSAIRGI RFLQILRMLH

241 VDRQGGTWRL LGSVVFIHRQ ELITTLYIGF LGLIFSSYFV

YLAEKDAVNE SGRVEFGSYA

301 DALWWGVVTV TTIGYGDKVP QTWVGKTIAS CFSVFAISFF

ALPAGILGSG FALKVQQKQR

361 QKHFNRQIPA AASLIQTAWR CYAAENPDSS TWKIYIRKAP

RSHTLLSPSP KPKKSVVVKK

421 KKFKLDKDNG VTPGEKMLTV PHITCDPPEE RRLDHFSVDG

YDSSVRKSPT LLEVSMPHFM

481 RTNSFAEDLD LEGETLLTPI THISQLREHH RATIKVIRRM

QYFVAKKKFQ QARKPYDVRD

541 VIEQYSQGHL NLMVRIKELQ RRLDQSIGKP SLFISVSEKS

KDRGSNTIGA RLNRVEDKVT

601 QLDQRLALIT DMLHQLLSLH GGSTPGSGGP PREGGAHITQ

PCGSGGSVDP ELFLPSNTLP

661 TYEQLTVPRR GPDEGS
```

By "KCNQ1 polynucleotide" is meant a polynucleotide encoding a KCNQ1 polypeptide or fragment thereof. An exemplary KCNQ1 polynucleotide sequence is provided at NCBI Ref: NM_000218.2. The sequence provided at NCBI Ref: NM_000218.2 is reproduced below:

```
  1 gcggcggggc tggcagcagt ggctgcccgc actgcgcccg ggcgctcgcc ttcgctgcag 61 ctcccggtgc cgccgctcgg gccggccccc cggcaggccc tcctcgttat ggccgcggcc
```

-continued

```
121 tcctccccgc ccagggccga gaggaagcgc tggggttggg gccgcctgcc aggcgcccgg 181 cggggcagcg cgggcctggc caagaagtgc cccttctcgc tggagctggc ggagggcggc 241 ccggcgggcg gcgcgctcta cgcgcccatc gcgcccggcg ccccaggtcc cgcgccccct 301 gcgtccccgg ccgcgcccgc cgcgcccca gttgcctccg accttggccc gcggccgccg 361 gtgagcctag acccgcgcgt ctccatctac agcacgcgcc gcccggtgtt ggcgcgcacc 421 cacgtccagg gccgcgtcta caacttcctc gagcgtccca ccggctggaa atgcttcgtt 481 taccacttcg ccgtcttcct catcgtcctg gtctgcctca tcttcagcgt gctgtccacc 541 atcgagcagt atgccgccct ggccacgggg actctcttct ggatggagat cgtgctggtg 601 gtgttcttcg ggacggagta cgtggtccgc ctctggtccg ccggctgccg cagcaagtac 661 gtgggcctct gggggcggct gcgctttgcc cggaagccca tttccatcat cgacctcatc 721 gtggtcgtgg cctccatggt ggtcctctgc gtgggctcca aggggcaggt gtttgccacg 781 tcggccatca ggggcatccg cttcctgcag atcctgagga tgctacacgt cgaccgccag 841 ggaggcacct ggaggctcct gggctccgtg gtcttcatcc accgccagga gctgataacc 901 accctgtaca tcggcttcct gggcctcatc ttctcctcgt actttgtgta cctggctgag 961 aaggacgcgg tgaacgagtc aggccgcgtg gagttcggca gctacgcaga tgcgctgtgg 1021 tggggggtgg tcacagtcac caccatcggc tatgggggaca aggtgcccca gacgtgggtc 1081 gggaagacca tcgcctcctg cttctctgtc tttgccatct ccttctttgc gctcccagcg 1141 gggattcttg gctcggggtt tgccctgaag gtgcagcaga agcagaggca gaagcacttc 1201 aaccggcaga tcccggcggc agcctcactc attcagaccg catggaggtg ctatgctgcc 1261 gagaaccccg actcctccac ctggaagatc tacatccgga aggcccccg gagccacact
```

-continued

```
1321 ctgctgtcac ccagccccaa acccaagaag tctgtggtgg taaagaaaaa aaagttcaag 1381 ctggacaaag acaatggggt gactcctgga gagaagatgc tcacagtccc ccatatcacg 1441 tgcgacccc cagaagagcg gcggctggac cacttctctg tcgacggcta tgacagttct 1501 gtaaggaaga gcccaacact gctggaagtg agcatgcccc atttcatgag aaccaacagc 1561 ttcgccgagg acctggacct ggaagggag actctgctga cacccatcac ccacatctca 1621 cagctgcggg aacaccatcg ggccaccatt aaggtcattc gacgcatgca gtactttgtg 1681 gccaagaaga aattccagca agcgcggaag ccttacgatg tgcgggacgt cattgagcag 1741 tactcgcagg gccacctcaa cctcatggtg cgcatcaagg agctgcagag gaggctggac 1801 cagtccattg ggaagccctc actgttcatc tccgtctcag aaaagagcaa ggatcgcggc 1861 agcaacacga tcggcgcccg cctgaaccga gtagaagaca aggtgacgca gctggaccag 1921 aggctggcac tcatcaccga catgcttcac cagctgctct ccttgcacgg tggcagcacc 1981 cccggcagcg gcggcccccc cagagagggc ggggcccaca tcacccagcc ctgcggcagt 2041 ggcggctccg tcgaccctga gctcttcctg cccagcaaca ccctgcccac ctacgagcag 2101 ctgaccgtgc ccaggagggg ccccgatgag gggtcctgag gaggggatgg ggctgggga 2161 tgggcctgag tgagaggga ggccaagagt ggccccacct ggccctctct gaaggaggcc 2221 acctcctaaa aggcccagag agaagagccc cactctcaga ggccccaata ccccatggac 2281 catgctgtct ggcacagcct gcacttgggg gctcagcaag gccacctctt cctggccggt 2341 gtggggggccc cgtctcaggt ctgagttgtt accccaagcg ccctggcccc cacatggtga 2401 tgttgacatc actggcatgg tggttgggac ccagtggcag ggcacagggc ctggcccatg 2461 tatggccagg aagtagcaca ggctgagtgc aggcccaccc tgcttggcc aggggggcttc
```

-continued

```
2521 ctgaggggag acagagcaac ccctggaccc cagcctcaaa tccaggaccc tgccaggcac 2581 aggcagggca ggaccagccc acgctgacta cagggccgcc ggcaataaaa gcccaggagc 2641 ccatttggag ggcctgggcc tggctccctc actctcagga aatgctgacc catgggcagg 2701 agactgtgga gactgctcct gagcccccag cttccagcag gagggacagt ctcaccattt 2761 ccccagggca cgtggttgag tggggggaac gcccacttcc ctgggttaga ctgccagctc 2821 ttcctagctg gagaggagcc ctgcctctcc gcccctgagc ccactgtgcg tggggctccc 2881 gcctccaacc cctcgcccag tcccagcagc cagccaaaca cacagaaggg gactgccacc 2941 tcccccttgcc agctgctgag ccgcagagaa gtgacggttc ctacacagga caggggttcc 3001 ttctgggcat tacatcgcat agaaatcaat aatttgtggt gatttggatc tgtgtttaa 3061 tgagtttcac agtgtgattt tgattattaa ttgtgcaagc ttttcctaat aaacgtggag 3121 aatcacaggc tgggctgggc actgctctca ccttggttcc tggggcatcc atggggtctc 3181 tcacagacag gacccctgca gttccctgg aagcagtgcc caggtggctg tggaatagga 3241 acgctaaaaa aaaaaaaaa aa
```

By "LGR5 polypeptide" is meant a protein or fragment thereof having at least 85%, at least 90%, at least 95%, at least 98%, or at least 99% amino acid sequence identity to the sequence provided at NCBI Accession No. NP_003658.1 (isoform 1), NP_001264155.1 (isoform 2), or NP_001264156.1 (isoform 3) and having transmembrane signaling receptor activity or G-protein coupled receptor activity. The amino acid sequence provided at NCBI Accession No. NP_003658.1 is shown below:

```
  1 MDTSRLGVLL SLPVLLQLAT GGSSPRSGVL LRGCPTHCHC

EPDGRMLLRV DCSDLGLSEL

61 PSNLSVFTSY LDLSMNNISQ LLPNPLPSLR FLEELRLAGN

ALTYIPKGAF TGLYSLKVLM

121 LQNNQLRHVP TEALQNLRSL QSLRLDANHI SYVPPSCFSG

LHSLRHLWLD DNALTEIPVQ

181 AFRSLSALQA MTLALNKIHH IPDYAFGNLS SLVVLHLHNN

RIHSLGKKCF DGLHSLETLD
```

```
241 LNYNNLDEFP TAIRTLSNLK ELGFHSNNIR SIPEKAFVGN

PSLITIHFYD NPIQFVGRSA

301 FQHLPELRTL TLNGASQITE FPDLTGTANL ESLILTGAQI

SSLPQTVCNQ LPNLQVLDLS

361 YNLLEDLPSF SVCQKLQKID LRHNEIYEIK VDTFQQLLSL

RSLNLAWNKI AIIHPNAFST

421 LPSLIKLDLS SNLLSSFPIT GLHGLTHLKL TGNHALQSLI

SSENFPELKV IEMPYAYQCC

481 AFGVCENAYK ISNQWNKGDN SSMDDLHKKD AGMFQAQDER

DLEDFLLDFE EDLKALHSVQ

541 CSPSPGPFKP CEHLLDGWLI RIGVWTIAVL ALTCNALVTS

TVFRSPLYIS PIKLLIGVIA

601 AVNMLTGVSS AVLAGVDAFT FGSFARHGAW WENGVGCHVI

GFLSIFASES SVFLLTLAAL

661 ERGFSVKYSA KFETKAPFSS LKVIILLCAL LALTMAAVPL

LGGSKYGASP LCLPLPFGEP

721 STMGYMVALI LLNSLCFLMM TIAYTKLYCN LDKGDLENIW

DCSMVKHIAL LLFTNCILNC

781 PVAFLSFSSL INLTFISPEV IKFILLVVVP LPACLNPLLY

ILFNPHFKED LVSLRKQTYV

841 WTRSKHPSLM SINSDDVEKQ SCDSTQALVT FTSSSITYDL

PPSSVPSPAY PVTESCHLSS

901 VAFVPCL
```

By "LGR5 polynucleotide" is meant a polynucleotide encoding a LGR5 polypeptide or fragment thereof. An exemplary LGR5 polynucleotide sequence is provided at NCBI Ref: NM_003667.3. The sequence provided at NCBI Ref: NM_003667.3 is reproduced below:

```
  1 aaaaaacgag cgtgcaagca gagatgctgc tccacaccgc tcaggccgcg agcagcagca 61 aggcgcaccg ccactgtcgc cgctgcagcc agggctgctc cgaaggccgg cgtggcggca 121 accggcacct ctgtccccgc cgcgcttctc ctcgccgccc acgccgtggg gtcaggaacg 181 cggcgtctgg cgctgcagac gcccgctgag ttgcagaagc ccacggagcg gcgcccggcg 241 cgccacggcc cgtagcagtc cggtgctgct ctccgcccgc gtccggctcg tggcccccta 301 cttcgggcac catggacacc tcccggctcg gtgtgctcct gtccttgcct gtgctgctgc
```

```
361 agctggcgac cggggggcagc tctcccaggt ctggtgtgtt gctgaggggc tgccccacac 421 actgtcattg cgagcccgac ggcaggatgt tgctcagggt ggactgctcc gacctggggc 481 tctcggagct gccttccaac ctcagcgtct tcacctccta cctagacctc agtatgaaca 541 acatcagtca gctgctcccg aatcccctgc ccagtctccg cttcctggag gagttacgtc 601 ttgcgggaaa cgctctgaca tacattccca agggagcatt cactggcctt tacagtctta 661 aagttcttat gctgcagaat aatcagctaa gacacgtacc cacagaagct ctgcagaatt 721 tgcgaagcct tcaatccctg cgtctggatg ctaaccacat cagctatgtg cccccaagct 781 gtttcagtgg cctgcattcc ctgaggcacc tgtggctgga tgacaatgcg ttaacagaaa 841 tccccgtcca ggcttttaga agtttatcgg cattgcaagc catgaccttg gccctgaaca 901 aaatacacca cataccagac tatgcctttg gaaacctctc cagcttggta gttctacatc 961 tccataacaa tagaatccac tccctgggaa agaaatgctt tgatgggctc cacagcctag 1021 agactttaga tttaaattac aataaccttg atgaattccc cactgcaatt aggacactct 1081 ccaaccttaa agaactagga tttcatagca acaatatcag gtcgatacct gagaaagcat 1141 ttgtaggcaa cccttctctt attacaatac atttctatga caatcccatc cagtttgttg 1201 ggagatctgc ttttcaacat ttacctgaac taagaacact gactctgaat ggtgcctcac 1261 aaataactga atttcctgat ttaactggaa ctgcaaacct ggagagtctg actttaactg 1321 gagcacagat ctcatctctt cctcaaaccg tctgcaatca gttacctaat ctccaagtgc 1381 tagatctgtc ttacaaccta ttagaagatt tacccagttt ttcagtctgc caaaagcttc 1441 agaaaattga cctaagacat aatgaaatct acgaaattaa agttgacact ttccagcagt 1501 tgcttagcct ccgatcgcta aatttggctt ggaacaaaat tgctattatt caccccaatg
```

-continued

```
1561 catttttccac tttgccatcc ctaataaagc tggacctatc gtccaacctc ctgtcgtctt 1621 ttcctataac tgggttacat ggtttaactc acttaaaatt aacaggaaat catgccttac 1681 agagcttgat atcatctgaa aactttccag aactcaaggt tatagaaatg ccttatgctt 1741 accagtgctg tgcatttgga gtgtgtgaga atgcctataa gatttctaat caatggaata 1801 aaggtgacaa cagcagtatg gacgaccttc ataagaaaga tgctggaatg tttcaggctc 1861 aagatgaacg tgaccttgaa gatttcctgc ttgactttga ggaagacctg aaagcccttc 1921 attcagtgca gtgttcacct tccccaggcc ccttcaaacc ctgtgaacac ctgcttgatg 1981 gctggctgat cagaattgga gtgtggacca tagcagttct ggcacttact tgtaatgctt 2041 tggtgacttc aacagttttc agatcccctc tgtacatttc ccccattaaa ctgttaattg 2101 gggtcatcgc agcagtgaac atgctcacgg gagtctccag tgccgtgctg gctggtgtgg 2161 atgcgttcac ttttggcagc tttgcacgac atggtgcctg gtgggagaat ggggttggtt 2221 gccatgtcat tggttttttg tccatttttg cttcagaatc atctgttttc ctgcttactc 2281 tggcagccct ggagcgtggg ttctctgtga aatattctgc aaaatttgaa acgaaagctc 2341 catttttctag cctgaaagta atcatttttgc tctgtgccct gctggccttg accatggccg 2401 cagttcccct gctgggtggc agcaagtatg gcgcctcccc tctctgcctg cctttgcctt 2461 ttggggagcc cagcaccatg ggctacatgg tcgctctcat cttgctcaat tccctttgct 2521 tcctcatgat gaccattgcc tacaccaagc tctactgcaa tttggacaag ggagacctgg 2581 agaatatttg ggactgctct atggtaaaac acattgccct gttgctcttc accaactgca 2641 tcctaaactg ccctgtggct ttcttgtcct ctcctctttt aataaacctt acatttatca 2701 gtcctgaagt aattaagttt atccttctgg tggtagtccc acttcctgca tgtctcaatc
```

-continued

```
2761 cccttctcta catcttgttc aatcctcact ttaaggagga tctggtgagc ctgagaaagc 2821 aaacctacgt ctggacaaga tcaaaacacc caagcttgat gtcaattaac tctgatgatg 2881 tcgaaaaaca gtcctgtgac tcaactcaag ccttggtaac ctttaccagc tccagcatca 2941 cttatgacct gcctcccagt tccgtgccat caccagctta tccagtgact gagagctgcc 3001 atctttcctc tgtggcattt gtcccatgtc tctaattaat atgtgaagga aaatgttttc 3061 aaaggttgag aacctgaaaa tgtgagattg agtatatcag agcagtaatt aataagaaga 3121 gctgaggtga aactcggttt aaaaaccaaa aaagaatctc tcagttagta agaaaaggct 3181 gaaaacctct tgatacttga gagtgaatat aagtctaaat gctgctttgt ataatttgtt 3241 cagctaaggg atagatcgat cacactattt aagtgagccc agatcaaaaa agcagattga 3301 aattttcttt agaaaagatt ctccatgatt tgaattgcat tctctttaaa ctcaccaatg 3361 taatcatttt gggaggaggg agaacccact tgctttccaa atgggtttat ttaaacccac 3421 aaactcaaga ggttgttggg ggaattagga aaataagggt tttcaatgac ctacattgct 3481 aggtagaggc tgtgatccat gggatttcat tctaatgacc atgtgaagat gtttgagtcc 3541 tcctttgcct ttcctcagaa agaatccttc taaggcacaa atcccttaga tggataatgt 3601 aaggtattgt taactcactc atattgagat catttttaga gataccaggt tttatgtatc 3661 agcactagat ggttccaccc tcatgggata aaactgctta caagtatttt gaaagaaaaa 3721 ctgaccaaaa ttcttaaatt gttactaagg caatcatgca caggtgacgt atgtcttatc 3781 tgatttgttt ttaactcctt ggtgcccaaa gctcagaagg gaattccact gccagcaatg 3841 aacatacctg gaaaagaaag taagcaatct gggatttttt ttctgggtta gtaaagaatt 3901 tttgcaataa gtttttatcag ttgattcaaa ctgatgtgca tcttaatgat caaatgtgca
```

-continued

```
3961 cattacataa attaagtcca ctgatacaac ttcttacaca tgtatctcta gtagctctgg 4021 caaacccaat atctgacacc actttggact caagagactc agtaacgtat tatcctgttt 4081 atttagcttg gttttagctg tgttctctct ggataaccca cttgatgtta ggaacattac 4141 ttctctgctt attccatatt aatactgtgt taggtatttt aagaagcaag ttattaaata 4201 agaaaagtca aagtattaat tcttaccttc tattatccta tattagcttc aatacatcca 4261 aaccaaatgg ctgttaggta gatttatttt tatataagca tgtttatttt gatcagatgt 4321 tttaacttgg atttgaaaaa atacatttat gagatgtttt ataagatgtg taaatataga 4381 actgtattta ttactatagt aaaggttcag taacattaag gaccatgata atgataataa 4441 accttgtaca gtggcatatt ctttgattta tattgtgttt ctctgcccat tttctttaaa 4501 ttcattaact gtatatatgt aaatatatag tacttgtaaa tagattccaa atttgctttt 4561 ctattgggta aaaaataaat ttgtaataaa atgtgtgact atgaaacaaa aaaaaaaaaa 4621 aaaaa
```

By "LDHA polypeptide" or "lactate dehydrogenase A polypeptide" is meant a protein or fragment thereof having at least 85%, at least 90%, at least 95%, at least 98%, or at least 99% amino acid sequence identity to the sequence provided at NCBI Accession No. NP_005557.1 (isoform 1), NP_001128711.1 (isoform 2), NP_001158886.1 (isoform 3), NP_001158887.1 (isoform 4), or NP_001158888.1 (isoform 5) and having dehydrogenase activity. The amino acid sequence provided at NCBI Accession No. NP_005557.1 is shown below:

```
  1 MATLKDQLIY NLLKEEQTPQ NKITVVGVGA VGMACAISIL

MKDLADELAL VDVIEDKLKG

61 EMMDLQHGSL FLRTPKIVSG KDYNVTANSK LVIITAGARQ

QEGESRLNLV QRNVNIFKFI

121 IPNVVKYSPN CKLLIVSNPV DILTYVAWKI SGFPKNRVIG

SGCNLDSARF RYLMGERLGV

181 HPLSCHGWVL GEHGDSSVPV WSGMNVAGVS LKTLHPDLGT

DKDKEQWKEV HKQVVESAYE
```

-continued

```
241 VIKLKGYTSW AIGLSVADLA ESIMKNLRRV HPVSTMIKGL

YGIKDDVFLS VPCILGQNGI

301 SDLVKVTLTS EEEARLKKSA DTLWGIQKEL QF
```

By "LDHA polynucleotide" or "lactate dehydrogenase A polynucleotide" is meant a polynucleotide encoding a LDHA polypeptide or fragment thereof. An exemplary LDHA polynucleotide sequence is provided at NCBI Ref: NM_005566.3. The sequence provided at NCBI Ref: NM_005566.3 is reproduced below:

```
  1 gtctgccggt cggttgtctg gctgcgcgcg ccacccgggc ctctccagtg ccccgcctgg 61 ctcggcatcc accccagcc cgactcacac gtgggttccc gcacgtccgc cggcccccc 121 cgctgacgtc agcatagctg ttccacttaa ggcccctccc gcgcccagct cagagtgctg 181 cagccgctgc cgccgattcc ggatctcatt gccacgcgcc cccgacgacc gcccgacgtg 241 cattcccgat tcctttggt tccaagtcca atatggcaac tctaaaggat cagctgattt 301 ataatcttct aaaggaagaa cagacccccc agaataagat tacagttgtt ggggttggtg 361 ctgttggcat ggcctgtgcc atcagtatct taatgaagga cttggcagat gaacttgctc 421 ttgttgatgt catcgaagac aaaattgaagg gagagatgat ggatctccaa catggcagcc 481 ttttccttag aacaccaaag attgtctctg gcaaagacta taatgtaact gcaaactcca 541 agctggtcat tatcacggct ggggcacgtc agcaagaggg agaaagccgt cttaatttgg 601 tccagcgtaa cgtgaacatc tttaaattca tcattcctaa tgttgtaaaa tacagcccga 661 actgcaagtt gcttattgtt tcaaatccag tggatatctt gacctacgtg gcttggaaga 721 taagtggttt tcccaaaaac cgtgttattg gaagcggttg caatctggat tcagcccgat 781 tccgttacct aatgggggaa aggctgggag ttcacccatt aagctgtcat gggtgggtcc 841 ttggggaaca tggagattcc agtgtgcctg tatggagtgg aatgaatgtt gctggtgtct 901 ctctgaagac tctgcaccca gatttaggga ctgataaaga taaggaacag tggaaagagg
```

-continued

```
 961 ttcacaagca ggtggttgag agtgcttatg aggtgatcaa actcaaaggc tacacatcct 1021 gggctattgg actctctgta gcagatttgg cagagagtat aatgaagaat cttaggcggg 1081 tgcacccagt ttccaccatg attaagggtc tttacggaat aaaggatgat gtcttcctta 1141 gtgttccttg cattttggga cagaatggaa tctcagacct tgtgaaggtg actctgactt 1201 ctgaggaaga ggcccgtttg aagaagagtg cagatacact ttgggggatc caaaaggagc 1261 tgcaatttta aagtcttctg atgtcatatc atttcactgt ctaggctaca acaggattct 1321 aggtggaggt tgtgcatgtt gtccttttta tctgatctgt gattaaagca gtaatatttt 1381 aagatggact gggaaaaaca tcaactcctg aagttagaaa taagaatggt ttgtaaaatc 1441 cacagctata tcctgatgct ggatggtatt aatcttgtgt agtcttcaac tggttagtgt 1501 gaaatagttc tgccacctct gacgcaccac tgccaatgct gtacgtactg catttgcccc 1561 ttgagccagg tggatgttta ccgtgtgtta tataacttcc tggctccttc actgaacatg 1621 cctagtccaa cattttttcc cagtgagtca catcctggga tccagtgtat aaatccaata 1681 tcatgtcttg tgcataattc ttccaaagga tcttattttg tgaactatat cagtagtgta 1741 cattaccata taatgtaaaa agatctacat acaaacaatg caaccaacta tccaagtgtt 1801 ataccaacta aaacccccaa taaaccttga acagtgacta ctttggttaa ttcattatat 1861 taagatataa agtcataaag ctgctagtta ttatattaat ttggaaatat taggctattc 1921 ttgggcaacc ctgcaacgat tttttctaac agggatatta ttgactaata gcagaggatg 1981 taatagtcaa ctgagttgta ttggtaccac ttccattgta agtcccaaag tattatatat 2041 ttgataataa tgctaatcat aattggaaag taacattcta tatgtaaatg taaaatttat 2101 ttgccaactg aatataggca atgatagtgt gtcactatag ggaacacaga tttttgagat
```

-continued

```
2161 cttgtcctct ggaagctggt aacaattaaa aacaatctta aggcagggaa aaaaaaaaa 2221 aaaaaa
```

By "MAFA polypeptide" is meant a protein or fragment thereof having at least 85%, at least 90%, at least 95%, at least 98%, or at least 99% amino acid sequence identity to the sequence provided at NCBI Accession No. NP_963883.2 and having transcription factor activity. The amino acid sequence provided at NCBI Accession No. NP_963883.2 is shown below:

```
  1 MAAELAMGAE LPSSPLAIEY VNDFDLMKFE VKKEPPEAER

FCHRLPPGSL SSTPLSTPCS

61 SVPSSPSFCA PSPGTGGGGG AGGGGGSSQA GGAPGPPSGG

PGAVGGTSGK PALEDLYWMS

121 GYQHHLNPEA LNLTPEDAVE ALIGSGHHGA HHGAHHPAAA

AAYEAFRGPG FAGGGGADDM

181 GAGHHHGAHH AAHHHHAAHH HHHHHHHHGG AGHGGGAGHH

VRLEERFSDD QLVSMSVREL

241 NRQLRGFSKE EVIRLKQKRR TLKNRGYAQS CRFKRVQQRH

ILESEKCQLQ SQVEQLKLEV

301 GRLAKERDLY KEKYEKLAGR GGPGSAGGAG FPREPSPPQA

GPGGAKGTAD FFL
```

By "MAFA polynucleotide" is meant a polynucleotide encoding a MAFA polypeptide or fragment thereof. An exemplary MAFA polynucleotide sequence is provided at NCBI Ref: NM_201589.3. The sequence provided at NCBI Ref: NM_201589.3 is reproduced below:

```
  1 gcgcggccgg gcgcgggccc cgggcgatgg ccgcggagct ggcgatgggc gccgagctgc 61 ccagcagccc gctggccatc gagtacgtca cgacttcga cctgatgaag ttcgaggtga 121 agaaggagcc tcccgaggcc gagcgcttct gccaccgcct gccgccaggc tcgctgtcct 181 cgacgccgct cagcacgccc tgctcctccg tgccctcctc gcccagcttc tgcgcgccca 241 gcccgggcac cggcggcggc ggcggcgcgg ggggcggcgg cggctcgtct caggccgggg 301 gcgcccccgg gccgccgagc gggggccccg gcgccgtcgg gggcacctcg gggaagccgg 361 cgctggagga tctgtactgg atgagcggct accagcatca cctcaacccc gaggcgctca
```

-continued

```
421 acctgacgcc cgaggacgcg gtggaggcgc tcatcggcag cggccaccac ggcgcgcacc 481 acggcgcgca ccacccggcg gccgccgcag cctacgaggc tttccgcggc ccgggcttcg 541 cgggcggcgg cggagcggac gacatgggcg ccggccacca ccacggcgcg caccacgccg 601 cccaccatca ccacgccgcc caccaccacc accaccacca ccaccaccat ggcggcgcgg 661 gacacggcgg tggcgcgggc caccacgtgc gcctggagga gcgcttctcc gacgaccagc 721 tggtgtccat gtcggtgcgc gagctgaacc ggcagctccg cggcttcagc aaggaggagg 781 tcatccggct caagcagaag cggcgcacgc tcaagaaccg cggctacgcg cagtcctgcc 841 gcttcaagcg ggtgcagcag cggcacattc tggagagcga gaagtgccaa ctccagagcc 901 aggtggagca gctgaagctg gaggtggggc gcctggccaa agagcgggac ctgtacaagg 961 agaaatacga gaagctggcg ggccggggcg gccccgggag cgcgggcggg gccggtttcc 1021 cgcgggagcc ttcgccgccg caggccggtc ccggcggggc caagggcacg gccgacttct 1081 tcctgtaggc gccggacccc gagcccgcgc cgccgtcgcc ggggacaagt tcgcgcaggc 1141 ctctcggggc ctcggctcgg actccgcggt acaggacgtg gacaccaggc ccggcccggc 1201 cgtgctggcc ccggtgccaa gtctgcgggc gcggggctgg aggcccttc gctcccggtc 1261 cccgttcgcg cgcgtcggcc cgggtcgccg tcctgaggtt gagcggagaa cggtgatttc 1321 taaggaaact tgagccaggt ctaacttctt tccaagcgtc cgcttgtaca tacgttgaac 1381 gtggttctcc gttcccacct tcgccctgcc agcctagagg gaccgcgctg ccgtcccttc 1441 ccgggtggcc cctgcctgcc cccgccctcc ttcgttctct tctcagcctc cctttccttg 1501 cctttttaa cttcccctcc ccgttttaaa atcggtctta ttttcgaagt atttataatt 1561 attatgcttg gtgattagaa aagaaaacct tggaggaagc cccttcttc cccagccggg
```

-continued

```
1621 gtccgccctc agtcgcgagt cacagcatga gtcgctcgcc aggaggggcc cggcccctgc 1681 ctgccccctc cccgcttgcc cccgaccctg ctaccggcgt tccttggagg tcgaagccag 1741 ggacgtcacc cgtgctgtgt ccaggcctgc tgtcctacta tgctcaaccg ggggtggggg 1801 gagggggggtg agtcctgtgc tcagtcgggt gggggctggc ccggatcccg agctgctgtc 1861 tctctatgca ccagaacata tctgtaactc ctggggaaat acatcttgtt ttaaccttca 1921 agagaagtga aagaaaaaag taatgcacag tatttctagc agaaaatttt ttttttttaag 1981 aggaggcttg ggccagagcc ttctggcatg gggcgggtgg agaaagtgtt tttattttaa 2041 tttaaattgt gtttcgtttt gtttgtggaa tctttctta atgcttcgtc gctctttgga 2101 ctagccggga gagagggcga ggaggcgggt gctccaggcc ctgtaggctg ggccaggcgc 2161 ctgggggatc tgcccgtttt cggaggccct caggggccat cagtgggatt ccagccgctc 2221 cacacccctc ccctgagcac tcggagtgga aggcgcgccg actcgttgaa agtttttgttg 2281 tgtagttggt tttcgttgag ttctttttc atttgctacg aaactgagaa aaagaaaaaa 2341 atacacaaaa taaatctgtt cagatccaag tca
```

As used herein, a "marker" is meant any protein or polynucleotide having an alteration in expression level or activity that is associated with a disease or disorder or that is associated with a particular cell type. In some embodiments, a marker for a beta cell is Pdx1, MafA, Pax4, Pax6, NeuroD1, Nkx6-1, Gata6, or Foxa2. In some embodiments, a marker for a hepatocyte is AFP, ALB, or Cyp3a7. In some other embodiments, a marker for a cardiomyocyte is hMlc2a, hNkx2-5, alphaMHC or KCNQ1. In still other embodiments, a marker for a small intestine cell is CDX2, Muc2, or Lgr5.

By "alphaMHC polypeptide" or "myosin heavy chain (MHC) alpha polypeptide" is meant a protein or fragment thereof having at least 85%, at least 90%, at least 95%, at least 98%, or at least 99% amino acid sequence identity to the sequence provided at NCBI Accession No. NP_002462.2 and having actin binding activity. The amino acid sequence provided at NCBI Accession No. NP_002462.2 is shown below:

```
  1 MTDAQMADFG AAAQYLRKSE KERLEAQTRP FDIRTECFVP

DDKEEFVKAK ILSREGGKVI
```

-continued

```
 61 AETENGKTVT VKEDQVLQQN PPKFDKIEDM AMLTFLHEPA

VLFNLKERYA AWMIYTYSGL

121 FCVTVNPYKW LPVYNAEVVA AYRGKKRSEA PPHIFSISDN

AYQYMLTDRE NQSILITGES

181 GAGKTVNTKR VIQYFASIAA IGDRGKKDNA NANKGTLEDQ

IIQANPALEA FGNAKTVRND

241 NSSRFGKFIR IHFGATGKLA SADIETYLLE KSRVIFQLKA

ERNYHIFYQI LSNKKPELLD

301 MLLVTNNPYD YAFVSQGEVS VASIDDSEEL MATDSAFDVL

GFTSEEKAGV YKLTGAIMHY

361 GNMKFKQKQR EEQAEPDGTE DADKSAYLMG LNSADLLKGL

CHPRVKVGNE YVTKGQSVQQ

421 VYYSIGALAK AVYEKMFNWM VTRINATLET KQPRQYFIGV

LDIAGFEIFD FNSFEQLCIN

481 FTNEKLQQFF NHHMFVLEQE EYKKEGIEWT FIDFGMDLQA

CIDLIEKPMG IMSILEEECM

541 FPKATDMIFK AKLYDNHLGK SNNFQKPRNI KGKQEAHFSL

IHYAGTVDYN ILGWLEKNKD

601 PLNETVVALY QKSSLKLMAT LFSSYATADT GDSGKSKGGK

KKGSSFQTVS ALHRENLNKL

661 MTNLRTTHPH FVRCIIPNER KAPGVMDNPL VMHQLRCNGV

LEGIRICRKG FPNRILYGDF

721 RQRYRILNPV AIPEGQFIDS RKGTEKLLSS LDIDHNQYKF

GHTKVFFKAG LLGLLEEMRD

781 ERLSRIITRM QAQARGQLMR IEFKKIVERR DALLVIQWNI

RAFMGVKNWP WMKLYFKIKP

841 LLKSAETEKE MATMKEEFGR IKETLEKSEA RRKELEEKMV

SLLQEKNDLQ LQVQAEQDNL

901 NDAEERCDQL IKNKIQLEAK VKEMNERLED EEEMNAELTA

KKRKLEDECS ELKKDIDDLE

961 LTLAKVEKEK HATENKVKNL TEEMAGLDEI IAKLTKEKKA

LQEAHQQALD DLQVEEDKVN

1021 SLSKSKVKLE QQVDDLEGSL EQEKKVRMDL ERAKRKLEGD

LKLTQESIMD LENDKLQLEE

1081 KLKKKEFDIN QQNSKIEDEQ VLALQLQKKL KENQARIEEL

EEELEAERTA RAKVEKLRSD

1141 LSRELEEISE RLEEAGGATS VQIEMNKKRE AEFQKMRRDL

EEATLQHEAT AAALRKKHAD

1201 SVAELGEQID NLQRVKQKLE KEKSEFKLEL DDVTSNMEQI

IKAKANLEKV SRTLEDQANE
```

-continued

```
1261 YRVKLEEAQR SLNDFTTQRA KLQTENGELA RQLEEKEALI

SQLTRGKLSY TQQMEDLKRQ

1321 LEEEGKAKNA LAHALQSARH DCDLLREQYE EETEAKAELQ

RVLSKANSEV AQWRTKYETD

1381 AIQRTEELEE AKKKLAQRLQ DAEEAVEAVN AKCSSLEKTK

HRLQNEIEDL MVDVERSNAA

1441 AAALDKKQRN FDKILAEWKQ KYEESQSELE SSQKEARSLS

TELFKLKNAY EESLEHLETF

1501 KRENKNLQEE ISDLTEQLGE GGKNVHELEK VRKQLEVEKL

ELQSALEEAA ASLEHEEGKI

1561 LRAQLEFNQI KAEIERKLAE KDEEMEQAKR NHQRVVDSLQ

TSLDAETRSR NEVLRVKKKM

1621 EGDLNEMEIQ LSHANRMAAE AQKQVKSLQS LLKDTQIQLD

DAVRANDDLK ENIAIVERRN

1681 NLLQAELEEL RAVVEQTERS RKLAEQELIE TSERVQLLHS

QNTSLINQKK KMESDLTQLQ

1741 SEVEEAVQEC RNAEEKAKKA ITDAAMMAEE LKKEQDTSAH

LERMKKNMEQ TIKDLQHRLD

1801 EAEQIALKGG KKQLQKLEAR VRELEGELEA EQKRNAESVK

GMRKSERRIK ELTYQTEEDK

1861 KNLLRLQDLV DKLQLKVKAY KRQAEEAEEQ ANTNLSKFRK

VQHELDEAEE RADIAESQVN

1921 KLRAKSRDIG AKQKMHDEE
```

By "alphaMHC polynucleotide" is meant a polynucleotide encoding a alphaMHC polypeptide or fragment thereof. An exemplary alphaMHC polynucleotide sequence is provided at NCBI Ref: NM_002471.3. The sequence provided at NCBI Ref: NM_002471.3 is reproduced below:

```
  1 agatagagag actcctgcgg cccagattct tcaggattct ccgtgaaggg ataaccaggg 61 gaagcaccaa gatgaccgat gcccagatgg ctgactttgg ggcagcggcc cagtacctcc 121 gcaagtcaga gaaggagcgt ctagaggccc agacccggcc ctttgacatt cgcactgagt 181 gcttcgtgcc cgatgacaag gaagagtttg tcaaagccaa gattttgtcc cgggagggag 241 gcaaggtcat tgctgaaacc gagaatggga agacggtgac tgtgaaggag gaccaggtgt 301 tgcagcagaa cccacccaag ttcgacaaga ttgaggacat ggccatgctg accttcctgc
```

-continued

```
 361 acgagcccgc ggtgctttc aacctcaagg agcgctacgc
     ggcctggatg atatatacct 421 actcgggcct cttctgtgtc actgtcaacc cctacaagtg
     gctgccggtg tacaatgccg 481 aggtggtggc cgcctaccgg ggcaagaaga ggagtgaggc
     cccgcccac atcttctcca 541 tctccgacaa cgcctatcag tacatgctga cagatcggga
     gaaccagtcc atcctcatca 601 cgggagaatc cggggcgggg aagactgtga acaccaagcg
     tgtcatccag tactttgcca 661 gcattgcagc cataggtgac cgtggcaaga aggacaatgc
     caatgcgaac aagggcaccc 721 tggaggacca gatcatccag gccaaccccg ctctggaggc
     cttcggcaat gccaagactg 781 tccggaacga caactcctcc cgctttggga aattcattag
     gatccacttt ggggccactg 841 gaaagctggc ttctgcagac atagagacct acctgctgga
     gaagtcccgg gtgatcttcc 901 agctgaaagc tgagagaaac taccacatct tctaccagat
     tctgtccaac aagaagccgg 961 agttgctgga catgctgctg gtcaccaaca atccctacga
     ctacgccttc gtgtctcagg 1021 gagaggtgtc cgtggcctcc attgatgact ccgaggagct
     catggccacc gatagtgcct 1081 ttgacgtgct gggcttcact tcagaggaga aagctggcgt
     ctacaagctg acgggagcca 1141 tcatgcacta cgggaacatg aagttcaagc agaagcagcg
     ggaggagcag gcggagccag 1201 acggcaccga agatgctgac aagtcggcct acctcatggg
     gctgaactca gctgacctgc 1261 tcaaggggct gtgccaccct cgggtgaaag tgggcaacga
     gtatgtcacc aaggggcaga 1321 gcgtgcagca ggtgtactac tccatcgggg ctctggccaa
     ggcagtgtat gagaagatgt 1381 tcaactggat ggtgacgcgc atcaacgcca ccctggagac
     caagcagcca cgccagtact 1441 tcataggagt cctggacatc gctggcttcg agatcttcga
     cttcaacagc tttgagcagc 1501 tctgcatcaa cttcaccaac gagaagctgc agcagttctt
     caaccaccac atgttcgtgc
```

-continued

```
1561 tggagcagga ggagtacaag aaggagggca ttgagtggac
     attcattgac tttggcatgg 1621 acctgcaggc ctgcattgac ctcatcgaga agcccatggg
     catcatgtcc atcctggagg 1681 aggagtgcat gttccccaag gccactgaca tgaccttcaa
     ggccaagctg tacgacaacc 1741 acctgggcaa gtccaacaat ttccagaagc cacgcaacat
     caaggggaag caggaagccc 1801 acttctccct gatccactac gccggcactg tggactacaa
     catcctgggc tggctggaaa 1861 aaaacaagga tcctctcaac gagactgttg tggccctgta
     ccagaagtcc tccctcaagc 1921 tcatggccac tctcttctcc tcctacgcaa ctgccgatac
     tggggacagt ggtaaaagca 1981 aaggaggcaa gaaaaagggc tcatccttcc agacggtgtc
     ggctctccac cgggaaaatc 2041 tcaacaagct aatgaccaac ctgaggacca cccatcctca
     ctttgtgcgt tgcatcatcc 2101 ccaatgacg gaaggctcca ggggtgatgg acaaccccct
     ggtcatgcac cagctgcgct 2161 gcaatggcgt gctggagggc atccgcatct gcaggaaggg
     cttccccaac cgcatcctct 2221 acggggactt ccggcagagg tatcgcatcc tgaacccagt
     ggccatccct gagggacagt 2281 tcattgatag caggaagggg acagagaagc tgctcagctc
     tctggacatt gatcacaacc 2341 agtacaagtt tggccacacc aaggtgttct tcaaggcagg
     gctgcttggg ctgctggagg 2401 agatgcggga tgagaggctg agccgcatca tcacgcgcat
     gcaggcccaa gcccgggggcc 2461 agctcatgcg cattgagttc aagaagatag tggaacgcag
     ggatgccctg ctggtaatcc 2521 agtggaacat tcgggccttc atgggggtca agaattggcc
     ctggatgaag ctctacttca 2581 agatcaagcc gctgctgaag agcgcagaga cggagaagga
     gatggccacc atgaaggaag 2641 agttcgggcg catcaaagag acgctggaga gtccgaggc
     tcgccgcaag gagctggagg 2701 agaagatggt gtccctgctg caggagaaga atgacctgca
     gctccaagtg caggcggaac
```

-continued

```
2761  aagacaacct caatgatgct gaggagcgct gcgaccagct
      gatcaaaaac aagattcagc 2821  tggaggccaa agtaaaggag atgaatgaga ggctggagga
      tgaggaggag atgaacgcgg 2881  agctcactgc caagaagcgc aagctggaag acgagtgctc
      agagctcaag aaggacattg 2941  atgacctgga gctgacactg gccaaggtgg agaaggagaa
      gcatgcaaca gagaacaagg 3001  tgaagaacct aacagaggag atggctgggc tggatgaaat
      catcgctaag ctgaccaagg 3061  agaagaaagc tctacaagag gcccatcagc aggccctgga
      tgaccttcag gttgaggaag 3121  acaaggtcaa cagcctgtcc aagtctaagg tcaagctgga
      gcagcaggtg gatgatctgg 3181  agggatccct agagcaagag aagaaggtgc gcatggacct
      ggagcgagca aagcggaaac 3241  tggagggcga cctgaagctg acccaggaga gcatcatgga
      cctggaaaat gataaactgc 3301  agctggaaga aaagcttaag aagaaggagt ttgacattaa
      tcagcagaac agtaagattg 3361  aggatgagca ggtgctggcc cttcaactac agaagaaact
      gaaggaaaac caggcacgca 3421  tcgaggagct ggaggaggag ctggaggccg agcgcaccgc
      cagggctaag gtggagaagc 3481  tgcgctcaga cctgtctcgg gagctggagg agatcagcga
      gcggctggaa gaggccggcg 3541  gggccacgtc cgtgcagatc gagatgaaca agaagcgcga
      ggccgagttc cagaagatgc 3601  ggcgggacct ggaggaggcc acgctgcagc acgaggccac
      tgccgcggcc ctgcgcaaga 3661  agcacgccga cagcgtggcc gagctgggcg agcagatcga
      caacctgcag cgggtgaagc 3721  agaagctgga gaaggagaag agcgagttca agctggagct
      ggatgacgtc acctccaaca 3781  tggagcagat catcaaggcc aaggcaaacc tggagaaagt
      gtctcggacg ctggaggacc 3841  aggccaatga gtaccgcgtg aagctagaag aggcccaacg
      ctccctcaat gatttcacca 3901  cccagcgagc caagctgcag accgagaatg gagagttggc
      ccggcagcta gaggaaaagg
```

-continued

```
3961  aggcgctaat ctcgcagctg acccggggga agctctctta
      tacccagcaa atggaggacc 4021  tcaaaaggca gctggaggag gagggcaagg cgaagaacgc
      cctggcccat gcactgcagt 4081  cggcccggca tgactgcgac ctgctgcggg agcagtacga
      ggaggagaca gaggccaagg 4141  ccgagctgca gcgcgtcctg tccaaggcca actcggaggt
      ggcccagtgg aggaccaagt 4201  atgagacgga cgccattcag cggactgagg agctcgaaga
      ggccaaaaag aagctggccc 4261  agcggctgca ggatgccgag gaggccgtgg aggctgttaa
      tgccaagtgc tcctcactgg 4321  agaagaccaa gcaccggcta cagaatgaga tagaggactt
      gatggtggac gtagagcgct 4381  ccaatgctgc tgctgcagcc ctggacaaga agcagagaaa
      ctttgacaag atcctggccg 4441  agtggaagca gaagtatgag gagtcgcagt ctgagctgga
      gtcctcacag aaggaggctc 4501  gctccctcag cacagagctc ttcaagctca gaacgcccta
      cgaggagtcc ctggagcacc 4561  tagagacctt caagcgggga aacaagaacc ttcaggagga
      aatctcggac cttactgagc 4621  agctaggaga aggaggaaag aatgtgcatg agctggagaa
      ggtccgcaaa cagctggagg 4681  tggagaagct ggagctgcag tcagccctgg aggaggcaga
      ggcctccctg gagcacgagg 4741  agggcaagat cctccgggcc cagctagagt tcaaccagat
      caaggcagag atcgagcgga 4801  agctggcaga gaaggacgag gagatggaac aggccaagcg
      caaccaccag cgggtggtgg 4861  actcgctgca gacctccctg gatgcagaga cacgcagccg
      caacgaggtc ctgagggtga 4921  agaagaagat ggaaggagac ctcaatgaga tggagatcca
      gctcagccac gccaaccgca 4981  tggctgccga ggcccagaag caagtcaaga gcctccagag
      cttgctgaag gacacccaga 5041  tccagctgga cgatgcggtc cgtgccaacg acgacctgaa
      ggagaacatc gccatcgtgg 5101  agcggcgcaa caacctgctg caggctgagc tggaggagct
      gcgtgccgtg gtggagcaga
```

-continued

```
5161 cagagcggtc ccggaagctg gcggagcagg agctgattga gaccagcgag cgggtgcagc 5221 tgctgcattc ccagaacacc agcctcatca accagaagaa gaagatggag tcggatctga 5281 cccagctcca gtcggaagtg gaggaggcag tgcaggagtg cagaaacgcc gaggagaagg 5341 ccaagaaggc catcacggat gccgccatga tggcagagga gctgaagaag gagcaggaca 5401 ccagcgccca cctggagcgc atgaagaaga acatggagca gaccattaag gacctgcagc 5461 accggctgga cgaggccgag cagatcgccc tcaagggagg caagaagcag ctgcagaagc 5521 tggaagcgcg ggtgcgggag ctggagggtg agctggaggc cgagcagaag cgcaacgcag 5581 agtcggtgaa gggcatgagg aagagcgagc ggcgcatcaa ggagctcacc taccagacag 5641 aggaagacaa aaagaacctg ctgcggctac aggacctggt ggacaagctg caactgaagg 5701 tcaaggccta caagcgccag gccgaggagg cggaggagca agccaacacc aacctgtcca 5761 agttccgcaa ggtgcagcat gagctggatg aggcagagga gcgggcggac atcgctgagt 5821 cccaggtcaa caagcttcga gccaagagcc gtgacattgg tgccaagcaa aaaatgcacg 5881 atgaggagtg acactgcctc gggaacctca ctcttgccaa cctgtaataa atatgagtgc 5941 c
```

By "MLC2A polypeptide" or "human MLSC2A
(hMLC2A) polypeptide" is meant a protein or fragment
thereof having at least 85%, at least 90%, at least 95%, at
least 98%, or at least 99% amino acid sequence identity to
the sequence provided at NCBI Accession No.
NP_067046.1 and having calcium binding activity. The
amino acid sequence provided at NCBI Accession No.
NP_067046.1 is shown below:

```
  1 MASRKAGTRG KVAATKQAQR GSSNVFSMFE QAQIQEFKEA

FSCIDQNRDG IICKADLRET
```

-continued

```
 61 YSQLGKVSVP EEELDAMLQE GKGPINFTVF LTLFGEKLNG

TDPEEAILSA FRMFDPSGKG

121 VVNKDEFKQL LLTQADKFSP AEVEQMFALT PMDLAGNIDY

KSLCYIITHG DEKEE
```

By "MLC2A polynucleotide" is meant a polynucleotide
encoding a MLC2A polypeptide or fragment thereof. An
exemplary MLC2A polynucleotide sequence is provided at
NCBI Ref: NM_021223.2. The sequence provided at NCBI
Ref: NM_021223.2 is reproduced below:

```
  1 tctgcagaga gaatggccag caggaaggcg gggaccccggg gcaaggtggc agccaccaag 61 caggcccaac gtggttcttc caacgtcttt tccatgtttg aacaagccca gatacaggag 121 ttcaaagaag ccttcagctg tatcgaccag aatcgtgatg gcatcatctg caaggcagac 181 ctgagggaga cctactccca gctggggaag gtgagtgtcc cagaggagga gctggacgcc 241 atgctgcaag agggcaaggg ccccatcaac ttcaccgtct tcctcacgct ctttggggag 301 aagctcaatg ggacagaccc cgaggaagcc atcctgagtg ccttccgcat gtttgacccc 361 agcggcaaag gggtggtgaa caaggatgag ttcaagcagc ttctcctgac ccaggcagac 421 aagttctctc cagctgaggt ggagcagatg ttcgccctga cacccatgga cctggcgggg 481 aacatcgact acaagtcact gtgctacatc atcacccatg gagacgagaa agaggaatga 541 ggggcagggc caggcccacg gggggggcacc tcaataaact ctgttgcaaa attggaaaaa 601 aaaaaaaaaa aaaaaaaaa
```

By "MUC2 polypeptide" is meant a protein or fragment
thereof having at least 85%, at least 90%, at least 95%, at
least 98%, or at least 99% amino acid sequence identity to
the sequence provided at NCBI Accession No.
NP_002448.3 and having and having a biological activity of
a MUC2 polypeptide. Exemplary biological activities of a
MUC2 polypeptide include polymerization into a gel and
coating of epithelia of the intestines and other mucus mem-
brane-containing organs. The amino acid sequence provided
at NCBI Accession No. NP_002448.3 is shown below:

```
  1 MGLPLARLAA VCLALSLAGG SELQTEGRTR NHGHNVCSTW GNFHYKTFDG DVFRFPGPCD

61 YNFASDCRGS YKEFAVHLKR GPGQAEAPAG VESILLTIKD DTIYLTRHLA VLNGAVVSTP

121 HYSPGLLIEK SDAYTKVYSR AGLTLMWNRE DALMLELDTK FRNHTCGLCG DYNGLQSYSE

181 FLSDGVLFSP LEFGNMQKIN QPDVVCEDPE EEVAPASCSE HRAECERLLT AEAFADCQDL
```

-continued

```
 241 VPLEPYLRAC QQDRCRCPGG DTCVCSTVAE FSRQCSHAGG RPGNWRTATL CPKTCPGNLV

301 YLESGSPCMD TCSHLEVSSL CEEHRMDGCF CPEGTVYDDI GDSGCVPVSQ CHCRLHGHLY

361 TPGQEITNDC EQCVCNAGRW VCKDLPCPGT CALEGGSHIT TFDGKTYTFH GDCYYVLAKG

421 DHNDSYALLG ELAPCGSTDK QTCLKTVVLL ADKKKNVVVF KSDGSVLLNE LQVNLPHVTA

481 SFSVFRPSSY HIMVSMAIGV RLQVQLAPVM QLFVTLDQAS QGQVQGLCGN FNGLEGDDFK

541 TASGLVEATG AGFANTWKAQ STCHDKLDWL DDPCSLNIES ANYAEHWCSL LKKTETPFGR

601 CHSAVDPAEY YKRCKYDTCN CQNNEDCLCA ALSSYARACT AKGVMLWGWR EHVCNKDVGS

661 CPNSQVFLYN LTTCQQTCRS LSEADSHCLE GFAPVDGCGC PDHTFLDEKG RCVPLAKCSC

721 YHRGLYLEAG DVVVRQEERC VCRDGRLHCR QIRLIGQSCT APKIHMDCSN LTALATSKPR

781 ALSCQTLAAG YYHTECVSGC VCPDGLMDDG RGGCVVEKEC PCVHNNDLYS SGAKIKVDCN

841 TCTCKRGRWV CTQAVCHGTC SIYGSGHYIT FDGKYYDFDG HCSYVAVQDY CGQNSSLGSF

901 SIITENVPCG TTGVTCSKAI KIFMGRTELK LEDKHRVVIQ RDEGHHVAYT TREVGQYLVV

961 ESSTGIIVIW DKRTTVFIKL APSYKGTVCG LCGNFDHRSN NDFTTRDHMV VSSELDFGNS

1021 WKEAPTCPDV STNPEPCSLN PHRRSWAEKQ CSILKSSVFS ICHSKVDPKP FYEACVHDSC

1081 SCDTGGDCEC FCSAVASYAQ ECTKEGACVF WRTPDLCPIF CDYYNPPHEC EWHYEPCGNR

1141 SFETCRTING IHSNISVSYL EGCYPRCPKD RPIYEEDLKK CVTADKCGCY VEDTHYPPGA

1201 SVPTEETCKS CVCTNSSQVV CRPEEGKILN QTQDGAFCYW EICGPNGTVE KHFNICSITT

1261 RPSTLTTFTT ITLPTTPTTF TTTTTTTTPT SSTVLSTTPK LCCLWSDWIN EDHPSSGSDD

1321 GDRETFDGVC GAPEDIECRS VKDPHLSLEQ LGQKVQCDVS VGFICKNEDQ FGNGPFGLCY

1381 DYKIRVNCCW PMDKCITTPS PPTTTPSPPP TSTTTLPPTT TPSPPTTTTT TPPPTTTPSP

1441 PITTTTTPPP TTTPSPPIST TTTPPPTTTP SPPTTTPSPP TTTPSPPTTT TTTPPPTTTP

1501 SPPTTTPITP PASTTTLPPT TTPSPPTTTT TTPPPTTTPS PPTTTPITPP TSTTTLPPTT

1561 TPSPPPTTTT TPPPTTTPSP PTTTTPSPPT ITTTTPPPTT TPSPPTTTTT TPPPTTTPSP

1621 PTTTPITPPT STTTLPPTTT PSPPPTTTTT PPPTTTPSPP TTTTPSPPIT TTTTPPPTTT

1681 PSSPITTTPS PPTTTMTTPS PTTTPSSPIT TTTTPSSTTT PSPPPTTMTT PSPTTTPSPP

1741 TTTMTTLPPT TTSSPLTTTP LPPSITPPTF SPFSTTTPTT PCVPLCNWTG WLDSGKPNFH

1801 KPGGDTELIG DVCGPGWAAN ISCRATMYPD VPIGQLGQTV VCDVSVGLIC KNEDQKPGGV

1861 IPMAFCLNYE INVQCCECVT QPTTMTTTTT ENPTPPTTTP ITTTTTVTPT PTPTGTQTPT

1921 TTPITTTTTV TPTPTPTGTQ TPTTTPITTT TTVTPTPTPT GTQTPTTTPI TTTTTVTPTP

1981 TPTGTQTPTT TPITTTTVT PTPTPTGTQT PTTTPITTTT TVTPTPTPTG TQTPTTTPIT

2041 TTTTVTPTPT PTGTQTPTTT PITTTTVTP TPTPTGTQTP TTTPITTTTT VTPTPTPTGT

2101 QTPTTTPITT TTTVTPTPTP TGTQTPTTTP ITTTTVTPT PTPTGTQTPT TTPITTTTTV

2161 TPTPTPTGTQ TPTTTPITTT TTVTPTPTPT GTQTPTTTPI TTTTTVTPTP TPTGTQTPTT

2221 TPITTTTTVT PTPTPTGTQT PTTTPITTTT TVTPTPTPTG TQTPTTTPIT TTTTVTPTPT

2281 PTGTQTPTTT PITTTTTVTP TPTPTGTQTP TTTPITTTTT VTPTPTPTGT QTPTTTPITT

2341 TTTVTPTPTP TGTQTPTTTP ITTTTTVTPT PTPTGTQTPT TTPITTTTTV TPTPTPTGTQ

2401 TPTTTPITTT TTVTPTPTPT GTQTPTTTPI TTTTTVTPTP TPTGTQTPTT TPITTTTTVT

2461 PTPTPTGTQT PTTTPITTTT TVTPTPTPTG TQTPTTTPIT TTTTVTPTPT PTGTQTPTTT

2521 PITTTTTVTP TPTPTGTQTP TTTPITTTTT VTPTPTPTGT QTPTTTPITT TTTVTPTPTP

2581 TGTQTPTTTP ITTTTTVTPT PTPTGTQTPT TPITTTTTV TPTPTPTGTQ TPTTTPITTT
```

-continued

```
2641 TTVTPTPTPT GTQTPTTTPI TTTTTVTPTP TPTGTQTPTT TPITTTTTVT PTPTPTGTQT

2701 PTTTPITTTT TVTPTPTPTG TQTPTTTPIT TTTTVTPTPT PTGTQTPTTT PITTTTTVTP

2761 TPTPTGTQTP TTTPITTTTT VTPTPTPTGT QTPTTTPITT TTTVTPTPTP TGTQTPTTTP

2821 ITTTTTVTPT PTPTGTQTPT TTPITTTTTV TPTPTPTGTQ TPTTTPITTT TTVTPTPTPT

2881 GTQTPTTTPI TTTTTVTPTP TPTGTQTPTT TPITTTTTVT PTPTPTGTQT PTTTPITTTT

2941 TVTPTPTPTG TQTPTTTPIT TTTTVTPTPT PTGTQTPTTT PITTTTTVTP TPTPTGTQTP

3001 TTTPITTTTT VTPTPTPTGT QTPTTTPITT TTTVTPTPTP TGTQTPTTTP ITTTTTVTPT

3061 PTPTGTQTPT TTPITTTTTV TPTPTPTGTQ TPTTTPITTT TTVTPTPTPT GTQTPTTTPI

3121 TTTTTVTPTP TPTGTQTPTT TPITTTTTVT PTPTPTGTQT PTTTPITTTT TVTPTPTPTG

3181 TQTPTTTPIT TTTTVTPTPT PTGTQTPTTT PITTTTTVTP TPTPTGTQTP TTTPITTTTT

3241 VTPTPTPTGT QTPTTTPITT TTTVTPTPTP TGTQTPTTTP ITTTTTVTPT PTPTGTQTPT

3301 TTPITTTTTV TPTPTPTGTQ TPTTTPITTT TTVTPTPTPT GTQTPTTTPI TTTTTVTPTP

3361 TPTGTQTPTT TPITTTTTVT PTPTPTGTQT PTTTPITTTT TVTPTPTPTG TQTPTTTPIT

3421 TTTTVTPTPT PTGTQTPTTT PITTTTTVTP TPTPTGTQTP TTTPITTTTT VTPTPTPTGT

3481 QTPTTTPITT TTTVTPTPTP TGTQTPTTTP ITTTTTVTPT PTPTGTQTPT TTPITTTTTV

3541 TPTPTPTGTQ TPTTTPITTT TTVTPTPTPT GTQTPTTTPI TTTTTVTPTP TPTGTQTPTT

3601 TPITTTTTVT PTPTPTGTQT PTTTPITTTT TVTPTPTPTG TQTPTTTPIT TTTTVTPTPT

3661 PTGTQTPTTT PITTTTTVTP TPTPTGTQTP TTTPITTTTT VTPTPTPTGT QTPTTTPITT

3721 TTTVTPTPTP TGTQTPTTTP ITTTTTVTPT PTPTGTQTPT TTPITTTTTV TPTPTPTGTQ

3781 TPTTTPITTT TTVTPTPTPT GTQTPTTTPI TTTTTVTPTP TPTGTQTPTT TPITTTTTVT

3841 PTPTPTGTQT PTTTPITTTT TVTPTPTPTG TQTPTTTPIT TTTTVTPTPT PTGTQTPTTT

3901 PITTTTTVTP TPTPTGTQTP TTTPITTTTT VTPTPTPTGT QTPTTTPITT TTTVTPTPTP

3961 TGTQTPTTTP ITTTTTVTPT PTPTGTQTPT TTPITTTTTV TPTPTPTGTQ TPTTTPITTT

4021 TTVTPTPTPT GTQTPTTTPI TTTTTVTPTP TPTGTQTPTT TPITTTTTVT PTPTPTGTQT

4081 PTTTPITTTT TVTPTPTPTG TQTPTTTPIT TTTTVTPTPT PTGTQTPTTT PITTTTTVTP

4141 TPTPTGTQTP TTTPITTTTT VTPTPTPTGT QTPTTTPITT TTTVTPTPTP TGTQTGPPTH

4201 TSTAPIAELT TSNPPPESST PQTSRSTSSP LTESTTLLST LPPAIEMTST APPSTPTAPT

4261 TTSGGHTLSP PPSTTTSPPG TPTRGTTTGS SSAPTPSTVQ TTTTSAWTPT PTPLSTPSII

4321 RTTGLRPYPS SVLICCVLND TYYAPGEEVY NGTYGDTCYF VNCSLSCTLE FYNWSCPSTP

4381 SPTPTPSKST PTPSKPSSTP SKPTPGTKPP ECPDFDPPRQ ENETWWLCDC FMATCKYNNT

4441 VEIVKVECEP PPMPTCSNGL QPVRVEDPDG CCWHWECDCY CTGWGDPHYV TFDGLYYSYQ

4501 GNCTYVLVEE ISPSVDNFGV YIDNYHCDPN DKVSCPRTLI VRHETQEVLI KTVHMMPMQV

4561 QVQVNRQAVA LPYKKYGLEV YQSGINYVVD IPELGVLVSY NGLSFSVRLP YHRFGNNTKG

4621 QCGTCTNTTS DDCILPSGEI VSNCEAAADQ WLVNDPSKPH CPHSSSTTKR PAVTVPGGGK

4681 TTPHKDCTPS PLCQLIKDSL FAQCHALVPP QHYYDACVFD SCFMPGSSLE CASLQAYAAL

4741 CAQQNICLDW RNHTHGACLV ECPSHREYQA CGPAEEPTCK SSSSQQNNTV LVEGCFCPEG

4801 TMNYAPGFDV CVKTCGCVGP DNVPREFGEH FEFDCKNCVC LEGGSGIICQ PKRCSQKPVT

4861 HCVEDGTYLA TEVNPADTCC NITVCKCNTS LCKEKPSVCP LGFEVKSKMV PGRCCPFYWC

4921 ESKGVCVHGN AEYQPGSPVY SSKCQDCVCT DKVDNNTLLN VIACTHVPCN TSCSPGFELM

4981 EAPGECCKKC EQTHCIIKRP DNQHVILKPG DFKSDPKNNC TFFSCVKIHN QLISSVSNIT

5041 CPNFDASICI PGSITFMPNG CCKTCTPRNE TRVPCSTVPV TTEVSYAGCT KTVLMNHCSG
```

-continued

```
5101 SCGTFVMYSA KAQALDHSCS CCKEEKTSQR EVVLSCPNGG SLTHTYTHIE SCQCQDTVCG

5161 LPTGTSRRAR RSPRHLGSG
```

By "MUC2 polynucleotide" is meant a polynucleotide encoding a MUC2 polypeptide or fragment thereof. An exemplary MUC2 polynucleotide sequence is provided at NCBI Ref: NM_002457.3. The sequence provided at NCBI Ref: NM_002457.3 is reproduced below:

```
   1 caacccacac cgcccctgcc agccaccatg gggctgccac tagcccgcct ggcggctgtg 61 tgcctggccc tgtctttggc aggggggctcg gagctccaga cagagggcag aacccgaaac 121 cacggccaca acgtctgcag cacctggggc aacttccact acaagacctt cgacggggac 181 gtcttccgct tccccggccc ctgcgactac aacttcgcct ccgactgccg aggctcctac 241 aaggaatttg ctgtgcacct gaagcggggt ccgggccagg ctgaggcccc cgccggggtg 301 gagtccatcc tgctgaccat caaggatgac accatctacc tcacccgcca cctggctgtg 361 cttaacgggg ccgtggtcag cacccgcac tacagccccg ggctgctcat tgagaagagc 421 gatgcctaca ccaaagtcta ctcccgcgcc ggcctcaccc tcatgtggaa ccgggaggat 481 gcactcatgc tggagctgga cactaagttc cggaaccaca cctgtggcct ctgcggggac 541 tacaacggcc tgcagagcta ttcagaattc ctctctgacg gcgtgctctt cagtcccctg 601 gagtttggga acatgcagaa gatcaaccag cccgatgtgg tgtgtgagga tcccgaggag 661 gaggtggccc ccgcatcctg ctccgagcac cgcgccgagt gtgagaggct gctgaccgcc 721 gaggccttcg cggactgtca ggacctggtg ccgctggagc cgtatctgcg cgcctgccag 781 caggaccgct gccggtgccc gggcggtgac acctgcgtct gcagcaccgt ggccgagttc 841 tcccgccagt gctcccacgc cggcggccgg cccgggaact ggaggaccgc cacgctctgc 901 cccaagacct gccccgggaa cctggtgtac ctggagagcg gctcgccctg catggacacc 961 tgctcacacc tggaggtgag cagcctgtgc gaggagcacc gcatggacgg ctgtttctgc 1021 ccagaaggca ccgtatatga cgacatcggg gacagtggct gcgttcctgt gagccagtgc 1081 cactgcaggc tgcacggaca cctgtacaca ccgggccagg agatcaccaa tgactgcgag 1141 cagtgtgtct gtaacgctgg ccgctgggtg tgcaaagacc tgccctgccc cggcacctgt 1201 gccctggaag gcggctccca catcaccacc ttcgatggga gacgtacac cttccacggg 1261 gactgctact atgtcctggc caagggtgac cacaacgatt cctacgctct cctgggcgag 1321 ctggcccct gtggctccac agacaagcag acctgcctga gacggtggt gctgctggct 1381 gacaagaaga agaatgtggt ggtcttcaag tccgatggca gtgtactgct caacgagctg 1441 caggtgaacc tgccccacgt gaccgcgagc ttctctgtct tccgcccgtc ttcctaccac 1501 atcatggtga gcatggccat tggcgtccgg ctgcaggtgc agctggcccc agtcatgcaa 1561 ctctttgtga cactggacca ggcctcccag gggcaggtgc agggcctctg cgggaacttc 1621 aacggcctgg aaggtgacga cttcaagacg gccagcgggc tggtggaggc cacggggggcc 1681 ggctttgcca cacctggaa ggcacagtca acctgccatg acaagctgga ctggttggac 1741 gatccctgct ccctgaacat cgagagcgcc aactacgccg agcactggtg ctccctcctg 1801 aagaagacag agaccccctt tggcaggtgc cactcggctg tggaccctgc tgagtattac 1861 aagaggtgca aatatgacac gtgtaactgt cagaacaatg aggactgcct gtgcgccgcc 1921 ctgtcctcct acgcgcgcgc ctgcaccgcc aagggcgtca tgctgtgggg ctggcgggag 1981 catgtctgca acaaggatgt gggctcctgc cccaactcgc aggtcttcct gtacaacctg 2041 accacctgcc agcagacctg ccgctccctc tccgaggccg acagccactg tctcgagggc
```

-continued

```
2101 tttgcgcctg tggacggctg cggctgccct gaccacacct tcctggacga gaagggccgc 2161 tgcgtacccc tggccaagtg ctcctgttac caccgcggtc tctacctgga ggcggggggac 2221 gtggtcgtca ggcaggaaga acgatgtgtg tgccgggatg ggcggctgca ctgtaggcag 2281 atccggctga tcggccagag ctgcacggcc ccaaagatcc acatggactg cagcaacctg 2341 actgcactgg ccacctcgaa gccccgagcc ctcagctgcc agacgctggc cgccggctat 2401 taccacacag agtgtgtcag tggctgtgtg tgccccgacg ggctgatgga tgacggccgg 2461 ggtggctgcg tggtggagaa ggaatgccct tgcgtccata caacgacct gtattcttcc 2521 ggcgccaaga tcaaggtgga ctgcaatacc tgcacctgca agagaggacg ctgggtgtgc 2581 acccaggctg tgtgccatgg cacctgctcc atttacggga gtggccacta catcaccttt 2641 gacgggaagt actacgactt tgacggacac tgctcctacg tggctgttca ggactactgc 2701 ggccagaact cctcactggg ctcattcagc atcatcaccg agaacgtccc ctgtggcact 2761 acgggcgtca cctgctccaa ggccatcaag atcttcatgg ggaggacgga gctgaagttg 2821 gaagacaagc accgtgtggt gatccagcgt gatgagggtc accacgtggc ctacaccacg 2881 cgggaggtgg gccagtacct ggtggtggag tccagcacgg gcatcatcgt catctgggac 2941 aagaggacca ccgtgttcat caagctggct ccctcctaca agggcaccgt gtgtggcctg 3001 tgtgggaact ttgaccaccg ctccaacaac gacttcacca cgcgggacca catggtggtg 3061 agcagcgagc tggacttcgg gaacagctgg aaggaggccc ccacctgccc agatgtgagc 3121 accaaccccg agccctgcag cctgaacccg caccgccgct cctgggccga gaagcagtgc 3181 agcatcctca aaagcagcgt gttcagcatc tgccacagca aggtggaccc caagcccttc 3241 tacgaggcct gtgtgcacga ctcgtgctcc tgtgacacgg gtggggactg tgagtgcttc 3301 tgctctgccg tggcctccta cgcccaggag tgtaccaaag aggggggcctg cgtgttctgg 3361 aggacgccgg acctgtgccc catattctgc gactactaca accctccgca tgagtgtgag 3421 tggcactatg agccatgtgg gaaccggagc ttcgagacct gcaggaccat caatggcatc 3481 cactccaaca tctccgtgtc ctacctggag ggctgctacc cccggtgccc caaggacagg 3541 cccatctatg aggaggatct gaagaagtgt gtcactgcag acaagtgtgg ctgctatgtc 3601 gaggacaccc actacccacc tggagcatcg gttcccaccg aggagacctg caagtcctgc 3661 gtgtgtacca actcctccca agtcgtctgc aggccggagg aaggaaagat tcttaaccag 3721 acccaggatg gcgccttctg ctactgggag atctgtggcc ccaacgggac ggtggagaag 3781 cacttcaaca tctgttccat tacgacacgc ccgtccaccc tgaccacctt caccaccatc 3841 accctcccca ccacccccac caccttcacc actaccacca ccaccaccac cccgacctcc 3901 agcacagttt tatcaacaac tccgaagctg tgctgcctct ggtctgactg gatcaatgag 3961 gaccacccca gcagtggcag cgacgacggt gaccgagaaa catttgatgg ggtctgcggg 4021 gcccctgagg acatcgagtg caggtcggtc aaggatcccc acctcagctt ggagcagcta 4081 ggccagaagg tgcagtgtga tgtctctgtt gggttcattt gcaagaatga agaccagttt 4141 ggaaatggac catttggact gtgttacgac tacaagatac gtgtcaattg ttgctggccc 4201 atggataagt gtatcaccac tcccagccct ccaactacca ctcccagccc tccaccaacc 4261 agcacgacca cccttccacc aaccaccacc cccagccctc caaccaccac cacaaccacc 4321 cctccaccaa ccaccacccc cagccctcca ataaccacca cgaccacccc tccaccaacc 4381 accactccca gccctccaat aagcaccaca accacccctc caccaaccac cactcccagc 4441 cctccaacca ccactcccag ccctccaacc accactccca gccctccaac aaccaccaca
```

-continued

```
4501 accaccoctc caccaaccac cactcccagc cctccaacga ctacgcccat cactccacca 4561 gccagcacta ccacccttcc accaaccacc actcccagcc ctccaacaac caccacaacc 4621 acccctccac caaccaccac tcccagtcct ccaacgacta cgcccatcac tccaccaacc 4681 agcactacta cccttccacc aaccaccact cccagccctc caccaaccac cacaaccacc 4741 cctccaccaa ccaccactcc cagccctcca acaaccacca ctcccagtcc tccaacaatc 4801 accacaacca cccctccacc aaccaccact cccagccctc caacaacgac cacaaccacc 4861 cctccaccaa ccaccactcc cagccctcca acgactacac ccatcactcc accaaccagc 4921 actaccaccc ttccaccaac caccactccc agccctccac caaccaccac aaccacccct 4981 ccaccaacca ccactcccag ccctccaaca accaccactc ccagccctcc aataaccacc 5041 acaaccaccc ctccaccaac caccactccc agctctccaa taaccaccac tcccagccct 5101 ccaacaacca ccatgaccac cccttcacca accaccaccc ccagctctcc aataaccacc 5161 acaaccaccc cttcctcaac taccactccc agccctccac caaccaccat gaccacccct 5221 tcaccaacca ccactcccag ccctccaaca accaccatga ccacccttcc accaaccacc 5281 acttccagcc ctctaacaac tactcctcta cctccatcaa taactcctcc tacattttca 5341 ccattctcaa cgacaacccc tactacccca tgcgtgcctc tctgcaattg gactggctgg 5401 ctggattctg gaaaacccaa ctttcacaaa ccaggtggag acacagaatt gattggagac 5461 gtctgtggac caggctgggc agctaacatc tcttgcagag ccaccatgta tcctgatgtt 5521 cccattggac agcttggaca aacagtggtg tgtgatgtct ctgtggggct gatatgcaaa 5581 aatgaagacc aaaagccagg tggggtcatc cctatggcct tctgcctcaa ctacgagatc 5641 aacgttcagt gctgtgagtg tgtcacccaa cccaccacca tgacaaccac caccacagag 5701 aacccaactc cgccaaccac gacacccatc accaccacca ctacggtgac cccaaccccca 5761 acacccaccg gcacacagac cccaaccacg acacccatca ccaccaccac tacggtgacc 5821 ccaaccccaa cacccaccgg cacacagacc ccaaccacga cacccatcac caccaccact 5881 acggtgaccc caaccccaac acccaccggc acacagaccc caaccacgac acccatcacc 5941 accaccacta cggtgacccc aaccccaaca cccaccggca cagacccca aaccacgaca 6001 cccatcacca ccaccactac ggtgacccca accccaacac ccaccggcac acagacccca 6061 accacgacac ccatcaccac caccactacg gtgaccccaa ccccaacacc caccggcaca 6121 cagaccccaa ccacgacacc catcaccacc accactacgg tgaccccaac cccaacaccc 6181 accggcacac agaccccaac cacgacaccc atcaccacca ccactacggt gaccccaacc 6241 ccaacaccca ccggcacaca gaccccaacc acgacaccca tcaccaccac cactacggtg 6301 accccaaccc caacacccac cggcacacag accccaacca cgacacccat caccaccacc 6361 actacggtga ccccaacccc aacacccacc ggcacacaga ccccaaccac gacacccatc 6421 accaccacca ctacggtgac cccaacccca cacccaccg gcacacagac cccaaccacg 6481 acacccatca ccaccaccac tacggtgacc caacccccaa cacccaccgg cacacagacc 6541 ccaaccacga cacccatcac caccaccact acggtgaccc caaccccaac acccaccggc 6601 acacagaccc caaccacgac acccatcacc accaccacta cggtgacccc aaccccaaca 6661 cccaccggca cagacccca aaccacgaca cccatcacca ccaccactac ggtgaccccca 6721 accccaacac caccggcac acagacccca accacgacac ccatcaccac caccactacg 6781 gtgaccccaa ccccaacacc caccggcaca cagaccccaa ccacgacacc catcaccacc 6841 accactacgg tgaccccaac cccaacaccc accggcacac agaccccaac cacgacacccc 6901 atcaccacca ccactacggt gaccccaacc ccaacacccca ccggcacaca gaccccaacc
```

-continued

```
6961 acgacaccca tcaccaccac cactacggtg accccaaccc caacacccac cggcacacag 7021 accccaacca cgacacccat caccaccacc actacggtga ccccaacccc aacacccacc 7081 ggcacacaga ccccaaccac gacacccatc accaccacca ctacggtgac cccaacccca 7141 acacccaccg gcacacagac cccaaccacg acacccatca ccaccaccac tacggtgacc 7201 ccaaccccaa cacccaccgg cacacagacc caaccacga cacccatcac caccaccact 7261 acggtgaccc caaccccaac acccaccggc acacagaccc caaccacgac acccatcacc 7321 accaccacta cggtgaccc aaccccaaca cccaccggca cagacccc aaccacgaca 7381 cccatcacca ccaccactac ggtgacccca accccaacac ccaccggcac acagacccca 7441 accacgacac ccatcaccac caccactacg gtgaccccaa ccccaacacc caccggcaca 7501 cagaccccaa ccacgacacc catcaccacc accactacgg tgaccccaac cccaacaccc 7561 accggcacac agacccaac cacgacaccc atcaccacca ccactacggt gaccccaacc 7621 ccaacacca ccggcacaca gaccccaacc acgacaccca tcaccaccac cactacggtg 7681 accccaaccc caacacccac cggcacacag accccaacca cgacacccat caccaccacc 7741 actacggtga ccccaacccc aacacccacc ggcacacaga ccccaaccac gacacccatc 7801 accaccacca ctacggtgac cccaaccca acacccaccg gcacacagac cccaaccacg 7861 acacccatca ccaccaccac tacggtgacc caaccccaa cacccaccgg cacacagacc 7921 ccaaccacga cacccatcac caccaccact acggtgaccc caaccccaac acccaccggc 7981 acacagaccc caaccacgac acccatcacc accaccacta cggtgacccc aaccccaaca 8041 cccaccggca cagacccc aaccacgaca cccatcacca ccaccactac ggtgacccca 8101 accccaacac ccaccggcac acagacccca accacgacac ccatcaccac caccactacg 8161 gtgaccccaa ccccaacacc caccggcaca cagaccccaa ccacgacacc catcaccacc 8221 accactacgg tgaccccaac cccaacaccc accggcacac agacccaac cacgacaccc 8281 atcaccacca ccactacggt gaccccaacc ccaacaccca ccggcacaca gaccccaacc 8341 acgacaccca tcaccaccac cactacggtg accccaaccc caacacccac cggcacacag 8401 accccaacca cgacacccat caccaccacc actacggtga ccccaacccc aacacccacc 8461 ggcacacaga ccccaaccac gacacccatc accaccacca ctacggtgac cccaacccca 8521 acacccaccg gcacacagac cccaaccacg acacccatca ccaccaccac tacggtgacc 8581 ccaaccccaa cacccaccgg cacacagacc caaccacga cacccatcac caccaccact 8641 acggtgaccc caaccccaac acccaccggc acacagaccc caaccacgac acccatcacc 8701 accaccacta cggtgacccc aaccccaaca cccaccggca cagacccc aaccacgaca 8761 cccatcacca ccaccactac ggtgacccca accccaacac ccaccggcac acagacccca 8821 accacgacac ccatcaccac caccactacg gtgaccccaa ccccaacacc caccggcaca 8881 cagaccccaa ccacgacacc catcaccacc accactacgg tgaccccaac cccaacaccc 8941 accggcacac agacccaac cacgacaccc atcaccacca ccactacggt gaccccaacc 9001 ccaacacca ccggcacaca gaccccaacc acgacaccca tcaccaccac cactacggtg 9061 accccaaccc caacacccac cggcacacag accccaacca cgacacccat caccaccacc 9121 actacggtga ccccaacccc aacacccacc ggcacacaga ccccaaccac gacacccatc 9181 accaccacca ctacggtgac cccaaccca acacccaccg gcacacagac cccaaccacg 9241 acacccatca ccaccaccac tacggtgacc caaccccaa cacccaccgg cacacagacc 9301 ccaaccacga cacccatcac caccaccact acggtgaccc caaccccaac acccaccggc
```

-continued

```
 9361 acacagaccc caaccacgac acccatcacc accaccacta cggtgacccc aaccccaaca 9421 cccaccggca cacagaccccc aaccacgaca cccatcacca ccaccactac ggtgaccccca 9481 accccaacac ccaccggcac acagaccccca accacgacac ccatcaccac caccactacg 9541 gtgaccccaa ccccaacacc caccggcaca cagacccccaa ccacgacacc catcaccacc 9601 accactacgg tgaccccaac cccaacaccc accggcacac agaccccaac cacgacaccc 9661 atcaccacca ccactacggt gaccccaacc ccaacaccca ccggcacaca gacccccaacc 9721 acgacaccca tcaccaccac cactacggtg accccaaccc caacacccac cggcacacag 9781 accccaacca cgacacccat caccaccacc actacggtga ccccaacccc aacacccacc 9841 ggcacacaga ccccaaccac gacacccatc accaccacca ctacggtgac cccaacccca 9901 acacccaccg gcacacagac cccaaccacg acacccatca ccaccaccac tacggtgacc 9961 ccaaccccaa cacccaccgg cacacagacc caaccacga cacccatcac caccaccact 10021 acggtgaccc caaccccaac acccaccggc acacagaccc caaccacgac acccatcacc 10081 accaccacta cggtgacccc aaccccaaca cccaccggca cacagaccccc aaccacgaca 10141 cccatcacca ccaccactac ggtgaccccca accccaacac ccaccggcac acagaccccca 10201 accacgacac ccatcaccac caccactacg gtgaccccaa ccccaacacc caccggcaca 10261 cagaccccaa ccacgacacc catcaccacc accactacgg tgaccccaac cccaacaccc 10321 accggcacac agaccccaac cacgacaccc atcaccacca ccactacggt gaccccaacc 10381 ccaacaccca ccggcacaca gaccccaacc acgacaccca tcaccaccac cactacggtg 10441 accccaaccc caacacccac cggcacacag accccaacca cgacacccat caccaccacc 10501 actacggtga ccccaacccc aacacccacc ggcacacaga ccccaaccac gacacccatc 10561 accaccacca ctacggtgac cccaacccca acacccaccg gcacacagac cccaaccacg 10621 acacccatca ccaccaccac tacggtgacc ccaaccccaa cacccaccgg cacacagacc 10681 ccaaccacga cacccatcac caccaccact acggtgaccc caaccccaac acccaccggc 10741 acacagaccc caaccacgac acccatcacc accaccacta cggtgacccc aaccccaaca 10801 cccaccggca cacagaccccc aaccacgaca cccatcacca ccaccactac ggtgacccca 10861 accccaacac ccaccggcac acagaccccca accacgacac ccatcaccac caccactacg 10921 gtgaccccaa ccccaacacc caccggcaca cagaccccaa ccacgacacc catcaccacc 10981 accactacgg tgaccccaac cccaacaccc accggcacac agaccccaac cacgacaccc 11041 atcaccacca ccactacggt gaccccaacc ccaacaccca ccggcacaca gacccccaacc 11101 acgacaccca tcaccaccac cactacggtg accccaaccc caacacccac cggcacacag 11161 accccaacca cgacacccat caccaccacc actacggtga ccccaacccc aacacccacc 11221 ggcacacaga ccccaaccac gacacccatc accaccacca ctacggtgac cccaacccca 11281 acacccaccg gcacacagac cccaaccacg acacccatca ccaccaccac tacggtgacc 11341 ccaaccccaa cacccaccgg cacacagacc caaccacga cacccatcac caccaccact 11401 acggtgaccc caaccccaac acccaccggc acacagaccc caaccacgac acccatcacc 11461 accaccacta cggtgacccc aaccccaaca cccaccggca cacagaccccc aaccacgaca 11521 cccatcacca ccaccactac ggtgaccccca accccaacac ccaccggcac acagaccccca 11581 accacgacac ccatcaccac caccactacg gtgaccccaa ccccaacacc caccggcaca 11641 cagaccccaa ccacgacacc catcaccacc accactacgg tgaccccaac cccaacaccc 11701 accggcacac agaccccaac cacgacaccc atcaccacca ccactacggt gaccccaacc 11761 ccaacaccca ccggcacaca gaccccaacc acgacaccca tcaccaccac cactacggtg
```

-continued

```
11821 accccaaccc caacacccac cggcacacag accccaacca cgacacccat caccaccacc 11881 actacggtga ccccaaccct aacacccacc ggcacacaga ccccaaccac gacacccatc 11941 accaccacca ctacggtgac cccaacccca acacccaccg gcacacagac cccaaccacg 12001 acacccatca ccaccaccac tacggtgacc ccaaccccaa cacccaccgg cacacagacc 12061 ccaaccacga cacccatcac caccaccact acggtgaccc caaccccaac acccaccggc 12121 acacagaccc caaccacgac acccatcacc accaccacta cggtgacccc aaccccaaca 12181 cccaccggca cacagacccc aaccacgaca cccatcacca ccaccactac ggtgaccccca 12241 accccaacac ccaccggcac acagacccca accacgacac ccatcaccac caccactacg 12301 gtgaccccaa ccccaacacc caccggcaca cagaccccaa ccacgacacc catcaccacc 12361 accactacgg tgaccccaac cccaacaccc accggcacac agaccccaac cacgacaccc 12421 atcaccacca ccactacggt gaccccaacc ccaacaccca ccggcacaca gaccccaacc 12481 acgacccca tcaccaccac cactacggtg accccaaccc caacacccac cggcacacag 12541 accccaacca cgacacccat caccaccacc actacggtga ccccaacccc aacacccacc 12601 ggcacacaga ccgggccccc cacccacaca agcacagcac cgattgctga gttgaccaca 12661 tccaatcctc cgcctgagtc ctcaacccct cagacctctc ggtccacctc ttccctctc 12721 acggagtcaa ccacccttct gagtacccta ccacctgcca ttgagatgac cagcacggcc 12781 ccaccctcca cacccacggc acccacgacc acgagcggag gccacacact gtctccaccg 12841 cccagcacca ccacgtcccc tccaggcacc cccactcgcg gtaccacgac tgggtcatct 12901 tcagccccca cccccagcac tgtgcagacg accaccacca gtgcctggac ccccacgccg 12961 accccactct ccacacccag catcatcagg accacaggcc tgaggcccta cccttcctct 13021 gtgcttatct gctgtgtcct gaacgacacc tactacgcac caggtgagga ggtgtacaac 13081 ggcacatacg gagacacctg ttatttcgtc aactgctcac tgagctgtac gttggagttc 13141 tataactggt cctgcccatc cacgccctcc ccaacacctca cgccctccaa gtcgacgccc 13201 acgccttcca agccatcgtc cacgccctcc aagccgacgc ccggcaccaa gccccccgag 13261 tgcccagact ttgatcctcc cagacaggag aacgagactt ggtggctgtg cgactgcttc 13321 atggccacgt gcaagtacaa caacacggtg gagatcgtga aggtggagtg tgagccgccg 13381 cccatgccca cctgctccaa cggcctccaa cccgtgcgcg tcgaggaccc cgacggctgc 13441 tgctggcact gggagtgcga ctgctactgc acgggctggg cgacccgca ctatgtcacc 13501 ttcgacggac tctactacag ctaccagggc aactgcacct acgtgctggt ggaggagatc 13561 agcccctccg tggacaactt cggagtttac atcgacaact accactgcga tcccaacgac 13621 aaggtgtcct gcccccgcac cctcatcgtg cgccacgaga cccaggaggt gctgatcaag 13681 accgtgcata tgatgcccat gcaggtgcag gtgcaggtga acaggcaggc ggtggcactg 13741 ccctacaaga gtacgggct ggaggtgtac cagtctggca tcaactacgt ggtggacatc 13801 cccgagctgg gtgtcctcgt ctcctacaat ggcctgtcct tctccgtcag gctgccctac 13861 caccggtttg gcaacaacac caagggccag tgtggcacct gcaccaacac cacctccgac 13921 gactgcattc tgcccagcgg ggagatcgtc tccaactgtg aggctgcggc tgaccagtgg 13981 ctggtgaacg acccctccaa gccacactgc ccccacagca gctccacgac caagcgcccg 14041 gccgtcactg tgcccggggg cggtaaaacg accccacaca aggactgcac cccatctccc 14101 ctctgccagc tcatcaagga cagcctgttt gcccagtgcc acgcactggt gcccccgcag 14161 cactactacg atgcctgcgt gttcgacagc tgcttcatgc cgggctcgag cctggagtgc
```

-continued

```
14221 gccagtctgc aggcctacgc agccctctgt gcccagcaga acatctgcct cgactggcgg 14281 aaccacacgc atggggcctg cttggtggag tgcccatctc acagggagta ccaggcctgt 14341 ggccctgcag aagagcccac gtgcaaatcc agctcctccc agcagaacaa cacagtcctg 14401 gtggaaggct gcttctgtcc tgagggcacc atgaactacg ctcctggctt tgatgtctgc 14461 gtgaagacct gcggctgtgt gggacctgac aatgtgccca gagagtttgg ggagcacttc 14521 gagttcgact gcaagaactg tgtctgcctg gagggtggaa gtggcatcat ctgccaaccc 14581 aagaggtgca gccagaagcc cgttacccac tgcgtggaag acggcaccta cctcgccacg 14641 gaggtcaacc ctgccgacac ctgctgcaac attaccgtct gcaagtgcaa caccagcctg 14701 tgcaaagaga gccctccgt gtgcccgctg ggattcgaag tgaagagcaa gatggtgcct 14761 ggaaggtgct gtcctttcta ctggtgtgag tccaaggggg tgtgtgttca cgggaatgct 14821 gagtaccagc ccggttctcc agtttattcc tccaagtgcc aggactgcgt gtgcacggac 14881 aaggtggaca acaacaccct gctcaacgtc atcgcctgca cccacgtgcc ctgcaacacc 14941 tcctgcagcc ctggcttcga actcatggag gcccccgggg agtgctgtaa gaagtgtgaa 15001 cagacgcact gtatcatcaa acggcccgac aaccagcacg tcatcctgaa gcccgggggac 15061 ttcaagagcg acccgaagaa caactgcaca ttcttcagct gcgtgaagat ccacaaccag 15121 ctcatctcgt ccgtctccaa catcacctgc cccaactttg atgccagcat ttgcatcccg 15181 ggctccatca cattcatgcc caatggatgc tgcaagacct gcacccctcg caatgagacc 15241 agggtgccct gctccaccgt ccccgtcacc acggaggttt cgtacgccgg ctgcaccaag 15301 accgtcctca tgaatcattg ctccgggtcc tgcgggacat ttgtcatgta ctcggccaag 15361 gcccaggccc tggaccacag ctgctcctgc tgcaaagagg agaaaaccag ccagcgtgag 15421 gtggtcctga gctgcccaa tggcggctcg ctgacacaca cctacacca catcgagagc 15481 tgccagtgcc aggacaccgt ctgcgggctc cccaccggca cctcccgccg ggcccggcgc 15541 tcccctaggc atctggggag cgggtgagcg gggtgggcac agccccttc actgccctcg 15601 acagctttac ctccccgga ccctctgagc ctcctaagct cggcttcctc tcttcagata 15661 tttattgtct gagtctttgt tcagtccttg ctttccaata ataaactcag ggggacatgc
```

By "NKX2-5 polypeptide" or "human NKX2-5 (hNKX2-5) polypeptide" is meant a protein or fragment thereof having at least 85%, at least 90%, at least 95%, at least 98%, or at least 99% amino acid sequence identity to the sequence provided at NCBI Accession 15 No. NP_004378.1 (isoform 1), NP_001159647.1 (isoform 2), or NP_001159648.1 (isoform 3) and having transcription factor activity. The amino acid sequence provided at NCBI Accession No. NP_004378.1 is shown below:

```
  1 MFPSPALTPT PFSVKDILNL EQQQRSLAAA

GELSARLEAT LAPSSCMLAA FKPEAYAGPE

61 AAAPGLPELR AELGRAPSPA KCASAFPAAP

AFYPRAYSDP DPAKDPRAEK KELCALQKAV

121 ELEKTEADNA ERPRARRRRK PRVLFSQAQV

YELERRFKQQ RYLSAPERDQ LASVLKLTST

181 QVKIWFQNRR YKCKRQRQDQ TLELVGLPPP

PPPPARRIAV PVLVRDGKPC LGDSAPYAPA
```

-continued
```
241 YGVGLNPYGY NAYPAYPGYG GAACSPGYSC

TAAYPAGPSP AQPATAAANN NEVNEGVGDL

301 NAVQSPGIPQ SNSGVSTLHG IRAW
```

By "NKX2-5 polynucleotide" is meant a polynucleotide encoding a NKX2-5 polypeptide or fragment thereof. An exemplary NKX2-5 polynucleotide sequence is provided at NCBI Ref: NM_004387.3. The sequence provided at NCBI Ref: NM_004387.3 is reproduced below:

```
  1 gctcctgtca tcgaggcccc tggcccaatg gcaggctgag tccccctcct ctggcctggt 61 cccgcctctc ctgcccttg tgctcagcgc tacctgctgc ccggacacat ccagagctgg 121 ccgacgggtg cgcgggcggg cggcggcacc atgcaggaa gctgccaggg gccgtgggca
```

-continued

```
181 gcgccgcttt ctgccgccca cctggcgctg tgagactggc gctgccacca tgttccccag 241 ccctgctctc acgcccacgc ccttctcagt caaagacatc ctaaacctgg aacagcagca 301 gcgcagcctg gctgccgccg gagagctctc tgcccgcctg gaggcgaccc tggcgccctc 361 ctcctgcatg ctggccgcct tcaagccaga ggcctacgct gggcccgagg cggctgcgcc 421 gggcctccca gagctgcgcg cagagctggg ccgcgcgcct tcaccggcca agtgtgcgtc 481 tgcctttccc gccgcccccg ccttctatcc acgtgcctac agcgacccc acccagccaa 541 ggaccctaga gccgaaaaga aagagctgtg cgcgctgcag aaggcggtgg agctggagaa 601 gacagaggcg gacaacgcgg agcggcccg ggcgcgacgg cggaggaagc cgcgcgtgct 661 cttctcgcag gcgcaggtct atgagctgga gcggcgcttc aagcagcagc ggtacctgtc 721 ggccccccgaa cgcgaccagc tggccagcgt gctgaaactc acgtccacgc aggtcaagat 781 ctggttccag aaccggcgct acaagtgcaa gcggcagcgg caggaccaga ctctggagct 841 ggtggggctg cccccgccgc cgccgccgcc tgcccgcagg atcgcggtgc cagtgctggt 901 gcgcgatggc aagccatgcc tagggggactc ggcgccctac gcgcctgcct acggcgtggg 961 cctcaatccc tacggttata acgcctaccc cgcctatccg ggttacggcg gcgcggcctg 1021 cagccctggc tacagctgca ctgccgctta ccccgccggg ccttccccag cgcagccggc 1081 cactgccgcc gccaacaaca acttcgtgaa cttcggcgtc ggggacttga atgcggttca 1141 gagccccggg attccgcaga gcaactcggg agtgtccacg ctgcatggta tccgagcctg 1201 gtagggaagg gaccgcgtg gcgcgaccct gaccgatccc acctcaacag ctccctgact 1261 ctcggggga gaaggggctc ccaacatgac cctgagtccc ctggattttg cattcactcc 1321 tgcggagacc taggaacttt ttctgtccca cgcgcgtttg ttcttgcgca cgggagagtt
```

-continued

```
1381 tgtggcggcg attatgcagc gtgcaatgag tgatcctgca gcctggtgtc ttagctgtcc 1441 ccccaggagt gccctccgag agtccatggg caccccggt tggaactggg actgagctcg 1501 ggcacgcagg gcctgagatc tggccgccca ttccgcgagc cagggccggg cgcccgggcc 1561 tttgctatct cgccgtcgcc cgcccacgca cccaccgta tttatgtttt tacctattgc 1621 tgtaagaaat gacgatcccc ttcccattaa agagagtgcg ttgaccccg
```

By "NEUROD1 polypeptide" is meant a protein or fragment thereof having at least 85%, at least 90%, at least 95%, at least 98%, or at least 99% amino acid sequence identity to the sequence provided at NCBI Accession No. NP_002491.2 and having transcription factor activity. The amino acid sequence provided at NCBI Accession No. NP_002491.2 is shown below:

```
  1 MTKSYSESGL MGEPQPQGPP SWTDECLSSQ

DEEHEADKKE DDLEAMNAEE DSLRNGGEEE

61 DEDEDLEEEE EEEEEDDDQK PKRRGPKKKK

MTKARLERFK LRRMKANARE RNRMHGLNAA

121 LDNLRKVVPC YSKTQKLSKI ETLRLAKNYI

WALSEILRSG KSPDLVSFVQ TLCKGLSQPT

181 TNLVAGCLQL NPRTFLPEQN QDMPPHLPTA

SASFPVHPYS YQSPGLPSPP YGTMDSSHVF

241 HVKPPPHAYS AALEPFFESP LTDCTSPSFD

GPLSPPLSIN GNFSFKHEPS AEFEKNYAFT

301 MHYPAATLAG AQSHGSIFSG TAAPRCEIPI

DNIMSFDSHS HHERVMSAQL NAIFHD
```

By "NEUROD1 polynucleotide" is meant a polynucleotide encoding a NEUROD1 polypeptide or fragment thereof. An exemplary NEUROD1 polynucleotide sequence is provided at NCBI Ref: NM_002500.4. The sequence provided at NCBI Ref: NM_002500.4 is reproduced below:

```
  1 ggggaggagg ggagaacggg gagcgcacag cctggacgcg tgcgcaggcg tcaggcgcat 61 agacctgcta gccctcagc tagcggcccc gcccgcgctt agcatcacta actgggctat 121 ataacctgag cgcccgcgcg gccacgacac gaggaattcg cccacgcagg aggcgcggcg 181 tccggaggcc ccagggttat gagactatca ctgctcagga cctactaaca acaaaggaaa
```

-continued

```
 241 tcgaaacatg accaaatcgt acagcgagag tgggctgatg ggcgagcctc agccccaagg 301 tcctccaagc tggacagacg agtgtctcag ttctcaggac gaggagcacg aggcagacaa 361 gaaggaggac gacctcgaag ccatgaacgc agaggaggac tcactgagga acgggggaga 421 ggaggaggac gaagatgagg acctggaaga ggaggaagaa gaggaagagg aggatgacga 481 tcaaaagccc aagagacgcg gccccaaaaa gaagaagatg actaaggctc gcctggagcg 541 ttttaaattg agacgcatga aggctaacgc ccgggagcgg aaccgcatgc acggactgaa 601 cgcggcgcta gacaacctgc gcaaggtggt gccttgctat tctaagacgc agaagctgtc 661 caaaatcgag actctgcgct tggccaagaa ctacatctgg gctctgtcgg agatcctgcg 721 ctcaggcaaa agcccagacc tggtctcctt cgttcagacg ctttgcaagg gcttatccca 781 acccaccacc aacctggttg cgggctgcct gcaactcaat cctcggactt ttctgcctga 841 gcagaaccag gacatgcccc cccacctgcc gacggccagc gcttccttcc ctgtacaccc 901 ctactcctac cagtcgcctg ggctgcccag tccgccttac ggtaccatgg acagctccca 961 tgtcttccac gttaagcctc cgccgcacgc ctacagcgca gcgctggagc ccttctttga 1021 aagccctctg actgattgca ccagcccttc ctttgatgga cccctcagcc cgccgctcag 1081 catcaatggc aacttctctt tcaaacacga accgtccgcc gagtttgaga aaaattatgc 1141 ctttaccatg cactatcctg cagcgacact ggcaggggcc caaagccacg gatcaatctt 1201 ctcaggcacc gctgccctc gctgcgagat ccccatagac aatattatgt ccttcgatag 1261 ccattcacat catgagcgag tcatgagtgc ccagctcaat gccatatttc atgattagag 1321 gcacgccagt ttcaccattt ccgggaaacg aacccactgt gcttacagtg actgtcgtgt 1381 ttacaaaagg cagcccttg ggtactactg ctgcaaagtg caaatactcc aagcttcaag
```

-continued

```
1441 tgatatatgt atttattgtc attactgcct ttggaagaaa caggggatca aagttcctgt 1501 tcaccttatg tattattttc tatagctctt ctatttaaaa aataaaaaaa tacagtaaag 1561 tttaaaaaat acaccacgaa tttggtgtgg ctgtattcag atcgtattaa ttatctgatc 1621 gggataacaa aatcacaagc aataattagg atctatgcaa tttttaaact agtaatgggc 1681 caattaaaat atatataaat atatattttt caaccagcat tttactactt gttacctttc 1741 ccatgctgaa ttattttgtt gtgattttgt acagaatttt taatgacttt ttataatgtg 1801 gatttcctat tttaaaacca tgcagcttca tcaatttta tacatatcag aaaagtagaa 1861 ttatatctaa tttatacaaa ataatttaac taatttaaac cagcagaaaa gtgcttagaa 1921 agttattgtg ttgccttagc acttcttttcc tctccaattg taaaaaaaaa aaaaaaaaaa 1981 aaaaaaaaaa aaaaattgca caatttgagc aattcatttc actttaaagt ctttccgtct 2041 ccctaaaata aaaaccagaa tcataatttt caagagaaga aaaaattaag agatacattc 2101 cctatcaaaa catatcaatt caacacatta cttgcacaag cttgtatata catattataa 2161 ataaatgcca acataccctt ctttaaatca aaagctgctt gactatcaca tacaatttgc 2221 actgttactt tttagtcttt tactcctttg cattccatga ttttacagag aatctgaagc 2281 tattgatgtt tccagaaaat ataaatgcat gattttatac atagtcacaa aaatggtggt 2341 ttgtcatata ttcatgtaat aaatctgagc ctaaatctaa tcaggttgtt aatgttggga 2401 tttatatcta tagtagtcaa ttagtacagt agcttaaata aattcaaacc atttaattca 2461 taattagaac aatagctatt gcatgtaaaa tgcagtccag aataagtgct gtttgagatg 2521 tgatgctggt accactggaa tcgatctgta ctgtaatttt gtttgtaatc ctgtatatta 2581 tggtgtaatg cacaatttag aaaacattca tccagttgca ataaaatagt attgaaagtg
```

-continued

```
2641 agagcaattg ttgcatttct tcttaaaggg attctgtttt tatttttggg gaaagtagtt 2701 gctttttttgc tgagttaaaa aatactaaac actatatgta gaataaaaga aaagaaaaaa 2761 gtttaccttg gcatatgctc ttgtctgttt atcttgcaca gggagtcacc agttctatgt 2821 agataatgaa aagacctaac tgatatttca ttatttggaa tatgggactg gacggcagta 2881 caaacagtgt gtttttttct ttgttttaag tggcttagcc tttaggtttt ttatttccat 2941 ttttaaaaat gattgttaca tgtttttcttc tatttctttt tttaaaaggt ggattttaat 3001 aa
```

By "NKX6-1 polypeptide" is meant a protein or fragment thereof having at least 85%, at least 90%, at least 95%, at least 98%, or at least 99% amino acid sequence identity to the sequence provided at NCBI Accession No. NP_006159.2 and having transcription factor activity. The amino acid sequence provided at NCBI Accession No. NP_006159.2 is shown below:

```
  1 MLAVGAMEGT RQSAFLLSSP PLAALHSMAE

MKTPLYPAAY PPLPAGPPSS SSSSSSSSSP

61 SPPLGTHNPG GLKPPATGGL SSLGSPPQQL

SAATPHGIND ILSRPSMPVA SGAALPSASP

121 SGSSSSSSS ASASSASAAA AAAAAAAAA

SSPAGLLAGL PRFSSLSPPP PPPGLYFSPS

181 AAAVAAVGRY PKPLAELPGR TPIFWPGVMQ

SPPWRDARLA CTPHQGSILL DKDGKRKHTR

241 PTFSGQQIFA LEKTFEQTKY LAGPERARLA

YSLGMTESQV KVWFQNRRTK WRKKHAAEMA

301 TAKKKQDSET ERLKGASENE EEDDDYNKPL

DPNSDDEKIT QLLKKHKSSS GGGGGLLLHA

361 SEPESSS
```

By "NKX6-1 polynucleotide" is meant a polynucleotide encoding a NKX6-1 polypeptide or fragment thereof. An exemplary NKX6-1 polynucleotide sequence is provided at NCBI Ref: NM_006168.2. The sequence provided at NCBI Ref: NM_006168.2 is reproduced below:

```
  1 cgtgggatgt tagcggtggg ggcaatggag ggcacccggc agagcgcatt cctgctcagc 61 agccctcccc tggccgccct gcacagcatg gccgagatga agacccccgct gtaccctgcc
```

-continued

```
121 gcgtatcccc cgctgcctgc cggccccccc tcctcctcgt cctcgtcgtc gtcctcctcg 181 tcgccctccc cgcctctggg cacccacaac ccaggcggcc tgaagccccc ggccacgggg 241 gggctctcat ccctcggcag cccccccgcag cagctctcgg ccgccacccc acacggcatc 301 aacgatatcc tgagccggcc ctccatgccc gtggcctcgg gggccgccct gccctccgcc 361 tcgccctccg gttcctcctc ctcctcttcc tcgtccgcct ctgcctcctc cgcctctgcc 421 gccgccgcgg ctgctgccgc ggccgcagcc gccgcctcat ccccggcggg gctgctggcc 481 ggactgccac gctttagcag cctgagcccg ccgccgccgc cgcccgggct ctacttcagc 541 cccagcgccg cggccgtggc cgccgtgggc cggtaccccca agccgctggc tgagctgcct 601 ggccggacgc ccatcttctg gcccggagtg atgcagagcc cgccctggag ggacgcacgc 661 ctggcctgta cccctcatca aggatccatt ttgttggaca aagacgggaa gagaaaacac 721 acgagaccca cttttttccgg acagcagatc ttcgccctgg agaagacttt cgaacaaaca 781 aaatacttgg cggggcccga gagggctcgt ttggcctatt cgttggggat gacagagagt 841 caggtcaagg tctggttcca gaaccgccgg accaagtgga ggaagaagca cgctgccgag 901 atggccacgg ccaagaagaa gcaggactcg gagacagagc gcctcaaggg ggcctcggag 961 aacgaggaag aggacgacga ctacaataag cctctggatc ccaactcgga cgacgagaaa 1021 atcacgcagc tgttgaagaa gcacaagtcc agcagcggcg gcggcggcgg cctcctactg 1081 cacgcgtccg agccggagag ctcatcctga acgccg
```

By "NDUFA4 polypeptide" is meant a protein or fragment thereof having at least 85%, at least 90%, at least 95%, at least 98%, or at least 99% amino acid sequence identity to the sequence provided at NCBI Accession No. NP_002480.1 and having NADH dehydrogenase activity and oxidoreductase activity. The amino acid sequence provided at NCBI Accession No. NP_002480.1 is shown below:

```
  1 MAAELAMGAE LPSSPLAIEY VNDFDLMKFE
    VKKEPPEAER FCHRLPPGSL SSTPLSTPCS
 61 SVPSSPSFCA PSPGTGGGGG AGGGGGSSQA
    GGAPGPPSGG PGAVGGTSGK PALEDLYWMS
121 GYQHHLNPEA LNLTPEDAVE ALIGSGHHGA
    HHGAHHPAAA AAYEAFRGPG FAGGGGADDM
181 GAGHHHGAHH AAHHHHAAHH HHHHHHHHGG
    AGHGGGAGHH VRLEERFSDD QLVSMSVREL
241 NRQLRGFSKE EVIRLKQKRR TLKNRGYAQS
    CRFKRVQQRH ILESEKCQLQ SQVEQLKLEV
301 GRLAKERDLY KEKYEKLAGR GGPGSAGGAG
    FPREPSPPQA GPGGAKGTAD FFL
```

By "NDUFA4 polynucleotide" is meant a polynucleotide encoding a NDUFA4 polypeptide or fragment thereof. An exemplary NDUFA4 polynucleotide sequence is provided at NCBI Ref: NM_002489.3. The sequence provided at NCBI Ref: NM_002489.3 is reproduced below:

```
   1 gggtccttca ggtaggaggt cctgggtgac
     tttggaagtc cgtagtgtct cattgcagat
  61 aatttttagc ttagggcctg gtggctaggt
     cggttctctc ctttccagtc ggagacctct
 121 gccgcaaaca tgctccgcca gatcatcggt
     caggccaaga agcatccgag cttgatcccc
 181 ctctttgtat ttattggaac tggagctact
     ggagcaacac tgtatctctt gcgtctggca
 241 ttgttcaatc cagatgtttg ttgggacaga
     aataacccag agccctggaa caaactgggt
 301 cccaatgatc aatacaagtt ctactcagtg
     aatgtggatt acagcaagct gaagaaggaa
 361 cgtccagatt tctaaatgaa atgtttcact
     ataacgctgc tttagaatga aggtcttcca
 421 gaagccacat ccgcacaatt ttccacttaa
     ccaggaaata tttctcctct aaatgcatga
 481 aatcatgttg gagatctcta ttgtaatctc
     tattggagat tacaatgatt aaatcaataa
 541 ataactgaaa cttgatatgt gtcacttttt
     tatgctgaaa gtatgctctg aactttagag
 601 tataggaaat taactattag aatttaaaga
     atttcttgaa tttctgtagt ttgaaaatac
```

```
 661 gactttaagc tgctttagta aaacacttcc
     attttgtgta tagactgttg gtaacttcac
 721 tagagcatac ataacaactg gaactggaaa
     ttatacaaaa gtaaattggg aaggatactc
 781 cagcatctga cactggcaaa atggaaacct
     ttgagtttct cttactggct gttgaagtgt
 841 gtgcagtttt taacaatggt ttttacttgg
     catctctttg ttgtgatttt caaggttata
 901 agttgctttg gtcctaggat tgaagttgaa
     atctgagttc atcagtgcta accatggtgc
 961 tagtagtcaa gagatcttga gaattttggc
     tgctgagtct tggtgcaggg tgcaggtttt
1021 cttttctttt ttctttttt tttttttgag
     atagtctctg tcacccaggc tggagtgcag
1081 tggtacaaac atggatcact gcagcctcta
     cctcccgggc ttaagtgatc ctcctgcctc
1141 agccctaag tagccgggac tacaggtatg
     tgccaccatg cccagttaat ttttgtaatt
1201 ttttttagag acagggtttt gccatgttgc
     ccaggctggt ctcaaactct tgagctcaag
1261 cgatccattc tcctcagcct cccagggtgc
     tgggattaca ggcgtgagcc attgcgctta
1321 gccatggtgc aggttttcaa aggccaggaa
     gtatattcat aattttaaga tggggaatat
1381 agcaagtttt cacataggtg tgtgtaagtc
     atcacatcat agaaacttga ggaattcagt
1441 gacattaatt ttggattttc atacgtaagt
     atacaattaa atgtttacag ggtagtagaa
1501 gcacatttta aatgtcagga actgaactaa
     gtatttgaat tacgtggatt atctcaaaaa
1561 ttttgaaatt gttaaacgag ttgaattact
     tgaattcatt ctgttagtca aatggtggat
1621 atttacaccc atgtagtttt gaatttagag
     tgtgtagagt gttttcagtt accagactcc
1681 atgcttttac ctcctatgtg tcaggtataa
     tttgaacctc taagaacagg gtttctcaac
1741 cttgccactg ttgactattt ctgaaagaca
     gtttggttta gcagaccatc ccatgcgctt
1801 tagcttgttt agtagctaac ttgggctctg
     ccactacaga caaaaagcac tctttccctc
```

```
                   -continued
1861 caattcccac aggctatgag aagaatggag acattaccaa atgtccattg gtgggcaaaa 1921 ttgcttcatt cctacctctg ttgagaatta ctctagatcc tttggcacaa attacctcaa 1981 agtttaaaat tgtgtaaaca aacagtgtgt catgtaattg aaaaacatta agcaactcca 2041 aataaatgct acattaag
```

As used herein, "obtaining" as in "obtaining an agent" includes synthesizing, purchasing, procuring, deriving, or otherwise acquiring the agent.

By "organ" is meant a collection of cells that perform a biological function. In one embodiment, an organ includes, but is not limited to, bladder, brain, nervous tissue, glial tissue, esophagus, fallopian tube, heart, pancreas, intestines, gallbladder, kidney, liver, lung, ovaries, prostate, spinal cord, spleen, stomach, testes, thymus, thyroid, trachea, urogenital tract, ureter, urethra, uterus, breast, skeletal muscle, skin, bone, and cartilage. The biological function of an organ can be assayed using standard methods known to the skilled artisan.

By "organoid" is meant an in vitro generated body that mimics organ structure and function. "Organoid" and "mini organ" are used interchangeably herein. An "islet-like organoid," "pancreatic islet organoid," "pancreatic islet," or "pancreatic organoid" is an in vitro generated cell cluster that mimics the structure and function of a pancreatic islet. Exemplary functions of a pancreatic islet include, without limitation, glucose-stimulated insulin secretion (GSIS), potassium chloride (KCl)-stimulated insulin secretion, GLP-1 stimulated insulin secretion, somatostatin secretion, or glucagon secretion. "Pancreatic islet organoid," "islet-like organoid," "pancreatic organoid" and "mini pancreatic islet" are used interchangeably herein. In an embodiment, a "pancreatic organoid" is an in vitro generated body that mimics structure and function of a pancreas. Exemplary functions of a pancreas include, without limitation, endocrine secretion of hormones, such as glucose and glucagon, that regulate glucose metabolism and blood glucose concentration, and exocrine secretion of digestive enzymes that help break down carbohydrates, proteins, and lipids. "Pancreatic organoid" and "mini pancreas" are also used interchangeably herein. In an embodiment, an organoid is a human islet-like organoid ("HILO") as described herein. In an embodiment, a HILO is generated from induced pluripotent stem cells (iPSCs). In an embodiment, the HILO is functionally mature and contains endocrine-like cell types that, upon transplantation, effectively re-establish glucose homeostasis, e.g., in a diabetic mouse model (NOD-SCID mouse). In an embodiment, the HILO is a WNT4-treated HILO (wHILOs). In an embodiment, overexpression of the checkpoint protein PD-L1 in HILOs allowed the HILOs to evade an immune reaction or surveillance by T cells such that they were able to maintain glucose homeostasis in immune-competent diabetic mice (NOD-SCID mice) for a long time period, e.g., at least 50 days. In an embodiment, induction of endogenous PD-L1 expression in HILOs following multiple intermittent ex vivo exposures to interferon gamma (IFNγ) over a given time period, e.g., at least 24 hours, restricts T cell activation and graft rejection. In embodiments, multiple intermittent exposure of cells or HILOs and the cells therein to IFNγ encompasses exposure (e.g., in culture, such as liquid culture or 3D matrix culture) of cells or HILOs and the cells therein to an amount (e.g., low levels) of IFNγ for multiple times, e.g., 2, 3, 4, 5, 6, 7, 8, 9, 10, or more times, over a given time period, with periods of no IFNγ exposure in between. In an embodiment, HILOs that have undergone multiple intermittent exposure to IFNγ so as to express PD-L1 polypeptide as described herein may be referred to as immune evasive HILOs, wHILOs or wHILO$^{ie}$ herein.

By "PD-L1 polypeptide" (also called CD274) is meant a protein or fragment thereof having at least 85%, at least 90%, at least 95%, at least 98%, or at least 99% amino acid sequence identity to the sequence provided at UniProt Accession No. Q9NZQ7-1 and having transcription factor activity. The amino acid sequence is provided at NCBI Accession No. NP_006184.2 is shown below:

```
MRIFAVFIFMTYWHLLNAFTVTVPKDLYVV

EYGSNMTIECKFPVEKQLDLAALIVYWEME

DKNIIQFVHGEEDLKVQHSSYRQRARLLKD

QLSLGNAALQITDVKLQDAGVYRCMISYGG

ADYKRITVKVNAPYNKINQRILVVDPVTSE

HELTCQAEGYPKAEVIWTSSDHQVLSGKTT

TTNSKREEKLFNVTSTLRINTTTNEIFYCT

FRRLDPEENHTAELVIPELPLAHPPNERTH

LVILGAILLCLGVALTFIFRLRKGRMMDVK

KCGIQDTNSKKQSDTHLEET
```

By "PD-L1 polynucleotide" is meant a polynucleotide encoding a PD-L1 polypeptide or fragment thereof. An exemplary PD-L1 polynucleotide sequence is provided at NCBI Accession No.: CCDS59118.1. The sequence provided at NCBI Accession No.: CCDS59118.1 is reproduced below:

Nucleotide Sequence (531 nt):

```
atgaggatatttgctgtctttatattcatgacctactggcatttgct gaacgccccatacaacaaaatcaaccaaagaattttggttgtggatc cagtcacctctgaacatgaactgacatgtcaggctgagggctacccc aaggccgaagtcatctggacaagcagtgaccatcaagtcctgagtgg taagaccaccaccaccaattccaagagagaggagaagcttttcaatg tgaccagcacactgagaatcaacacaacaactaatgagattttctac tgcacttttaggagattagatcctgaggaaaaccatacagctgaatt ggtcatcccagaactacctctggcacatcctccaaatgaaaggactc acttggtaattctgggagccatcttattatgccttggtgtagcactg acattcatcttccgtttaagaaaagggagaatgatggatgtgaaaaa atgtggcatccaagatacaaactcaaagaagcaaagtgatacacatt tggaggagacgtaa
```

By "PAX4 polypeptide" is meant a protein or fragment thereof having at least 85%, at least 90%, at least 95%, at least 98%, or at least 99% amino acid sequence identity to the sequence provided at NCBI Accession No. NP_006184.2 and having transcription factor activity. The amino acid sequence is provided at NCBI Accession No. NP_006184.2 is shown below:

```
  1 MNQLGGLFVN GRPLPLDTRQ QIVRLAVSGM
    RPCDISRILK VSNGCVSKIL GRYYRTGVLE
 61 PKGIGGSKPR LATPPVVARI AQLKGECPAL
    FAWEIQRQLC AEGLCTQDKT PSVSSINRVL
121 RALQEDQGLP CTRLRSPAVL APAVLTPHSG
    SETPRGTHPG TGHRNRTIFS PSQAEALEKE
181 FQRGQYPDSV ARGKLATATS LPEDTVRVWF
    SNRRAKWRRQ EKLKWEMQLP GASQGLTVPR
241 VAPGIISAQQ SPGSVPTAAL PALEPLGPSC
    YQLCWATAPE RCLSDTPPKA CLKPCWGHLP
301 PQPNSLDSGL LCLPCPSSHC HLASLSGSQA
    LLWPGCPLLY GLE
```

By "PAX4 polynucleotide" is meant a polynucleotide encoding a PAX4 polypeptide or fragment thereof. An exemplary PAX4 polynucleotide sequence is provided at NCBI Ref: NM_006193.2. The sequence provided at NCBI Ref: NM_006193.2 is reproduced below:

```
  1 caaagactca cccgtgagcc agctctcaaa
    gaaagcagct tgcgttgaca gcctgggggc
 61 agcaaggatg cagtctccca ggagaggatg
    cactcggtgg tgggaagcca ggctggaggg
121 gcctgagtga ccctctccac aggcgggcag
    ggcagtggga gaggtggtgt gtggatacct
181 ctgtctcacg cccagggatc agcagcatga
    accagcttgg ggggctcttt gtgaatggcc
241 ggcccctgcc tctggatacc cggcagcaga
    ttgtgcggct agcagtcagt ggaatgcggc
301 cctgtgacat ctcacggatc cttaaggtat
    ctaatggctg tgtgagcaag atcctagggc
361 gttactaccg cacaggtgtc ttggagccaa
    agggcattgg gggaagcaag ccacggctgg
421 ctacacccc tgtggtggct cgaattgccc
    agctgaaggg tgagtgtcca gccctctttg
481 cctgggaaat ccaacgccag ctttgtgctg
    aagggctttg cacccaggac aagactccca
541 gtgtctcctc catcaaccga gtcctgcggg
    cattacagga ggaccaggga ctaccgtgca
601 cacggctcag gtcaccagct gttttggctc
    cagctgtcct cactcccat agtggctctg
```

```
 661 agactccccg gggtacccac ccagggaccg
     gccaccggaa tcggactatc ttctccccaa
 721 gccaagcaga ggcactggag aaagagttcc
     agcgtgggca gtatcctgat tcagtggccc
 781 gtggaaagct ggctactgcc acctctctgc
     ctgaggacac ggtgagggtc tggttttcca
 841 acagaagagc caaatggcgt cggcaagaga
     agctcaagtg ggaaatgcag ctgccaggtg
 901 cttcccaggg gctgactgta ccaagggttg
     ccccaggaat catctctgca cagcagtccc
 961 ctggcagtgt gcccacagca gccctgcctg
     ccctggaacc actgggtccc tcctgctatc
1021 agctgtgctg ggcaacagca ccagaaaggt
     gtctgagtga caccccacct aaagcctgtc
1081 tcaagccctg ctggggccac ttgcccccac
     agccgaattc cctggactca ggactgcttt
1141 gccttccttg cccttcctcc cactgtcacc
     tggccagtct tagtggctct caggccctgc
1201 tctggcctgg ctgcccacta ctgtatggct
     tggaatgagg caggagtggg aaggagatgg
1261 catagagaag atctaatacc atcctgccca
     ttgtccttac cgtcctgccc atacagactg
1321 tggctccttc ctccttcctg tgattgctcc
     ctcctgtgtg gacgttgcct ggccctgcct
1381 cgatgcctct ctggcgcatc acctgattgg
     aggggctggt aaagcaacac ccacccactt
1441 ctcacactag ccttaagagg cctccactca
     gcagtaataa aagctgtttt tattagcagt
1501 agttctgttg tccatcatgt tttccctatg
     agcacccta tgcccactct aatattcaac
1561 aattatagac aatttgccct atcatttatt
     tacatctatg tatctaccat ctaatctatg
1621 catgtatgta ggcaatacat gtatctaaac
     aatgtatttg tcaatgcatc aatttaccta
1681 ctctatgtat gcatctatat gtgtattatg
     tatgcgtgca tgcgtgcgcg cacacacaca
1741 cacacacaca cacactgaca ttatatcatg
     gcattttatt cctaaatctt ccagcatgca
1801 tccccaaaaa acaagaaact tgtcttacat
     aatcacaata atatatccac atctaagaaa
```

-continued

```
1861 atttactgta acttcttaat ctaagaaaat tatgtatttt tgtcatatgt attttgtcat 1921 atgtattttg tatttgcata tgtattttgt atttgcatat gtatttttgt catagcagca 1981 aacagagtga aatgccattt ttcatattct
```

By "PAX6 polypeptide" is meant a protein or fragment thereof having at least 85%, at least 90%, at least 95%, at least 98%, or at least 99% amino acid sequence identity to the sequence provided at NCBI Accession No. NP_001297090.1 and having transcription factor activity. The amino acid sequence provided at NCBI Accession No. NP_001297090.1 is shown below:

```
  1 MGADGMYDKL RMLNGQTGSW GTRPGWYPGT

SVPGQPTQDG CQQQEGGGEN TNSISSNGED
```

-continued

```
 61 SDEAQMRLQL KRKLQRNRTS FTQEQIEALE

KEFERTHYPD VFARERLAAK IDLPEARIQV

121 WFSNRRAKWR REEKLRNQRR QASNTPSHIP

ISSSFSTSVY QPIPQPTTPV SSFTSGSMLG

181 RTDTALTNTY SALPPMPSFT MANNLPMQPP

VPSQTSSYSC MLPTSPSVNG RSYDTYTPPH

241 MQTHMNSQPM GTSGTTSTGL ISPGVSVPVQ

VPGSEPDMSQ YWPRLQ
```

By "PAX6 polynucleotide" is meant a polynucleotide encoding a PAX6 polypeptide or fragment thereof. An exemplary PAX6 polynucleotide sequence is provided at NCBI Ref: NM_001310161.1. The sequence provided at NCBI Ref: NM_001310161.1 is reproduced below:

```
   1 cttttcaatt agccttccat gcatgatccg gagcgacttc cgcctatttc cagaaattaa 61 gctcaaactt gacgtgcagc tagtttttatt ttaaagacaa atgtcagaga ggctcatcat 121 attttccccc ctcttctata tttggagctt atttattgct aagaagctca ggctcctggc 181 gtcaatttat cagtaggctc caaggagaag agaggagagg agaggagagc tgaacaggga 241 gccacgtctt ttcctgggag ggctgctatc taagtcgggg ctgcaggtca cagcggagtg 301 aatcagctcg gtggtgtctt tgtcaacggg cggccactgc cggactccac ccggcagaag 361 attgtagagc tagctcacag cggggcccgg ccgtgcgaca tttcccgaat tctgcagacc 421 catgcagatg caaaagtcca agtgctggac aatcaaaacg tgtccaacgg atgtgtgagt 481 aaaattctgg gcaggtatta cgagactggc tccatcagac ccagggcaat cggtggtagt 541 aaaccgagag tagcgactcc agaagttgta agcaaaatag cccagtataa gcgggagtgc 601 ccgtccatct ttgcttggga aatccgagac agattactgt ccgagggggt ctgtaccaac 661 gataacatac caagcgtgtc atcaataaac agagttcttc gcaacctggc tagcgaaaag 721 caacagatgg gcgcagacgg catgtatgat aaactaagga tgttgaacgg gcagaccgga 781 agctggggca cccgccctgg ttggtatccg gggacttcgg tgccagggca acctacgcaa 841 gatggctgcc agcaacagga aggaggggga gagaatacca actccatcag ttccaacgga 901 gaagattcag atgaggctca aatgcgactt cagctgaagc ggaagctgca aagaaataga 961 acatccttta cccaagagca aattgaggcc ctggagaaag agtttgagag aacccattat 1021 ccagatgtgt ttgcccgaga agactagca gccaaaatag atctacctga agcaagaata 1081 caggtatggt tttctaatcg aagggccaaa tggagaagag aagaaaaact gaggaatcag 1141 agaagacagg ccagcaacac acctagtcat attcctatca gcagtagttt cagcaccagt 1201 gtctaccaac caattccaca acccaccaca ccggtttcct ccttcacatc tggctccatg 1261 ttgggccgaa cagacacagc cctcacaaac acctacagcg ctctgccgcc tatgcccagc 1321 ttcaccatgg caaataacct gcctatgcaa cccccagtcc ccagccagac ctcctcatac 1381 tcctgcatgc tgcccaccag cccttcggtg aatgggcgga gttatgatac ctacacccc 1441 ccacatatgc agacacacat gaacagtcag ccaatgggca cctcgggcac cacttcaaca 1501 ggactcattt cccctggtgt gtcagttcca gttcaagttc ccggaagtga acctgatatg 1561 tctcaatact ggccaagatt acagtaaaaa aaaaaaaaaa aaaaaaagg aaaggaaata
```

-continued

```
1621 ttgtgttaat tcagtcagtg actatgggga cacaacagtt gagctttcag gaaagaaaga 1681 aaaatggctg ttagagccgc ttcagttcta caattgtgtc ctgtattgta ccactgggga 1741 aggaatggac ttgaaacaag gacctttgta tacagaaggc acgatatcag ttggaacaaa 1801 tcttcatttt ggtatccaaa ctttttattca ttttggtgta ttatttgtaa atgggcattt 1861 gtatgttata atgaaaaaaa gaacaatgta gactggatgg atgtttgatc tgtgttggtc 1921 atgaagttgt tttttttttt tttaaaaaga aaaccatgat caacaagctt tgccacgaat 1981 ttaagagttt tatcaagata tatcgaatac ttctacccat ctgttcatag tttatggact 2041 gatgttccaa gtttgtatca ttcctttgca tataattaaa cctggaacaa catgcactag 2101 atttatgtca gaaatatctg ttggtttttcc aaaggttgtt aacagatgaa gtttatgtgc 2161 aaaaaagggt aagatataaa ttcaaggaag aaaaaaagtt gatagctaaa aggtagagtg 2221 tgtcttcgat ataatccaat ttgtttttatg tcaaaatgta agtatttgtc ttccctagaa 2281 atcctcagaa tgatttctat aataaagtta atttcattta tatttgacaa gaatatagat 2341 gttttataca cattttcatg caatcatacg tttcttttttt ggccagcaaa agttaattgt 2401 tcttagatat agttgtatta ctgttcacgg tccaatcatt ttgtgcatct agagttcatt 2461 cctaatcaat taaaagtgct tgcaagagtt ttaaacttaa gtgttttgaa gttgttcaca 2521 actacatatc aaaattaacc attgttgatt gtaaaaaacc atgccaaagc ctttgtatttt 2581 cctttattat acagttttct ttttaacctt atagtgtggt gttacaaatt ttatttccat 2641 gttagatcaa cattctaaac caatggttac tttcacacac actctgtttt acatcctgat 2701 gatccttaaa aaataatcct tatagatacc ataaatcaaa aacgtgttag aaaaaaattc 2761 cacttacagc agggtgtaga tctgtgccca tttataccca caacatatat acaaaatggt 2821 aacatttccc agttagccat ttaattctaa agctcaaagt ctagaaataa tttaaaaatg 2881 caacaagcga ttagctagga attgtttttt gaattaggac tggcatttttc aatctgggca 2941 gatttccatt gtcagcctat ttcaacaatg atttcactga agtatattca aaagtagatt 3001 tcttaaagga gactttctga aagctgttgc cttttttcaaa taggccctct ccctttttctg 3061 tctccctccc ctttgcacaa gaggcatcat ttcccattga accactacag ctgttcccat 3121 ttgaatcttg ctttctgtgc ggttgtggat ggttggaggg tggagggggg atgttgcatg 3181 tcaaggaata atgagcacag acacatcaac agacaacaac aaagcagact gtgactggcc 3241 ggtgggaatt aaaggccttc agtcattggc agcttaagcc aaacattccc aaatctatga 3301 agcagggccc attgttggtc agttgttatt tgcaatgaag cacagttctg atcatgttta 3361 aagtggaggc acgcagggca ggagtgcttg agcccaagca aaggatggaa aaaaataagc 3421 ctttgttggg taaaaaagga ctgtctgaga ctttcatttg ttctgtgcaa catataagtc 3481 aatacagata agtcttcctc tgcaaacttc actaaaaagc ctgggggttc tggcagtcta 3541 gattaaaatg cttgcacatg cagaaacctc tggggacaaa gacacacttc cactgaatta 3601 tactctgctt taaaaaaatc cccaaaagca aatgatcaga aatgtagaaa ttaatggaag 3661 gatttaaaca tgaccttctc gttcaatatc tactgttttt tagttaagga attacttgtg 3721 aacagataat tgagattcat tgctccggca tgaaatatac taataattttt attccaccag 3781 agttgctgca catttggaga caccttccta agttgcagtt tttgtatgtg tgcatgtagt 3841 tttgttcagt gtcagcctgc actgcacagc agcacatttc tgcaggggag tgagcacaca 3901 tacgcactgt tggtacaatt gccggtgcag acatttctac ctcctgacat tttgcagcct 3961 acattccctg agggctgtgt gctgagggaa ctgtcagaga agggctatgt gggagtgcat
```

-continued

```
4021 gccacagctg ctggctggct tacttcttcc ttctcgctgg ctgtaatttc caccacggtc 4081 aggcagccag ttccggccca cggttctgtt gtgtagacag cagagacttt ggagacccgg 4141 atgtcgcacg ccaggtgcaa gaggtgggaa tgggagaaaa ggagtgacgt gggagcggag 4201 ggtctgtatg tgtgcacttg ggcacgtata tgtgtgctct gaaggtcagg attgccaggg 4261 caaagtagca cagtctggta tagtctgaag aagcggctgc tcagctgcag aagccctctg 4321 gtccggcagg atgggaacgg ctgccttgcc ttctgcccac accctaggga catgagctgt 4381 ccttccaaac agagctccag gcactctctt ggggacagca tggcaggctc tgtgtggtag 4441 cagtgcctgg gagttggcct tttactcatt gttgaaataa tttttgttta ttatttattt 4501 aacgatacat atatttatat atttatcaat ggggtatctg cagggatgtt ttgacaccat 4561 cttccaggat ggagattatt tgtgaagact tcagtagaat cccaggacta aacgtctaaa 4621 ttttttctcc aaacttgact gacttgggaa aaccaggtga atagaataag agctgaatgt 4681 tttaagtaat aaacgttcaa actgctctaa gtaaaaaaat gcattttact gcaatgaatt 4741 tctagaatat ttttccccca aagctatgcc tcctaaccct taaatggtga acaactggtt 4801 tcttgctaca gctcactgcc atttcttctt actatcatca ctaggtttcc taagattcac 4861 tcatacagta ttatttgaag attcagcttt gttctgtgaa tgtcatctta ggattgtgtc 4921 tatattcttt tgcttatttc ttttttactct gggcctctca tactagtaag atttaaaaa 4981 gcctttttctt ctctgtatgt ttggctcacc aaggcgaaat atatattctt ctcttttttca 5041 tttctcaaga ataaacctca tctgcttttt tgttttttctg tgttttggct tggtactgaa 5101 tgactcaact gctcggtttt aaagttcaaa gtgtaagtac ttagggttag tactgcttat 5161 ttcaataatg ttgacggtga ctatctttgg aaagcagtaa catgctgtct tagaaatgac 5221 attaataatg ggcttaaaca aatgaatagg ggggtccccc cactctcctt ttgtatgcct 5281 atgtgtgtct gatttgttaa aagatggaca gggaattgat tgcagagtgt cgcttccttc 5341 taaagtagtt ttattttgtc tactgttagt atttaaagat cctggaggtg gacataagga 5401 ataaatggaa gagaaaagta gatattgtat ggtggctact aaaaggaaat tcaaaaagtc 5461 ttagaacccg agcacctgag caaactgcag tagtcaaaat atttatctca tgttaaagaa 5521 aggcaaatct agtgtaagaa atgagtacca tatagggttt tgaagttcat atactagaaa 5581 cacttaaaag atatcatttc agatattacg tttggcattg ttcttaagta tttatatctt 5641 tgagtcaagc tgataattaa aaaaaatctg ttaatggagt gtatatttca taatgtatca 5701 aaatggtgtc tatacctaag gtagcattat tgaagagaga tatgtttatg tagtaagtta 5761 ttaacataat gagtaacaaa taatgtttcc agaagaaagg aaaacacatt ttcagagtgc 5821 gtttttatca gaggaagaca aaaatacaca cccctctcca gtagcttatt tttacaaagc 5881 cggcccagtg aattagaaaa acaaagcact tggatatgat ttttggaaag cccaggtaca 5941 cttattattc aaaatgcact tttactgagt ttgaaaagtt tcttttatat ttaaaataag 6001 ggttcaaata tgcatattca attttttatag tagttatcta tttgcaaagc atatattaac 6061 tagtaattgg ctgttaattt tatagacatg gtagccaggg aagtatatca atgacctatt 6121 aagtattttg acaagcaatt tacatatctg atgacctcgt atctcttttt cagcaagtca 6181 aatgctatgt aattgttcca ttgtgtgttg tataaaatga atcaacacgg taagaaaaag 6241 gttagagtta ttaaaataat aaactgacta aaatactcat ttgaatttat tcagaatgtt 6301 cataatgctt tcaaaggaca tagcagagct tttgtggagt atccgcacaa cattatttat 6361 tatctatgga ctaaatcaat ttttgaagt tgctttaaaa tttaaaagca ccttttgctta 6421 atataaagcc ctttaatttt aactgacaga tcaattctga aactttattt tgaaaagaaa
```

-continued

```
6481 atggggaaga atctgtgtct ttagaattaa aagaaatgaa aaaaataaac ccgacattct 6541 aaaaaaatag aataagaaac ctgatttta gtactaatga aatagcgggt gacaaaatag 6601 ttgtcttttt gattttgatc acaaaaaata aactggtagt gacaggatat gatggagaga 6661 tttgacatcc tggcaaatca ctgtcattga ttcaattatt ctaattctga ataaaagctg 6721 tatacagtaa aa
```

By "PDX1 polypeptide" is meant a protein or fragment thereof having at least 85%, at least 90%, at least 95%, at least 98%, or at least 99% amino acid sequence identity to the sequence provided at NCBI Accession No. NP_000200.1 and having transcription factor 15 activity. The amino acid sequence provided at NCBI Accession No. NP_000200.1 is shown below:

```
  1 MNGEEQYYAA TQLYKDPCAF QRGPAPEFSA

SPPACLYMGR QPPPPPPHPF PGALGALEQG

61 SPPDISPYEV PPLADDPAVA HLHHHLPAQL

ALPHPPAGPF PEGAEPGVLE EPNRVQLPFP
```

-continued

```
121 WMKSTKAHAW KGQWAGGAYA AEPEENKRTR

TAYTRAQLLE LEKEFLFNKY ISRPRRVELA

181 VMLNLTERHI KIWFQNRRMK WKKEEDKKRG

GGTAVGGGGV AEPEQDCAVT SGEELLALPP

241 PPPPGGAVPP AAPVAAREGR LPPGLSASPQ

PSSVAPRRPQ EPR
```

By "PDX1 polynucleotide" is meant a polynucleotide encoding a PDX1 polypeptide or fragment thereof. An exemplary PDX1 polynucleotide sequence is provided at NCBI Ref: NM_000209.3. The sequence provided at NCBI Ref: NM_000209.3 is reproduced below:

```
   1 gggtggcgcc gggagtggga acgccacaca gtgccaaatc cccggctcca gctcccgact 61 cccggctccc ggctcccggc tcccggtgcc caatcccggg ccgcagccat gaacggcgag 121 gagcagtact acgcggccac gcagctttac aaggacccat gcgcgttcca gcgaggcccg 181 gcgccggagt tcagcgccag cccccctgcg tgcctgtaca tgggccgcca gccccccgccg 241 ccgccgccgc acccgttccc tggcgccctg ggcgcgctgg agcagggcag cccccccggac 301 atctccccgt acgaggtgcc ccccctcgcc gacgaccccg cggtggcgca ccttcaccac 361 cacctcccgg ctcagctcgc gctcccccac ccgcccgccg ggcccttccc ggagggagcc 421 gagccgggcg tcctggagga gcccaaccgc gtccagctgc ctttcccatg gatgaagtct 481 accaaagctc acgcgtggaa aggccagtgg gcaggcggcg cctacgctgc ggagccggag 541 gagaacaagc ggacgcgcac ggcctacacg cgcgcacagc tgctagagct ggagaaggag 601 ttcctattca acaagtacat ctcacggccg cgccgggtgg agctggctgt catgttgaac 661 ttgaccgaga gacacatcaa gatctggttc caaaaccgcc gcatgaagtg gaaaaaggag 721 gaggacaaga gcgcggcgg cgggacagct gtcgggggtg gcggggtcgc ggagcctgag 781 caggactgcg ccgtgacctc cggcgaggag cttctggcgc tgccgccgcc gccgcccccc 841 ggaggtgctg tgccgcccgc tgcccccgtt gccgcccgag agggccgcct gccgcctggc 901 cttagcgcgt cgccacagcc ctccagcgtc gcgcctcggc ggccgcagga accacgatga 961 gaggcaggag ctgctcctgg ctgaggggct tcaaccactc gccgaggagg agcagagggc 1021 ctaggaggac cccgggcgtg gaccacccgc cctggcagtt gaatggggcg gcaattgcgg 1081 ggcccacctt agaccgaagg ggaaaacccg ctctctcagg cgcatgtgcc agttggggcc 1141 ccgcgggtag atgccggcag gccttccgga agaaaaagag ccattggttt ttgtagtatt 1201 ggggccctct tttagtgata ctggattggc gttgtttgtg gctgttgcgc acatccctgc 1261 cctcctacag cactccacct tgggacctgt ttagagaagc cggctcttca aagacaatgg 1321 aaactgtacc atacacattg gaaggctccc taacacacac agcggggaag ctgggccgag
```

-continued

```
1381 taccttaatc tgccataaag ccattcttac tcgggcgacc cctttaagtt tagaaataat 1441 tgaaaggaaa tgtttgagtt ttcaaagatc ccgtgaaatt gatgccagtg gaatacagtg 1501 agtcctcctc ttcctcctcc tcctcttccc cctcccttc ctcctcctcc tcttcttttc 1561 cctcctcttc ctcttcctcc tgctctcctt tcctccccct cctcttttcc ctcctcttcc 1621 tcttcctcct gctctccttt cctccccctc ctctttctcc tcctcctcct cttcttcccc 1681 ctcctctccc tcctcctctt cttcccctc ctctccctcc tcctcttctt ctccctcctc 1741 ttcctcttcc tcctcttcca cgtgctctcc tttcctcccc ctcctcttgc tccccttctt 1801 ccccgtcctc ttcctcctcc tcctcttctt ctccctcctc ttcctcctcc tctttcttcc 1861 tgacctcttt ctttctcctc ctcctccttc tacctcccct tctcatccct cctcttcctc 1921 ttctctagct gcacacttca ctactgcaca tcttataact tgcacccctt tcttctgagg 1981 aagagaacat cttgcaaggc agggcgagca gcggcagggc tggcttagga gcagtgcaag 2041 agtccctgtg ctccagttcc acactgctgg cagggaaggc aaggggggac gggcctggat 2101 ctgggggtga gggagaaaga tggacccctg ggtgaccact aaaccaaaga tattcggaac 2161 tttctattta ggatgtggac gtaattcctg ttccgaggta gaggctgtgc tgaagacaag 2221 cacagtggcc tggtgcgcct tggaaaccaa caactattca cgagccagta tgaccttcac 2281 atctttagaa attatgaaaa cgtatgtgat tggagggttt ggaaaaccag ttatcttatt 2341 taacatttta aaaattacct aacagttatt tacaaacagg tctgtgcatc ccaggtctgt 2401 cttcttttca aggtctgggc cttgtgctcg ggttatgttt gtgggaaatg cttaataaat 2461 actgataata tgggaagaga tgaaaactga ttctcctcac tttgtttcaa acctttctgg 2521 cagtgggatg attcgaattc acttttaaaa ttaaattagc gtgttttgtt ttg
```

By "PTF1 polypeptide" is meant a protein or fragment thereof having at least 85%, at least 90%, at least 95%, at least 98%, or at least 99% amino acid sequence identity to the sequence provided at NCBI Accession No. NP_835455.1 and having transcription factor activity. The amino acid sequence provided at NCBI Accession No. NP_835455.1 is shown below.

```
  1 MDAVLLEHFP GGLDAFPSSY FDEDDFFTDQ

SSRDPLEDGD ELLADEQAEV EFLSHQLHEY

61 CYRDGACLLL QPAPPAAPLA LAPPSSGGLG

EPDDGGGGGY CCETGAPPGG FPYSPGSPPS

121 CLAYPCAGAA VLSPGARLRG LSGAAAAAAR

RRRRVRSEAE LQQLRQAANV RERRRMQSIN
```

-continued

```
181 DAFEGLRSHI PTLPYEKRLS KVDTLRLAIG

YINFLSELVQ ADLPLRGGGA GGCGGPGGGG

241 RLGGDSPGSQ AQKVIICHRG TRSPSPSDPD

YGLPPLAGHS LSWTDEKQLK EQNIIRTAKV

301 WTPEDPRKLN SKSSFNNIEN EPPFEFVS
```

By "PTF1 polynucleotide" is meant a polynucleotide encoding a PTF1 polypeptide or fragment thereof. An exemplary PTF1 polynucleotide sequence is provided at NCBI Ref: NM_178161.2. The sequence provided at NCBI Ref: NM_178161.2 is reproduced below:

```
  1 atggacgcgg tgttgctgga gcacttcccc ggggggcctag acgcctttcc ttcttcgtac 61 ttcgacgagg acgacttctt caccgaccag tcttcacggg accccctgga ggacggcgat 121 gagctgctgg cggacgagca ggccgaggtg gagttcctta gccaccagct ccacgagtac 181 tgctaccgcg acggggcgtg cctgctgctg cagcccgcgc ccccggccgc cccgctagcg 241 ctcgccccgc cgtcctcggg gggcctcggt gagccagacg acggcggcgg cggcggctac 301 tgctgcgaga cggggcgccc ccaggcggc ttcccctact cgcccggctc gccgccctcg 361 tgcctggcct accgtgcgc cggggcggca gtactgtctc ccgggcgcg gctgcgcggc
```

```
                         -continued
 421 ctgagcggag cggcggctgc ggcggcgcgg cgccggcggc gggtgcgctc cgaggcggag 481 ctgcagcagc tgcggcaggc ggccaacgtg cgcgagcggc ggcgcatgca gtccatcaac 541 gacgccttcg aggggctgcg ctcgcacatc cccacgctgc cctacgagaa gcgcctctcc 601 aaggtggaca cgctgcgcct ggccatcggc tacatcaact tcctcagcga gctcgtgcag 661 gccgacctgc ccttgcgcgg cggtggcgcg ggcggctgcg ggggccgggg cggcggcggg 721 cgcctgggcg gggacagccc gggcagccag gcccagaagg tcatcatctg ccatcggggc 781 acccggtccc cctcccccag cgaccctgat tatggcctcc ctcccctagc aggacactct 841 ctctcatgga ctgatgaaaa acaactcaag gaacaaaata ttatccgaac agccaaagtc 901 tggaccccag aggaccccag aaaactcaac agcaaatctt ccttcaacaa catagaaaac 961 gaaccaccat ttgagtttgt gtcctgagaa gtcccagact cggctgaaga tctgattatg 1021 tctctgtgca tattgtacat gtaaatatct ataatgtaaa tgtaatttaa gaatcaaatt 1081 tttcgaatgg caatcaactg tttattattt atctatttat tatcctgttg agttgatgaa 1141 atagatgatt tctttttaaa tatataattt atataactta tcctgatttt ctgaaaatat 1201 gcaatagcct atgattttcc tgaactctgt gttgttggga gaactctggc cagaaaacgt 1261 cctgcttatt tattgccaga tatggtttat ttctaagcgt tgtcaataaa tgctatttac 1321 accttttcct gaaaaaaaa
```

By "Wnt3a polynucleotide" is meant a polynucleotide encoding a Wnt3a polypeptide or a fragment thereof. An exemplary human Wnt3a polynucleotide sequence is provided at NCBI GenBank Accession No. AB060284.1. The polynucleotide sequence provided at NCBI GenBank Accession No. AB060284.1 is reproduced below:

```
   1 cggcgatggc cccactcgga tacttcttac tcctctgcag cctgaagcag gctctgggca 61 gctacccgat ctggtggtcg ctggctgttg ggccacagta ttcctccctg ggctcgcagc 121 ccatcctgtg tgccagcatc ccgggcctgg tccccaagca gctccgcttc tgcaggaact 181 acgtggagat catgcccagc gtggccgagg gcatcaagat tggcatccag gagtgccagc 241 accagttccg cggccgccgg tggaactgca ccaccgtcca cgacagcctg gccatcttcg 301 ggcccgtgct ggacaaagct accagggagt cggcctttgt ccacgccatt gcctcagccg 361 gtgtggcctt tgcagtgaca cgctcatgtg cagaaggcac ggccgccatc tgtggctgca 421 gcagccgcca ccagggctca ccaggcaagg gctggaagtg gggtggctgt agcgaggaca 481 tcgagtttgg tgggatggtg tctcgggagt tcgccgacgc ccgggagaac cggccagatg 541 cccgctcagc catgaaccgc cacaacaacg aggctgggcg ccaggccatc gccagccaca 601 tgcacctcaa gtgcaagtgc cacgggctgt cgggcagctg cgaggtgaag acatgctggt 661 ggtcgcaacc cgacttccgc gccatcggtg acttcctcaa ggacaagtac gacagcgcct 721 cggagatggt ggtggagaag caccgggagt cccgcggctg ggtggagacc ctgcggccgc 781 gctacaccta cttcaaggtg cccacggagc gcgacctggt ctactacgag gcctcgccca 841 acttctgcga gcccaaccct gagacgggct ccttcggcac gcgcgaccgc acctgcaacg 901 tcagctcgca cggcatcgac ggctgcgacc tgctgtgctg cggccgcggc cacaacgcgc 961 gagcggagcg gcgccgggag aagtgccgct gcgtgttcca ctggtgctgc tacgtcagct 1021 gccaggagtg cacgcgcgtc tacgacgtga cacctgcaa gtaggcaccg gccgcggctc 1081 ccctggacg gggcgggccc tgcctgaggg tgggctttc cctgggtgga gcaggactcc 1141 cacctaaacg gggcagtact cctccctggg ggcgggactc ctccctgggg gtggggctcc 1201 tacctggggg cagaactcct acctgaaggc agggctcctc cctggagcta gtgtctcctc
```

-continued

```
1261 tctggtggct gggctgctcc tgaatgaggc ggagctccag gatggggagg ggctctgcgt 1321 tggcttctcc ctggggacgg ggctcccctg gacagaggcg gggctacaga ttgggcgggg 1381 cttctcttgg gtgggacagg gcttctcctg cggggcgag gccctccca gtaagggcgt 1441 ggctctgggt gggcggggca ctaggtaggc ttctacctgc aggcggggct cctcctgaag 1501 gaggcggggc tctaggatgg ggcacggctc tggggtaggc tgctccctga gggcg
```

By "Wnt3a polypeptide" is meant a Wnt3a polypeptide or a fragment thereof, or a polypeptide having at least 85%, at least 90%, at least 95%, at least 98%, or at least 99% amino acid sequence identity to the human Wnt3a polypeptide sequence. An exemplary human Wnt3a polypeptide sequence is provided at NCBI GenBank: AAI03924.1. The sequence provided at GenBank: AAI03924.1 is reproduced below:

```
  1 MAPLGYFLLL CSLKQALGSY PIWWSLAVGP

QYSSLGSQPI LCASIPGLVP KQLRFCRNYV

61 EIMPSVAEGI KIGIQECQHQ FRGRRWNCTT

VHDSLAIFGP VLDKATRESA FVHAIASAGV

121 AFAVTRSCAE GTAAICGCSS RHQGSPGKGW

KWGGCSEDIE FGGMVSREFA DARENRPDAR
```

-continued

```
181 SAMNRHNNEA GRQAIASHMH LKCKCHGLSG

SCEVKTCWWS QPDFRAIGDF LKDKYDSASE

241 MVVEKHRESR GWVETLRPRY TYFKVPTERD

LVYYEASPNF CEPNPETGSF GTRDRTCNVS

301 SHGIDGCDLL CCGRGHNARA ERRREKCRCV

FHWCCYVSCQ ECTRVYDVHT CKNPGSRAGN

361 SAHQPPHPQP PVRFHPPLRR AGKVP
```

By "Wnt4 polynucleotide" is meant a polynucleotide encoding Wnt4 polypeptide or a fragment thereof. An exemplary human Wnt4 polynucleotide sequence is provided at NCBI GenBank Accession No. AY009398.1. Accession number NCBI Ref NG_008974.1 is a reference standard Wnt4a polynucleotide sequence. The polynucleotide sequence provided at NCBI GenBank Accession No. AY009398.1 is reproduced below:

```
   1 atgagtcccc gctcgtgcct gcgttcgctg cgcctcctcg tcttcgccgt cttctcagcc 61 gccgcgagca actggctgta cctggccaag ctgtcgtcgg tggggagcat ctcagaggag 121 gagacgtgcg agaaactcaa gggcctgatc cagaggcagg tgcagatgtg caagcggaac 181 ctggaagtca tggactcggt gcgccgcggt gcccagctgg ccattgagga gtgccagtac 241 cagttccgga accggcgctg gaactgctcc acactcgact ccttgcccgt cttcggcaag 301 gtggtgacgc aagggattcg ggaggcggcc ttggtgtacg ccatctcttc ggcaggtgtg 361 gcctttgcag tgacgcgggc gtgcagcagt ggggagctgg agaagtgcgg ctgtgacagg 421 acagtgcatg gggtcagccc acagggcttc cagtggtcag gatgctctga caacatcgcc 481 tacggtgtgg ccttctcaca gtcgtttgtg gatgtgcggg agagaagcaa gggggcctcg 541 tccagcagag ccctcatgaa cctccacaac aatgaggccg gcaggaaggc catcctgaca 601 cacatgcggg tggaatgcaa gtgccacggg gtgtcaggct cctgtgaggt aaagacgtgc 661 tggcgagccg tgccgccctt ccgccaggtg ggtcacgcac tgaaggagaa gtttgatggt 721 gccactgagg tggagccacg ccgcgtgggc tcctccaggg cactggtgcc acgcaacgca 781 cagttcaagc cgcacacaga tgaggacttg gtgtacttgg agcctagccc cgacttctgt 841 gagcaggaca tgcgcagcgg cgtgctgggc acgaggggcc gcacatgcaa caagacgtcc 901 aaggccatcg acggctgtga gctgctgtgc tgtggccgcg gcttccacac ggcgcaggtg 961 gagctggctg aacgctgcag ctgcaaattc cactggtgct gcttcgtcaa gtgccggcag 1021 tgccagcggc tcgtggagtt gcacacgtgc cgatga
```

By "Wnt4 polypeptide" is meant a Wnt4 polypeptide or a fragment thereof, or a polypeptide having at least 85%, at least 90%, at least 95%, at least 98%, or at least 99% amino acid sequence identity to the human Wnt4 polypeptide sequence. An exemplary human Wnt4 polypeptide sequence is provided at NCBI GenBank Accession No.: AAG38658.1. The sequence provided at GenBank Accession No.: AAG38658.1 is reproduced below:

```
  1 MSPRSCLRSL RLLVFAVFSA AASNWLYLAK

LSSVGSISEE ETCEKLKGLI QRQVQMCKRN

61 LEVMDSVRRG AQLAIEECQY QFRNRRWNCS

TLDSLPVFGK VVTQGIREAA LVYAISSAGV

121 AFAVTRACSS GELEKCGCDR TVHGVSPQGF

QWSGCSDNIA YGVAFSQSFV DVRERSKGAS

181 SSRALMNLHN NEAGRKAILT HMRVECKCHG

VSGSCEVKTC WRAVPPFRQV GHALKEKFDG

241 ATEVEPRRVG SSRALVPRNA QFKPHTDEDL

VYLEPSPDFC EQDMRSGVLG TRGRTCNKTS

301 KAIDGCELLC CGRGFHTAQV ELAERCSCKF

HWCCFVKCRQ CQRLVELHTC R
```

By "Wnt5a polynucleotide" is meant a polynucleotide encoding Wnt5a polypeptide or a fragment thereof. An exemplary polynucleotide sequence coding for human Wnt5a is provided at NCBIRef: GenBank NM_003392, a reference standard sequence. Nucleotides 658-1800 of the Wnt5a genomic sequence having 6194 nucleotides codes for a human Wnt5a polypeptide. The polynucleotide sequence of the human Wnt5a coding sequence provided at bases 658-1800 of NCBI Ref: GenBank NM_003392 is reproduced below:

```
 658 atg 661 aagaagtcca ttggaatatt aagcccagga gttgctttgg ggatggctgg aagtgcaatg 721 tcttccaagt tcttcctagt ggctttggcc atatttttct ccttcgccca ggttgtaatt 781 gaagccaatt cttggtggtc gctaggtatg aataaccctg ttcagatgtc agaagtatat 841 attataggag cacagcctct ctgcagccaa ctggcaggac tttctcaagg acagaagaaa 901 ctgtgccact tgtatcagga ccacatgcag tacatcggag aaggcgcgaa gacaggcatc 961 aaagaatgcc agtatcaatt ccgacatcga aggtggaact gcagcactgt ggataacacc 1021 tctgtttttg gcagggtgat gcagataggc agccgcgaga cggccttcac atacgcggtg
```

```
1081 agcgcagcag gggtggtgaa cgccatgagc cgggcgtgcc gcgagggcga gctgtccacc 1141 tgcggctgca gccgcgccgc gcgccccaag gacctgccgc gggactggct ctggggcggc 1201 tgcggcgaca acatcgacta tggctaccgc tttgccaagg agttcgtgga cgcccgcgag 1261 cgggagcgca tccacgccaa gggctcctac gagagtgctc gcatcctcat gaacctgcac 1321 aacaacgagg ccggccgcag gacggtgtac aacctggctg atgtggcctg caagtgccat 1381 ggggtgtccg gctcatgtag cctgaagaca tgctggctgc agctggcaga cttccgcaag 1441 gtgggtgatg ccctgaagga gaagtacgac agcgcggcgg ccatgcggct caacagccgg 1501 ggcaagttgg tacaggtcaa cagccgcttc aactcgccca ccacacaaga cctggtctac 1561 atcgacccca gccctgacta ctgcgtgcgc aatgagagca ccggctcgct gggcacgcag 1621 ggccgcctgt gcaacaagac gtcggagggc atggatggct gcgagctcat gtgctgcggc 1681 cgtggctacg accagttcaa gaccgtgcag acggagcgct gccactgcaa gttccactgg 1741 tgctgctacg tcaagtgcaa gaagtgcacg gagatcgtgg accagtttgt gtgcaagtag
```

By "Wnt5a polypeptide" is meant a Wnt5a polypeptide or a fragment thereof, or a polypeptide having at least 85%, at least 90%, at least 95%, at least 98%, or at least 99% amino acid sequence identity to the human Wnt5a polypeptide sequence. An exemplary human Wnt5a (isoform 1) polypeptide sequence is provided at UniProtKB Identifier: P41221-1. The sequence provided at UniProtKB Identifier: P41221-1 is reproduced below:

```
  1 MKKSIGILSP GVALGMAGSA MSSKFFLVAL

AIFFSFAQVV IEANSWWSLG

51 MNNPVQMSEV YIIGAQPLCS QLAGLSQGQK

KLCHLYQDHM QYIGEGAKTG

101 IKECQYQFRH RRWNCSTVDN TSVFGRVMQI

GSRETAFTYA VSAAGVVNAM

151 SRACREGELS TCGCSRAARP KDLPRDWLWG

GCGDNIDYGY RFAKEFVDAR

201 ERERIHAKGS YESARILMNL HNNEAGRRTV

YNLADVACKC HGVSGSCSLK
```

```
                   -continued
    251 TCWLQLADFR KVGDALKEKY DSAAAMRLNS

RGKLVQVNSR FNSPTTQDLV

301 YIDPSPDYCV RNESTGSLGT QGRLCNKTSE

GMDGCELMCC GRGYDQFKTV

351 QTERCHCKFH WCCYVKCKKC TEIVDQFVCK
```

An "immune checkpoint protein or molecule" or "immune checkpoint" refers to a specific subtype of transmembrane protein molecule that provides fine-tuning of the immune response. In normal tissues, immune checkpoints are inhibitory signals and play an important role in immune cell function by preventing autoimmunity. In a subject with a tumor or cancer, up-regulation of immune checkpoint proteins on the tumor or cancer cells allows tumors and cancers to escape immune surveillance and evade anti-tumor immunity. Nonlimiting examples of immune checkpoint proteins that have been the focus of clinical immunotherapeutics are cytotoxic T-lymphocyte-associated antigen 4 (CTLA-4), programmed cell death protein 1 (PD-1), and programmed cell death protein ligand 1 (PD-L1). CTLA-4, also known as CD152, is essential for the activation of CD4$^+$ T cells and the priming phase of the immune response. PD-1, also known as CD279 and formerly as B7.1, is a key immune checkpoint receptor expressed by activated T cells, B cells and myeloid cells, and mediates immunosuppression. PD-L1, also known as CD274 and formerly as B7-H1, is an immune regulatory protein that plays a significant role in suppressing the immune system during certain disease states, including cancer and autoimmune disease. PD-L1 is the cognate ligand that binds to PD-1 to modulate activation or inhibition of immune cells. Under normal circumstances, the immune system reacts to foreign antigens that are associated with exogenous or endogenous agents, e.g., microorganisms or cells, which triggers the proliferation of antigen-specific cytotoxic CD8+ T cells and/or CD4+ helper T cells. The binding of PD-L1 to PD-1 transmits an inhibitory signal that reduces the proliferation of the antigen-specific T cells in lymph nodes, while simultaneously reducing apoptosis in regulatory T cells (anti-inflammatory, suppressive T cells).

The $K_d$ (dissociation constant), which reflects the binding affinity between PD-L1 and PD-1, is 770 nM. PD-L1 also has an appreciable affinity for the costimulatory molecule CD80 (B7-1), but not for CD86 (B7-2). The affinity of PD-L1 of CD80 is 1.4 µM, which is a value that is intermediate between the affinity of PD-L1 for CD28 and CTLA-4 (4.0 µM and 400 nM, respectively). The related molecule PD-L2 does not have affinity for CD80 or CD86, but shares PD-1 as a receptor (with a stronger $K_d$ of 140 nM). PD-1 is up-regulated on activated CD4 T-cells and can bind to PD-L1-expressing monocytes to induce the production of IL-10. (E. A. Said et al., 2010, *Nature Medicine*, 16(4):452-459). The interaction of PD-L1 with its receptor PD-1 on T cells delivers a signal that inhibits T cell receptor (TCR)-mediated activation of IL-2 production and T cell proliferation. The PD-1/PD-L1 interaction has been implicated in autoimmunity. By way of example, NOD mice, an animal model for autoimmunity, exhibit a susceptibility to spontaneous development of type I diabetes and other autoimmune diseases and have been shown to develop a precipitated onset of diabetes from the blockade of PD-1 or PD-L1 (but not PD-L2), (M. J. Ansari et al., 2003, *J. Exp. Med.*, 198(1):63-69).

By "immune surveillance" or "immunological surveillance" is meant a monitoring process by cells of the immune system to detect and destroy cells that are recognized as non-self, other, or allogeneic in the tissues and organs of the body. For example, such non-self cells may be virally-infected, mutated, neoplastically transformed, or may express a cell surface molecule that is not recognized as a self or autologous molecule by cells of the immune system.

By "progenitor cell" is meant a cell that a multipotent stem cell that is capable of generating (e.g., by differentiation or division) an endothelial cell. A progenitor cell that is capable of generating an endothelial cell may express this capability when grown under appropriate in vitro or in vivo conditions, such as those described herein.

By "progeny" is meant a cell derived from a multipotent stem cell of the invention. Progeny include without limitation progenitor cells, differentiated cells, and terminally differentiated cells.

By "derived from" is meant "obtained from" or the process of obtaining a progeny cell.

By "reduces" is meant a negative alteration of at least 10%, 25%, 50%, 75%, or 100%.

By "reference" or "control" is meant a standard condition. For example, an untreated or healthy (nondiseased) cell, tissue, or organ that is used as a reference.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, at least about 20 amino acids, or at least about 25 amino acids. The length of the reference polypeptide sequence can be about 35 amino acids, about 50 amino acids, or about 100 amino acids. For nucleic acids, the length of the reference nucleic acid sequence will generally be at least about 50 nucleotides, at least about 60 nucleotides, or at least about 75 nucleotides. The length of the reference nucleic acid sequence can be about 100 nucleotides, about 300 nucleotides or any integer thereabout or therebetween.

A "somatic" cell refers to a cell that is obtained from a tissue of a subject. Such subjects are at a post-natal stage of development (e.g., adult, infant, child). In contrast, an "embryonic cell" or "embryonic stem cell" is derived from an embryo at a pre-natal stage of development.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, or at least about 50% formamide. Stringent temperature conditions will ordinarily include temperatures of at least about 30° C., at least about 37° C., and at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In another embodiment, hybridization will occur at 37° C. in 500 mM NaCl, 50 mM trisodium citrate, 1% SDS, 35% formamide, and 100 µg/ml denatured salmon sperm DNA (ssDNA). In yet another embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will be less than about 30 mM NaCl and 3 mM trisodium citrate, or less than about 15 mM NaCl and 1.5 mM trisodium citrate. Stringent temperature conditions for the wash steps will ordinarily include a temperature of at least about 25° C., at least about 42° C., and at least about 68° C. In one embodiment, wash steps will occur at 25° C. in 30 mM NaCl, 3 mM trisodium citrate, and 0.1% SDS. In another embodiment, wash steps will occur at 42 C in 15 mM NaCl, 1.5 mM trisodium citrate, and 0.1% SDS. In yet another embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Such a sequence is at least 60%, at least 80%, at least 85%, at least 90%, at least 95% or even at least 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

The term "self-renewal" as used herein refers to the process by which a stem cell divides to generate one (asymmetric division) or two (symmetric division) daughter cells with development potentials that are indistinguishable from those of the mother cell. Self renewal involves both proliferation and the maintenance of an undifferentiated state.

The term "stem cell" is meant a pluripotent cell or multipotent stem cell having the capacity to self-renew and to differentiate into multiple cell lineages.

By "subject" is meant a mammal, including, but not limited to, a human or non-human mammal, such as a non-human primate, bovine, equine, canine, ovine, rodent, or feline. In a particular embodiment, a subject is a human subject, such as a human patient.

Ranges provided herein are understood to be shorthand for all of the values within the range, inclusive of the first and last values. By way of nonlimiting example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

By "tissue" is meant a collection of cells having a similar morphology and function.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

By "vascularized" is meant having a blood vessel. In some embodiments, the pancreatic islet organoid or pancreatic organoid is vascularized.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided and described herein.

BRIEF DESCRIPTION OF THE DRAWINGS

FIG. 1A (top) shows the results of a Principal Component analysis of transcriptomes from human iPSCs (hiPSCs), primary human pancreatic epithelial cells (hPanc Epithelial), human adipose-derived stem cells (hADSCs), human pancreatic fibroblasts (hPanc Fibroblast), human umbilical vein endothelial cells (HUVECs) and human pancreatic microvascular endothelial cells (hPanc Endothelial). FIG. 1A (bottom) shows a time course of human adipose-derived stem cell (hADSC) culture in Matrigel (1:1 dilution in hADSC medium, 2 million cells in 300 μl) showing intrinsic self-organization (Scale bar 1 mm). FIG. 1B shows a schematic of the generation of multicellular islet-like spheroids (MCS) and islet-like spheroid (IS). hiPSC-derived endocrine progenitor cells (EP) were co-cultured with hADSC and endothelial cells (ECs, HUVECs) in gellan gum-based 3D culture system (left). EPs are multipotent cells that differentiate into endocrine cells including α, β, δ, ε, pancreatic polypeptide and G cells, as defined by the expression of neurogenin 3, neurod1, Nkx2.2 and Pax4 biomarkers (Rezania, A. et al., 2014, *Nature Biotechnology*, 32:1121-1133). MCS generated in the matrigel environment show the incorporation of ECs (mCherry expression) and insulin expression as detected by Green Fluorescent Protein (GFP) expression, right). (Scale bar 100 sm). FIG. 1C illustrates multicellular islet-like spheroids (MCS) cultured in the 3D gellan gum system showing insulin expression (GFP, upper panel). Electron microscopy images of MCS showing insulin granules (lower right) and lipid droplets in hADSC (lower right). FIG. 1D presents graphs of gene expression in sorted insulin-expressing cells (GFP⁺) in islet-like spheroids (IS; hiPSC derived β-like cells generated in the absence of hADSCs and ECs), MCSs, or human islets (hislets). FIG. 1E presents a graph demonstrating human c-peptide secretion in response to 3 mM (G3) or 20 mM (G20) glucose from IS, MCS and hislets. FIG. 1F presents a graph demonstrating random fed blood glucose levels in STZ-induced diabetic NOD-SCID mice after sham treatment or transplantation of MCS (500) or human islets. FIG. 1G presents a graph demonstrating serum human c-peptide levels during feeding, fasting, and refeeding cycles in mice from 4 weeks after transplantation. Error bars represent SEM. *p<0.05, p<0.01, *p<0.001.

FIGS. 2A-2F provide a heat map, graphs and plots demonstrating the expression of non-canonical Wnts in endocrine and supportive cells in human islets. FIG. 2A presents a heatmap of expression changes during hADSC culture in Matrigel. A significantly affected gene ontology category is presented at the right, namely, Wnt5a and downstream signaling (5.1e-03). FIG. 2B presents a graph showing tSNE clustering of temporal expression of WNTs during hADSC self organization as shown in FIG. 2A. FIG.

2C presents a graph and heatmap showing relative expression of WNTs in human islets (n=5). FIG. 2D shows t-SNE clustering of human islet single cell transcriptomes (n=3245). Annotated cell types are assigned based on known marker gene expression. FIGS. 2E and 2F show a single cell plot and violin plots, respectively, of WNT2B, WNT4, WNT5A, WNT7A, WNT7B and WN79A expression in human islets. Error bar represents ±SEM.

FIGS. 3A-3K provide schematics, images, heatmaps and graphs related to the generation of human islets like organoids (HILOs) and the induction of functional maturation of HILOs by WNT4. FIG. 3A presents a schematic of human islet-like organoid (HILO) generation. FIG. 3B shows representative images of HILOs in 3D culture (left) and insulin expression (human insulin promoter driven GFP (right, scale bar 100 μm). FIG. 3C depicts electron microscopy images showing insulin and glucagon granules in β and α cells, respectively, in WNT4-treated HILOs ("wHILOs") and human islets. Scale bar, 1 μm. FIG. 3D-1 presents a heatmap of relative expression of key islets genes in hiPSCs, HILOs treated with PBS (P) or WNT4 (W), and in human islets (log₂ expression with Z-score). FIG. 3D-2 presents plots showing the relative expression of ISL1, SYT7, PDX1, GCK, NEUROD1, NKX2-2, INSULIN, NKX6-1, MAFA, MAFB and UCN3 in wHILOs and human islets as determined by qPCR (n=8 per sample type). FIG. 3E is a gene ontology map of genes that are up- and down-regulated in HILOs by treatment with WNT4 (100 ng/ml from day26 to day33). FIG. 3F shows the relative expression of ERRγ, NDUFA7 and COX7A2 in HILOs treated with increasing concentrations of WNT4 (0, 10, 25, 50, 200 ng/ml) for 5 days. FIG. 3G presents a heatmap of relative expressions of oxidative phosphorylation genes in 3D cultured hiPSCs, HILOs with PBS and HILOs with WNT4 treatment (wHILOs), and human islets (Z-Score). FIG. 3H is a graph demonstrating oxygen consumption rates (OCRs) measured in hiPSC spheroids on day 0 (upside down triangle), PBS treated HILOs (upright triangle), WNT4 treated HILOs (square) and human islets (circle). FIG. 3I presents a graph showing in vitro human c-peptide secretion in response to 3 mM (G3) or 20 mM (G20) glucose or 20 mM KCl (K20) from HILOs generated with and without WNT4 treatment. FIG. 3J presents a cartoon schematic depicting culture conditions for commercially available hiPSC-derived β-like cells (left) and light microscopy images of cultured cells (right). FIG. 3K presents a bar graph showing in vitro c-peptide secretion in response to 3 mM (G3) and 20 mM (G20) glucose from cultures described in FIG. 7D-2.

FIG. 4A shows tSNE clustering of single cell transcriptomes from WNT4 treated HILOs (wHILOs, n=4840). FIG. 4B is a graph showing relative cell type populations in HILOs and human islets. FIG. 4C presents a graph demonstrating random fed blood glucose levels after transplantation of wHILOs with or without PD-L1 expression (in kidney/kidney capsule of induced diabetic C57BL6J mice (n=11 and 9 mice, respectively). The top plot on the graph represents wHILOs (–); the middle plot on the graph represents wHILOs (PD-L1 expression); the bottom plot on the graph represents mislets. FIG. 4D presents flow cytometric analysis of insulin-expressing and mouse immune (CD45⁺) cells recovered from kidney capsule grafts 27 days after transplantation of wHILOs with and without PD-L1 expression. Grafts containing HILOs expressing PD-L1, which can potentially bind to PD-1 on T cells (e.g., CD45+ cells), thereby suppressing T cell activation and killing activity, show fewer infiltrating CD45+ T cells compared with grafts containing HILOs that do not express PD-L1. FIG. 4E shows the quantification of the analysis of blood glucose levels in STZ-induced diabetic mice after transplantation of wHILOs with or without PD-L1 expression, as shown in FIG. 4D (Error bars represent SEM. *p<0.05, p<0.01, *p<0.001). FIG. 4F presents a flow cytometry analysis of insulin expressing and mouse immune (CD45$^+$) cells recovered from kidney capsule grafts 27 days after transplantation of wHILOs with and without PD-L1 expression. CD45$^+$ cells were further categorized as B cells (CD19$^+$), T cells (CD3$^+$) and NK cells (NK1.1$^+$). FIG. 4G shows dot plots of the quantification of the analysis described for FIG. 4F (n=6 and 6). FIG. 4H shows an image of wHILO (PD-L1) cells in a kidney graft 27 days after transplantation (insulin promoter driven GFP expression). Scale bar, 100 μm Error bars represent ±SEM. *p<0.05. FIG. 4I presents a schematic showing transplantation of wHILOs with and without PD-L1 overexpression (500 HILOs per mouse) into multi low dose streptozotocin (MLD-STZ, 50 mg/kg/day for 5 days) induced diabetic Hu-PBMC-NSG mice. FIG. 4J presents a flow cytometric analysis of human T cells (CD4$^+$ and CD8$^+$ cells in CD45$^+$/CD3$^+$ population) in PBMC from Hu-PBMC-NSG mice (n=15 mice) 3 weeks after human PBMC transplantation. FIG. 4K shows a graph of random fed blood glucose levels in MLD-STZ induced diabetic Hu-PBMC-NSG mice after transplantation of wHILOs with or without PD-L1 expression (n=6 and 6 mice). FIG. 4L shows a graph of serum human c-peptide levels in mice described in FIG. 4K FIG. 4M presents a flow cytometric analysis of insulin-expressing and human CD45$^+$ immune cells recovered from kidney capsule grafts 27 days after transplantation of wHILOs, with and without PD-L1 expression.

FIG. 5A presents a graph showing PD-L1 expression in islet (wHILOs) cells sorted by flow cytometry based on insulin expression (GFP+ and GFP−, respectively) after IFNγ treatment (10 ng/ml, 12 hours). The GFP+ cells comprise β-like cells; the GFP− cells comprise alpha (α), delta (δ) and epsilon (ε) cells. FIG. 5B presents a graph showing temporal PD-L1 expression in wHILOs after a single IFNγ treatment (10 ng/ml, 2 hours). FIG. 5C is a schematic illustrating IFNγ (10 ng/ml) pulse treatment of wHILOs. (MPS treatment). FIG. 5D presents a graph showing PD-L1 expression induced by indicated cycles of IFNγ treatment, 7 days after last treatment. FIG. 5E presents a graph of PD-L1 protein levels 1 and 7 days after indicated IFNγ (10 ng/ml) treatments. PD-L1 overexpressing wHILOs (PDL1OE) and a single 12 h exposure to IFNγ was used as a positive control. FIG. 5F presents a dot plot showing human c-peptide secretion from IFNγ treated wHILOs in response to 3 mM (G3) or 20 mM (G20) glucose. FIG. 5G is a schematic illustrating IFNγ treatment in combination with an IL-1β treatment challenge (10 ng/ml for 24 hours) to induce β cell dedifferentiation. FIG. 5H presents a graph showing INS and UCN3 expression after the indicated IFNγ and IL-1β treatments (10 ng/ml, 24 hours) of wHILOs. FIG. 5I presents a schematic of an experimental protocol for in vivo transplantation of wHILOs into induced diabetic animals. High dose streptozotocin (HD-STZ, 180 mg/kg)

induced diabetic C57BL6J mice received transplants of wHILOs that had or had not been subjected to the IFNγ treatment protocol shown in FIG. 5C, (n=6 and 6, 500 wHILOs/mouse). FIG. 5J presents a graph showing blood glucose levels in recipient mice (STZ-treated (180 mg/kg) diabetic C57BL6J mice) at day 17 following kidney capsule transplantation of wHILOs and IFNγ pulse stimulated wHILO ("immune evasive wHILOs" or "wHILO$^{ie}$"). FIG. 5K presents a graph showing serum human c-peptide levels in mice treated as described in FIG. 5I. Error bars represent SEM. *p<0.05, **p<0.01.

FIGS. 6A-6F provide images, graphs and results related to multicellular spheroids (MCSs) as described herein. FIG. 6A shows a 3D gellan gum suspension of multicellular spheroids (MCS, top), light microscopy images of single MCS (lower left) and hislets (lower right). FIG. 6B shows images of insulin promoter driven GPF expression, and endothelial cells (EC, marked by mCherry expression) in MCS. FIG. 6C presents images showing the progressive development of vascular-like structures in MCSs that were cultured with endothelial growth media in the Matrigel system. FIG. 6D is a schematic for single cell RNA-seq analyses. FIG. 6E presents a heatmap of expression of the top 10 signature genes in human islet cell clusters from FIG. 2D. FIG. 6F present plots showing t-SNE_2 single cell expression of signature hormonal and cell type specific genes in human islets. Relative expression scale: low (0.5, least intense), to high (5, most intense).

FIGS. 7A-7F provide a schematic, graphs, images, and data related to the characterization of mature HILOs. FIG. 7A depicts a diagram of CRISPR-Cas9-based knockin for human insulin promoter driven GFP expression in hiPSC. FIG. 7B presents a differential interference contrast (DIC) image of wHILOs with insulin-GFP and UCN3-RFP expression (scale bar, 100 μm). FIG. 7C presents a Seahorse analysis of extracellular acidification rate (ECAR) measured in day 0 hiPSC spheroids (open square), HILOs (Vehicle/PBS-treated, filled triangle), wHILOs (Wnt4 treated, filled circle) and human islets (open circle). 20 mM glucose (Glu), oligomycin (Olig), Fccp, antimycin+Rotenon (Ant+Rot) were treated in order. FIG. 7D-1 presents a graph showing the kinetics of human c-peptide secretion from WNT4 treated HILOs in response to progressive exposure of the HILOs to 3 mM glucose, 20 mM glucose, 20 mM glucose+100 mM GLP-1, 3 mM glucose, and 3 mM glucose+20 mM KCl over time. FIG. 7D-2 presents a bar graph showing glucose stimulated human c-peptide secretion from wHILOs treated with and without XAV939 to promote β-catenin degradation (XAV939, 1 μM for 3 days). FIG. 7E presents data illustrating motif enrichment in chromatin regions with enhanced accessibility upon WNT4 treatment. FIG. 7F depicts chromatin accessibility at ERRγ target genes (determined by ATAC-Seq) in insulin expressing cells sorted from HILO treated with PBS or WNT4 for 7 days (fold change>1.5).

FIG. 8A presents representative images of mitochondrial content, indicated by MitoTracker (red) staining, in PBS and WNT4 treated HILOs (scale bar, 100 μm). FIG. 8B presents graphs of flow cytometry quantification of insulin expression (GFP) and mitochondrial content in HILOs treated with recombinant human WNT4 (rhWNT4), WNT5A (rhWNT5A), or conditioned medium (CM) from control or WNT5A overexpressing fibroblasts (n=3). Error bars represent SEM. *p<0.05. FIG. 8C presents a gene ontology of transcriptional changes induced by WNT4 treatment (100 ng/ml WNT4 from day26 to day33) in HILOs. FIG. 8D presents a graph demonstrating blood glucose levels in STZ-induced diabetic NOD-SCID mice after transplantation (TP) of 500 wHILOs or hislets, or sham surgery was performed at day 3 (n=7, wHILOs; n=6, hislets; n=3, Sham). Error bars represent SEM. *p<0.05. FIG. 8E presents a Venn diagram showing overlap between WNT4-induced increases in chromatin accessibility in GFP$^+$ cells and increases in HILO gene expression (upper panel), and gene ontology pathways enriched in the intersection gene set. FIG. 8F shows motifs that are enriched in the intersection gene set shown in FIG. 8E. FIGS. 8G and 8H demonstrate the results of experiments in which postnatal islets (day P11-14) from WT and β cell specific ERRγKO mice were cultured with or without rhWNT4 (100 ng/ml) for >5 days. FIG. 8G shows relative gene expression measured by qPCR, and FIG. 8H shows insulin secretion in response to 3 mM and 20 mM glucose. *p<0.05, ***p<0.001. For FIGS. 8G and 8H, postnatal islets (day P11-14) from WT and β cell specific ERRγKO mice were cultured with or without rhWNT4 (100 ng/ml) for >5 days.

FIGS. 9AB, 9C and 9D present confocal images of wHILOs stained for C-peptide. FIG. 9A shows representative immunofluorescent staining results for glucagon, somatostatin and pancreatic polypeptide (PP) in wHILOs. FIG. 9B presents confocal images of wHILOs stained for C-peptide. FIG. 9C presents confocal images of wHILOs stained for β cell enriched markers NKX2-2, NKX6-1, MAFA, MAFB, PDX1. Images are representative of three independent experiments. FIG. 9D presents confocal images of wHILOs stained for endocrine markers chromogranin A (CHGA), Synaptophysin (red, middle images) with Insulin-GFP (green, left images) visualization. Hoechst nuclei staining is shown in the right (Merge) panels. Scale bar, 100 μm. Images are representative of three independent experiments. FIG. 9E shows representative flow cytometry results for ß cell and endocrine marker co-staining in HILOs with and without WNT4 treatment. FIG. 9F graphically depicts the quantification of results presented in FIG. 9E (n=6 and 6). FIG. 9G shows tSNE clustering of single cell transcriptomes from WNT4 treated HILOs (wHILOs, n=4840). FIGS. 9H and 9I show Violin Plots (9H) and single cell expression (9I) of INS, CHGA, SOX9, HES1 in wHILOs. FIG. 9J shows expression of β cell-enriched (INS, PDX1, NKX6-1, NKX2-2, NEU-ROD1, NPTX2, ITGA1, PCSK1, MAFA, MAFB, UCN3, CHGA), a cell-enriched (GCG, ARX) and 6 cell-enriched genes (SST, RBP4) overlaid on tSNE clustering. FIG. 9K presents a heatmap of the top 10 differentially-expressed genes in each cell cluster. FIG. 9L presents tSNE clusters according to cell type (Panc P=pancreatic progenitor, Rep=replicating, UK=unknown). FIG. 9M presents tSNE clustering of combined HILOs and wHILO single cell data sets (right panel) and clustering analysis-defined cell types.

FIG. 10A shows plots illustrating a correlation of number of detected genes and UMIs in HILO, wHILO and human islets. FIG. 10B presents tSNE clustering of combined wHILO (blue dots, n=4840) and human islet (red dots, n=3245) single cell transcriptomes (left panel) and clustering analysis-defined cell types (left). FIG. 10C shows the expression of endocrine specific genes (INS, NKX2-2, GCG, SST, PPY), duct marker (KRT19) and stellate cell marker (ACTA2) in tSNE visualization of merged single cell data sets for wHILO and hislets.

FIG. 11A is a scheme of plate based scRNA-seq. Dissociated single cells from wHILO were sorted by FACS into 96 well tissue culture plate (microplate). FIGS. 11B and 11C: A box plot showing average gene counts per cells (FIG. 11B) and identification of 45 single cells with high quality gene detection (FIG. 11C). FIG. 11D illustrates that single cell RNA-seq revealed single hormone expressing insulin, glucagon, somatostain cells in wHILOs.

FIG. 12A (left) shows tSNE endogenous expression of PD-L1 in human islet cells (β cells are outlined), and (right) a heatmap of the top differentially expressed genes between PD-L1+ and PD-L1– β cells. FIG. 12B presents immunohistochemistry results overlap of lentiviral-driven PD-L1 expression and insulin promoter-driven GFP expression in wHILOs (scale bar, 100 μm). FIG. 12C presents bar graphs showing human PD-L1 expression (left) and human insulin expression (right) in wHILOs, with and without lentiviral PD-L1 overexpression, as measured by qPCR. FIG. 12D (top) presents a schematic depiction of an in vivo experimental study conducted in induced diabetic C57BL6J mice. High dose streptozotocin (HD-STZ, 180 mg/kg) induced diabetic C57BL6J mice received transplants of wHILOs with and without PD-L1 overexpression (n=500), or mouse islets; FIG. 12D (bottom) shows results following transplantation of PD-L1-overexpressing wHILOs into the kidney capsule of STZ-induced diabetic mice. FIG. 12E presents a bar graph showing PD-L1 expression in wHILOs 12 hours after indicated IFNγ stimulation. Error bars represent SEM. *p<0.001. FIG. 12F presents a bar graph showing PD-L1 gene expression in human islets 12 hours after INFγ (ng/ml) stimulation. Error bars represent SEM. *p<0.001.

FIGS. 14A-14D present a Venn diagram, heatmap, gene ontology chart and browser track related to studies investigating IFNγ-induced changes in wHILOs. FIG. 14A shows a Venn diagram of differentially regulated genes upon acute (12 h at 10 ng/ml) and multi pulse stimulated (MPS), (2 h at 10 ng/ml for 3 days) IFNγ treatment of wHILOs. In the diagram, the leftmost circle represents "MPS IFNγ treatment" and the rightmost circle represents "acute IFNγ treatment." FIG. 14B shows a heatmap of differentially expressed genes upon acute and MPS IFNγ stimulation. Sustainable PD-L1 genes expression by MPS are highlighted. FIG. 14C shows gene ontology of selectively regulated genes upon MPS-IFNγ (top panel) and acute IFNγ (bottom panel) treatments. FIG. 14D shows panels of browser tracks indicating chromatin accessibility at selected genes 7 days after the last IFNγ treatment in the MPS method, or 12 hours after acute IFNγ stimulation in wHILOs.

FIG. 15A shows a schematic of a treatment regimen involving multi low dose streptozotocin treatment (MLD-STZ, 50 mg/kg/day for 5 days) of Hu-PBMC-NSG mice to produce an immune competent diabetic animal model. MPS induced PD-L1 expressed wHILOs (n=500) were transplanted under kidney capsule. FIG. 15B shows a graph of random fed blood glucose levels in STZ-induced diabetic Hu-PBMC-NSG mice after transplantation of wHILOs that had undergone or had not undergone MPS (n=6 mice, respectively). wHILOs (−) data from FIG. 4K and FIG. 4G are replicated, since those experiments were performed parallelly. FIG. 15C shows a flow cytometry analysis of insulin-expressing and human immune (CD45$^+$) cells recovered from kidney capsule grafts 27 days after transplantation of wHILOs with or without MPS. Error bars represent ±SEM. *p<0.05, p<0.01, *p<0.001.

DETAILED DESCRIPTION OF THE EMBODIMENTS

Figure 1A:
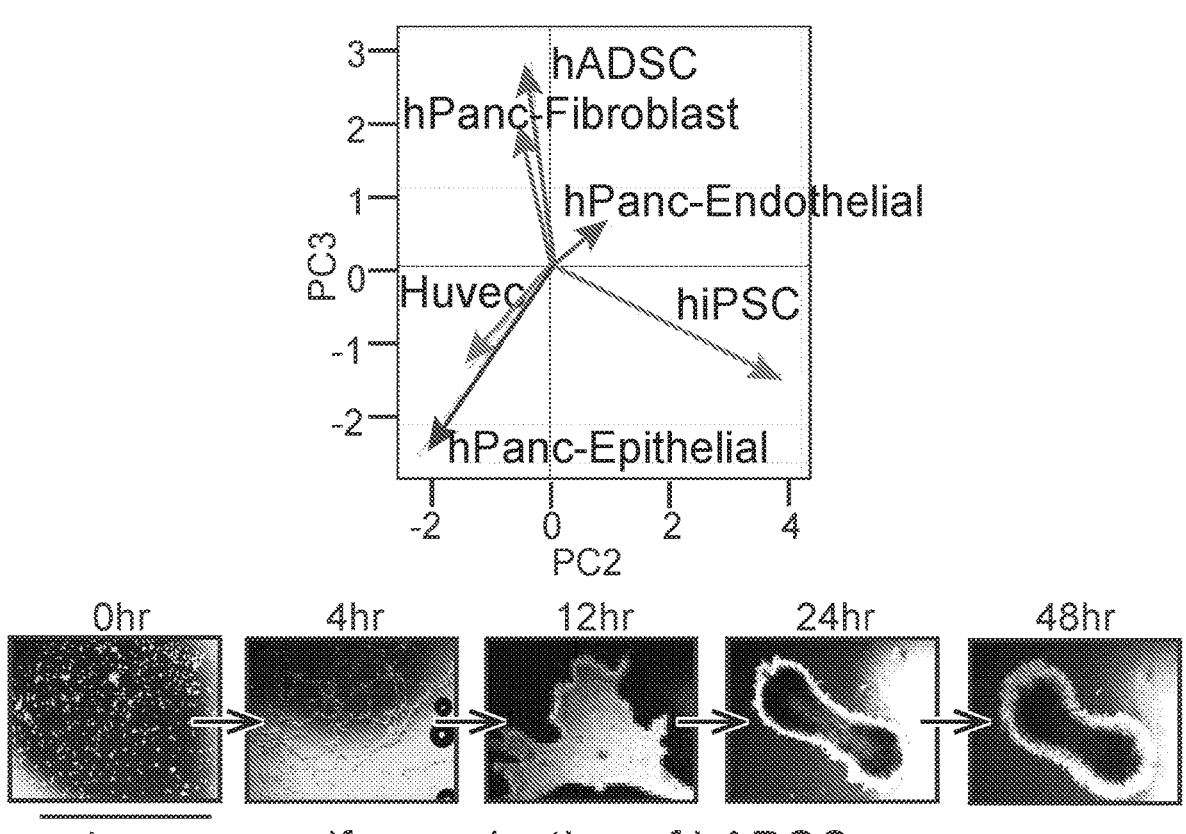
FIGS. 1A-1G provide images, a schematic diagram, and graphs related to enhancement of the functionality of hiPSC-derived β-like cells via cellular crosstalk in polymer-based cultures.

Featured herein are methods and systems for the generation and utilization of stem cell-derived human islets and human islet-like organoids, which provide a promising strategy for the therapeutic treatment of diseases and pathologies, such as pancreatic diseases and insulin dependent diabetes, a disease caused by the loss of endogenous insulin-producing p cells. Advantageously, the methods and systems as described can generate biological products, e.g., cells, human islet-like organoids and cells thereof, as therapeutics that can alleviate the shortage of donor-matched cadaveric human islets, which are currently being used to treat patients.

As described herein, functional human islet-like organoids (HILOs) are generated from human pluripotent stem cells, such as induced pluripotent stem cells (iPSCs). In an embodiment, a culture system which allows for non-canonical WNT4 signaling is employed to generate HILOs. Without wishing to be bound by theory, WNT4 signaling in cells such as iPSCs, human islet and HILO cells drives metabolic maturation necessary for robust glucose stimulated insulin secretion (GSIS). The stem-cell derived islets and HILOs as described herein achieve functional maturity and exhibit robust, glucose-stimulated insulin secretion (GSIS) through enhanced glucose-responsive oxidative capacity, which is regulated by the WNT4-ERR (Estrogen-Related Receptor) metabolic pathway. The functionally mature HILOs contain endocrine-like cell types that, upon transplantation, rapidly re-establish glucose homeostasis in diabetic NOD-SCID mice (e.g., Examples 4 and 5). In an embodiment and as described herein, the HILOs and cells thereof avoid rejection by immune cells under immune-competent conditions.

In an aspect, single cell RNA (scRNA)-sequencing analysis of functional HILOs, as well as human cadaveric islets, revealed transcriptional heterogeneity of HILO-derived cells, including a small population of immune-evasive β cells. As described in an aspect herein, HILOs were molecularly engineered to express a checkpoint protein, e.g., PD-L1, in order to mimic the transcriptional program of immune-evasive β cells. When the PD-L1-expressing HILOs were assessed, it was found that PD-L1 expression overcame autoimmune rejection of the HILOs, which had been transplanted in immune-competent mice with type 1 diabetes. Thus, the generation, in a scalable fashion, of functional β cells and HILOs that can avoid immune detection, autoimmune activation, and transplant or implant rejection afford advantageous and beneficial treatments and therapies for diabetes, in particular, type 1 diabetes and late stage type 2 diabetes. In an embodiment, β cells, human HILOs and human islets are molecularly engineered (e.g., transduced or transfected) to express a checkpoint protein such as PD-L1. In an embodiment, β cells, human HILOs and human islets are induced to express the PD-L1 protein as described herein.

Methods of Protecting Islets, Organoids and the Cells Therein from Immune Surveillance and Immune Cell Killing and Clearance In an aspect, methods, particularly in vitro or ex vivo methods, are provided for generating islets and organoids, including the cells therein, (e.g., donor cells, islet and organoid cells) that survive, have reduced cell death and/or can better evade immune detection by cells of the immune system, especially after transplantation, implantation, or transfer into a subject, such as a recipient individual. In an embodiment, the transplantation, implantation, or transfer involves allogeneic cells, islets, and/or organoids that survive and have reduced killing and detection by immune cells, e.g., T cells, β cells, monocytes, macrophages and the like, subsequent to the practice of the methods described herein.

In an aspect, the expression (or upregulated expression) of a checkpoint protein-encoding gene and/or its encoded product, in particular, PD-L1 and/or the PD-L1 protein, in or by IFNγ receptor-expressing islets, organoids (e.g., HILOs), or cells (e.g., β cells of HILOs) following multiple intermittent exposures to interferon gamma (IFNγ) over a given time period (such as at least 24 hours) allows the HILOs to maintain glucose homeostasis, e.g., in immune-competent diabetic mice for a long time period, e.g., at least 50 days, as well as to evade an immune response by activated T cells and/or graft rejection. In an embodiment, the islets, organoids, or cells are human islets, organoids, or cells. In embodiments, such islets, organoids, or cells express IFNγ receptors and/or are responsive to treatment with IFN 7. In an embodiment, the islets, organoids, or cells naturally express IFNγ receptors. In an embodiment, IFNγ receptors may be introduced into the islets, organoids, or cells, for example, without limitation, by recombinant, viral, or molecular biology techniques as known and practiced in the art. In an embodiment, PD-L1 gene and/or protein expression (or upregulated expression) in the IFNγ receptor-expressing islets, organoids, and cells constitutes a detectable marker, which is indicative of the response of the islets, organoids, and cells to IFNγ exposure. PD-L1 expression or upregulated expression of PD-L1 as a marker of IFNγ responsiveness following exposure of islets, organoids, and cells to IFNγ may be assayed by polynucleotide and/or protein detection methods routinely used and known in the art, and are not intended to be limiting.

In embodiments, the method comprises stimulating the cells with interferon gamma (IFNγ) in low amounts or doses, e.g., 0.5-100 ng/ml, 1-50 ng/ml, 1-25 ng/ml, 1-20 ng/ml, 1-10 ng/ml, 10 ng/ml or 20 ng/ml. In an embodiment, this is achieved by subjecting the islets, organoids, and/or cells, e.g., HILOs, to IFNγ for discrete time periods, e.g., 1, 2, 3, 4, 5, 6, 7, 8, 9, 10, 11, 12, 13, 14, or 15 hours, or more, in particular, for about or equal to 2 hours or 12 hours, for example, multiple times, e.g., 2 times, 3 times, 4 times, 5 times, 6 times or more, over a given time period. In some embodiments, the multiple exposures or pulses are performed over at least a 24-hour period of time (about 1 day), a 48-hour period, a 72-hour period, or over the course of 4, 5, 6, 7, 8, 9, or 10 days. In some embodiments, the cells are exposed to IFNγ for a total of 0.5-3 hours, 0.5-4 hours, 0.5-5 hours, 0.5-6 hours, 0.5-7 hours, or 0.5-10 hours. Between IFNγ exposures or pulses the cells are allowed to 'rest,' e.g., in culture medium or 3D matrix, in the absence of IFNγ between the time periods of exposure to IFNγ. In some embodiments, the cells are allowed to 'rest' in the absence of IFNγ for at least about 0.5, 1, 2, 3, 4, 5, 6, 7, 8, 9, 10, 11, 12, 13, 14, 15, 16, 17, 18, 19, 20, 21, 22, 23, or 24 hours between exposure to IFNγ. In other embodiments, the cells are allowed to 'rest' in the absence of IFNγ for about 1, 2, 3, 4 or 5 days. In one embodiment, the IFNγ treatment causes a constitutive (prolonged) upregulation and expression (and maintenance) of PD-L1 expression in the islets, organoids, and/or cells, e.g., HILOs. This procedure involves multiple pulse stimulation (MPS), also referred to as intermittent exposure, of cells, islets, organoids, e.g., HILOs or islets and the cells therein, to IFNγ. Expression of PD-L1 by the cells, islets, and/or organoids, is long-lasting following MPS, particularly, if the islets, organoids, and/or cells (e.g., HILOs) experience at least 3 pulses or intermittent exposures to IFNγ (e.g., 10 ng/ml) for about or equal to a 2-hour time period per pulse of IFNγ. For example, by this regimen, sustained expression of PD-L1 is found in the islets, organoids and/or cells, e.g., HILOs, for at least 7 days following subjecting the islets, organoids and/or cells, e.g., HILOs, to the MPS procedure. In an embodiment, islets, organoids, (e.g., HILOs), or cells generated by the method survive in a recipient subject following transplantation, implantation, or transfer for at least about or equal to 50 days.

Without wishing or intending to be bound by theory, the MPS IFNγ exposure procedure results in PD-L1 expression (or upregulation of PD-L1 expression) in islets, organoids and/or cells (e.g., HILOs and the cells therein (e.g., β cells)), which involves a mechanism of transcriptional memory. The described procedure comprising MPS IFNγ exposure of cells, islets, and/or organoids may stimulate or create an intracellular signaling cascade in which the de-differentiation of the cells, islets and/or organoids is inhibited or blocked. The short pulses of IFNγ (MPS IFNγ) to which the cells, islets or organoids are exposed in the methods may ultimately involve an alteration of chromatin structure, thereby protecting the cells, islets or organoids from de-differentiation and affording the MPS IFNγ exposed cells, islets, or organoids, with the ability to survive (e.g. by reduced cell death by cells of the immune system), as well as to be immune to the effects of inflammatory cytokines and chemokines, e.g., Interleukin-1B (IL-1B) as described infra, so as to provide an anti-inflammatory effect for the cells, islets, or organoids. The absence or reduction of inflammation associated with MPS IFNγ exposed cells, islets, or organoids generated from the described methods may enhance their potential for survival and reduction in killing by immune cells post transplantation, implantation, or transfer into a subject. The described methods thus generate donor cells, islets and organoids that have improved survival and retain their functionalities following transplant, implant, or transfer into a subject and offer a number of beneficial advantages in their use as therapeutics.

In a particular embodiment, a method is provided for generating human islets, organoids (e.g., HILOs) and various primary or differentiated cells (of different lineages) that survive, have reduced cell death, and can better evade immune detection or autoimmunity in which the method involves (a) contacting the human islets, organoids (e.g., HILOs), or cells with interferon gamma (IFNγ) for greater than one hour at a predetermined time point; repeating step (a) at least about two times during a given time period, e.g., a time period of about or equal to 72-hours; wherein the human islets, organoids (e.g., HILOs), or cells are maintained in the absence of IFNγ between times of contact with IFNγ; and wherein steps (a) and (b) induce sustained expression of PD-L1 in the human islets, organoids (e.g., HILOs), or cells. In an embodiment of the method, the human islets, organoids (e.g., HILOs), or cells are contacted with IFNγ for a time period of about or equal to at least 1 hour, or at least 2 hours, or more than 2 hours in step (a). In a particular embodiment of the method, the human islets, organoids (e.g., HILOs), or cells are contacted with IFNγ for a time period of about or equal to 2 hours or about or equal to 12 hours in step (a). In another particular embodiment of the method, step (a) is repeated three times for at least about or equal to 2 hours each time in the given time period, e.g., an about or equal to 72-hour time period. In another embodiment of the method, the human islets, organoids (e.g., HILOs), or cells are washed to remove the presence of IFNγ between step (a) and step (b). In another embodiment of the method, IFNγ is used in an amount of 1-25 ng/ml. In another embodiment of the method, IFNγ is used in an amount of 10 ng/ml. In another embodiment of the method, PD-L1 expression in the human islets, organoids (e.g., HILOs), or cells is maintained following step (b) for greater than about or equal to 7 days. In an embodiment, the method generates human cadaveric islets (e.g., syngeneic or allogeneic) that are protected from destruction or clearance by the immune system.

In another particular aspect, a method of generating various cells, islets, or organoids (e.g., HILOs), including human cells, islets, or organoids, that survive, have reduced cell death, and/or evade immune detection or autoimmunity is provided in which the method involves (a) contacting the cells, human islets, or organoids (e.g., HILOs) with interferon gamma (IFNγ) in an amount of about 1 ng/ml to 25 ng/ml for greater than 1 hour at a first time point during a given time period, e.g., a time period of about or equal to 24-hours; and (b) contacting the cells, human islets, or HILOs with IFNγ in an amount of about 1 ng/ml to 25 ng/ml for greater than about or equal to 0.5 hours or more, or about or equal to 1 hour at at least two additional time points during a following time period, e.g., a 48-hour time period, following step (a); wherein the islets or organoids (e.g., HILOs) are washed and rested in medium in the absence of IFNγ between being contacted with IFNγ; and wherein steps (a) and (b) induce sustained expression of PD-L1 in the islets or organoids (e.g., HILOs). In a particular embodiment of the method, the cells, islets, or organoids (e.g., HILOs) are contacted with IFNγ in an amount of 10 ng/ml for at least 2 hours in step (a) and step (b). In another particular embodiment of the method, the cells, islets, or organoids (e.g., HILOs) are contacted with IFNγ for at least about or equal to 2 hours at 3 time points (different time points) during a 72-hour time period.

The practice of the above-described methods for immune evasion of IFNγ receptor-expressing islets, organoids, and cells provide advantages for such islets, organoids and cells, particularly, human cells, islets and organoids, used for transplants, implants, or transfer from one subject to another as therapeutics and therapeutic treatment of diseases, disorders and pathologies. The practice of the described methods provides immunoprotection and enhanced survival of islets, organoids and cells that are transplanted, implant, or transferred into a recipient subject (e.g., an adoptive recipient, transplant recipient, and the like), such that the transplanted, implanted, or transferred islets, organoids, or cells are maintained and are functional in the recipient for several days, or weeks, or longer, for example, for about 2 days or longer to 1, 2, 3, 4, or more weeks, or longer.

The methods and systems described herein are suitable for use with a variety of cells and cell types, or donor cells for transplantation, particularly, IFNγ receptor-expressing cells, derived from different lineages, as well as islets, and organoids, e.g., to provide immune protection after transplant, implant, administration or transfer into a recipient subject. In general, by way of nonlimiting example, stem cells, primary cells, differentiated cells of various lineages and types, or cells of one type derived from cells of a different source may be used. In embodiments, such suitable cells express IFNγ receptors and/or are responsive to treatment with IFN γ may be used in accordance with the above-described methods. Responsiveness to IFNγ treatment in the described methods may be determined or identified by assaying for detectable expression of PD-L1 or the PD-L1 protein by the IFNγ receptor-expressing cells, islets, or organoids (and cells therein).

By way of particular, yet nonlimiting, example, the methods described herein, which involve induction of sustained PD-L1 expression by IFNγ MPS, may be suitable or applicable for use with a variety of cells and cell types, or donor cells for transplantation, including, without limitation, cardiac cells, colon cells, kidney cells, bladder cells, liver cells (hepatocytes), gastrointestinal cells, gastric (stomach) cells, lung cells, ovarian cells, cervical cells, uterine cells, testicular cells, pancreatic cells, pancreatic β cells, muscle cells, hematopoietic cells, immune cells (B cells, T cells), retinal cells, corneal cells, brain cells, chimeric antigen receptor-T cells (CAR-T cells), bone marrow cells, e.g., mononuclear cells, neurons, neuronal cells, insulin-producing pancreatic β cells derived from human skin cells (e.g., as reported by L1, K. et al., 2014, *Cell Stem Cell*, 14(2):228-236); umbilical cord blood (UCB) cells, adipose derived mesenchymal stromal (stem) cells, cardiac stem cells, colon stem cells, kidney stem cells, liver (hepatocyte) stem cells, gastrointestinal stem cells, gastric (stomach) stem cells, lung stem cells, pancreatic stem cells, pancreatic β stem cells, muscle stem cells, hematopoietic stem cells, immune cell (T cell or B cell) stem cells, bone marrow stem cells, CD133+ stem cells, CD34+ hematopoietic cells, CD34+ stem cells, mesenchymal stem cells, umbilical cord mesenchymal stem cells, retinal stem cells, neuronal stem cells, and the like, as well as islets and organoids generated from or containing such cells. By way of example, the following types of organoids are suitable for use in the methods: intestinal organoids, hepatic organoids, neural organoids, pulmonary organoids, for example, as may be produced using art-described procedures, or commercially available, e.g., Stemcell™ Technology, Cambridge, MA Other suitable cells are those derived from embryonic stem cells which give rise to various differentiated cell types, for example, ectoderm-derived cells, such as neuronal cells, dopaminergic neuronal cells (e.g., immortalized dopaminergic neuronal precursor cells (LUHMES) commercially available from abm, Vancouver, British Columbia); corneal-derived cells (e.g., normal human corneal epithelial cells, commercially available from LifeLine Cell Technology, Oceanside, CA); endoderm-derived cells, such as liver cells (e.g., human hepatocytes wild type, available from Defini-GEN, Cambridge, UK); and mesoderm-derived cells, such as muscle cells, bone marrow cells, kidney cells and skeletal muscle cells (e.g., human skeletal muscle cells (skMDC), commercially available from Cook MyoSite®, Pittsburgh, PA). Nonlimiting examples of β cells (e.g., having pancreatic β-cell characteristics/function) or islets which may be used in the described methods may be found, for example, in WO 2016/100898, WO 2016/100909, WO 2016/100921, WO 2016/100925, WO 2016/100930, WO 2014/145625.

Accordingly, the methods, systems and compositions as featured and described herein are useful and applicable for generating cells, tissues and organoids, which exhibit long-lasting viability and functional activity following administration, e.g., via transplantation, implantation, injection, and the like, to a subject in need thereof, based on the sustained expression of a checkpoint protein, such as PD-L1 by the cells, tissues and organoids, and their resultant evasion of and protection from immune surveillance and destruction by cells of the immune system, e.g., as occurs in graft versus host reaction.

In a particular aspect, the methods, systems and compositions as featured and described herein are useful for generating in vitro scalable, functional, vascularized organoids, particularly human pancreatic or pancreatic islet organoids (HILOs), that can evade immune detection following transplantation or implantation. In an embodiment, the culturing of iPSC-derived beta-like cells, which express an immune checkpoint protein, with human adipose-derived stem cells (hADSC) and human umbilical vein endothelial cells (Huvec) in a three-dimensional matrix containing gellan gum generated functional pancreatic and pancreatic islet organoids is also provided.

The HILOs generated in accordance with the described methods were vascularized and exhibited functional properties, such as glucose-stimulated insulin secretion (GSIS). While recent studies have reported the possibility of generating glucose-responsive, insulin-producing, beta-like cells from human Pluripotent Stem Cells (PSCs), the generation of functional, vascularized pancreatic islets organoids from PSCs that secrete insulin, glucagon and somatostatin in response to nutrients and that are capable of evading immune detection and graft or transplantation or implantation rejection by cells of the immune system for substantial periods of time is advantageously provided herein.

As described herein, the self-organizing function of human adipose-derived stem cells (hADSC), HUVEC, and human iPSC-derived beta-like cells allows for the in vitro generation of glucose-responsive insulin secreting islet-like organoids with the ability to form functional vasculature. In addition, successful scaling of islet-like organoids production through the use of Gellan gum based 3D culture systems is achieved. Using a Gaussia luciferase reporter to measure insulin secretion, the functional heterogeneity in hiPSC-derived islet-like organoids was characterized. Without intending to be bound by theory, results herein suggest that the human islet-like organoids (HILOs) which express a checkpoint protein may offer a beneficial therapeutic treatment for diabetes and a new treatment for organ failure, as well as a platform for drug screening, genome editing, and the modeling of organogenesis and pathogenesis of diabetes.
Immune Checkpoint Proteins Maintaining immune homeostasis is critical for host survival. Overt or uncontrolled immune responses to pathogens or to mutated, modified, or over-expressed self-antigens can cause inflammatory tissue damage and autoimmune diseases. To prevent this, the breadth and magnitude of the immune response is regulated by a balance between co-stimulatory and inhibitory signals. These signals are collectively referred to as immune checkpoints, which are necessary for maintaining self-tolerance and protecting a subject from tissue damage.

Activated T cells are the primary mediators of immune effector functions and as such, they express multiple co-inhibitory receptors such as, e.g., lymphocyte-activation gene 3 (LAG-3), programmed cell death protein 1 (PD-1) and cytotoxic T-lymphocyte-associated protein 4 (CTLA-4). These immune checkpoint molecules have been shown to modulate T cell responses to 'self' proteins, as well as to chronic infections and tumor antigens. Of note, the pathways utilized by these checkpoint proteins are unique and non-redundant, thus, reflecting the important role of immune checkpoints in regulating immune homeostasis, As noted supra, an immune checkpoint protein" or "immune checkpoint molecule," or simply, "checkpoint protein or molecule" is a protein or molecule that regulates the immune system and frequently binds to or interact with ligands (cognate ligands), which may cause a given effect, e.g., cell stimulation, anergy, or apoptosis. In an embodiment, the immune checkpoint protein is one that binds a cognate ligand (e.g., a receptor ligand) on the membrane surface of an immune cell, e.g., a T cell surface receptor. In a specific embodiment, an immune checkpoint protein is PD-L1 or a binding portion thereof, where the cognate ligand of PD-L1 is PD-1, e.g., as expressed on the surface of T cells. In an embodiment, the checkpoint protein is the extracellular domain of the protein.

In an aspect, a checkpoint protein binds to its cognate ligand, which may also be a checkpoint protein receptor on an immune cell, such as a T cell, and blocks or interrupts signaling, activity, or function of the cell that expresses the cognate ligand or receptor. Alternatively, immune checkpoint inhibitors, which include antibodies and fragments of the antibodies that retain binding to checkpoint proteins, can bind to checkpoint proteins on cells, such as immune cells (e.g., effector T cells) and block or interrupt signaling, activity, or function of the cell. The binding of a checkpoint protein inhibitor to a checkpoint protein expressed on a cell can cause inactivation of the normal activity of the cell expressing the checkpoint protein. In embodiments, a checkpoint protein inhibitor is an antibody, such as a monoclonal antibody, a humanized antibody, a human antibody, a single chain antibody, etc., or a fragment thereof that binds to a checkpoint protein (cognate ligand).

Nonlimiting examples of immune checkpoint proteins, or cognate ligand binding portions thereof, that may be expressed in a cell, an iPSC, beta-cell, and the like, or an organoid, e.g., HILOs and other organoids as described herein, include PD-1, programmed cell-death protein 1, PD-L1, programmed cell-death ligand 1, which is the cognate binding ligand of PD-1; PD-L2, programmed cell-death ligand 2, which also binds PD-1; CTLA-4 (cytotoxic T-lymphocyte protein 4, also called CD152); LAG-3, lymphocyte activation gene 3 protein; KIR, killer cell immunoglobulin-like receptor; IDO1, indoleamine 2,3-dioxygenase 1; 4-1BB, a tumor necrosis factor receptor superfamily member 9, (also known as CD137); 4-1BBL (binds to 4-1BB); GITR, "glucocorticoid-induced TNFR family related gene; TIM-3, "T-cell immunoglobulin domain and mucin domain;" OX40, tumor necrosis factor receptor superfamily member 4, (also known as CD134); OX40L (binds to OX40), CD40, CD40L, A2AR, adenosine A2A receptor; B7-H3 (also called CD276); B7-H4 (also called VTCN1); B7-1/B7-2; BTLA (also called CD272); VISTA, "V-domain Ig suppressor of T cell activation;" and the like.

In embodiments, the immune checkpoint protein molecule is, without limitation, PD-L1 or the extracellular domain of PD-L1, which binds to PD-1 expressed by T cells. In an embodiment, a polynucleotide encoding an immune checkpoint protein is utilized to molecularly engineer a cell to express a checkpoint protein, or one or more checkpoint proteins, such as by infecting the cell with a viral or bacterial vector containing the checkpoint protein-encoding polynucleotide. In some embodiments, a cell (e.g., a beta-cell, or HILO cell) expresses more than one immune checkpoint protein, or a ligand binding portion thereof. In some embodiments, the cell is molecularly engineered to contain one, or more than one immune checkpoint protein, or ligand binding portion thereof, which is expressed by the cell. In an embodiment, the cell is infected with a viral vector, e.g., a lentiviral vector or adeno-associated viral vector, or more than one viral vector, that contains one or more polynucleotide(s) that encode(s) one or more immune checkpoint proteins or a ligand binding portion thereof, using procedures and methods that are well-known in the art. In an embodiment, the cell is transformed or transfected with a plasmid vector, or more than one plasmid vector, that contains one or more polynucleotide(s) that encode(s) one or more immune checkpoint proteins or a ligand binding portion thereof, using procedures and methods that are well-known in the art.

PD-1, the Programmed Death 1 (PD-1) protein, is a key immune checkpoint protein (receptor protein) that is expressed by activated T cells, as well as B cells, antigen presenting cells (APCs) and natural killer cells (NK cells) and mediates immunosuppression. PD-1 functions mainly in peripheral tissues where T cells may encounter the immunosuppressive PD-1 ligands PD-L1 (B7-H1) and PD-L2 that are expressed by other cells, such as cells molecularly engineered to express PD-L1, as well as, e.g., tumor cells, stromal cells, or both. Without intending to be limited by theory and by way of particular, nonlimiting example, PD-L1 expressed by transplanted, implanted, or engrafted beta($\beta$)-cells, organoid cells, including HILO cells as described herein, binds to PD-1 expressed by effector T cells, thus effectively suppressing a T cell response directed against the beta-cells, organoid cells, or HILO cells and mediating the normal T cell response so as to tamp down or block autoimmunity and inactivate the immune response against the beta-cells, organoid cells, or HILOs. In an embodiment, the beta-cells, organoid cells, or HILOs express the immune checkpoint protein in situ, in the localized area of a transplant, implant, or graft; therefore, the ability of the cells and HILOs to evade autoimmunity occurs in and around the localized area of the transplant, implant, or graft and results in less risk of a systemic or more widespread modulation of immune cell activity in a recipient subject.

Pancreas

In some aspects, a pancreatic organoid or a pancreatic islet organoid, also called a human islet-like organoid, or HILO, herein, is provided. The pancreas is an organ that lies in the abdomen and has endocrine and exocrine functions. The portion of the pancreas having an endocrine role are cell clusters called "pancreatic islets" (also known as islets of Langerhans). Pancreatic endocrine secretions include hormones that regulate glucose metabolism and blood glucose concentration. Four main cell types are present in the islets: alpha cells, which secrete glucagon (a hormone that increases blood glucose concentration); beta cells, which secrete insulin (a hormone that decreases blood glucose concentration); delta cells, which secrete somatostatin (a hormone that regulates alpha and beta cells), and gamma cells, which secrete pancreatic polypeptide.

The portion of the pancreas that has an exocrine role is referred to as the exocrine component. The exocrine pancreatic secretions contain digestive enzymes that pass into the small intestine and help break down carbohydrates, proteins, and lipids. The exocrine component has ducts arranged in clusters called pancreatic acini. Pancreatic exocrine secretions are secreted into the lumen of the acinus; the secretions accumulate and drain into the pancreatic duct and duodenum.

Pancreatic islet organoids, pancreatic organoids and HILOs as described herein mimic the structure of a pancreatic islet and a pancreas, respectively. In some embodiments, the pancreatic islet organoid or pancreatic organoid contains any one or more of the following cells: an iPSC-derived beta-like cell, an iPSC-derived alpha-like cell, an iPSC derived delta-like cell, and an iPSC-derived duct-like cell. In some embodiments, the pancreatic organoid contains an iPSC-derived exocrine component. In some embodiments, the iPSC is a human iPSC (hiPSC). Human embryonic stem cells and human induced pluripotent stem cells are commercially available (e.g., from WiCell, which provides iPS (IMR-90)-1, iPS(IMR-90)-4 and iPS(Foreskin)-1). Human induced pluripotent stem cells can also be generated using methods known in the art from a variety of somatic cell types (Yu, J., K. Hu, et al. (2009). "Human induced pluripotent stem cells free of vector and transgene sequences." *Science*, 324(5928): 797-801).

Pancreatic islet organoids, pancreatic organoids and HILOs as described herein also exhibit function(s) of a pancreatic islet and a pancreas. In certain embodiments, the pancreatic islet organoid or pancreatic organoid exhibits any one or more of the following functions: glucose-stimulated insulin secretion (GSIS), KCl-stimulated insulin secretion, GLP-1 stimulated insulin secretion, somatostatin secretion, and glucagon secretion. In some embodiments, the pancreatic islet or pancreatic organoid expresses any one or more of the transcription factors Pdx1, MafA, Pax4, Pax6, NeuroD1, Nkx6-1, Gata6, and Foxa2. In some embodiments, the HILOs express a checkpoint protein, or a functional portion thereof, that functions to allow the HILOs to evade immune detection and destruction by cells of the immune system. In some embodiments, the HILOs express more than one type of checkpoint protein or molecule, or a functional portion thereof.

Generation of Pancreatic and Pancreatic Islet Organoids

In other aspects, methods of generating a pancreatic or pancreatic islet organoid are described. Recent studies have shown that while it was possible to generate glucose-responsive, insulin-producing, beta-like cells, efforts to generate pancreatic islets which are capable of secreting insulin, glucagon and somatostatin in response to nutrients, as well as efforts to obtain vascularization from stem cells, have not succeeded. Described herein are results demonstrating that using the self-organizing function of human adipose-derived stem cells (hADSCs), human umbilical vein endothelial cells (HUVECs), and human iPSC-derived beta-like cells, glucose responsive insulin secreting islet-like organoids (HILOs) capable of functional vascularization are successfully generated in vitro. Further, islet-like organoid generation methods were successfully scaled up using gellan gum based 3D culture systems. The functional heterogeneity in hiPSC-derived human islet-like organoids was also investigated using a Gaussia luciferase reporter to measure insulin secretion.

Generation of functional human organs provides new therapeutic strategies in drug-screening, disease modeling and inhibiting or preventing end point organ failure. Efficient stepwise differentiation methods from human embryonic stem cells (hESC) and human induced pluripotent stem cells (hiPSC) to insulin producing β-like cells have been demonstrated. For example, D'Amour et al. and Kroon E. et al. reported the efficient differentiation of hESCs into insulin producing cells which, after 4 to 5 months of in vivo maturation, were able to secrete insulin in response to glucose (D'Amour et al., 2006, *Nature Biotechnology*, 24, 1392-1401; Kroon et al., 2008, *Nature Biotechnology*, 26, 443-452). Recently, Rezania et al. and Pagliuca et al. reported in vitro differentiation methods that induced the formation of mature human beta-like cells that expressed the terminal β-cell markers MAFA and Nkx6-1, and exhibited partial functionality (e.g., insulin secretion) (Rezania et al., 2014, *Nature Biotechnology*, 32(11):1121-33; Pagliuca et al., 2014, *Cell*, 159, 428-439). However, in contrast to cadaveric human islets, those beta-like cells required in vivo functional maturation for a few months, and lacked the functionality provided by the other pancreatic islet cell types, such as glycemic control by α-cells (glucagon secretion) and δ-cells (somatostatin secretion). Further, the beta-like cells lacked both a mesenchyme and vascularized endothelial cells, which human islets naturally have. These crucial differences between hPSCs derived beta-like cells and human islets may compromise the ability of hPSCs-based therapies to treat insulin dependent diabetes (such as type 1 or late stage type 2 diabetes).

Figure 13:
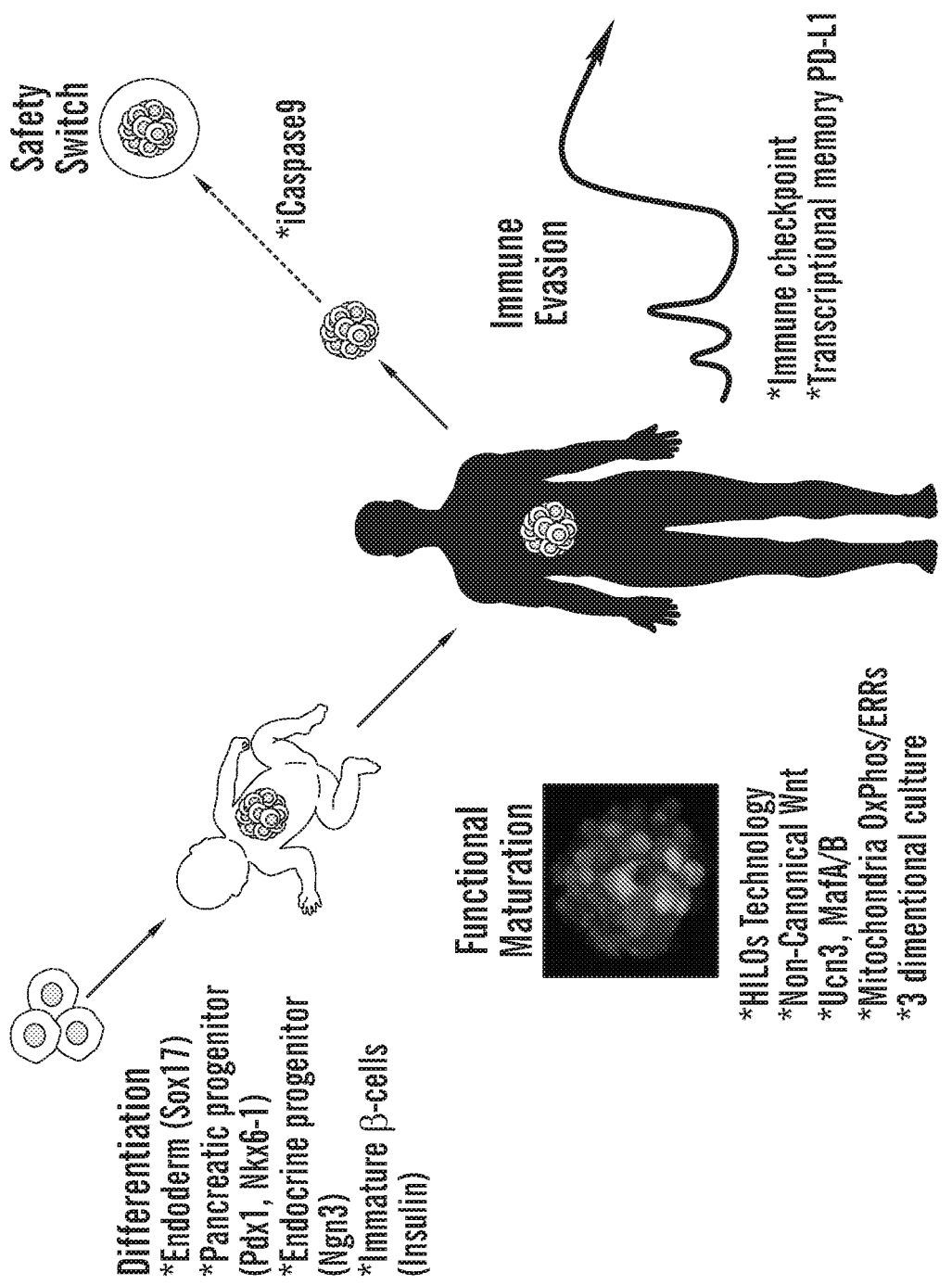
FIG. 13 provides a schematic diagram of the strategy for generation of mature, immune evasive wHILOs (wHILO$^{ie}$s).

Previously, it was identified that a metabolic transition occurs during the neonatal to adult maturation of β-cells in which the orphan nuclear receptor Estrogen-related receptor γ (ERRγ) regulates an increase in oxidative metabolism required for fully functional β cells. Consistent with this result, human iPSC-derived β like cells expressing insulin, MAFA, and Nkx6-1 can be metabolically matured through the overexpression of ERRγ to increase their oxidative metabolism and thereby enhance their glucose stimulated insulin secretion (GSIS) functionality. These results indicated that, in addition to the expression of lineage determination factors such as PDX1, MAFA, Nkx6-1 and insulin, further cellular signaling which mature the β-cells' metabolism is required to generate fully functional β-cells. (FIG. 13).

During early pancreas organogenesis, newly specified pancreatic cells originate from the foregut endodermal sheet and form a pancreatic bud, a condensed tissue mass that is soon vascularized. A similar progression has been observed in liver organogenesis as well. Such large-scale morphogenetic changes depend on the exquisite orchestration of signals between endodermal epithelial, mesenchymal, and endothelial progenitors before blood perfusion. Takebe et al. successfully generated hepatic organ buds by culturing hepatic endoderm cells with endothelial and mesenchymal linages which rapidly vascularized and functionally matured in vivo (Takebe et al., 2013, *Nature*, 499:481-484).

Previous work did not reveal the possibility of generating in vitro other organoid tissue types, such as pancreas organoids, which were mature, functional, and vascularized. Further, previous work showed a lack of scalability because the organoids were generated using MATRIGEL® matrix, which is not efficient to use for scaled-up production.

Figure 1B:
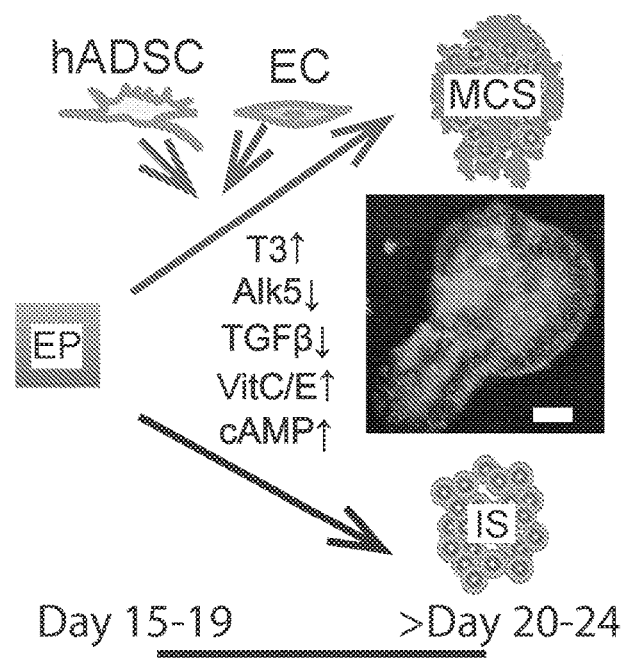

Described herein are studies demonstrating successful large-scale generation of human islet-like organoids (HILOs) that can secrete insulin and are vascularized, as seen in human islets, and that express one or more immune checkpoint proteins, thus affording the HILOs the ability to evade autoimmunity or immune detection by surveilling immune cells, e.g., T cells. It is demonstrated herein that (1) human adipose derived mesenchymal stem cells (hADSCs) have a self-organizing capacity (FIGS. 1A and 1B); (2) late stage pancreatic progenitors are capable of forming an islet-like cluster (organ buds) when co-cultured with HUVECs and hADSCs with comparable efficiency to beta-like cells; (FIGS. 1A-1C, FIG. 1E and FIGS. 3A-3C); (3) human islet-like organoids had improved expression of lineage determination factors, as well as metabolic regulatory genes including ERRγ; (4) islet insulin secretion assays revealed that human islet-like organoids contain functional cells capable of secreting insulin in response to glucose (e.g., Example 8); (5) human islet-like organoids (HILOs) exhibited vascularization (FIG. 6C); (6) human islet-like organoids derived from hiPSC as described herein recaptured human islet organogenesis and pathogenesis of type 1 and type 2 diabetes in a dish; (7) human islet-like organoids derived from hiPSC as described herein offered a new replaceable resource for human islet transplantation to treat type 1 and type 2 diabetes; (8) human islet-like organoids transplanted into an STZ-induced NODSCID mouse model of type 1 diabetes ameliorated type 1 diabetes in the recipient animals (FIGS. 1F and 1G); and (9) Wnt4 and Wnt5a increased the number of mitochondria-enriched β cells in HILOs (FIGS. 8A-8D), thus suggesting that both Wnt4 and Wnt5a (derived from pancreatic endocrine cells and supportive cells, respectively) enhance mitochondrial metabolic function to promote β cell maturation and sustainable GSIS function.

Also described herein are studies in which the role of certain Wnt (also "WNT" herein) proteins was assessed in developing human islet-like organoids which are capable of secreting insulin and which are vascularized, as seen in human islets. The WNT gene family consists of structurally related genes that encode secreted signaling proteins, which have been implicated in oncogenesis and in several developmental processes, including regulation of cell fate and patterning during embryogenesis. Wnt proteins comprise a major family of signaling molecules that orchestrate and influence a variety of cell biological and developmental processes. Wnt proteins undergo a complex set of posttranslational modifications involving several highly specialized processing enzymes. Upon release from the cell, the Wnt proteins interact with a number of molecules in the extracellular environment, such as glycans, protein-binding partners (e.g., WIF, Sfrp) and cell surface receptors. (Willert, K. et al., 2012, Cold Spring Harbor, *Perspectives in Biology,* 2012). From studies described herein, Wnt5a is the predominant Wnt protein that induces the self-organization of hADSCs; (2) Wnt5a, as well as Wnt4, activate the ERRγ-mitochondrial metabolic pathway; (3) Wnt4 is sufficient to induce in vitro functional maturation of hiPSC-derived islet-like organoids in the absence of additional cell types such as hADSC and HUVECs.

Generation of Mature HILOs that Evade Immune Detection

In vivo, β cells become functionally mature via a long, postnatal maturation process. To date, human induced pluripotent stem cells (hiPSCs) have not been successfully transformed into fully functional β cells by duplicating this process in vitro. Moreover, even though β cells derived from hiPSCs are immune-matched to the patient, life-long immune suppression may still be required to protect against transplant rejection after β cells are transplanted into a patient, particularly, patients with type 1 diabetes who generally have a hyper-reactive immune system. Thus, the generation of universal PSCs that resist immune rejection by expressing one or more checkpoint molecules is highly beneficial, as this would obviate a need for costly personalized therapies.

A self-organized, three-dimensional (3D) tissue architecture is required for organ formation and the terminal differentiation of organ-specific cell types. As described herein, 3D structured organoids comprising human pancreatic islet tissue were generated. The production of functional β cells requires cellular diversity within the developing islet, as well as cellular interactions that may influence the functional differentiation of islets from hiPSCs.

As described herein, a method for the scalable generation of human islet-like organoids (HILOs) from hiPSC is provided. The method utilizes a differentiation pathway that results in enhanced functional maturation and endows the resulting HILOs with immune evasive function. Advantageously, the described method does not require the use of instruments, such as a magnetic spinner or an air-liquid surface, thereby resulting in a simplified and highly reproducible procedure. The scalability of the system allows for both large- and small-scale production of mature HILOs. Tissue maturity is critical for recapitulating all aspects of pancreatic islet function. Since hiPSC-derived pancreatic progenitors or β-like cells reach functional maturation with physiological levels of insulin secretion in vivo within a few months, the in vitro differentiated β-like cells have the potential to be fully functional, mature β-like cells.

The scalable process for generating islet-like organoids from hiPSCs as described herein includes effective signals for functional maturation of the cells, and cellular heterogeneity. In an aspect, a functional, polymer-based, 3-dimensional (3D) culture system and activation of non-canonical Wnt (e.g., Wnt4) signaling are provided to generate 3D structured human islet-like organoids (HILOs) that contain critical pancreatic islet cell types, including beta (β) cells (insulin), alpha (α) cells (glucagon), delta (δ) cells (somatostatin), gamma (γ) cells (PPY), and E cells (ghrelin (GHRL)).

The scalable, 3D system for generating mature human islet-like organoids (HILOs) involves stimulating the non-canonical Wnt pathway to achieve mitochondrial OxPhos function and functional insulin secretion as described herein provides medically useful, therapeutic biological material for the treatment of diseases, such as diabetes. As described herein, the stem cell derived, mature islets or HILOs can express an immune check point molecule; therefore, they are capable of evading allogenic immune rejection and thus provide a fundamental cure for insulin dependent diabetes, without resorting to immunosuppressants. Such HILOs may serve as universal (allogeneic) pancreatic islets, instead of patient-specific or autologous islets, leading to greater availability of therapeutic biological materials and cost reductions in the treatment of insulin dependent diabetes.

Figure 5A:
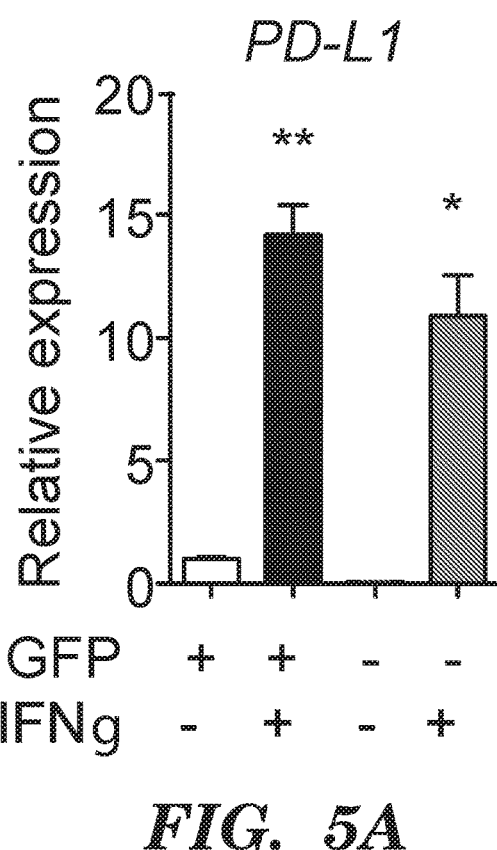
FIGS. 5A-5K provide graphs and schematic diagrams demonstrating that immune tolerance is induced by epigenetic memory.
Figure 5B:
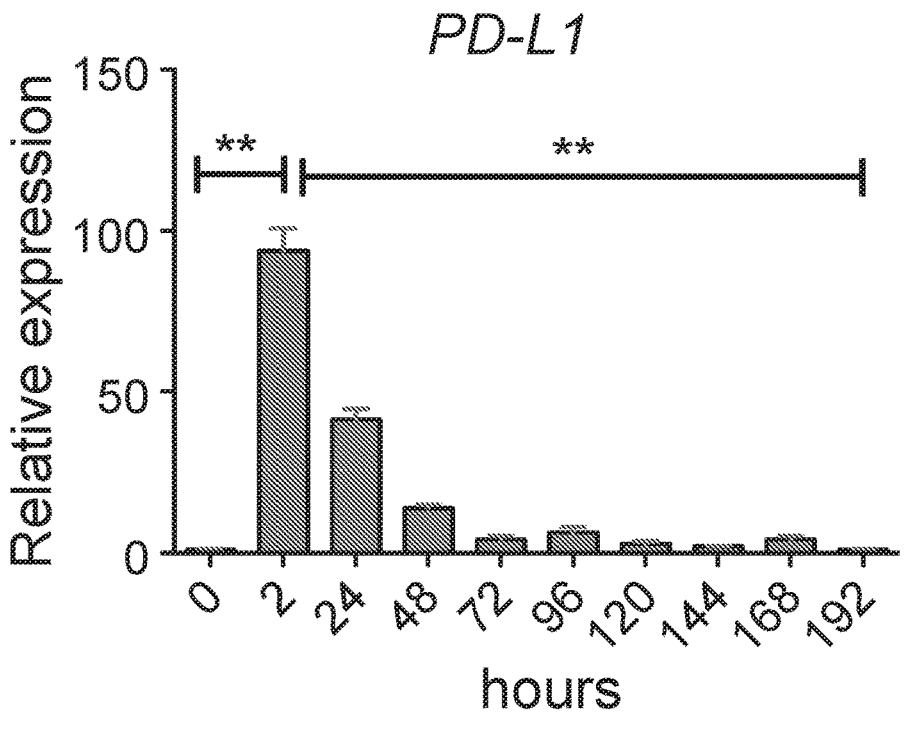
Figure 5D:
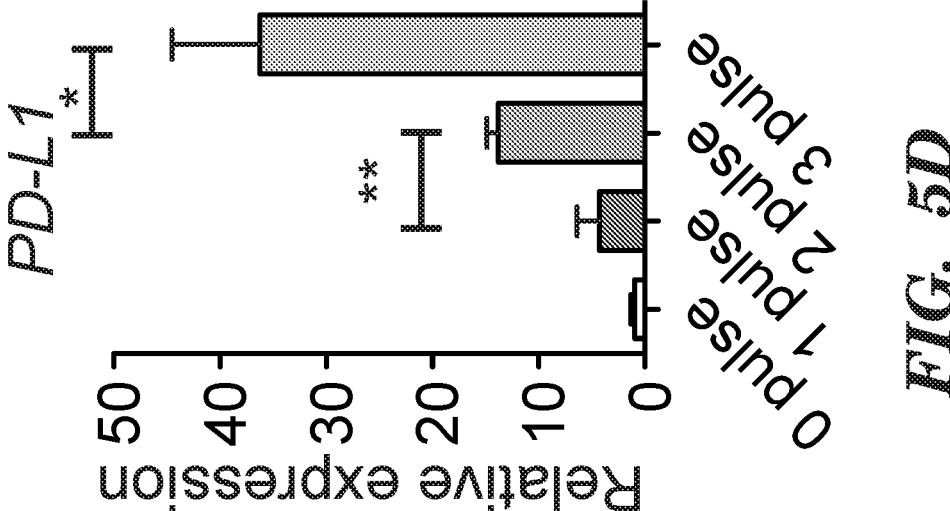
Figure 5C:
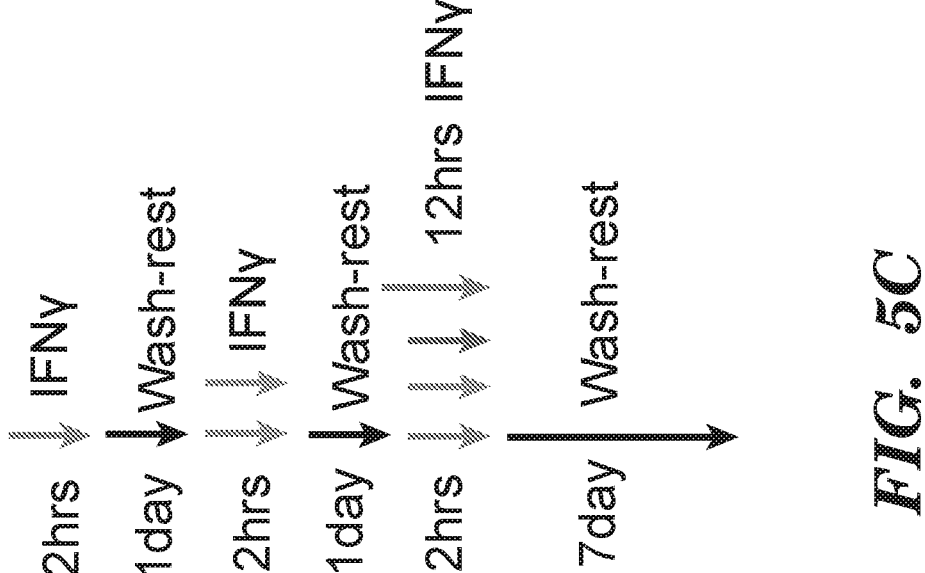
Figure 12A:
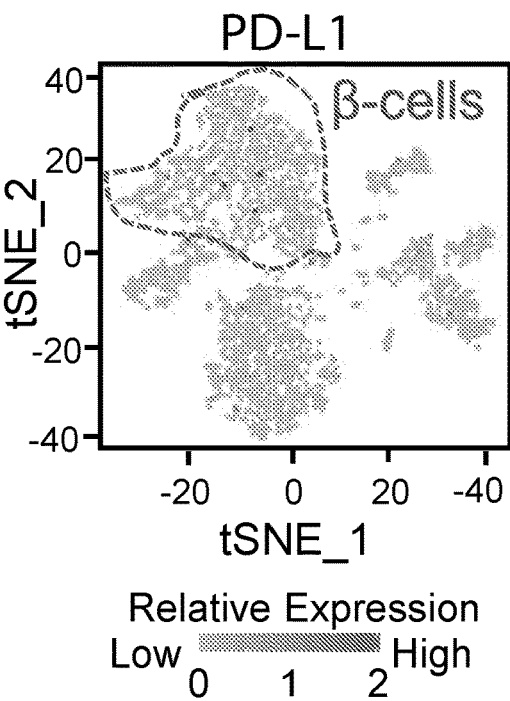
FIGS. 12A-12F provide graphs and images related to PD-L1 gene and protein expression in β cells and HILOs.
Figure 12A:
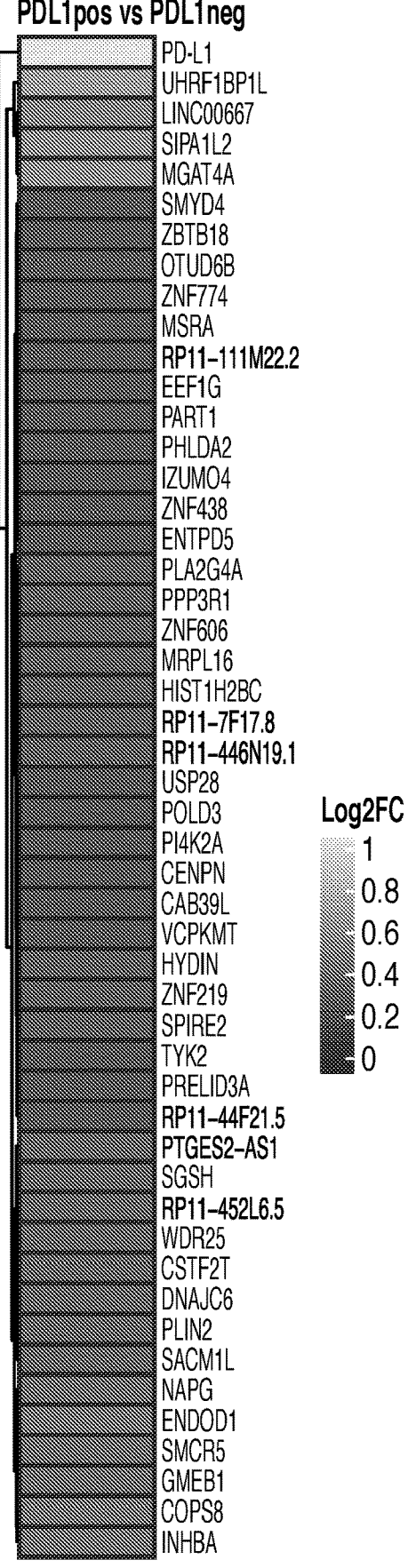
Figure 12B:
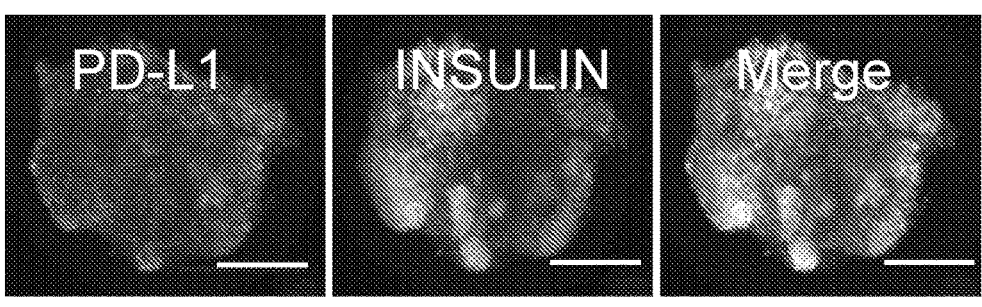
Figure 12C:
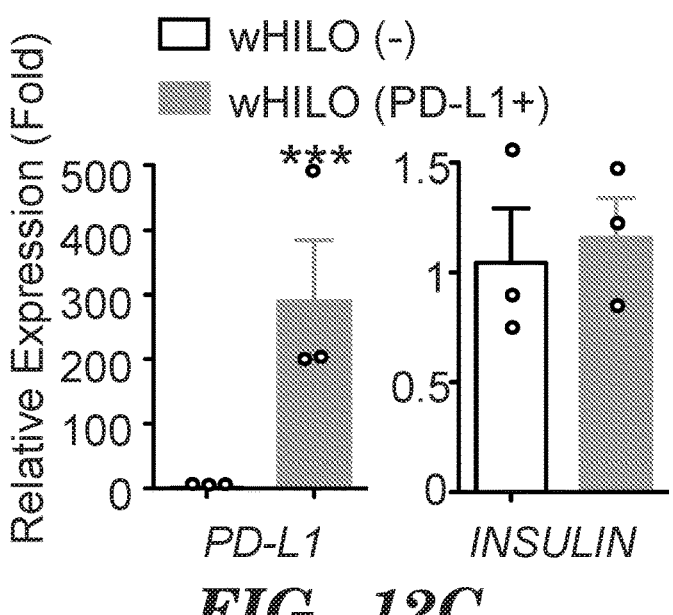
Figure 12D:
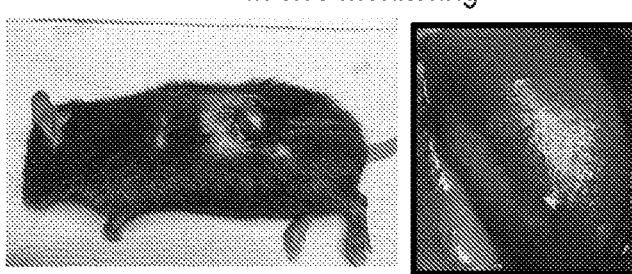
Figure 12F:
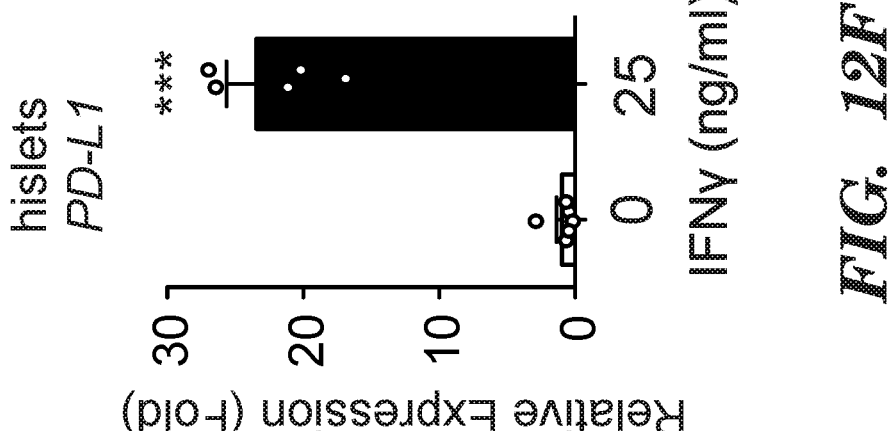
Figure 12E:
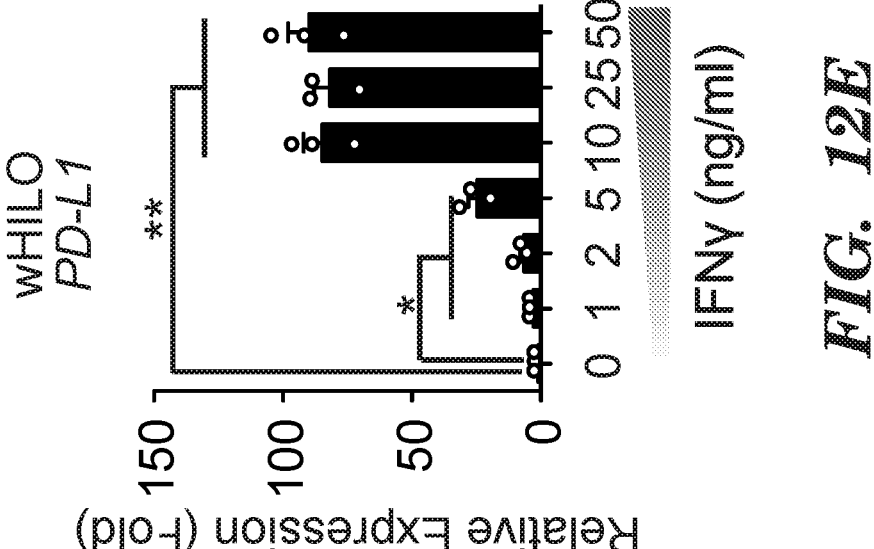

As described herein, the IFNγ pathway was assessed for the ability to minimize host immune responses against transplanted or implanted wHILOs. Following a short exposure of wHILOs to IFNγ stimulation, it was found that IFNγ rapidly and robustly induced PD-L1 expression in wHILOs (FIGS. 12E and 12F). Notably, IFNγ induced PD-L1 expression to levels similar to those in both insulin-expressing and insulin non-expressing cells (GFP+ and GFP− cells, respectively), (FIGS. 5A and 5B). Repeated exposure of HILOs to IFNγ (IFNγ stimulation) induced a similar effect in wHILOs, specifically, a sustained induction of PD-L1 in the HILOs. In an aspect, repeated short exposures to IFNγ (multiple pulse stimulation, MPS) led to sustained PD-L1 expression and concomitant increases in PD-L1 protein levels (FIGS. 5C, 5D and 5E). In embodiments, human islets or HILOs, e.g., mature islets or HILOs are exposed to (contacted with) IFNγ for at least 0.5-5 hours, at least 1-5 hours, at least 1-3 hours, at least 1-2.5 hours, or at least 1-2 hours. In particular embodiments, human islets or HILOs, e.g., mature islets or HILOs are exposed to (contacted with) IFNγ for greater than 1 hour, greater than 2 hours, for 1 hour, for 2 hours, or for 3 hours, prior to washing the islets or HILOs and allowing them to rest in medium without IFNγ. In embodiments, each exposure of the human islets or HILOs to IFNγ is termed a "pulse." In embodiments, the human islets or HILOs are exposed to, contacted or pulsed with IFNγ at least one time, at least two times, at least three times, at least four times, at least five times, etc., or 1, 2, 3, 4, or 5 times, in a one-day or a multi-day (e.g., over a 72 hour time period, or a longer time period) protocol in which cells are allowed to recover (e.g., in medium or matrix without IFNγ) between IFNγ pulses for about 24 hours. In a particular embodiment, the human islets or HILOs are pulsed with IFNγ three times over 3 days, (72 hours), for 2 hours per pulse period, to achieve a constitutive level of PD-L1 expression in the islets or HILOs. Following this IFNγ MPS regimen, the IFNγ-stimulated human islets or HILOs showed high levels of PD-L1 protein expression at 7 days post MPS. In embodiments, the human islets or HILOs are exposed to (contacted or pulsed with) IFNγ in an amount of 1-100 ng/ml, 1-50 ng/ml, 1-25 ng/ml, 1-20 ng/ml, 1-10 ng/ml, or 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 ng/ml. In a particular embodiment, IFNγ is in an amount of 10 ng/ml or 20 ng/ml for each exposure or pulse period. In a particular embodiment, the human islets or HILOs, including mature human islets or HILOs, are exposed to, contacted or pulsed with 2 pulses of IFNγ for 2 hours per pulse in a 2-day period. In a particular embodiment, the human islets or HILOs, including mature human islets or HILOs, are exposed to, contacted or pulsed with 3 pulses of IFNγ for 2 hours per pulse over a 3-day (day3) period.

Figure 5F:
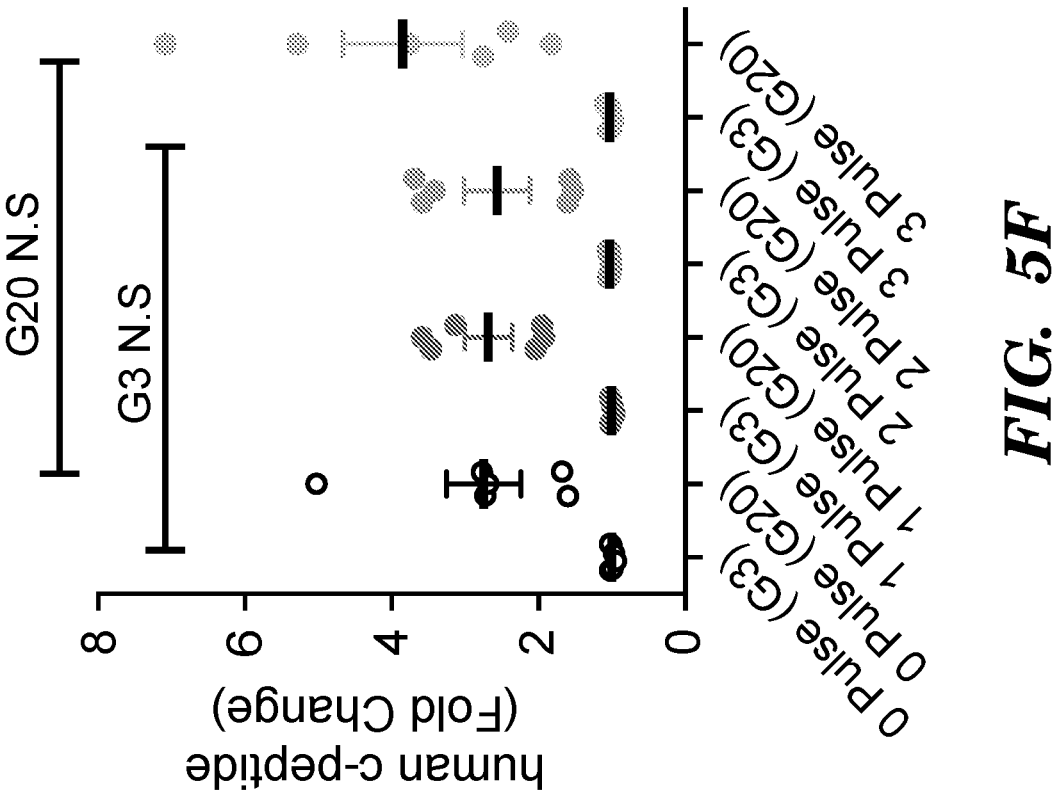
Figure 5E:
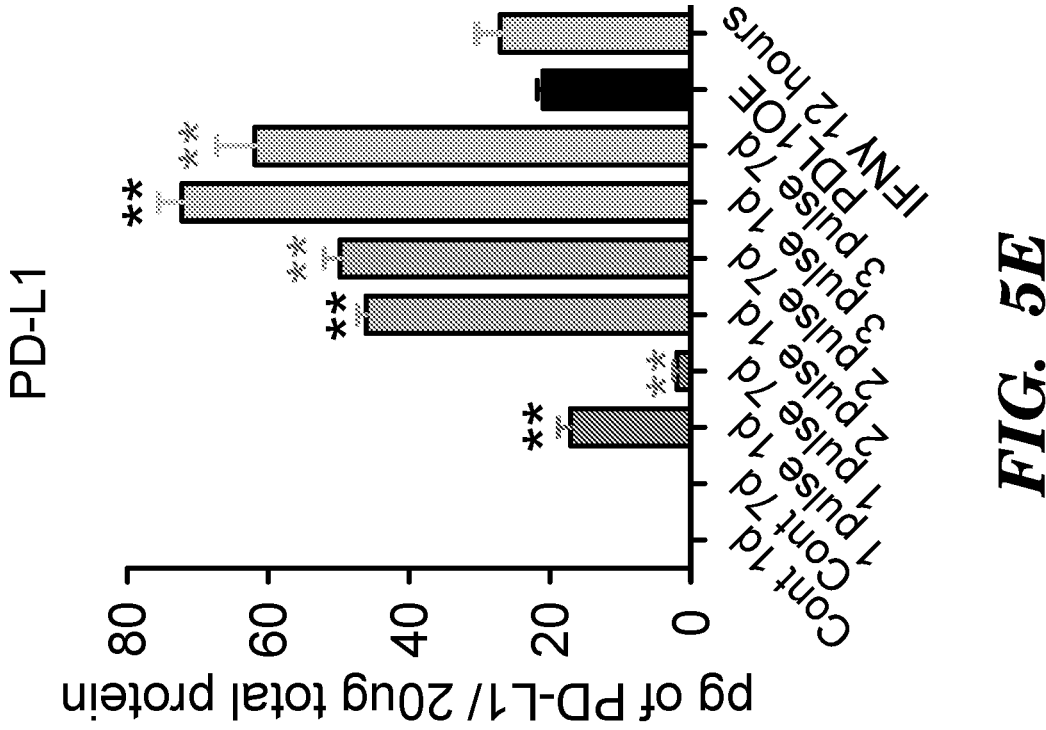
Figure 5H:
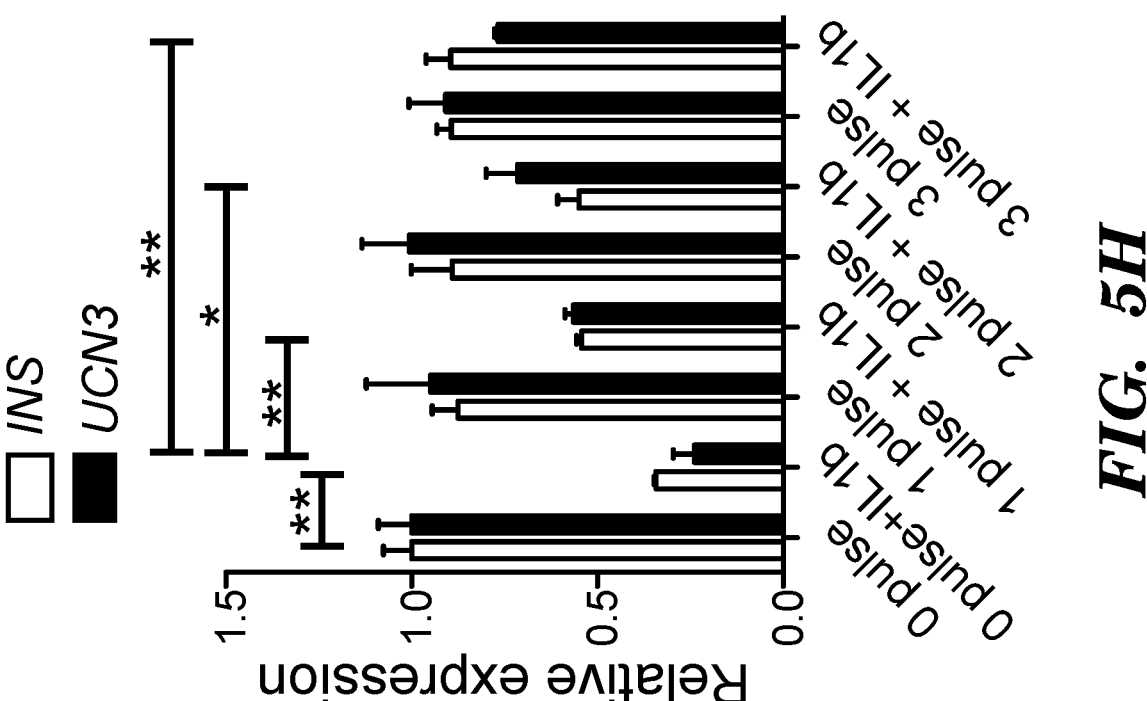

GSIS functionality was not compromised by exposure of the wHILOs to MPS by IFNγ (FIG. 5F). Furthermore, IFNγ-treated wHILOs were protected against IL-1β-induced β cell dedifferentiation, as revealed by the expression of the β cell identity markers INS and UCN3 (FIG. 5H).

Normal, in utero development of a human pancreas takes more than 280 days, and full functional maturity is not reached until a few years after birth; therefore, gaining a complete understanding of the complex pathways involved in the development and maturation of human islets is a necessary step toward generating functional islets in vitro. A pivotal aspect for functional maturity of β cells is the activation of the mitochondrial metabolic pathway, which occurs naturally in postnatal maturation and is required for functional β cells nutritional sensing insulin secretion function. For HILOs, sustainable mitochondrial activation may be achieved through Wnt4 driven mitochondria metabolic regulation.

In an aspect, enhancing the ability of transplanted β cells to evade immune detection as described herein provides an alternative or adjunct strategy to MHC matching (A. Morizane et al., 2017, *Nature communications,* 8:385) for reducing the risk of autoimmune rejection of transplanted islet cells, pancreatic islets, organoids and HILOS. Stem cell-, islets- and organoid-based treatments for diabetes must achieve protection of the transplanted cells, islets and organoids from autoimmune rejection, in addition to their functional maturity. When PD-L1 negative mature HILOs were transplanted into diabetic immune-competent C57BU6J mice, the xenograft was rejected and failed to produce detectable amounts of human c-peptide. In contrast, mature HILOs that expressed PD-L1 (either via molecular engineering or induction of expression of PD-L1 in organoid cells as described herein), successfully survived more than 50 days following transplantation into immune competent animals. (FIGS. 4D-4E and FIGS. 12A-12C). Moreover, acquisition of immune tolerance did not require the presence of Tregs. Thus, in an aspect, additional immune protection may be achieved by co-culturing Tregs in the gel-based system used to produce mature HILOs. During antigen presentation, interactions between cytotoxic T-lymphocyte antigen-4 (CTLA-4) and B7 molecules, as well as programed death 1 (PD-1) protein and its ligand PD-L1, negatively regulate immune responses in a non-redundant manner. As described herein, PD-L1 negative, control HILOs were rejected in T and B cell competent C57BL6J mice, but were not rejected in T and B cell-deficient NOD-SCID mice (e.g., Example 8), suggesting that allogenic rejection for PD-L1 negative control mature HILOs were mainly through T cells and B cells reaction in vivo.

The generation of iPSCs by somatic cell reprogramming provides a source of patient-specific cells (e.g., autologous cells) that may be differentiated into any lineage. Moreover, generating insulin-producing cells from iPSCs provides an invaluable tool for autologous transplantation, which would greatly reduce the risk for autoimmune rejection. While allogenic transplantation of MHC-matching grafts has proven effective in reducing immune responses and is useful, this technique may not result in complete evasion of the immune system and immune surveillance, even in less immunological sites, such as the brain. Thus, a combination of MHC matching and the induction of immune tolerance may provide a further approach to controlling immune responses against transplanted stem cells, islets and organoids. In some cases, such procedures may obviate a need for immunosuppressive drugs.

Because ongoing autoimmunity in patients with type 1 diabetes could still result in immunogenicity when patient-specific, stem cell-derived islets are transplanted, or stem cell-based islet cell replacement approaches are used, employing allogeneic hiPSCs together with immunosuppressive or tolerogenic treatments (for controlling both alloreactivity and autoreactivity) provide advantageous therapies for patients with type 1 diabetes. In addition, co-stimulation blockade procedures involving the expression of one or more checkpoint inhibitor molecules as well as a checkpoint protein to evade immune surveillance, e.g., CTLA4Ig- and PD-L1-expressing human stem cells, β cells, islets cells, or organoid cells, may provide clinically relevant materials for successful transplantation/implantation in subjects for diabetes treatment. By protecting HILOs via PD-L1 expression to promote graft/transplant/implant survival, HILO allografts can experience reduced immune cell infiltration, in the absence of immunosuppressive drugs. However, it will be appreciated that one or more immunosuppressive may be used if medically required or desired.

Methods of Treatment

Islet transplantation is a therapy for treating insulin deficient diabetes such as type 1 and late stage type 2 diabetes. Thus, in an aspect, a method of treating a pancreatic disease such as type 1 or type 2 diabetes are provided, in which the method comprises administering a pancreatic or pancreatic islet organoid, in particular, a HILO expressing a checkpoint protein as described, to a subject (e.g., a mammalian subject, such as a human or human patient) by transplantation (or implantation). In an embodiment, the method treats a subject suffering from, susceptible to, or at risk of having, a pancreatic disease (e.g., type 1 diabetes), disorder, or symptom thereof. The method includes the step of transplanting a pancreatic or pancreatic islet organoid (HILO) in the mammal sufficient to treat the disease, disorder, or symptom thereof, under conditions such that the disease, disorder, or symptom is treated.

As used herein, the terms "treat," "treating," "treatment," and the like refer to reducing, diminishing, ameliorating, abrogating, or alleviating a disease, disorder and/or the symptoms associated therewith. It will be appreciated that, although not precluded, treating a disease, disorder, condition, or symptom thereof does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of, or susceptible to, developing or having a disorder or condition.

The therapeutic methods (which include prophylactic treatment) generally comprise administration, in particular, transplantation or implantation, of an effective amount of a pancreatic islet or pancreatic islet organoid (e.g., a HILO) to a subject (e.g., animal, mammal, human) in need thereof, including a mammal, particularly a human. In particular, the pancreatic islet or pancreatic islet organoid (e.g., HILO) is molecularly engineered to express one or more checkpoint proteins. In an embodiment, the checkpoint protein is PD-L1. In an embodiment, a cell, islet, or organoid is subjected to multiple intermittent exposures to interferon gamma (IFNγ), (multiple pulse stimulation or MPS), according to the methods described herein. The MPS methods yield cells, islets, or organoids in which the expression of a checkpoint protein such as PD-L1 is sustained over long time periods following transplantation or administration to a subject, thereby allowing the transplanted or administered cells, islets, or organoids to function while avoiding autoimmunity or immune detection. In an embodiment, the administration of a pancreatic islet or pancreatic islet organoid (e.g., HILO) may be by any suitable means that results in an amount of the organoid that, combined with other components, is effective in ameliorating, reducing, abrogating, diminishing, or stabilizing a pancreatic disease such as type 1 or type 2 diabetes.

In certain aspects, the subject may be further administered an immunosuppressant. The immunosuppressant can be administered to the subject before, during, or after the subject is administered (e.g., transplanted or implanted) with the organoid. The immunosuppressive agent can be an agent that inhibits or prevents rejection (e.g., acute rejection) of the transplanted organoid upon transplantation, or an agent that maintains immunosuppression after the transplantation. Immunosuppressants include, but are not limited to, basiliximab, antithymocyte globulin, alemtuzumab, prednisone, azathioprine, mycophenolate, cyclosporine, sirolimus, and tacrolimus.

In some embodiments, at least about 100,000, at least about 200,000, at least about 300,000, at least about 400,000, at least about 500,000, at least about 600,000, at least about 700,000, at least about 800,000, at least about 900,000 or at least about 1 million pancreatic islet organoids (HILOs) are transplanted or implanted into the subject. In some embodiments, islets of the subject are removed prior to transplanting or implanting the organoids of the invention. In some other embodiments, pancreatic islet organoids (HILOs) are transplanted or implanted into a subject by injection into the upper abdomen of the subjects. In some embodiments, the pancreatic islet organoids (HILOs) are injected into the liver. The pancreatic islet organoids can be injected into the subject using a catheter. In some other embodiments, the pancreatic organoid or pancreatic islet organoid (HILO) is administered to the subject by surgery, e.g., transplant surgery. In another embodiment, pancreatic islet organoids (HILOs) are transplanted onto the omentum. For omentum transplantation, a layering technique can be used in which the islet organoid (or cells thereof) are combined with autologous plasma and are laparoscopically layered onto the omentum. A solution (20 ml) containing recombinant thrombin (1000 U/ml) is next layered over the islet organoid, followed by another layer of autologous plasma to produce a biodegradable biologic scaffold that can survive and function in the patient for at least a year (See, e.g., Baidal, D. et al., 2017, *N. Engl. J. Med.,* 376:19). In another embodiment, hydrogel biomaterials that mitigate an immune response by the recipient can be used for islet organoid transplantation. (See, e.g., Vegas, A. et al., 2016, *Nature Biotechnology,* 34:345-352).

While organoids, pancreatic organoids, or pancreatic islet organoids (e.g., HILOs) are preferably engineered to express one or more checkpoint proteins as described herein, an immune reaction to the transplanted organoid (e.g., HILO) may be further reduced in the subject by encapsulating the organoid, pancreatic organoid, or pancreatic islet organoid (HILO) in a hydrogel prior to transplanting in the subject. Such methods of transplantation are further described in Vegas et al., 2016, *Nature Medicine.* doi:10.1038/nm.4030; Vegas et al., 2016, *Nature Biotechnology,* doi:10.1038/nbt.3462. In some embodiments, the hydrogel contains an alginate or alginate derivative (e.g., triazole-thiomorpholine dioxide). Various modifications of alginate hydrogels that substantially reduce inflammatory or fibrotic effects of alginate hydrogels have also been identified (Vegas et al., 2016, *Nature Biotechnology,* doi:10.1038/nbt.3462). Thus, in some other embodiments, the hydrogel contains a chemical modification that reduces an inflammatory effect of the transplanted organoid in the subject.

Screening Assays

Pancreatic islet organoids and pancreatic organoids (HILOs) as described herein can be employed to model diseases of the pancreas in vitro or in vivo. Such pancreas disease models can identify drugs that are useful for treatment of a pancreatic disease. Thus, in some aspects, the invention provides methods for identifying modulators, i.e., candidate or test compounds or agents (e.g., proteins, peptides, peptidomimetics, peptoids, polynucleotides, small molecules or other drugs) that can treat a pancreatic disease, particularly type 2 diabetes and/or pancreatic cancer. In one embodiment, the compound or agent modulates an activity of a pancreatic organoid or pancreatic islet organoid (HILO) as described herein.

The test compounds or agents can be obtained singly or using any of the numerous approaches in combinatorial library methods known in the art, including, but not limited to, biological libraries; peptoid libraries (libraries of molecules having the functionalities of peptides, but with a novel, non-peptide backbone which are resistant to enzymatic degradation and remain bioactive; see, e.g., Zuckermann, R. N. et al., 1994, *J. Med. Chem.,* 37:2678-85; spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.,* 12:145).

Examples of methods for the synthesis of molecular libraries can be found in the art, for example in: DeWitt et al., 1993, *Proc. Nal. Acad. Sci. U.S.A.,* 90:6909; Erb et al., 1994, *Proc. Nal. Acad. Sci. USA,* 91:11422; Zuckermann et al., 1994, *J. Med. Chem.,* 37:2678; Cho et al., 1993, *Science,* 261:1303; Carrell et al., 1994, *Angew. Chem. Int. Ed. Engl.,* 33:2059; Carell et al., 1994, *Angew. Chem. Int. Ed. Engl.,* 33:2061; and Gallop et al., 1994, *J. Med. Chem.,* 37:1233.

Libraries of compounds may be presented in solution (e.g., Houghten, 1992, *Biotechniques*, 13:412-421), or on beads (Lam, 1991, *Nature*, 354:82-84), chips (Fodor, 1993, *Nature*, 364:555-556), bacteria (Ladner, U.S. Pat. No. 5,223, 409), spores (Ladner U.S. Pat. No. 5,223,409), plasmids (Cull et al., 1992, *Proc Natl Acad Sci USA*, 89:1865-1869) or on phage (Scott and Smith, 1990, *Science*, 249:386-390; Devlin, 1990, *Science*, 249:404-406; Cwirla et al., 1990, *Proc. Natl. Acad. Sci. USA*, 87:6378-6382; Felici, 1991, *J. Mol. Biol.*, 222:301-310; and Ladner, Ibid., supra).

Chemical compounds to be used as test agents (i.e., potential inhibitors, antagonists, agonists) can be obtained from commercial sources or can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, 1989, *Comprehensive Organic Transformations*, VCH Publishers; T. W. Greene and P. G. M. Wuts, *Protective Groups in Organic Synthesis*, 2nd ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Combinations of substituents and variables in compounds encompassed by these methods are only those that result in the formation of stable compounds. The term "stable", as used herein, refers to compounds that possess stability sufficient to allow manufacture and that maintain the integrity of the compound for a sufficient period of time to be useful for the purposes detailed herein (e.g., transport, storage, assaying, activity, therapeutic administration to a subject).

The compounds described herein can contain one or more asymmetric centers and thus occur as racemates and racemic mixtures, single enantiomers, individual diastereomers and diastereomeric mixtures. All such isomeric forms of these compounds are expressly included in the described methods. The compounds described herein can also be represented in multiple tautomeric forms, all of which are included herein. The compounds can also occur in cis- or trans- or E- or Z-double bond isomeric forms. All such isomeric forms of such compounds are expressly included.

Test agents, molecules and compounds can also be peptides (e.g., growth factors, cytokines, receptor ligands) or polynucleotides encoding such peptides, and the like.

Screening methods identify agents that increase or decrease a biological activity of pancreatic organoids and pancreatic islet organoids (e.g., HILOs) as described herein. In some embodiments, a pancreatic disease, such as diabetes, (e.g., type 2 diabetes) or pancreatic cancer, is induced or mimicked in the pancreatic islet organoid (e.g., HILO) or pancreatic organoid. Type 2 diabetes in the pancreatic organoid or pancreatic islet organoid (e.g., HILO) can be induced, for example, by contacting the organoid with free fatty acids (FFAs), glucose, and cytokines (in particular, high levels of glucose and/or high levels of FFAs). In one embodiment, a pancreatic organoid or pancreatic islet organoid (e.g., HILO) is co-cultured with pancreatic cancer cells, stellate cells and immune cells to create a human pancreatic cancer microenvironment in vitro.

In some embodiments, the organoid is contacted with a candidate agent, molecule, or compound, and an effect of the candidate agent, molecule, or compound on a biological activity, function, or event is assayed. In some embodiments, the candidate agent, molecule, or compound is a drug approved by the Food and Drug Administration (FDA). For example, biological activities of a pancreatic organoid or pancreatic islet organoid (e.g., HILO) assayed in the screening methods include insulin secretion (e.g., glucose-stimulated insulin secretion (GSIS)), beta cell apoptosis, LDHA activity, K(ATP) channel activity, mitochondrial function, level or activity of NDUFA4, ESRRG, KCNK3, or MAFA polypeptides or encoding polynucleotides, cell death, cell growth, and metastasis. In some embodiments, the agent, molecule, or compound increases GSIS.

In other embodiments, pancreatic islet cells, pancreatic organoid, or pancreatic islet organoid (e.g., HILO) is transplanted or implanted into a host to model pancreatic disease, such as type 2 diabetes or pancreatic cancer, in vivo. Methods of transplanting or implanting an organ or organoid are known in the art. The host can be any non-human mammal, such as a rat or mouse.

In addition to the expression of a checkpoint protein in cells, islets, organoids, pancreatic islet cells, pancreatic organoids, or pancreatic islet organoids (e.g., HILOs) for evading autoimmunity and immune detection, a recipient's immune reaction to the transplanted biological material, such as an organoid (e.g., HILO), can be further reduced, if desired, by encapsulating the organoid (e.g., HILO) in a hydrogel and then transplanting the encapsulated organoid (e.g., HILO) in the animal. Such methods of transplantation are described in Vegas et al., 2016, *Nature Medicine*, doi: 10.1038/nm.4030; and Vegas et al., 2016, *Nature Biotechnology*, doi:10.1038/nbt.3462. In some embodiments, the hydrogel contains an alginate or alginate derivative (e.g., triazole-thiomorpholine dioxide). Various modifications of alginate hydrogels that substantially reduce inflammatory or fibrotic effects of alginate hydrogels have also been identified (Vegas et al., 2016, *Nature Biotechnology*, Ibid.). In still other embodiments, the hydrogel contains a chemical modification that reduces an inflammatory effect of the transplanted organoid in the host.

In some embodiments, a pancreatic organoid or pancreatic islet organoid (e.g., HILO) and liver organoid are co-transplanted or implanted in the animal. The liver is a major target organ for metastasis of pancreatic cancer. In mice, in vivo endothelial cells in the mini pancreas and in the mini liver are connected to each other and create a pancreas-liver vasculature network for pancreatic cancer metastasis. Therefore, an animal co-transplanted with a a pancreatic organoid or pancreatic islet organoid (e.g., HILO) and a liver organoid can be useful for studies of human pancreatic cancer metastasis into human liver. In some embodiments, the co-transplanted organoids are subjected to multiple intermittent exposures to IFNγ (MPS procedure) according to the methods as described herein.

In some embodiments, an animal transplanted with an organoid (e.g., HILO) as described herein is administered an environmental stress (e.g., a high fat/high glucose diet or is administered pancreatic cancer cells) to induce or mimic pancreatic disease in the animal. In some other embodiments, the animal is transplanted with a pancreatic islet, pancreatic organoid, or pancreatic islet organoid (e.g., HILO) and/or a liver organoid in which a disease (e.g., type 2 diabetes or pancreatic cancer) has been induced.

In some embodiments, a candidate agent, molecule, or compound is administered to an animal. In certain embodiments, the candidate agent, molecule, or compound is a drug approved by the Food and Drug Administration (FDA). In some embodiments, an effect of the candidate agent, molecule, or compound on a phenotype in the animal (such as biological activity or function associated with the pancreas, or activities associated with a disease such as pancreatic disease) is assayed. Exemplary, yet nonlimiting, biological activities include one or more of insulin secretion (e.g., glucose-stimulated insulin secretion (GSIS)), beta cell apoptosis, lactate dehydrogenase (LDHA) activity, K(ATP) channel activity, mitochondrial function, level or activity of NDUFA4 (Cytochrome c oxidase subunit NDUFA4), ESRRG, or MAFA (musculoaponeurotic fibrosarcoma oncogene family, protein A) polypeptide or encoding polynucleotide, cell death, cell growth, and metastasis. In some embodiments, the candidate agent, molecule, or compound increases GSIS.

In any one of the embodiments herein, the effect of the candidate agent, molecule, or compound (i.e., ability to modulate a pancreatic activity or function) is measured relative to a reference or control. The reference can be, for example, an untreated pancreatic organoid or pancreatic islet organoid. In some embodiments, the reference is a host transplanted with an organoid (e.g, HILO) as described herein, where the host is not administered a candidate agent, molecule, or compound.

Agents, molecules, or compounds useful in the methods as described herein can also be detected by identifying an increase in expression of a desirable marker (e.g., MAFA as a beta cell fate marker). The level of expression can be measured in a number of ways, including, but not limited to, measuring the mRNA encoded by the genetic markers; measuring the amount of protein encoded by the genetic markers; or measuring the activity of the protein encoded by the genetic markers.

The level of mRNA corresponding to a marker can be determined both by in situ and by in vitro formats. The isolated mRNA can be used in hybridization or amplification assays that include, but are not limited to, Southern or Northern analyses, polymerase chain reaction (PCR) analyses and probe arrays. In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. The skilled practitioner can adapt known mRNA detection methods for use in detecting the level of mRNA encoded by the markers described herein.

The level of mRNA in a sample can be evaluated with nucleic acid amplification, e.g., by rtPCR (C. Mullis, 1987, U.S. Pat. No. 4,683,202), ligase chain reaction (Barany, 1991, *Proc. Natl. Acad. Sci. USA*, 88:189-193), self-sustained sequence replication (Guatelli et al., 1990, *Proc. Natl. Acad. Sci. USA*, 87:1874-1878), transcriptional amplification system (Kwoh et al., 1989, *Proc. Natl. Acad. Sci. USA*, 86:1173-1177), Q-Beta Replicase (Lizardi et al., 1988, *Bio/Technology*, 6:1197), rolling circle replication (Lizardi et al., U.S. Pat. No. 5,854,033), or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length.

Under appropriate conditions and with appropriate reagents, such primers permit the amplification of a nucleic acid molecule (polynucleotide) comprising the nucleotide sequence flanked by the primers.

Kits

Also provided are kits containing an immunoprotected cell, human islet-like organoid or pancreatic islet organoid as described herein, or a pharmaceutically acceptable composition (therapeutic composition) containing the immunoprotected cell, human islet-like organoid or pancreatic islet organoid and a pharmaceutically acceptable carrier, diluent, or excipient, for administering to, or transplanting into, a subject in need thereof. As will be appreciated by the skilled practitioner in the art, such a kit comprises a sterile container which contains the therapeutic composition; such containers can be boxes, ampoules, bottles, vials, tubes, bags, pouches, or other suitable container forms known in the art. The containers can be made of plastic, glass, or other materials suitable for holding biological medicaments. In some embodiments, a kit may include multiple containers that house the immunoprotected cell, human islet-like organoid or pancreatic islet organoid, a composition thereof, diluents, vehicles, or excipients, as necessary, and instructions for use. The instructions will generally include information about the use of the immunoprotected cell, human islet-like organoid or pancreatic islet organoid or composition thereof for treating a disease, such as a pancreatic disease or diabetes. In other embodiments, the instructions include at least one of the following: description of the therapeutic agent (immunoprotected cell, human islet-like organoid or pancreatic islet organoid); dosage schedule and administration for treatment of the disease, or transplantation; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

Advantages and Applicability of the Embodiments

A combination of genetic and environmental factors underlies the autoimmune destruction of ß cells, and while exogenous insulin provides glycemic control, the long-term complications associated with Type 1 diabetes are a continuing concern. Thus, the ability to generate ß cells suitable for transplantation has the potential to significantly improve patients' lives. While cadaveric islet cell transplantation offers one mode of therapy, alternative stem cell-based approaches continue to face numerous challenges in generating GSIS competent ß cells on a large-scale and protecting transplanted cells from auto-immunity and allogenic rejection. For the latter, it is generally considered that self-contained transplantation devices, immune suppressive therapies, or both are required.

Figure 3A:
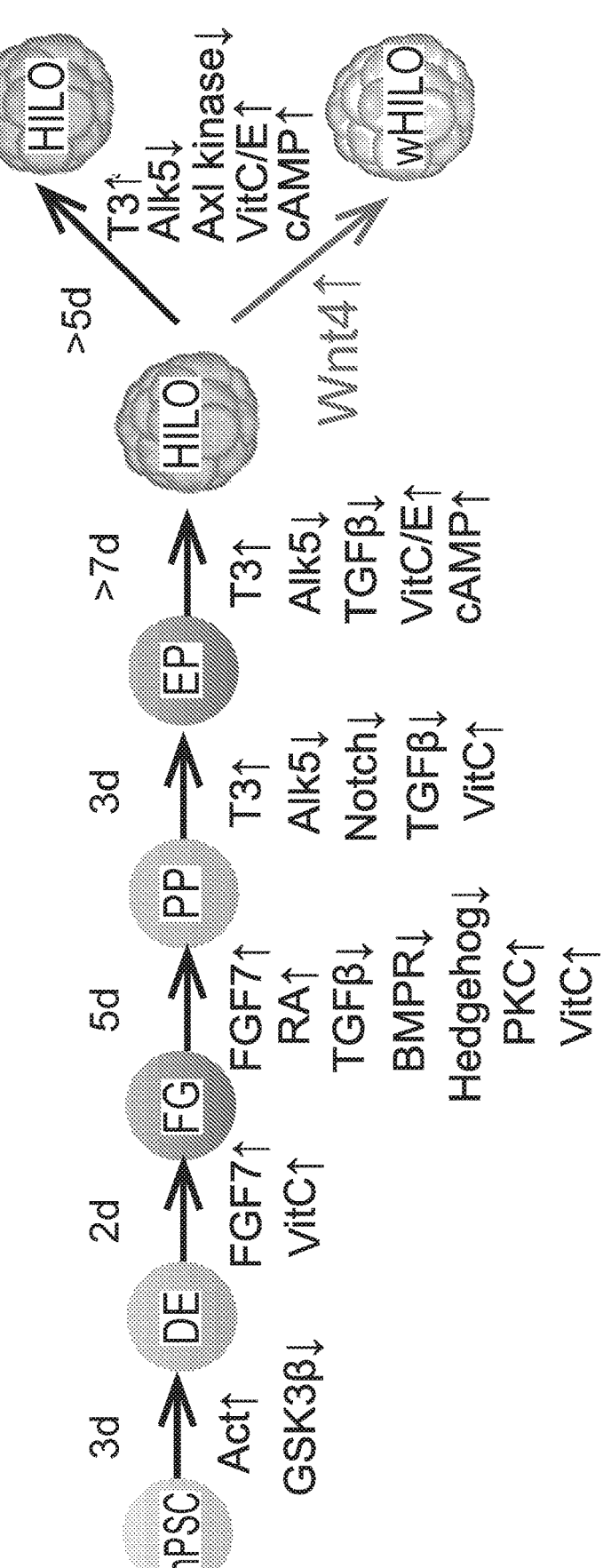
Figure 3B:
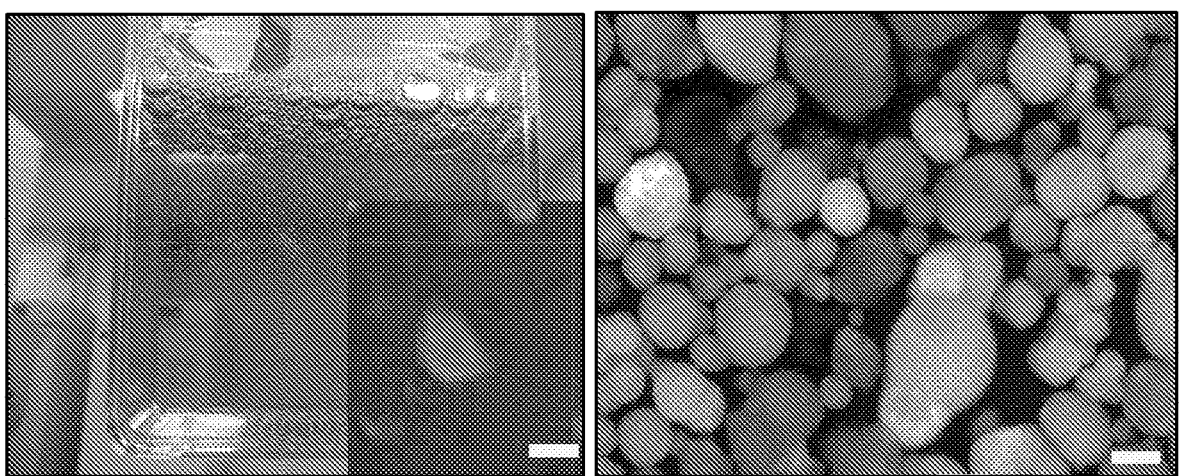
Figure 3C:
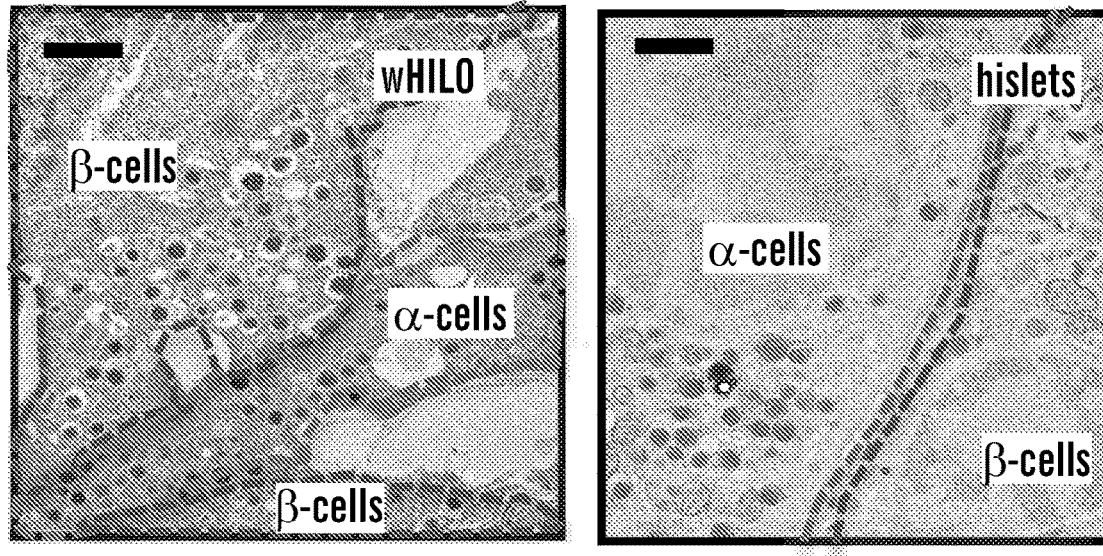

The methods and systems described herein provide useful protocols, such as 3D culturing conditions that systematically drive the differentiation of pluripotent stem cells (e.g., hiPSCs), stem cells, or embryonic stem (ES) cells, into insulin-positive, glucose-sensitive ß-like cells, and lead to the generation of metabolically mature, immune evasive human islet-like organoids (wHILO$^{ie}$) capable of secreting insulin in response to a glucose challenge. Furthermore, these functionally mature HILOs rapidly reestablish glucose homeostasis upon transplantation into diabetic, immune-competent mice. A feature of the described protocols furthers the inventors' discoveries that oxidative mitochondrial metabolism was central for postnatal ß cell maturation and that the transcription factor ERRγ was necessary and sufficient for this metabolic program. The identification of WNT4 as a potent maturation factor for inducing both ERRγ expression and for enhancing mitochondrial oxidative phosphorylation allowed for the production of wHILOs in fully chemically defined medium (FIGS. 3F and 3H).

Figures 7A, 7B:
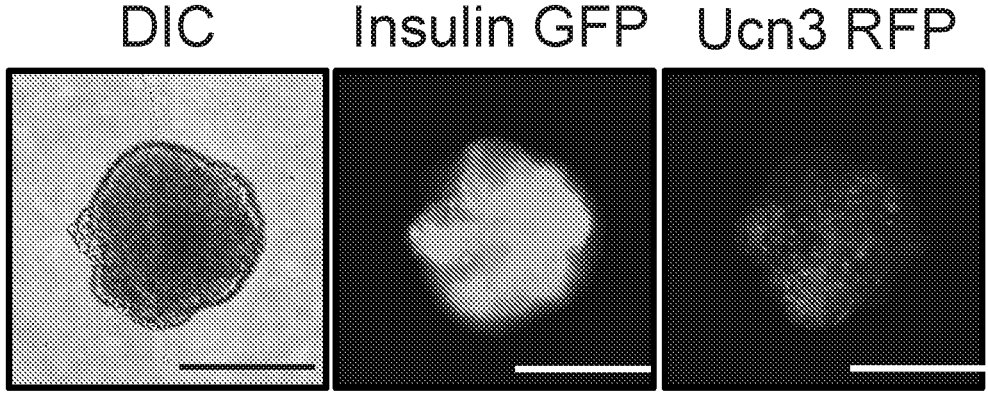
Figures 1, 7C, 7D:
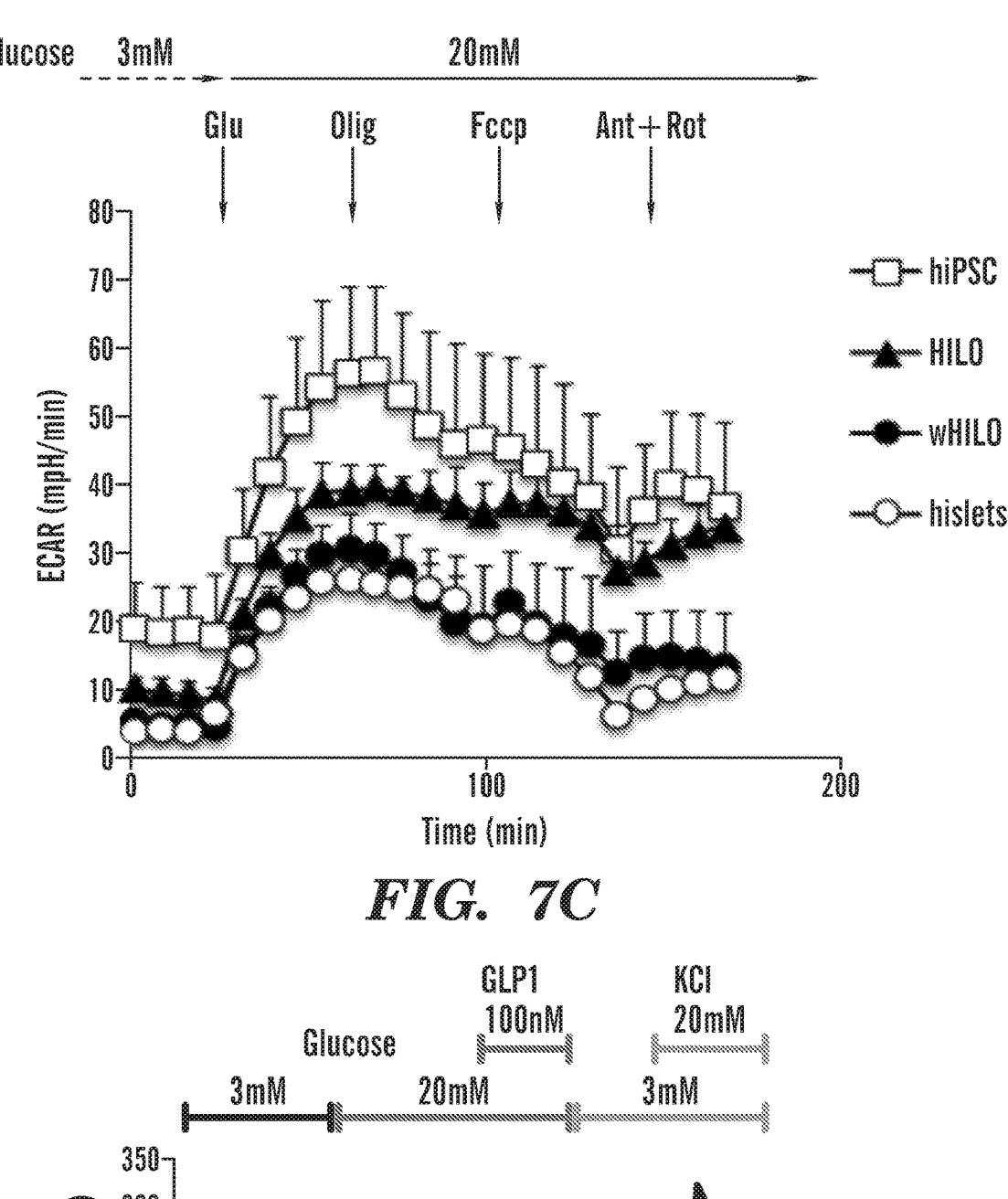

As would be appreciated by the skilled practitioner, challenges for stem cell-based therapeutics include autoimmune rejection of transplanted cells, in addition to metabolic and functional maturity of the cells. However, the methods, systems, and biological products generated and provided herein provide advantageous solutions to such challenges. By way of example, the finding that wHILOs maintained functionality in NOD-SCID but not in C57BL6J mice implicates T cells and B cells in the xenograft rejection (FIG. 3K and FIG. 7C). During antigen presentation, interactions between cytotoxic T-lymphocyte antigen-4 (CTLA-4) and B7 molecules, as well as programmed cell death protein 1 (PD1) receptor and its ligand PD-L1, negatively regulate immune responses in a non-redundant manner. As described and exemplified herein, HILOs, such as wHILOs, overexpressing PD-L1 are protected from xenograft (FIG. 4C) and allogenic (FIG. 4K) rejection. As further described and exemplified herein, methods and systems were developed in which multiple, repeated exposures to limited IFNγ concentrations (IFNγ MPS treatment method) over period of time led to sustained, endogenous PD-L1 expression without compromising the GSIS activity of the cells (e.g., ß-cells), HILOs and the cells therein. Notably, the resultant immune evasive HILOs maintained glucose homeostasis in immune-competent as well as in humanized diabetic mice in the absence of a transplantation device.

The generation of iPSCs by somatic cell reprogramming provides a source of patient-specific syngeneic or autologous cells that can potentially be differentiated into any lineage. Thus, generating insulin-producing cells from iPSCs for autologous transplantation might dramatically reduce the risk for autoimmune rejection. However, in practical terms, generating clinical-grade autologous transplants that meet manufacturing standards, quality assurance, and regulatory compliance involves expensive and time-consuming procedures. Although the allogenic transplantation of MHC-matching grafts has proven effective in reducing immune responses, this technique generally does not result in complete evasion of the immune system, even in less immunological sites such as the brain. Furthermore, the possible destruction of the transplanted insulin-producing cells by autoreactive T cells remains. Thus, the present methods and their resulting cells and products (e.g., immune evasive HILOs and cells) provide beneficial and long-lasting therapeutics that maintain function (e.g., GSIS) and integrity for significant time periods after transplantation or administration to a subject in need. In embodiments, MHC matching and/or the induction of immune tolerance may further be employed to control immune responses, optimally without immunosuppressive drugs.

Provided and described in an embodiment herein are advantageous methods and culture systems (e.g., a 3D culture system) for the generation of human islet-like organoids (HILOs). The methods and systems incorporate non-canonical WNT signaling to promote metabolic maturation and glucose-sensitive insulin secretion in HILOs and the cells therein, and limited IFNγ exposure, namely, multiple pulse stimulation with IFNγ, to drive the sustained expression of endogenous PD-L1 in the HILOs and cells therein. The ability to generate functional immune evasive HILOs, e.g., wHILO$^{ie}$, that are capable of avoiding immune detection over a significant period of time (over 50 days or longer) represents a major advance that offers a viable alternative to current cadaveric islet use or device-dependent technologies.

The practice of the methods and protocols described herein employs, unless otherwise indicated, conventional techniques of molecular biology (including recombinant techniques), microbiology, cell biology, biochemistry and immunology, which are well within the purview of the skilled artisan. Such techniques are explained fully in the literature, such as in "Molecular Cloning: A Laboratory Manual", second edition (Sambrook, 1989), as well as subsequent editions; "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides described herein, and, as such, may be considered and employed in making and practicing the invention.

Particularly useful techniques for particular embodiments are discussed in the following examples, which are set forth to provide those of ordinary skill in the art with a complete disclosure and description of how to make and use the products, assays, procedures, screening, and therapeutic methods as described, without intending to limit the description and disclosure herein.

EXAMPLES

Example 1: Generation and Characterization of Pancreatic and Pancreatic Islet Organoids Although an animal disease model can yield insight into the pathogenesis of diseases, drugs identified from screens using animal models often fail to be adopted in human patients. Generation of functional human organoids provides a new therapeutic strategy in drug-screening and disease modeling. Described herein is a technique to generate a 3D human pancreatic mini-organ, or organoid (e.g., HILO), in a dish. Using this technique, diseases such as human type 2 diabetes can be modeled in vitro to find effective drugs in genetic, patient or environmental specific diseases such as human type 2 diabetes.

Developing Gellan Gum Based 3D Culture System for β-Like Cells Differentiation

It is known that 3 dimensional (3D) culture systems contribute to facilitating self-organization and integration of cells. Therefore, MATRIGEL® matrix containing extracellular matrix components such as collagen and fibronectin is often used as the basement of a 3D culture system. However, MATRIGEL® matrix-based 3D culture systems are not ideal for large-scale human organoid generation because of their cost and difficulties in scale up. Described hereinbelow are Gellan-gum based 3D culture systems and methods for β-like cell differentiation, which are cost effective and easily scalable. In an embodiment, using a fully chemically-defined stepwise differentiation protocol, human pluripotent cells (hPSCs) are differentiated into insulin producing islet-like spherical cell clusters with high efficiency and reproducibility in Gellan-gum based 3D culture systems. Single dissociated pluripotent stem cells (PSCs) successfully formed into spheres within 5 days in Gellan gum containing STEMCELL™ TeSR™ media. Fifteen (15) to 21 days after differentiation in Gellan gum-containing Custom TeSR™ with defined small molecule stimulation, insulin positive GFP clusters were observed. Global transcriptome analysis by RNA-seq revealed the stepwise differentiation of hiPSCs into insulin positive cells expressing β cell lineage specific marker genes including Pdx1, Nkx6-1, GATA6 and MAFB. The differentiation of hiPSCs, as well as the human ESC lines HuES8 and H1ES, into islet-like cell clusters was further confirmed by the progressive loss of the pluripotent marker Nanog, the induction of the β cell specific marker Nkx6-1, and the progressive induction of the endocrine hormones insulin, somatostatin and glucagon, as determined by qPCR. These results demonstrated that the Gellan-gum based 3D culture systems is suitable for the generation of large-scale islet-like organoids from hPSCs.

Generation of Scalable, Human Islet-Like Organoids In Vitro

β-like cells derived from human embryonic stem cells (hESC) or human induced pluripotent stem cells (hiPSC) have limited functionality and lack the morphological and functional feature of human islets. Previous studies revealed that co-culturing hiPSC derived hepatocyte with human umbilical vein endothelial cells (HUVECs) and human bone marrow-derived mesenchymal stem cells (hMSC) generates self-organized 3D liver-bud spheres in matrigel (Takebe et al., 2013, *Nature*, 499:481-484). This study found that the liver "organoids" had superior expression of lineage determinant factors compared to the differentiation of isolated hepatocytes and that these organoids rapidly vascularized and functionally matured in vivo.

Studies have found that hiPSC-derived pancreatic progenitor cells (hiPSC-PP) generated using a 2D differentiation protocol (Yoshihara et al, 2016, *CellMetab.* 23, 622-634) did not self-organize in 3D MATRIGEL® matrix. (See, e.g., WO 2017/205511). In contrast, HUVEC cells rapidly formed a vasculature-like structure while human adipocyte-derived stem cells (hADSCs) self-organized in 3D MATRIGEL® matrix. In MATRIGEL® matrix, dispersed hADSC cells projected processes within 4 hours, formed a cloth-like wrapper within 12 hours, and adopted a sphere-like formation within 24 to 48 hours. Furthermore, a minimum cell density for self-organization was identified (i.e., ~10,000-20,000 cells in 300 μl of MATRIGEL® matrix in ~2 cm² well. RNA-seq analysis identified dynamic transcriptional changes during hADSC 3D self-organization, suggesting that the ability to self-organize under 3D culture conditions is an inherent feature of naïve hADSCs. These results identify the mesenchymal hADSC as a resource for generating self-organizing organoids.

To explore pancreatic organogenesis, hiPSC-PP ($1 \times 10^6$ cells) cells were co-cultured with HUVECs ($7 \times 10^5$ cells) and hADSCs ($1-2 \times 10^5$ cells) (FIGS. 1A and 1B) in Matrigel matrix. This co-culture yielded macroscopically visible 3D cell clusters 48 hours after seeding. Furthermore, insulin expression, based on the expression of a GFP reporter, was detected 5 days after seeding and increased with time in culture in the human islet-like organoids. In addition, HUVECs-based endothelial cells are integrated inside the organoids as shown by fluorescence-labeled (mCherry) HUVECs. The limitations of MATRIGEL® matrix for organoid production include high cost, difficult organoid recovery, scaling restrictions, and batch to batch variabilities.

Methods to generate morphologically identical human islet-like organoids using gellan gum based 3D cultures are described herein below and in WO 2017/205511. Human induced pluripotent stem cells derived pancreatic progenitors (hiPSC-PPs) ($1 \times 10^8$ cells) were cultivated with a stromal cell population such as human umbilical vein endothelial cells (HUVECs) ($2-7 \times 10^6$ cells) and human adipose-derived stem cells (hADSCs) ($2-7 \times 10^6$) in 50 ml of gellan gum based 3D culture media. HiPSC-PP rapidly formed isle-like sphere formation with HUVECs and hADSCs within 5 days after seeding into the gellan gum based 3D culture media. Human islets like mini-organs expressed human insulin GFP reporter in 5 days after seeding with gradually enhancing GFP intensity. Co-culturing hiPSC-PP, hADSCs, and HUVECs according to this method, generated human islet-like organoids with high reproducibility that were morphologically similar to human islets. In addition, the generated human islet-like organoids contained insulin granules in β-like cells. Gene expression analyses revealed increased expression of β cell fate determinant genes (Insulin, Nkx6-1, PCSK1 and UCN3) and mitochondrial related metabolic genes (Esrrg, Ndufal, Ndufa 12, Cox7a2. Atp5b) in the insulin expressing cell population (GFP enriched (GFP+)) in islet-like organoids compared to those prepared without hADSC and HUVEC co-culture. Glucose-stimulated human c-peptide secretion assay revealed that islet-like organoids generated by this method are able to secrete human c-peptide in response to high (20 mM) glucose.

An in vitro functional vascularization test was performed. Islet-like mini organs generated in gellan gum were transferred to MATRIGEL® matrix and cultured in endothelial growth media (EGM). Green fluorescence indicates expression of insulin genes. Within 24 hours to 48 hours after stimulation by EGM, the outgrowth of HUVEC cells was observed, indicating that human islet-like organoids generated by the method possessed the ability to form vascular structures.

Establishment of Single Islet Insulin Secretion Assay Using Proinsulin-NanoLuc Gaussia Luciferase Assay System It was previously published that a reporter construct, in which the Gaussia luciferase is placed within the c-peptide portion of proinsulin accurately measures insulin secretion without affecting β-cell function (Burns et al., 2015, *Cell metabolism,* 21, 126-137). Using a lentiviral system, INS-1 cells stably expressing this Gaussia luciferase were generated. Luciferase secretion from INS-1 cells stably expressing Proinsulin-NanoLuc increased with high-glucose (20 mM), high glucose with Exendin-4 (G20 mM+Ex4), and the depolarizing agent, potassium chloride, confirming the utility of this reporter system. Next, the usefulness of this reporter to measure insulin secretion in mouse or human islets transiently infected with the Proinsulin-NanoLuc reporter was evaluated. Luciferase secretion in response to 20 mM high glucose was detected in both transiently infected mouse and human islets were detected. Importantly, the assay sensitivity was sufficient that insulin secretion could be qualified at the level of single islets. These results indicate that the Proinsulin-NanoLuc luciferase reporter based insulin secretion assay is applicable to not only the rat beta cell line INS-1 cells, but also to primary mouse and human primary β cells. (See, e.g., WO 2017/205511).

Establishment of hiPSC and hESC Cells Incorporating Dual Lineage and Functional Reporters Human iPSCs and hESCs stably expressing reporters for β cell lineage (human insulin reporter) and β cell function (proinsulin-NanoLuc reporter) were generated, hiPSC$^{hINS-GFP/Sec-Luc}$ and hESC$^{hINS-GFP/Sec-Luc}$, respectively. First, a neomycin resistant construct of human insulin GFP reporter was generated by inserting human insulin promoter sequence of pGreenZeo lenti-reporter (SR10028PA-1, System Bioscience) into pGreenFire Lenti-Reporter plasmid (TR019PA-1, System Bioscience) (named as hINS-GFP-EF1a-Neo). hINS-GFP-EF1a-Neo lenti virus was infected into hiPSC and hESC by spin fection (800 g, 1 hour, 37° C.) followed by a medium changed to fresh STEMCELL™ TeSR™ medium. Three (3) days after the first infection, the cells were treated with 100 µg/ml G418 in STEMCELL™ TeSR™ medium for 7 days. Selected hiPSC and hESC cells stably expressing hINS-GFP– EF1a-Neo were subsequently infected with the Proinsulin-NanoLuc (Addgene, Plasmid #62057) lenti-virus by spin fection (800 g, 1 hour, 37° C.) followed by a medium change to fresh STEMCELL™ TeSR™ medium. Three (3) days after the second infection, the cells were treated with 5 µg/ml blasticysin and 100 µg/ml G418 in STEMCELL™ TeSR™ medium for 7 days. Subsequently, cells were maintained in STEMCELL™ TeSR™ medium. The generated stable cell lines incorporating the dual reporters maintained self-renewal and pluripotency capabilities, as well as the capacity to differentiate into insulin producing p like cells (see, e.g., WO 2017/205511).

Pooled Human Islet-Like Organoid Cultures Display Consistent Insulin Secretion Despite Variable Functionality Seen in Individual Organoids Recent studies have reported the generation of insulin producing β-like cells from hESC and hiPSC capable of secreting insulin in response to glucose (Pagliuca et al., 2014, *Cell*, 159, 428-439; Rezania et al., 2014, *Nature Biotechnology*, 32(11):1121-33; Russ et al., 2015, *EMBO Journal*, 34:1759-1772). However, fully functional human islet-like clusters able to appropriately secrete insulin in response to nutritional signals including glucose, amino acids, fatty acids and incretins such as GLP-1 have yet to be demonstrated. To date, efforts have focused on the independent generation of insulin producing β-like cells, glucagon producing α-like cells, and somatostatin producing 6-like cells from hPSC. However, these approaches lack the supporting cells important for regulation, such as mesenchymal cells, adipose cells, and vasculature cells. Since the 3D structure of islets naturally enhances their function, these missing cellular components may compromise the functionality of islet-like cells clusters. In addition, organogenesis of pancreatic islets involves clonal expansion of β-cells, suggesting that these cells may have multiple functions in islet-like organoids. To test this idea, single organoid proinsulin secretion assays were performed. Human islet-like organoids generated by methods described herein are morphologically identical with human islet. However, significant variability was seen in the glucose-stimulated insulin secretion (GSIS) capabilities of individual human islet-like organoids compared to human islets, as measured by proinsulin luciferase secretion assay. Consistent GSIS functionality was demonstrated in pooled organoids (10 to 100 organoids for assay). Furthermore, pooled human islet like organoids demonstrate enhanced GSIS when co-stimulation with GLP-1, as well as robust KCl-stimulated insulin secretion.

In vitro cultured iPSC-derived human pancreatic islet-like organoids generated herein retained their ability to respond to glucose, GLP1 and KCl after extended time (133 days) in culture.

Example 2: Transplantation of Functional Pancreatic Islet Organoids Rescued Type 1 Diabetic Mice Expression of specific functional islets markers such as MAFA, UCN3 and mitochondrial oxidative genes such as ERRγ (Esrrg), Ndufa 1, Ndufa 12, Cox7a2 and Atp5b in hiPSC-derived human islet-like organoids was observed, as further described in the below Examples. Notably, these islet-like organoids recapture in a dish both human islets development as well as the pathogenesis of diabetes. Transplantation of these functional islet-like organoids rescue type 1 diabetic mice with long survival, rapid vascularization, and reduced immune rejection.

Example 3: Wnt Proteins in the Metabolic Maturation of iPSC-Derived Islet Organoids Fltp and Esrrg genes were found to be expressed in iPSC-derived islet organoids (day 21, generated without co-culture with hADSCs or HUVECs) after treatment with PBS, WNT3a (500 ng/ml), recombinant human (rh)WNT4 (100 ng/ml), or rhWNT5a (400 ng/ml) for 5 days. Esrrg gene expression was induced in hiPSC-derived islet organoids that were generated in the absence of supporting hADSC or HUVECs, in response to increasing doses of rhWNT4 (0, 10, 25, 50, 100, 200 ng/ml) and rhWNT5a (0, 25, 50, 100, 200, 400 ng/ml). In addition, mitochondrial genes involved in oxidative phosphorylation (Cox7a2, Ndufal, Ndufa7), lactate dehydrogenase (Ldha) and Fltp (a Wnt/planar cell polarity (PCP) effector and reporter gene) were induced in hiPSC-derived islet organoids that were generated in the absence of supporting hADSC or HUVECs, in response to increasing doses of rhWNT4 (0, 10, 25, 50, 100, 200 ng/ml) and rhWNT5a (0, 25, 50, 100, 200, 400 ng/ml). Mitochondrial (Mitotracker; Mito-Red) and insulin (Insulin-GFP) levels were increased in hiPSC-derived islet organoids (day 27) after 8 days treatment with PBS or WNT4 (100 ng/ml). Human iPSC-derived islet organoids (day 27) were generated after 8 days treatment with PBS or WNT4 (100 ng/ml). Insulin production was found in hiPSC-derived islet organoids (day 27) after 8 days treatment with rhWNT4 (100 ng/ml), rhWNT5a (400 ng/ml), or WNT5a secreting fibroblast conditioned media (50%), compared with PBS and control fibroblast conditioned media (50%). Human iPSC (hiPSC)-derived islet organoids (day 22) treated with rhWnt4 (100 ng/ml) for 12 days showed functional maturation based on their secretion of human c-peptide, as measured in response to low glucose (3 mM, "G3 mM"), high glucose (20 mM, "G20 mM"), or high KCl levels (20 mM, "KCL20 mM"), (see, e.g., WO 2017/205511).

Example 4: Generation of Functional Human Islet-Like Organoids (HILOs) from Induced Pluripotent Stem Cells (iPSC) Using a Functional Polymer-Based 3D Culture System Stem cell-derived human islets hold promise as a therapy for insulin dependent diabetes. This Example describes the generation of human islet-like organoids (HILOs) from induced pluripotent stem cells (iPSCs) and shows that activation of the non-canonical WNT pathway drives a metabolic maturation step necessary for robust glucose-stimulated insulin secretion. These functionally mature HILOs containing multiple endocrine cell types maintain glucose homeostasis upon transplantation into diabetic NOD-SCID mice. Furthermore, overexpression of PD-L1 generated immune evasive, immunologically protected HILOs that maintained glucose homeostasis in immune-competent type 1 diabetic mice for at least 50 days. The ability to generate, in a scalable fashion, functional islet-like organoids that avoid immune detection provides an advantageous and beneficial new therapy for diabetes.

Islet transplantation provides superior long-term blood glucose control for type 1 and late-stage type 2 diabetics; however, the availability and quality of cadaveric islets is currently limiting. While the differentiation of induced pluripotent stem cells (iPSCs) into insulin-producing β-like cells represents an advance in the field, the methods for generating functional β-like cells appropriate for human therapy and treatment provided herein provide biologically functional cell and HILO products suitable for use as therapeutics and in transplantation.

Figures 1C, 1D:
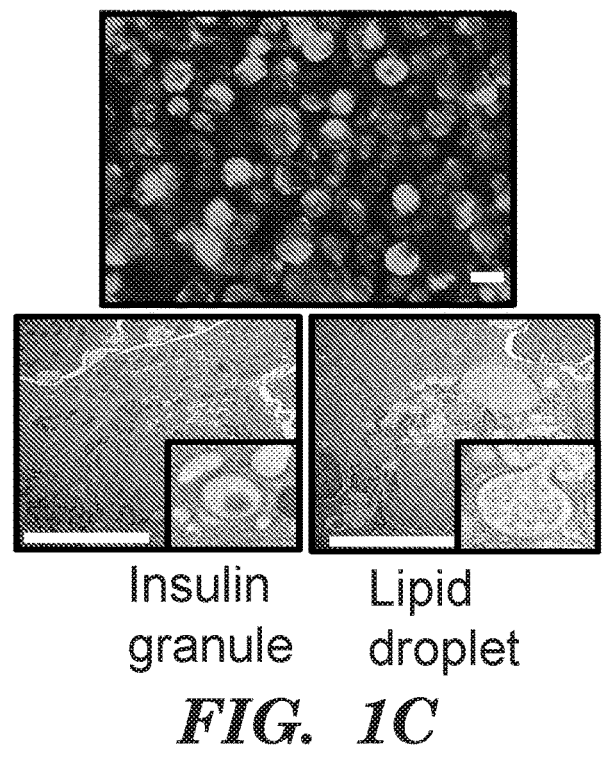
Figure 1E:
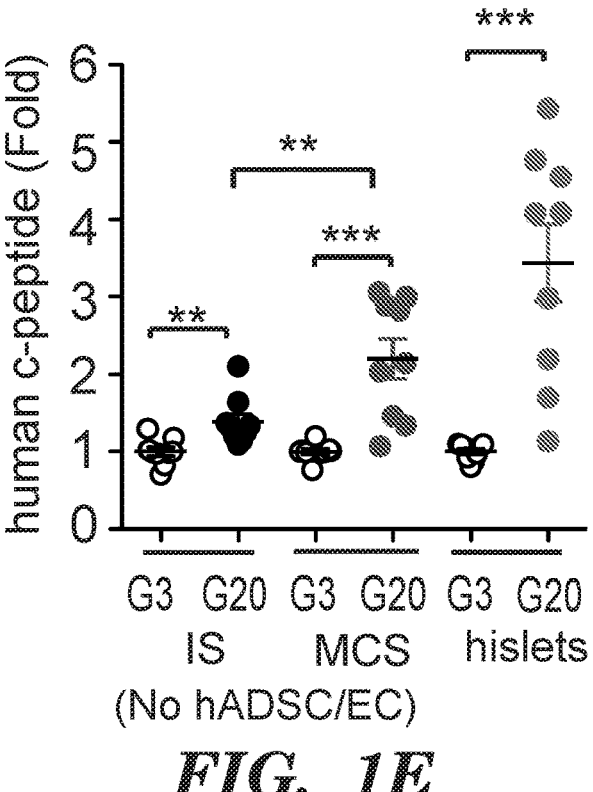
Figure 1F:
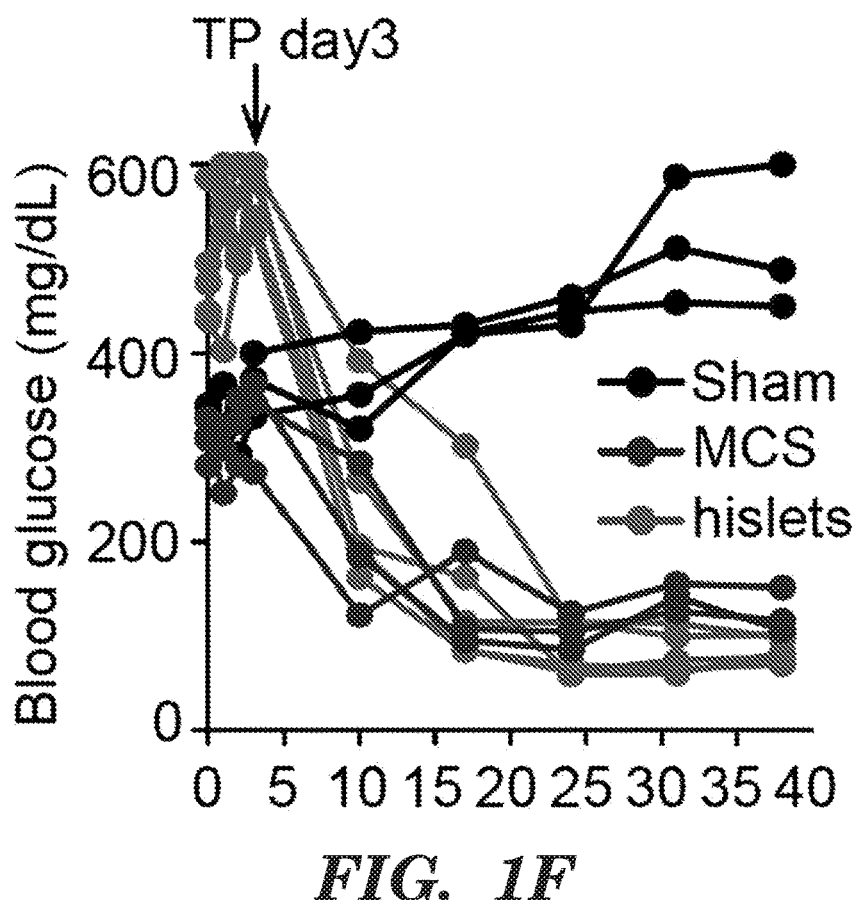
Figure 1G:
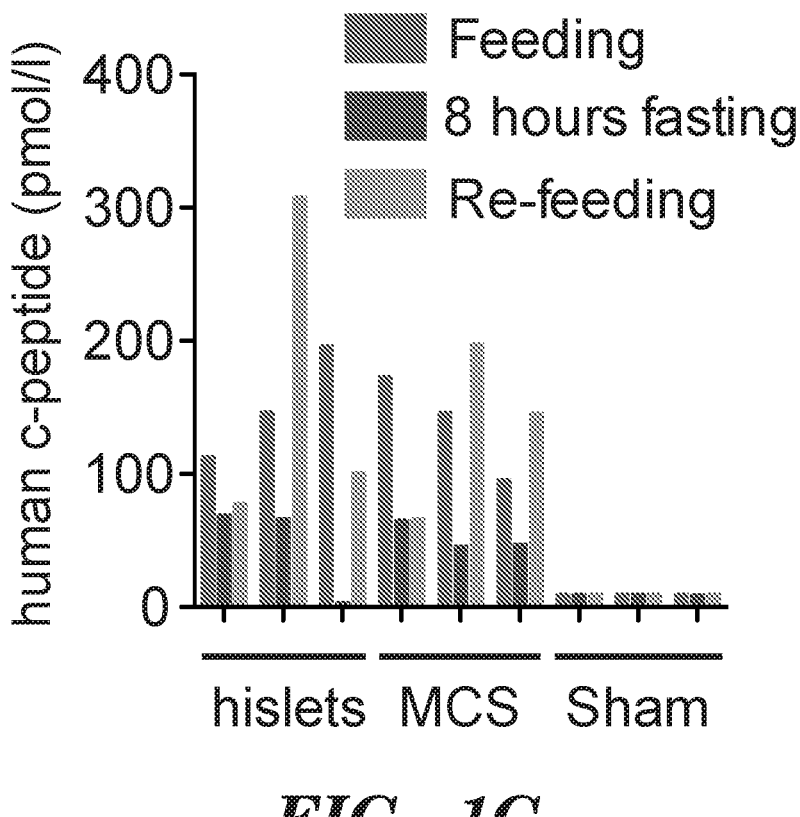
Figures 6D, 6E:
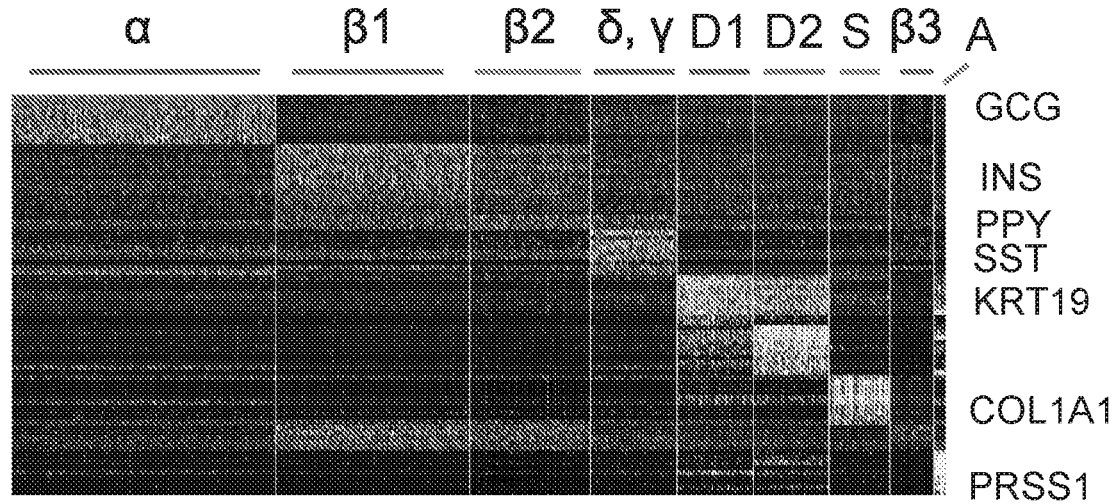

As described, an ERRγ-driven, postnatal metabolic maturation step is necessary for β cell glucose stimulated insulin secretion (GSIS). In addition, ERRγ overexpression in iPSC-derived β-like cells was sufficient for in vitro and in vivo functionality. To generate functional cells suitable for transplantation, culture conditions that replicate the cellular architecture, as well as the cell type complexity of islets, were developed. Accordingly, as transcriptionally-similar models of pancreatic fibroblast and epithelial cells, human adipose derived stem cells (hADSCs) and human umbilical vein endothelial cells (HUVECs) were used for their cell-intrinsic abilities of to form organ-like and vascular structures, respectively, when grown in 3 dimensional (3D) Matrigel cultures (FIG. 1A). Incorporating hADSCs and HUVECs during the differentiation of human induced pluripotent stem cell (hiPSC)-derived endocrine progenitors (EPs) in a 3-dimensional polysaccharide based gel (gellan gum) led to the formation of multicellular spheroids (MCSs), comparable in size to human islets. (FIG. 1B; FIGS. 6A-6F). These MCSs contain insulin-producing cells, as seen from the expression of GFP driven by the insulin promoter and the presence of insulin granules (FIG. 1C); the incorporation of hADSCs was confirmed by the presence of cells containing lipids in droplet-like structures. (FIG. 1E). Compared to endocrine progenitors (EPs) differentiated in the absence of hADSCs and HUVECS (IS), the expression of ERRγ and the mitochondrial genes NDUFA1 and COX7A2 were increased in MCSs, consistent with functional metabolic maturation (FIG. 1D). Consistent with their functional maturation, the MCSs displayed improved insulin secretion in response to a glucose challenge (measured by c-peptide secretion), (FIG. 1E). In addition, MCSs developed vascular-like structures when stimulated with endothelial growth media, suggesting the possibility of extended in vivo functionality (FIG. 6C). Indeed, MCSs transplanted into the kidney capsule were able to maintain glucose homeostasis for approximately 40 days in STZ-induced diabetic NOD-SCID mice (diabetic mouse model), displaying similar efficacy to human islet transplantations (FIG. 1F). Furthermore, transplanted MCSs remained glucose responsive, appropriately regulating insulin secretion in the fed, fasted, and refed states as indicated by c-peptide levels (FIG. 1G); (mouse insulin levels were <0.2 ng/ml, not shown).

Figure 2A:
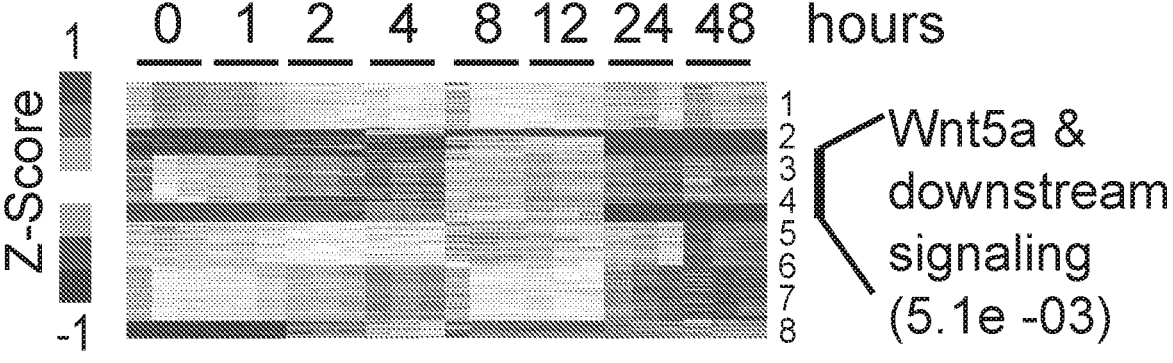

The results obtained support the role of 3D multicellular interactions in organogenesis, as previously shown for liver organoids. The transcriptional changes induced during the initial 48 hours of hADSC single cell type 3D culture were assessed to understand the molecular signals driving the cell-intrinsic ability to self-assemble (FIG. 2A). Gene ontology analysis identified metabolic and cytokine signaling pathways, as well as WNT signaling, enriched in the altered transcripts (FIG. 2A). Consistent with this, the temporal expressions of WNTs during hADSC self-assembly revealed a transient, approximately 2-fold increase in WNT5a expression that coincided with the initial cell-cell interactions observed in three dimensional (3D) cultures (FIG. 2B).

Figure 2D:
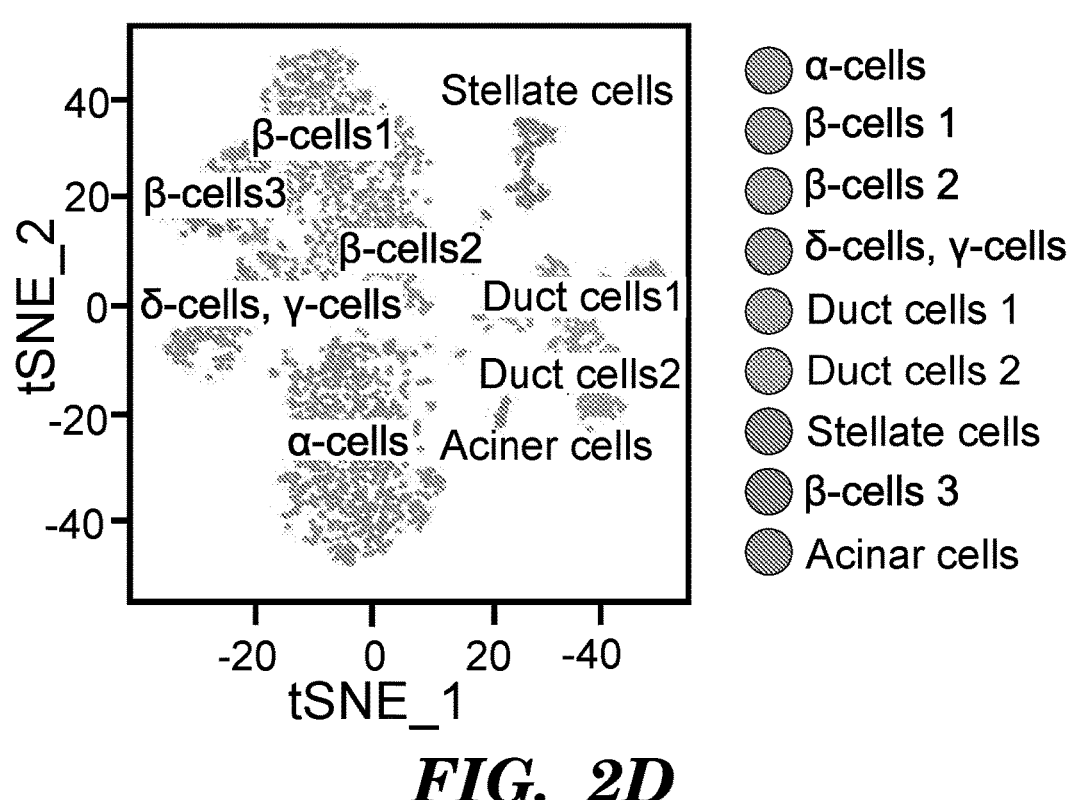
Figure 2E:
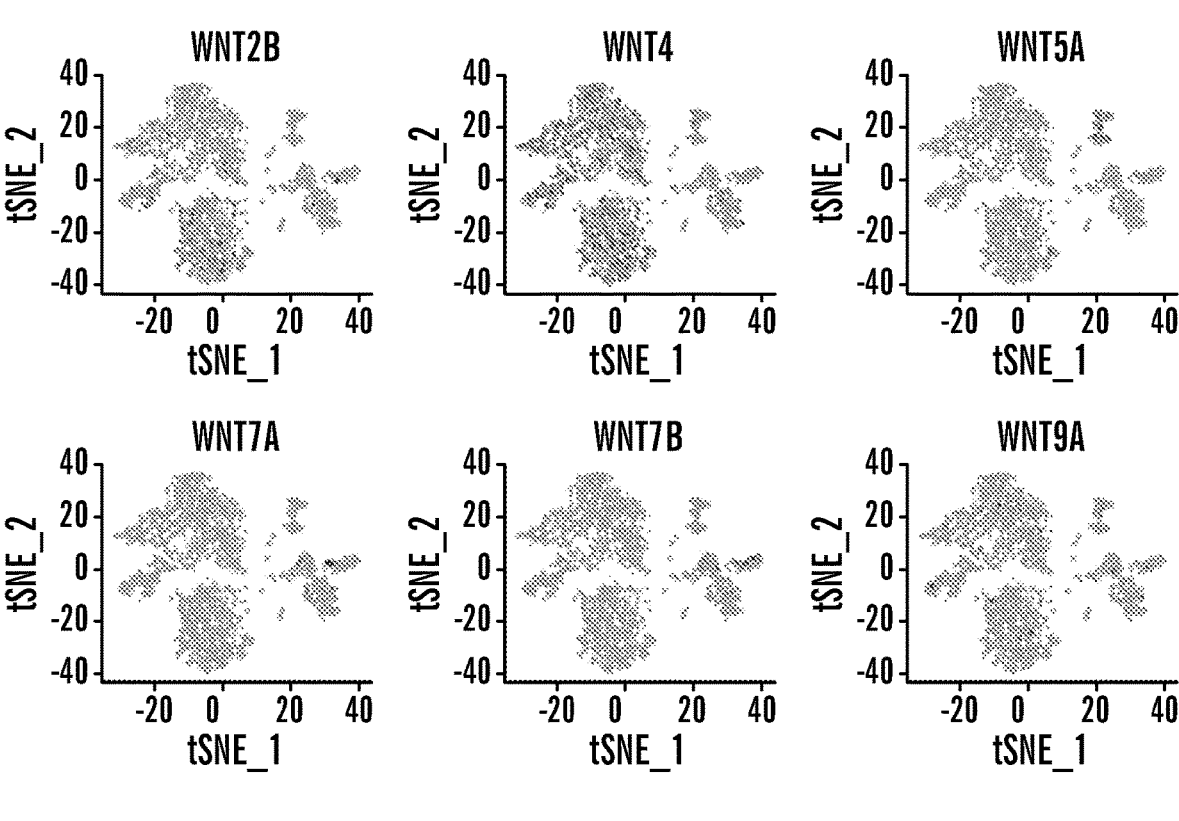
Figure 2F:
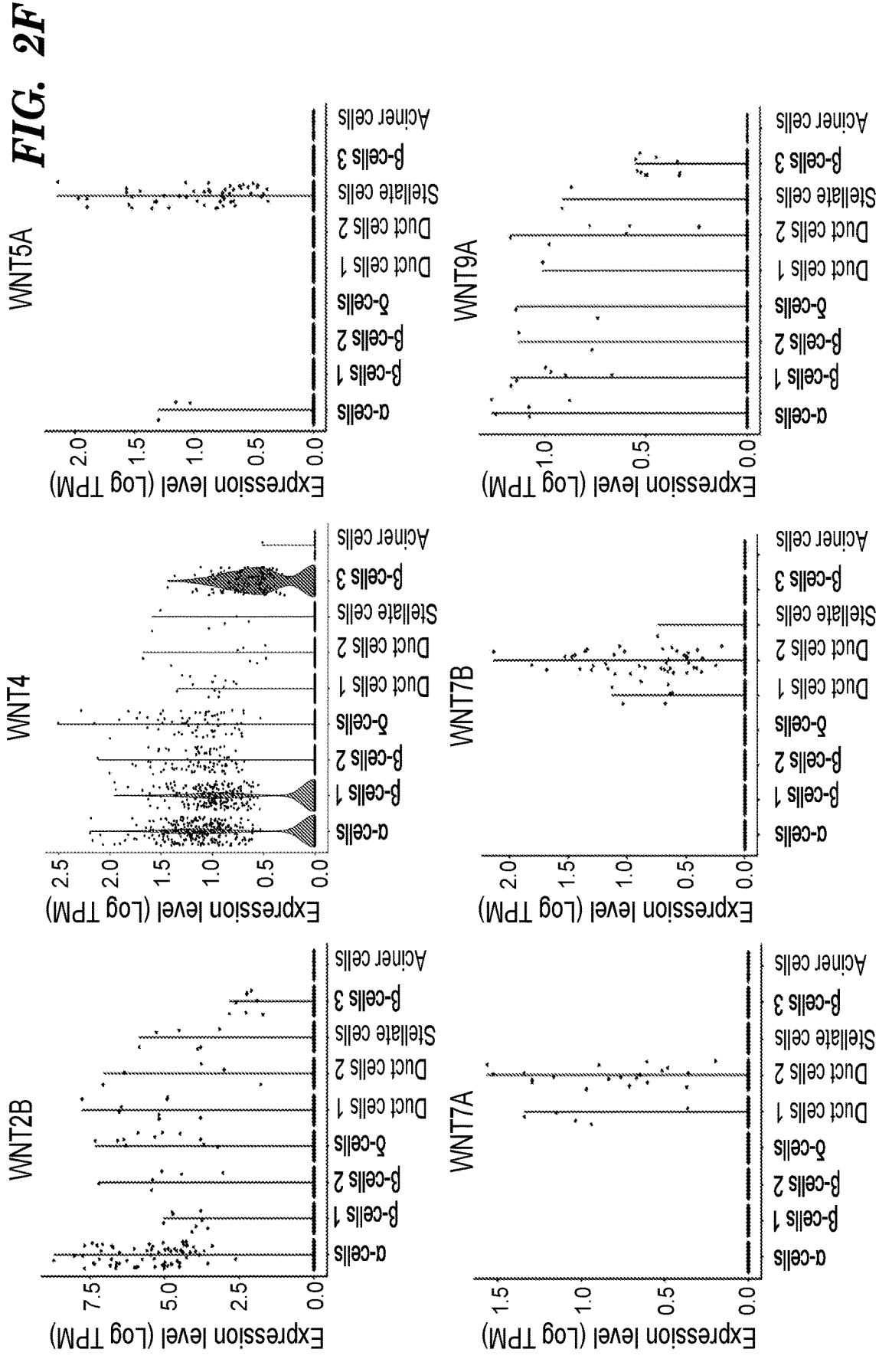
Figure 6F:
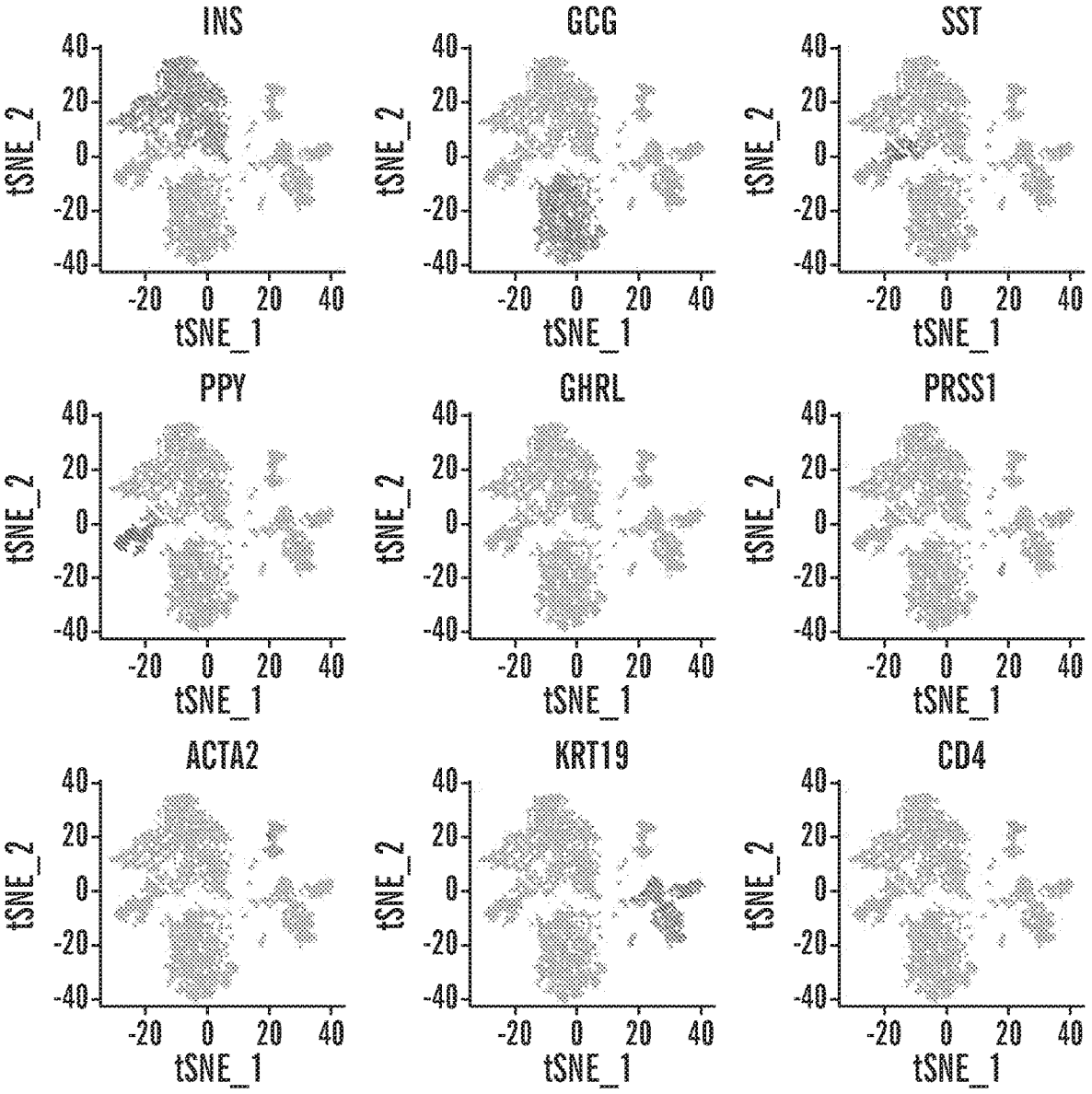

Example 5: The Non-Canonical Wnt Pathway Regulates Gene Expression to Enable Oxidative Phosphorylation and Maturation of HILOs The non-canonical WNT pathway is a marker for non-proliferative, mature β cells, and WNT4 expression is enhanced during the postnatal functional maturation of mouse islets. In experimental studies using human islets, WNT4 was discovered to be highly expressed in the human islets (FIG. 2C), in agreement with these findings. Moreover, single cell sequencing of human islets identified widespread expression of WNT4 in β and α cells, along with more restricted WNT5A expression predominantly in stellate cells (FIGS. 2D, 2E, 2F; FIGS. 6D-6F). To demonstrate that non-canonical WNT signaling was sufficient for the functional maturation of iPSC-derived β cells or β-like cells, CRISPR-Cas9 genome editing was used to insert the GFP coding sequences downstream of the insulin promoter in hiPSCs (FIG. 7A), to generate a reporter for endogenous insulin promoter activity and to allow endogenous insulin promoter activity to be visualized. These engineered hiPSCs were subsequently differentiated in a fully chemically-defined 3D culture system that incorporated WNT4 in the final endocrine progenitor (EP) maturation step (FIG. 3A). This optimized 3D differentiation protocol led to the formation of human islet-like organoids (HILOs) that expressed insulin (FIGS. 3A and 3B). In addition, expression of Urocortin-3, secreted from β cells to regulate δ (delta) cell somatostatin secretion, co-localized with insulin in HILOs (FIG. 2B). The analysis of the HILOs by electron microscopy revealed structural similarity to human islets, most notably, by the presence of insulin and glucagon granules in the HILOs (FIG. 3C).

Figures 1, 3D:
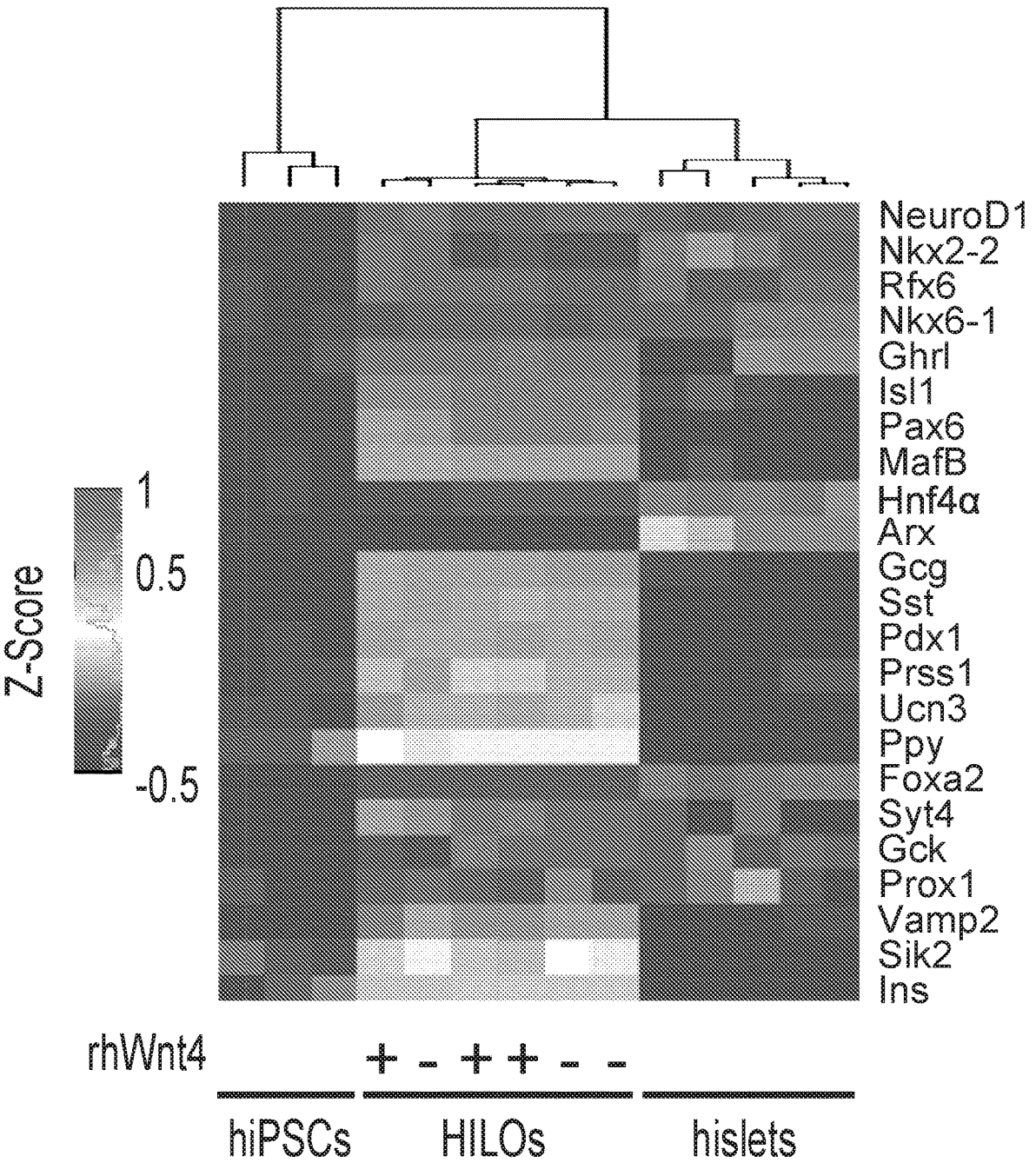
Figures 2, 3D:
Figures 3E, 3F:
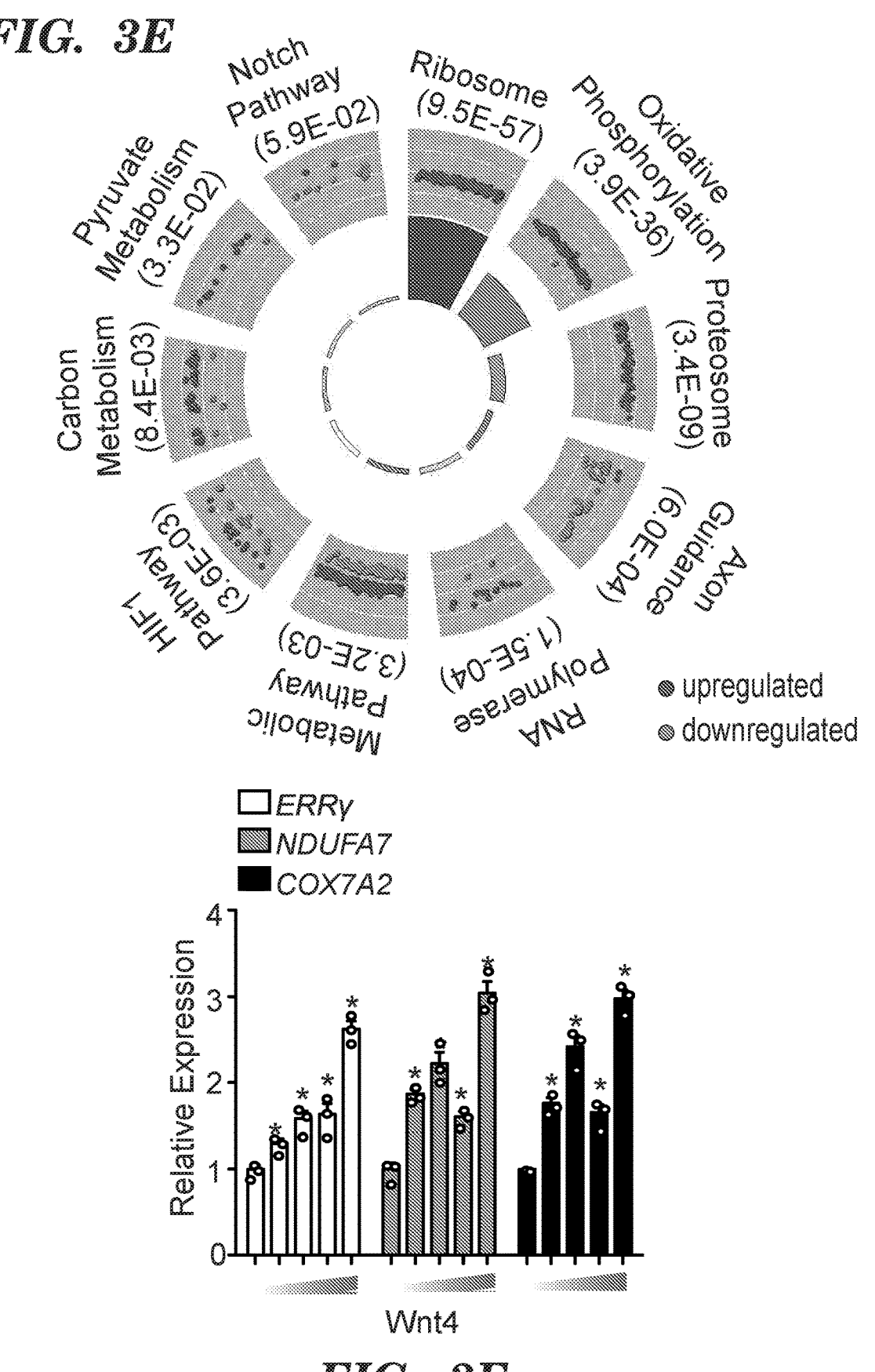
Figure 3G:
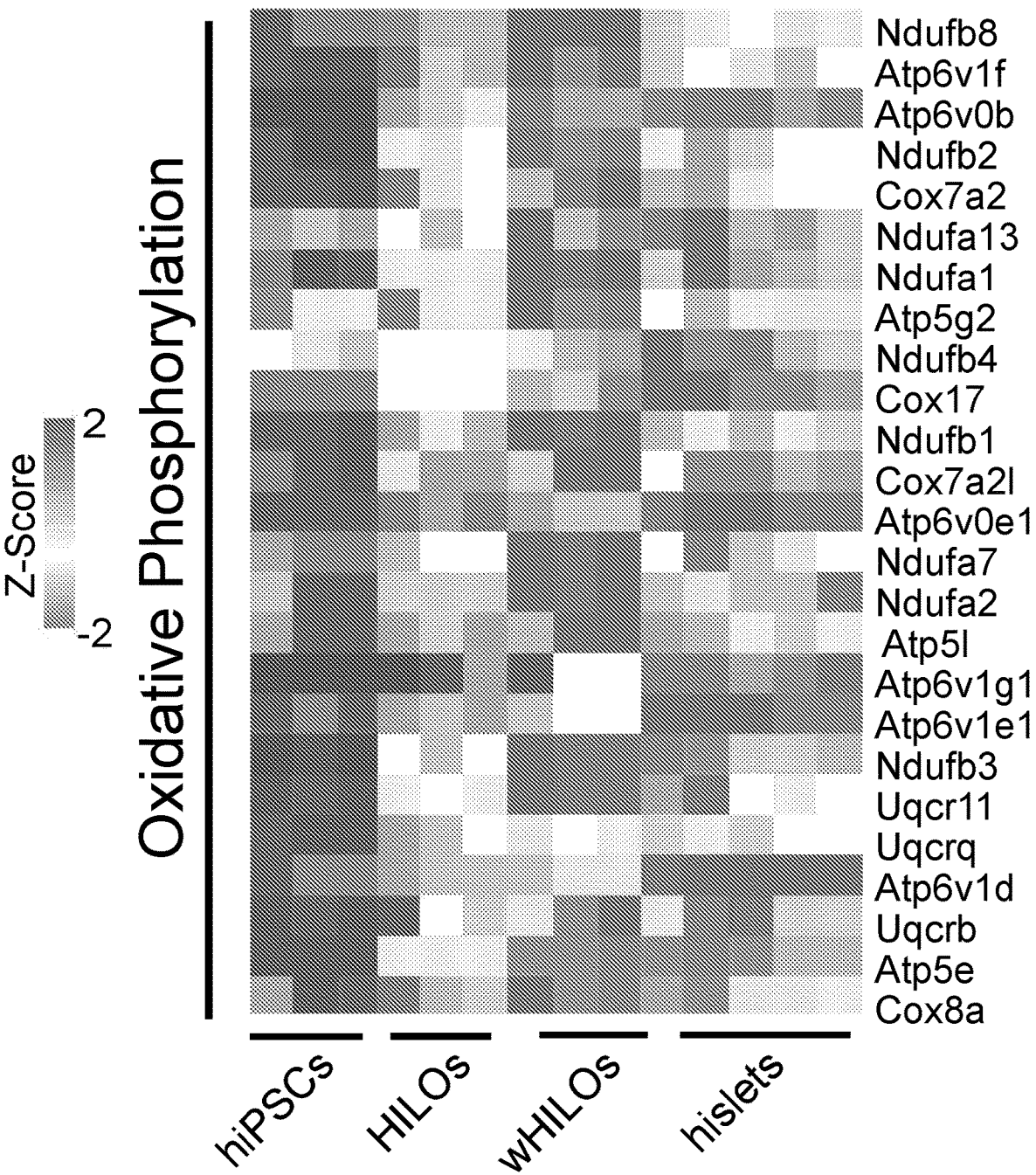
Figure 3H:
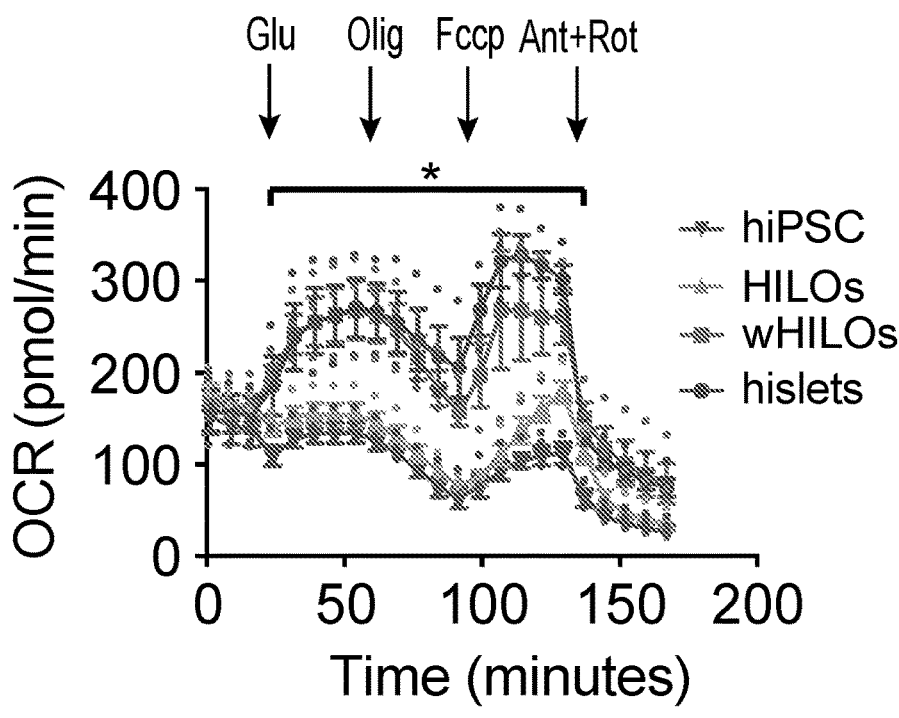
Figure 3I:
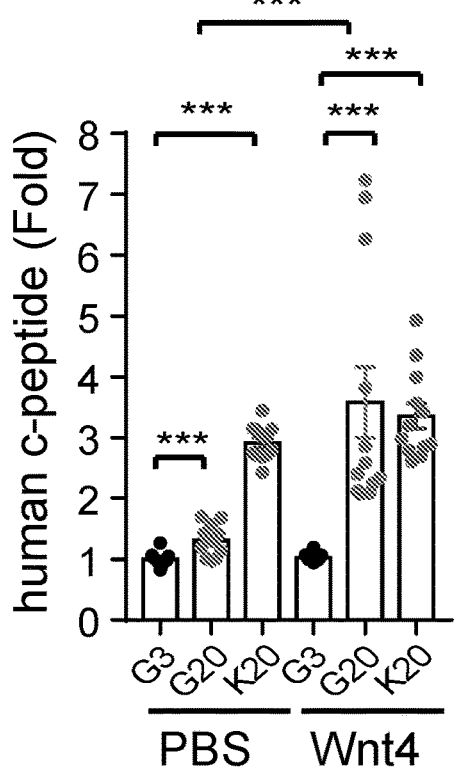
Figure 3J:
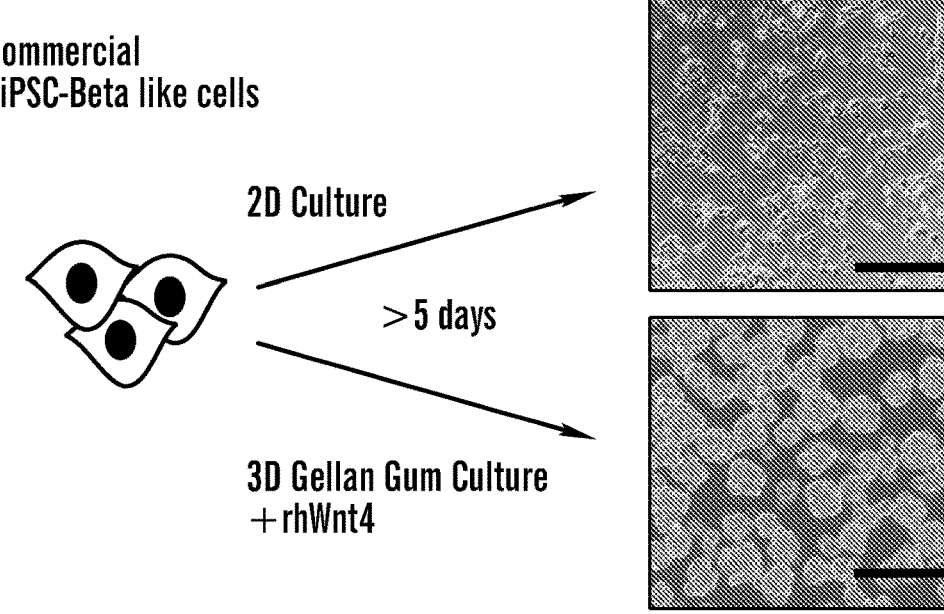
Figure 3K:
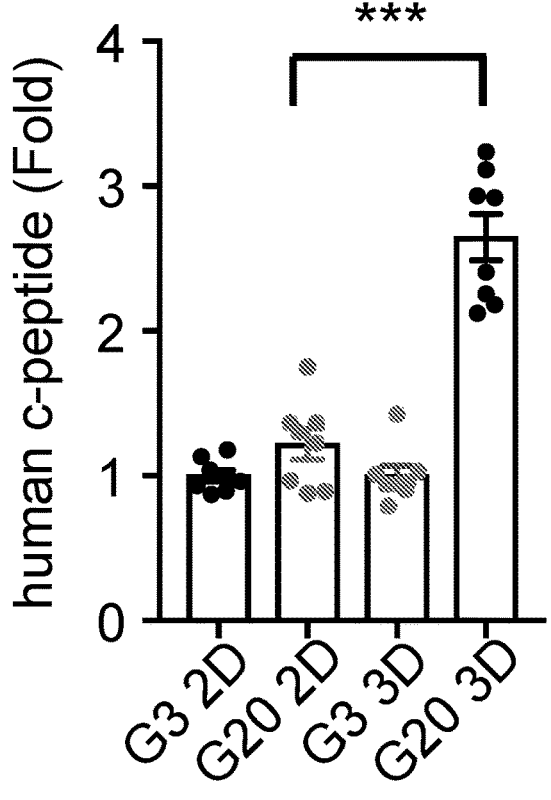
Figure 8A:
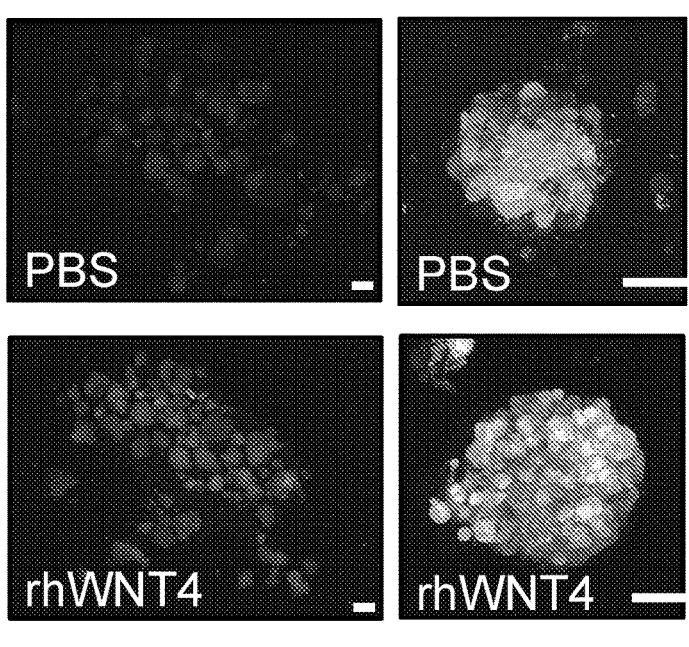
FIGS. 8A-8H provide images, graphs, a schematic and a diagram showing results related to WNT4 mediated insulin-GFP expression and WNT4-driven metabolic maturation.
Figure 8B:
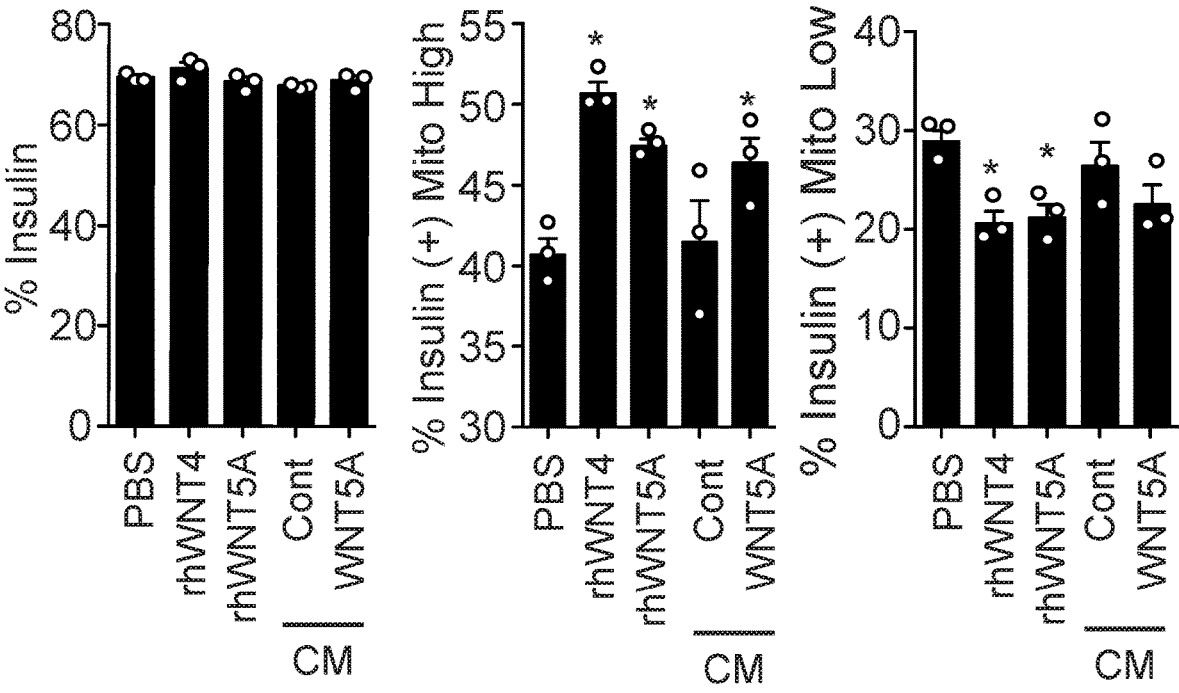
Figure 8C:
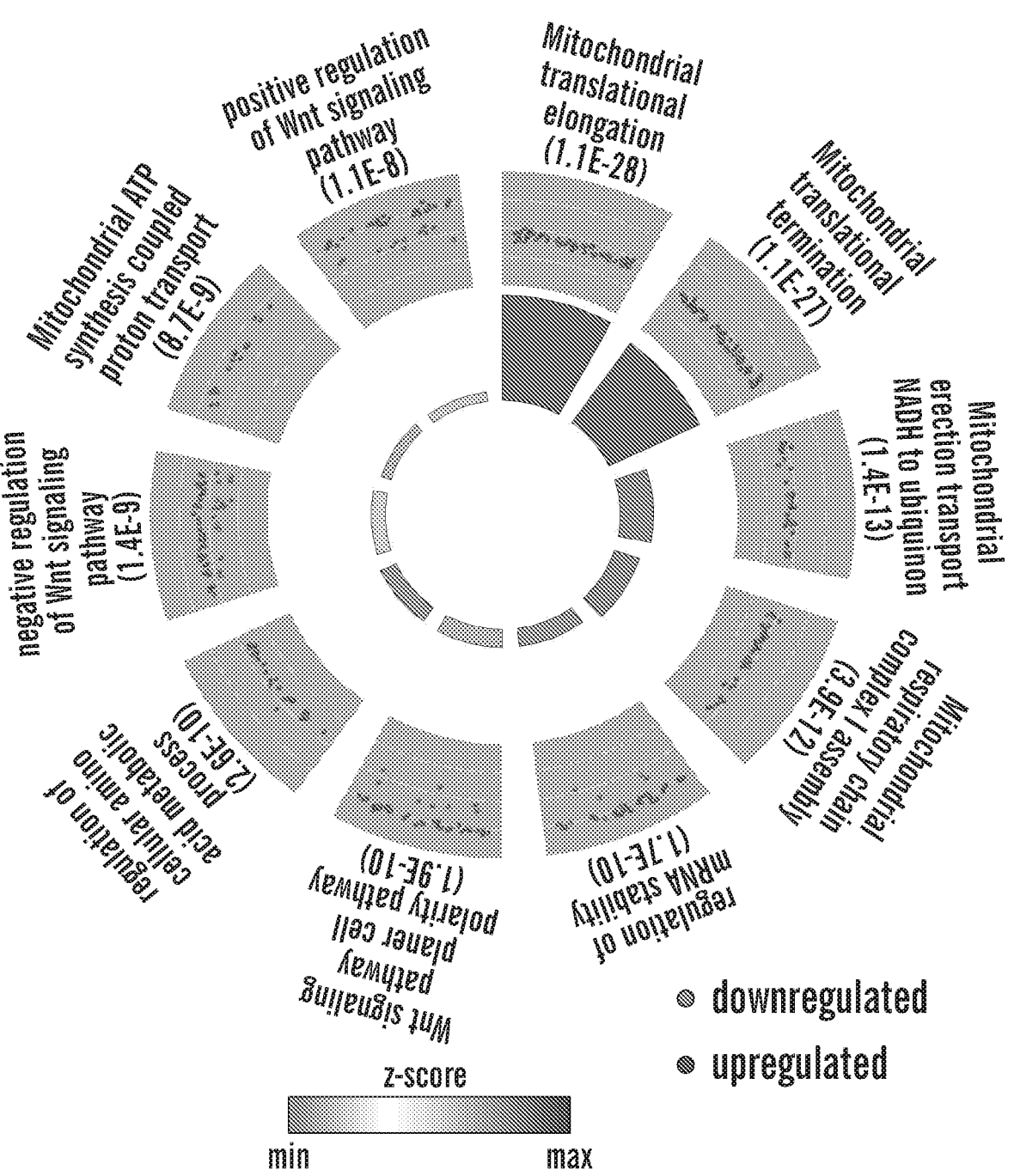
Figure 8D:
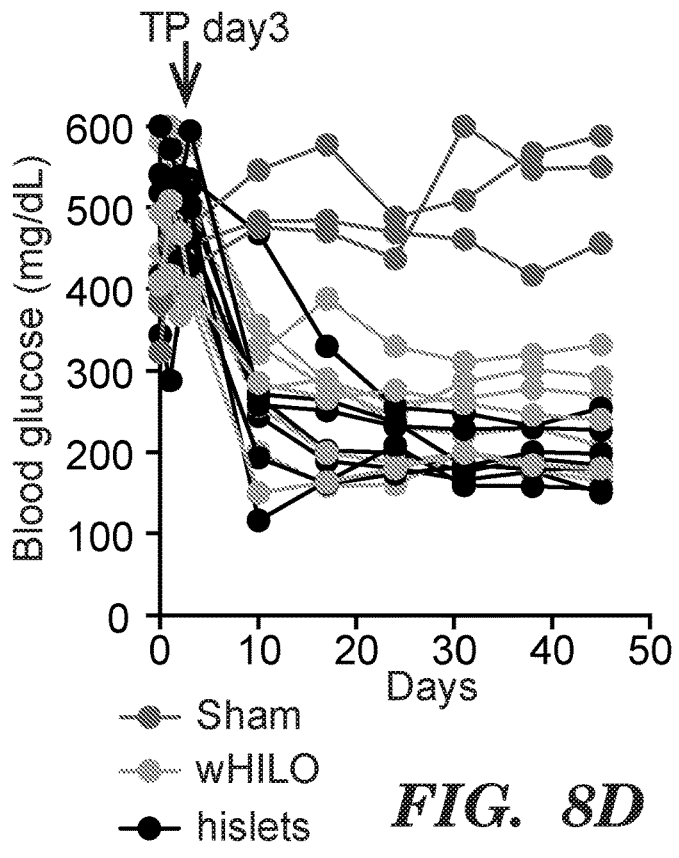

Comparative transcriptional analyses confirmed the induction of key islet cell markers in WNT4-treated HILOs (wHILOs) to levels comparable to those seen in human islets, including β cell specific genes (NKX2-2, NEUROD1, RFX6, GCK) and a cell-specific genes (ARX), (FIGS. 3D-1 and 3D-2). Importantly, the expression of β cell lineage specification markers, including INS, NKX6-1, UCN3, MAFB and SYT4, was not affected by the addition of WNT4, thus indicating that this non-canonical WNT signaling was not affecting cell fate determination. In contrast, WNT4 dose-dependently increased the expression of ERRγ (encoded by ESRRG), as well as components of the mitochondrial respiratory chain NDUFA7 and COX7A2 in HILOs (FIG. 3F). Consistent with these inductions, HILOs generated in the presence of WNT4 displayed increased oxidative metabolism, as measured by an increase in oxygen consumption rate (OCR) and decreased extracellular acidification rate (ECAR), replicating the metabolic characteristics of healthy human islets (FIG. 3H and FIG. 7C). WNT4 treated HILOs showed improved in vitro GSIS; an effect that was not blocked by the β-catenin inhibitor XAV939 (FIG. 3I; FIGS. 7D-1 and 7D-2). Similarly, culturing commercially-available hiPSC-derived β like cells in 3D differentiation medium containing WNT4 promoted pseudo-islet formation and GSIS functionality. (FIG. 3J and FIG. 3K). Importantly, wHILOs (i.e., HILOs cultured in culture or differentiation medium containing WNT4) restored glycemic control upon transplantation into STZ-induced NOD-SCID diabetic mice and maintained glucose homeostasis for more than 6 weeks (FIG. 8D). In combination, these results indicate that non-canonical WNT signaling is sufficient to induce a metabolic maturation of HILOs needed for robust GSIS, in a manner that mimics the postnatal maturation of human islets. Accordingly, culturing stem cells (e.g., hiP- SCs, PSCs, or embryonic stem (ES) cells) in medium containing WNT (e.g., WNT4) generates islets and islet like organoids (wHILOs) which are functionally mature and islet-like and which express more mature ß-cell markers and produce insulin.

To understand the molecular transformations driving the maturation of HILOs, the transcriptional changes induced by WNT4 treatment of HILOs were assessed. The expression of 1581 and 1354 genes were increased and decreased, respectively, by WNT4 treatment (100 ng/ml for days 26-33). Gene ontology analysis identified metabolic pathways, most notably oxidative phosphorylation, enriched in this gene set FIG. 3E. Genes associated with the ribosome include mitochondrial translation and elongation gene clusters, as determined by GOTERM_BP analysis by DAVID, FIG. 8C). Consistent with an effect on cellular metabolism, WNT4 treatment comprehensively increased the expression of OxPhos genes in HILOs to levels similar to those seen in human islets, and increased mitochondrial number (FIG. 3G and FIG. 8A).

Figure 7F:
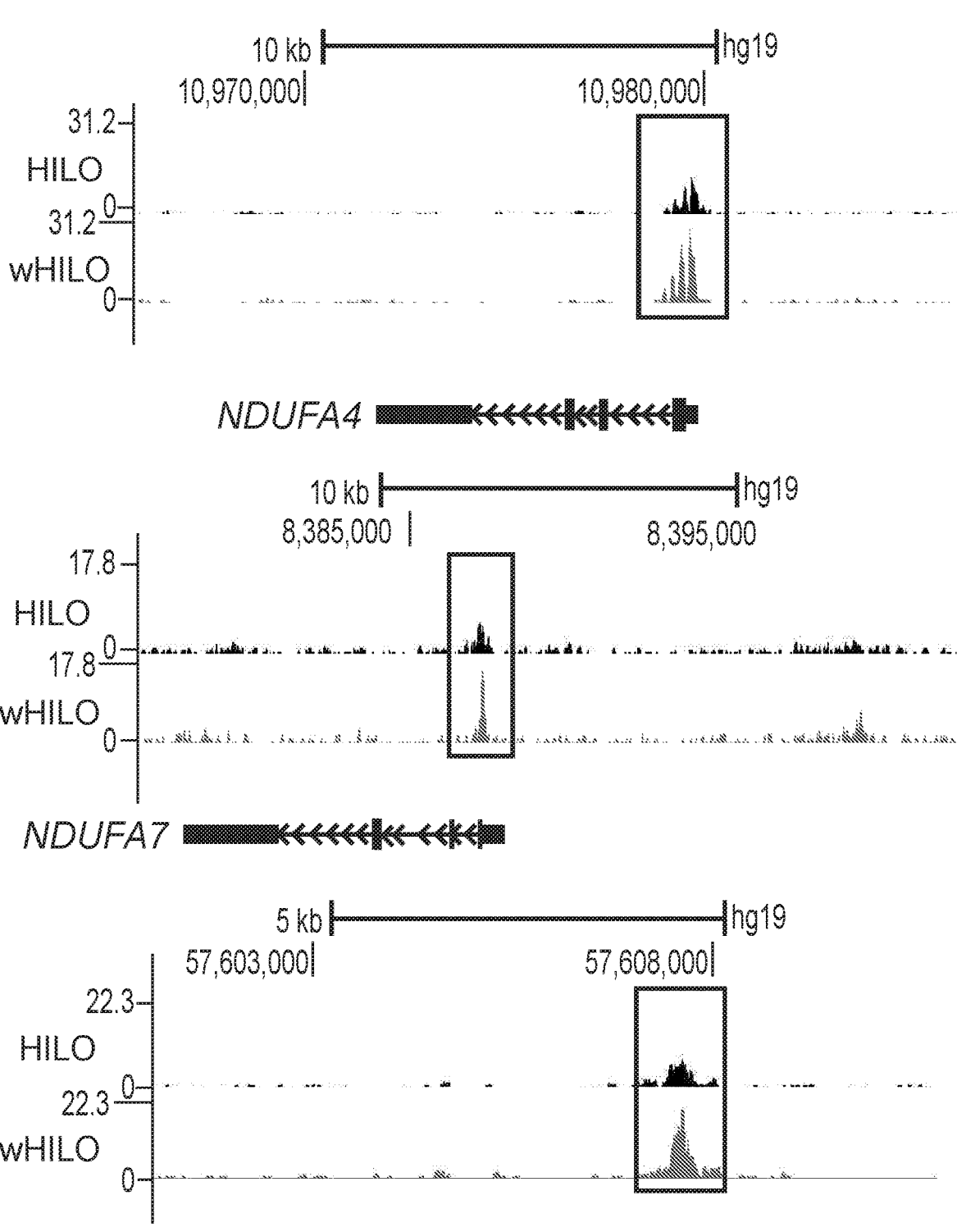
Figure 8E:
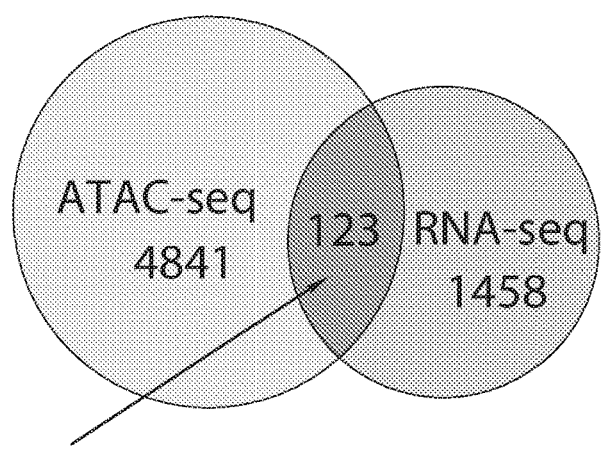
Figures 8F, 8G:
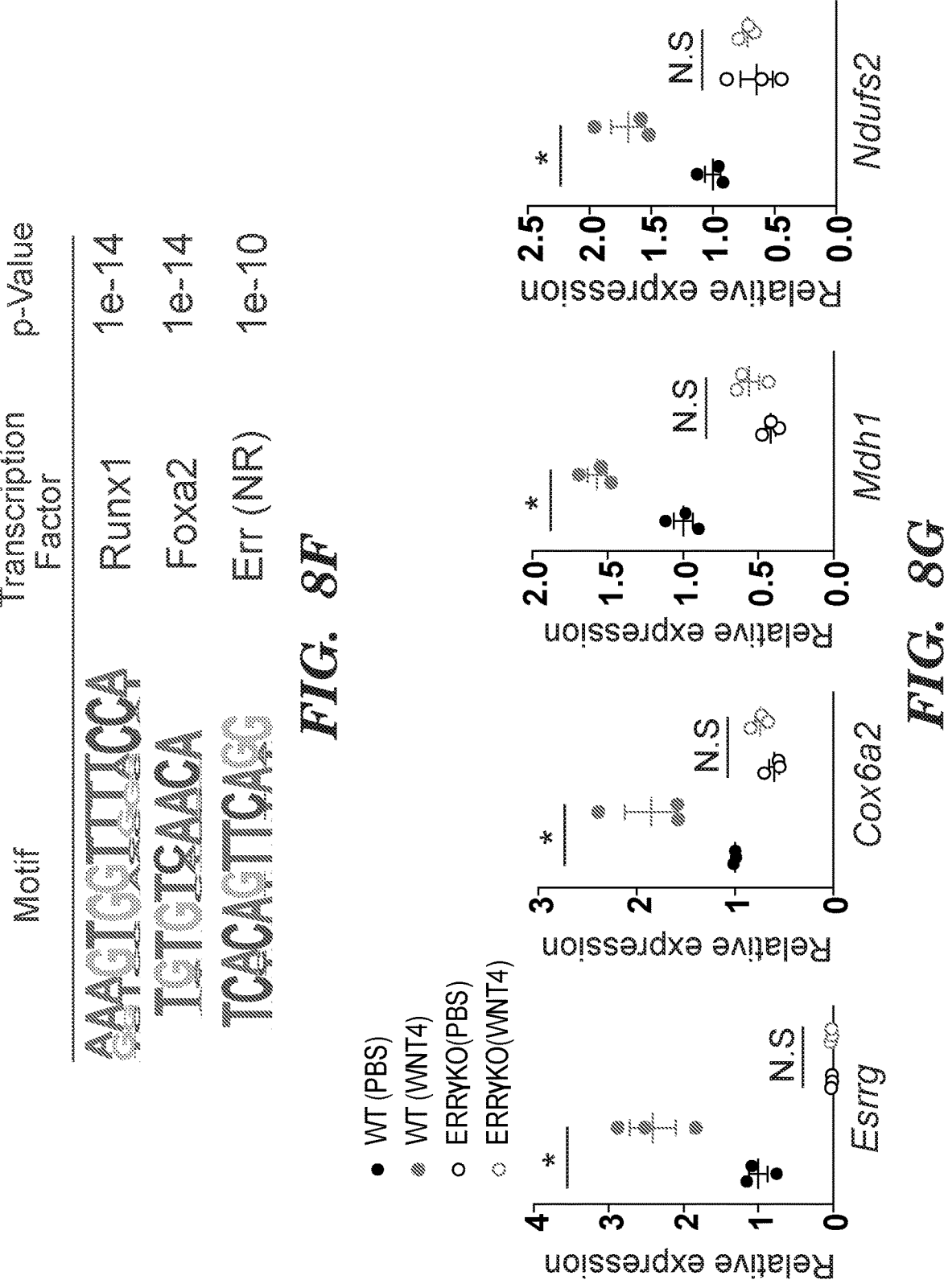
Figure 8H:
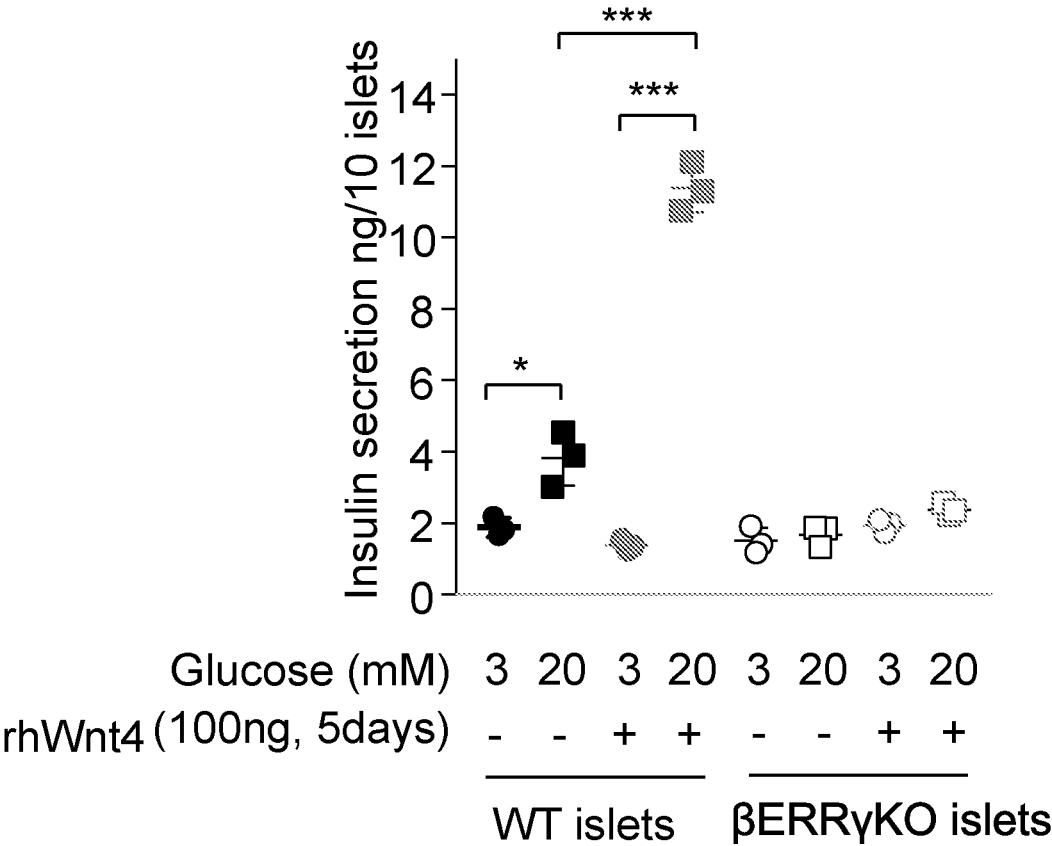

To examine the specific effects on the β-like cell population, insulin-expressing cells were sorted based on GFP expression from HILOs with and without WNT4 or WNT5a treatment. The proportion of insulin expressing cells was not affected by WNT treatment, in agreement with the invariant β cell lineage marker expression during HILO maturation (FIG. 8B). However, WNT4 and WNT5a treatment increased the mitochondrial content of the insulin-expressing cells, supporting the notion of a metabolic maturation of β cells (FIG. 8B). To identify genetic effectors of this maturation step, the WNT4-induced changes in chromatin accessibility were mapped in the sorted, GFP+ cells by ATAC-Seq. Widespread alterations in chromatin accessibility were seen with WNT4 treatment, in agreement with the extent of transcriptional changes. An overlap of the regions with increased chromatin accessibility with the HILO genes induced by WNT4 treatment identified 123 genes (FIG. 8E). Gene ontology identified metabolic pathways, including oxidative phosphorylation, enriched in this gene set. Furthermore, motif analysis in genes where increased chromatin accessibility corresponded with increased gene expression identified R cell maturation factors including Foxa2 and ERRs. (FIG. 8F). Consistent with this, WNT4-induced increases in chromatin accessibility were seen at oxidative phosphorylation genes including ERRγ target genes NDUFA4, NDUFA7 and ATP5E (FIG. 7F). Further supporting the essential role of ERRγ signaling, WNT4 (100 ng/ml for 5 days) induced the expression of mitochondrial metabolic genes and improved GSIS function in isolated neonatal islets from WT, but not from ERRγ ß cell specific knockout (KO) mice (ERRγKO mice), (FIG. 8G and FIG. 8H). Without wishing to be bound by theory, these results, taken together, support the concept that non-canonical WNT4 signaling enhances mitochondrial function, in large part through the induction of ERRγ, to drive the metabolic maturation of β-like cells.

Example 6: Cellular Complexity of Mature HILOs

Figure 9A:
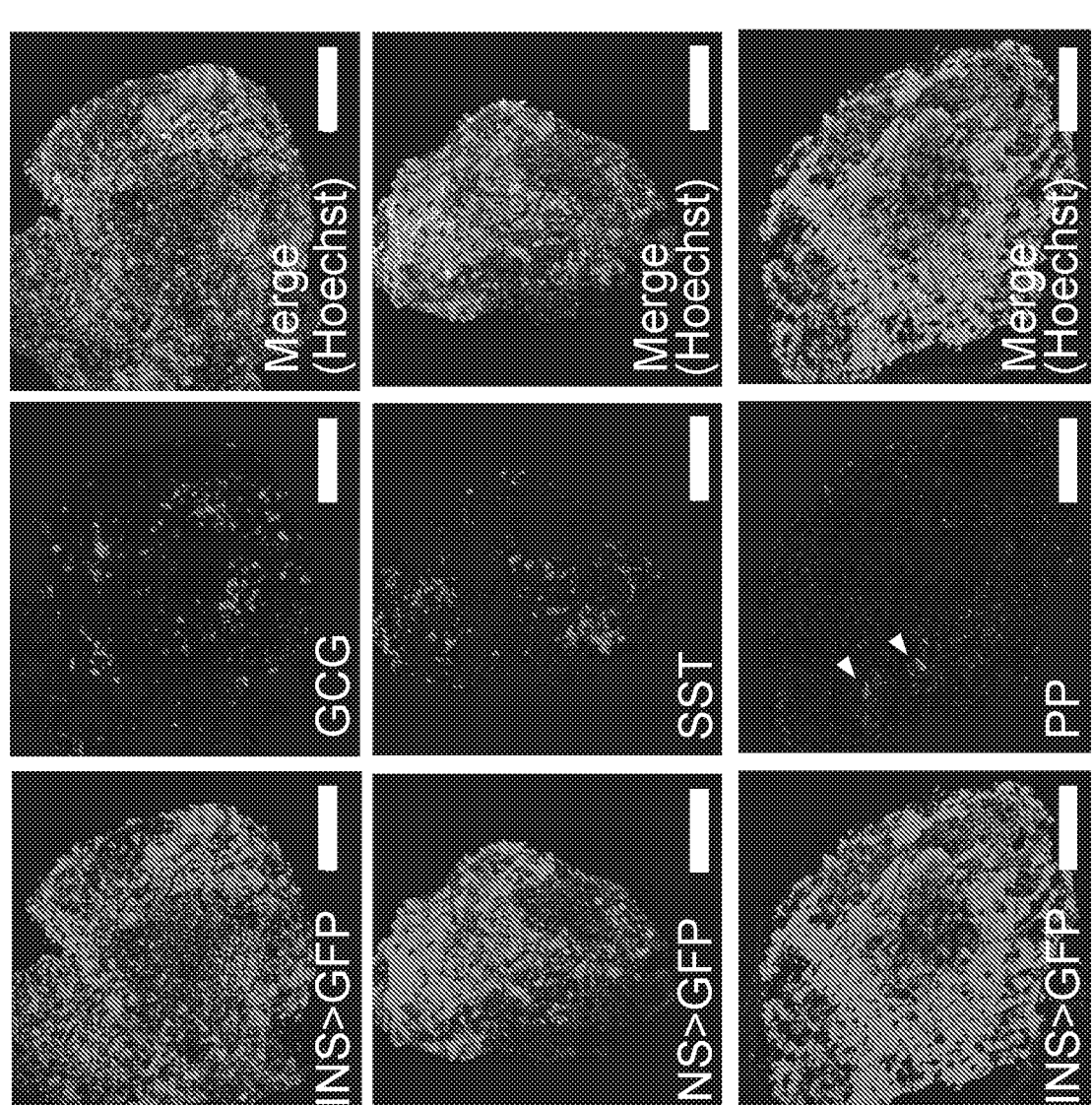
FIGS. 9A-9M provide microscopy (confocal) images, plots, heatmaps and graphs demonstrating immunofluorescent characterization of wHILOs, flow cytometry analysis of HILOs, and single cell analysis of wHILOs.
Figure 9B:
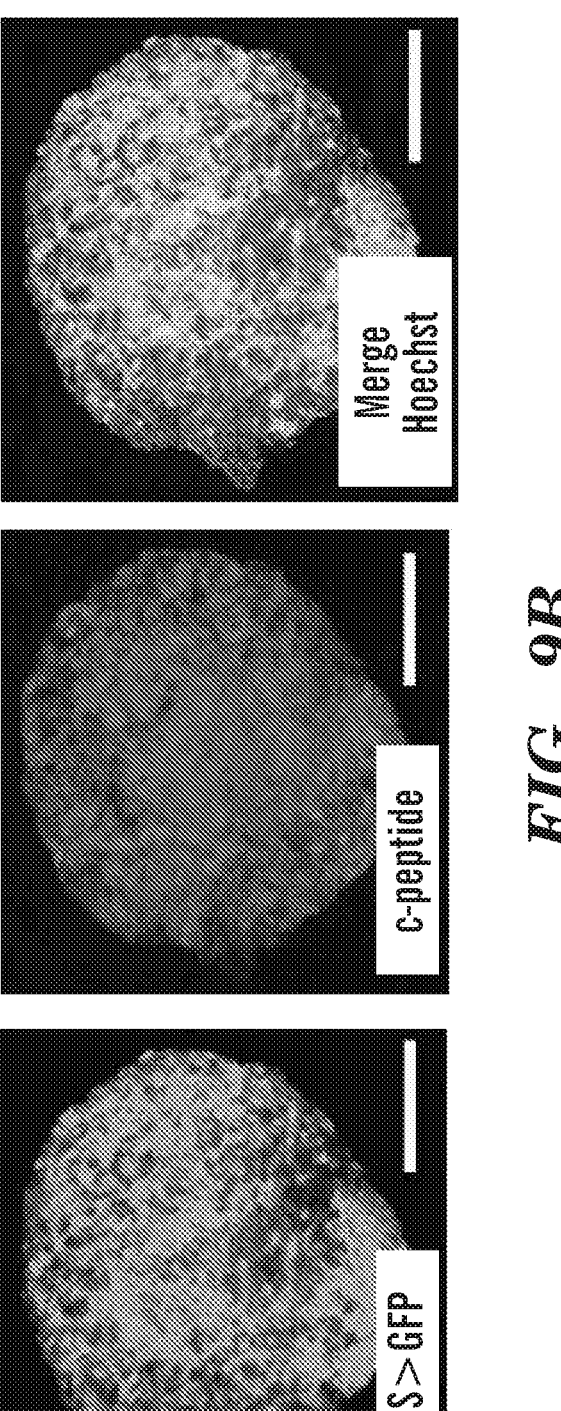
Figure 9C:
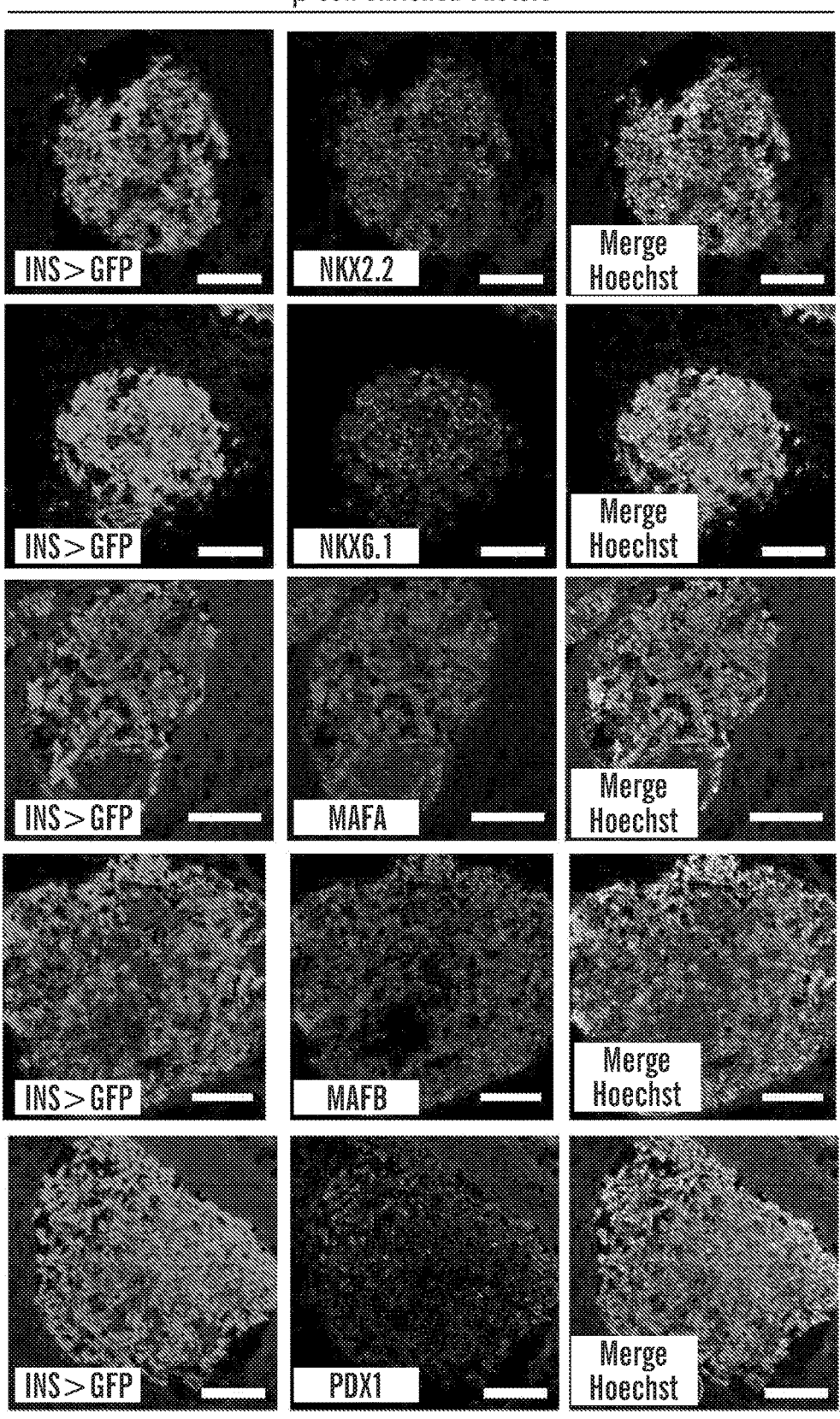
Figure 9D:
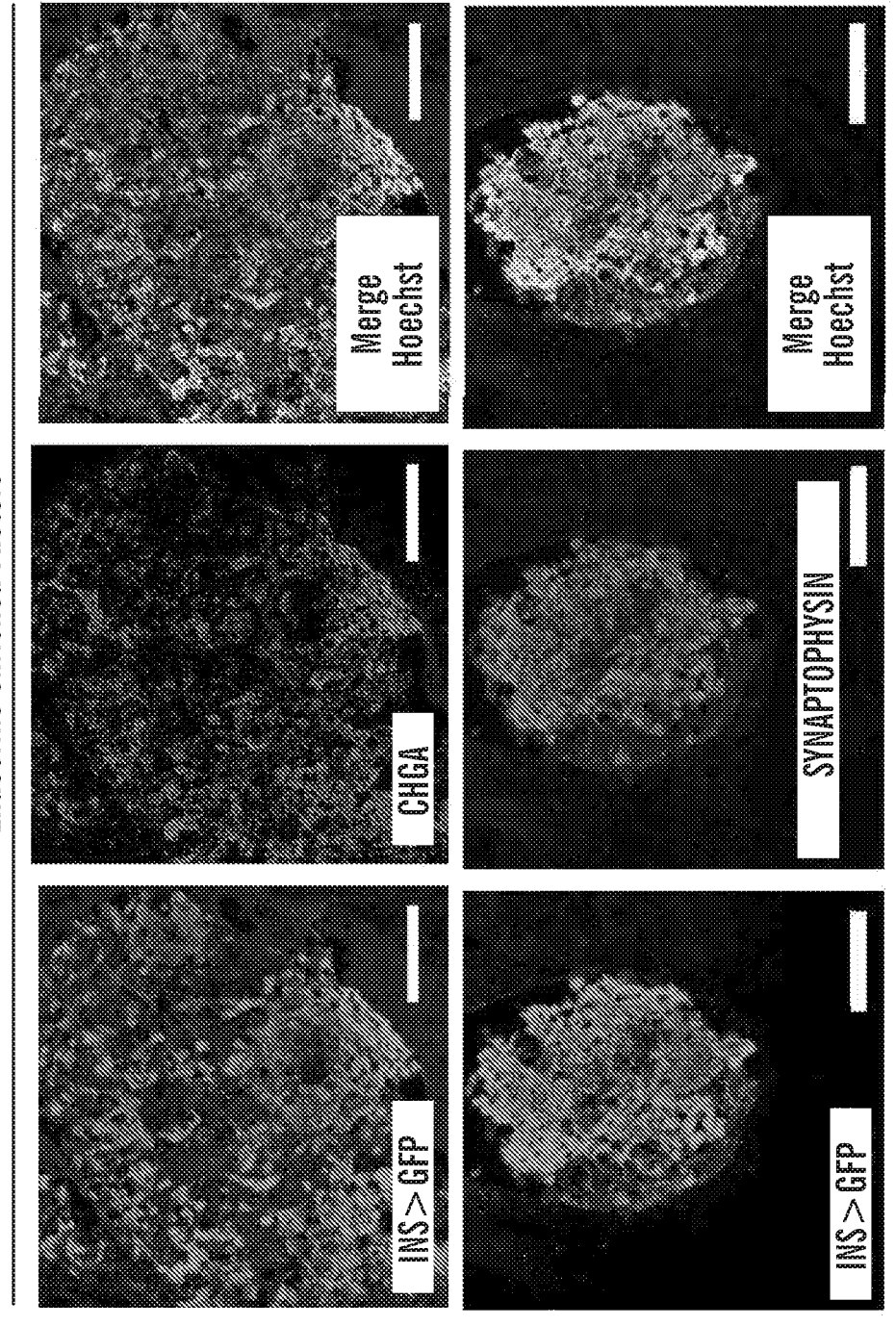
Figure 9E:
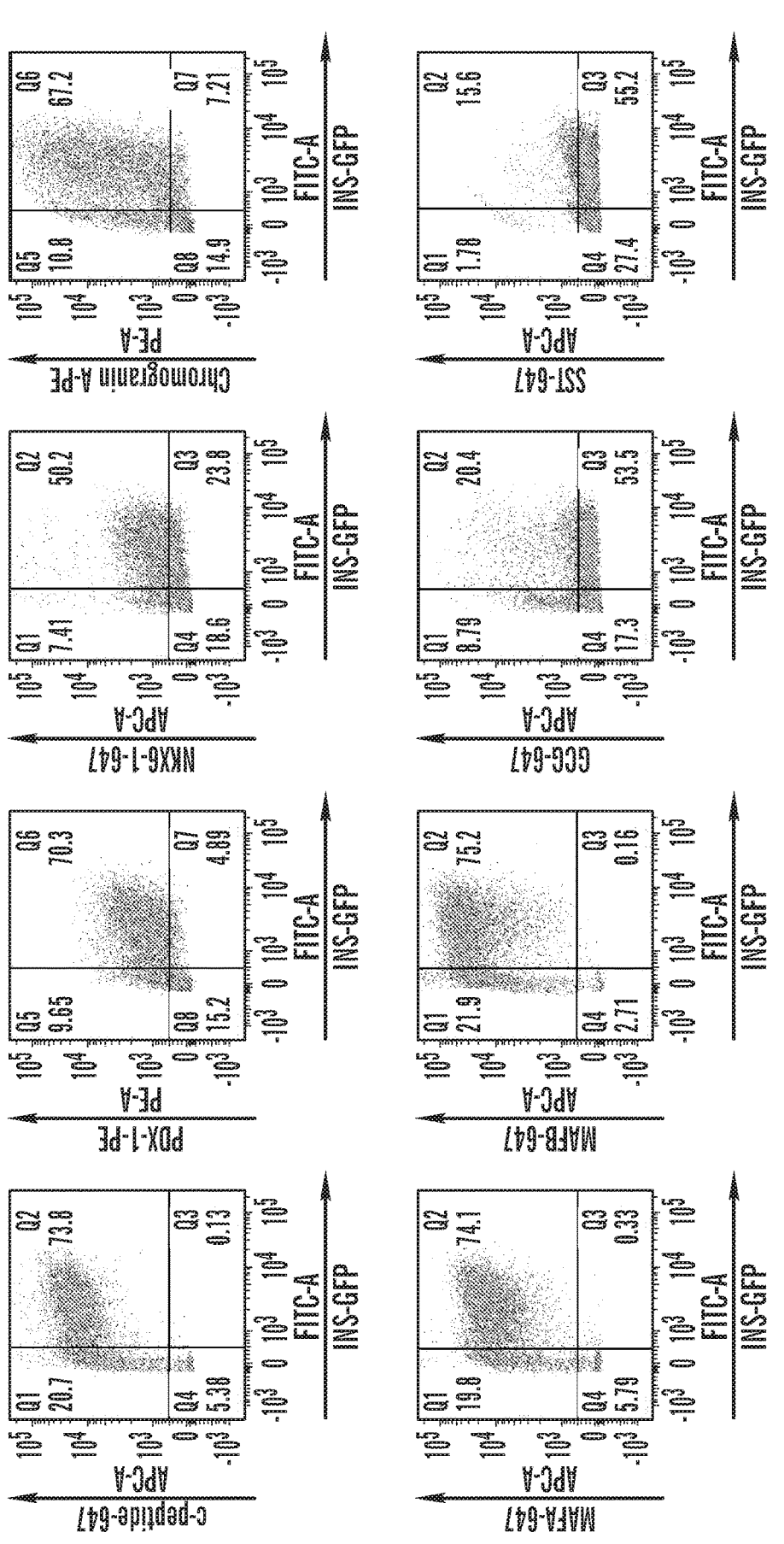
Figure 9F:
Figure 9F:
Figures 9G, 9H:
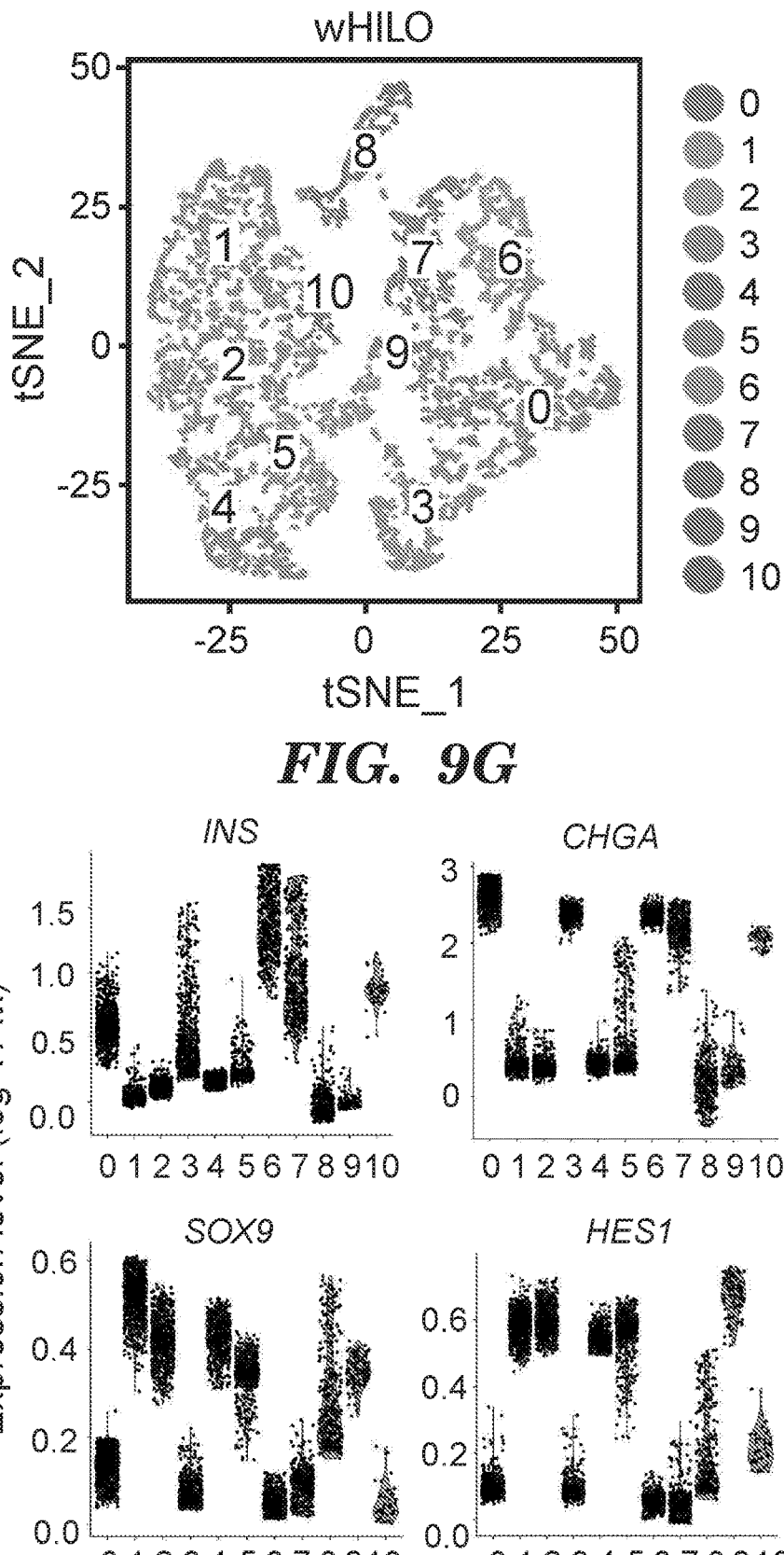
Figures 9I, 9J:
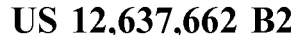
Figure 9K:
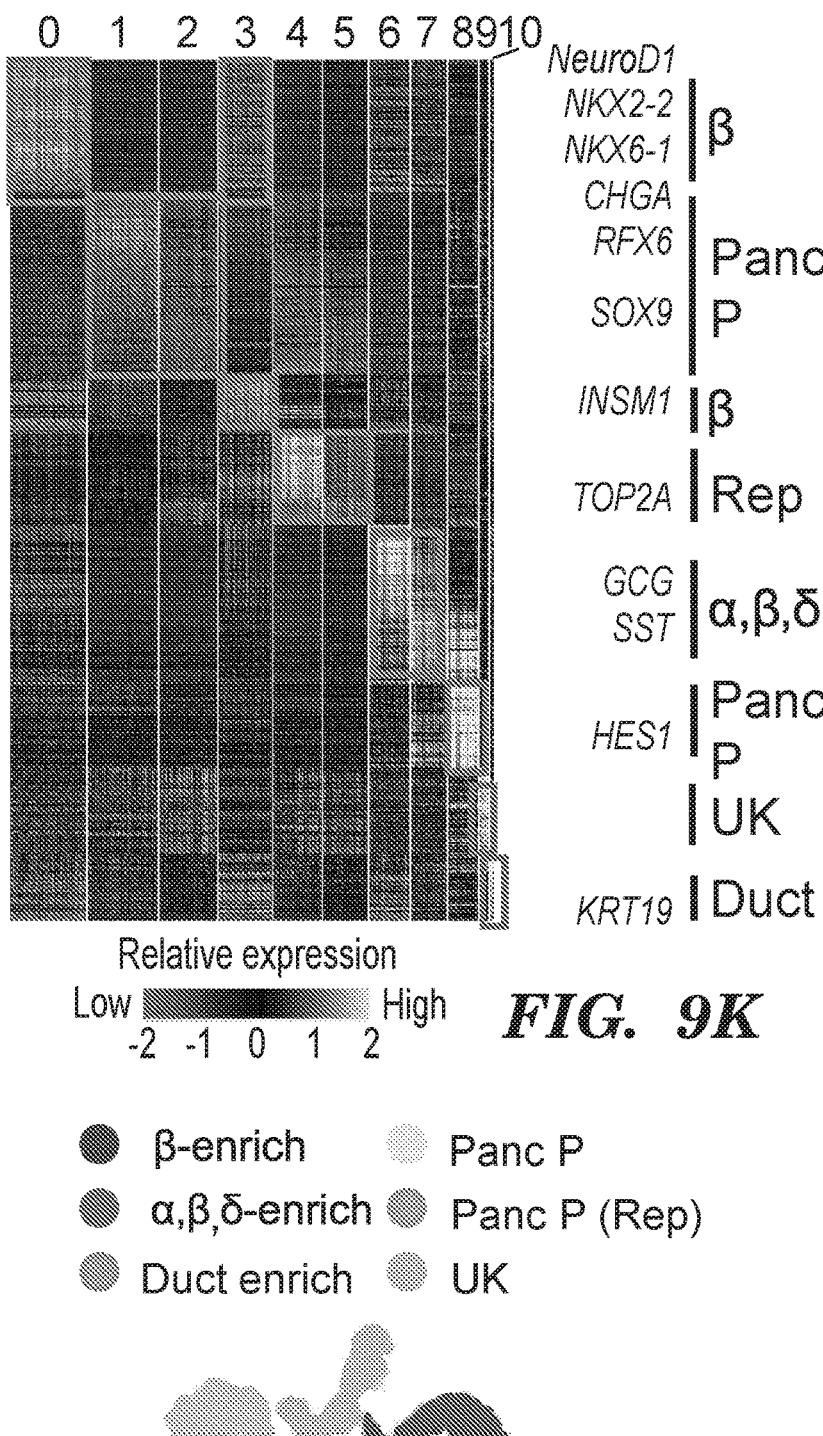
Figure 9L:
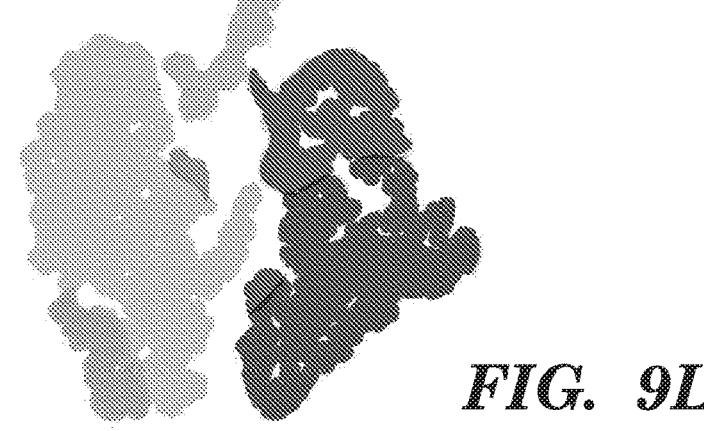
Figure 9M:
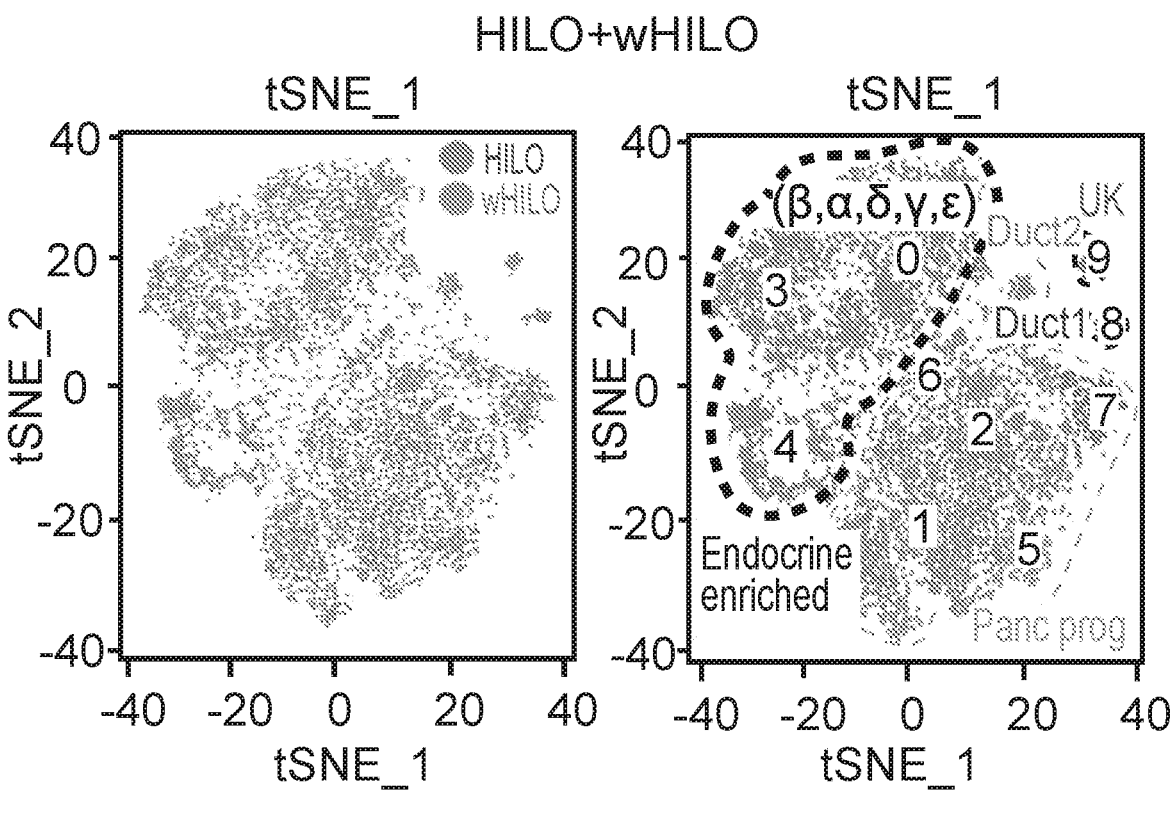
Figure 10A:
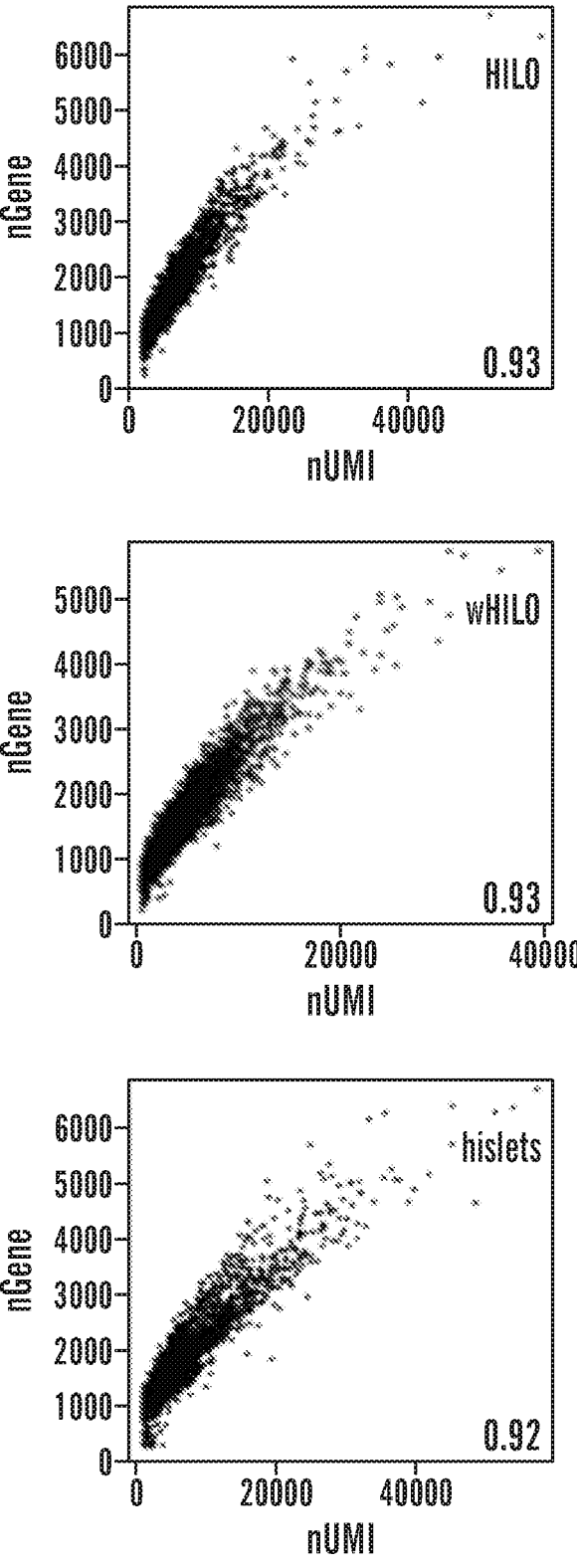
FIGS. 10A-10C provide plots showing quality analyses of scRNA-seq.
Figure 10B:
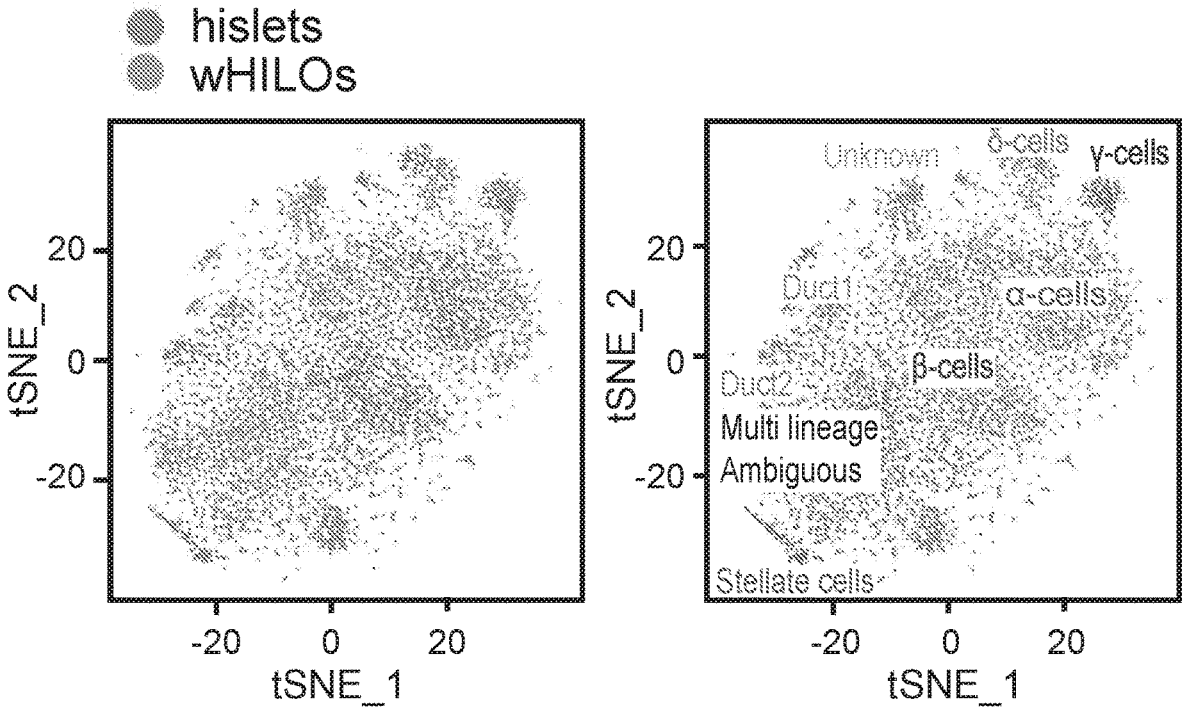
Figure 10C:
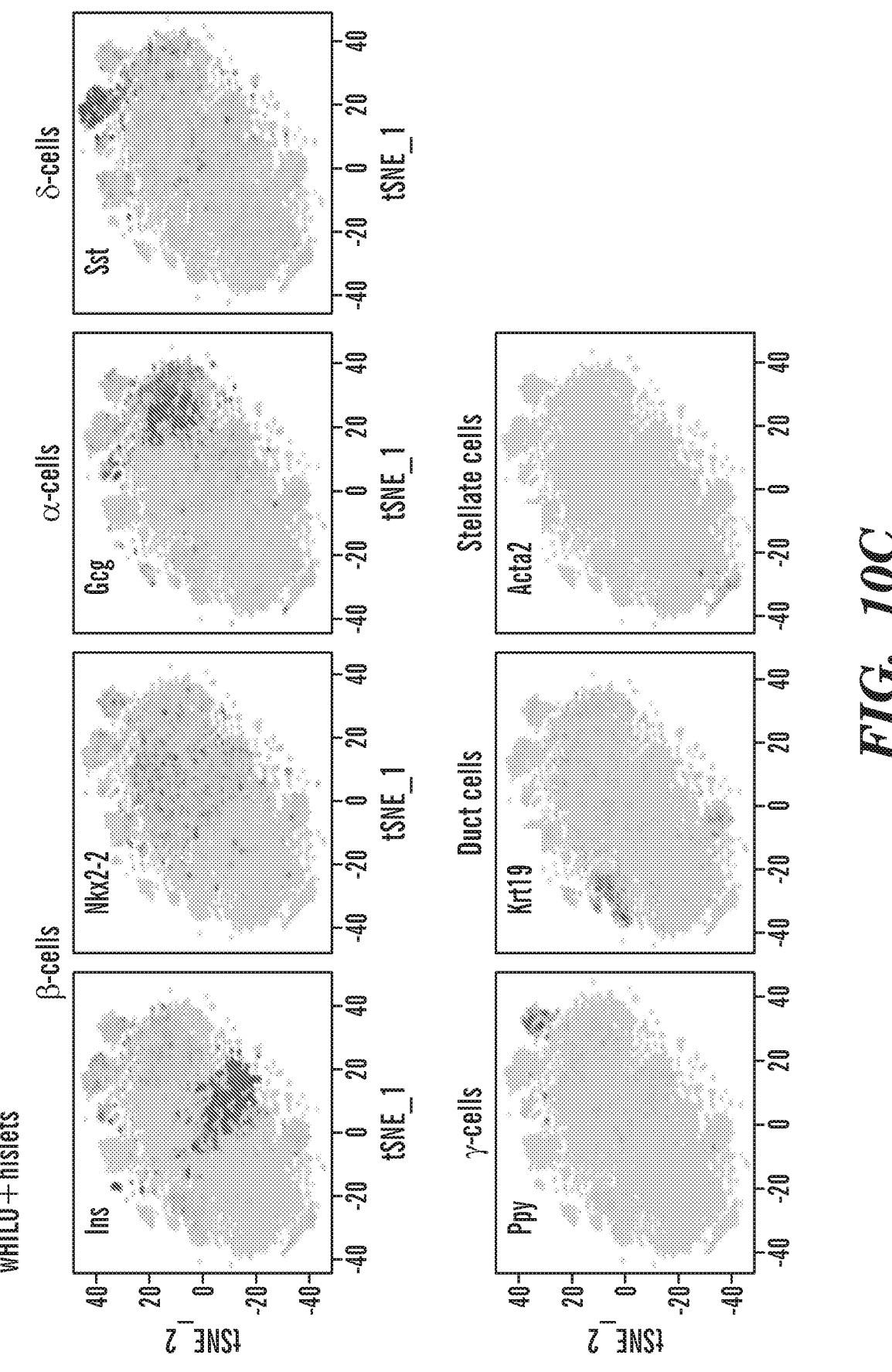
Figure 11B:
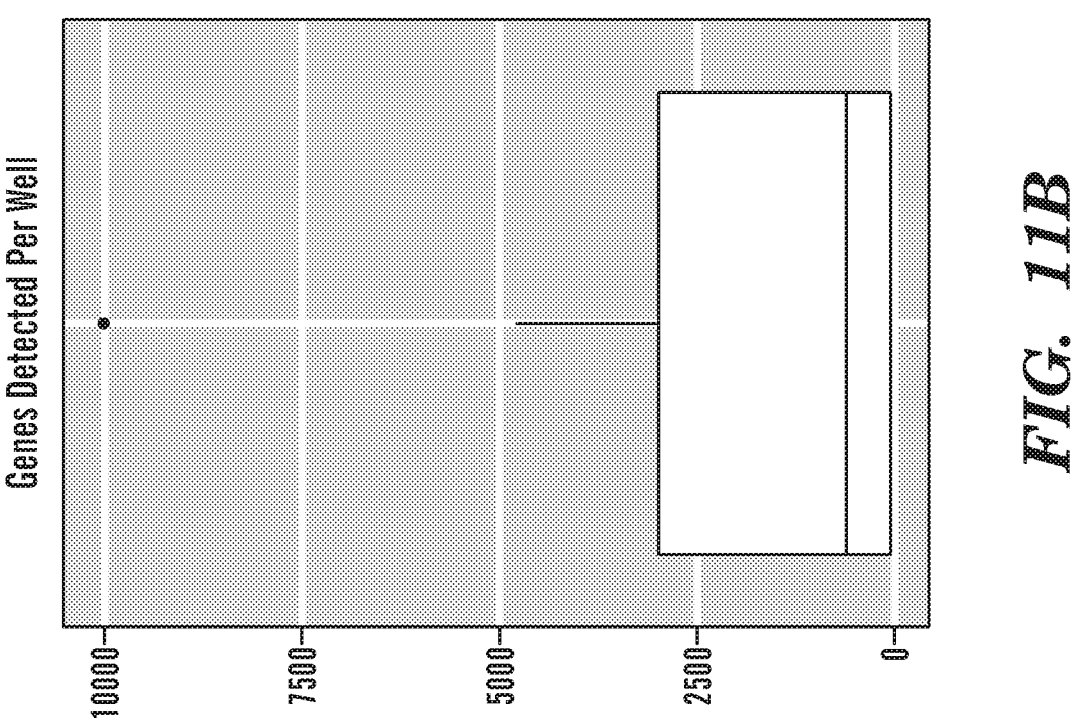
FIGS. 11A-11D provide a schematic depiction, graphs and plots related to plate based scRNA-seq analysis.
Figure 11A:
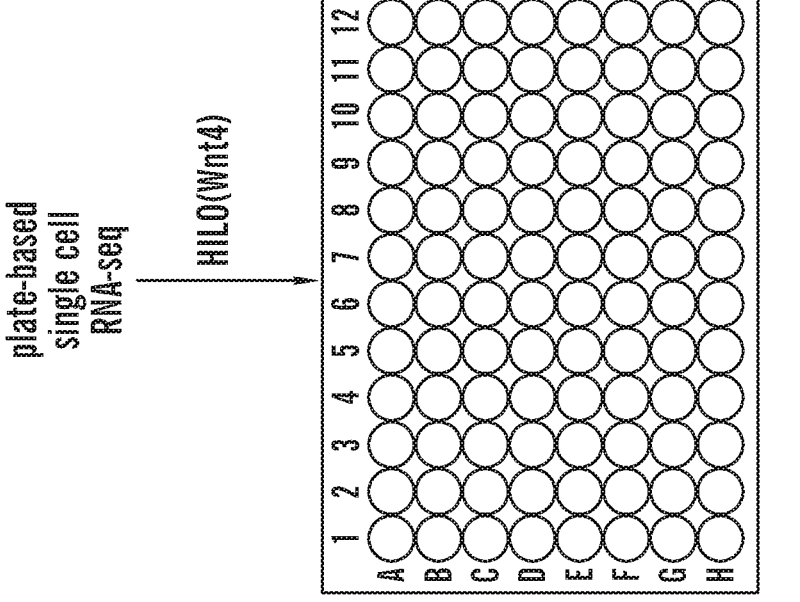
Figure 11C:
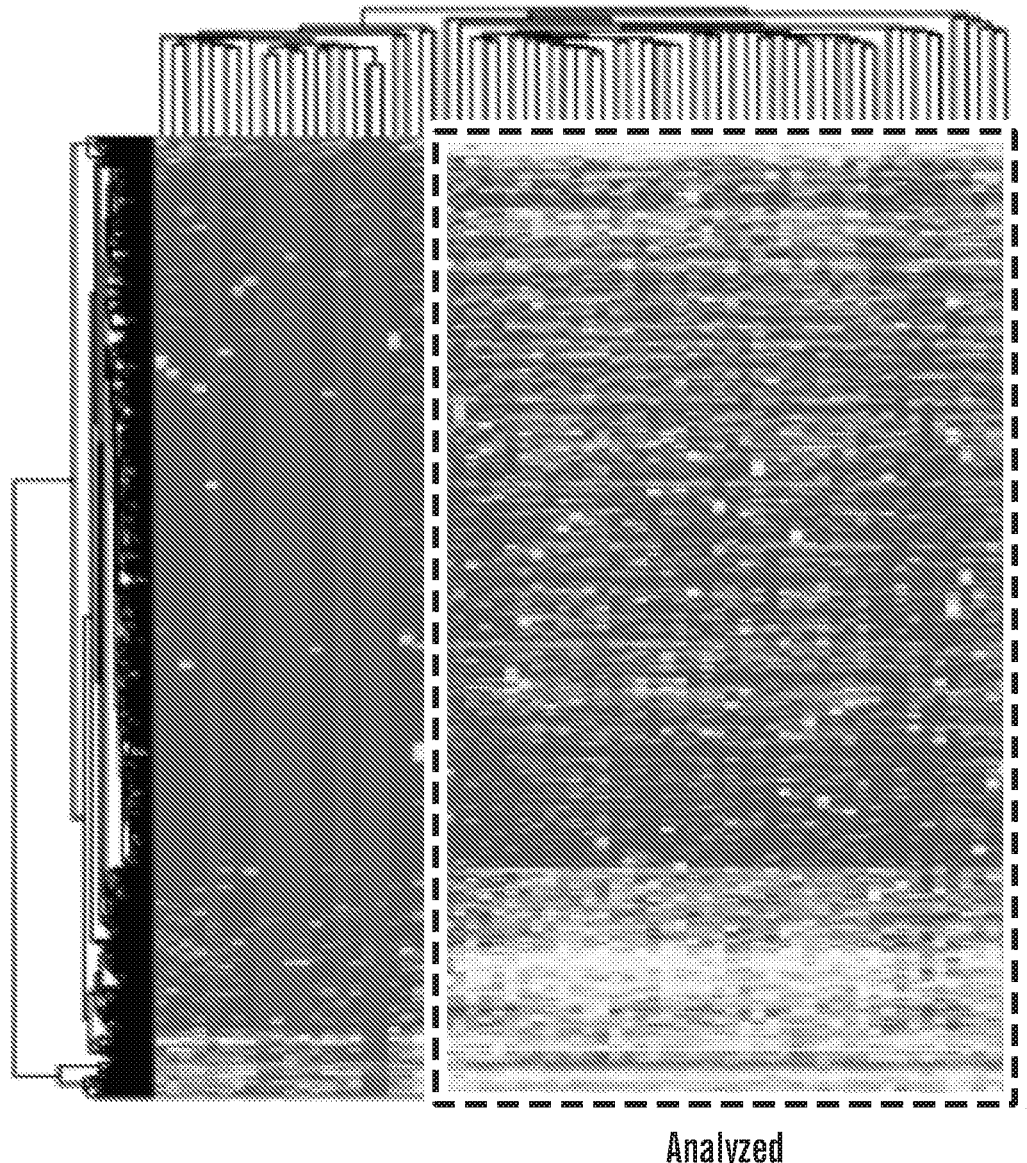
Figure 11D:
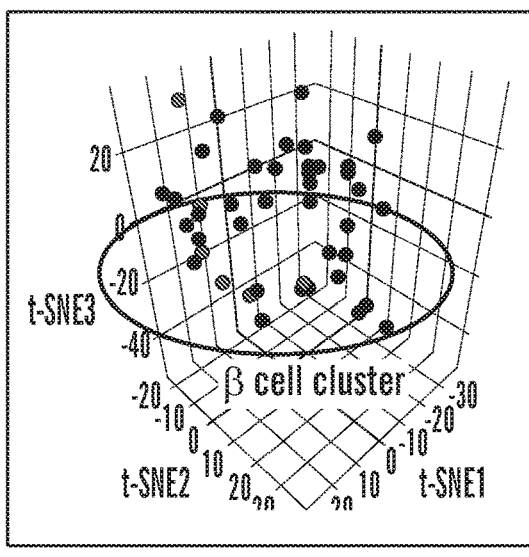
Figure 11D:
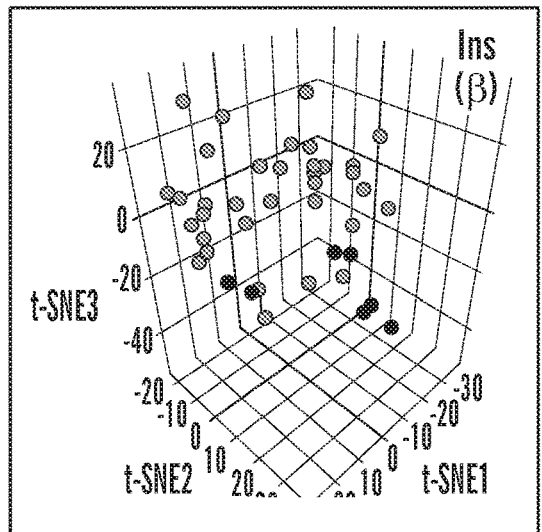
Figure 11D:
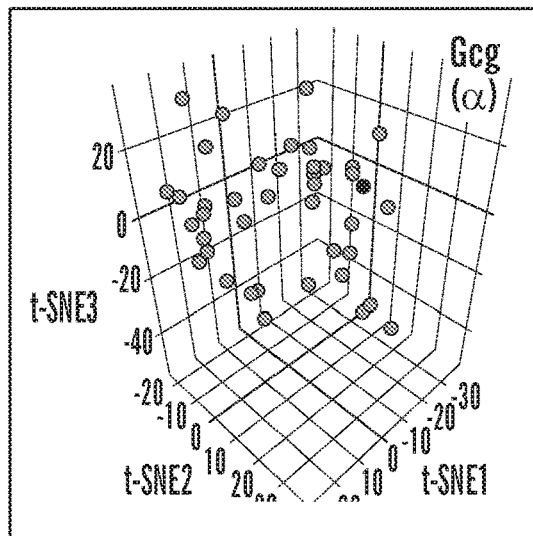
Figure 11D:
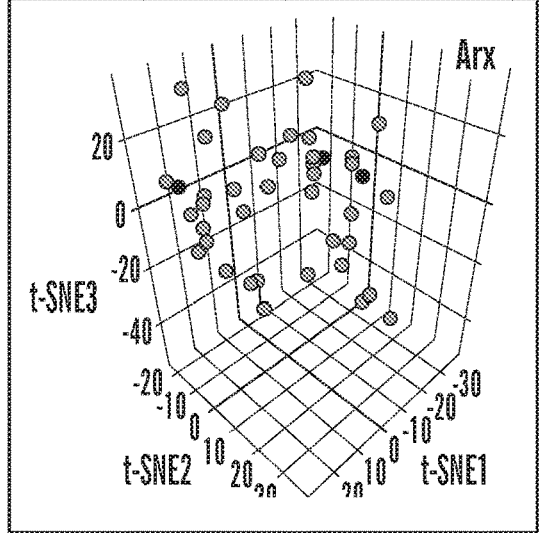
Figure 11D:
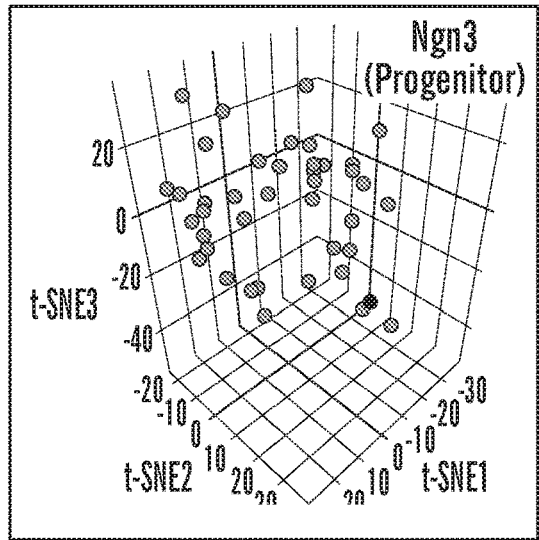
Figure 11D:
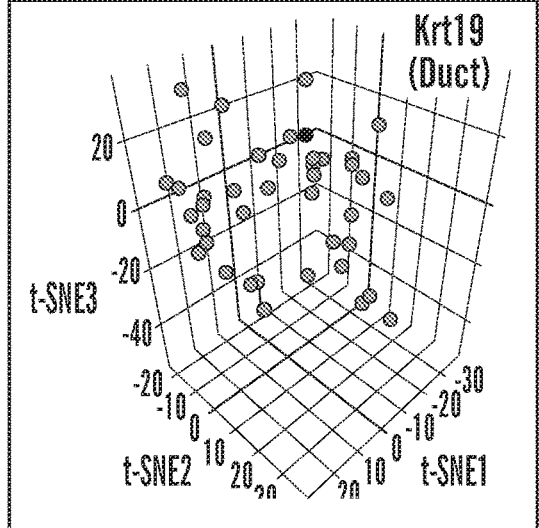
Figure 11D:
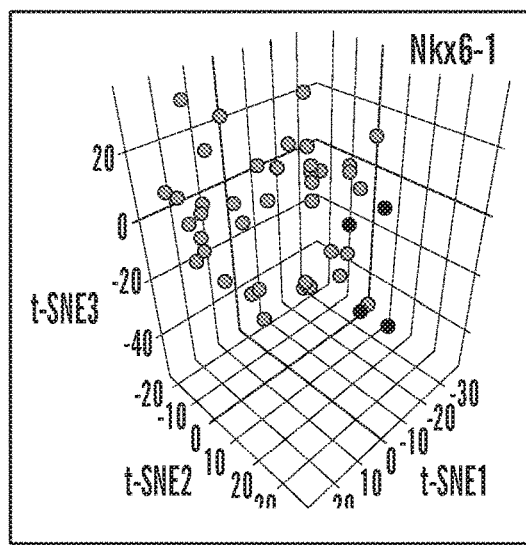
Figure 11D:
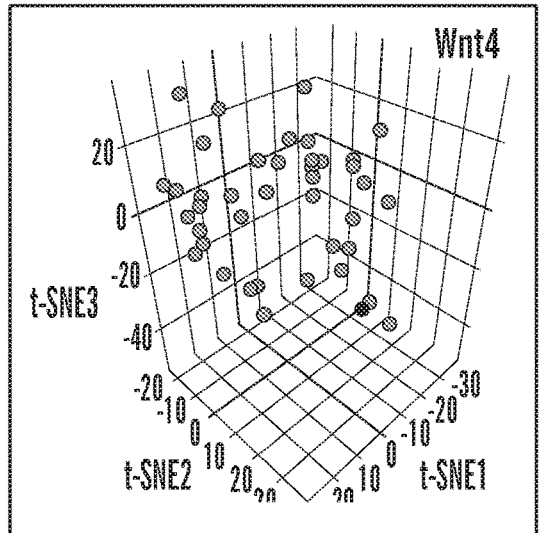
Figure 11D:
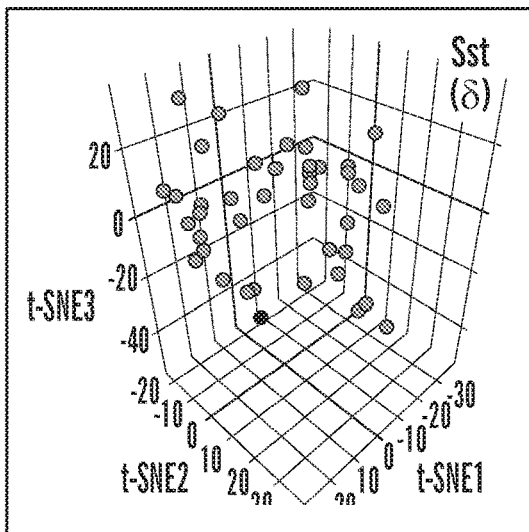
Figure 11D:
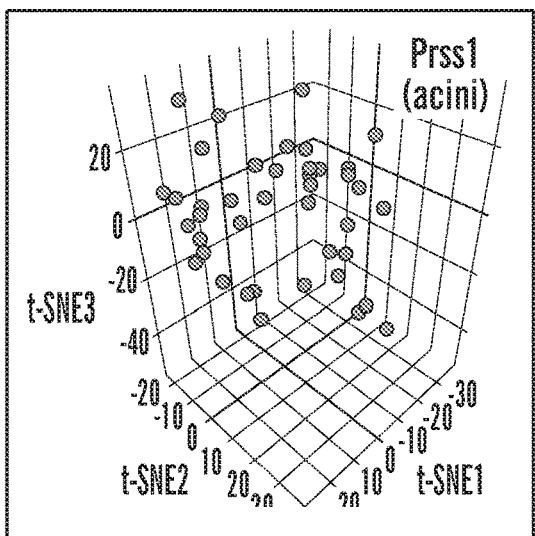
Figure 11D:
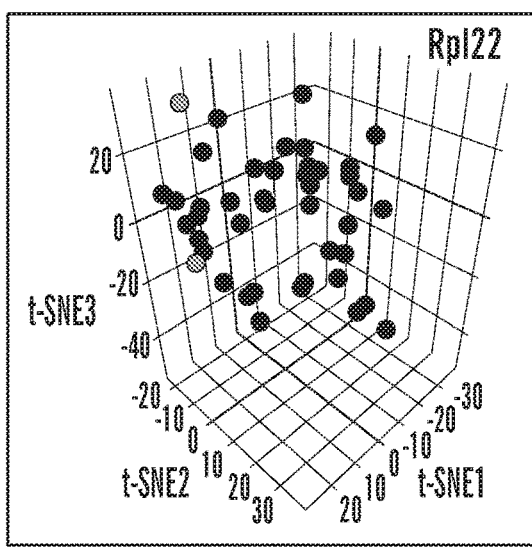

Immunohistochemical and flow cytometric analyses revealed that approximately 50-60% of wHILO cells co-expressed insulin and β cell markers, as well as low levels of additional endocrine cells (glucagon+, somatostatin+, pancreatic polypeptide+ (PP+)) (FIGS. 9A-9F). In agreement with the transcriptional comparisons, the cellular composition of HILOs was not altered by WNT4 treatment (FIG. 9F). To comprehensively characterize the cellular complexity of metabolically mature HILOs and gain insight into the in vitro maturation program, the single cell transcriptomes of HILOs (PBS-treated, n=4078) and wHILOs (WNT4-treated, n=4840) were compared with those of human islets (n=3245) (Table 1). Cellular transcriptomes in each analysis were clustered by principal component analysis of read counts with dimensionality reduction using t-distributed stochastic neighbor embedding (t-SNE). Clustering of wHILOs revealed populations enriched in β cell markers, as well as in Sox9+HES1+ pancreatic progenitor clusters (FIGS. 9G-9J). Signature gene expression analyses further distinguished non-replicating and replicating ductal-endocrine bipotent cells (+/−TOP2A), hormone positive endocrine enriched cells (GCG+, SST+), ductal-like cells (KRT19+) and a small population of cells with unknown function (UK). (FIG. 9K and FIG. 9L). Co-clustering of HILO and wHILO data sets provided additional evidence for the presence of multiple endocrine-like cell types (based on the highly expressed genes in each cluster) that were largely independent of WNT4 treatment (FIG. 9M). To confirm the presence of multiple endocrine-like cell types, an integrated analysis of the combined wHILO and human islet single cell data sets was performed (FIGS. 10A-10C). While differences were evident, wHILO cells were found clustering with islet endocrine cells including β, α, δ and γ cells, indicating transcriptional similarities (FIG. 10B). Notably, a functional classification based on co-clustering with islet cell types revealed a predominance of β- and α-like cells in wHILOs (FIG. 10B).

TABLE 1

| Sample identification | HILO | wHILO | H-ISLETS |
|---|---|---|---|
| Estimated Number of Cells | 4,078 | 4,840 | 3,245 |
| Fraction Reads in Cells | 88.90% | 89.20% | 79.70% |
| Mean Reads per Cell | 16,482 | 13,496 | 22,195 |
| Median Genes per Cell | 1,582 | 1,455 | 1,486 |
| Total Genes Detected | 22,003 | 22,076 | 21,007 |
| Median UMI Counts per Cell | 4,754 | 4,220 | 5,618 |
| Number of Reads | 67,216,051 | 65,324,121 | 72,025,806 |
| Valid Barcodes | 98.50% | 98.50% | 98.60% |
| Reads Mapped Confidently to Transcriptome | 58.30% | 58.10% | 64.40% |
| Reads Mapped Confidently to Exonic Regions | 62.20% | 62.00% | 68.10% |
| Reads Mapped Confidently to Intergenic Regions | 24% | 23.70% | 19.00% |
| Reads Mapped Confidently to Intergenic Regions | 4.70% | 4.70% | 4.20% |

TABLE 1-continued

| Sample identification | HILO | wHILO | H-ISLETS |
|---|---|---|---|
| Reads Mapped Antisense to Gene | 4.10% | 4.00% | 4.40% |
| Sequencing Saturation | 32.30% | 27.00% | 38.60% |
| Q30 Bases in Barcode | 96.80% | 96.80% | 96.80% |
| Q30 Bases in RNA Read | 80.50% | 79.40% | 80.40% |
| Q30 Bases in UMI | 96.40% | 96.40% | 96.40% |
| Genomic Modification | CRISPR-InsulinGFP Reporter | | None |
| Transcriptome | | GRCh38 | |
| Chemistry | | Single Cell 3' v2 | |
| Cell Ranger Version | | 2.0.2 | |

Example 7: PD-L1 Provides Immune Protection for HILOs

Figure 4A:
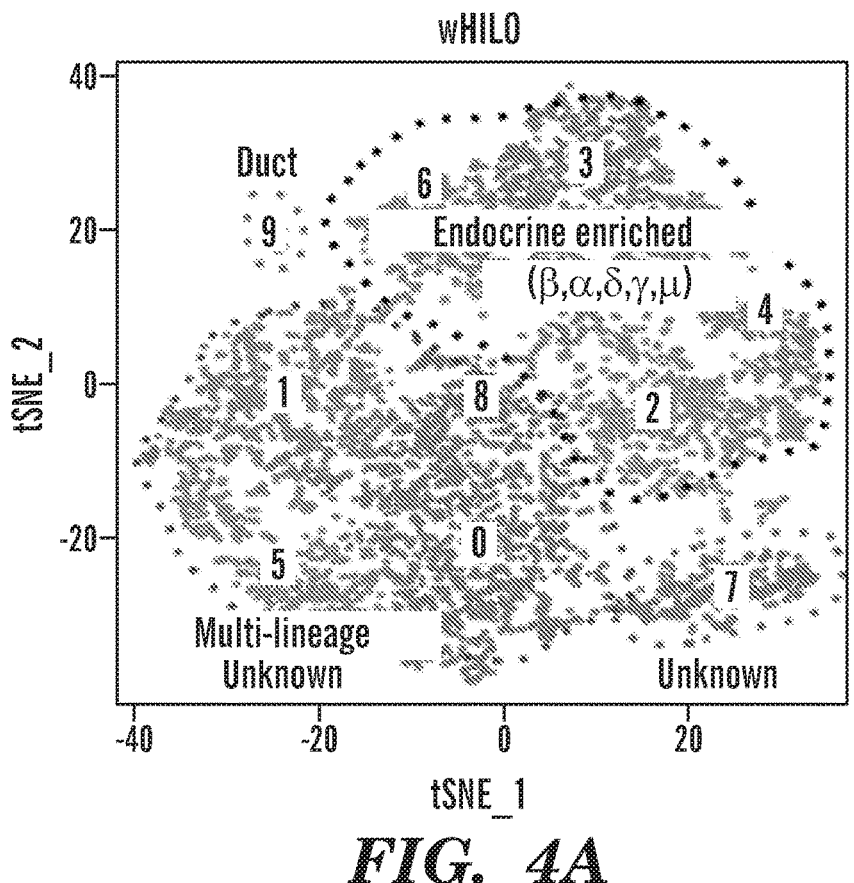
FIGS. 4A-4M provide plots, graphs, a microscopy image, flow cytometry results and a schematic related to studies of PD-L1-expressing wHILOs extended functionality and glucose control in immune competent mice and immune profiling of wHILO grafts in C57BL6J mice.
Figure 4B:
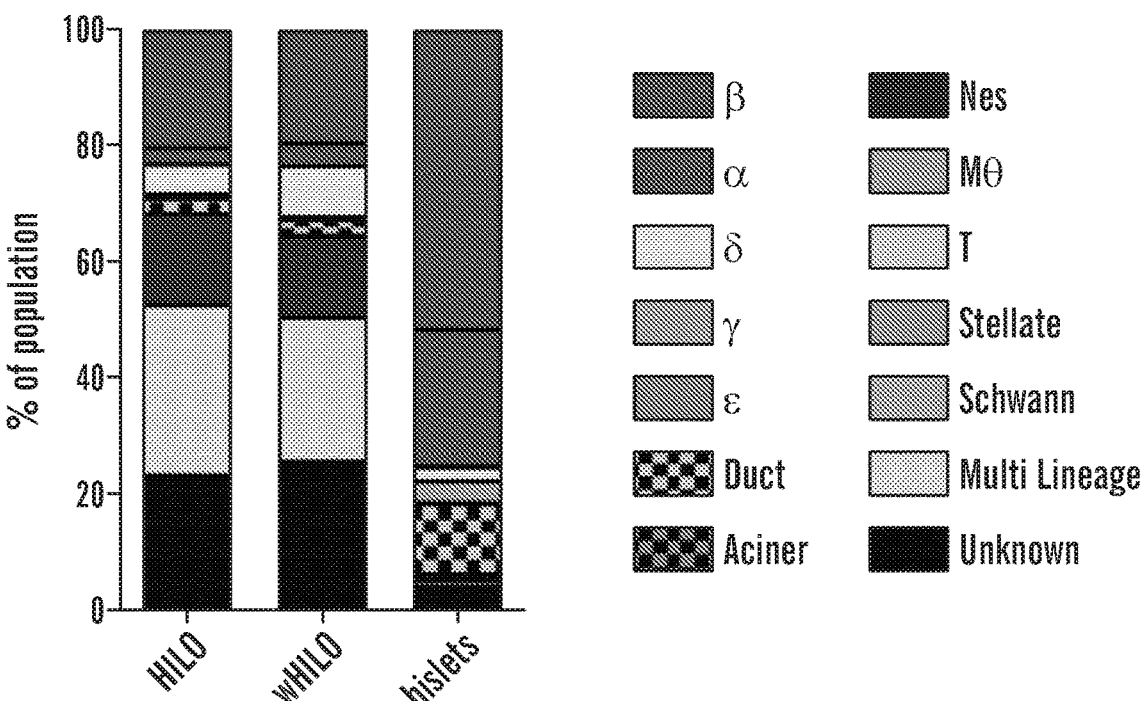
Figure 4C:
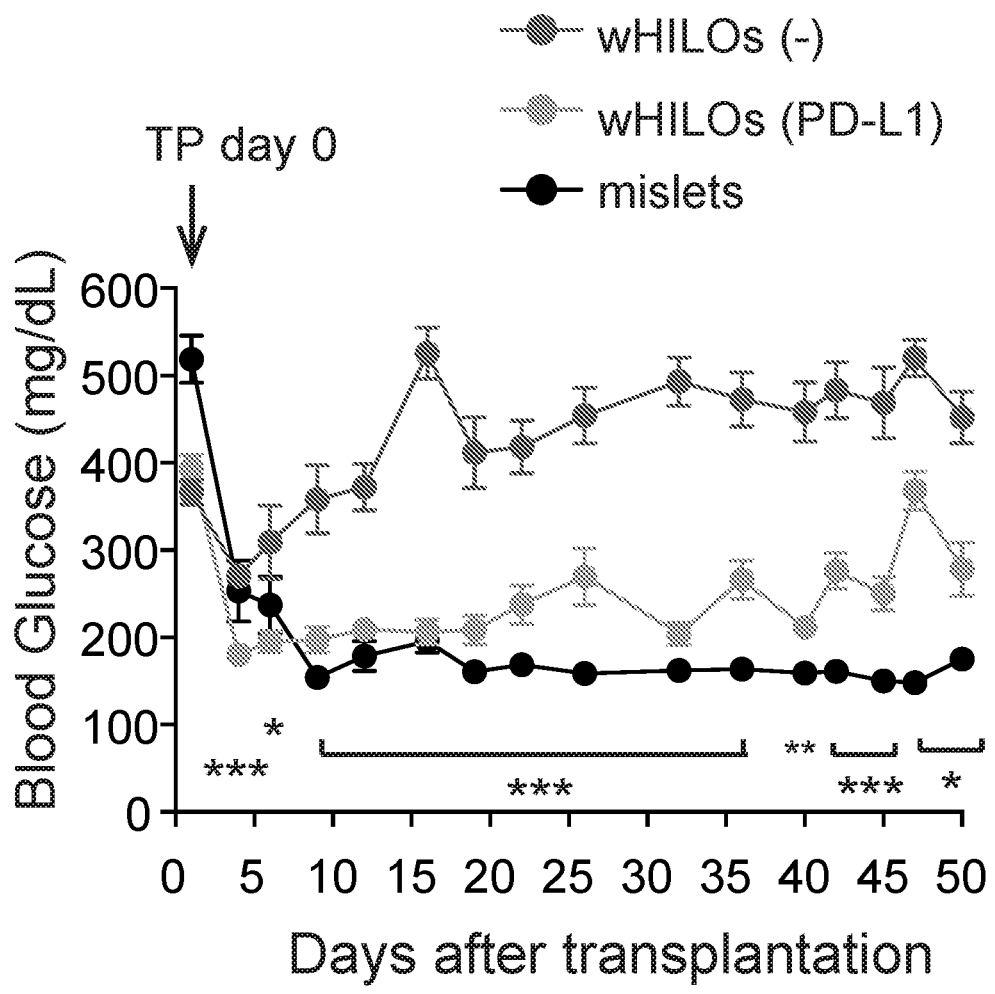

The clinical utility of transplanted islets is limited by both allogenic and autoimmune responses. Given the ability of checkpoint molecules to suppress immune responses, the endogenous expression of immune checkpoint proteins in human islets was investigated. A small subset of β cells in healthy islets showed a unique gene expression signature that included PD-L1 expression (FIG. 12A), a determinant of immune tolerance in β cells. To create wHILOs that exhibited exogenous PD-L1 expression to thereby protect them upon transplantation, PD-L1-expressing hiPSC clones were generated using a lentiviral system and subsequently differentiated into metabolically mature wHILOs, as delineated in FIG. 3A. PD-L1 over-expression in the HILOs did not affect insulin expression (FIGS. 12B and 12C). PD-L1-expressing wHILOs and those that did not express PD-L1 were transplanted into the kidney capsules of immune competent diabetic mice (STZ-treated C57BL6J mice), (FIG. 12D). wHILOs with and without PD-L1 overexpression were able to restore glycemic control within days of transplantation with similar efficacy (FIG. 4C). However, the functionality of wHILOs lacking PD-L1 expression was progressively lost over a period of weeks, as monitored by the increases in blood glucose levels. By contrast, the PD-L1$^+$ wHILOs were able to maintain glucose homeostasis for >50 days in the absence of immunosuppressive drugs (FIG. 4C).

Figure 4D:
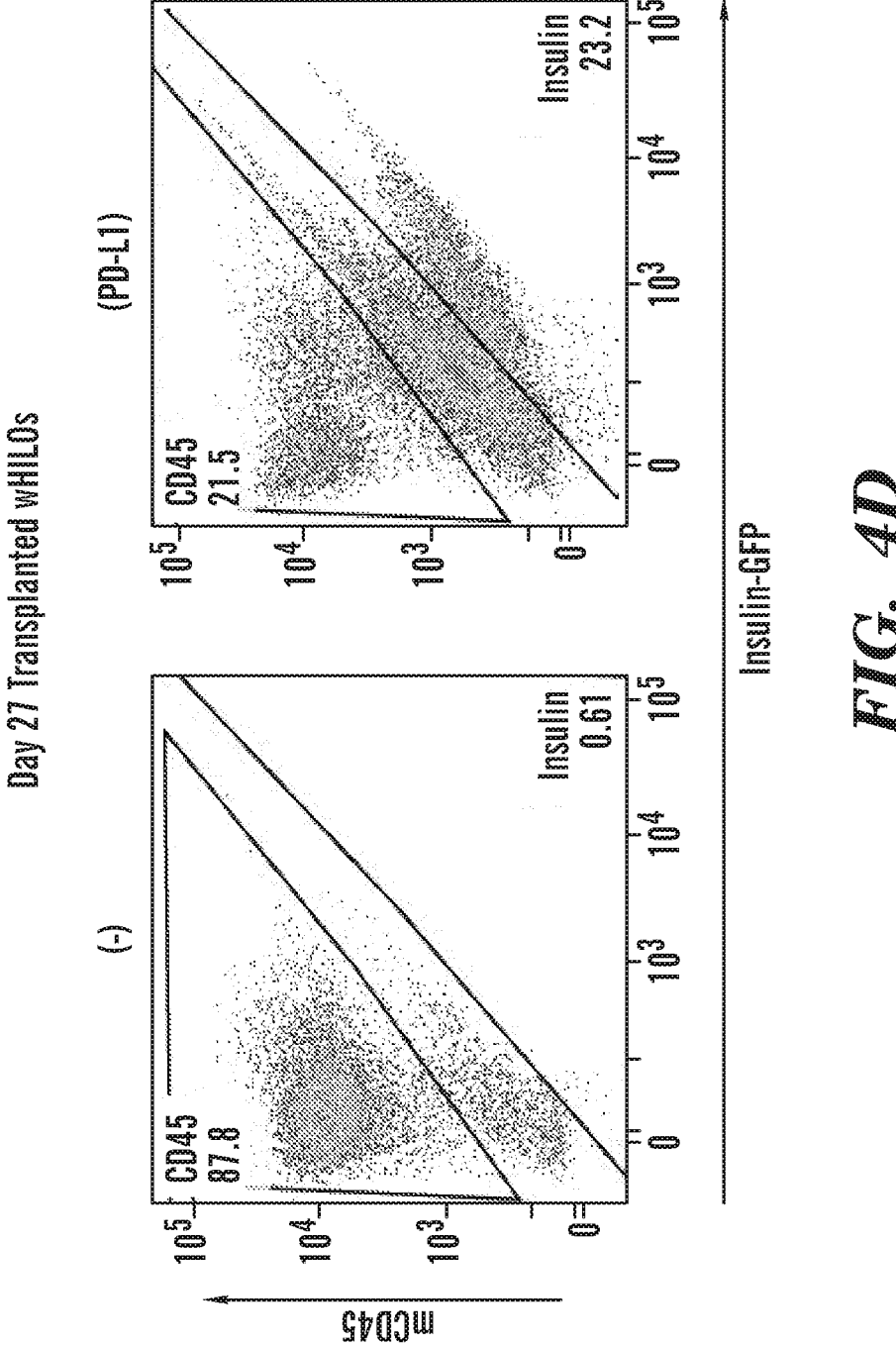
Figure 4E:
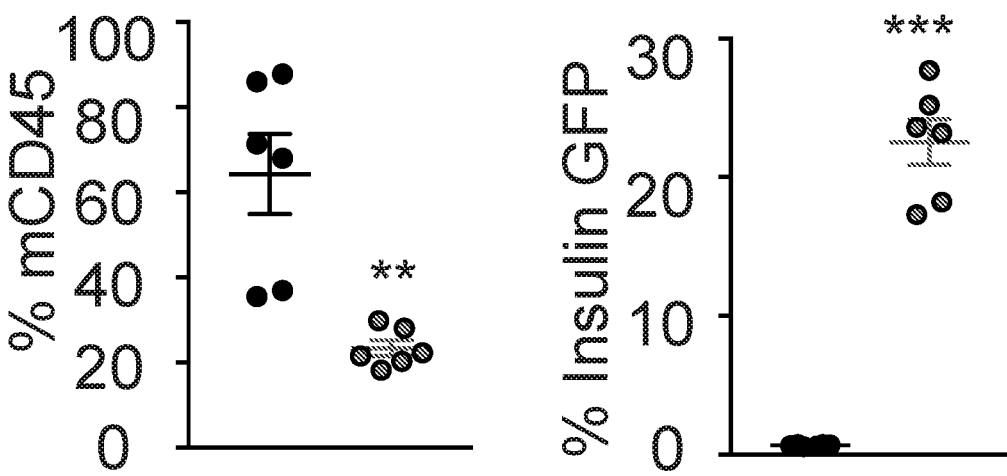
Figure 4F:
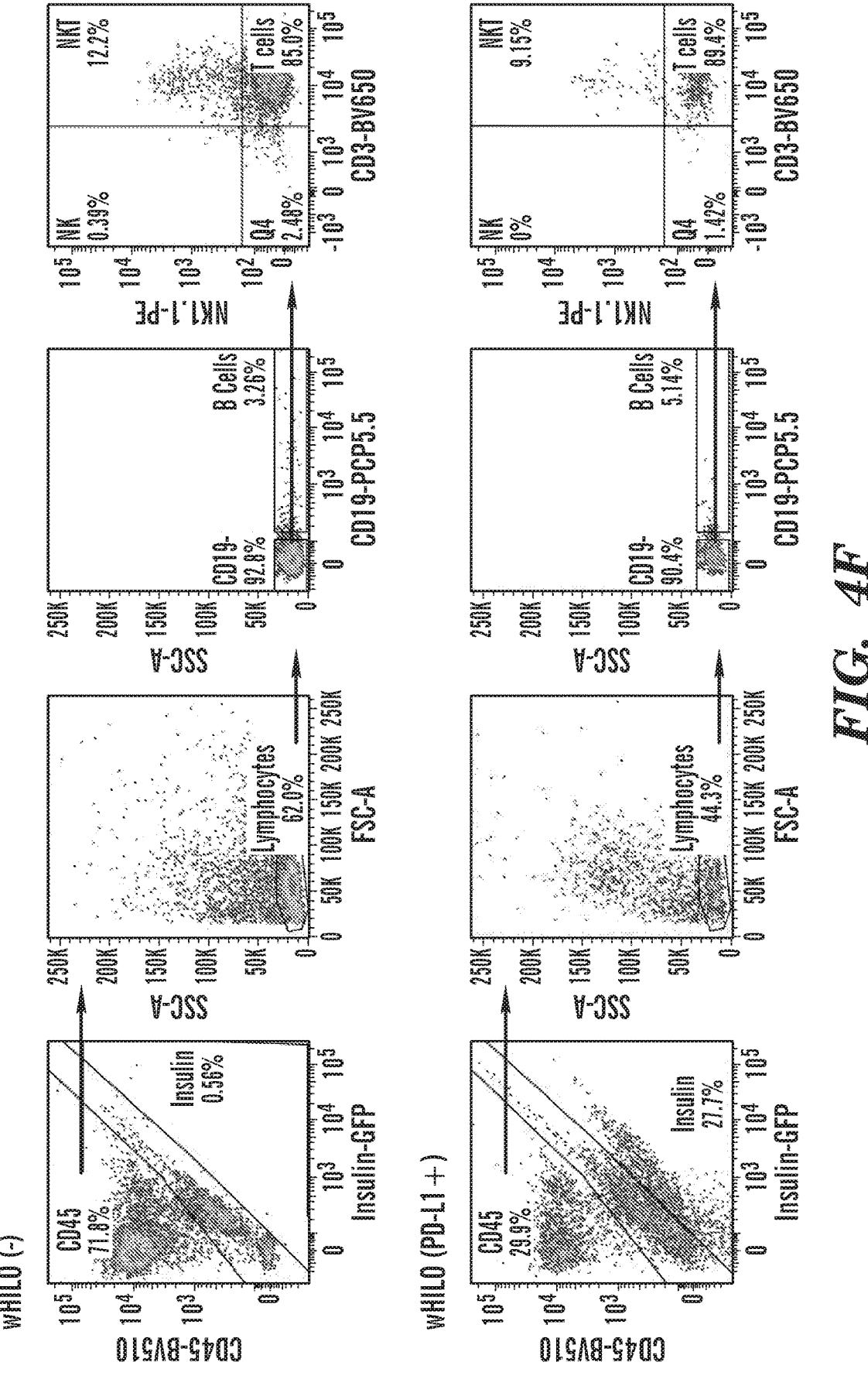
Figures 4G, 4H:
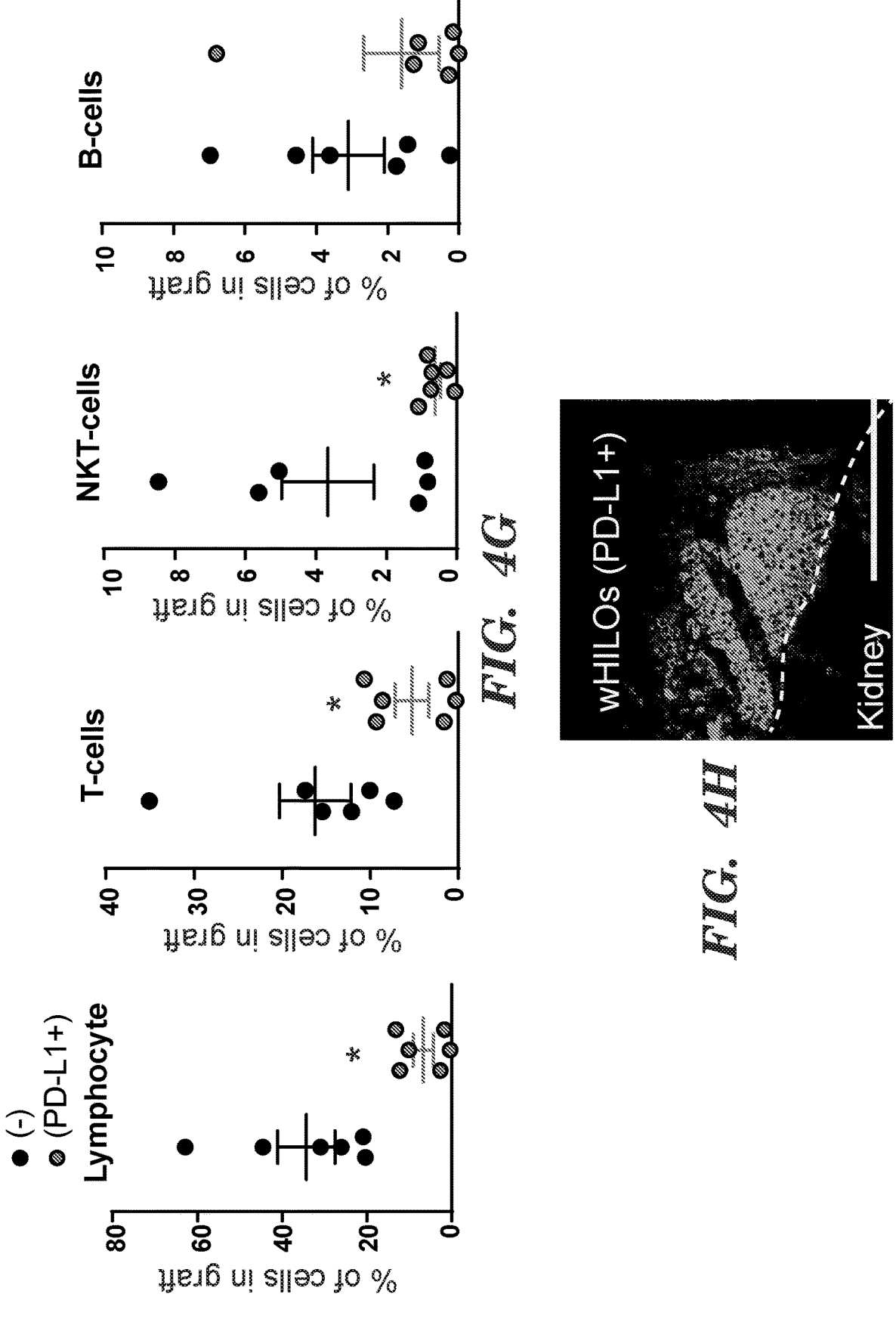

To confirm the immune-suppressive actions of PD-L1, transplanted wHILOs were recovered from recipient mice 27 days after transplantation, and the cellular compositions were compared by flow cytometry. The infiltration of CD45$^+$ immune cells, including T and NKT cells, was markedly decreased in grafts that had received wHILOs that expressed PD-L1 (FIGS. 4D-4G). Furthermore, negligible numbers of insulin-expressing cells were found in grafts that had received wHILOs lacking PD-L1 expression, in agreement with the largely unregulated blood glucose levels observed 27 days after transplantation (FIG. 4D, FIG. 4F and FIG. 4H).

Figures 4I, 4J:
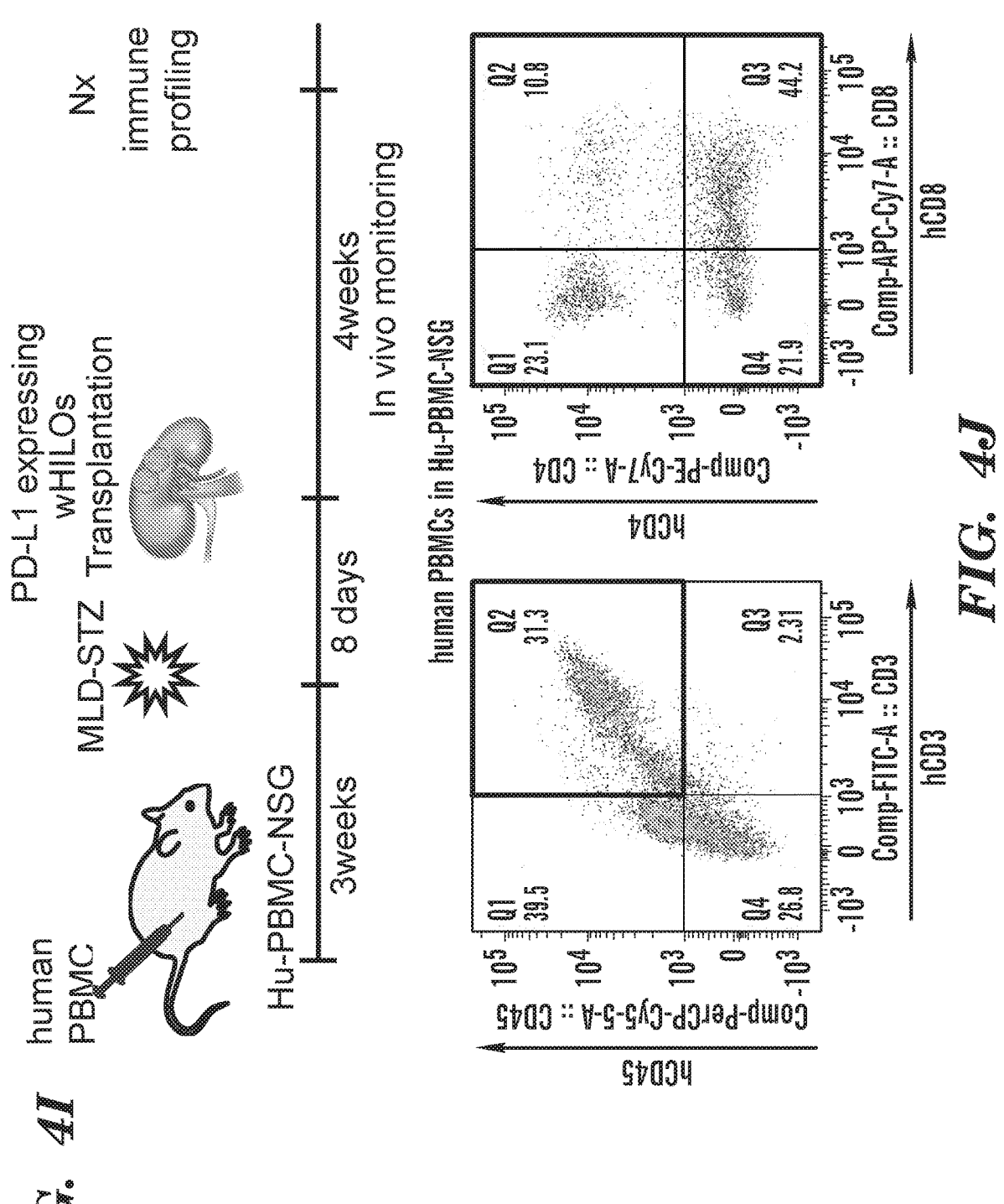
Figure 4K:
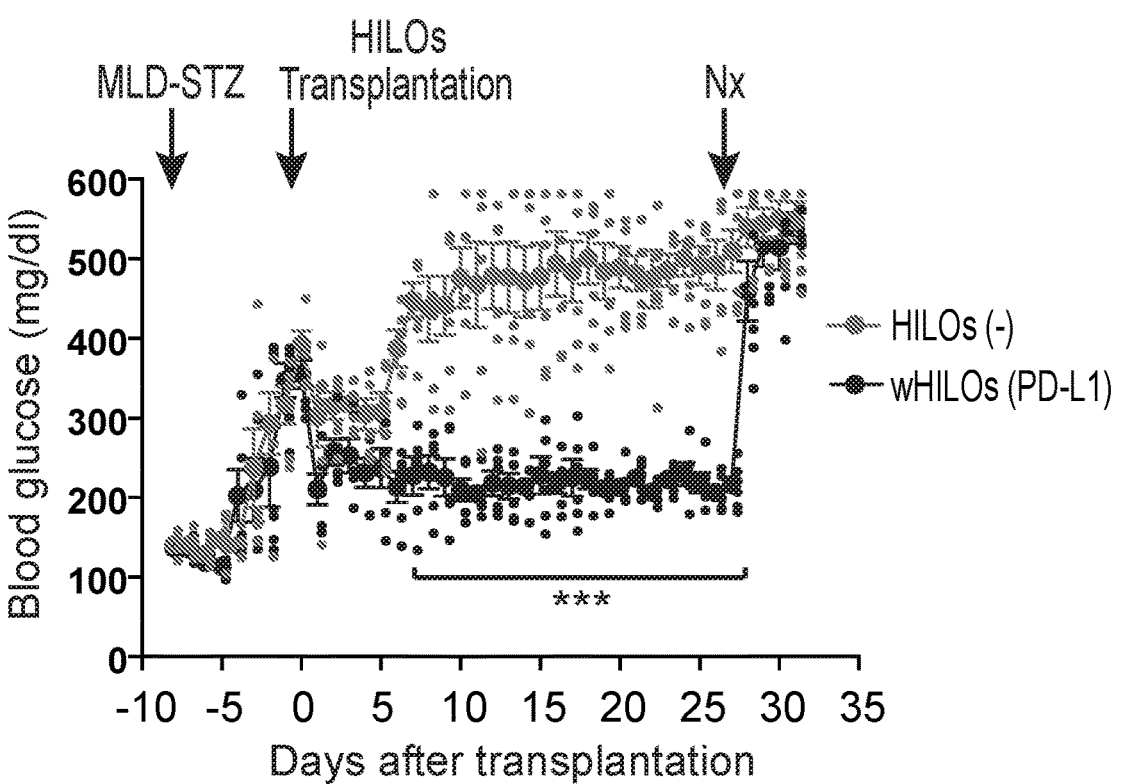
Figure 4L:
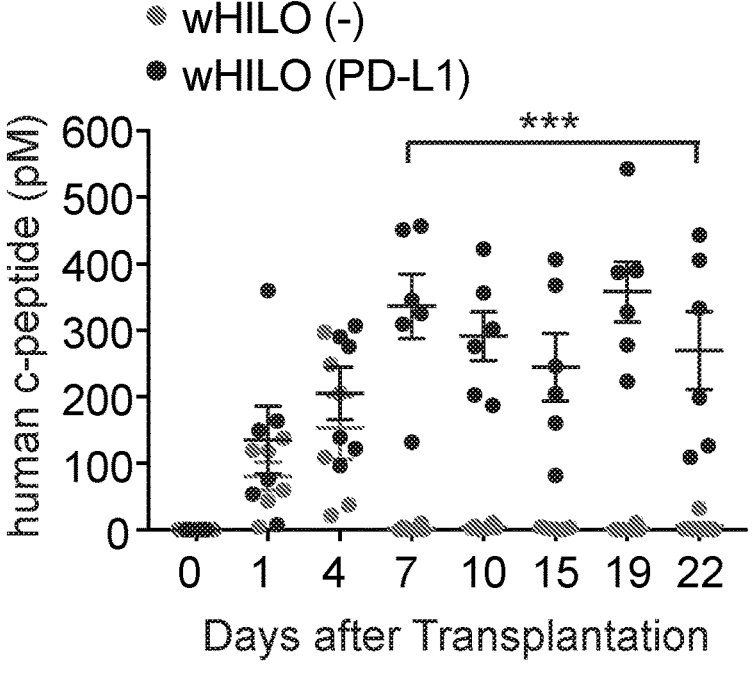
Figure 4M:
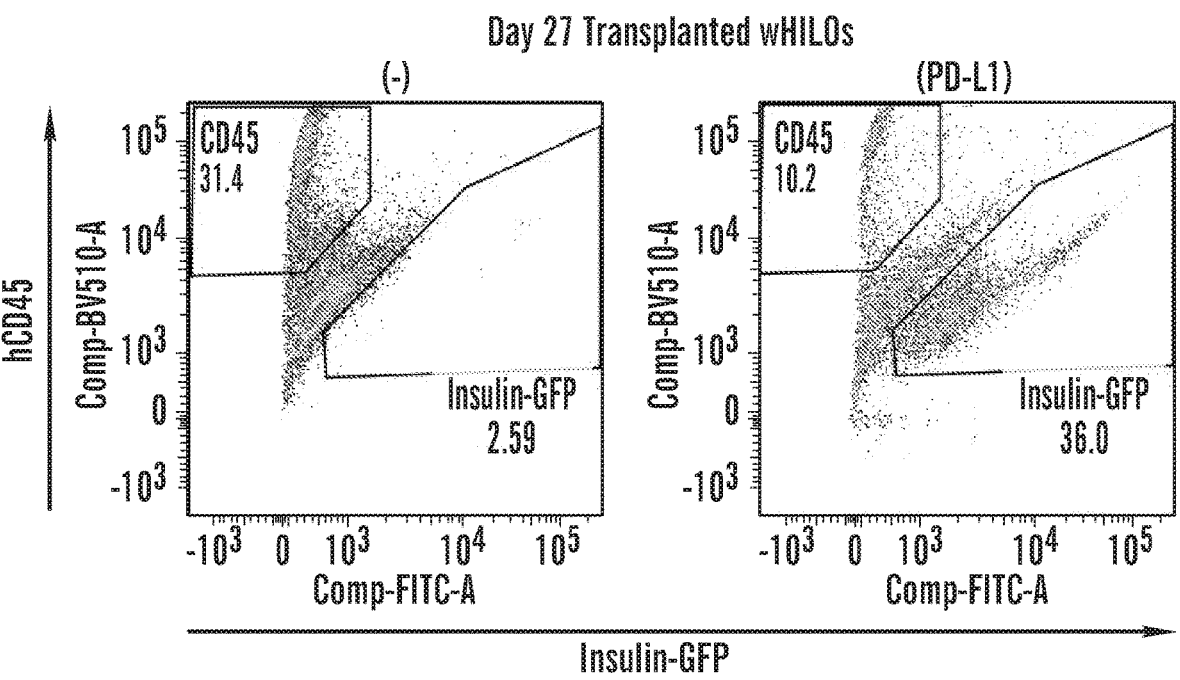
Figure 4N:
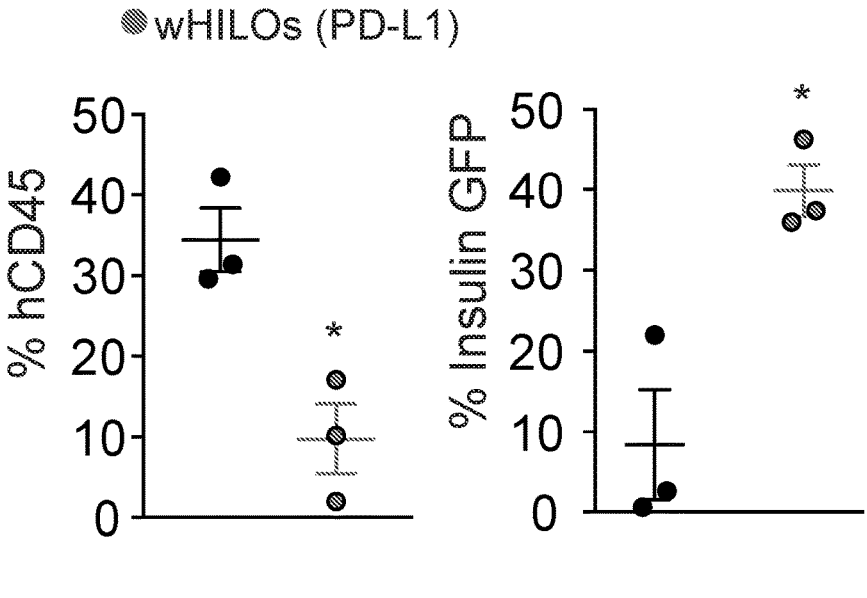
FIG. 4N presents dot plot graphs that quantify the results of analyses shown in FIG. 4M. (Error bars represent SEM. *p<0.05, p<0.01, *p<0.001).

The persistence of wHILO (PD-L1) as xenografts led to an assessment of their functionality in a model incorporating a reconstituted human T cell repertoire. After confirming the presence of human T cells, HuPBMS-NSG-SGM3 mice were rendered diabetic by multi low dose STZ treatment (50 mg/kg/day for 5 days, MLD-STZ) and were subsequently transplanted with wHILO (FIG. 4I and FIG. 4J). Transplanted wHILOs (PD-L1) provided sustained blood glucose control compared to those lacking PD-L1 expression, with human c-peptide levels correlating with the extent of glycemic control (FIG. 4K and FIG. 4L). The rapid development of hyperglycemia upon surgical removal of the transplanted kidneys implicated graft-derived insulin as the primary effector (FIG. 4K). Subsequent analysis of the recovered grafts revealed a marked reduction in the number of insulin expressing cells in wHILOs and a corresponding increase in human lymphocytes (FIG. 4E and FIG. 4M).

Example 8: Epigenetic Memory Drives Immune Tolerant wHILOs

Figure 5G:
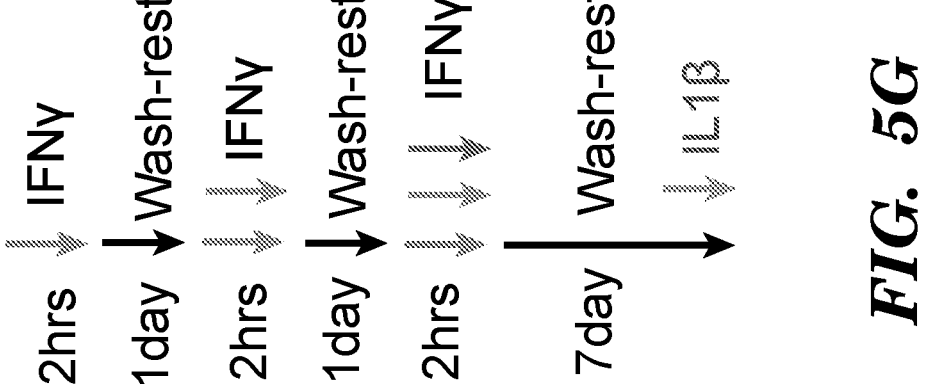

PD-L1 expression is induced by IFNγ stimulation in multiple cancers; however, extended exposure to cytokines, including IFNγ, has been found to induce β-cell death and/or de-differentiation. In this Example, experiments were performed to assess whether the IFNγ pathway was capable of minimizing host immune responses against transplanted wHILOs. Following exposure of wHILOs to IFNγ stimulation, it was found that IFNγ rapidly and robustly induced PD-L1 expression in wHILOs (FIGS. 12E and 12F). In particular, an approximately 20-fold increase in PD-L1 expression was observed 12 hours after IFNγ treatment. (FIG. 12F). Notably, IFNγ induced PD-L1 expression in wHILOs to similar levels in both insulin-expressing and insulin non-expressing cells (GFP+ and GFP- cells, respectively), (FIG. 5A). Subsequent dose-escalating studies in wHILOs identified maximum PD-L1 induction after a 2-hour, 10 ng/ml IFNγ exposure. (FIG. 12E). However, the induction was transient, with PD-L1 expression rapidly decreasing in the days following exposure to IFNγ (FIG. 5B). Because tolerance to inflammatory stimuli such as lipopolysaccharide has been associated with epigenetic changes, experiments were performed to investigate whether sequential IFNγ stimulation induced longer term or sustained effects in wHILOs, specifically, a sustained induction of PD-L1 in the HILOs. Indeed, it was discovered that repeated short exposures (intermittent exposure) to IFNγ (multiple pulse stimulation, "MPS") led to sustained PD-L1 expression and concomitant increases in PD-L1 protein levels (FIGS. 5C, 5D and 5E). Importantly, GSIS functionality was not compromised by exposure of the wHILOs to MPS IFNγ (FIG. 5F). Furthermore, MPS IFNγ-treated wHILOs were protected against IL-1β-induced β cell dedifferentiation, as revealed by the expression of the β cell identity markers INS and UCN3 (FIG. 5G and FIG. 5H).

Figure 14A:
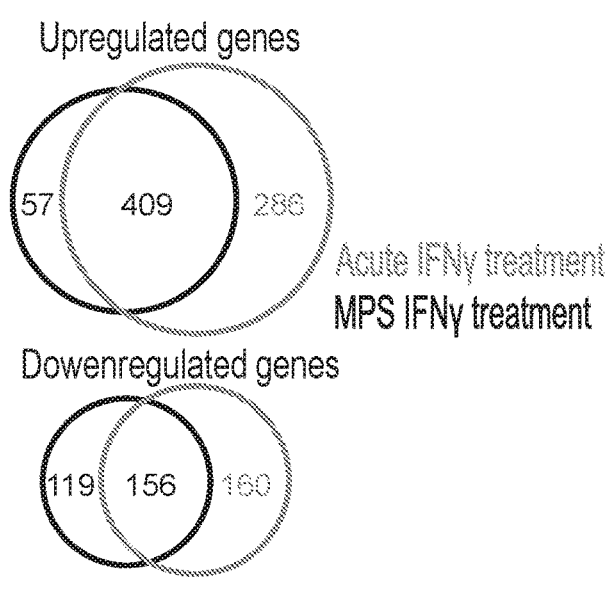
Figure 14B:
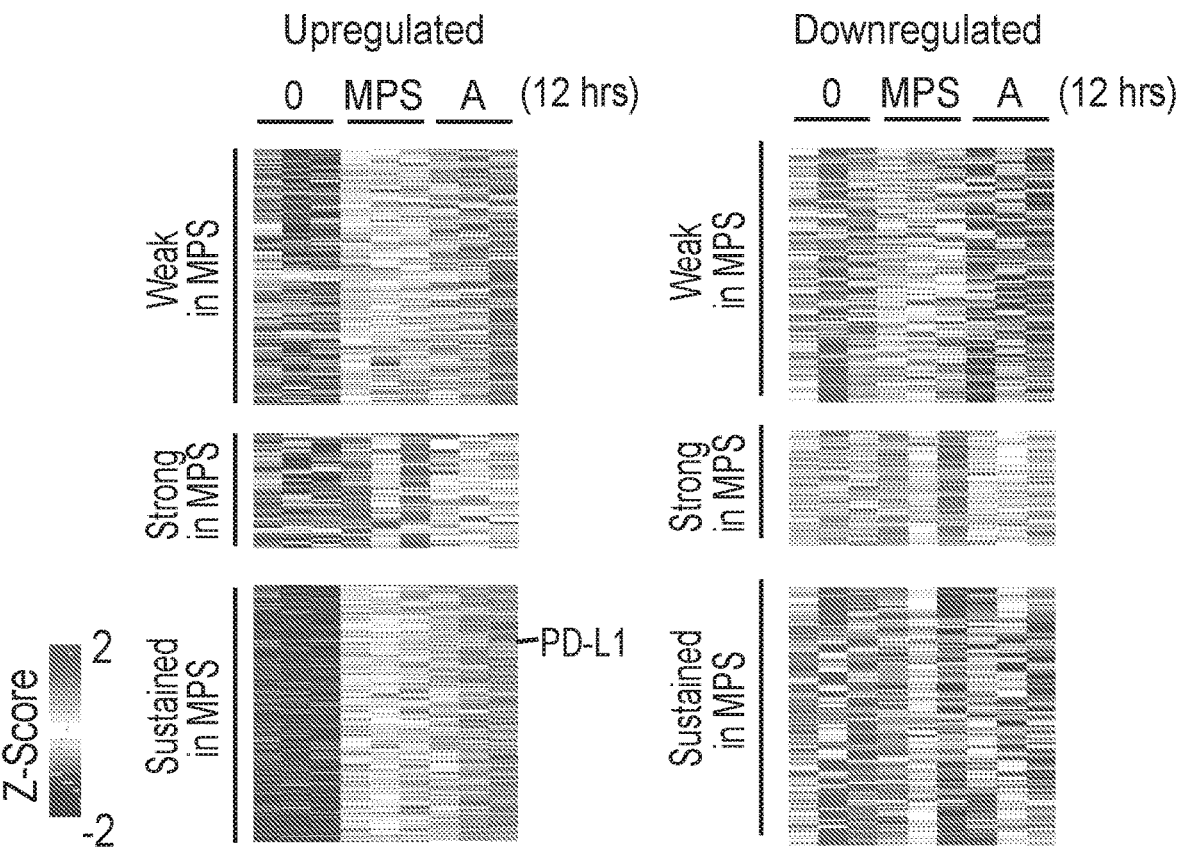
Figure 14C:
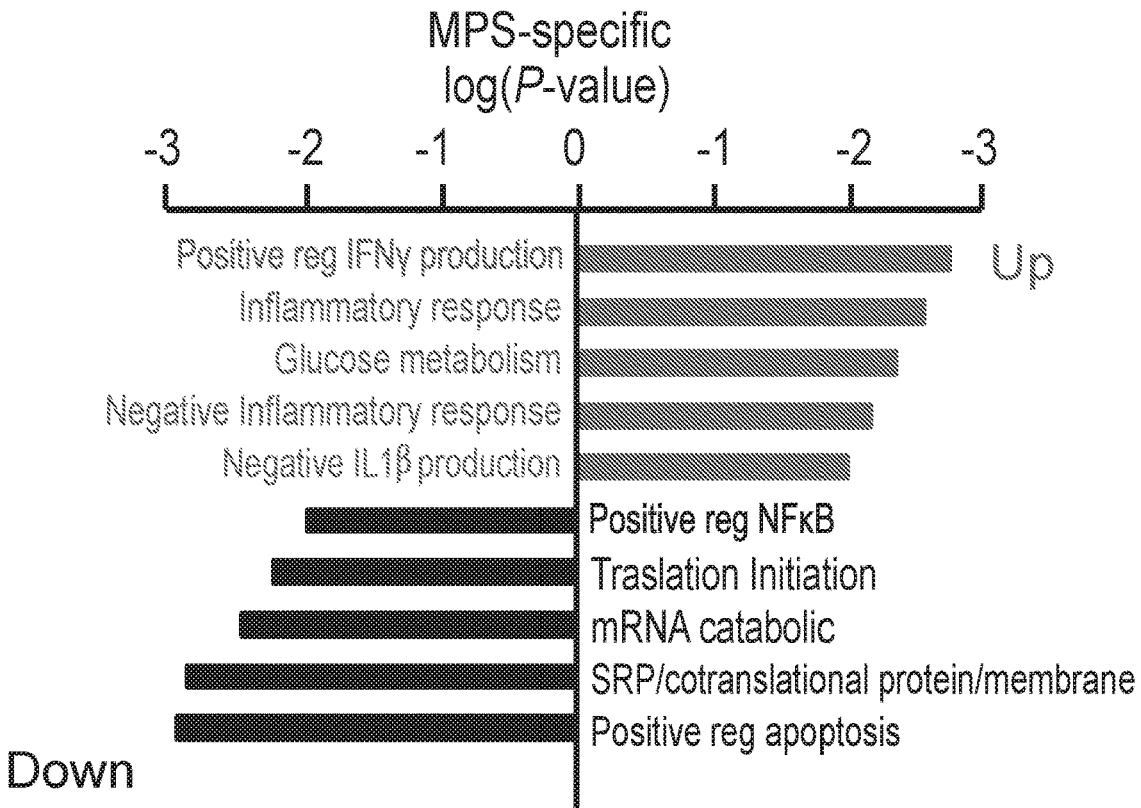
Figure 14C:
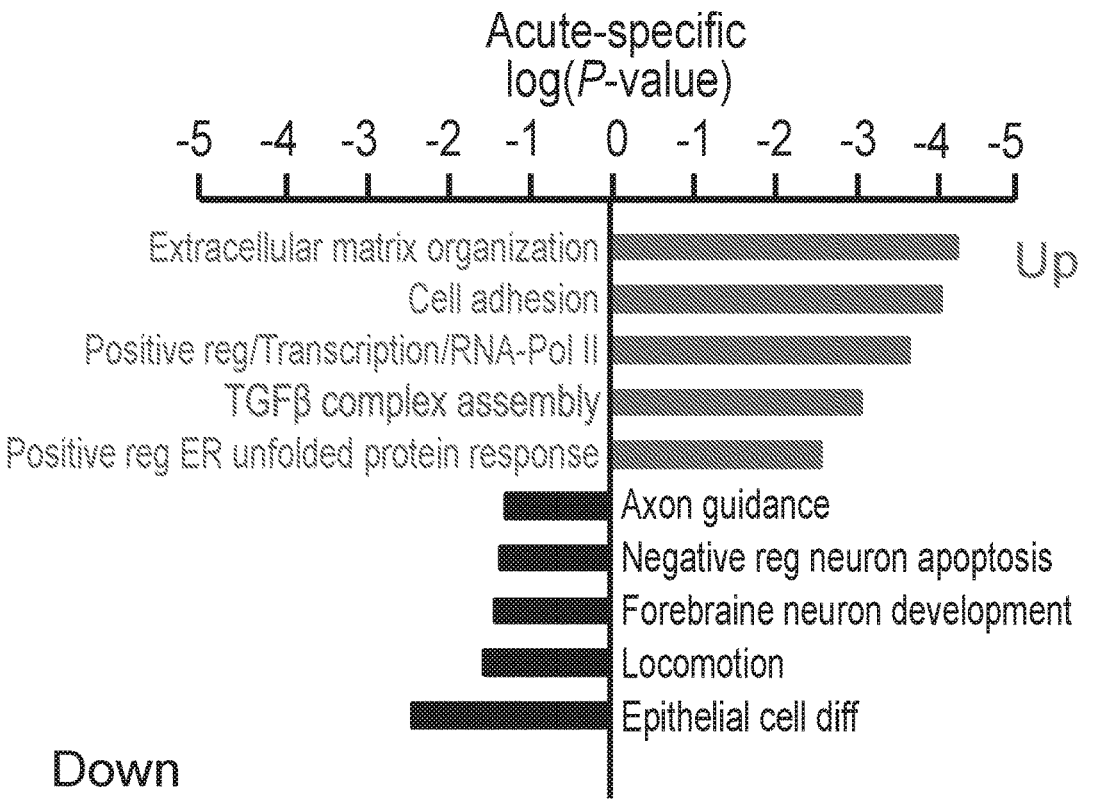

ATAC-Seq was used in studies to provide mechanistic insight into the IFNγ-driven changes in wHILOs. As measured by ATAC-Seq, the genome-wide transcriptional changes induced by acute (12 h exposure) and MPS treatments were associated with alterations in chromatin accessibility. Largely overlapping gene sets were induced by the IFNγ treatments that included PD-L1, while approximately half of the downregulated genes were commonly affected (FIG. 14A and FIG. 14B). Gene ontology of the commonly upregulated gene set identified IFNγ pathways (not shown). In contrast, pathways that reflect the cell inflammation status including negative regulation of IL-1ß production and inflammatory pathways were identified only in the MPS-upregulated gene set, while positive regulation of NFkB signaling and apoptosis were found selectively in the MPS-downregulated gene set (FIG. 14C). Overlaying changes in chromatin accessibility revealed persistent increases at gene loci including PD-L1, IRF9, JUNB, and JUND after MPS IFNγ treatment, in agreement with the sustained increases in gene transcript levels. In contrast, while increased accessibility was seen at known IFNγ-responsive genes, including IRF1 and STAT1, after the acute treatment, these increases were not sustained (FIG. 14D).

Figures 5I, 5J:
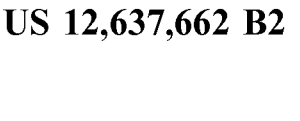
Figure 5K:
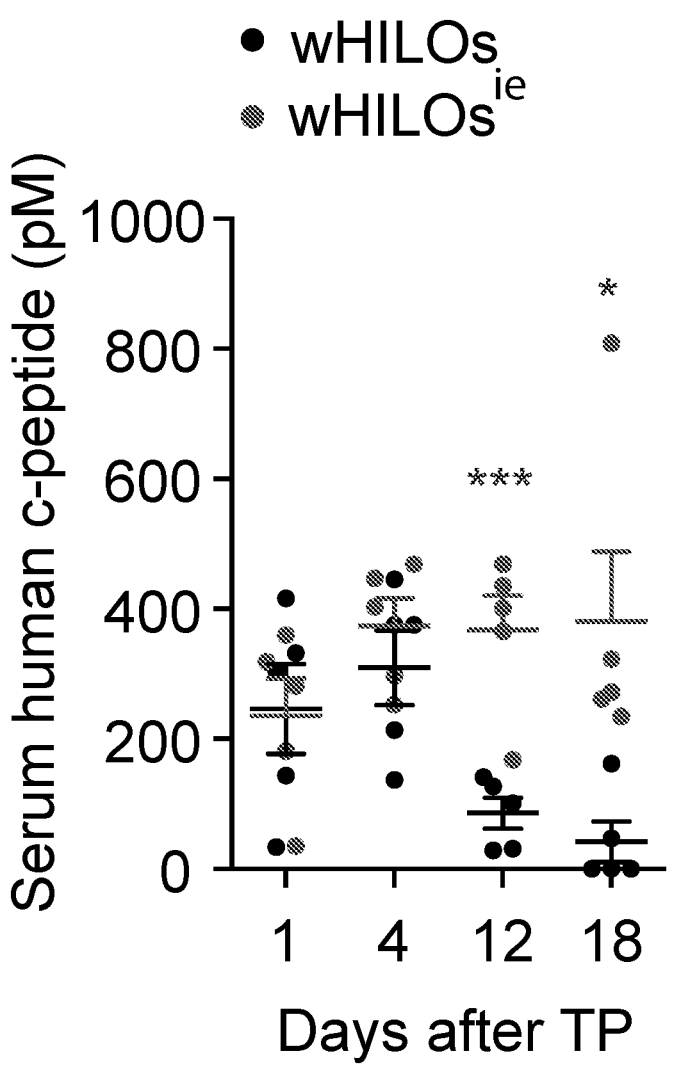
Figure 15A:
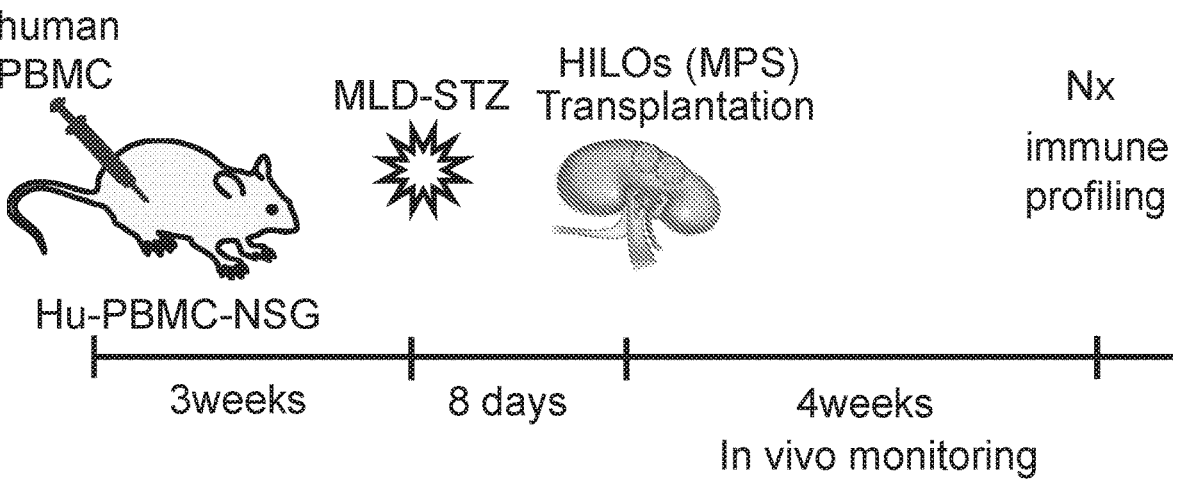
FIGS. 15A-15C present a schematic, graph and flow cytometry plots related to studies demonstrating the immune evasiveness of wHILOs by enhanced endogenous PD-L1 expression.
Figure 15B:
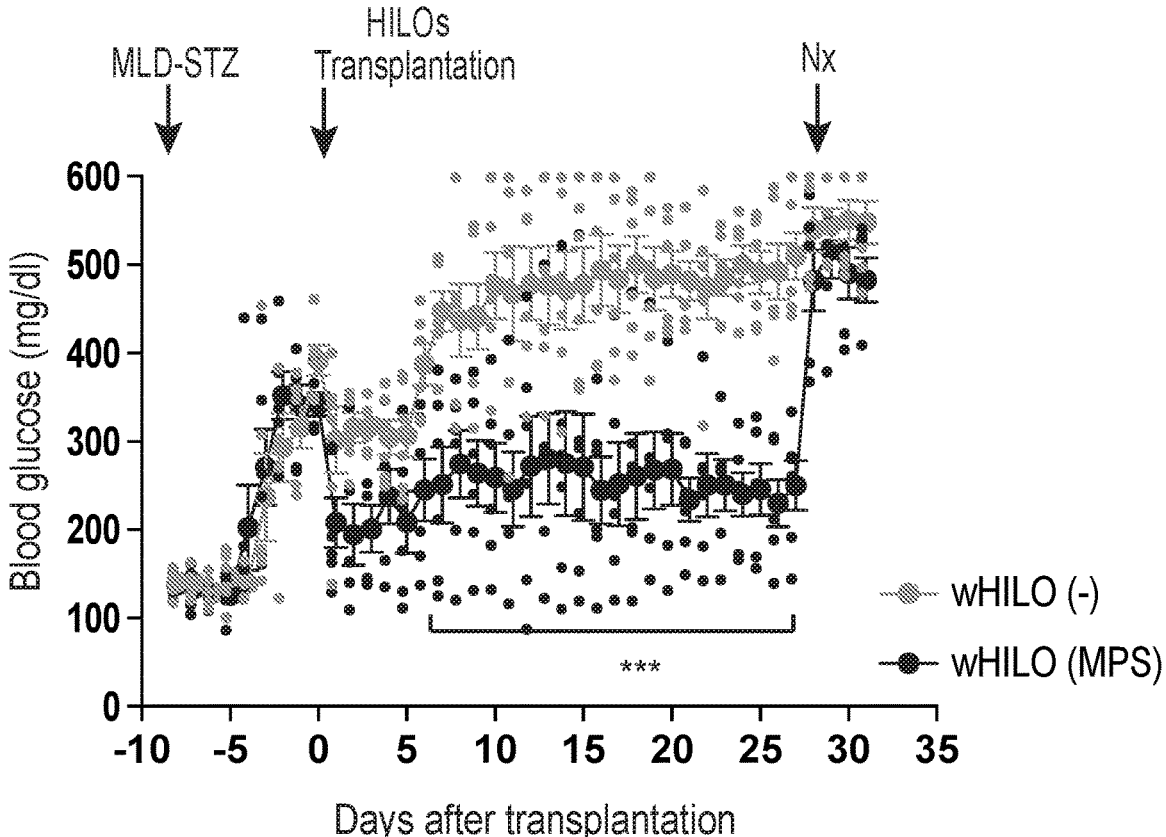
Figure 15C:
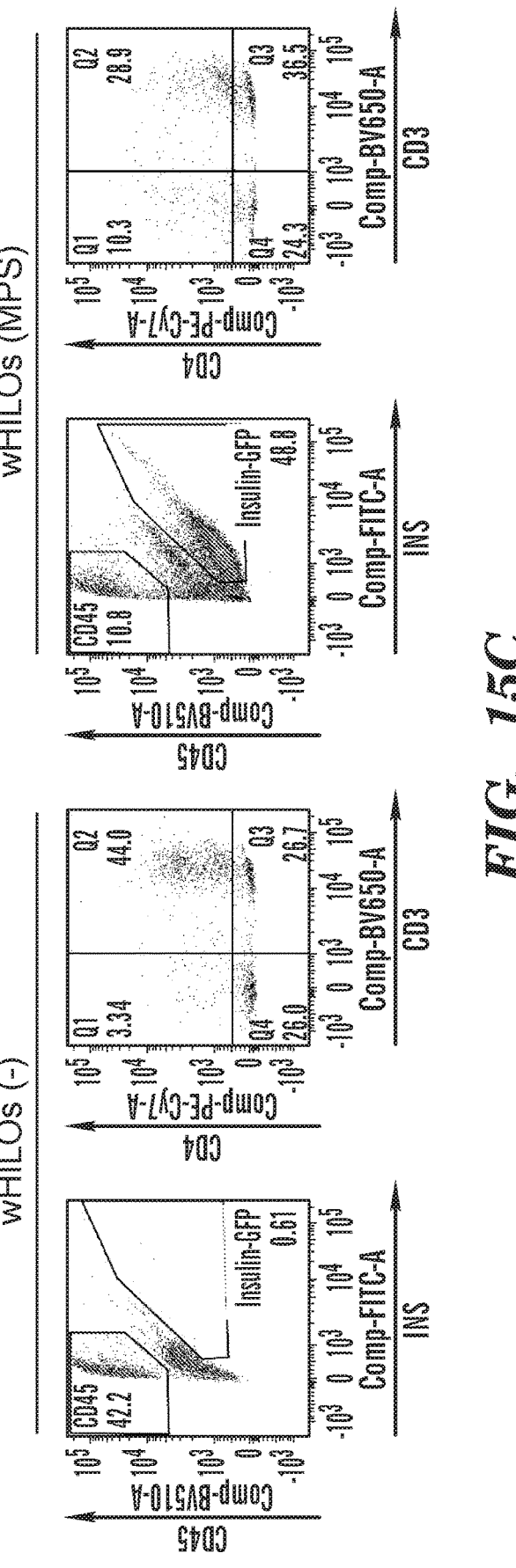

To confirm that IFNγ treatment generated immune evasive wHILOs (wHILO$^{ie}$), the ability of wHILO$^{ie}$ to provide long term glucose regulation in immune competent mice was assessed. Transplantation of wHILO$^{ie}$ into STZ-induced diabetic C56BL6J mice lowered blood glucose levels in the mice within days and maintained reduced levels for >40 days (FIG. 5I, FIG. 5J). In contrast, the efficacy of transplanted, naive wHILOs (no IFNγ exposure) progressively decreased, which was consistent with the reduced levels of human c-peptide observed in the serum of recipient mice (FIG. 5K). Similar results were found with transplantation into humanized diabetic mice. Notably, the reduced glucose levels achieved with wHILO (MPS treated) transplantation were lost upon surgical removal of the recipient kidney (FIGS. 15A and 15B). As support for the immunosuppressive role of IFNγ-induced PD-L1 in the transplanted wHILOs, reduced lymphocyte infiltration, as well as a decrease in the relative number of activated T helper cells (CD4$^+$CD3$^+$), were observed in the recovered grafts. Moreover, the number of insulin expressing cells was markedly increased in wHILO (MPS treated) grafts (FIG. 15C).

Without intending to be bound by theory, the results described herein suggest that prior IFNγ stimulation, namely, exposure of cells, such as wHILOs, to the MPS IFNγ protocol, induces an epigenetic memory that leads to cytokine tolerance and sustained de novo PD-L1 expression in wHILOs. Such IFNγ stimulated wHILOs (wHILO$^{ie}$) offer utility of as a therapy to alleviate diseases, such as pancreatic diseases, or insulin dependent diabetes, for example, type 1 or type 2 diabetes.

The findings, based on the above-described experiments, that wHILOs maintained functionality in NOD-SCID but not in C57BL6J mice implicates T cells and B cells in their allogenic rejection. During antigen presentation, interactions between cytotoxic T-lymphocyte antigen-4 (CTLA-4) and B7 molecules, as well as programmed cell death protein 1 (PD1) and its ligand PD-L1, negatively regulate immune responses in a non-redundant manner. The results of the experiments demonstrate that wHILOs that express PD-L1, such as by induction or overexpression as described herein, are protected from allogenic rejection. Furthermore, as described supra, a protocol is provided in which repeated exposure to limited IFNγ concentrations leads to sustained, endogenous PD-L1 expression without compromising glucose stimulated insulin secretion (GSIS) activity. Of note and unexpectedly, the resultant immune evasive HILOs described herein were able to maintain glucose homeostasis in immune-competent type 1 diabetic mice for ~50 days in the absence of a transplantation device. The immune evasive cells (such as in HILOs) that result from IFNγ exposure according to the method described herein not only exhibit metabolic and functional maturity, but they overcome auto-immune rejection of transplanted cells, which provides a solution to a general problem that exists for other stem cell-based therapeutics.

Example 9: Methods Used in the Above-Described Examples

Maintenance of Mouse Lines

Animals were maintained in a specific pathogen-free animal facility on a 12 hour light-dark cycle at an ambient temperature of 23° C. Water and food were provided ad libitum. Animal experiments used age- and background-matched male C57BL6J (Stock No 000664), NOD-SCID mice (NOD.Cg-Prkdcscid Il2rgtm1Wjl/SzJ, Stock No 005557), ß cell specific ERRγ knockout mice (Yoshihara, E. Pt al., 2016, Cell metabolism 23, 622-634, doi:10.2016r.c-met.2016.03.005), hu-PBMC-SGM3 mice, called 'humanized mice'. Female NSG™ mice were injected with human peripheral blood mononuclear cells (PBMCs) in NSG-SGM3 (Jackson 013062) strain) All procedures involving animals were performed in accordance with protocols approved by the IACUC and Animal Resources Department of the Salk Institute for Biological Studies.

Generation of Human Insulin Reporter and PD-L Overexpressing Human PSC Lines To mark β cell specification, human induced pluripotent stem cells (hiPSCs) derived from HUVECs were infected with a human insulin GFP reporter, as described by E. Yoshihara et al. (2016, Cell metabolism, 23:622-634). To visualize endogenous insulin promoter activity, CRISPR/Cas9 genome editing was used to knockin GFP into the insulin promoter (Tables 1 and 2).

TABLE 2

| NCBI or Primer Bank (PB) ID | Genes | Species | Primers (Forward) | Primers (Reverse) |
|---|---|---|---|---|
| NM_206594.2 | ESRRG (ERRy) | hu* | gctaacactgtcgcagtttga | cgaacagctggaatcaatgtg |
| 316659406c1 (PB) | NDUFA7 | hu | tgcagctacgctaccagga | ggaggctgagttcgcttgg |
| 103472000b1 (PB) | COX7A2 | hu | ctcggaggtagttccggttc | tctgcccaatctgacgaagag |
| 316659406c1 (PB) | NDUFA1 | hu | atgctccgccagatcatcg | tgccagacgcaagagatacag |
| NM_002509.4 | NKX2-2 | hu | ggccttcagtactccctgca | gggacttggagcttgagtcct |
| 115387113c1 (PB) | ISL1 | hu | gcggagtgtaatcag tatttgga | gcatttgatcccgtacaacct |

TABLE 2-continued

| NCBI or Primer Bank (PB) ID | Genes | Species* | Primers (Forward) | Primers (Reverse) |
|---|---|---|---|---|
| NM_005461.4 | MAFB | hu | gcctgcgctaattgtaggag | cgcacttgaaagttgcaaaa |
| NM_020783.3 | STY4 | hu | ttcaggacggggtgagttac | tttggcatggtacaggttca |
| NM_000162.3 | GlucoKinase | hu | gctggaatcaatttcccaga | ctccccacacaggatgagtt |
| NM_000207.2 | INSULIN | hu | agcctttgtgaaccaacacc | gctggtagagggagcagatg |
| NM_002054.4 | GLUCAGON | hu | aggcagacccactcagtga | aacaatggcgacctcttctg |
| NM_001048.3 | SOMATOSTATIN | hu | gtacttcttggcagagc tgctg | cagaagaaattcttgc agccag |
| NM_000209.3 | PDX-1 | hu | ggatgaagtctaccaaa gctcacgc | ccagatcttgatgtgt ctctcggtc |
| NM_201589 | MAFA | hu | cttcagcaaggaggag gtcatc | ctcgtatttctccttg tacaggtcc |
| NM_006168.2 | NKX6-1 | hu | attcgttggggatgacagag | tcaacagctgcgtgatttttc |
| NM_053049.3 | UCN3 | hu | gatgggcttggctttgtaga | ggagggaagtccactctgc |
| NM_002500.4 | NEUROD1 | hu | gttctcaggacgaggagcac | cttgggcttttgatcgtcat |
| NM_014143.3 | CD274 (PD-L1) | hu | tatggtggtgccgactacaa | tgcttgtccagatgacttcg |
| NM_001002.3 | U3664 (RPLP0) | hu/mo | gtgctgatgggcaagaac | aggtcctccttggtgaac |
| NM_021893.3 | CD274 (PD-L1) | mo | tgctgcataatcagctacgg | gctggtcacattgagaagca |
| NM_001243792.1 | Esrrg (ERR) | mo | gcaaggcattcttcaagagg | ggctgggcagctgtactcta |
| NM_009943.2 | COX6a2 | mo | ctctcgactgggtgaaggag | gaagagccagcacaaaggtc |
| NM_008618.3 | MDH1 | mo | gaagccctgaaagacgacag | tcgacacgaactctccctct |
| NM_153064.4 | NDUFS2 | mo | gatccgagtgctctttggag | atgtcatccagaagcccaag |

Species*: hu: human; mo: mouse

TABLE 3

| Sequence Name | Sequence | Vector |
|---|---|---|
| Human insulin guide 1 | GTGGTTGACGC TGTCCGTCA | pCas-Guide-EF1a-GFP vector (Origene 100018) |
| Human insulin guide 2 | CTGTTCGTCCT TCATCAAGA | pCas-Guide-EF1a-GFP vector (Origene 100018) |
| Left Arm | ATAAGACACAGTTATGCTT ATGGAAGCGTGCTGACAAA CAGTAATTACAGAGCTGAG GATCATCTGTTCAGTCTTG AAAATAAAAGTTTTATTCT GCTCATAATAAAATGATTG CAGCATCAGAATGAGGAAG GAAAGGTAGAATGAGGATA AATACAATTTTAGAAATGG TATAGACTTTGCAAATCAC CACCTCTTCCATTGATAAA TTTAGAATCTAGAGTTGAG TTAGATATTGACACTGGTT CTCCAAGAGAAAGGTAAAA | Luc-LoxP-PGK-Puro-LoxP |

TABLE 3-continued

| Sequence Name | Sequence | Vector |
|---|---|---|
|  | TAAAAGCAATCGGACTCTT TAGAGCTTTTGTTTATGGC CTGTCTGGGCCCTTTGTTG TAACCCTGTCATGCCCTTA TGCTGATTACCTTCTTGTA GAACAAGAAGTATTGACTA GAGAATGAATGATGTGTAG TCCCTAGCCCTTAGGAAAC TCTCTCAAAGAGCAATGTC TTTAACATATGAATTCTGT TTTTTTCCTCCTTTTACCT TTCCCTTTCCCTTTCTCTA TTTTTCACCATCTCTTTTG TTTCTACCTCTTTTGGTCT CTGTGCTTGACACTCTCTC CTCTTTCTGTCTCTCTTTG TATCTCCTCAATCTCAGGC TTCTCTGCAGA |  |
| Right Arm | CTGGTGGCTCTTCAGACGC CAGTGGGAGCTACAGTTCA ACCATGAATGGCCATCAGA ACGGACTTGACTCGCCACC TCTCTACCCTTCTGCTCCT ATCCTGGGAGGTAGTGGGC CTGTCAGGAAACTGTATGA TGACTGCTCCAGCACCATT GTTGAAGATCCCCAGACCA |  |

TABLE 3-continued

| Sequence Name | Sequence | Vector |
|---|---|---|
| | AGTGTGAATACATGCTCAA | |
| | CTCGATGCCCAAGAGACTG | |
| | TGTTTAGTGTGTGGTGACA | |
| | TCGCTTCTGGGTACCACTA | |
| | TGGGGTAGCATCATGTGAA | |
| | GCCTGCAAGGCATTCTTCA | |
| | AGAGGACAATTCAAGGTTA | |
| | GTGTCGGACCTGGGAATAC | |
| | TCTCCCCACTTCCAACCTC | |
| | ACATGATGGGTTTTTGTTT | |
| | TTCCTTATTCTTATTCTCA | |
| | TAAGTCAAGTATCATAGTT | |
| | TTAATTCTCTCTTGAGTAG | |
| | AAAATGGAAATAGATTACA | |
| | ATTGATAGTGGAAGATTTA | |
| | TAGAATAAAATCCCCCCAG | |
| | ATATACTCCATATCTATTA | |
| | ATTTTCCTCTTACTGTTAA | |
| | GCTTTAATGGTGCAAGGAT | |
| | AATAAACTTTGGGTAGAGT | |
| | TTACAAGAGCATAGTTATT | |
| | ATTAGAGCAATGTGGGTCT | |
| | ATATAGCAACT | |

PD-L1 expressing hiPSCs were generated by infecting hiPSCs with a lentivirus (abm, LV113090) encoding human CD274 (PD-L1) with puromycin selection (Table 4). The human UCN3 proximal promoter sequence (−1298/+103) was introduced by In-Fusion cloning (Clonetech) into the promoterless pLV-Cherry-Picker1 backbone (Clontech, 632574) using the ApaI/NotI restriction enzyme sites. Primer sequences for PCR amplification of the promoter sequence from genomic DNA were 5'-GTCCATGCTGATC-CATCCTT-3' (forward) and 5'-TGCTTCTCCGGTAT-TGTTCC-3' (reverse). A dual reporter line for human UCN3 mcherry and human insulin GFP (hINS-GFP-EF1α-Neo), Yoshihara et al., Ibid., was generated in hiPSC.

TABLE 4

Plasmid Information

| System | Name (Donor)/ Catalog # | Spe-cies | Char-acter | Sequence Primer Fw/Rv |
|---|---|---|---|---|
| Lentivirus | CD274 (PD-L1) Lentivirus Vector/ (abm LV113090) | human | Over-expres-sion | |
| Lentivirus | UCN3-Cherry reporter | human | mCherry reporter | 5'-GTCCA TGCTGATC CATCCTT-3' (forward) 5'-TGCTTC TCCGGTATT GTTCC-3' (reverse) |

Virus Production

Lentiviruses were produced using second- or third-generation lentiviral systems in HEK293T cell line using methods as described herein (e.g., Example 10 methods) and as known and practiced by those skilled in the art.

3D Gellan Gum (3 DKG) Culture Medium

Aqueous solutions of low acyl gellan gum (Kelcogel F GG-LA), (Modernist pantry), 0.3% w/v, were sterilized by autoclaving prior to dilution in mTeSR1 or Custom TeSR medium (StemCell Technologies, final concentration 0.015%) and the addition of methylcellulose (R&D systems, final concentration 0.3%) and penicillin/streptozocin.

More specifically, by way of example, Kelcogel F low acyl GG GG-LA (Modernist pantry) was suspended in pure water 0.3% (w/v) and dissolved by stirring at 90° C. or by microwave. The aqueous solution was sterilized at 121° C. for 20 minutes in an autoclave. The solution was added to TeSR or Custam TeSR at a final concentration of 0.015%. Methylcellulose (MC) stock solution was added to a final concentration of 0.3% (R&D systems) (e.g., 0.3% Kelcogel stock; Kelcogel F low acyl GG GG-LA 300 mg+MilliQ water 100 ml: 3 DKG Stem TeSR Base Medium; Stem TeSR 95 ml+0.3% Kelcogel 5 ml+MC stock solution 300 μl. A 1% final concentration of Penicillin/streptozocin was added for 3 DKG Stem TeSR.

Human Multicellular Spheroids (MCSs)

Pancreatic endocrine (PE) cells were prepared from human iPSC as described in the publication of Yoshihara, E. et al. (2016, Cell Metabolism, 23(4):622-634). In brief, HUVEC-derived hiPSC, obtained from the Salk Stem Cell Core Facility, were maintained on matrigel (BD)-coated dishes in complete Stem TeSR Medium at 37° C. in a humidified 5% $CO_2$ incubator. Prior to pancreatic differentiation, hiPSC were infected with a human insulin reporter lentivirus (pGreenZero lenti reporter human insulin, System Biosciences) by Spinfection (800 g, 1 hour), and then the cell medium was changed to 100 ng/ml human Activin (R&D Systems), 3 μM CHIR99021 (Selleckchem) in differentiation medium (800 ml DMEM/F12, 13.28 g BSA, 10 ml Glutamax, 560 mg $NaHCO_3$, 330 mg thiamine, 100 mg reduced glutathione, 3300 mg Vitamin C, 14 μg Selenium, 10 ml NEAA, 2 ml Trace Element B, 1 ml Trace Element C, 7μ 1 β-ME, 2 ml DLC, 2 ml GABA, 2 ml LiCl, 129.7 μg PA, Insulin 2 mg, made up to 1000 ml) for 2 days, and then the cells were maintained in 100 ng/ml human Activin in differentiation medium for another 2 days (Stage 1, Pancreatic Endoderm). Subsequently, this medium was replaced with differentiation medium containing 1p M dorsomorphin (Calbiochem), 2 μM Retinoic Acid (Sigma), 10 μM SB431542 and 1% of B27 supplement for 7 days (Stage 2). The medium was then replaced with differentiation medium containing 10 μM forskolin (Sigma), 10 μM dexamethasone (Stemgent), 10 μM TGFβ RI Kinase inhibitor II/Alk5 inhibitor II (Calbiochem or Enzo), 10 μM Nicotinamide (Sigma), 1 μM 3,3',5-Triiodo-L-thyronine sodium salt (T3) and 1% of B27 supplement for 4-5 days (day15-day19, Pancreatic endocrine progenitors developed). The medium was replaced every day (stage 1), and then every other day (stage 2 and stage 3).

Primary HUVEC cells and human adipose-derived stem cells (hADSC) (Invitrogen or PromoCell) were cultured in 15 cm dishes with EBM Media (Lonza, cc-3121) or MesenProRS Media (GIBCO, 12747-010 or Preadipocyte Growth Medium Kit, C-27417), respectively, at 37° C. in a humidified 5% $CO_2$ incubator. For co-culturing experiments, pancreatic endocrine progenitors derived from human iPSC were treated with Accutase, while HUVECs and hADSC were treated with TrypLE (GIBCO, 12604-013). Cells were collected into 50 ml tubes. hiPSC-EP ($1 \times 10^6$ cells), HUVECs ($7 \times 10^6$ cells) and hADSCs ($1$-$2 \times 10^5$ cells) were co-cultured in a single well of a 24 well plate with 300 μl of matrigel.

For MCS generation, hiPSC-EP (day15-day21, $1 \times 10^6$ cells), HUVECs ($7 \times 10^6$ cells) and hADSCs ($1$-$2 \times 10^5$ cells) were co-cultured in 3D Kelco Gel Custom TeSR with 10 μM forskolin (Sigma), 10 µM dexamethasone (Stemgent), 10 µM TGFβ RI Kinase inhibitor II/Alk5 inhibitor II (Calbiochem or Enzo), 10 µM Nicotinamide (Sigma), 1 µM 3,3',5-Triiodo-L-thyronine sodium salt (T3) and 1% of B27 supplement, R428 (2 µM), Zinc sulfate (10 µM) and N-Cys (1 mM). The medium was changed every other day, and islet-like clusters formed within a few days. (FIGS. 6A-6F).

Human Pancreatic Islet-Like Organoid (HILO) Cultures hiPSCs were cultured in matrigel-coated plates. Single cell suspensions were prepared using Accutase, washed in PBS, and collected by centrifugation (1000-1300 rpm for 5 min). Cells were re-suspended with 3D Kelco Gel Stem TeSR™ Base Medium in the presence of the ROCK inhibitor (10 µM Y-27632, StemCell) for 5 to 7 days until spheroids reached 50-100 µm diameter. The medium was then replaced with 0.015% Kelco gel containing 0.3% methylcellulose and supplemented with 100 ng/ml human Activin A (R&D Systems), 3 µM CHIR99021 (Axon or Selleckchem) in differentiation medium (S1) for 1 day, and then 100 ng/ml human Activin in differentiation medium (S1) for another 2 days (Stage 1, Definitive Endoderm). Subsequently, the medium was replaced with differentiation medium (S2) with 50 ng/ml FGF7 (R&D Systems) for 2 days, differentiation medium (S3) with 50 ng/ml FGF7, 0.25 µM SANT-1 (Sigma), 1 µM Retinoic Acid (Sigma), 100 nM LDN193189, 10 µM Alk5 inhibitor II and 200 nM of the ß-Amyloid Precursor Protein modulator TPB for 3 days, then 50 ng/ml FGF7, 0.25 µM SANT-1 (Sigma), 1 µM Retinoic Acid (Sigma), 100 nM LDN193189, 10 µM Alk5 inhibitor II and 100 nM of the ß-Amyloid Precursor Protein modulator TPB for 2 days. Subsequently the medium was replaced with differentiation medium (S4) with 0.25 µM SANT-1, 50 nM retinoic acid, 100 nM LDN193189, 10 µM Alk5 inhibitor II, 1 µM T3 for 3 days. Subsequently, the medium was replaced with differentiation medium (S5) with 100 nM LDN193189, 100 nM 7-secretase inhibitor XX (GSiXX, Millipore), 10 µM Alk5 inhibitor IL, 1 µM T3 for 7 days. Subsequently, the medium was replaced with differentiation media (S5) with 10 µM Trolox (Calbiochem), 2 µM R428 (Selleckchem), 1 mM N-acetyl cysteine, 10 µM Alk5 inhibitor II, 1 µM T3 for an additional 7 to 20 days. After confirmation of insulin expression by qPCR or reporter activity (typically days 20-30), the medium was changed to differentiation medium (S5) with 10 µM Trolox (Calbiochem), 2 µM R428 (Selleckchem), 1 mM N-acetyl cysteine, 10 µM Alk5 inhibitor II, 1 µM T3 and 100 ng/ml rhWnt4 (R&D Systems) with or without the addition of laminins (LM-511/521 and LM-411/421) for 5-10 days.

WNT5A Conditional Medium

WNT5A-producing fibroblasts (ATCC CRL-2814) and control fibroblasts (ATCC CRL-2648) were cultured in DMEM containing 10% FBS and 1% penicillin/Streptomycin (Complete Medium). Upon reaching confluency, cells were washed with PBS prior to incubation in Complete Medium for one week. Conditioned medium was subsequently collected, filtered through a 0.2 µm sterile filter, and frozen at −80° C. in 50 ml aliquots. Conditioned medium was mixed with Differentiation Medium (S5 with 10 µM Trolox, 2 µM R428, 1 mM N-acetyl cysteine, 10 µM Alk5 inhibitor IL, 1 µM T3) at a 1:1 ratio, and then was used to treat HILOs for 5-10 days.

PD-L1 Induction in Human Islets and wHILOs

PD-L1 expression was induced by recombinant human IFNγ (R&D Systems, 285-IF, 2-12 hours treatment at 1-50 ng/ml final concentration). For acute treatment, wHILOs were treated with 10 ng/ml IFNγ in the differentiation medium (S5 with 10 µM Trolox, 2 µM R428, 1 mM N-acetyl cysteine, 10 µM Alk5 inhibitor II, 1 µM T3 and 100 ng/ml rhWnt4 (recombinant human Wnt4)) for 2 hours. Cells were then washed twice with PBS prior to culturing in differentiation medium (S5 with 10 µM Trolox, 2 µM R428, 1 mM N-acetyl cysteine, 10 µM Alk5 inhibitor II, 1 µM T3 and 100 ng/ml rhWnt4) (single pulse stimulation). IFNγ exposure was repeated 3 times with washing and 24 hours resting time in differentiation medium (S5 with 10 µM Trolox, 2 µM R428, 1 mM N-acetyl cysteine, 10 µM Alk5 inhibitor II, 1 µM T3 and 100 ng/ml rhWnt4) between each IFNγ exposure (MPS stimulation) to generate wHILO[ie]. After the final IFNγ pulse, cells were cultured in the tissue culture incubator for a week prior to the RNA-seq analyses (FIGS. 14A-14C), ATAC-seq analyses (FIG. 14D) and transplantation into STZ-induced diabetic C57BL6J mice (FIG. 5J) or humanized mice (FIG. 15B).

Isolation of Pancreatic Islets

Mouse pancreatic islets were isolated as previously described by E. Yoshihara et al., 2010, Nature communications, 1:127, with slight modifications. Briefly, 0.5 mg/ml collagenase P (Roche REF11213873001, diluted in HBSS buffer, GIBCO, 14170-112) was injected through the common bile duct, and the perfused pancreas was dissected and incubated at 37° C. for 21 minutes. Digested exocrine cells and intact islets were separated via centrifugation over Histopaque-1077 (Sigma, H8889) at 900×g for 15 minutes, and intact islets were manually selected. Human islets were provided by the Integrated Islets Distribution Program under an approved protocol.

Insulin/c-Peptide Secretion Assays

Insulin release from intact islets was monitored using batch incubation methods as reported by E. Yoshihara et al., 2016, Cell metabolism, 23:622-634. Briefly, overnight-cultured, isolated pancreatic islets (RPMI-1640 medium supplemented with 10% (v/v) fetal bovine serum and 1% (v/v) Antibiotic-Antimycotic (Gibco)) were pre-cultured at 37° C. for 30 minutes in Krebs-Ringer bicarbonate buffer (KRBB) containing 129.4 mM NaCl, 3.7 mM KCl, 2.7 mM CaCl₂), 1.3 mM KH₂PO₄, 1.3 mM MgSO₄, 24.8 mM NaHCO₃ (equilibrated with 5% CO₂, 95% O₂, pH 7.4), 10 mM HEPES and 0.2% (v/v) BSA (fraction V, Sigma) (KRBH) with 3 mM glucose). Pancreatic islets were incubated in Krebs-Ringer bicarbonate HEPES (KRBH) buffer (500 µl/10 islets) with 3 mM or 20 mM glucose for 30 minutes to determine insulin secretion levels. After 30 minutes, the islets were pelleted by centrifugation and secreted insulin levels were determined in the medium by Enzyme Linked Immunosorbent Assay (ELISA), (Rat/mouse Insulin ELISA KIT (Millipore) and Human Insulin ELISA KIT or ultrasensitive human c-peptide ELISA Kit (Millipore) for mouse and human islets, respectively). For human iPSC derived cells, the cells (1×10⁶ cells/well in 24 well culture plates) were pre-cultured in 3 mM glucose KRBH buffer (500 µl/well). The cells were then incubated in KRBB (200 µl/well) with 3 mM or 20 mM glucose for 30 minutes to determine c-peptide secretion levels as an indicator of insulin secretion levels. After 30 minutes, the cells were pelleted by centrifugation and c-peptide levels were determined in the supernatant medium using the human c-peptide ELISA KIT (Millipore). (e.g., FIGS. 7D-1 and 7D-2).

Oxygen Consumption and Extracellular Acidifcation Rates

Oxygen consumption rate (OCR) and extracellular acidification rate (ECAR) (e.g., of islets) were recorded in 24-well plates using an XF24 sea horse (Seahorse Biosciences). (FIG. 7C). Briefly, 70 size matched, human islets, hiPSC spheroids, or HILOs were pre-cultured in 3 mM glucose XF DMEM medium (pH 7.4) supplemented to contain 1 mM sodium pyruvate (Base Medium) for 1 hour prior to transfer to XF24 islet culture plates in Base Medium. OCRs (reported as percent change compared to 3 mM glucose) were recorded during the incremental addition of glucose, up to a final concentration of 20 mM glucose. Subsequently, mitochondrial stress reagents (oligomycin, Fccp, Rotenone, and Antimycin A), were added as instructed in the Mitostress Kit (Seahorse Biosciences).

Islet and HILO Transplantation Studies

Immunodeficient NOD-SCID, C57BL6J and Hu-PBMC-SGM3 mice were purchased from Jackson Laboratory and maintained in autoclaved cages in a SPF facility at the Salk Institute. Mice were rendered diabetic by a single high dose (180 mg/kg) injection or 5 times with a multi low dose (MLD, 50 mg/kg) injection of streptozotocin (STZ; i.p., Sigma S0130-500MG). One week after the STZ injection, mice with blood glucose levels higher than 300 mg/dl were used as transplant recipients. Human and mouse islets (200-500 islets or 500-1,000 IEQ for mouse islets, 500-1,000 islets or 1,000-2,000 IEQ for human islets per animal) or HILOs (500 clusters) were resuspended in 200 μl RPMI-1640 medium, loaded into laboratory tubing (SiLastic, 508-004), and centrifuged (400×g for 1-2 minutes) to generate cell clusters in the center of the tubing. Cell clusters were transplanted (approximately 30-50 μl) under the kidney capsules in 8 to 16-week-old STZ-injected diabetic mice. Ketamine (80 mg/kg) and xylazine (10 mg/kg) were used as surgical anesthetics, and mice were placed on 37° C. heating pads to recover. Blood glucose levels were monitored by using a commercially available blood glucose/ketone monitor (Nova Max Plus). Nephrectomy (Nx) for graft removal experiments were carried out to confirm the efficacy for glucose regulation in the transplanted wHILOs. The kidney with graft was ligated at the renal hilum using 4-0 silk (LOOK, SP116), and then was resected. Removed grafts were processed for analyses of immune profiling.

ATAC-Seq

ATAC-seq was performed on 5×10$^4$ GFP-positive (GFP+) cells isolated using Fluorescence Activated Cell Sorting (FACS) from HILOs treated with PBS or with 100 ng/ml rhWnt4 from day 27 to day 34 as described in J. D. Buenrostro et al., 2015, *Current Protocols in Molecular Biology*, 109:21-29. Reads were aligned by Bowtie to hg19, and peaks were called by HOMER using default settings. Differential peaks and motif analyses from 2 biological duplicates were identified using HOMER essentially as instructed (see, e.g., S. Heinz et al., 2010, *J. Mol. Cell*, 38:576-589). Detailed methods for HOMER are freely available, e.g., at http://http://homer.salk.edu/homer/. Briefly, the program searches against the target and background sequences for enrichment of known motifs, and returns motifs enriched with a threshold of 1.5-fold change and a p-value of less than 0.05. Promoter regions, defined as 1 kilobase (kB) upstream from the transcription start site, of genes with enhanced chromatin accessibility upon Wnt4 treatment, were interrogated for enriched motifs of 8-16 bp using HOMER motif analysis.

Bulk RNA-Seq Library Generation

Total RNA was isolated from cell pellets treated with RNAlater (Invitrogen) using the RNeasy micro kit (Qiagen) and treated with DNaseI (Qiagen) for 30 minutes at room temperature. Sequencing libraries were prepared from 100-500 ng total RNA using the TruSeq RNA Sample Preparation Kit v2 (Illumina) according to the manufacturer's protocol. Briefly, mRNA was purified, fragmented, and used for first- and second-strand cDNA synthesis followed by adenylation of 3' ends. Samples were ligated to unique adapters and PCR amplified. Libraries were then validated using the 2100 BioAnalyzer (Agilent), normalized and pooled for sequencing.

High-Throughput Sequencing and Analysis

RNA-Seq libraries prepared from 3 biological replicates for each experimental condition were sequenced on the Illumina HiSeq 2500 using bar-coded multiplexing and a 100 bp read length. Image analysis and base calling were automatically generated with the Illumina HiSeq Real-Time Analysis Software. This yielded a median of 29.9M usable reads per sample. Short read sequences were mapped to a UCSC hg19 reference sequence using the RNA-Seq aligner STAR (A. Dobin et al., 2013, *Bioinformatics*, 29:15-21). Known splice junctions from hg19 were supplied to the aligner and de novo junction discovery was also permitted. Differential gene expression analysis, statistical testing and annotation were performed using Cuffdiff 2 (C. Trapnell et al., 2013, *Nature Biotechnology*, 31:46-53). Transcript expression was calculated as gene-level relative abundance in fragments per kilobase of exon model per million (fpkm) mapped fragments and employed correction for transcript abundance bias (A. Roberts et al., 2011, *Bioinformatics*, 27:2325-2329). RNA-Seq results for genes of interest were also explored visually using the UCSC Genome Browser. Heatmaps were generated by R-Script with heatmap.2 (gplot) software or Cluster with Javatree view software. Scale of heatmaps was determined by Z-score (FIG. 2A, FIG. 3D and FIG. 3G).

Droplet-Based Single-Cell RNA Sequence

Three biological replicates (200 clusters per replicate) of hiPSC-derived endocrine progenitor cells (day15), HILOs, and WNT4-treated HILOs (100 ng/ml rhWNT4 for 5 days), as well as human islets (IIDP donor ID 1874), were dissociated into single cell suspensions using TrypLE. Single cells were processed through the Chromium Single Cell Platform using the GemCode Gel Bead, Chip and Library Kits (10× Genomics) as per the manufacturer's protocol. In brief, 8,800 single cells were sorted into 0.4% BSA in PBS for a targeted 5000 cell recovery. Cells were transferred into Gel Beads (Chromium Single Cell 3" v2) in Emulsion in the Chromium instrument, where cell lysis and barcoded reverse transcription of RNA was carried out, followed by amplification, shearing and 5' adaptor and sample index attachment. Libraries were sequenced on an Illumina HiSeq 4000 instrument.

scRNA-Seq Data Analysis

Initial data processing, including de-multiplexing, alignment to the GRCh38 transcriptome and unique molecular identifier (UMI)-collapsing, were performed using Cell Ranger software (10× Genomics, ver2.0.2). An overview of single cell sample information was generated from the results of Cell Ranger pipelines. R studio (https:www.rstudio.com), Cell Ranger R Kit, Seurat, monocle and other custom R scripts were used. For the identification of cell types, the cluster cell function of monocle was used. (FIG. 4B). Clustering of cells was performed using the Seurat R package in two iterative rounds of principal component analysis.

Cells having unique gene counts less than 200 were removed (FilterCells function) prior to normalization of digital gene expression matrices by total expression, multipled by a scale factor (default setting of 10,000) and log-transformed (NormalizeData function). A set of variable genes was then identified by binning the average expression of all genes and dispersion (variance divided by the mean) for each gene, placing these genes into bins, and then calculating z-score for dispersion within each bin (FindVariableGenes Function). Linear dimensional reduction was performed using the default setting of RunPCA, and the principal components were evaluated for statistically significant gene expression signals using the Jackstraw method (JackStraw function, not shown). At most, 12 principal components were used in this second round of clustering. t-distributed stochastic neighbor embedding (t-SNE) mapping was used to visualize scRNA-seq results.

Clustered cell populations were classified, and the top10 differentially expressed genes were identified (FindAllMarkers function). Cell types within the clustered cell populations were verified by examining the expression of canonical marker genes, including insulin (β-cells), glucagon (α-cells), somatostain (δ-cells), pancreatic polypeptide (γ-cells), ghrelin (ε-cells), Prss1 (aciner cells), Krt19 (duct cells) and Acta2 (stellate cells). (FIGS. 2D, 2E, FIG. 4A and FIGS. 6D-6F).

scRNA-seq data from WNT4-treated HILOs (4,840 cells) and human islets (7,248 cells) were combined in 1 Seurat object, and the highly variable genes were identified as described above. Cell types within the clustered populations were identified by reference to differentially expressed genes in human islet cells. The β-cell populations identified in WNT4-treated HILOs and human islets were compared to identify differentially expressed genes. (FIGS. 10A-10C; FIGS. 11A-11D).

Software and Program for Bioinformatics Analysis

The following software or programs were used for genomic data analysis: R studio (https://www.rstudio.com/); Cell Ranger R Kit (https://support.10xgenomics.com/single-cell-gene-expression/software/pipelines/latest/rkit); Seurat (https://satijalab.org/seurat/); Monocle (http://cole-trapnell-lab.github.io/monocle-release/); DAVID (https://david.ncifcrf.gov/home.jsp); GOplot (https://wencke.github.io); UCSC genome browser (http://genome.ucsc.edu); and Homer (http://homer.ucsd.edu/homer/).

Immunohistochemistry (IHC)

Immunohistochemistry (IHC) of frozen or paraffin-embedded sections of pancreas and human islets or iβeta cells in the kidney capsule (4% PFA-fixed cells) was performed using antibodies to insulin (anti-Insulin antibody, 1/100, Abcam ab7842)), c-peptide (anti-c-peptide antibody, 1/100, Abcam ab30477), glucagon (anti-glucagon antibody, 1/100, Abcam ab10988), somatostatin (anti-somatostatin antibody, 1/100, Abcam ab103790), pancreatic polypeptide (anti-pancreatic polypeptide antibody, 1/100, Abcam, ab113694), NKX2-2 (anti-NKX2-2 antibody, 1/100, DSHB, 74.5A5), NKX6-1 (anti-NKX6-1 antibody, 1/100, DSHB, F55A12), MAFA (anti-MAFA antibody, 1/100, Abcam, ab26405), MAFB (anti-MAFB antibody, 1/100, Abcam, ab26405), PDX-1 (anti-PDX-1 antibody, 1/100, R&D, AF2419), CHGA (anti-CHGA antibody, 1/100, Abcam, ab15160), Synaptophysin (anti-Synaptophysin antibody, 1/100, Biogenex, MU363-UC) and PD-L1 (anti-PD-L1 antibody, 1/100, Abcam, ab20592), (Table 5). Secondary antibodies were coupled to Alexa 568, 647 (Life Technologies), and IHC staining was visualized by confocal microscopy (ZEISS) or fluorescence microscopy. Hoechst 33342 (Thermo Scientific, 62249, 1 µg/ml final concentration) was used for nuclear staining.

TABLE 5

| Antibody (Ab) Name | Species* | Host | Ab Type | Applications | Source/ Company | Catalog ID |
|---|---|---|---|---|---|---|
| Insulin | H, M, R | Guinea pig | Polyclonal | IHC | abcam | ab7842 |
| c-peptide | H, M | Guinea pig | Polyclonal | IHC | abcam | ab30477 |
| Glucagon | H, M, R | Mouse | Monoclonal | IHC | abcam | ab10988 |
| Somatostatin | H, M, R | Rabbit | Polyclonal | IHC | abcam | ab103790 |
| Insulin | H, M, R | Guinea pig | Polyclonal | IHC | abcam | ab7842 |
| Pancreatic Polypeptide | H | Rabbit | Polycronal | IHC | abcam | ab113694 |
| NKX2-2 | H, M, R, C | Chicken | Monoclonal | IHC | DSHB | 74.5A5 |
| NKX6-1 | H, M, R | Rat | Monoclonal | IHC | DSHB | F55A12 |
| MAFA | H, M | Rabbit | Polyclonal | IHC/Flow cytometry | Novus Biologicals | NB400-137 |
| MAFB | H, M, R | Rabbit | Polyclonal | IHC/Flow cytometry | abcam | ab66506 |
| PDX-1 | H, M | Goat | Polyclonal | IHC | R&D Systems | AF2419 |
| ChromograninA | H, M, Mon | Rabbit | Polyclonal | IHC | abcam | ab15160 |
| Synaptophysin | H | Mouse | Monoclonal/ Polyclonal | IHC | BioGenex | MU363-UC |
| PD-L1 antybody | H | Rabbit | Monoclonal | IHC | abcam | ab205921 |
| ChromograninA-PE | H | Mouse | Monoclonal/ Polyclonal | Flow cytometry | BD Bioscience | 564563 |
| NKX6-1-Alexa647 | H, M | Mouse | Monoclonal/ Polyclonal | Flow cytometry | BD Bioscience | 563338 |
| PDX-1-PE | H, M | Mouse | Monoclonal/ Polyclonal | Flow cytometry | BD Bioscience | 562161 |
| anti-mouse CD45-510 | M | Rat | Monoclonal | Flow cytometry | BioLegend | 103138 |
| anti-mouse CD3-650 | M | Rat | Monoclonal | Flow cytometry | BioLegend | 100229 |
| anti-mouse CD19-PerCP/Cy5.5 | M | Rat | Monoclonal | Flow cytometry | BioLegend | 115533 |
| anti-mouse NK1.1-PE | M | Mouse | Monoclonal | Flow cytometry | eBioscience | 12-5941-82 |
| anti-mouse FoxP3-APC | M | Rat | Monoclonal | Flow cytometry | eBioscience | 17-5773-80 |
| anti-human CD45-510 | H | Mouse | Monoclonal | Flow cytometry | BioLegend | 368526 |

TABLE 5-continued

| Antibody (Ab) Name | Species* | Host | Ab Type | Applications | Source/ Company | Catalog ID |
|---|---|---|---|---|---|---|
| anti-human CD3-650 | H | Mouse | Monoclonal | Flow cytometry | BioLegend | 317324 |
| anti-human-CD4-PE/Cy7 | H | Rat | Monoclonal | Flow cytometry | BioLegend | 357410 |
| anti-human-CD8-FITC | H | Mouse | Monoclonal | Flow cytometry | BioLegend | 368524 |
| anti-human CD19-PerCP/Cy5.5 | H | Mouse | Monoclonal | Flow cytometry | BioLegend | 363016 |

Species*: H = Human; M = mouse; R = Rat; C = Chicken; Mon = Monkey

Flow Cytometry

Clusters at indicated stages were dissociated with TrypLE (GIBCO) with 20 ug/ml DNase for 12 minutes at 37° C. and then were fixed with 4% PFA for 10 minutes at room temperature. Clusters were then permeabilized with 0.2% Triton X for 10 min, blocking with 10% goat serum for 30 min and stained for various intracellular markers with antibodies, c-peptide, (1/100, abcam, ab30477), PDX-1 (1/100, BD, 562161), NKX6-1 (1/100, BD, 563338), Chromogranin A (1/100, BD, 564583), MAFA (1/100, abcam, ab264583), MAFB (1/100, abcam, ab66506), Glucagon (1/100, abcam, ab82270), Somatostatin (1/100, abcam, 108456) for analysis on a BD Biosciences LSRII instrument. Data were analysed by FlowJo software. Secondary antibodies for c-peptide, Glucagon and Somatostatin were coupled to Alexa 647 (Life Technologies).

Electron Microscopy (EM) Analysis

Human islets and HILOs in suspension were pelleted in 2% low melting point agarose and subsequently fixed in 2.5% glutaraldehyde with 2% paraformaldehyde in 0.15M cacodylate buffer containing 2 mM calcium chloride (pH 7.4) for one hour at 4° C. Excess agarose was removed, and the pellet was washed in buffer prior to secondary fixing in 1% osmium tetroxide/0.3% potassium ferrocyanide in buffer. After washing in water, the pellet was en bloc stained with 2% uranyl acetate, followed by graded dehydration in ethanol (35%, 50%, 70%, 90%, 100%, 100%). Samples were then rapidly infiltrated in Spurr's resin using a Pelco BioWave microwave processing unit (Ted Pella, Redding, CA), embedded in Pelco Pyramid tip mold (Ted Pella, Redding, CA), and cured at 60° C. overnight. 70 nm ultrathin sections were cut on a Leica UC7 ultramicrotome (Leica, Vienna) and examined on a Libra120 (Zeiss, Oberkochen, Germany) at 120V.

Immune Profiling of Transplanted HILOs

Transplanted HILOs were harvested at day 26 after transplantation and were dissociated into single cells using TrypLE. After blocking a common epitope found in extracellular regions of mouse Fc-receptors by Fc block (Anti-mouse CD16/CD32 (Fc Shield) (70-0161-U500) staining, antibodies (1:100 dilution) to the cell surface markers CD19 (PerCP/Cy5.5 anti-mouse CD19, BioLegend, 115533), Nk1.1 (anti-mouse Nk1.1PE, eBioscience, 12-5941-81), CD45 (brilliant violet510 anti-mouse CD45, BioLegend, 103138), CD3 (brilliant violet650 anti-mouse CD3, BioLegend, 100229), Cd11b (anti-human/mouse APC-cyanine, TONBO, 25-0112U100) were used for FACS-based immune profiling. For flow cytometry analyses, data were collected using a BD Biosciences LSRII. For cell sorting, a BD Influx was used (100 micron nozzle tip and 1×PBS sheath fluid with sheath pressure set to 18.5 PSI) with sample and collection cooling set to 4 degrees C. Viable (Zombie-UV dye negative) single cells were selected for FACS or analyses using Forward scatter (FSC) and Side scatter (SSC) gating, followed by pulse-width discrimination for FSC and SSC.

The described protocol assays infiltration of lymphocytes (T cells, B cells) into an organ or tissue, e.g., kidney or kidney capsule, following transplant, implant, or transfer of donor cells, islets, organoids (and cells therein). The reduced numbers of CD45+ T cells that infiltrate into tissue such as kidney following transplantation of insulin-producing PD-L1+ wHILOs versus insulin-producing PD-L1—wHILOs demonstrates that the HILOs (and cells therein) expressing PD-L1 are protected from recognition as foreign by T cells and from T cell killing after transplantation (e.g., 27 days after transplantation), (FIGS. 4D and 4E).

Detecting Immunoprotected Cells, Islets, or Organoids (and Cells Therein) Following Transplant, Implant, or Transfer into a Recipient Subject Primary human cells, islets, and/or organoids derived from human tissues are labeled via infection with a lentiviral-mediated TYF-CMV-eGFP (green fluorescent protein), (Mao, Y. et al., 2015, International Journal of Medical Sciences, 12(5), 407-15. doi:10.7150/ijms.11270), which has been shown to produce sustained, high GFP expression. GFP-expressing cells/islets/organoids are then exposed to 2-3 IFNγ treatments (e.g., MPS IFNγ exposures described supra), and the subsequent induction of PDL-1 expression is confirmed by qPCR. IFNγ-exposed cells, islets and/or organoids are transplanted into the kidney capsule of an immune-competent mouse, with naïve cells/islets//organoids (i.e., no IFNγ exposure) transplanted into the ipsilateral kidney capsule as controls Mice are sacrificed 2-3 weeks after transplantation and kidney resident GFP-positive cells are quantified by fluorescence activated cell sorting (FACS) analysis. Increases in cells/islets/organoids that survive following IFNγ exposure are determined quantitatively, based on the numbers of GFP+ cells in each kidney as determined from individual mice.

Quantitative RT-PCR Analysis

Total RNA was extracted using TRIzol reagent (Invitrogen) and RNeasy KIT (Qiagen). Reverse transcription was performed with a SuperScript III First-Strand Synthesis System kit (Invitrogen) or PrimeScript RT reagent kit (TAKARA). Real time quantitative RT-PCR (qPCR) was performed using SYBR Green (Bio-Rad). Primer information is listed in Table 2.

In Vitro Vascularization

Human multicellular spheroids (MCSs) were embedded in 300 μl of Matrigel with EBM medium (Ronza, cc-3121) in 24 well tissue culture plates. Vascularization was observed over the following 24-72 hours.

Statistical Methods

Results were expressed as the mean±SEM. Statistical comparisons were made using Student's t test. Statistically significant differences are indicated as *p<0.05, p<0.01, *p<0.001.

Example 10: Human Islet-Like Organoids

The generation of functional human organs according to methods described herein provides new strategies for drug-screening and disease modeling. Specifically, functional organoids can be used as models of type 2 diabetes for drug screening. Human islet-like organoids responded to amyloid polypeptide (hIAPP) toxicity, an inducer of β cell loss in type 2 diabetic patients and islet dysfunction after transplantation in hyperglycemic patients, hIAPP dose-dependently induced G0/G1 arrest in 24 hours in human islet-like organoids (See, e.g., WO 2017/205511). Such human-like organoids may also be induced to express PD-L1 according to the methods and systems described herein, so as to avoid immune detection and destruction when used for transplantation, implantation, or administration to a subject in need thereof.

In an exemplary assay, 3D mini organs are exposed to stressors that induce type 2 diabetes, such as high levels of free fatty acids (FFAs) and/or, glucose and selected cytokines. The stressed 3D mini organs are then treated with various drugs. In some embodiments, the drug is approved by the Food and Drug Administration (FDA).

As output, the following are assayed in human pancreatic islet organoids: insulin secretion, beta cell apoptosis (PI stain), lactate dehydrogenase A (LDHA) expression via a luciferase reporter, and changes in expression of marker genes including NDUFA4 (Mitochondrial oxidative phosphorylation), ESRRG (Mitochondrial function), KCNK3 (Katp channel activity) and MAFA (beta cell fate marker). For the human pancreas organoid, amylase secretion and apoptosis of exocrine cells (PI stain) are assayed.

In an exemplary assay for modeling human pancreatic cancer tumorigenesis and metastasis in a dish and the potential to screen for drugs that target those diseases, a 3D mini human pancreas is co-cultured with pancreatic cancer cells, stellate cells, and immune cells to create human pancreatic cancer microenvironment in a dish. Various drugs (e.g., FDA-approved drugs) are then screened to find compounds which effectively suppress pancreatic cancer growth or metastasis in a mini human pancreas microenvironment. As output, the following are measured for the pancreas organoid: apoptosis of exocrine cells (PI stain), collagen synthesis (Trichrome stain) and stellate cells activation (GFAP-reporter). Potential candidate drugs identified in these assays are tested in pancreatic cancer tumorigenesis and metastasis mouse models. Genes expression and morphology as well as the degree of cell death, cell growth, and metastasis are investigated.

In an exemplary assay for modeling of human Type 2 diabetes in mice, human islet organoids and/or human liver organoids are transplanted into mice. The mice are then administered various stressors that induce type 2 diabetes, such as a high fat diet (HFD) or cytokines injection. The potential candidate drugs identified in this assay are further tested in human type 2 diabetic mouse model. Genes expression and morphology as well as the degree of diabetes are investigated.

In an exemplary assay for modeling of human pancreatic cancer tumorigenesis and metastasis in mice, human pancreas organoids and/or human liver organoids are transplanted into mice. Mice transplanted with a mini pancreas are used to study human pancreatic cancer growth in human pancreas microenvironment. In another exemplary assay, a mini pancreas and mini liver are co-transplanted in mice. The liver is a major site for metastasis of pancreatic cancer. In vivo, endothelial cells in the mini pancreas and in the mini liver create a pancreas-liver vasculature network for pancreatic cancer metastasis. Thus, mice co-transplanted with a mini pancreas and mini liver are used to study the metastasis of human pancreatic cancer into the human liver. The generation of functional organ-like clusters from pluripotent stem cells (PSC) and human islets and HILOs as described herein provides insight into the mechanisms underlying human diseases, as well as biological therapeutics that function following introduction or transplant into a recipient subject.

The results hereinabove were obtained using the following materials and methods:

3D KELCOGEL® (3 DKG) Culture Medium

KELCOGEL® F low acyl gellan gum (GG-LA) obtained from Modernist Pantry was suspended in pure water 0.3% (w/v) and dissolved by stirring at 90° C. or by microwave. The aqueous solution was sterilized at 121° C. for 20 minutes in an autoclave. The solution was added to TeSR™ medium (Ludwid et al., Nature Methods, 3, 637-646) or custom TeSR™ medium (800 ml DMEM/F12, 13.28 g BSA. 10 ml Glutamax, 560 mg NaHCO$_3$, 330 mg thiamine, 100 mg reduced glutathione, 3300 mg Vitamin C, 14 μg Selenium, 10 ml NEAA, 2 ml Trace Element B, 1 ml Trace Element C, 7 μl β-ME, 2 ml DLC, 2 ml GABA, 2 ml LiCl, 129.7 μg pipecolic acid, Insulin 2 mg up to 1000 ml) at a final concentration of 0.015%. Methylcellulose (MC) stock solution was added to a final concentration of 0.3% (R&D systems) (e.g., 0.3% KELCOGEL® stock: KELCOGEL® F low acyl GG-LA 300 mg+MilliQ water 100 ml; 3D-KEL-COGEL® (3 DKG) Stem TeSR™ Base Medium: STEM-CELL™ TeSR™ 95 ml+0.3% KELCOGEL® stock 5 ml+MC stock solution 300 ul; 3 DKG Custom TeSR™ Base Medium: custom TeSR™ media 95 ml+0.3% KELCO-GEL® stock 5 ml+MC stock solution 300 ul; 1% final concentration of Penicillin/streptozocin was added for 3 DKG medium.

Preparation of Human Pancreatic Endocrine Progenitors and β-Like Cells In Vitro

Pancreatic endocrine cells (hiPSC-PEs) were prepared from human iPSC using differentiation methods as previously described. Briefly, human induced pluripotent stem cells (hiPSC) derived from HUVECs were obtained from the Stem Cell Core (Salk Institute). Cells were maintained on MATRIGEL® (BD)-coated dishes in complete STEM-CELL™ TeSR™ medium at 37° C. in a humidified 5% CO$_2$ incubator. For pancreatic differentiation, hiPSC were infected with a human insulin reporter lentivirus (pGreen-Zero lenti reporter human insulin, System Biosciences) by Spinfection (800 g, 1 hour). Methods 1: Medium was changed to 100 ng/ml human Activin (R&D Systems), 25 ng/ml recombinant human Wnt3a (R&D Systems) in custom TeSR™ medium (800 ml DMEM/F12, 13.28 g BSA, 10 ml Glutamax, 560 mg NaHCO$_3$, 330 mg thiamine, 100 mg reduced glutathione, 3300 mg Vitamin C, 14 μg Selenium, 10 ml NEAA, 2 ml Trace Element B, 1 ml Trace Element C, 7 μl β-ME, 2 ml DLC, 2 ml GABA, 2 ml LiCl, 129.7 μg PA, Insulin 2 mg up to 1000 ml) for 2 days and then 100 ng/ml human Activin in differentiation medium for another 2 days (Stage 1, Pancreatic Endoderm). Subsequently, the medium was replaced with custom TeSR™ medium with 1 μM dorsomorphin (Calbiochem), 2 μM Retinoic Acid (Sigma), 10sM SB431542 and 1% of B27 supplement for 7 days (Stage 2). Medium was then replaced with custom TeSR™ medium with 10 uM forskolin (Sigma), 10 sM dexamethasone (Stemgent), 10sM TGFβ RI Kinase inhibitor II/Alk5 inhibitor II (Calbiochem or Enzo), 10 μM Nicotinamide (Sigma), 1 μM 3,3',5-Triiodo-L-thyronine sodium salt (T3) and 1% of B27 supplement for 4-5 days (day 15-day 21, Pancreatic endocrine progenitors). Medium was replaced every day (stage 1) or every other day (stage 2 & stage 3).

Methods 2: Medium was changed to 100 ng/ml human Activin (R&D Systems), 25 ng/ml recombinant human Wnt3a (R&D Systems) or 3 μM CHIR99021 (Axon or Selleckchem) in differentiation medium (S1) for 1 day and then 100 ng/ml human Activin in differentiation medium (S1) for another 2 days (Stage 1, Pancreatic Endoderm). Subsequently, medium was replaced with differentiation medium (S2) with 50 ng/ml FGF7 (R&D Systems) for 2 days and then differentiation medium (S3) with 50 ng/ml FGF7, 0.25 μM SANT-1 (Sigma), 1 μM Retinoic Acid (Sigma), 100 nM LDN193189 and 100 nM α-Amyloid Precursor Protein Modulator TPB for 3 days. Subsequently, medium was replaced with differentiation medium (S4) with 0.25 μM SANT-1, 50 nM Retinoic Acid, 10 μM Alk5 inhibitor II, 1 μM T3 for 3 days. Subsequently, medium was replaced with differentiation medium (S5) with 100 nM LDN193189, 100 nM Gamma Secretase inhibitor XX GSiXX (Millipore), 10 μM Alk5 inhibitor II, 1 μM T3 for 7 days. Subsequently, medium was replaced with differentiation medium (S5) with 10 μM Trolox (Calbiochem), 2 μM R428 (Selleckchem), 1 mM N-acetyl cysteine, 10 μM Alk5 inhibitor II, 1 μM T3 for additional 7 to 20 days.

S1 Medium (MCDB131 Medium, 8 mM glucose, 2.46 g/L NaHCO$_3$, 2% Fatty acid free BSA, 0.25 mM L-Ascorbic acid 0.002% Insulin-Transferrin-Selenium ITS-X (GIBCO), 2 mM Glutamax, 1% Penicillin-Streptomycin), S2 Medium (MCDB131 Medium, 8 mM glucose, 1.23 g/L NaHCO$_3$, 2% Fatty acid free BSA, 0.25 mM L-Ascorbic acid, 0.002% Insulin-Transferrin-Selenium ITS-X (GIBCO), 2 mM Glutamax, 1% Penicillin-Streptomycin), S3 Medium (MCDB131 Medium, 8 mM glucose, 1.23 g/L NaHCO$_3$, 2% Fatty acid free BSA, 0.25 mM L-Ascorbic acid, 0.5% Insulin-Transferrin-Selenium ITS-X (GIBCO), 2 mM Glutamax, 1% Penicillin-Streptomycin), S4 Medium (MCDB131 Medium, 8 mM glucose, 1.23 g/L NaHCO$_3$, 2% Fatty acid free BSA, 0.25 mM L-Ascorbic acid, 0.002% Insulin-Transferrin-Selenium ITS-X (GIBCO), 2 mM Glutamax, 1% Penicillin-Streptomycin, 10 μg/ml Heparin, 10 μM Zinc Sulfate), S5 Medium (MCDB131 Medium or BLAR Medium, 20 mM glucose, 1.754 g/L NaHCO$_3$, 2% Fatty acid free BSA, 0.25 mM L-Ascorbic acid, 0.002% Insulin-Transferrin-Selenium ITS-X (GIBCO), 2 mM Glutamax, 1% Penicillin-Streptomycin). For 3-dimensional (3D) culture, hiPSC or hESC were cultured in 3 DKG Stem TeSR™ Base Medium with 10 μM Y-27632 for 5 to 7 days and then the medium was replaced each Differentiation medium with 0.015% Kelcogel and 0.3% Methylcellulose. Generation of Three-Dimensional Pancreatic Islet Bud In Vitro: Islet-Like Organoids in Matrigel Through Co-Culture with hADSCs and HUVECs Primary HUVECs and human Adipose-derived stem cells (hADSC) (Invitrogen or PromoCell) were cultured in 15 cm dish with EBM Medium (Ronza, cc-3121) or Mesen-ProRS™ Medium (GIBCO, 12747-010 or Preadipocyte Growth Medium Kit, C-27417), respectively, at 37° C. in a humidified 5% CO$_2$ incubator. For co-culturing experiments, pancreatic endocrine progenitors derived from human iPSC were treated with Accutase, while HUVECs and hADSC were treated with TrypLE (GIBCO, 12604-013) and cells collected into a 50 ml tube, respectively. After the cells were counted, 1×10$^6$ cells of hiPS-PP, 7×10$^6$ cells of HUVEC and 1-2×10$^5$ cells of hADSC were co-cultured in 1 well of 24 well with 300 ul of MATRIGEL® matrix. For the purpose of scalable generation of human islets like organoids, 1×10$^6$ cells of hiPS-PP (day 15-day 21), 7×10$^6$ cells of HUVEC and 1-2×10$^5$ cells of hADSC were co-cultured in 3 DKG Custom TeSR® media with 10 μM forskolin (Sigma), 10 μM dexamethasone (Stemgent), 10 μM TGFβ RI Kinase inhibitor II/Alk5 inhibitor II (Calbiochem or Enzo), 10 μM Nicotinamide (Sigma), 1 uM 3,3',5-Triiodo-L-thyronine sodium salt (T3) and 1% of B27 supplement, R428 (2 μM), Zinc sulfate (10 μM) and N-Cys (1 mM). (Methods 1) or co-cultured in differentiation medium (S5) with 100 nM LDN193189, 100 nM Gamma Secretase inhibitor XX GSiXX (Millipore), 10 μM Alk5 inhibitor II, 1 μM T3 for 7 days. Subsequently, medium was replaced with differentiation medium (S5) with 10 μM Trolox (Calbiochem), 2 μM R428 (Selleckchem), 1 mM N-acetyl cysteine, 10 μM Alk5 inhibitor II, 1 μM T3 for an additional 7 to 20 days (Methods 2). Mixed cells formed spherical, islet-like clusters within a few days. The medium was changed every other day.
Generation of 3D (Three-Dimensional) Pancreatic Islet Buds In Vitro: Islet-Like Organoids in Scalable Gellan Gum Through Co-Culture with hADSCs and HUVECs Cells were prepared as described above. Briefly, 1×10$^8$ cells of hiPS-PP, 2-7×10$^7$ cells of HUVECs and 5-7×10$^6$ cells of hADSC were co-cultured in 60-100 ml of 3 DKG Custom TeSR™ with 10 μM forskolin (Sigma), 10 μM dexamethasone (Stemgent), 10 μM TGFβ RI Kinase inhibitor II/Alk5 inhibitor II (Calbiochem or Enzo), 10 μM Nicotinamide (Sigma), 1 μM 3,3',5-Triiodo-L-thyronine sodium salt (T3) and 1% of B27 supplement, R428 (2 μM), Zinc sulfate (10 μM) and N-Cys (1 mM) (Methods 1) or co-cultured in differentiation media (S5) with 100 nM LDN193189, 100 nM Gamma Secretase inhibitor XX GSiXX (Millipore), 10 μM Alk5 inhibitor II, 1 μM T3 for 7 days. Subsequently, media was replaced with differentiation media (S5) with 10 μM Trolox (Calbiochem), 2 μM R428 (Selleckchem), 1 mM N-acetyl cysteine, 10 μM Alk5 inhibitor II, 1 μM T3 for additional 7 to 20 days (Methods 2). Mixed cells formed spherical, islet-like clusters within a few days. Media was changed every day or every other day.
Generation of 3D (Three-Dimensional) Pancreatic Islets Bud In Vitro: Islet-Like Organoids in Scalable Gellan Gum 3D Culture Methods without (w/o) Using hADSC and HUVECs Human PSCs, including iPSC or ESC, were initially cultured in matrigel-coated plates (2 dimensional (2D) cultures. Cells were then treated with Accutase (Innovative Cell Technologies, Inc., San Diego, CA) to generate a single cell suspension, washed with PBS and centrifuged at 1000-1300 rpm for 5 minutes to pellet cells. Cells were resuspended with 3 DKG Stem TeSR™ Base Medium (Stemcell Technologies, Cambridge, MA) with 10sM Y-27632 (a RHO/ROCK pathway inhibitor compound) and cultured for an additional for 5 to 7 days until PSC sphere growth reached 50-100 μm diameter. Media was then replaced with differentiation media supplemented with 0.015% Kelcogel and 0.3% Methylcellulose. The culture medium was changed to differentiation medium (S1) containing 100 ng/ml human Activin (R&D Systems), 25 ng/ml recombinant human Wnt3a (R&D Systems) or 3sM CHIR99021, a glycogen synthase kinase GSK-3 inhibitor (Axon Medchem, Reston, VA; or Selleckchem) for 1 day and then to differentiation medium (S1) containing 100 ng/ml human Activin for another 2 days (Stage 1, Pancreatic Endoderm). Subsequently, the medium was replaced with differentiation medium (S2) containing 50 ng/ml FGF7 (R&D Systems) for 2 days, and then with differentiation medium (S3) containing 50 ng/ml FGF7, 0.25 uM SANT-1 (Sigma), 1 sM Retinoic Acid (Sigma), 100 nM LDN193189 (an ALK2 and ALK3 inhibitor, Sigma) and 100 nM α-Amyloid Precursor Protein Modulator TPB for 3 days. Subsequently, this medium was replaced with differentiation medium (S4) containing 0.25 sM SANT-1, 50 nM Retinoic Acid, 10 µM Alk5 inhibitor II, 1 sM T3 for 3 days. Subsequently, the medium was replaced with differentiation medium (S5) containing 100 nM LDN193189, 100 nM Gamma Secretase inhibitor XX GSiXX (Millipore) 10 sM Alk5 inhibitor II, 1 µM T3 for 7 days. Subsequently, the medium was replaced with differentiation medium (S5) containing 10 µM Trolox (Calbiochem), 2 sM R428 (Selleckchem), 1 mM N-acetyl cysteine, 10 sM Alk5 inhibitor II, 1 µM T3 for an additional 7 to 20 days.

After confirmation of the insulin gene expression by either reporter expression or qPCR (typically on day 20-30), the medium was changed to differentiation medium (S5) containing 10 µM Trolox (Calbiochem), 2 µM R428 (Selleckchem), 1 mM N-acetyl cysteine, 10 sM Alk5 inhibitor II, 1 µM T3 and 100 ng/ml recombinant human (rh)Wnt4 (R&D Systems), 400 ng/ml rhWnt5a, or 50% Wnt5a conditioned medium for 1-20 days. Wnt5a conditioned medium was prepared by culturing an L-Wnt5a cell line (ATCC, CRL-2814) in DMEM with 10% FBS, 1% Penicillin-streptomycin for 4 days after cells had reached 70-100% confluence in T175-T225 cell culture flasks.

Generation of 3D (Three-Dimensional) Liver Bud In Vitro: Organ Buds

Hepatocyte cells (hiPSC-HEs) from human iPSC were prepared using differentiation methods as previously described. Briefly, hiPSCs were maintained on MATRI-GEL® (BD)-coated dishes in complete STEMCELL™ TeSR™ medium at 37° C. in a humidified 5% $CO_2$ incubator. For hepatic differentiation, hiPSC (90% confluence in 6 well) were cultured with 100 ng/ml human Activin (Sigma) and 25 ng/ml recombinant human Wnt3a (R&D systems) or 3sM CHIR99021 and 1% B27 supplement minus Insulin in RPMI-1640 medium for 1 day and then 100 ng/ml human Activin and 1% B27 supplement minus Insulin in RPMI medium for another 4 days (Stage 1 Hepatic-Endoderm). Subsequently, the medium was replaced with differentiation medium with 10 ng/ml bFGF, 20 ng/ml BMP4 and 1% of B27 supplement in RPMI-1640 medium for 3 days (Stage 2). The medium was then replaced with differentiation medium with 0.1 µM Dexamethasone, 20 ng/ml Oncostat-inM (R&D Systems) and 10-20 ng/ml Hepatic Growth Factor (HGF, R&D Systems) and 1% of B27 supplement in Hepatocyte Culture Media (Lonza, MD, CC-3198, withdraw EGF and Gentamicin/Amphotericin-B) for 4-22 days (day15-day19, Pancreatic endocrine progenitors). The medium was replaced every day (stage 1) or every other day (stage 2 & stage 3). Primary HUVECs cells and human Adipose-derived stem cells (hADSC) (InVitrogen or Pro-moCell) were cultured in 15 cm dish with EBM Medium (Ronza, cc-3121) or MesenProRS Medium (GIBCO, 12747-010 or Preadipocyte Growth Medium Kit, C-27417), respectively, at 37° C. in a humidified 5% $CO_2$ incubator. For co-culturing experiments, day 10-hepatocytes derived from human iPSC were treated with Accutase, while HUVECs and hADSC were treated with TrypLE (GIBCO, 12604-013) and cells were collected into 50 ml tubes, respectively. After the cells were counted, $1\times10^6$ cells of hiPS-PP, $7\times10^6$ cells of HUVEC and $1$-$2\times10^5$ cells of hADSC were co-cultured in 1 well of 24 well with 300 ul of matrigel. Liver-like organoids were formed within 1 to 2 days. Then, liver-like organoids were taken out from MATRIGEL® matrix and cultured in in 3 DKG Custom TeSR™. In an embodiment, cells (hepatocytes) of the liver-like organoids were molecularly engineered to express one or more checkpoint proteins.

Generation of 3D (Three-Dimensional) Heart Bud In Vitro: Organ Buds

Cardiomyocyte cells (hiPSC-CDs) were prepared from human iPSC using differentiation methods as previously described. Briefly, hiPSCs were maintained on MATRI-GEL® (BD)-coated dishes in complete Stemcell™ TeSR™ media at 37° C. in a humidified 5% $CO_2$ incubator. For cardiac differentiation, hiPSC (90% confluence in 6 well) were cultured with 100 ng/ml human Activin (R&D Systems) and 10 µM CHIR99021 and 1% B27 supplement minus Insulin in RPMI1640 media for 1 days and then 1% B27 supplement minus Insulin in RPMI media for another 2 days (Stage 1 cardiac-Mesoderm). Subsequently, medium was replaced with RPMI1640 with 5 µM IWP-2 and 1% B27 supplement minus Insulin in RPMI medium for 1 days (Stage 2). The medium was then replaced with 1% B27 supplement minus Insulin in RPMI Medium for 6 days or more (Stage 3). Cardiac contraction started around day 13. The medium was replaced every day (stage 1) or every other day (stage 2 & stage 3). Primary HUVECs cells and human Adipose-derived stem cells (hADSC) (Invitrogen or Promo-Cell) were cultured in 15 cm dish with EBM Medium (Ronza, cc-3121) or MesenProRS™ Media (GIBCO, 12747-010 or Preadipocyte Growth Medium Kit, C-27417), respectively, at 37° C. in a humidified 5% $CO_2$ incubator. For co-culturing experiments, day 13 to day 15 cardiomyocytes derived from human iPSC were treated with Dispase, while HUVECs and hADSC were treated with TrypLE (GIBCO, 12604-013) and cells collected into 50 ml tubes, respectively. After the cells were counted, $1\times10^6$ cells of hiPS-PP, $7\times10^6$ cells of HUVEC and $1$-$2\times10^5$ cells of hADSC were co-cultured in 3 DKG Custom TeSR™ medium. Mini heart like organs capable of contracting were formed within a few days. In an embodiment, cells (cardiomyocytes) of the mini-heart-like organoids were molecularly engineered to express one or more checkpoint proteins.

Generation of 3D (Three-Dimensional) Intestine Bud In Vitro: Organ Buds

Intestinal cells (hiPSC-ITs) were prepared from human iPSC using differentiation methods as previously described. Briefly, hiPSCs were maintained on Matrigel® (BD)-coated dishes in complete Stemcell™ TeSR™ Medium at 37° C. in a humidified 5% $CO_2$ incubator. For intestinal cell differentiation, hiPSC (90% confluence in 6 well plates) were cultured with 100 ng/ml human Activin (R&D Systems), 3 µM CHIR99021, 2 mM Glutamax and 1% B27 supplement minus Insulin in RPMI1640 medium for 1 day and then 100 ng/ml human Activin (R&D Systems), 2 mM Glutamax and 1% B27 supplement minus Insulin in RPMI1640 medium for another 3 days (Stage 1 Forgut-Endoderm). Subsequently, medium was replaced with 500 ng/ml Wnt3a, 500 ng/ml FGF4 and 1% B27 supplement in RPMI 1640 medium for 4 days (Stage 2). Cells were transferred to Matrigel® matrix and then a 3D-spheroid Matrigel® dorm was made in the bottom of 24 well. The medium was then replaced with 1% B27 supplement, 1% N2 supplement, 500 ng/ml R-spondin, 100 ng/ml Noggin, 50 ng/ml EGF, 2 mM Glutamax™ supplement, 10 µM HEPES in DMEM/F12 Medium for 7 days or more (stage3). Intestinal-like organoid spheroids were observed within a week. The medium was replaced every day (stage 1) and every other day (stage 2 & stage 3). Primary HUVECs cells and human Adipose-derived stem cells (hADSC) (Invitrogen or PromoCell) were cultured in a 15 cm dish with EBM Media (Ronza, cc-3121) or MesenProRS™ Medium (GIBCO®, 12747-010 or Pre-adipocyte Growth Medium Kit, C-27417), respectively, at 37° C. in a humidified 5% $CO_2$ incubator. For co-culturing experiments, intestinal progenitors (day 7) derived from human iPSC were treated with Accutase, while HUVECs and hADSC were treated with TrypLE (GIBCO®, 12604-013) and cells were collected into 50 ml tubes, respectively. After counting the cells, $1 \times 10^6$ cells of hiPS-PP, $7 \times 10^6$ HUVEC cells and $1-2 \times 10^5$ hADSC cells were co-cultured in 3 DKG Custom TeSR™ medium. In an embodiment, intestinal cells of the intestine-like organoids were molecularly engineered to express one or more checkpoint proteins.

Insulin Secretion Assay (Primary Mouse and Human Pancreatic Islets and Human iPSC-Derived Cells)

Insulin release from intact islets was monitored using batch incubation methods (Yoshihara et al., 2010, *Nat. Commun.* 1:127). Briefly, overnight-cultured isolated pancreatic islets (RPMI-1640 supplemented with 10% (v/v) fetal bovine serum and 1% (v/v) Antibiotic-Antimycotic (Gibco)) were pre-cultured at 37° C. for 30 min (Krebs-Ringer bicarbonate buffer (KRBB) containing 129.4 mM NaCl, 3.7 mM KCl, 2.7 mM $CaCl_2$), 1.3 mM $KH_2PO_4$, 1.3 mM $MgSO_4$, 24.8 mM $NaHCO_3$(equilibrated with 5% $CO_2$, 95% $O_2$, pH7.4), 10 mM HEPES and 0.2% (v/v) BSA (fraction V, Sigma) (KRBH) with 3 mM glucose). Pancreatic islets were then incubated in KRBH buffer (500 µl/10 islets) with 3 mM or 20 mM glucose to determine insulin secretion levels. After 30 min, islets were pelleted by centrifugation and insulin levels determined by ELISA (Rat/mouse Insulin ELISA KIT (Millipore) and Human Insulin ELISA KIT (Millipore) for mouse and human islets, respectively). For human iPSC derived cells, the cells ($1 \times 10^6$ cells/well in 24 well) were pre-cultured in 3 mM glucose KRBH buffer (500 µl/well). The cells were then incubated in KRBB (200 µl/well) with 3 mM or 20 mM glucose to determine c-peptide secretion levels as indicator of insulin secretion levels. After 30 min, the cells were pelleted by centrifugation and c-peptide levels were determined by human c-peptide ELISA KIT (Millipore).

Example 10 Methods

Quantitative RT-PCR Analysis

Total RNA was extracted using TRIzol reagent (Invitrogen) and RNeasy KIT (Qiagen). Reverse transcription was performed with a SuperScript III First-Strand Synthesis System kit (Invitrogen) or PrimeScript RT reagent kit (TA-KARA). Real time quantitative RT-PCR (qPCR) was performed using SYBR Green (Bio-Rad).

Lentivirus Production for Proinsulin-NanoLuc

Proinsulin-NanoLuc in pLX304 (Addgene, #62057) was obtained from Addgene. Proinsulin-NanoLuc lentivirus was produced using a second-generation viral packaging system. Briefly, 14 µg of Proinsulin-NanoLuc, 6.6 µg of PsPAX2 packaging plasmid (Addgene 12260), 5.4 µg of pMD2.G envelope plasmid (Addgene 12259) and 54 µl Lipofectamin2000 (Invitrogen) were used to transfect a T75 flask of HEK293LTV packaging cells. Twenty-four (24) hours after transfection, media was changed to fresh DMEM with 10% FBS and 1% Penicillin/Streptozocine. Forty-eight (48) hours and 96 hours after transfection, viruses were collected as day 1 and day 3, respectively and passed through 0.2 µm cellulose acetate filters (VWR). Viruses were aliquoted and frozen at −80° C. until use.

Gaussia Luciferase Assay for Insulin Secretion Measurement

Mouse islets, human islets and human islets like organoids were plated in their respective growth media with 10 µg/ml Polybrene® polymer (Santacruz). Viruses were then added. After overnight culture, cells were placed in fresh growth media. Forty-eight (48) to 72 hours after infection, mouse islets, human islets and human islet-like organoids were picked up by hand and then placed into 96 wells with single islet or organoid. Then, insulin secretion assays were performed. Briefly, a single islet or organoid was pre-incubated with 3 mM glucose KRBB at 37° C. for 30 min to 1 hour. The cells were then incubated in KRBB (100 µl/well) with 3 mM for 30 min and then sequentially incubated with 20 mM glucose with or without 100 nM Exendin-4 or 3 mM glucose with 20 mM KCl (100 µl/well). To determine Gaussia Luciferase activity as indicator of insulin secretion levels, 10 µl of samples are used for Luciferase assay using Pierce Gaussia Luciferase Flash Assay Kit (Prod #16159, Thermo Scientific).

INS-1 cells were infected with the virus by spinfection (800 g, 1 hour at 37° C. and then changed to fresh INS-1 growth media. Seventy-two (72) hours after transfection, INS-1 cells were treated with 5 µg/ml Blasticidin (Invitrogen) for 7 days to select for Proinsulin-NanoLuc expressing cells. For insulin secretion assay, the cells ($5 \times 10^4 - 1 \times 10^5$ cells/well in 96 well) were pre-cultured in 3 mM glucose KRBB (100 µl/well). The cells were then incubated in KRBB (100 µl/well) with 3 mM and then sequentially incubated with 20 mM glucose with or without 100 nM Exendine-4 or 3 mM glucose with 20 mM KCl (100 µl/well). To determine Gaussia Luciferase activity as indicator of insulin secretion levels, 10 µl of samples are used for Luciferase assay using Pierce Gaussia Luciferase Flash Assay Kit (Prod #16159, Thermo Scientific).

Vascularization Test In Vitro

Human islet-like organoids were embedded in 1 well of 24 well plate with 300 µl of Matrigel® matrix with EBM Media (Ronza, cc-3121). Vascularization was observed within 24-72 hours.

3D Culture of hADSCs and WNT Protein Expression hADSCs undergo changes in the expression of Wnt genes, in particular genes in the Wnt5a pathway, during the spontaneous self-organization that occurs in 3D culture. Wnt5a was found to be the predominant protein expressed among the Wnt proteins in hADSC 3D culture over time.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. An in vitro or ex vivo method of increasing survival or reducing cell death of a transplanted pancreatic islet-like organoid that has been administered to, or transplanted or implanted in, a subject, the method comprising:

contacting the donor pancreatic islet-like organoid or a pancreatic islet cell, pancreatic β-like islet cell, or pancreatic organoid cell thereof, in vitro or ex vivo, with multiple, intermittent exposures to interferon gamma (IFNγ), said multiple, intermittent in vitro or ex vivo exposures to IFNγ comprising at least 2 or 3 exposures to IFNγ in an amount of about 0.5-100 ng/ml for about 2-12 hours per exposure for a time period of at least about 1- to 3-days; wherein the donor pancreatic islet-like organoid or a pancreatic islet cell, pancreatic B-like islet cell, or pancreatic organoid cell thereof is washed and/or rested between the exposures to IFNγ;

culturing the pancreatic islet-like organoid or a pancreatic islet cell, pancreatic β-like islet cell, pancreatic organoid cell thereof in culture medium comprising about 5-200 ng/ml of Wnt4 or about 25-400 ng/ml of Wnt5a protein for at least about 8 days prior to administration, transplantation, or implantation;

wherein the multiple intermittent exposures to IFNγ increase survival or reduce cell death of the donor pancreatic islet-like organoid or a pancreatic islet cell, pancreatic β-like islet cell, or pancreatic organoid cell thereof following administration, transplantation, or implantation in the subject; and wherein the pancreatic islet-like organoid contacted with the multiple, intermittent exposures to IFNγ avoids immune detection; exhibits at least one of KCl-stimulated insulin secretion, GLP-1 stimulated insulin secretion, somatostatin secretion, and glucagon secretion; and maintains glucose homeostasis in the subject following administration, transplantation, or implantation in the subject.

2. The method of claim 1, wherein the donor pancreatic islet-like organoid or pancreatic islet cell, pancreatic β-like islet cell, or pancreatic organoid cell thereof, is a human pancreatic islet-like organoid, pancreatic islet cell, pancreatic β-like islet cell, or pancreatic organoid cell.

3. The method of claim 2, wherein administration, transplantation, or implantation of the pancreatic islet organoid increases survival or reduces death of the subject for at least 50 days.

4. The method of claim 2, wherein the pancreatic islet-like organoid expresses a beta cell lineage marker selected from the group consisting of NKX2-2, NEUROD1, RFX6, GCK, INS, NKX6-1, UCN3, MAFB and SYT4 and an ARX alpha cell lineage marker.

5. The method of claim 2, wherein the pancreatic islet-like organoid comprises an induced pluripotent stem cell (iPSC)-derived β cell which exhibits increased expression of Estrogen Related Receptor gamma (ERRγ) or increased oxidative metabolism characterized by increased oxygen consumption rate (OCR) and decreased cellular acidification rate (ECAR).

6. The method of claim 1, wherein the donor pancreatic islet-like organoid or the pancreatic islet cell, pancreatic β-like islet cell, or pancreatic organoid cell is exposed to IFNγ at least two times over an at least two-day time period;

is exposed to IFNγ at least three times over an at least three-day time period;

is exposed to IFNγ for greater than one hour at least two times over an at least two-day time period; is exposed to IFNγ for greater than one hour at least three times over an at least three-day time period; or is exposed to IFNγ for two hours at least three times over an at least three-day time period.

7. The method of claim 1, wherein the donor pancreatic islet-like organoid or the pancreatic islet cell, pancreatic β-like islet cell, or pancreatic organoid cell is syngeneic, autologous, allogeneic, or xenogeneic.

8. The method of claim 1, wherein the subject is immune competent or is immunosuppressed.

9. The method of claim 1, wherein the donor pancreatic islet-like organoid or the pancreatic islet cell, pancreatic β-like islet cell, or pancreatic organoid cell is derived from induced pluripotent stem cells (iPSC) or embryonic stem cells.

10. The method of claim 1, wherein the donor pancreatic islet-like organoid or the pancreatic islet cell, pancreatic β-like islet cell, or pancreatic organoid cell is contacted in vitro or ex vivo with multiple intermittent exposures to interferon gamma (IFNγ) in an amount of about 10 ng/ml.

11. The method of claim 1, wherein the Wnt4 or Wnt5a protein is selected from the group consisting of recombinant Wnt4 protein, recombinant Wnt5a protein, human Wnt4 protein, human Wnt5a protein, recombinant human Wnt4 protein, recombinant human Wnt5a protein, and conditioned medium containing Wnt4 or Wnt5a produced by a Wnt4 or Wnt5a-producing cell.

* * * * *

SEQUENCE LISTING

```
<160> NUMBER OF SEQ ID NOS: 110

<210> SEQ ID NO 1
<211> LENGTH: 609
<212> TYPE: PRT
<213> ORGANISM: Homo sapiens

<400> SEQUENCE: 1

Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
    50                  55                  60

Lys Met Val Lys Asp Ala Leu Thr Ala Ile Glu Lys Pro Thr Gly Asp
65                  70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
            115                 120                 125

Lys Lys Pro Thr Pro Ala Ser Ile Pro Leu Phe Gln Val Pro Glu Pro
        130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
            195                 200                 205

Val Thr Lys Glu Leu Arg Glu Ser Ser Leu Leu Asn Gln His Ala Cys
        210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly
            260                 265                 270

Asp Val Leu Asp Cys Leu Gln Asp Gly Glu Lys Ile Met Ser Tyr Ile
        275                 280                 285

Cys Ser Gln Gln Asp Thr Leu Ser Asn Lys Ile Thr Glu Cys Cys Lys
    290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335
```

```
Arg Asp Phe Asn Gln Phe Ser Ser Gly Glu Lys Asn Ile Phe Leu Ala
        340                 345                 350

Ser Phe Val His Glu Tyr Ser Arg Arg His Pro Gln Leu Ala Val Ser
        355                 360                 365

Val Ile Leu Arg Val Ala Lys Gly Tyr Gln Glu Leu Leu Glu Lys Cys
    370                 375                 380

Phe Gln Thr Glu Asn Pro Leu Glu Cys Gln Asp Lys Gly Glu Glu Glu
385                 390                 395                 400

Leu Gln Lys Tyr Ile Gln Glu Ser Gln Ala Leu Ala Lys Arg Ser Cys
                405                 410                 415

Gly Leu Phe Gln Lys Leu Gly Glu Tyr Tyr Leu Gln Asn Ala Phe Leu
            420                 425                 430

Val Ala Tyr Thr Lys Lys Ala Pro Gln Leu Thr Ser Ser Glu Leu Met
            435                 440                 445

Ala Ile Thr Arg Lys Met Ala Ala Thr Ala Ala Thr Cys Cys Gln Leu
        450                 455                 460

Ser Glu Asp Lys Leu Leu Ala Cys Gly Glu Gly Ala Ala Asp Ile Ile
465                 470                 475                 480

Ile Gly His Leu Cys Ile Arg His Glu Met Thr Pro Val Asn Pro Gly
                485                 490                 495

Val Gly Gln Cys Cys Thr Ser Ser Tyr Ala Asn Arg Arg Pro Cys Phe
            500                 505                 510

Ser Ser Leu Val Val Asp Glu Thr Tyr Val Pro Pro Ala Phe Ser Asp
            515                 520                 525

Asp Lys Phe Ile Phe His Lys Asp Leu Cys Gln Ala Gln Gly Val Ala
        530                 535                 540

Leu Gln Thr Met Lys Gln Glu Phe Leu Ile Asn Leu Val Lys Gln Lys
545                 550                 555                 560

Pro Gln Ile Thr Glu Glu Gln Leu Glu Ala Val Ile Ala Asp Phe Ser
                565                 570                 575

Gly Leu Leu Glu Lys Cys Cys Gln Gly Gln Glu Gln Glu Val Cys Phe
            580                 585                 590

Ala Glu Glu Gly Gln Lys Leu Ile Ser Lys Thr Arg Ala Ala Leu Gly
        595                 600                 605

Val
```

```
<210> SEQ ID NO 2
<211> LENGTH: 2057
<212> TYPE: DNA
<213> ORGANISM: Homo sapiens

<400> SEQUENCE: 2
atattgtgct tccaccactg ccaataacaa aataactagc aaccatgaag tgggtggaat       60
caattttttt aattttccta ctaaattttta ctgaatccag aacactgcat agaaatgaat      120
atggaatagc ttccatattg gattcttacc aatgtactgc agagataagt ttagctgacc      180
tggctaccat attttttgcc cagtttgttc aagaagccac ttacaaggaa gtaagcaaaa      240
tggtgaaaga tgcattgact gcaattgaga aacccactgg agatgaacag tcttcagggt      300
gtttagaaaa ccagctacct gcctttctgg aagaactttg ccatgagaaa gaaattttgg      360
agaagtacgg acattcagac tgctgcagcc aaagtgaaga gggaagacat aactgttttc      420
ttgcacacaa aaagcccact ccagcatcga tcccactttt ccaagttcca gaacctgtca      480
caagctgtga agcatatgaa gaagacaggg agacattcat gaacaaattc atttatgaga      540
```

```
tagcaagaag gcatcccttc ctgtatgcac ctacaattct tctttgggct gctcgctatg    600
acaaaataat tccatcttgc tgcaaagctg aaaatgcagt tgaatgcttc caaacaaagg    660
cagcaacagt tacaaaagaa ttaagagaaa gcagcttgtt aaatcaacat gcatgtgcag    720
taatgaaaaa ttttgggacc cgaactttcc aagccataac tgttactaaa ctgagtcaga    780
agtttaccaa agttaatttt actgaaatcc agaaactagt cctggatgtg gcccatgtac    840
atgagcactg ttgcagagga gatgtgctgg attgtctgca ggatgggaa aaatcatgt     900 cctacatatg ttctcaacaa gacactctgt caaacaaaat aacagaatgc tgcaaactga    960
ccacgctgga acgtggtcaa tgtataattc atgcagaaaa tgatgaaaaa cctgaaggtc   1020
tatctccaaa tctaaacagg ttttttaggag atagagattt taaccaattt tcttcagggg   1080
aaaaaaatat cttcttggca agttttgttc atgaatattc aagaagacat cctcagcttg   1140
ctgtctcagt aattctaaga gttgctaaag ataccaggga gttattggag aagtgtttcc   1200
agactgaaaa ccctcttgaa tgccaagata aaggagaaga agaattacag aaatacatcc   1260
aggagagcca agcattggca aagcgaagct gcggcctctt ccagaaacta ggagaatatt   1320
acttacaaaa tgcgtttctc gttgcttaca caaagaaagc ccccagctg acctcgtcgg     1380 agctgatggc catcaccaga aaaatggcag ccacagcagc cacttgttgc caactcagtg    1440
aggacaaact attggcctgt ggcgagggag cggctgacat tattatcgga cacttatgta    1500
tcagacatga aatgactcca gtaaaccctg gtgttggcca gtgctgcact tcttcatatg    1560
ccaacaggag gccatgcttc agcagcttgg tggtggatga aacatatgtc cctcctgcat    1620
tctctgatga caagttcatt ttccataagg atctgtgcca agctcagggt gtagcgctgc    1680
aaacgatgaa gcaagagttt ctcattaacc ttgtgaagca aaagccacaa ataacagagg    1740
aacaacttga ggctgtcatt gcagatttct caggcctgtt ggagaaatgc tgccaaggcc    1800
aggaacagga agtctgcttt gctgaagagg acaaaaact gatttcaaaa actcgtgctg     1860
ctttgggagt ttaaattact tcaggggaag agaagacaaa acgagtcttt cattcggtgt    1920 gaactttct ctttaatttt aactgattta acacttttg tgaattaatg aaatgataaa     1980 gactttatg tgagatttcc ttatcacaga ataaaatat ctccaaatgt ttcctttca      2040 aaaaaaaaaa aaaaaaa                                                  2057
```

<210> SEQ ID NO 3
<211> LENGTH: 609
<212> TYPE: PRT
<213> ORGANISM: Homo sapiens

<400> SEQUENCE: 3

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95
```

```
Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
        130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
        210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
            245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
            325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
            405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
```

```
                    515             520                 525

Glu Thr Phe Thr Phe His Ala Asp Ile Cys Thr Leu Ser Glu Lys Glu
    530             535             540

Arg Gln Ile Lys Lys Gln Thr Ala Leu Val Glu Leu Val Lys His Lys
545             550             555             560

Pro Lys Ala Thr Lys Glu Gln Leu Lys Ala Val Met Asp Asp Phe Ala
                565             570             575

Ala Phe Val Glu Lys Cys Cys Lys Ala Asp Asp Lys Glu Thr Cys Phe
            580             585             590

Ala Glu Glu Gly Lys Lys Leu Val Ala Ala Ser Gln Ala Ala Leu Gly
        595             600             605

Leu

<210> SEQ ID NO 4
<211> LENGTH: 2264
<212> TYPE: DNA
<213> ORGANISM: Homo sapiens

<400> SEQUENCE: 4
agtatattag tgctaatttc cctccgtttg tcctagcttt tctcttctgt caaccccaca      60
cgcctttggc acaatgaagt gggtaacctt tatttccctt cttttttctct ttagctcggc     120 ttattccagg ggtgtgtttc gtcgagatgc acacaagagt gaggttgctc atcggtttaa     180
agatttggga gaagaaaatt tcaaagcctt ggtgttgatt gcctttgctc agtatcttca     240
gcagtgtcca tttgaagatc atgtaaaatt agtgaatgaa gtaactgaat ttgcaaaaac     300
atgtgttgct gatgagtcag ctgaaaattg tgacaaatca cttcataccc tttttggaga     360
caaattatgc acagttgcaa ctcttcgtga aacctatggt gaaatggctg actgctgtgc     420
aaaacaagaa cctgagagaa atgaatgctt cttgcaacac aaagatgaca acccaaacct     480
cccccgattg gtgagaccag aggttgatgt gatgtgcact gcttttcatg acaatgaaga     540 gacattttttg aaaaaatact tatatgaaat tgccagaaga catccttact tttatgcccc     600
ggaactcctt ttctttgcta aaaggtataa agctgctttt acagaatgtt gccaagctgc     660
tgataaagct gcctgcctgt tgccaaagct cgatgaactt cgggatgaag ggaaggcttc     720
gtctgccaaa cagagactca agtgtgccag tctccaaaaa tttggagaaa gagctttcaa     780
agcatgggca gtagctcgcc tgagccagag atttcccaaa gctgagtttg cagaagtttc     840
caagttagtg acagatctta ccaaagtcca cacggaatgc tgccatggag atctgcttga     900
atgtgctgat gacagggcgg accttgccaa gtatatctgt gaaaatcaag attcgatctc     960
cagtaaactg aaggaatgct gtgaaaaacc tctgttggaa aaatcccact gcattgccga    1020
agtggaaaat gatgagatgc ctgctgactt gccttcatta gctgctgatt ttgttgaaag    1080
taaggatgtt tgcaaaaact atgctgaggc aaaggatgtc ttcctgggca tgtttttgta    1140
tgaatatgca agaaggcatc ctgattactc tgtcgtgctg ctgctgagac ttgccaagac    1200
atatgaaacc actctagaga agtgctgtgc cgctgcagat cctcatgaat gctatgccaa    1260
agtgttcgat gaatttaaac ctcttgtgga agagcctcag aatttaatca aacaaaattg    1320
tgagcttttt gagcagcttg gagagtacaa attccagaat gcgctattag ttcgttacac    1380
caagaaagta ccccaagtgt caactccaac tcttgtagag gtctcaagaa acctaggaaa    1440
agtgggcagc aaatgttgta aacatcctga agcaaaaaga atgccctgtg cagaagacta    1500
tctatccgtg gtcctgaacc agttatgtgt gttgcatgag aaaacgccag taagtgacag    1560
```

```
agtcaccaaa tgctgcacag aatccttggt gaacaggcga ccatgctttt cagctctgga      1620
agtcgatgaa acatacgttc ccaaagagtt taatgctgaa acattcacct tccatgcaga      1680
tatatgcaca ctttctgaga aggagagaca aatcaagaaa caaactgcac ttgttgagct      1740
cgtgaaacac aagcccaagg caacaaaaga gcaactgaaa gctgttatgg atgatttcgc      1800 agctttgta gagaagtgct gcaaggctga cgataaggag acctgctttg ccgaggaggg      1860
taaaaaactt gttgctgcaa gtcaagctgc cttaggctta taacatcaca tttaaaagca      1920
tctcagccta ccatgagaat aagagaaaga aaatgaagat caaaagctta ttcatctgtt      1980 tttcttttc gttggtgtaa agccaacacc ctgtctaaaa aacataaatt tctttaatca      2040
ttttgcctct tttctctgtg cttcaattaa taaaaaatgg aaagaatcta atagagtggt      2100
acagcactgt tatttttcaa agatgtgttg ctatcctgaa aattctgtag gttctgtgga      2160
agttccagtg ttctctctta ttccacttcg gtagaggatt tctagtttct tgtgggctaa      2220
ttaaataaat cattaatact cttctaaaaa aaaaaaaaaa aaaa                        2264
```

<210> SEQ ID NO 5
<211> LENGTH: 313
<212> TYPE: PRT
<213> ORGANISM: Homo sapiens

<400> SEQUENCE: 5

```
Met Tyr Val Ser Tyr Leu Leu Asp Lys Asp Val Ser Met Tyr Pro Ser
1               5                   10                  15

Ser Val Arg His Ser Gly Gly Leu Asn Leu Ala Pro Gln Asn Phe Val
            20                  25                  30

Ser Pro Pro Gln Tyr Pro Asp Tyr Gly Gly Tyr His Val Ala Ala Ala
        35                  40                  45

Ala Ala Ala Ala Ala Asn Leu Asp Ser Ala Gln Ser Pro Gly Pro Ser
    50                  55                  60

Trp Pro Ala Ala Tyr Gly Ala Pro Leu Arg Glu Asp Trp Asn Gly Tyr
65                  70                  75                  80

Ala Pro Gly Gly Ala Ala Ala Ala Asn Ala Val Ala His Gly Leu
            85                  90                  95

Asn Gly Gly Ser Pro Ala Ala Ala Met Gly Tyr Ser Ser Pro Ala Asp
            100                 105                 110

Tyr His Pro His His Pro His His His Pro His His Pro Ala Ala
            115                 120                 125

Ala Pro Ser Cys Ala Ser Gly Leu Leu Gln Thr Leu Asn Pro Gly Pro
    130                 135                 140

Pro Gly Pro Ala Ala Thr Ala Ala Ala Glu Gln Leu Ser Pro Gly Gly
145                 150                 155                 160

Gln Arg Arg Asn Leu Cys Glu Trp Met Arg Lys Pro Ala Gln Gln Ser
            165                 170                 175

Leu Gly Ser Gln Val Lys Thr Arg Thr Lys Asp Lys Tyr Arg Val Val
            180                 185                 190

Tyr Thr Asp His Gln Arg Leu Glu Leu Glu Lys Glu Phe His Tyr Ser
        195                 200                 205

Arg Tyr Ile Thr Ile Arg Arg Lys Ala Glu Leu Ala Ala Thr Leu Gly
        210                 215                 220

Leu Ser Glu Arg Gln Val Lys Ile Trp Phe Gln Asn Arg Arg Ala Lys
225                 230                 235                 240

Glu Arg Lys Ile Asn Lys Lys Lys Leu Gln Gln Gln Gln Gln Gln
            245                 250                 255
```

-continued

```
Pro Pro Gln Pro Pro Pro Pro Pro Pro Gln Pro Pro Gln Pro Gln Pro
        260              265              270

Gly Pro Leu Arg Ser Val Pro Glu Pro Leu Ser Pro Val Ser Ser Leu
        275              280              285

Gln Ala Ser Val Ser Gly Ser Val Pro Gly Val Leu Gly Pro Thr Gly
    290              295              300

Gly Val Leu Asn Pro Thr Val Thr Gln
305              310

<210> SEQ ID NO 6
<211> LENGTH: 2370
<212> TYPE: DNA
<213> ORGANISM: Homo sapiens

<400> SEQUENCE: 6
ctccaaccat tggtgtctgt gtcattacta atagagtctt gtaaacactc gttaatcacg        60
gaaggccgcc ggcctggggc tccgcacgcc agcctgtggc gggtcttccc cgcctctgca       120
gcctagtggg aaggaggtgg gaggaaagaa ggaagaaagg gagggaggga ggaggcaggc       180
cagagggagg gaccgcctcg gaggcagaag agccgcgagg agccagcgga gcaccgcggg       240
ctggggcgca gccacccgcc gctcctcgag tcccctcgcc cctttccctt cgtgccccct       300
ggcagcctcc agcgtcggtc cccaggcagc atggtgaggt ctgctcccgg accctcgcca       360
ccatgtacgt gagctacctc ctggacaagg acgtgagcat gtaccctagc tccgtgcgcc       420
actctggcgg cctcaacctg gcgccgcaga acttcgtcag ccccccgcag tacccggact       480
acggcggtta ccacgtggcg gccgcagctg cagcggcagc gaacttggac agcgcgcagt       540 ccccgggggcc atcctggccg gcagcgtatg gcgccccact ccgggaggac tggaatggct       600
acgcgcccgg aggcgccgcg gccgccgcca acgccgtggc tcacggcctc aacggtggct       660
ccccggccgc agccatgggc tacagcagcc ccgcagacta ccatccgcac caccacccgc       720
atcaccaccc gcaccacccg gccgccgcgc cttcctgcgc ttctgggctg ctgcaaacgc       780
tcaaccccgg ccctcctggg cccgccgcca ccgctgccgc cgagcagctg tctcccggcg       840
gccagcggcg gaacctgtgc gagtggatgc ggaagccggc gcagcagtcc ctcggcagcc       900
aagtgaaaac caggacgaaa gacaaatatc gagtggtgta cacggaccac cagcggctgg       960
agctggagaa ggagtttcac tacagtcgct acatcaccat ccggaggaaa gccgagctag      1020
ccgccacgct ggggctctct gagaggcagg ttaaaatctg gtttcagaac cgcagagcaa      1080
aggagaggaa aatcaacaag aagaagttgc agcagcaaca gcagcagcag ccaccacagc      1140
cgcctccgcc gccaccacag cctccccagc ctcagccagg tcctctgaga agtgtcccag      1200
agcccttgag tccggtgtct tccctgcaag cctcagtgtc tggctctgtc cctggggttc      1260
tggggccaac tgggggggtg ctaaacccca ccgtcaccca gtgacccacc gggttctgca      1320
gcggcagagc aattccaggc tgagccatga ggagcgtgga ctctgctaga ctcctcagga      1380
gagaccccta ccctcccacc cacagccata gacctacaga cctggctctc agaggaaaaa      1440
tgggagccag gagtaagaca agtgggattt ggggcctcaa gaaatatact ctcccagatt      1500 tttactttt cccatctggc tttttctgcc actgaggaga cagaaagcct ccgctgggct      1560
tcattccgga ctggcagaag cattgcctgg actgaccaca ccaaccaggc cttcatcctc      1620
ctccccagct cttctcttcc tagatctgca ggctgcacct ctggctagag ccgagggggag      1680 agagggactc aagggaaagg caagcttgag gccaagatgg ctgctgcctg ctcatggccc      1740
```

```
tcggaggtcc agctgggcct cctgcctccg ggcaggcaag gtttacactg cggaagccaa      1800
aggcagctaa gatagaaagc tggactgacc aaagactgca gaaccccag gtggcctgcg       1860 tctttttct cttcccttcc cagaccagga aaggcttggc tggtgtatgc acagggtgtg      1920
gtatgagggg gtggttattg gactccaggc ctgaccaggg ggcccgaaca gggacttgtt      1980
tagagagcct gtcaccagag cttctctggg ctgaatgtat gtcagtgcta taaatgccag     2040
agccaacctg gacttcctgt cattttcaca atcttggggc tgatgaagaa ggggggtgggg    2100 ggagtttgtg ttgttgttgc tgctgtttgg gttgttggtc tgtgtaacat ccaagccaga     2160 gttttttaaag ccttctggat ccatgggggg agaagtgata tggtgaaggg aagtggggag    2220
tatttgaaca cagttgaatt ttttctaaaa agaaaaagag ataaatgagc tttccagatt     2280
tcagattctg tatttatctt cagattttgt ctgcaactat tttttatttt ttaaagaaat     2340
gaaatatctt caaaaaaaaa aaaaaaaaa                                       2370
```

<210> SEQ ID NO 7
<211> LENGTH: 503
<212> TYPE: PRT
<213> ORGANISM: Homo sapiens

<400> SEQUENCE: 7

```
Met Asp Leu Ile Pro Asn Leu Ala Val Glu Thr Trp Leu Leu Leu Ala
1               5                   10                  15

Val Ser Leu Ile Leu Leu Tyr Leu Tyr Gly Thr Arg Thr His Gly Leu
            20                  25                  30

Phe Lys Lys Leu Gly Ile Pro Gly Pro Thr Pro Leu Pro Phe Leu Gly
        35                  40                  45

Asn Ala Leu Ser Phe Arg Lys Gly Tyr Trp Thr Phe Asp Met Glu Cys
    50                  55                  60

Tyr Lys Lys Tyr Arg Lys Val Trp Gly Ile Tyr Asp Cys Gln Gln Pro
65                  70                  75                  80

Met Leu Ala Ile Thr Asp Pro Asp Met Ile Lys Thr Val Leu Val Lys
                85                  90                  95

Glu Cys Tyr Ser Val Phe Thr Asn Arg Arg Pro Phe Gly Pro Val Gly
            100                 105                 110

Phe Met Lys Asn Ala Ile Ser Ile Ala Glu Asp Glu Glu Trp Lys Arg
        115                 120                 125

Ile Arg Ser Leu Leu Ser Pro Thr Phe Thr Ser Gly Lys Leu Lys Glu
    130                 135                 140

Met Val Pro Ile Ile Ala Gln Tyr Gly Asp Val Leu Val Arg Asn Leu
145                 150                 155                 160

Arg Arg Glu Ala Glu Thr Gly Lys Pro Val Thr Leu Lys His Val Phe
                165                 170                 175

Gly Ala Tyr Ser Met Asp Val Ile Thr Ser Thr Ser Phe Gly Val Ser
            180                 185                 190

Ile Asp Ser Leu Asn Asn Pro Gln Asp Pro Phe Val Glu Asn Thr Lys
        195                 200                 205

Lys Leu Leu Arg Phe Asn Pro Leu Asp Pro Phe Val Leu Ser Ile Lys
    210                 215                 220

Val Phe Pro Phe Leu Thr Pro Ile Leu Glu Ala Leu Asn Ile Thr Val
225                 230                 235                 240

Phe Pro Arg Lys Val Ile Ser Phe Leu Thr Lys Ser Val Lys Gln Ile
                245                 250                 255

Lys Glu Gly Arg Leu Lys Glu Thr Gln Lys His Arg Val Asp Phe Leu
```

```
                260               265               270
Gln Leu Met Ile Asp Ser Gln Asn Ser Lys Asp Ser Glu Thr His Lys
         275               280               285
Ala Leu Ser Asp Leu Glu Leu Met Ala Gln Ser Ile Ile Phe Ile Phe
     290               295               300
Ala Gly Tyr Glu Thr Thr Ser Ser Val Leu Ser Phe Ile Ile Tyr Glu
305               310               315               320
Leu Ala Thr His Pro Asp Val Gln Gln Lys Val Gln Lys Glu Ile Asp
             325               330               335
Thr Val Leu Pro Asn Lys Ala Pro Pro Thr Tyr Asp Thr Val Leu Gln
             340               345               350
Leu Glu Tyr Leu Asp Met Val Val Asn Glu Thr Leu Arg Leu Phe Pro
         355               360               365
Val Ala Met Arg Leu Glu Arg Val Cys Lys Lys Asp Val Glu Ile Asn
     370               375               380
Gly Met Phe Ile Pro Lys Gly Val Val Val Met Ile Pro Ser Tyr Val
385               390               395               400
Leu His His Asp Pro Lys Tyr Trp Thr Glu Pro Glu Lys Phe Leu Pro
             405               410               415
Glu Arg Phe Ser Lys Lys Asn Lys Asp Asn Ile Asp Pro Tyr Ile Tyr
             420               425               430
Thr Pro Phe Gly Ser Gly Pro Arg Asn Cys Ile Gly Met Arg Phe Ala
             435               440               445
Leu Val Asn Met Lys Leu Ala Leu Val Arg Val Leu Gln Asn Phe Ser
     450               455               460
Phe Lys Pro Cys Lys Glu Thr Gln Ile Pro Leu Lys Leu Arg Phe Gly
465               470               475               480
Gly Leu Leu Leu Thr Glu Lys Pro Ile Val Leu Lys Ala Glu Ser Arg
             485               490               495
Asp Glu Thr Val Ser Gly Ala
             500
```

```
<210> SEQ ID NO 8
<211> LENGTH: 2099
<212> TYPE: DNA
<213> ORGANISM: Homo sapiens

<400> SEQUENCE: 8
aatcactgct gtgcagggca ggaaagctcc acacacacag cccagcaaac agcagcacgc      60
tgctgaaaaa aagactcaga ggagagagat aaggaaggaa agtagtgatg gatctcatcc     120
caaacttggc cgtggaaacc tggcttctcc tggctgtcag cctgatactc ctctatctat     180
atggaacccg tacacatgga cttttttaaga agcttggaat tccagggccc acacctctgc    240
cttttttggg aaatgctttg tccttccgta agggctattg gacgtttgac atggaatgtt     300
ataaaaagta tagaaaagtc tggggtattt atgactgtca acagcctatg ctggctatca     360
cagatcccga catgatcaaa acagtgctag tgaaagaatg ttattctgtc ttcacaaacc     420
ggaggccttt cgggccagtg ggatttatga aaaatgccat ctctatagct gaggatgaag     480
aatggaagag aatacgatca ttgctgtctc caacattcac cagcggaaaa ctcaaggaga     540
tggtccctat cattgcccag tatggagatg tgttggtgag aaatctgagg cgggaagcag     600
agacaggcaa gcctgtcacc ttgaaacacg tctttgggGc ctacagcatg gatgtgatca     660
ctagcacatc atttggagtg agcatcgact ctctcaacaa tccacaagac ccctttgtgg     720
```

```
aaaacaccaa gaagctttta agatttaatc cattagatcc attcgttctc tcaataaaag   780
tctttccatt ccttacccca attcttgaag cattaaatat cactgtgttt ccaagaaaag   840
ttataagttt tctaacaaaa tctgtaaaac agataaaaga aggtcgcctc aaagagacac   900
aaaagcaccg agtggatttc cttcagctga tgattgactc tcagaattca aaagactctg   960
agacccacaa agctctgtct gatctggagc tcatggccca atcaattatc tttatttttg  1020
ctggctatga aaccacgagc agtgttctct ccttcattat atatgaactg gccactcacc  1080
ctgatgtcca gcagaaagtg cagaaggaaa ttgatacagt tttacccaat aaggcaccac  1140
ccacctatga tactgtgcta cagttggagt atcttgacat ggtggtgaat gaaacactca  1200
gattattccc agttgctatg agacttgaga gggtctgcaa aaaagatgtt gaaatcaatg  1260
ggatgtttat tcccaaaggg gtggtggtga tgattccaag ctatgttctt catcatgacc  1320
caaagtactg gacagagcct gagaagttcc tccctgaaag gttcagtaaa aagaacaagg  1380
acaacataga tccttacata tacacaccct ttggaagtgg acccagaaac tgcattggca  1440
tgaggtttgc tctcgtgaac atgaaacttg ctctagtcag agtccttcag aacttctcct  1500
tcaaaccttg taaagaaaca cagatccccc tgaaattacg ctttggagga cttcttctaa  1560
cagaaaaacc cattgttcta aaggctgagt caagggatga gaccgtaagt ggagcctgat  1620
ttccctaagg acttctggtt tgctcttttaa gaaagctgtg ccccagaaca ccagagacct  1680
caaattactt tacaaataga accctgaaat gaagacgggc ttcatccaat gtgctgcata  1740
aataatcagg gattctgtac gtgcattgtg ctctctcatg gtctgtatag agtgttatac  1800
ttggtaatat agaggagatg accaaatcag tgctggggaa gtagatttgg cttctctgct  1860
tctcatagga ctatctccac caccccagt tagcaccatt aactcctcct gagctctgat  1920
aacataatta acatttctca ataatttcaa ccacaatcat taataaaaat aggaattatt  1980
ttgatggctc taacagtgac atttatatca tgtgttatat ctgtagtatt ctatagtaag  2040
ctttatatta agcaaatcaa taaaaacctc tttacaaaag taaaaaaaaa aaaaaaaaa   2099
```

<210> SEQ ID NO 9
<211> LENGTH: 435
<212> TYPE: PRT
<213> ORGANISM: Homo sapiens

<400> SEQUENCE: 9

```
Met Ser Asn Lys Asp Arg His Ile Asp Ser Ser Cys Ser Ser Phe Ile
1               5                  10                  15

Lys Thr Glu Pro Ser Ser Pro Ala Ser Leu Thr Asp Ser Val Asn His
            20                  25                  30

His Ser Pro Gly Gly Ser Ser Asp Ala Ser Gly Ser Tyr Ser Ser Thr
        35                  40                  45

Met Asn Gly His Gln Asn Gly Leu Asp Ser Pro Pro Leu Tyr Pro Ser
    50                  55                  60

Ala Pro Ile Leu Gly Gly Ser Gly Pro Val Arg Lys Leu Tyr Asp Asp
65                  70                  75                  80

Cys Ser Ser Thr Ile Val Glu Asp Pro Gln Thr Lys Cys Glu Tyr Met
                85                  90                  95

Leu Asn Ser Met Pro Lys Arg Leu Cys Leu Val Cys Gly Asp Ile Ala
            100                 105                 110

Ser Gly Tyr His Tyr Gly Val Ala Ser Cys Glu Ala Cys Lys Ala Phe
        115                 120                 125

Phe Lys Arg Thr Ile Gln Gly Asn Ile Glu Tyr Ser Cys Pro Ala Thr
```

```
           130                 135                 140
Asn Glu Cys Glu Ile Thr Lys Arg Arg Arg Lys Ser Cys Gln Ala Cys
145                 150                 155                 160

Arg Phe Met Lys Cys Leu Lys Val Gly Met Leu Lys Glu Gly Val Arg
                165                 170                 175

Leu Asp Arg Val Arg Gly Gly Arg Gln Lys Tyr Lys Arg Arg Ile Asp
                180                 185                 190

Ala Glu Asn Ser Pro Tyr Leu Asn Pro Gln Leu Val Gln Pro Ala Lys
            195                 200                 205

Lys Pro Tyr Asn Lys Ile Val Ser His Leu Leu Val Ala Glu Pro Glu
        210                 215                 220

Lys Ile Tyr Ala Met Pro Asp Pro Thr Val Pro Asp Ser Asp Ile Lys
225                 230                 235                 240

Ala Leu Thr Thr Leu Cys Asp Leu Ala Asp Arg Glu Leu Val Val Ile
                245                 250                 255

Ile Gly Trp Ala Lys His Ile Pro Gly Phe Ser Thr Leu Ser Leu Ala
                260                 265                 270

Asp Gln Met Ser Leu Leu Gln Ser Ala Trp Met Glu Ile Leu Ile Leu
            275                 280                 285

Gly Val Val Tyr Arg Ser Leu Ser Phe Glu Asp Glu Leu Val Tyr Ala
        290                 295                 300

Asp Asp Tyr Ile Met Asp Glu Asp Gln Ser Lys Leu Ala Gly Leu Leu
305                 310                 315                 320

Asp Leu Asn Asn Ala Ile Leu Gln Leu Val Lys Lys Tyr Lys Ser Met
                325                 330                 335

Lys Leu Glu Lys Glu Glu Phe Val Thr Leu Lys Ala Ile Ala Leu Ala
            340                 345                 350

Asn Ser Asp Ser Met His Ile Glu Asp Val Glu Ala Val Gln Lys Leu
            355                 360                 365

Gln Asp Val Leu His Glu Ala Leu Gln Asp Tyr Glu Ala Gly Gln His
        370                 375                 380

Met Glu Asp Pro Arg Arg Ala Gly Lys Met Leu Met Thr Leu Pro Leu
385                 390                 395                 400

Leu Arg Gln Thr Ser Thr Lys Ala Val Gln His Phe Tyr Asn Ile Lys
                405                 410                 415

Leu Glu Gly Lys Val Pro Met His Lys Leu Phe Leu Glu Met Leu Glu
            420                 425                 430

Ala Lys Val
        435
```

```
<210> SEQ ID NO 10
<211> LENGTH: 5559
<212> TYPE: DNA
<213> ORGANISM: Homo sapiens

<400> SEQUENCE: 10
aagctccaat cggggcttta agtccttgat taggagagtg tgagagcttt ggtcccaact      60
ggctgtgcct ataggcttgt cactaggaga acatttgtgt taattgcact gtgctctgtc     120
aaggaaactt tgatttatag ctggggtgca caaataatgg ttgccggtcg cacatggatt     180
cggtagaact ttgccttcct gaatcttttt ccctgcacta cgaggaagag tagacttgaa     240
tgagacctgc ctcatcagtc atgggatcat agtgtcacag atggaaaagc aactatcagc     300
tgaattgtac tgaactacac acttggctaa ttcatcttat tgctctacac atctaaagga     360
```

```
aggctcattc tgttcttgga gtctagacag catcaggagt tgggctcagt gaacaaaact    420
ttaatgtcta gagcatttat gagggtttta atgattggaa aatctatcct gagaatgtgg    480
tcaccatatg tgacagcctt gctttctatc ttgtcttcag tttctggggc ttctctgcag    540
aatgtcaaac aaagatcgac acattgattc cagctgttcg tccttcatca agacggaacc    600
ttccagccca gcctccctga cggacagcgt caaccaccac agccctggtg gctcttcaga    660
cgccagtggg agctacagtt caaccatgaa tggccatcag aacggacttg actgccacc    720 tctctaccct tctgctccta tcctgggagg tagtgggcct gtcaggaaac tgtatgatga    780
ctgctccagc accattgttg aagatcccca gaccaagtgt gaatacatgc tcaactcgat    840
gcccaagaga ctgtgtttag tgtgtggtga catcgcttct gggtaccact atggggtagc    900
atcatgtgaa gcctgcaagg cattcttcaa gaggacaatt caaggcaata tagaatacag    960
ctgccctgcc acgaatgaat gtgaaatcac aaagcgcaga cgtaaatcct gccaggcttg   1020
ccgcttcatg aagtgtttaa aagtgggcat gctgaaagaa ggggtgcgtc ttgacagagt   1080
acgtggaggt cggcagaagt acaagcgcag gatagatgcg gagaacagcc catacctgaa   1140
ccctcagctg gttcagccag ccaaaaagcc atataacaag attgtctcac atttgttggt   1200
ggctgaaccg gagaagatct atgccatgcc tgaccctact gtccccgaca gtgacatcaa   1260
agccctcact acactgtgtg acttggccga ccgagagttg gtggttatca ttggatgggc   1320
gaagcatatt ccaggcttct ccacgctgtc cctggcggac cagatgagcc ttctgcagag   1380
tgcttggatg gaaattttga tccttggtgt cgtataccgg tctctttcgt ttgaggatga   1440
acttgtctat gcagacgatt atataatgga cgaagaccag tccaaattag caggccttct   1500
tgatctaaat aatgctatcc tgcagctggt aaagaaatac aagagcatga gctggaaaa   1560 agaagaattt gtcaccctca aagctatagc tcttgctaat tcagactcca tgcacataga   1620
agatgttgaa gccgttcaga agcttcagga tgtcttacat gaagcgctgc aggattatga   1680
agctggccag cacatggaag accctcgtcg agctggcaag atgctgatga cactgccact   1740
cctgaggcag acctctacca aggccgtgca gcatttctac aacatcaaac tagaaggcaa   1800
agtcccaatg cacaaacttt ttttggaaat gttggaggcc aaggtctgac taaaagctcc   1860
ctgggccttc ccatccttca tgttgaaaaa gggaaaataa acccaagagt gatgtcgaag   1920
aaacttagag tttagttaac aacatcaaaa atcaacagac tgcactgata atttagcagc   1980
aagactatga agcagctttc agattcctcc ataggttcct gatgagtttc tttctacttt   2040
ctccatcatc ttctttcctc tttcttccca catttctctt tctctttatt ttttctcctt   2100
ttcttctttc acctcccctta tttctttgct tctttcattc ctagttccca ttctcctttta   2160 ttttcttccc gtctgcctgc cttctttctt ttctttacct actctcattc ctctcttttc   2220
tcatccttcc cctttttttct aaatttgaaa tagctttagt ttaaaaaaaa atcctccctt   2280
ccccctttcc tttcccttttc tttccttttt ccctttcctt ttcccttttcc tttccttttcc   2340 tcttgacctt ctttccatct ttctttttct tccttctgct gctgaacttt taaaagaggt   2400
ctctaactga agagagatgg aagccagccc tgccaaagga tggagatcca taatatggat   2460
gccagtgaac ttattgtgaa ccatactgtc cccaatgact aaggaatcaa agagagagaa   2520
ccaacgttcc taaaagtaca gtgcaacata tacaaattga ctgagtgcag tattagattt   2580
catgggagca gcctctaatt agacaactta agcaacgttg catcggctgc ttcttatcat   2640
tgcttttcca tctagatcag ttacagccat ttgattcctt aattgttttt tcaagtcttc   2700
caggtatttg ttagtttagc tactatgtaa ctttttcagg gaatagttta agctttattc   2760
```

-continued

```
attcatgcaa tactaaagag aaataagaat actgcaattt tgtgctggct ttgaacaatt    2820
acgaacaata atgaaggaca aatgaatcct gaaggaagat tttttaaaaat gttttgtttc    2880 ttcttacaaa tggagatttt tttgtaccag ctttaccact tttcagccat ttattaatat    2940
gggaatttaa cttactcaag caatagttga agggaaggtg catattatca cggatgcaat    3000
ttatgttgtg tgccagtctg gtcccaaaca tcaatttctt aacatgagct ccagtttacc    3060
taaatgttca ctgacacaaa ggatgagatt acacctacag tgactctgag tagtcacata    3120
tataagcact gcacatgaga tatagatccg tagaattgtc aggagtgcac ctctctactt    3180
gggaggtaca attgccatat gatttctagc tgccatggtg gttaggaatg tgatactgcc    3240
tgtttgcaaa gtcacagacc ttgcctcaga aggagctgtg agccagtatt catttaagag    3300
gcaataaggc aaatgccaga attaaaaaaa aaaatcatca aagacagaaa atgcctgacc    3360
aaattctaaa acctaatcca tataagttta ttcatttagg aatgttcgtt taaattaatc    3420
tgcagttttt accaagagct aagccaatat atgtgctttt caaccagtat tgtcacagca    3480
tgaaagtcaa gtcaggttcc agactgttaa gaggtgtaat ctaatgaaga aatcaattag    3540
atgccccgaa atctacagtc gctgaataac caataaacag taacctccat caaatgctat    3600
accaatggac cagtgttagt agctgctccc tgtattatgt gaacagtctt attctatgta    3660
cacagatgta attaaaattg taatcctaac aaacaaaaga aatgtagttc agcttttcaa    3720
tgtttcatgt ttgctgtgct tttctgaatt ttatgttgca ttcaaagact gttgtcttgt    3780
tcttgtggtg tttggattct tgtggtgtgt gcttttagac acagggtaga attagagaca    3840
atattggatg tacaattcct caggagacta cagtagtata ttctattcct taccagtaat    3900
aaggttcttc ctaataataa ttaagagatt gaaactccaa acaagtattc attatgaaca    3960
gatacacatc aaaatcataa taatattttc aaaacaagga ataatttctc taatggttta    4020
ttatagaata ccaatgtata gcttagaaat aaaactttga atatttcaag aatatagata    4080
agtctaattt ttaaatgctg tatatatggc tttcactcaa tcatctctca gatgttgtta    4140
ttaactcgct ctgtgttgtt gcaaaacttt ttggtgcaga ttcgtttcca aaactattgc    4200
tactttgtgt gctttaaaca aaataccttg ggttgatgaa acatcaaccc agtgctagga    4260
atactgtgta tctatcatta gctatatggg actatattgt agattgtggt ttctcagtag    4320
agaagtgact gtagtgtgat tctagataaa tcatcattag caattcattc agatggtcaa    4380
taacttgaaa tttatagctg tgataggagt tcagaaattg gcacatccct ttaaaaataa    4440
caacagaaaa tacaactcct gggaaaaaag gtgctgattc tataagatta tttatatatg    4500
taagtgttta aaaagattat tttccagaaa gtttgtgcag ggtttaagtt gctactattc    4560
aactacacta tatataaata aaatatatac aatatataca ttgtttttcac tgtatcacat    4620 taaagtactt gggcttcaga agtaagagcc aaccaactga aaacctgaga tggagatatg    4680
ttcaaagaat gagatacaat tttttagttt tcagtttaag taactctcag cattacaaaa    4740
gagtaagtat ctcacaaata ggaaataaaa ctaaaacgtg gatttaaaaa gaactgcacg    4800
ggctttaggg taaatgctca tcttaaacct cactagaggg aagtcttctc aagtttcaag    4860
caagaccatt tacttaatgt gaagtttttgg aaagttataa aggtgtatgt tttagccata    4920
tgattttaat tttaatttttg cttctttttag gttcgttctt atttaaagca atatgattgt    4980
gtgactcctt gtagttacac ttgtgtttca atcagatcag attgttgtat ttattccact    5040
attttgcatt taaatgataa cataaaagat ataaaaaatt taaaactgct attttttctta    5100
```

```
tagaagagaa aatgggtgtt ggtgattgta ttttaattat ttaagcgtct ctgtttacct      5160
gcctaggaaa acattttatg gcagtcttat gtgcaaagat cgtaaaagga caaaaaattt      5220
aaactgctta taataatcca ggagttgcat tatagccagt agtaaaaata ataataataa      5280
taataaaacc atgtctatag ctgtagatgg gcttcacatc tgtaaagcaa tcaattgtat      5340 attttttgtga tgtgtaccat actgtgtgct ccagcaaatg tccatttgtg taaatgtatt      5400
tattttatat tgtatatatt gttaaatgca aaaaggagat atgattctgt aactccaatc      5460
agttcagatg tgtaactcaa attattatgc ctttcaggat gatggtagag caatattaaa      5520
caagcttcca cttttgactg ctaaaaaaaa aaaaaaaaa                           5559
```

```
<210> SEQ ID NO 11
<211> LENGTH: 463
<212> TYPE: PRT
<213> ORGANISM: Homo sapiens

<400> SEQUENCE: 11

Met His Ser Ala Ser Ser Met Leu Gly Ala Val Lys Met Glu Gly His
1               5                   10                  15

Glu Pro Ser Asp Trp Ser Ser Tyr Tyr Ala Glu Pro Glu Gly Tyr Ser
                20                  25                  30

Ser Val Ser Asn Met Asn Ala Gly Leu Gly Met Asn Gly Met Asn Thr
            35                  40                  45

Tyr Met Ser Met Ser Ala Ala Ala Met Gly Ser Gly Ser Gly Asn Met
        50                  55                  60

Ser Ala Gly Ser Met Asn Met Ser Ser Tyr Val Gly Ala Gly Met Ser
65                  70                  75                  80

Pro Ser Leu Ala Gly Met Ser Pro Gly Ala Gly Ala Met Ala Gly Met
                85                  90                  95

Gly Gly Ser Ala Gly Ala Ala Gly Val Ala Gly Met Gly Pro His Leu
            100                 105                 110

Ser Pro Ser Leu Ser Pro Leu Gly Gly Gln Ala Ala Gly Ala Met Gly
        115                 120                 125

Gly Leu Ala Pro Tyr Ala Asn Met Asn Ser Met Ser Pro Met Tyr Gly
        130                 135                 140

Gln Ala Gly Leu Ser Arg Ala Arg Asp Pro Lys Thr Tyr Arg Arg Ser
145                 150                 155                 160

Tyr Thr His Ala Lys Pro Pro Tyr Ser Tyr Ile Ser Leu Ile Thr Met
                165                 170                 175

Ala Ile Gln Gln Ser Pro Asn Lys Met Leu Thr Leu Ser Glu Ile Tyr
                180                 185                 190

Gln Trp Ile Met Asp Leu Phe Pro Phe Tyr Arg Gln Asn Gln Gln Arg
            195                 200                 205

Trp Gln Asn Ser Ile Arg His Ser Leu Ser Phe Asn Asp Cys Phe Leu
        210                 215                 220

Lys Val Pro Arg Ser Pro Asp Lys Pro Gly Lys Gly Ser Phe Trp Thr
225                 230                 235                 240

Leu His Pro Asp Ser Gly Asn Met Phe Glu Asn Gly Cys Tyr Leu Arg
                245                 250                 255

Arg Gln Lys Arg Phe Lys Cys Glu Lys Gln Leu Ala Leu Lys Glu Ala
            260                 265                 270

Ala Gly Ala Ala Gly Ser Gly Lys Lys Ala Ala Ala Gly Ala Gln Ala
        275                 280                 285

Ser Gln Ala Gln Leu Gly Glu Ala Ala Gly Pro Ala Ser Glu Thr Pro
```

-continued

```
            290              295              300
Ala Gly Thr Glu Ser Pro His Ser Ser Ala Ser Pro Cys Gln Glu His
305                  310              315              320

Lys Arg Gly Gly Leu Gly Glu Leu Lys Gly Thr Pro Ala Ala Ala Leu
                 325              330              335

Ser Pro Pro Glu Pro Ala Pro Ser Pro Gly Gln Gln Gln Ala Ala
             340              345              350

Ala His Leu Leu Gly Pro Pro His His Pro Gly Leu Pro Pro Glu Ala
         355              360              365

His Leu Lys Pro Glu His His Tyr Ala Phe Asn His Pro Phe Ser Ile
     370              375              380

Asn Asn Leu Met Ser Ser Glu Gln Gln His His His Ser His His His
385                  390              395              400

His Gln Pro His Lys Met Asp Leu Lys Ala Tyr Glu Gln Val Met His
                 405              410              415

Tyr Pro Gly Tyr Gly Ser Pro Met Pro Gly Ser Leu Ala Met Gly Pro
                 420              425              430

Val Thr Asn Lys Thr Gly Leu Asp Ala Ser Pro Leu Ala Ala Asp Thr
         435              440              445

Ser Tyr Tyr Gln Gly Val Tyr Ser Arg Pro Ile Met Asn Ser Ser
     450              455              460
```

```
<210> SEQ ID NO 12
<211> LENGTH: 2428
<212> TYPE: DNA
<213> ORGANISM: Homo sapiens

<400> SEQUENCE: 12
cccgcccact tccaactacc gcctccggcc tgcccaggga gagagaggga gtggagccca     60
gggagaggga gcgcgagaga gggagggagg aggggacggt gctttggctg actttttttt    120
aaaagagggt gggggtgggg ggtgattgct ggtcgtttgt tgtggctgtt aaattttaaa    180
ctgccatgca ctcggcttcc agtatgctgg gagcggtgaa gatggaaggg cacgagccgt    240
ccgactggag cagctactat gcagagcccg agggctactc ctccgtgagc aacatgaacg    300
ccggcctggg gatgaacggc atgaacacgt acatgagcat gtcggcggcc gccatgggca    360
gcggctcggg caacatgagc gcgggctcca tgaacatgtc gtcgtacgtg ggcgctggca    420
tgagcccgtc cctggcgggg atgtcccccg gcgcgggcgc catggcgggc atgggcggct    480
cggccggggc ggccggcgtg gcgggcatgg ggccgcactt gagtcccagc ctgagcccgc    540
tcggggggca ggcggccggg gccatgggcg gcctggcccc ctacgccaac atgaactcca    600
tgagccccat gtacgggcag gcgggcctga gccgcgcccg cgaccccaag acctacaggc    660
gcagctacac gcacgcaaag ccgccctact cgtacatctc gctcatcacc atggccatcc    720
agcagagccc caacaagatg ctgacgctga gcgagatcta ccagtggatc atggacctct    780
tccccttcta ccggcagaac cagcagcgct ggcagaactc catccgccac tcgctctcct    840
tcaacgactg tttcctgaag gtgcccgct cgcccgacaa gcccggcaag ggctccttct    900
ggaccctgca ccctgactcg ggcaacatgt tcgagaacgg ctgctacctg cgccgccaga    960
agcgcttcaa gtgcgagaag cagctggcgc tgaaggaggc cgcaggcgcc gccggcagcg   1020
gcaagaaggc ggccgccgga gcccaggcct cacaggctca actcggggag gccgccgggc   1080
cggcctccga gactccggcg ggcaccgagt cgcctcactc gagcgcctcc ccgtgccagg   1140
agcacaagcg aggggggcctg ggagagctga aggggacgcc ggctgcggcg ctgagccccc   1200
```

-continued

```
cagagccggc gccctctccc gggcagcagc agcaggccgc ggcccacctg ctgggcccgc    1260
cccaccaccc gggcctgccg cctgaggccc acctgaagcc ggaacaccac tacgccttca    1320 accaccgtt ctccatcaac aacctcatgt cctcggagca gcagcaccac cacagccacc    1380
accaccacca accccacaaa atggacctca aggcctacga acaggtgatg cactaccccg    1440
gctacggttc ccccatgcct ggcagcttgg ccatgggccc ggtcacgaac aaaacgggcc    1500
tggacgcctc gccctggcc gcagatacct cctactacca gggggtgtac tcccggccca    1560
ttatgaactc ctcttaagaa gacgacggct tcaggcccgg ctaactctgg caccccggat    1620
cgaggacaag tgagagagca agtggggggtc gagactttgg ggagacggtg ttgcagagac    1680
gcaagggaga agaaatccat aacacccca ccccaacacc cccaagacag cagtcttctt    1740
cacccgctgc agccgttccg tcccaaacag agggccacac agatacccca cgttctatat    1800
aaggaggaaa acgggaaaga atataaagtt aaaaaaaagc ctccggtttc cactactgtg    1860
tagactcctg cttcttcaag cacctgcaga ttctgatttt tttgttgttg ttgttctcct    1920
ccattgctgt tgttgcaggg aagtcttact taaaaaaaaa aaaaaatttt gtgagtgact    1980
cggtgtaaaa ccatgtagtt ttaacagaac cagaggggttg tactattgtt taaaaacagg    2040
aaaaaaaata atgtaagggt ctgttgtaaa tgaccaagaa aaagaaaaaa aaagcattcc    2100
caatcttgac acggtgaaat ccaggtctcg ggtccgatta atttatggtt tctgcgtgct    2160
ttatttatgg cttataaatg tgtattctgg ctgcaagggc cagagttcca caaatctata    2220
ttaaagtgtt atacccggtt ttatcccttg aatcttttct tccagatttt tcttttcttt    2280
acttggctta caaaatatac aggcttggaa attatttcaa gaaggaggga gggataccct    2340
gtctggttgc aggttgtatt ttattttggc ccagggagtg ttgctgtttt cccaacattt    2400
tattaataaa attttcagac ataaaaaa                                      2428
```

```
<210> SEQ ID NO 13
<211> LENGTH: 595
<212> TYPE: PRT
<213> ORGANISM: Homo sapiens

<400> SEQUENCE: 13

Met Ala Leu Thr Asp Gly Gly Trp Cys Leu Pro Lys Arg Phe Gly Ala
1               5                   10                  15

Ala Gly Ala Asp Ala Ser Asp Ser Arg Ala Phe Pro Ala Arg Glu Pro
            20                  25                  30

Ser Thr Pro Pro Ser Pro Ile Ser Ser Ser Ser Ser Cys Ser Arg
        35                  40                  45

Gly Gly Glu Arg Gly Pro Gly Gly Ala Ser Asn Cys Gly Thr Pro Gln
    50                  55                  60

Leu Asp Thr Glu Ala Ala Ala Gly Pro Pro Ala Arg Ser Leu Leu Leu
65                  70                  75                  80

Ser Ser Tyr Ala Ser His Pro Phe Gly Ala Pro His Gly Pro Ser Ala
                85                  90                  95

Pro Gly Val Ala Gly Pro Gly Gly Asn Leu Ser Ser Trp Glu Asp Leu
            100                 105                 110

Leu Leu Phe Thr Asp Leu Asp Gln Ala Ala Thr Ala Ser Lys Leu Leu
        115                 120                 125

Trp Ser Ser Arg Gly Ala Lys Leu Ser Pro Phe Ala Pro Glu Gln Pro
    130                 135                 140

Glu Glu Met Tyr Gln Thr Leu Ala Ala Leu Ser Ser Gln Gly Pro Ala
```

-continued

```
145              150              155              160

Ala Tyr Asp Gly Ala Pro Gly Gly Phe Val His Ser Ala Ala Ala Ala
             165              170              175

Ala Ala Ala Ala Ala Ala Ala Ser Ser Pro Val Tyr Val Pro Thr Thr
             180              185              190

Arg Val Gly Ser Met Leu Pro Gly Leu Pro Tyr His Leu Gln Gly Ser
             195              200              205

Gly Ser Gly Pro Ala Asn His Ala Gly Gly Ala Gly Ala His Pro Gly
         210              215              220

Trp Pro Gln Ala Ser Ala Asp Ser Pro Pro Tyr Gly Ser Gly Gly Gly
225              230              235              240

Ala Ala Gly Gly Gly Ala Ala Gly Pro Gly Gly Ala Gly Ser Ala Ala
             245              250              255

Ala His Val Ser Ala Arg Phe Pro Tyr Ser Pro Ser Pro Pro Met Ala
             260              265              270

Asn Gly Ala Ala Arg Glu Pro Gly Gly Tyr Ala Ala Ala Gly Ser Gly
             275              280              285

Gly Ala Gly Gly Val Ser Gly Gly Gly Ser Ser Leu Ala Ala Met Gly
         290              295              300

Gly Arg Glu Pro Gln Tyr Ser Ser Leu Ser Ala Ala Arg Pro Leu Asn
305              310              315              320

Gly Thr Tyr His His His His His His His His His Pro Ser Pro
             325              330              335

Tyr Ser Pro Tyr Val Gly Ala Pro Leu Thr Pro Ala Trp Pro Ala Gly
             340              345              350

Pro Phe Glu Thr Pro Val Leu His Ser Leu Gln Ser Arg Ala Gly Ala
             355              360              365

Pro Leu Pro Val Pro Arg Gly Pro Ser Ala Asp Leu Leu Glu Asp Leu
         370              375              380

Ser Glu Ser Arg Glu Cys Val Asn Cys Gly Ser Ile Gln Thr Pro Leu
385              390              395              400

Trp Arg Arg Asp Gly Thr Gly His Tyr Leu Cys Asn Ala Cys Gly Leu
             405              410              415

Tyr Ser Lys Met Asn Gly Leu Ser Arg Pro Leu Ile Lys Pro Gln Lys
             420              425              430

Arg Val Pro Ser Ser Arg Arg Leu Gly Leu Ser Cys Ala Asn Cys His
             435              440              445

Thr Thr Thr Thr Thr Leu Trp Arg Arg Asn Ala Glu Gly Glu Pro Val
         450              455              460

Cys Asn Ala Cys Gly Leu Tyr Met Lys Leu His Gly Val Pro Arg Pro
465              470              475              480

Leu Ala Met Lys Lys Glu Gly Ile Gln Thr Arg Lys Arg Lys Pro Lys
             485              490              495

Asn Ile Asn Lys Ser Lys Thr Cys Ser Gly Asn Ser Asn Asn Ser Ile
             500              505              510

Pro Met Thr Pro Thr Ser Thr Ser Ser Asn Ser Asp Asp Cys Ser Lys
             515              520              525

Asn Thr Ser Pro Thr Thr Gln Pro Thr Ala Ser Gly Ala Gly Ala Pro
         530              535              540

Val Met Thr Gly Ala Gly Glu Ser Thr Asn Pro Glu Asn Ser Glu Leu
545              550              555              560

Lys Tyr Ser Gly Gln Asp Gly Leu Tyr Ile Gly Val Ser Leu Ala Ser
             565              570              575
```

Pro Ala Glu Val Thr Ser Ser Val Arg Pro Asp Ser Trp Cys Ala Leu
        580                      585                  590

Ala Leu Ala
        595

<210> SEQ ID NO 14
<211> LENGTH: 3785
<212> TYPE: DNA
<213> ORGANISM: Homo sapiens

<400> SEQUENCE: 14
agttccgacc cacagcctgg cacccttcgg cgagcgctgt ttgtttaggg ctcggtgagt        60
ccaatcagga gcccaggctg cagttttccg gcagagcagt aagaggcgcc tcctctctcc       120
tttttattca ccagcagcgc ggcgcagacc ccggactcgc gctcgcccgc tggcgccctc       180
ggcttctctc cgcgcctggg agcaccctcc gccgcggccg ttctccatgc gcagcgcccg       240
cccgaggagc tagacgtcag cttggagcgg cgccggaccg tggatggcct tgactgacgg       300
cggctggtgc ttgccgaagc gcttcggggc cgcgggtgcg gacgccagcg actccagagc       360
ctttccagcg cgggagccct ccacgccgcc ttcccccatc tcttcctcgt cctcctcctg       420
ctcccggggc ggagagcggg gccccggcgg cgccagcaac tgcgggacgc ctcagctcga       480
cacggaggcg gcggccggac ccccggcccg ctcgctgctg ctcagttcct acgcttcgca       540
tcccttcggg gctccccacg gaccttcggc gcctggggtc gcgggccccg ggggcaacct       600
gtcgagctgg gaggacttgc tgctgttcac tgacctcgac caagccgcga ccgccagcaa       660
gctgctgtgg tccagccgcg gcgccaagct gagccccttc gcacccgagc agccggagga       720
gatgtaccag accctcgccg ctctctccag ccagggtccg gccgcctacg acggcgcgcc       780
cggcggcttc gtgcactctg cggccgcggc ggcagcagcc gcggcggcgg ccagctcccc       840
ggtctacgtg cccaccaccc gcgtgggttc catgctgccc ggcctaccgt accacctgca       900
ggggtcgggc agtgggccag ccaaccacgc gggcggcgcg ggcgcgcacc ccggctggcc       960
tcaggcctcg gccgacagcc ctccatacgg cagcggaggc ggcgcggctg cggcgggggc      1020
cgcggggcct ggcggcgctg gctcagccgc ggcgcacgtc tcggcgcgct tcccctactc      1080
tcccagcccg cccatggcca acggcgccgc gcgggagccg ggaggctacg cggcggcggg      1140
cagtgggggc gcgggaggcg tgagcggcgg cggcagtagc ctggcggcca tgggcggccg      1200
cgagccccag tacagctcgc tgtcggccgc gcggccgctg aacgggacgt accaccacca      1260
ccaccaccac caccaccacc atccgagccc ctactcgccc tacgtggggg cgccactgac      1320
gcctgcctgg cccgccggac ccttcgagac cccggtgctg cacagcctgc agagccgcgc      1380
cggagccccg ctcccggtgc cccgggggtcc cagtgcagac ctgctggagg acctgtccga      1440
gagccgcgag tgcgtgaact gcggctccat ccagacgccg ctgtggcggc gggacggcac      1500
cggccactac ctgtgcaacg cctgcgggct ctacagcaag atgaacggcc tcagccggcc      1560
cctcatcaag ccgcagaagc gcgtgccttc atcacggcgg cttggattgt cctgtgccaa      1620
ctgtcacacc acaactacca ccttatggcg cagaaacgcc gagggtgaac ccgtgtgcaa      1680
tgcttgtgga ctctacatga aactccatgg ggtgcccaga ccacttgcta tgaaaaaaga      1740
gggaattcaa accaggaaac gaaaacctaa gaacataaat aaatcaaaga cttgctctgg      1800
taatagcaat aattccattc ccatgactcc aacttccacc tcttctaact cagatgattg      1860
cagcaaaaat acttccccca caacacaacc tacagcctca ggggcgggtg ccccggtgat      1920

-continued

```
gactggtgcg ggagagagca ccaatcccga gaacagcgag ctcaagtatt cgggtcaaga    1980
tgggctctac ataggcgtca gtctcgcctc gccggccgaa gtcacgtcct ccgtgcgacc    2040
ggattcctgg tgcgccctgg ccctggcctg agcccacgcc gccaggaggc agggagggct    2100
ccgccgcggg cctcactcca ctcgtgtctg cttttgtgca gcggtccaga cagtggcgac    2160
tgcgctgaca gaacgtgatt ctcgtgcctt tattttgaaa gagatgtttt tcccaagagg    2220
cttgctgaaa gagtgagaga agatggaagg gaagggccag tgcaactggg cgcttgggcc    2280
actccagcca gcccgcctcc ggggcggacc ctgctccact tccagaagcc aggactagga    2340
cctgggcctt gcctgctatg gaatattgag agagattttt taaaaaagat tttgcatttt    2400
gtccaaaatc atgtgcttct tctgatcaat tttggttgtt ccagaatttc ttcatacctt    2460
ttccacatcc agatttcatg tgcgttcatg gagaagatca cttgaggcca tttggtacac    2520
atctctggag gctgagtcgg ttcatgaggt ctcttatcaa aaatattact cagtttgcaa    2580
gactgcattg taactttaac atacactgtg actgacgttt ctcaaagttc atattgtgtg    2640
gctgatctga agtcagtcgg aatttgtaaa caggtagca  aacaagatat ttttcttcca    2700
tgtatacaat aattttttta aaaagtgcaa tttgcgttgc agcaatcagt gttaaatcat    2760
ttgcataaga tttaacagca ttttttataa tgaatgtaaa cattttaact taatggtact    2820
taaaataatt taaagaaaa  atgttaactt agacattctt atgcttcttt tacaactaca    2880
tcccatttta tatttccaat tgttaaagaa aaatatttca agaacaaatc ttctctcagg    2940
aaaattgcct ttctctattt gttaagaatt tttatacaag aacaccaata tacccccttt    3000
attttactgt ggaatatgtg ctggaaaaat tgcaacaaca ctttactacc taacggatag    3060
catttgtaaa tactctaggt atctgtaaac actctgatga agtctgtata gtgtgactaa    3120
cccacaggca ggttggttta cattaatttt tttttttgaa tgggatgtcc tatggaaacc    3180
tatttcacca gagttttaaa aataaaaagg gtattgtttt gtcttctgta cagtgagttc    3240 cttcccttt  caaagctttc ttttttatgct gtatgtgact atagatattc atataaaaca    3300
agtgcacgtg aagtttgcaa aatgctttaa ggccttcctt tcaaagcata gtcctttttgg    3360 agccgttttg tacctttat  accttggctt atttgaagtt gacacatggg gttagttact    3420
actctccatg tgcattgggg acagttttta taagtgggaa ggactcagta ttattatatt    3480
tgagatgata agcattttgt ttgggaacaa tgcttaaaaa tattccagaa agttcagatt    3540 tttttttcttt gtgaatgaaa tatattctgg cccacgaaca gggcgatttc ctttcagttt    3600 tttcctttg  caacgtgcct tgaagtctca aagctcacct gaggttgcag acgttacccc    3660
caacagaaga taggtagaaa tgattccagt ggcctctttg tattttcttc attgttgagt    3720
agatttcagg aaatcaggag gtgtttcaca atacagaatg atggcctttta actgtgaaaa    3780 aaaaa                                                                3785
```

```
<210> SEQ ID NO 15
<211> LENGTH: 394
<212> TYPE: PRT
<213> ORGANISM: Homo sapiens

<400> SEQUENCE: 15

Met Lys Arg Gln Asn Val Arg Thr Leu Ala Leu Ile Val Cys Thr Phe
1               5                   10                  15

Thr Tyr Leu Leu Val Gly Ala Ala Val Phe Asp Ala Leu Glu Ser Glu
            20                  25                  30

Pro Glu Leu Ile Glu Arg Gln Arg Leu Glu Leu Arg Gln Gln Glu Leu
```

```
                 35                40                45
Arg Ala Arg Tyr Asn Leu Ser Gln Gly Gly Tyr Glu Glu Leu Glu Arg
    50                55                60
Val Val Leu Arg Leu Lys Pro His Lys Ala Gly Val Gln Trp Arg Phe
65                70                75                80
Ala Gly Ser Phe Tyr Phe Ala Ile Thr Val Ile Thr Thr Ile Gly Tyr
                85                90                95
Gly His Ala Ala Pro Ser Thr Asp Gly Gly Lys Val Phe Cys Met Phe
            100               105               110
Tyr Ala Leu Leu Gly Ile Pro Leu Thr Leu Val Met Phe Gln Ser Leu
            115               120               125
Gly Glu Arg Ile Asn Thr Leu Val Arg Tyr Leu Leu His Arg Ala Lys
    130               135               140
Lys Gly Leu Gly Met Arg Arg Ala Asp Val Ser Met Ala Asn Met Val
145               150               155               160
Leu Ile Gly Phe Phe Ser Cys Ile Ser Thr Leu Cys Ile Gly Ala Ala
            165               170               175
Ala Phe Ser His Tyr Glu His Trp Thr Phe Phe Gln Ala Tyr Tyr Tyr
            180               185               190
Cys Phe Ile Thr Leu Thr Thr Ile Gly Phe Gly Asp Tyr Val Ala Leu
            195               200               205
Gln Lys Asp Gln Ala Leu Gln Thr Gln Pro Gln Tyr Val Ala Phe Ser
    210               215               220
Phe Val Tyr Ile Leu Thr Gly Leu Thr Val Ile Gly Ala Phe Leu Asn
225               230               235               240
Leu Val Val Leu Arg Phe Met Thr Met Asn Ala Glu Asp Glu Lys Arg
            245               250               255
Asp Ala Glu His Arg Ala Leu Leu Thr Arg Asn Gly Gln Ala Gly Gly
            260               265               270
Gly Gly Gly Gly Gly Ser Ala His Thr Thr Asp Thr Ala Ser Ser Thr
            275               280               285
Ala Ala Ala Gly Gly Gly Gly Phe Arg Asn Val Tyr Ala Glu Val Leu
    290               295               300
His Phe Gln Ser Met Cys Ser Cys Leu Trp Tyr Lys Ser Arg Glu Lys
305               310               315               320
Leu Gln Tyr Ser Ile Pro Met Ile Ile Pro Arg Asp Leu Ser Thr Ser
            325               330               335
Asp Thr Cys Val Glu Gln Ser His Ser Ser Pro Gly Gly Gly Gly Arg
            340               345               350
Tyr Ser Asp Thr Pro Ser Arg Arg Cys Leu Cys Ser Gly Ala Pro Arg
    355               360               365
Ser Ala Ile Ser Ser Val Ser Thr Gly Leu His Ser Leu Ser Thr Phe
    370               375               380
Arg Gly Leu Met Lys Arg Arg Ser Ser Val
385               390
```

<210> SEQ ID NO 16
<211> LENGTH: 3978
<212> TYPE: DNA
<213> ORGANISM: Homo sapiens

<400> SEQUENCE: 16
ggcggcggcg gcggcggcgg ccccgggcgc tgagcgggtg cccggcgcgg agagcggcga      60
gcgcagccat gccccaggcc gcctccgggg cagcagcagc ggcggccggg gccgaggcgc     120

-continued

```
gggccggggg cgccggggggg ccggcggcgg cccgggcggg acgatgaagc ggcagaacgt      180
gcgcacgctg gcgctcatcg tgtgcacctt cacctacctg ctggtggggcg ccgcggtctt      240 cgacgcgctg gagtcggagc ccgagctgat cgagcggcag cggctggagc tgcggcagca      300
ggagctgcgg gcgcgctaca acctcagcca gggcggctac gaggagctgg agcgcgtcgt      360
gctgcgcctc aagccgcaca aggccggcgt gcagtggcgc ttcgccggct ccttctactt      420
cgccatcacc gtcatcacca ccatcggcta cgggcacgcg gcacccagca cggatggcgg      480
caaggtgttc tgcatgttct acgcgctgct gggcatcccg ctcacgctcg tcatgttcca      540
gagcctgggc gagcgcatca acaccttggt gaggtacctg ctgcaccgcg ccaagaaggg      600
gctgggcatg cggcgcgccg acgtgtccat ggccaacatg gtgctcatcg gcttcttctc      660
gtgcatcagc acgctgtgca tcggcgccgc cgccttctcc cactacgagc actggacctt      720
cttccaggcc tactactact gcttcatcac cctcaccacc atcggcttcg gcgactacgt      780
ggcgctgcag aaggaccagg ccctgcagac gcagccgcag tacgtggcct tcagcttcgt      840
ctacatcctt acgggcctca cggtcatcgg cgccttcctc aacctcgtgg tgctgcgctt      900
catgaccatg aacgccgagg acgagaagcg cgacgccgag caccgcgcgc tgctcacgcg      960
caacgggcag gcgggcggcg gcggagggggg tggcagcgcg cacactacgg acaccgcctc     1020
atccacggcg gcagcgggcg gcggcggctt ccgcaacgtc tacgcggagg tgctgcactt     1080
ccagtccatg tgctcgtgcc tgtggtacaa gagccgcgag aagctgcagt actccatccc     1140
catgatcatc ccgcgggacc tctccacgtc cgacacgtgc gtggagcaga gccactcgtc     1200
gccgggaggg ggcggccgct acagcgacac gccctcgcga cgctgcctgt gcagcggggc     1260
gccacgctcc gccatcagct cggtgtccac gggtctgcac agcctgtcca ccttccgcgg     1320
cctcatgaag cgcaggagct ccgtgtgact gccccgaggg gcctggagca cctgggggcg     1380
cgggcggggg acccctgctg ggaggccagg agactgcccc tgctgccttc tgcccagtgg     1440
gaccccgcac aacatccctc accactctcc cccagcaccc ccatctccga ctgtgcctgc     1500
ttgcaccagc cggcaggagg ccgggctctg aggacccctg gggcccccat cggagccctg     1560
caaattccga gaaatgtgaa acttggtggg gtcagggagg aaaggcagaa gctgggagcc     1620
tcccttccct ttgaaaatct aagaagctcc cagtcctcag agaccctgct ggtacccaga     1680
cccccacctt cggaggggac ttcatgttcc gtgtacgttt gcatctctat ttatacctct     1740
gtcctgctag gtctcccacc ttcccttggt tccaaaagcc agggtgtcta tgtccaagtc     1800 accccctactc agcccactc cccttcctca tccccagctg tgtctcccaa cctcccttcg     1860
tgttgttttg catggctttg cagttatgga gaaagtggaa acccagcagt ccctaaagct     1920
ggtccccaga aagcaggaca gaaagaagga gggacaggca ggcagcagga ggggcgagct     1980
gggaggcagg aggcagcggc ctgtcagtct gcagaatggt cgcactggag gttcaagcta     2040
actggcctcc agccacattc tcatagcagg taggacttca gccttccaga cactgccctt     2100
agaatctgga acagaagact tcagactcac cataattgct gataattacc cactcttaaa     2160
tttgtcgagt gattttttagc ctctgaaaac tctatgctgg ccactgattc ctttgagtct     2220
cacaaaaccc tacttaggtc atcagggcag gagttctcac tcccatttta cagatgagaa     2280
tactgaggcc tggacaggtg aagtgaccag agagcaaaag gcaaaggggt gggggctggg     2340
tgcagtggct cacacctgta ttcccaacac ttttggaggc tgaggttgga ggattgcttg     2400
agcccaggaa tttgagacca gcctaggtga catagtgaga ccccatctct acaaaaaata     2460
```

```
aaaaattaac caggtgtggt ggcacgtgcc tgggagtccc agcgacttgg gaggctgagg    2520
tgggaggatt gtttgagcct gggaggtcga ggctgtagtg agccctgatt gcaccactgt    2580
actccagcct gggtgacagg gcaagaccct gtctcaaaaa aaaaaaaaaa aatggcaaag    2640
ggagacaaga gcccagcctg cttgttgcta gccaaagtgt tctttccttc cagcttggcc    2700
tgctcttaaa agcaaagctc ctgcagtgta catcctggca ttgtgtggct acctgggttt    2760
taaaccagaa tcagaagtcc cggatcagag ggcactgctg aggttcagcc tcttctcttc    2820
ttggccagga ggcagcagct ctgaatgggc ccctgaggct gcacaggggc ctttgtcact    2880
ggggcgcatg cttacaaaca gtgcagttct tgggaccgag gtaagcaggg ctgggtctca    2940
tggcagaaag gccaggatct ggggctctag gaatttggga attgggcaga gtggccaaga    3000
aagctggcag gcatatccta tgggacatca cacctggcac cattgtcatt gttggtgcct    3060
gtgtcccaag tagctagtga taagctgagg ctgcagcaag aaacaccctt cccaggtggg    3120
ggagtttgga ccagaggtgc cctctgccca ccacacctgc aacccagaag cccagatgga    3180
acgcagctga cgaaggtgat gcttgaggct cacttttggg gccccacagc tggagccggt    3240
ataatgactg ggacaacatc aagggggtgga tgaggggcct ctcctcccgc aacactgcct    3300
tcccatgctg ttcccctgcc agctccttaa cactgccgac caaggccagc cctggcattc    3360
agggaaattg gagggcagca cccgtagggt ggccagcctc aggcccccacc ccagctgtgt    3420 cctctagtct ctggggaccc ctggggggaa gaagtctacc ctgcttgtga gtcccgtctc    3480
agtgtggagg aactggctgc acgtgggacc tgaaggtgcc ctctgtgttt atgttggggg    3540 tggggggggca gtgctggctg cctctgtcct gtgtgtgacc ctgccctcga agggtcctgt    3600
cctgtcagtc ccgagggagc cacaaccaaa gctgcggaga gaaggtgggg aagggtgcag    3660
aatggccgtg gggcacagcg tggcagactg ttcagtctct gctgggtctt tcctagggac    3720
ctggaaggcc agtgttgctt cccccctcact ccctttcact gcaggcagcc tctctgcttc    3780
cccaatgcct tatgcctggg cacactgcca cagaatatgc aatatgtgtg ggtgaccatg    3840
ccctcacgac cacacccccca ccccgggcag cccccggact ccaaaggtcg tggctgccac    3900
agcctccctc agctcttcct gcctatctgt cttcacactg agaatggcgc ccaataaatg    3960
ctatccacgg agaccagg                                                  3978
```

```
<210> SEQ ID NO 17
<211> LENGTH: 676
<212> TYPE: PRT
<213> ORGANISM: Homo sapiens

<400> SEQUENCE: 17

Met Ala Ala Ala Ser Ser Pro Pro Arg Ala Glu Arg Lys Arg Trp Gly
1               5                   10                  15

Trp Gly Arg Leu Pro Gly Ala Arg Arg Gly Ser Ala Gly Leu Ala Lys
            20                  25                  30

Lys Cys Pro Phe Ser Leu Glu Leu Ala Glu Gly Gly Pro Ala Gly Gly
        35                  40                  45

Ala Leu Tyr Ala Pro Ile Ala Pro Gly Ala Pro Gly Pro Ala Pro Pro
    50                  55                  60

Ala Ser Pro Ala Ala Pro Ala Ala Pro Pro Val Ala Ser Asp Leu Gly
65                  70                  75                  80

Pro Arg Pro Pro Val Ser Leu Asp Pro Arg Val Ser Ile Tyr Ser Thr
                85                  90                  95

Arg Arg Pro Val Leu Ala Arg Thr His Val Gln Gly Arg Val Tyr Asn
```

-continued

```
                100                 105                 110
Phe Leu Glu Arg Pro Thr Gly Trp Lys Cys Phe Val Tyr His Phe Ala
            115                 120                 125
Val Phe Leu Ile Val Leu Val Cys Leu Ile Phe Ser Val Leu Ser Thr
            130                 135                 140
Ile Glu Gln Tyr Ala Ala Leu Ala Thr Gly Thr Leu Phe Trp Met Glu
145                 150                 155                 160
Ile Val Leu Val Val Phe Phe Gly Thr Glu Tyr Val Val Arg Leu Trp
                165                 170                 175
Ser Ala Gly Cys Arg Ser Lys Tyr Val Gly Leu Trp Gly Arg Leu Arg
                180                 185                 190
Phe Ala Arg Lys Pro Ile Ser Ile Ile Asp Leu Ile Val Val Val Ala
            195                 200                 205
Ser Met Val Val Leu Cys Val Gly Ser Lys Gly Gln Val Phe Ala Thr
            210                 215                 220
Ser Ala Ile Arg Gly Ile Arg Phe Leu Gln Ile Leu Arg Met Leu His
225                 230                 235                 240
Val Asp Arg Gln Gly Gly Thr Trp Arg Leu Leu Gly Ser Val Val Phe
                245                 250                 255
Ile His Arg Gln Glu Leu Ile Thr Thr Leu Tyr Ile Gly Phe Leu Gly
                260                 265                 270
Leu Ile Phe Ser Ser Tyr Phe Val Tyr Leu Ala Glu Lys Asp Ala Val
            275                 280                 285
Asn Glu Ser Gly Arg Val Glu Phe Gly Ser Tyr Ala Asp Ala Leu Trp
            290                 295                 300
Trp Gly Val Val Thr Val Thr Thr Ile Gly Tyr Gly Asp Lys Val Pro
305                 310                 315                 320
Gln Thr Trp Val Gly Lys Thr Ile Ala Ser Cys Phe Ser Val Phe Ala
                325                 330                 335
Ile Ser Phe Phe Ala Leu Pro Ala Gly Ile Leu Gly Ser Gly Phe Ala
                340                 345                 350
Leu Lys Val Gln Gln Lys Gln Arg Gln Lys His Phe Asn Arg Gln Ile
            355                 360                 365
Pro Ala Ala Ala Ser Leu Ile Gln Thr Ala Trp Arg Cys Tyr Ala Ala
            370                 375                 380
Glu Asn Pro Asp Ser Ser Thr Trp Lys Ile Tyr Ile Arg Lys Ala Pro
385                 390                 395                 400
Arg Ser His Thr Leu Leu Ser Pro Ser Pro Lys Pro Lys Lys Ser Val
                405                 410                 415
Val Val Lys Lys Lys Lys Phe Lys Leu Asp Lys Asp Asn Gly Val Thr
            420                 425                 430
Pro Gly Glu Lys Met Leu Thr Val Pro His Ile Thr Cys Asp Pro Pro
            435                 440                 445
Glu Glu Arg Arg Leu Asp His Phe Ser Val Asp Gly Tyr Asp Ser Ser
            450                 455                 460
Val Arg Lys Ser Pro Thr Leu Leu Glu Val Ser Met Pro His Phe Met
465                 470                 475                 480
Arg Thr Asn Ser Phe Ala Glu Asp Leu Asp Leu Glu Gly Glu Thr Leu
                485                 490                 495
Leu Thr Pro Ile Thr His Ile Ser Gln Leu Arg Glu His His Arg Ala
            500                 505                 510
Thr Ile Lys Val Ile Arg Arg Met Gln Tyr Phe Val Ala Lys Lys Lys
            515                 520                 525
```

-continued

```
Phe Gln Gln Ala Arg Lys Pro Tyr Asp Val Arg Asp Val Ile Glu Gln
    530                 535                 540

Tyr Ser Gln Gly His Leu Asn Leu Met Val Arg Ile Lys Glu Leu Gln
545                 550                 555                 560

Arg Arg Leu Asp Gln Ser Ile Gly Lys Pro Ser Leu Phe Ile Ser Val
                565                 570                 575

Ser Glu Lys Ser Lys Asp Arg Gly Ser Asn Thr Ile Gly Ala Arg Leu
                580                 585                 590

Asn Arg Val Glu Asp Lys Val Thr Gln Leu Asp Gln Arg Leu Ala Leu
                595                 600                 605

Ile Thr Asp Met Leu His Gln Leu Leu Ser Leu His Gly Gly Ser Thr
    610                 615                 620

Pro Gly Ser Gly Gly Pro Pro Arg Glu Gly Gly Ala His Ile Thr Gln
625                 630                 635                 640

Pro Cys Gly Ser Gly Gly Ser Val Asp Pro Glu Leu Phe Leu Pro Ser
                645                 650                 655

Asn Thr Leu Pro Thr Tyr Glu Gln Leu Thr Val Pro Arg Arg Gly Pro
                660                 665                 670

Asp Glu Gly Ser
        675

<210> SEQ ID NO 18
<211> LENGTH: 3262
<212> TYPE: DNA
<213> ORGANISM: Homo sapiens

<400> SEQUENCE: 18
gcggcggggc tggcagcagt ggctgcccgc actgcgcccg ggcgctcgcc ttcgctgcag      60
ctcccggtgc cgccgctcgg gccggccccc cggcaggccc tcctcgttat ggccgcggcc     120
tcctccccgc ccagggccga gaggaagcgc tggggttggg gccgcctgcc aggcgcccgg     180
cggggcagcg cgggcctggc caagaagtgc cccttctcgc tggagctggc ggagggcggc     240 ccggcggggcg cgcgctcta cgcgcccatc gcgcccggcg ccccaggtcc cgcgccccct     300
gcgtccccgg ccgcgcccgc cgcgcccca gttgcctccg accttggccc gcggccgccg     360
gtgagcctag accgcgcgt ctccatctac agcacgcgcc gcccggtgtt ggcgcgcacc     420
cacgtccagg gccgcgtcta caacttcctc gagcgtccca ccggctggaa atgcttcgtt     480
taccacttcg ccgtcttcct catcgtcctg gtctgcctca tcttcagcgt gctgtccacc     540
atcgagcagt atgccgccct ggccacgggg actctcttct ggatggagat cgtgctggtg     600
gtgttcttcg ggacggagta cgtggtccgc ctctggtccg ccggctgccg cagcaagtac     660
gtgggcctct gggggcggct cgctttgcc cggaagccca tttccatcat cgacctcatc     720
gtggtcgtgg cctccatggt ggtcctctgc gtgggctcca aggggcaggt gtttgccacg     780
tcggccatca gggcatccg cttcctgcag atcctgagga tgctacacgt cgaccgccag     840
ggaggcacct ggaggctcct gggctccgtg gtcttcatcc accgccagga gctgataacc     900
accctgtaca tcggcttcct gggcctcatc ttctcctcgt actttgtgta cctggctgag     960
aaggacgcgg tgaacgagtc aggccgcgtg gagttcggca gctacgcaga tgcgctgtgg    1020 tgggggggtgg tcacagtcac caccatcggc tatgggggaca aggtgcccca gacgtgggtc    1080
gggaagacca tcgcctcctg cttctctgtc tttgccatct ccttctttgc gctcccagcg    1140
gggattcttg gctcggggtt tgccctgaag gtgcagcaga agcagaggca gaagcacttc    1200
```

-continued

```
aaccggcaga tcccggcggc agcctcactc attcagaccg catggaggtg ctatgctgcc      1260
gagaaccccg actcctccac ctggaagatc tacatccgga aggcccccg gagccacact        1320 ctgctgtcac ccagccccaa acccaagaag tctgtggtgg taaagaaaaa aaagttcaag      1380
ctggacaaag acaatggggt gactcctgga gagaagatgc tcacagtccc ccatatcacg      1440
tgcgaccccc cagaagagcg gcggctggac cacttctctg tcgacggcta tgacagttct       1500
gtaaggaaga gcccaacact gctggaagtg agcatgcccc atttcatgag aaccaacagc      1560
ttcgccgagg acctggacct ggaaggggag actctgctga cacccatcac ccacatctca       1620
cagctgcggg aacaccatcg ggccaccatt aaggtcattc gacgcatgca gtactttgtg      1680
gccaagaaga aattccagca agcgcggaag ccttacgatg tgcgggacgt cattgagcag      1740
tactcgcagg gccacctcaa cctcatggtg cgcatcaagg agctgcagag gaggctggac      1800
cagtccattg ggaagccctc actgttcatc tccgtctcag aaaagagcaa ggatcgcggc      1860
agcaacacga tcggcgcccg cctgaaccga gtagaagaca aggtgacgca gctggaccag      1920
aggctggcac tcatcaccga catgcttcac cagctgctct ccttgcacgg tggcagcacc      1980
cccggcagcg gcggccccccc cagagagggc ggggcccaca tcacccagcc ctgcggcagt      2040
ggcggctccg tcgaccctga gctcttcctg cccagcaaca ccctgcccac ctacgagcag      2100
ctgaccgtgc ccaggagggg ccccgatgag gggtcctgag gaggggatgg ggctggggga      2160
tgggcctgag tgagagggga ggccaagagt ggccccacct ggccctctct gaaggaggcc      2220
acctcctaaa aggcccagag agaagagccc cactctcaga ggccccaata ccccatggac      2280
catgctgtct ggcacagcct gcacttgggg gctcagcaag gccacctctt cctggccggt      2340
gtgggggccc cgtctcaggt ctgagttgtt accccaagcg ccctggcccc cacatggtga      2400
tgttgacatc actggcatgg tggttgggac ccagtggcag ggcacagggc ctggcccatg      2460
tatggccagg aagtagcaca ggctgagtgc aggcccaccc tgcttggccc aggggggcttc     2520 ctgaggggag acagagcaac ccctggaccc cagcctcaaa tccaggaccc tgccaggcac      2580
aggcagggca ggaccagccc acgctgacta cagggccgcc ggcaataaaa gcccaggagc      2640
ccatttggag ggcctgggcc tggctccctc actctcagga aatgctgacc catgggcagg      2700
agactgtgga gactgctcct gagcccccag cttccagcag gagggacagt ctcaccattt      2760
ccccagggca cgtggttgag tggggggaac gcccacttcc ctgggttaga ctgccagctc      2820
ttcctagctg gagaggagcc ctgcctctcc gccctgagc ccactgtgcg tggggctccc       2880
gcctccaacc cctcgcccag tcccagcagc cagccaaaca cacagaaggg gactgccacc      2940
tccccttgcc agctgctgag ccgcagagaa gtgacggttc ctacacagga cagggggttcc     3000 ttctgggcat tacatcgcat agaaatcaat aatttgtggt gatttggatc tgtgtttttaa     3060 tgagtttcac agtgtgattt tgattattaa ttgtgcaagc ttttcctaat aaacgtggag      3120
aatcacaggc tgggctgggc actgctctca ccttggttcc tggggcatcc atggggtctc      3180
tcacagacag gacccctgca gttcccctgg aagcagtgcc caggtggctg tggaatagga      3240
acgctaaaaa aaaaaaaaaa aa                                               3262
```

<210> SEQ ID NO 19
<211> LENGTH: 907
<212> TYPE: PRT
<213> ORGANISM: Homo sapiens

<400> SEQUENCE: 19

Met Asp Thr Ser Arg Leu Gly Val Leu Leu Ser Leu Pro Val Leu Leu

-continued

```
1                   5                    10                   15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
            35                  40                  45

Arg Val Asp Cys Ser Asp Leu Gly Leu Ser Glu Leu Pro Ser Asn Leu
        50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
            115                 120                 125

Val Pro Thr Glu Ala Leu Gln Asn Leu Arg Ser Leu Gln Ser Leu Arg
            130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
            180                 185                 190

Leu Ala Leu Asn Lys Ile His His Ile Pro Asp Tyr Ala Phe Gly Asn
            195                 200                 205

Leu Ser Ser Leu Val Val Leu His Leu His Asn Asn Arg Ile His Ser
            210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
            260                 265                 270

Pro Glu Lys Ala Phe Val Gly Asn Pro Ser Leu Ile Thr Ile His Phe
            275                 280                 285

Tyr Asp Asn Pro Ile Gln Phe Val Gly Arg Ser Ala Phe Gln His Leu
            290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
                325                 330                 335

Gly Ala Gln Ile Ser Ser Leu Pro Gln Thr Val Cys Asn Gln Leu Pro
            340                 345                 350

Asn Leu Gln Val Leu Asp Leu Ser Tyr Asn Leu Leu Glu Asp Leu Pro
            355                 360                 365

Ser Phe Ser Val Cys Gln Lys Leu Gln Lys Ile Asp Leu Arg His Asn
            370                 375                 380

Glu Ile Tyr Glu Ile Lys Val Asp Thr Phe Gln Gln Leu Leu Ser Leu
385                 390                 395                 400

Arg Ser Leu Asn Leu Ala Trp Asn Lys Ile Ala Ile Ile His Pro Asn
                405                 410                 415

Ala Phe Ser Thr Leu Pro Ser Leu Ile Lys Leu Asp Leu Ser Ser Asn
            420                 425                 430
```

```
Leu Leu Ser Ser Phe Pro Ile Thr Gly Leu His Gly Leu Thr His Leu
        435                 440             445

Lys Leu Thr Gly Asn His Ala Leu Gln Ser Leu Ile Ser Ser Glu Asn
        450                 455             460

Phe Pro Glu Leu Lys Val Ile Glu Met Pro Tyr Ala Tyr Gln Cys Cys
465                 470             475             480

Ala Phe Gly Val Cys Glu Asn Ala Tyr Lys Ile Ser Asn Gln Trp Asn
                485             490             495

Lys Gly Asp Asn Ser Ser Met Asp Asp Leu His Lys Lys Asp Ala Gly
            500             505             510

Met Phe Gln Ala Gln Asp Glu Arg Asp Leu Glu Asp Phe Leu Leu Asp
        515             520             525

Phe Glu Glu Asp Leu Lys Ala Leu His Ser Val Gln Cys Ser Pro Ser
    530             535             540

Pro Gly Pro Phe Lys Pro Cys Glu His Leu Leu Asp Gly Trp Leu Ile
545             550             555             560

Arg Ile Gly Val Trp Thr Ile Ala Val Leu Ala Leu Thr Cys Asn Ala
                565             570             575

Leu Val Thr Ser Thr Val Phe Arg Ser Pro Leu Tyr Ile Ser Pro Ile
            580             585             590

Lys Leu Leu Ile Gly Val Ile Ala Ala Val Asn Met Leu Thr Gly Val
            595             600             605

Ser Ser Ala Val Leu Ala Gly Val Asp Ala Phe Thr Phe Gly Ser Phe
        610             615             620

Ala Arg His Gly Ala Trp Trp Glu Asn Gly Val Gly Cys His Val Ile
625             630             635             640

Gly Phe Leu Ser Ile Phe Ala Ser Glu Ser Ser Val Phe Leu Leu Thr
                645             650             655

Leu Ala Ala Leu Glu Arg Gly Phe Ser Val Lys Tyr Ser Ala Lys Phe
            660             665             670

Glu Thr Lys Ala Pro Phe Ser Ser Leu Lys Val Ile Ile Leu Leu Cys
        675             680             685

Ala Leu Leu Ala Leu Thr Met Ala Ala Val Pro Leu Leu Gly Gly Ser
        690             695             700

Lys Tyr Gly Ala Ser Pro Leu Cys Leu Pro Leu Pro Phe Gly Glu Pro
705             710             715             720

Ser Thr Met Gly Tyr Met Val Ala Leu Ile Leu Leu Asn Ser Leu Cys
                725             730             735

Phe Leu Met Met Thr Ile Ala Tyr Thr Lys Leu Tyr Cys Asn Leu Asp
            740             745             750

Lys Gly Asp Leu Glu Asn Ile Trp Asp Cys Ser Met Val Lys His Ile
        755             760             765

Ala Leu Leu Leu Phe Thr Asn Cys Ile Leu Asn Cys Pro Val Ala Phe
        770             775             780

Leu Ser Phe Ser Ser Leu Ile Asn Leu Thr Phe Ile Ser Pro Glu Val
785             790             795             800

Ile Lys Phe Ile Leu Leu Val Val Val Pro Leu Pro Ala Cys Leu Asn
                805             810             815

Pro Leu Leu Tyr Ile Leu Phe Asn Pro His Phe Lys Glu Asp Leu Val
            820             825             830

Ser Leu Arg Lys Gln Thr Tyr Val Trp Thr Arg Ser Lys His Pro Ser
        835             840             845
```

-continued

```
Leu Met Ser Ile Asn Ser Asp Asp Val Glu Lys Gln Ser Cys Asp Ser
    850             855             860

Thr Gln Ala Leu Val Thr Phe Thr Ser Ser Ser Ile Thr Tyr Asp Leu
865             870             875             880

Pro Pro Ser Ser Val Pro Ser Pro Ala Tyr Pro Val Thr Glu Ser Cys
                885             890             895

His Leu Ser Ser Val Ala Phe Val Pro Cys Leu
            900             905
```

```
<210> SEQ ID NO 20
<211> LENGTH: 4625
<212> TYPE: DNA
<213> ORGANISM: Homo sapiens

<400> SEQUENCE: 20
aaaaaacgag cgtgcaagca gagatgctgc tccacaccgc tcaggccgcg agcagcagca      60
aggcgcaccg ccactgtcgc cgctgcagcc agggctgctc cgaaggccgg cgtggcggca     120
accggcacct ctgtccccgc cgcgcttctc ctcgccgccc acgccgtggg gtcaggaacg     180
cggcgtctgg cgctgcagac gcccgctgag ttgcagaagc ccacggagcg gcgcccggcg     240
cgccacggcc cgtagcagtc cggtgctgct ctccgcccgc gtccggctcg tggcccccta     300
cttcgggcac catggacacc tcccggctcg gtgtgctcct gtccttgcct gtgctgctgc     360
agctggcgac cggggggcagc tctcccaggt ctggtgtgtt gctgaggggc tgccccacac     420
actgtcattg cgagcccgac ggcaggatgt tgctcagggt ggactgctcc gacctggggc     480
tctcggagct gccttccaac ctcagcgtct tcacctccta cctagacctc agtatgaaca     540
acatcagtca gctgctcccg aatcccctgc ccagtctccg cttcctggag gagttacgtc     600
ttgcgggaaa cgctctgaca tacattccca agggagcatt cactggcctt acagtctta     660 aagttcttat gctgcagaat aatcagctaa gacacgtacc cacagaagct ctgcagaatt     720
tgcgaagcct tcaatccctg cgtctggatg ctaaccacat cagctatgtg cccccaagct     780
gtttcagtgg cctgcattcc ctgaggcacc tgtggctgga tgacaatgcg ttaacagaaa     840
tccccgtcca ggcttttaga agtttatcgg cattgcaagc catgaccttg ccctgaaca     900 aaatacacca cataccagac tatgcctttg aaaacctctc cagcttggta gttctacatc     960
tccataacaa tagaatccac tccctgggaa agaaatgctt tgatgggctc cacagcctag    1020
agactttaga tttaaattac aataaccttg atgaattccc cactgcaatt aggacactct    1080
ccaaccttaa agaactagga tttcatagca acaatatcag gtcgatacct gagaaagcat    1140
ttgtaggcaa cccttctctt attacaatac atttctatga caatcccatc cagtttgttg    1200
ggagatctgc tttttcaacat ttacctgaac taagaacact gactctgaat ggtgcctcac    1260
aaataactga atttcctgat ttaactggaa ctgcaaacct ggagagtctg actttaactg    1320
gagcacagat ctcatctctt cctcaaaccg tctgcaatca gttacctaat ctccaagtgc    1380
tagatctgtc ttacaaccta ttagaagatt acccagtttt ttcagtctgc caaaagcttc    1440
agaaaattga cctaagacat aatgaaatct acgaaattaa agttgacact ttccagcagt    1500
tgcttagcct ccgatcgctg aatttggctt ggaacaaaat tgctattatt caccccaatg    1560
cattttccac tttgccatcc ctaataaagc tggacctatc gtccaacctc ctgtcgtctt    1620
ttcctataac tgggttacat ggtttaactc acttaaaatt aacaggaaat catgccttac    1680
agagcttgat atcatctgaa aactttccag aactcaaggt tatagaaatg ccttatgctt    1740
accagtgctg tgcatttgga gtgtgtgaga atgcctataa gatttctaat caatggaata    1800
```

```
aaggtgacaa cagcagtatg gacgaccttc ataagaaaga tgctggaatg tttcaggctc    1860
aagatgaacg tgaccttgaa gatttcctgc ttgactttga ggaagacctg aaagcccttc    1920
attcagtgca gtgttcacct tccccaggcc ccttcaaacc ctgtgaacac ctgcttgatg    1980
gctggctgat cagaattgga gtgtggacca tagcagttct ggcacttact tgtaatgctt    2040
tggtgacttc aacagttttc agatcccctc tgtacatttc ccccattaaa ctgttaattg    2100
gggtcatcgc agcagtgaac atgctcacgg gagtctccag tgccgtgctg gctggtgtgg    2160
atgcgttcac tttttggcagc tttgcacgac atggtgcctg gtgggagaat ggggttggtt    2220
gccatgtcat tggttttttg tccatttttg cttcagaatc atctgttttc ctgcttactc    2280
tggcagccct ggagcgtggg ttctctgtga atattctgc aaaatttgaa acgaaagctc      2340
cattttctag cctgaaagta atcatttgc tctgtgccct gctggccttg accatggccg       2400
cagttcccct gctgggtggc agcaagtatg gcgcctcccc tctctgcctg cctttgcctt    2460
ttggggagcc cagcaccatg ggctacatgg tcgctctcat cttgctcaat tcccttttgct    2520 tcctcatgat gaccattgcc tacaccaagc tctactgcaa tttggacaag ggagacctgg    2580
agaatatttg ggactgctct atggtaaaac acattgccct gttgctcttc accaactgca    2640
tcctaaactg ccctgtggct ttcttgtcct tctcctcttt aataaacctt acatttatca    2700
gtcctgaagt aattaagttt atccttctgg tggtagtccc acttcctgca tgtctcaatc    2760
cccttctcta catcttgttc aatcctcact ttaaggagga tctggtgagc ctgagaaagc    2820
aaacctacgt ctggacaaga tcaaaacacc caagcttgat gtcaattaac tctgatgatg    2880
tcgaaaaaca gtcctgtgac tcaactcaag ccttggtaac ctttaccagc tccagcatca    2940
cttatgacct gcctcccagt tccgtgccat caccagctta tccagtgact gagagctgcc    3000
atctttcctc tgtggcattt gtcccatgtc tctaattaat atgtgaagga aaatgttttc    3060
aaaggttgag aacctgaaaa tgtgagattg agtatatcag agcagtaatt aataagaaga    3120
gctgaggtga aactcggttt aaaaaccaaa aaagaatctc tcagttagta agaaaaggct    3180
gaaaacctct tgatacttga gagtgaatat aagtctaaat gctgctttgt ataatttgtt    3240
cagctaaggg atagatcgat cacactattt aagtgagccc agatcaaaaa agcagattga    3300
aattttcttt agaaaagatt ctccatgatt tgaattgcat tctctttaaa ctcaccaatg    3360
taatcatttt gggaggaggg agaacccact tgctttccaa atgggtttat ttaaacccac    3420
aaactcaaga ggttgttggg ggaattagga aaataagggt tttcaatgac ctacattgct    3480
aggtagaggc tgtgatccat gggatttcat tctaatgacc atgtgaagat gtttgagtcc    3540
tcctttgcct ttcctcagaa agaatccttc taaggcacaa atcccttaga tggataatgt    3600
aaggtattgt taactcactc atattgagat cattttaga gataccaggt tttatgtatc     3660
agcactagat ggttccaccc tcatgggata aaactgctta caagtatttt gaaagaaaaa    3720
ctgaccaaaa ttcttaaatt gttactaagg caatcatgca caggtgacgt atgtcttatc    3780
tgatttgttt ttaactcctt ggtgcccaaa gctcagaagg gaattccact gccagcaatg    3840
aacatacctg gaaaagaaag taagcaatct gggattttttt ttctgggtta gtaaagaatt    3900
tttgcaataa gttttatcag ttgattcaaa ctgatgtgca tcttaatgat caaatgtgca    3960
cattacataa attaagtcca ctgatacaac ttcttacaca tgtatctcta gtagctctgg    4020
caaacccaat atctgacacc actttggact caagagactc agtaacgtat tatcctgttt    4080
atttagcttg gttttagctg tgttctctct ggataaccca cttgatgtta ggaacattac    4140
```

-continued

```
ttctctgctt attccatatt aatactgtgt taggtatttt aagaagcaag ttattaaata    4200
agaaaagtca aagtattaat tcttaccttc tattatccta tattagcttc aatacatcca    4260
aaccaaatgg ctgttaggta gatttatttt tatataagca tgtttatttt gatcagatgt    4320
tttaacttgg atttgaaaaa atacatttat gagatgtttt ataagatgtg taaatataga    4380
actgtattta ttactatagt aaaggttcag taacattaag gaccatgata atgataataa    4440
accttgtaca gtggcatatt ctttgattta tattgtgttt ctctgcccat tttctttaaa    4500
ttcattaact gtatatatgt aaatatatag tacttgtaaa tagattccaa atttgctttt    4560
ctattgggta aaaataaat ttgtaataaa atgtgtgact atgaaacaaa aaaaaaaaaa    4620
aaaaa                                                                4625
```

```
<210> SEQ ID NO 21
<211> LENGTH: 332
<212> TYPE: PRT
<213> ORGANISM: Homo sapiens

<400> SEQUENCE: 21

Met Ala Thr Leu Lys Asp Gln Leu Ile Tyr Asn Leu Leu Lys Glu Glu
1               5                   10                  15

Gln Thr Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

Lys Asp Tyr Asn Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
            115                 120                 125

Pro Asn Cys Lys Leu Leu Ile Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Met Asn Val Ala Gly
            195                 200                 205

Val Ser Leu Lys Thr Leu His Pro Asp Leu Gly Thr Asp Lys Asp Lys
    210                 215                 220

Glu Gln Trp Lys Glu Val His Lys Gln Val Val Glu Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Val Ser Thr Met Ile Lys Gly Leu Tyr Gly Ile Lys Asp Asp Val Phe
    275                 280                 285
```

```
Leu Ser Val Pro Cys Ile Leu Gly Gln Asn Gly Ile Ser Asp Leu Val
    290                 295                 300

Lys Val Thr Leu Thr Ser Glu Glu Glu Ala Arg Leu Lys Lys Ser Ala
305                 310                 315                 320

Asp Thr Leu Trp Gly Ile Gln Lys Glu Leu Gln Phe
                325                 330

<210> SEQ ID NO 22
<211> LENGTH: 2226
<212> TYPE: DNA
<213> ORGANISM: Homo sapiens

<400> SEQUENCE: 22
gtctgccggt cggttgtctg gctgcgcgcg ccacccgggc ctctccagtg ccccgcctgg      60
ctcggcatcc accccagcc cgactcacac gtgggttccc gcacgtccgc cggcccccc      120 cgctgacgtc agcatagctg ttccacttaa ggccctccc gcgcccagct cagagtgctg      180
cagccgctgc cgccgattcc ggatctcatt gccacgcgcc cccgacgacc gcccgacgtg      240
cattcccgat tccttttggt tccaagtcca atatggcaac tctaaaggat cagctgattt      300
ataatcttct aaaggaagaa cagacccccc agaataagat tacagttgtt ggggttggtg      360
ctgttggcat ggcctgtgcc atcagtatct taatgaagga cttggcagat gaacttgctc      420
ttgttgatgt catcgaagac aaattgaagg gagagatgat ggatctccaa catggcagcc      480
ttttccttag aacaccaaag attgtctctg gcaaagacta taatgtaact gcaaactcca      540
agctggtcat tatcacggct ggggcacgtc agcaagaggg agaaagccgt cttaatttgg      600
tccagcgtaa cgtgaacatc tttaaattca tcattcctaa tgttgtaaaa tacagcccga      660
actgcaagtt gcttattgtt tcaaatccag tggatatctt gacctacgtg gcttggaaga      720
taagtggttt tcccaaaaac cgtgttattg gaagcggttg caatctggat tcagcccgat      780
tccgttacct aatgggggaa aggctgggag ttcaccatt aagctgtcat gggtgggtcc      840
ttggggaaca tggagattcc agtgtgcctg tatggagtgg aatgaatgtt gctggtgtct      900
ctctgaagac tctgcaccca gatttaggga ctgataaaga taaggaacag tggaaagagg      960
ttcacaagca ggtggttgag agtgcttatg aggtgatcaa actcaaaggc tacacatcct     1020
gggctattgg actctctgta gcagatttgg cagagagtat aatgaagaat cttaggcggg     1080
tgcacccagt ttccaccatg attaagggtc tttacggaat aaaggatgat gtcttcctta     1140
gtgttccttg cattttggga cagaatggaa tctcagacct tgtgaaggtg actctgactt     1200
ctgaggaaga ggcccgtttg aagaagagtg cagatacact ttgggggatc caaaaggagc     1260 tgcaattta aagtcttctg atgtcatatc atttcactgt ctaggctaca acaggattct     1320
aggtggaggt tgtgcatgtt gtccttttta tctgatctgt gattaaagca gtaatatttt     1380
aagatggact gggaaaaaca tcaactcctg aagttagaaa taagaatggt ttgtaaaatc     1440
cacagctata tcctgatgct ggatggtatt aatcttgtgt agtcttcaac tggttagtgt     1500
gaaatagttc tgccacctct gacgcaccac tgccaatgct gtacgtactg catttgcccc     1560
ttgagccagg tggatgttta ccgtgtgtta tataacttcc tggctccttc actgaacatg     1620
cctagtccaa catttttcc cagtgagtca catcctggga tccagtgtat aaatccaata     1680
tcatgtcttg tgcataattc ttccaaagga tcttattttg tgaactatat cagtagtgta     1740
cattaccata taatgtaaaa agatctacat acaaacaatg caaccaacta ccaagtgtt     1800 ataccaacta aaaccccaa taaaccttga acagtgacta ctttggttaa ttcattatat     1860
```

-continued

```
taagatataa agtcataaag ctgctagtta ttatattaat ttggaaatat taggctattc   1920
ttgggcaacc ctgcaacgat tttttctaac agggatatta ttgactaata gcagaggatg   1980
taatagtcaa ctgagttgta ttggtaccac ttccattgta agtcccaaag tattatatat   2040
ttgataataa tgctaatcat aattggaaag taacattcta tatgtaaatg taaaatttat   2100
ttgccaactg aatataggca atgatagtgt gtcactatag ggaacacaga tttttgagat   2160
cttgtcctct ggaagctggt aacaattaaa aacaatctta aggcagggaa aaaaaaaaaa   2220
aaaaaa                                                                     2226
```

```
<210> SEQ ID NO 23
<211> LENGTH: 353
<212> TYPE: PRT
<213> ORGANISM: Homo sapiens

<400> SEQUENCE: 23

Met Ala Ala Glu Leu Ala Met Gly Ala Glu Leu Pro Ser Ser Pro Leu
1               5                   10                  15

Ala Ile Glu Tyr Val Asn Asp Phe Asp Leu Met Lys Phe Glu Val Lys
            20                  25                  30

Lys Glu Pro Pro Glu Ala Glu Arg Phe Cys His Arg Leu Pro Pro Gly
        35                  40                  45

Ser Leu Ser Ser Thr Pro Leu Ser Thr Pro Cys Ser Ser Val Pro Ser
    50                  55                  60

Ser Pro Ser Phe Cys Ala Pro Ser Pro Gly Thr Gly Gly Gly Gly Gly
65                  70                  75                  80

Ala Gly Gly Gly Gly Gly Ser Ser Gln Ala Gly Gly Ala Pro Gly Pro
                85                  90                  95

Pro Ser Gly Gly Pro Gly Ala Val Gly Gly Thr Ser Gly Lys Pro Ala
            100                 105                 110

Leu Glu Asp Leu Tyr Trp Met Ser Gly Tyr Gln His His Leu Asn Pro
        115                 120                 125

Glu Ala Leu Asn Leu Thr Pro Glu Asp Ala Val Glu Ala Leu Ile Gly
    130                 135                 140

Ser Gly His His Gly Ala His His Gly Ala His His Pro Ala Ala Ala
145                 150                 155                 160

Ala Ala Tyr Glu Ala Phe Arg Gly Pro Gly Phe Ala Gly Gly Gly Gly
                165                 170                 175

Ala Asp Asp Met Gly Ala Gly His His His Gly Ala His His Ala Ala
            180                 185                 190

His His His His Ala Ala His His His His His His His His His His
        195                 200                 205

Gly Gly Ala Gly His Gly Gly Gly Ala Gly His His Val Arg Leu Glu
        210                 215                 220

Glu Arg Phe Ser Asp Asp Gln Leu Val Ser Met Ser Val Arg Glu Leu
225                 230                 235                 240

Asn Arg Gln Leu Arg Gly Phe Ser Lys Glu Glu Val Ile Arg Leu Lys
                245                 250                 255

Gln Lys Arg Arg Thr Leu Lys Asn Arg Gly Tyr Ala Gln Ser Cys Arg
            260                 265                 270

Phe Lys Arg Val Gln Gln Arg His Ile Leu Glu Ser Glu Lys Cys Gln
        275                 280                 285

Leu Gln Ser Gln Val Glu Gln Leu Lys Leu Glu Val Gly Arg Leu Ala
    290                 295                 300
```

-continued

```
Lys Glu Arg Asp Leu Tyr Lys Glu Lys Tyr Glu Lys Leu Ala Gly Arg
305                 310             315             320

Gly Gly Pro Gly Ser Ala Gly Gly Ala Gly Phe Pro Arg Glu Pro Ser
            325             330             335

Pro Pro Gln Ala Gly Pro Gly Gly Ala Lys Gly Thr Ala Asp Phe Phe
        340             345             350

Leu

<210> SEQ ID NO 24
<211> LENGTH: 2373
<212> TYPE: DNA
<213> ORGANISM: Homo sapiens

<400> SEQUENCE: 24
gcgcggccgg gcgcgggccc cgggcgatgg ccgcggagct ggcgatgggc gccgagctgc      60
ccagcagccc gctggccatc gagtacgtca acgacttcga cctgatgaag ttcgaggtga     120
agaaggagcc tcccgaggcc gagcgcttct gccaccgcc gccgccaggc tcgctgtcct     180
cgacgccgct cagcacgccc tgctcctccg tgccctcctc gcccagcttc tgcgcgccca     240
gcccgggcac cggcggcggc ggcggcgcgg ggggcggcgg cggctcgtct caggccgggg     300
gcgcccccgg gccgccgagc gggggcccccg gcgccgtcgg gggcacctcg gggaagccgg     360
cgctggagga tctgtactgg atgagcggct accagcatca cctcaacccc gaggcgctca     420
acctgacgcc cgaggacgcg gtggaggcgc tcatcggcag cggccaccac ggcgcgcacc     480
acggcgcgca ccacccggcg gccgccgcag cctacgagct tttccgcggc ccgggcttcg     540
cgggcggcgg cggagcggac gacatgggcg ccggccacca ccacggcgcg caccacgccg     600
cccaccatca ccacgccgcc caccaccacc accaccacca ccaccaccat ggcggcgcgg     660
gacacggcgg tggcgcgggc caccacgtgc gcctggagga gcgcttctcc gacgaccagc     720
tggtgtccat gtcggtgcgc gagctgaacc ggcagctccg cggcttcagc aaggaggagg     780
tcatccggct caagcagaag cggcgcacgc tcaagaaccg cggctacgcg cagtcctgcc     840
gcttcaagcg ggtgcagcag cggcacattc tggagagcga gaagtgccaa ctccagagcc     900
aggtggagca gctgaagctg gaggtggggc gcctggccaa agagcgggac ctgtacaagg     960
agaaatacga gaagctggcg ggccggggcg gcccccgggag cgcgggcggg gccggtttcc    1020
cgcgggagcc ttcgccgccg caggccggtc ccggcggggc caagggcacg gccgacttct    1080
tcctgtaggc gccggacccc gagcccgcgc gccgtcgcc ggggacaagt tcgcgcaggc    1140
ctctcggggc ctcggctcgg actccgcggt acaggacgtg gacaccaggc ccggcccggc    1200
cgtgctggcc ccggtgccaa gtctgcgggc gcggggctgg aggcccctttc gctcccggtc    1260 cccgttcgcg cgcgtcggcc cgggtcgccg tcctgaggtt gagcggagaa cggtgatttc    1320
taaggaaact tgagccaggt ctaacttctt tccaagcgtc cgcttgtaca tacgttgaac    1380
gtggttctcc gttcccacct tcgccctgcc agcctagagg gaccgcgctg ccgtcccttc    1440
ccgggtggcc cctgcctgcc cccgccctcc ttcgttctct tctcagcctc cctttccttg    1500
ccttttttaa cttcccctcc ccgttttaaa atcggtctta ttttcgaagt atttataatt    1560
attatgcttg gtgattagaa aagaaaacct tggaggaagc cccttctttc cccagccggg    1620
gtccgccctc agtcgcgagt cacagcatga gtcgctcgcc aggaggggcc cggcccctgc    1680 ctgcccccctc cccgcttgcc cccgaccctg ctaccgcgcgt tccttggagg tcgaagccag    1740
ggacgtcacc cgtgctgtgt ccaggcctgc tgtcctacta tgctcaaccg ggggtggggg    1800
```

```
gagggggggtg agtcctgtgc tcagtcgggt gggggctggc ccggatcccg agctgctgtc    1860
tctctatgca ccagaacata tctgtaactc ctggggaaat acatcttgtt ttaaccttca    1920
agagaagtga aagaaaaaag taatgcacag tatttctagc agaaaatttt ttttttttaag    1980 aggaggcttg ggccagagcc ttctggcatg gggcgggtgg agaaagtgtt tttatttaa    2040 tttaaattgt gtttcgtttt gtttgtggaa tctttctta atgcttcgtc gctctttgga    2100
ctagccggga gagagggcga ggaggcgggt gctccaggcc ctgtaggctg gccaggcgc    2160 ctgggggatc tgcccgtttt cggaggccct caggggccat cagtgggatt ccagccgctc    2220
cacacccctc ccctgagcac tcggagtgga aggcgcgccg actcgttgaa agttttgttg    2280
tgtagttggt tttcgttgag ttcttttttc atttgctacg aaactgagaa aaagaaaaaa    2340
atacacaaaa taaatctgtt cagatccaag tca                                 2373
```

<210> SEQ ID NO 25
<211> LENGTH: 1939
<212> TYPE: PRT
<213> ORGANISM: Homo sapiens

<400> SEQUENCE: 25

```
Met Thr Asp Ala Gln Met Ala Asp Phe Gly Ala Ala Ala Gln Tyr Leu
1               5                   10                  15

Arg Lys Ser Glu Lys Glu Arg Leu Glu Ala Gln Thr Arg Pro Phe Asp
            20                  25                  30

Ile Arg Thr Glu Cys Phe Val Pro Asp Asp Lys Glu Glu Phe Val Lys
        35                  40                  45

Ala Lys Ile Leu Ser Arg Glu Gly Gly Lys Val Ile Ala Glu Thr Glu
    50                  55                  60

Asn Gly Lys Thr Val Thr Val Lys Glu Asp Gln Val Leu Gln Gln Asn
65                  70                  75                  80

Pro Pro Lys Phe Asp Lys Ile Glu Asp Met Ala Met Leu Thr Phe Leu
                85                  90                  95

His Glu Pro Ala Val Leu Phe Asn Leu Lys Glu Arg Tyr Ala Ala Trp
            100                 105                 110

Met Ile Tyr Thr Tyr Ser Gly Leu Phe Cys Val Thr Val Asn Pro Tyr
            115                 120                 125

Lys Trp Leu Pro Val Tyr Asn Ala Glu Val Val Ala Ala Tyr Arg Gly
        130                 135                 140

Lys Lys Arg Ser Glu Ala Pro Pro His Ile Phe Ser Ile Ser Asp Asn
145                 150                 155                 160

Ala Tyr Gln Tyr Met Leu Thr Asp Arg Glu Asn Gln Ser Ile Leu Ile
                165                 170                 175

Thr Gly Glu Ser Gly Ala Gly Lys Thr Val Asn Thr Lys Arg Val Ile
            180                 185                 190

Gln Tyr Phe Ala Ser Ile Ala Ala Ile Gly Asp Arg Gly Lys Lys Asp
        195                 200                 205

Asn Ala Asn Ala Asn Lys Gly Thr Leu Glu Asp Gln Ile Ile Gln Ala
    210                 215                 220

Asn Pro Ala Leu Glu Ala Phe Gly Asn Ala Lys Thr Val Arg Asn Asp
225                 230                 235                 240

Asn Ser Ser Arg Phe Gly Lys Phe Ile Arg Ile His Phe Gly Ala Thr
                245                 250                 255

Gly Lys Leu Ala Ser Ala Asp Ile Glu Thr Tyr Leu Leu Glu Lys Ser
            260                 265                 270
```

-continued

```
Arg Val Ile Phe Gln Leu Lys Ala Glu Arg Asn Tyr His Ile Phe Tyr
        275                 280                 285

Gln Ile Leu Ser Asn Lys Lys Pro Glu Leu Leu Asp Met Leu Leu Val
        290                 295                 300

Thr Asn Asn Pro Tyr Asp Tyr Ala Phe Val Ser Gln Gly Glu Val Ser
305                 310                 315                 320

Val Ala Ser Ile Asp Asp Ser Glu Glu Leu Met Ala Thr Asp Ser Ala
                325                 330                 335

Phe Asp Val Leu Gly Phe Thr Ser Glu Glu Lys Ala Gly Val Tyr Lys
                340                 345                 350

Leu Thr Gly Ala Ile Met His Tyr Gly Asn Met Lys Phe Lys Gln Lys
                355                 360                 365

Gln Arg Glu Glu Gln Ala Glu Pro Asp Gly Thr Glu Asp Ala Asp Lys
        370                 375                 380

Ser Ala Tyr Leu Met Gly Leu Asn Ser Ala Asp Leu Leu Lys Gly Leu
385                 390                 395                 400

Cys His Pro Arg Val Lys Val Gly Asn Glu Tyr Val Thr Lys Gly Gln
                405                 410                 415

Ser Val Gln Gln Val Tyr Tyr Ser Ile Gly Ala Leu Ala Lys Ala Val
                420                 425                 430

Tyr Glu Lys Met Phe Asn Trp Met Val Thr Arg Ile Asn Ala Thr Leu
                435                 440                 445

Glu Thr Lys Gln Pro Arg Gln Tyr Phe Ile Gly Val Leu Asp Ile Ala
        450                 455                 460

Gly Phe Glu Ile Phe Asp Phe Asn Ser Phe Glu Gln Leu Cys Ile Asn
465                 470                 475                 480

Phe Thr Asn Glu Lys Leu Gln Gln Phe Phe Asn His His Met Phe Val
                485                 490                 495

Leu Glu Gln Glu Glu Tyr Lys Lys Glu Gly Ile Glu Trp Thr Phe Ile
                500                 505                 510

Asp Phe Gly Met Asp Leu Gln Ala Cys Ile Asp Leu Ile Glu Lys Pro
        515                 520                 525

Met Gly Ile Met Ser Ile Leu Glu Glu Glu Cys Met Phe Pro Lys Ala
        530                 535                 540

Thr Asp Met Thr Phe Lys Ala Lys Leu Tyr Asp Asn His Leu Gly Lys
545                 550                 555                 560

Ser Asn Asn Phe Gln Lys Pro Arg Asn Ile Lys Gly Lys Gln Glu Ala
                565                 570                 575

His Phe Ser Leu Ile His Tyr Ala Gly Thr Val Asp Tyr Asn Ile Leu
                580                 585                 590

Gly Trp Leu Glu Lys Asn Lys Asp Pro Leu Asn Glu Thr Val Val Ala
                595                 600                 605

Leu Tyr Gln Lys Ser Ser Leu Lys Leu Met Ala Thr Leu Phe Ser Ser
        610                 615                 620

Tyr Ala Thr Ala Asp Thr Gly Asp Ser Gly Lys Ser Lys Gly Gly Lys
625                 630                 635                 640

Lys Lys Gly Ser Ser Phe Gln Thr Val Ser Ala Leu His Arg Glu Asn
                645                 650                 655

Leu Asn Lys Leu Met Thr Asn Leu Arg Thr Thr His Pro His Phe Val
                660                 665                 670

Arg Cys Ile Ile Pro Asn Glu Arg Lys Ala Pro Gly Val Met Asp Asn
                675                 680                 685
```

-continued

```
Pro Leu Val Met His Gln Leu Arg Cys Asn Gly Val Leu Glu Gly Ile
    690                 695                 700

Arg Ile Cys Arg Lys Gly Phe Pro Asn Arg Ile Leu Tyr Gly Asp Phe
705                 710                 715                 720

Arg Gln Arg Tyr Arg Ile Leu Asn Pro Val Ala Ile Pro Glu Gly Gln
                725                 730                 735

Phe Ile Asp Ser Arg Lys Gly Thr Glu Lys Leu Leu Ser Ser Leu Asp
                740                 745                 750

Ile Asp His Asn Gln Tyr Lys Phe Gly His Thr Lys Val Phe Phe Lys
            755                 760                 765

Ala Gly Leu Leu Gly Leu Leu Glu Glu Met Arg Asp Glu Arg Leu Ser
    770                 775                 780

Arg Ile Ile Thr Arg Met Gln Ala Gln Ala Arg Gly Gln Leu Met Arg
785                 790                 795                 800

Ile Glu Phe Lys Lys Ile Val Glu Arg Arg Asp Ala Leu Leu Val Ile
                805                 810                 815

Gln Trp Asn Ile Arg Ala Phe Met Gly Val Lys Asn Trp Pro Trp Met
                820                 825                 830

Lys Leu Tyr Phe Lys Ile Lys Pro Leu Leu Lys Ser Ala Glu Thr Glu
                835                 840                 845

Lys Glu Met Ala Thr Met Lys Glu Glu Phe Gly Arg Ile Lys Glu Thr
    850                 855                 860

Leu Glu Lys Ser Glu Ala Arg Arg Lys Glu Leu Glu Glu Lys Met Val
865                 870                 875                 880

Ser Leu Leu Gln Glu Lys Asn Asp Leu Gln Leu Gln Val Gln Ala Glu
                885                 890                 895

Gln Asp Asn Leu Asn Asp Ala Glu Glu Arg Cys Asp Gln Leu Ile Lys
                900                 905                 910

Asn Lys Ile Gln Leu Glu Ala Lys Val Lys Glu Met Asn Glu Arg Leu
            915                 920                 925

Glu Asp Glu Glu Glu Met Asn Ala Glu Leu Thr Ala Lys Lys Arg Lys
    930                 935                 940

Leu Glu Asp Glu Cys Ser Glu Leu Lys Lys Asp Ile Asp Asp Leu Glu
945                 950                 955                 960

Leu Thr Leu Ala Lys Val Glu Lys Glu Lys His Ala Thr Glu Asn Lys
                965                 970                 975

Val Lys Asn Leu Thr Glu Glu Met Ala Gly Leu Asp Glu Ile Ile Ala
                980                 985                 990

Lys Leu Thr Lys Glu Lys Lys Ala  Leu Gln Glu Ala His  Gln Gln Ala
            995                 1000                1005

Leu Asp  Asp Leu Gln Val Glu  Glu Asp Lys Val Asn  Ser Leu Ser
    1010                1015                1020

Lys Ser  Lys Val Lys Leu Glu  Gln Gln Val Asp Asp  Leu Glu Gly
    1025                1030                1035

Ser Leu  Glu Gln Glu Lys Lys  Val Arg Met Asp Leu  Glu Arg Ala
    1040                1045                1050

Lys Arg  Lys Leu Glu Gly Asp  Leu Lys Leu Thr Gln  Glu Ser Ile
    1055                1060                1065

Met Asp  Leu Glu Asn Asp Lys  Leu Gln Leu Glu Glu  Lys Leu Lys
    1070                1075                1080

Lys Lys  Glu Phe Asp Ile Asn  Gln Gln Asn Ser Lys  Ile Glu Asp
    1085                1090                1095

Glu Gln  Val Leu Ala Leu Gln  Leu Gln Lys Lys Leu  Lys Glu Asn
```

```
        1100            1105            1110

Gln Ala  Arg Ile Glu Glu Leu  Glu Glu Glu Leu Glu  Ala Glu Arg
    1115            1120            1125

Thr Ala  Arg Ala Lys Val Glu  Lys Leu Arg Ser Asp  Leu Ser Arg
    1130            1135            1140

Glu Leu  Glu Glu Ile Ser Glu  Arg Leu Glu Glu Ala  Gly Gly Ala
    1145            1150            1155

Thr Ser  Val Gln Ile Glu Met  Asn Lys Lys Arg Glu  Ala Glu Phe
    1160            1165            1170

Gln Lys  Met Arg Arg Asp Leu  Glu Glu Ala Thr Leu  Gln His Glu
    1175            1180            1185

Ala Thr  Ala Ala Ala Leu Arg  Lys Lys His Ala Asp  Ser Val Ala
    1190            1195            1200

Glu Leu  Gly Glu Gln Ile Asp  Asn Leu Gln Arg Val  Lys Gln Lys
    1205            1210            1215

Leu Glu  Lys Glu Lys Ser Glu  Phe Lys Leu Glu Leu  Asp Asp Val
    1220            1225            1230

Thr Ser  Asn Met Glu Gln Ile  Ile Lys Ala Lys Ala  Asn Leu Glu
    1235            1240            1245

Lys Val  Ser Arg Thr Leu Glu  Asp Gln Ala Asn Glu  Tyr Arg Val
    1250            1255            1260

Lys Leu  Glu Glu Ala Gln Arg  Ser Leu Asn Asp Phe  Thr Thr Gln
    1265            1270            1275

Arg Ala  Lys Leu Gln Thr Glu  Asn Gly Glu Leu Ala  Arg Gln Leu
    1280            1285            1290

Glu Glu  Lys Glu Ala Leu Ile  Ser Gln Leu Thr Arg  Gly Lys Leu
    1295            1300            1305

Ser Tyr  Thr Gln Gln Met Glu  Asp Leu Lys Arg Gln  Leu Glu Glu
    1310            1315            1320

Glu Gly  Lys Ala Lys Asn Ala  Leu Ala His Ala Leu  Gln Ser Ala
    1325            1330            1335

Arg His  Asp Cys Asp Leu Leu  Arg Glu Gln Tyr Glu  Glu Glu Thr
    1340            1345            1350

Glu Ala  Lys Ala Glu Leu Gln  Arg Val Leu Ser Lys  Ala Asn Ser
    1355            1360            1365

Glu Val  Ala Gln Trp Arg Thr  Lys Tyr Glu Thr Asp  Ala Ile Gln
    1370            1375            1380

Arg Thr  Glu Glu Leu Glu Glu  Ala Lys Lys Lys Leu  Ala Gln Arg
    1385            1390            1395

Leu Gln  Asp Ala Glu Glu Ala  Val Glu Ala Val Asn  Ala Lys Cys
    1400            1405            1410

Ser Ser  Leu Glu Lys Thr Lys  His Arg Leu Gln Asn  Glu Ile Glu
    1415            1420            1425

Asp Leu  Met Val Asp Val Glu  Arg Ser Asn Ala Ala  Ala Ala Ala
    1430            1435            1440

Leu Asp  Lys Lys Gln Arg Asn  Phe Asp Lys Ile Leu  Ala Glu Trp
    1445            1450            1455

Lys Gln  Lys Tyr Glu Glu Ser  Gln Ser Glu Leu Glu  Ser Ser Gln
    1460            1465            1470

Lys Glu  Ala Arg Ser Leu Ser  Thr Glu Leu Phe Lys  Leu Lys Asn
    1475            1480            1485

Ala Tyr  Glu Glu Ser Leu Glu  His Leu Glu Thr Phe  Lys Arg Glu
    1490            1495            1500
```

-continued

```
Asn Lys Asn Leu Gln Glu Glu  Ile Ser Asp Leu Thr  Glu Gln Leu
    1505             1510             1515

Gly Glu Gly Gly Lys Asn Val  His Glu Leu Glu Lys  Val Arg Lys
    1520             1525             1530

Gln Leu Glu Val Glu Lys Leu  Glu Leu Gln Ser Ala  Leu Glu Glu
    1535             1540             1545

Ala Glu Ala Ser Leu Glu His  Glu Glu Gly Lys Ile  Leu Arg Ala
    1550             1555             1560

Gln Leu Glu Phe Asn Gln Ile  Lys Ala Glu Ile Glu  Arg Lys Leu
    1565             1570             1575

Ala Glu Lys Asp Glu Glu Met  Glu Gln Ala Lys Arg  Asn His Gln
    1580             1585             1590

Arg Val Val Asp Ser Leu Gln  Thr Ser Leu Asp Ala  Glu Thr Arg
    1595             1600             1605

Ser Arg Asn Glu Val Leu Arg  Val Lys Lys Lys Met  Glu Gly Asp
    1610             1615             1620

Leu Asn Glu Met Glu Ile Gln  Leu Ser His Ala Asn  Arg Met Ala
    1625             1630             1635

Ala Glu Ala Gln Lys Gln Val  Lys Ser Leu Gln Ser  Leu Leu Lys
    1640             1645             1650

Asp Thr Gln Ile Gln Leu Asp  Asp Ala Val Arg Ala  Asn Asp Asp
    1655             1660             1665

Leu Lys Glu Asn Ile Ala Ile  Val Glu Arg Arg Asn  Asn Leu Leu
    1670             1675             1680

Gln Ala Glu Leu Glu Glu Leu  Arg Ala Val Val Glu  Gln Thr Glu
    1685             1690             1695

Arg Ser Arg Lys Leu Ala Glu  Gln Glu Leu Ile Glu  Thr Ser Glu
    1700             1705             1710

Arg Val Gln Leu Leu His Ser  Gln Asn Thr Ser Leu  Ile Asn Gln
    1715             1720             1725

Lys Lys Lys Met Glu Ser Asp  Leu Thr Gln Leu Gln  Ser Glu Val
    1730             1735             1740

Glu Glu Ala Val Gln Glu Cys  Arg Asn Ala Glu Glu  Lys Ala Lys
    1745             1750             1755

Lys Ala Ile Thr Asp Ala Ala  Met Met Ala Glu Glu  Leu Lys Lys
    1760             1765             1770

Glu Gln Asp Thr Ser Ala His  Leu Glu Arg Met Lys  Lys Asn Met
    1775             1780             1785

Glu Gln Thr Ile Lys Asp Leu  Gln His Arg Leu Asp  Glu Ala Glu
    1790             1795             1800

Gln Ile Ala Leu Lys Gly Gly  Lys Lys Gln Leu Gln  Lys Leu Glu
    1805             1810             1815

Ala Arg Val Arg Glu Leu Glu  Gly Glu Leu Glu Ala  Glu Gln Lys
    1820             1825             1830

Arg Asn Ala Glu Ser Val Lys  Gly Met Arg Lys Ser  Glu Arg Arg
    1835             1840             1845

Ile Lys Glu Leu Thr Tyr Gln  Thr Glu Glu Asp Lys  Lys Asn Leu
    1850             1855             1860

Leu Arg Leu Gln Asp Leu Val  Asp Lys Leu Gln Leu  Lys Val Lys
    1865             1870             1875

Ala Tyr Lys Arg Gln Ala Glu  Glu Ala Glu Glu Gln  Ala Asn Thr
    1880             1885             1890
```

```
Asn Leu  Ser Lys Phe Arg Lys  Val Gln His Glu Leu  Asp Glu Ala
    1895                 1900              1905

Glu Glu  Arg Ala Asp Ile Ala  Glu Ser Gln Val Asn  Lys Leu Arg
    1910             1915              1920

Ala Lys  Ser Arg Asp Ile Gly  Ala Lys Gln Lys Met  His Asp Glu
    1925             1930              1935

Glu
```

<210> SEQ ID NO 26
<211> LENGTH: 5941
<212> TYPE: DNA
<213> ORGANISM: Homo sapiens

<400> SEQUENCE: 26

```
agatagagag actcctgcgg cccagattct tcaggattct ccgtgaaggg ataaccaggg     60
gaagcaccaa gatgaccgat gcccagatgg ctgactttgg ggcagcggcc cagtacctcc    120
gcaagtcaga gaaggagcgt ctagaggccc agacccggcc cttttgacatt cgcactgagt    180 gcttcgtgcc cgatgacaag gaagagtttg tcaaagccaa gattttgtcc cgggagggag    240
gcaaggtcat tgctgaaacc gagaatggga agacggtgac tgtgaaggag gaccaggtgt    300
tgcagcagaa cccacccaag ttcgacaaga ttgaggacat ggccatgctg accttcctgc    360
acgagcccgc ggtgctttc aacctcaagg agcgctacgc ggcctggatg atatatacct    420
actcgggcct cttctgtgtc actgtcaacc cctacaagtg gctgccggtg tacaatgccg    480
aggtggtggc cgcctaccgg ggcaagaaga ggagtgaggc cccgccccac atcttctcca    540
tctccgacaa cgcctatcag tacatgctga cagatcggga gaaccagtcc atcctcatca    600
cgggagaatc cggggcgggg aagactgtga caccaagcg tgtcatccag tactttgcca    660
gcattgcagc cataggtgac cgtggcaaga aggacaatgc caatgcgaac aagggcaccc    720
tggaggacca gatcatccag gccaaccccg ctctggaggc cttcggcaat gccaagactg    780
tccggaacga caactcctcc cgctttggga aattcattag gatccacttt ggggccactg    840
gaaagctggc ttctgcagac atagagacct acctgctgga gaagtcccgg gtgatcttcc    900
agctgaaagc tgagagaaac taccacatct tctaccagat tctgtccaac aagaagccgg    960
agttgctgga catgctgctg gtcaccaaca tccctacga ctacgccttc gtgtctcagg   1020
gagaggtgtc cgtggcctcc attgatgact ccgaggagct catggccacc gatagtgcct   1080
ttgacgtgct gggcttcact tcagaggaga agctggcgt ctacaagctg acgggagcca   1140
tcatgcacta cgggaacatg aagttcaagc agaagcagcg ggaggagcag gcggagccag   1200
acggcaccga agatgctgac aagtcggcct acctcatggg gctgaactca gctgacctgc   1260
tcaaggggct gtgccaccct cgggtgaaag tgggcaacga gtatgtcacc aagggccaga   1320
gcgtgcagca ggtgtactac tccatcgggg ctctggccaa ggcagtgtat gagaagatgt   1380
tcaactggat ggtgacgcgc atcaacgcca ccctggagac caagcagcca cgccagtact   1440
tcataggagt cctggacatc gctggcttcg agatcttcga cttcaacagc tttgagcagc   1500
tctgcatcaa cttcaccaac gagaagctgc agcagttctt caaccaccac atgttcgtgc   1560
tggagcagga ggagtacaag aaggagggca ttgagtggac attcattgac tttggcatgg   1620
acctgcaggc ctgcattgac ctcatcgaga gcccatggg catcatgtcc atcctggagg   1680
aggagtgcat gttccccaag gccactgaca tgacttcaa ggccaagctg tacgacaacc   1740
acctgggcaa gtccaacaat ttccagaagc cacgcaacat caaggggaag caggaagccc   1800
```

-continued

```
acttctccct gatccactac gccggcactg tggactacaa catcctgggc tggctggaaa    1860
aaaacaagga tcctctcaac gagactgttg tggccctgta ccagaagtcc tccctcaagc    1920
tcatggccac tctcttctcc tcctacgcaa ctgccgatac tggggacagt ggtaaaagca    1980
aaggaggcaa gaaaaagggc tcatccttcc agacggtgtc ggctctccac cgggaaaatc    2040
tcaacaagct aatgaccaac ctgaggacca cccatcctca ctttgtgcgt tgcatcatcc    2100
ccaatgagcg gaaggctcca ggggtgatgg acaaccccct ggtcatgcac cagctgcgct    2160
gcaatggcgt gctggagggc atccgcatct gcaggaaggg cttccccaac cgcatcctct    2220
acggggactt ccggcagagg tatcgcatcc tgaacccagt ggccatccct gagggacagt    2280
tcattgatag caggaagggg acagagaagc tgctcagctc tctggacatt gatcacaacc    2340
agtacaagtt tggccacacc aaggtgttct tcaaggcagg gctgcttggg ctgctggagg    2400
agatgcggga tgagaggctg agccgcatca tcacgcgcat gcaggcccaa gcccgggggcc    2460 agctcatgcg cattgagttc aagaagatag tggaacgcag ggatgccctg ctggtaatcc    2520
agtggaacat tcgggccttc atgggggtca agaattggcc ctggatgaag ctctacttca    2580
agatcaagcc gctgctgaag agcgcagaga cggagaagga gatggccacc atgaaggaag    2640
agttcgggcg catcaaagag acgctggaga agtccgaggc tcgccgcaag gagctggagg    2700
agaagatggt gtccctgctg caggagaaga atgacctgca gctccaagtg caggcggaac    2760
aagacaacct caatgatgct gaggagcgct gcgaccagct gatcaaaaac aagattcagc    2820
tggaggccaa agtaaaggag atgaatgaga ggctggagga tgaggaggag atgaacgcgg    2880
agctcactgc caagaagcgc aagctggaag acgagtgctc agagctcaag aaggacattg    2940
atgacctgga gctgacactg gccaaggtgg agaaggagaa gcatgcaaca gagaacaagg    3000
tgaagaacct aacagaggag atggctgggc tggatgaaat catcgctaag ctgaccaagg    3060
agaagaaagc tctacaagag gcccatcagc aggccctgga tgaccttcag gttgaggaag    3120
acaaggtcaa cagcctgtcc aagtctaagg tcaagctgga gcagcaggtg gatgatctgg    3180
agggatccct agagcaagag aagaaggtgc gcatggacct ggagcgagca aagcggaaac    3240
tggagggcga cctgaagctg acccaggaga gcatcatgga cctggaaaat gataaactgc    3300
agctggaaga aaagcttaag aagaaggagt ttgacattaa tcagcagaac agtaagattg    3360
aggatgagca ggtgctggcc cttcaactac agaagaaact gaaggaaaac caggcacgca    3420
tcgaggagct ggaggaggag ctggaggccg agcgcaccgc cagggctaag gtggagaagc    3480
tgcgctcaga cctgtctcgg gagctggagg agatcagcga gcggctggaa gaggccggcg    3540
gggccacgtc cgtgcagatc gagatgaaca agaagcgcga ggccgagttc cagaagatgc    3600
ggcgggacct ggaggaggcc acgctgcagc acgaggccac tgccgcggcc ctgcgcaaga    3660
agcacgccga cagcgtggcc gagctgggcg agcagatcga caacctgcag cgggtgaagc    3720
agaagctgga gaaggagaag agcgagttca agctggagct ggatgacgtc acctccaaca    3780
tggagcagat catcaaggcc aaggcaaacc tggagaaagt gtctcggacg ctggaggacc    3840
aggccaatga gtaccgcgtg aagctagaag aggcccaacg ctccctcaat gatttcacca    3900
cccagcgagc caagctgcag accgagaatg agagttggc ccggcagcta gaggaaaagg    3960
aggcgctaat ctcgcagctg acccggggga agctctctta tacccagcaa atggaggacc    4020
tcaaaaggca gctggaggag gagggcaagg cgaagaacgc cctggcccat gcactgcagt    4080
cggcccggca tgactgcgac ctgctgcggg agcagtacga ggaggagaca gaggccaagg    4140
ccgagctgca gcgcgtcctg tccaaggcca actcggaggt ggcccagtgg aggaccaagt    4200
```

```
atgagacgga cgccattcag cggactgagg agctcgaaga ggccaaaaag aagctggccc    4260
agcggctgca ggatgccgag gaggccgtgg aggctgttaa tgccaagtgc tcctcactgg    4320
agaagaccaa gcaccggcta cagaatgaga tagaggactt gatggtggac gtagagcgct    4380
ccaatgctgc tgctgcagcc ctggacaaga agcagagaaa ctttgacaag atcctggccg    4440
agtggaagca gaagtatgag gagtcgcagt ctgagctgga gtcctcacag aaggaggctc    4500
gctccctcag cacagagctc ttcaagctca agaacgccta cgaggagtcc ctggagcacc    4560
tagagacctt caagcgggag aacaagaacc ttcaggagga aatctcggac cttactgagc    4620
agctaggaga aggaggaaag aatgtgcatg agctggagaa ggtccgcaaa cagctggagg    4680
tggagaagct ggagctgcag tcagccctgg aggaggcaga ggcctccctg gagcacgagg    4740
agggcaagat cctccgggcc cagctagagt tcaaccagat caaggcagag atcgagcgga    4800
agctggcaga gaaggacgag gagatggaac aggccaagcg caaccaccag cgggtggtgg    4860
actcgctgca gacctccctg gatgcagaga cacgcagccg caacgaggtc ctgaggtgtga    4920 agaagaagat ggaaggagac ctcaatgaga tggagatcca gctcagccac gccaaccgca    4980
tggctgccga ggcccagaag caagtcaaga gcctccagag cttgctgaag gacacccaga    5040
tccagctgga cgatgcggtc cgtgccaacg acgacctgaa ggagaacatc gccatcgtgg    5100
agcggcgcaa caacctgctg caggctgagc tggaggagct cgcgtgccgtg gtggagcaga    5160 cagagcggtc ccggaagctg gcggagcagg agctgattga gaccagcgag cgggtgcagc    5220
tgctgcattc ccagaacacc agcctcatca accagaagaa gaagatggag tcggatctga    5280
cccagctcca gtcggaagtg gaggaggcag tgcaggagtg cagaaacgcc gaggagaagg    5340
ccaagaaggc catcacggat gccgccatga tggcagagga gctgaagaag gagcaggaca    5400
ccagcgccca cctggagcgc atgaagaaga acatggagca gaccattaag gacctgcagc    5460
accggctgga cgaggccgag cagatcgccc tcaaggagg caagaagcag ctgcagaagc    5520
tggaagcgcg ggtgcgggag ctggaggtg agctggaggc cgagcagaag cgcaacgcag    5580
agtcggtgaa gggcatgagg aagagcgagc ggcgcatcaa ggagctcacc taccagacag    5640
aggaagacaa aaagaacctg ctgcggctac aggacctggt ggacaagctg caactgaagg    5700
tcaaggccta caagcgccag gccgaggagg cggaggagca agccaacacc aacctgtcca    5760
agttccgcaa ggtgcagcat gagctggatg aggcagagga gcgggcggac atcgctgagt    5820
cccaggtcaa caagcttcga gccaagagcc gtgacattgg tgccaagcaa aaaatgcacg    5880
atgaggagtg acactgcctc gggaacctca ctcttgccaa cctgtaataa atatgagtgc    5940
c                                                                     5941
```

<210> SEQ ID NO 27
<211> LENGTH: 175
<212> TYPE: PRT
<213> ORGANISM: Homo sapiens

<400> SEQUENCE: 27

```
Met Ala Ser Arg Lys Ala Gly Thr Arg Gly Lys Val Ala Ala Thr Lys
1               5                   10                  15

Gln Ala Gln Arg Gly Ser Ser Asn Val Phe Ser Met Phe Glu Gln Ala
            20                  25                  30

Gln Ile Gln Glu Phe Lys Glu Ala Phe Ser Cys Ile Asp Gln Asn Arg
        35                  40                  45

Asp Gly Ile Ile Cys Lys Ala Asp Leu Arg Glu Thr Tyr Ser Gln Leu
```

```
      50              55              60

Gly Lys Val Ser Val Pro Glu Glu Leu Asp Ala Met Leu Gln Glu
65              70              75              80

Gly Lys Gly Pro Ile Asn Phe Thr Val Phe Leu Thr Leu Phe Gly Glu
              85              90              95

Lys Leu Asn Gly Thr Asp Pro Glu Glu Ala Ile Leu Ser Ala Phe Arg
              100             105             110

Met Phe Asp Pro Ser Gly Lys Gly Val Val Asn Lys Asp Glu Phe Lys
        115             120             125

Gln Leu Leu Leu Thr Gln Ala Asp Lys Phe Ser Pro Ala Glu Val Glu
        130             135             140

Gln Met Phe Ala Leu Thr Pro Met Asp Leu Ala Gly Asn Ile Asp Tyr
145             150             155             160

Lys Ser Leu Cys Tyr Ile Ile Thr His Gly Asp Glu Lys Glu Glu
              165             170             175
```

```
<210> SEQ ID NO 28
<211> LENGTH: 619
<212> TYPE: DNA
<213> ORGANISM: Homo sapiens

<400> SEQUENCE: 28
tctgcagaga gaatggccag caggaaggcg gggacccggg gcaaggtggc agccaccaag      60
caggcccaac gtggttcttc caacgtcttt tccatgtttg aacaagccca gatacaggag     120
ttcaaagaag ccttcagctg tatcgaccag aatcgtgatg gcatcatctg caaggcagac     180
ctgagggaga cctactccca gctggggaag gtgagtgtcc cagaggagga gctggacgcc     240
atgctgcaag agggcaaggg ccccatcaac ttcaccgtct tcctcacgct ctttggggag     300
aagctcaatg gacagaccc cgaggaagcc atcctgagtg ccttccgcat gtttgacccc      360
agcggcaaag gggtggtgaa caaggatgag ttcaagcagc ttctcctgac ccaggcagac     420
aagttctctc cagctgaggt ggagcagatg ttcgccctga cacccatgga cctggcgggg     480
aacatcgact acaagtcact gtgctacatc atcacccatg gagacgagaa agaggaatga     540
ggggcagggc caggcccacg ggggggcacc tcaataaact ctgttgcaaa attggaaaaa     600
aaaaaaaaaa aaaaaaaaa                                                   619
```

```
<210> SEQ ID NO 29
<211> LENGTH: 5179
<212> TYPE: PRT
<213> ORGANISM: Homo sapiens

<400> SEQUENCE: 29

Met Gly Leu Pro Leu Ala Arg Leu Ala Ala Val Cys Leu Ala Leu Ser
1               5               10              15

Leu Ala Gly Gly Ser Glu Leu Gln Thr Glu Gly Arg Thr Arg Asn His
              20              25              30

Gly His Asn Val Cys Ser Thr Trp Gly Asn Phe His Tyr Lys Thr Phe
        35              40              45

Asp Gly Asp Val Phe Arg Phe Pro Gly Pro Cys Asp Tyr Asn Phe Ala
        50              55              60

Ser Asp Cys Arg Gly Ser Tyr Lys Glu Phe Ala Val His Leu Lys Arg
65              70              75              80

Gly Pro Gly Gln Ala Glu Ala Pro Ala Gly Val Glu Ser Ile Leu Leu
              85              90              95
```

```
Thr Ile Lys Asp Asp Thr Ile Tyr Leu Thr Arg His Leu Ala Val Leu
            100             105             110

Asn Gly Ala Val Val Ser Thr Pro His Tyr Ser Pro Gly Leu Leu Ile
        115             120             125

Glu Lys Ser Asp Ala Tyr Thr Lys Val Tyr Ser Arg Ala Gly Leu Thr
    130             135             140

Leu Met Trp Asn Arg Glu Asp Ala Leu Met Leu Glu Leu Asp Thr Lys
145             150             155             160

Phe Arg Asn His Thr Cys Gly Leu Cys Gly Asp Tyr Asn Gly Leu Gln
                165             170             175

Ser Tyr Ser Glu Phe Leu Ser Asp Gly Val Leu Phe Ser Pro Leu Glu
            180             185             190

Phe Gly Asn Met Gln Lys Ile Asn Gln Pro Asp Val Val Cys Glu Asp
        195             200             205

Pro Glu Glu Glu Val Ala Pro Ala Ser Cys Ser Glu His Arg Ala Glu
    210             215             220

Cys Glu Arg Leu Leu Thr Ala Glu Ala Phe Ala Asp Cys Gln Asp Leu
225             230             235             240

Val Pro Leu Glu Pro Tyr Leu Arg Ala Cys Gln Gln Asp Arg Cys Arg
            245             250             255

Cys Pro Gly Gly Asp Thr Cys Val Cys Ser Thr Val Ala Glu Phe Ser
            260             265             270

Arg Gln Cys Ser His Ala Gly Gly Arg Pro Gly Asn Trp Arg Thr Ala
        275             280             285

Thr Leu Cys Pro Lys Thr Cys Pro Gly Asn Leu Val Tyr Leu Glu Ser
    290             295             300

Gly Ser Pro Cys Met Asp Thr Cys Ser His Leu Glu Val Ser Ser Leu
305             310             315             320

Cys Glu Glu His Arg Met Asp Gly Cys Phe Cys Pro Glu Gly Thr Val
            325             330             335

Tyr Asp Asp Ile Gly Asp Ser Gly Cys Val Pro Val Ser Gln Cys His
            340             345             350

Cys Arg Leu His Gly His Leu Tyr Thr Pro Gly Gln Glu Ile Thr Asn
        355             360             365

Asp Cys Glu Gln Cys Val Cys Asn Ala Gly Arg Trp Val Cys Lys Asp
    370             375             380

Leu Pro Cys Pro Gly Thr Cys Ala Leu Glu Gly Gly Ser His Ile Thr
385             390             395             400

Thr Phe Asp Gly Lys Thr Tyr Thr Phe His Gly Asp Cys Tyr Tyr Val
            405             410             415

Leu Ala Lys Gly Asp His Asn Asp Ser Tyr Ala Leu Leu Gly Glu Leu
        420             425             430

Ala Pro Cys Gly Ser Thr Asp Lys Gln Thr Cys Leu Lys Thr Val Val
        435             440             445

Leu Leu Ala Asp Lys Lys Lys Asn Val Val Val Phe Lys Ser Asp Gly
    450             455             460

Ser Val Leu Leu Asn Glu Leu Gln Val Asn Leu Pro His Val Thr Ala
465             470             475             480

Ser Phe Ser Val Phe Arg Pro Ser Ser Tyr His Ile Met Val Ser Met
            485             490             495

Ala Ile Gly Val Arg Leu Gln Val Gln Leu Ala Pro Val Met Gln Leu
            500             505             510

Phe Val Thr Leu Asp Gln Ala Ser Gln Gly Gln Val Gln Gly Leu Cys
```

```
              515              520              525

Gly Asn Phe Asn Gly Leu Glu Gly Asp Asp Phe Lys Thr Ala Ser Gly
    530              535              540

Leu Val Glu Ala Thr Gly Ala Gly Phe Ala Asn Thr Trp Lys Ala Gln
545              550              555              560

Ser Thr Cys His Asp Lys Leu Asp Trp Leu Asp Asp Pro Cys Ser Leu
            565              570              575

Asn Ile Glu Ser Ala Asn Tyr Ala Glu His Trp Cys Ser Leu Leu Lys
            580              585              590

Lys Thr Glu Thr Pro Phe Gly Arg Cys His Ser Ala Val Asp Pro Ala
            595              600              605

Glu Tyr Tyr Lys Arg Cys Lys Tyr Asp Thr Cys Asn Cys Gln Asn Asn
    610              615              620

Glu Asp Cys Leu Cys Ala Ala Leu Ser Ser Tyr Ala Arg Ala Cys Thr
625              630              635              640

Ala Lys Gly Val Met Leu Trp Gly Trp Arg Glu His Val Cys Asn Lys
            645              650              655

Asp Val Gly Ser Cys Pro Asn Ser Gln Val Phe Leu Tyr Asn Leu Thr
            660              665              670

Thr Cys Gln Gln Thr Cys Arg Ser Leu Ser Glu Ala Asp Ser His Cys
            675              680              685

Leu Glu Gly Phe Ala Pro Val Asp Gly Cys Gly Cys Pro Asp His Thr
    690              695              700

Phe Leu Asp Glu Lys Gly Arg Cys Val Pro Leu Ala Lys Cys Ser Cys
705              710              715              720

Tyr His Arg Gly Leu Tyr Leu Glu Ala Gly Asp Val Val Val Arg Gln
            725              730              735

Glu Glu Arg Cys Val Cys Arg Asp Gly Arg Leu His Cys Arg Gln Ile
            740              745              750

Arg Leu Ile Gly Gln Ser Cys Thr Ala Pro Lys Ile His Met Asp Cys
            755              760              765

Ser Asn Leu Thr Ala Leu Ala Thr Ser Lys Pro Arg Ala Leu Ser Cys
    770              775              780

Gln Thr Leu Ala Ala Gly Tyr Tyr His Thr Glu Cys Val Ser Gly Cys
785              790              795              800

Val Cys Pro Asp Gly Leu Met Asp Asp Gly Arg Gly Gly Cys Val Val
            805              810              815

Glu Lys Glu Cys Pro Cys Val His Asn Asn Asp Leu Tyr Ser Ser Gly
            820              825              830

Ala Lys Ile Lys Val Asp Cys Asn Thr Cys Thr Cys Lys Arg Gly Arg
            835              840              845

Trp Val Cys Thr Gln Ala Val Cys His Gly Thr Cys Ser Ile Tyr Gly
    850              855              860

Ser Gly His Tyr Ile Thr Phe Asp Gly Lys Tyr Tyr Asp Phe Asp Gly
865              870              875              880

His Cys Ser Tyr Val Ala Val Gln Asp Tyr Cys Gly Gln Asn Ser Ser
            885              890              895

Leu Gly Ser Phe Ser Ile Ile Thr Glu Asn Val Pro Cys Gly Thr Thr
            900              905              910

Gly Val Thr Cys Ser Lys Ala Ile Lys Ile Phe Met Gly Arg Thr Glu
            915              920              925

Leu Lys Leu Glu Asp Lys His Arg Val Val Ile Gln Arg Asp Glu Gly
    930              935              940
```

```
His His Val Ala Tyr Thr Thr Arg Glu Val Gly Gln Tyr Leu Val Val
945                 950                 955                 960

Glu Ser Ser Thr Gly Ile Ile Val Ile Trp Asp Lys Arg Thr Thr Val
                965                 970                 975

Phe Ile Lys Leu Ala Pro Ser Tyr Lys Gly Thr Val Cys Gly Leu Cys
            980                 985                 990

Gly Asn Phe Asp His Arg Ser Asn Asn Asp Phe Thr Thr Arg Asp His
        995                 1000                1005

Met Val Val Ser Ser Glu Leu Asp Phe Gly Asn Ser Trp Lys Glu
    1010            1015                1020

Ala Pro Thr Cys Pro Asp Val Ser Thr Asn Pro Glu Pro Cys Ser
    1025            1030                1035

Leu Asn Pro His Arg Arg Ser Trp Ala Glu Lys Gln Cys Ser Ile
    1040            1045                1050

Leu Lys Ser Ser Val Phe Ser Ile Cys His Ser Lys Val Asp Pro
    1055            1060                1065

Lys Pro Phe Tyr Glu Ala Cys Val His Asp Ser Cys Ser Cys Asp
    1070            1075                1080

Thr Gly Gly Asp Cys Glu Cys Phe Cys Ser Ala Val Ala Ser Tyr
    1085            1090                1095

Ala Gln Glu Cys Thr Lys Glu Gly Ala Cys Val Phe Trp Arg Thr
    1100            1105                1110

Pro Asp Leu Cys Pro Ile Phe Cys Asp Tyr Tyr Asn Pro Pro His
    1115            1120                1125

Glu Cys Glu Trp His Tyr Glu Pro Cys Gly Asn Arg Ser Phe Glu
    1130            1135                1140

Thr Cys Arg Thr Ile Asn Gly Ile His Ser Asn Ile Ser Val Ser
    1145            1150                1155

Tyr Leu Glu Gly Cys Tyr Pro Arg Cys Pro Lys Asp Arg Pro Ile
    1160            1165                1170

Tyr Glu Glu Asp Leu Lys Lys Cys Val Thr Ala Asp Lys Cys Gly
    1175            1180                1185

Cys Tyr Val Glu Asp Thr His Tyr Pro Pro Gly Ala Ser Val Pro
    1190            1195                1200

Thr Glu Glu Thr Cys Lys Ser Cys Val Cys Thr Asn Ser Ser Gln
    1205            1210                1215

Val Val Cys Arg Pro Glu Glu Gly Lys Ile Leu Asn Gln Thr Gln
    1220            1225                1230

Asp Gly Ala Phe Cys Tyr Trp Glu Ile Cys Gly Pro Asn Gly Thr
    1235            1240                1245

Val Glu Lys His Phe Asn Ile Cys Ser Ile Thr Thr Arg Pro Ser
    1250            1255                1260

Thr Leu Thr Thr Phe Thr Thr Ile Thr Leu Pro Thr Thr Pro Thr
    1265            1270                1275

Thr Phe Thr Thr Thr Thr Thr Thr Thr Thr Pro Thr Ser Ser Thr
    1280            1285                1290

Val Leu Ser Thr Thr Pro Lys Leu Cys Cys Leu Trp Ser Asp Trp
    1295            1300                1305

Ile Asn Glu Asp His Pro Ser Ser Gly Ser Asp Asp Gly Asp Arg
    1310            1315                1320

Glu Thr Phe Asp Gly Val Cys Gly Ala Pro Glu Asp Ile Glu Cys
    1325            1330                1335
```

```
Arg Ser  Val Lys Asp Pro His  Leu Ser Leu Glu Gln  Leu Gly Gln
    1340             1345              1350

Lys Val  Gln Cys Asp Val Ser  Val Gly Phe Ile Cys  Lys Asn Glu
    1355             1360              1365

Asp Gln  Phe Gly Asn Gly Pro  Phe Gly Leu Cys Tyr  Asp Tyr Lys
    1370             1375              1380

Ile Arg  Val Asn Cys Cys Trp  Pro Met Asp Lys Cys  Ile Thr Thr
    1385             1390              1395

Pro Ser  Pro Pro Thr Thr Thr  Pro Ser Pro Pro Thr  Thr Ser Thr
    1400             1405              1410

Thr Thr  Leu Pro Pro Thr Thr  Thr Pro Ser Pro Pro  Thr Thr Thr
    1415             1420              1425

Thr Thr  Thr Pro Pro Pro Thr  Thr Thr Pro Ser Pro  Pro Ile Thr
    1430             1435              1440

Thr Thr  Thr Thr Pro Pro Pro  Thr Thr Thr Pro Ser  Pro Pro Ile
    1445             1450              1455

Ser Thr  Thr Thr Thr Pro Pro  Pro Thr Thr Thr Pro  Ser Pro Pro
    1460             1465              1470

Thr Thr  Thr Pro Ser Pro Pro  Thr Thr Thr Pro Ser  Pro Pro Thr
    1475             1480              1485

Thr Thr  Thr Thr Thr Pro Pro  Pro Thr Thr Thr Pro  Ser Pro Pro
    1490             1495              1500

Thr Thr  Thr Pro Ile Thr Pro  Pro Ala Ser Thr Thr  Thr Leu Pro
    1505             1510              1515

Pro Thr  Thr Thr Pro Ser Pro  Pro Thr Thr Thr Thr  Thr Thr Pro
    1520             1525              1530

Pro Pro  Thr Thr Thr Pro Ser  Pro Pro Thr Thr Thr  Pro Ile Thr
    1535             1540              1545

Pro Pro  Thr Ser Thr Thr Thr  Leu Pro Pro Thr Thr  Thr Pro Ser
    1550             1555              1560

Pro Pro  Pro Thr Thr Thr Thr  Thr Pro Pro Pro Thr  Thr Thr Pro
    1565             1570              1575

Ser Pro  Pro Thr Thr Thr Thr  Pro Ser Pro Pro Thr  Ile Thr Thr
    1580             1585              1590

Thr Thr  Pro Pro Pro Thr Thr  Thr Pro Ser Pro Pro  Thr Thr Thr
    1595             1600              1605

Thr Thr  Thr Pro Pro Pro Thr  Thr Thr Pro Ser Pro  Pro Thr Thr
    1610             1615              1620

Thr Pro  Ile Thr Pro Pro Thr  Ser Thr Thr Thr Leu  Pro Pro Thr
    1625             1630              1635

Thr Thr  Pro Ser Pro Pro Pro  Thr Thr Thr Thr Thr  Pro Pro Pro
    1640             1645              1650

Thr Thr  Thr Pro Ser Pro Pro  Thr Thr Thr Thr Pro  Ser Pro Pro
    1655             1660              1665

Ile Thr  Thr Thr Thr Thr Pro  Pro Pro Thr Thr Thr  Pro Ser Ser
    1670             1675              1680

Pro Ile  Thr Thr Thr Pro Ser  Pro Pro Thr Thr Thr  Met Thr Thr
    1685             1690              1695

Pro Ser  Pro Thr Thr Thr Pro  Ser Ser Pro Ile Thr  Thr Thr Thr
    1700             1705              1710

Thr Pro  Ser Ser Thr Thr Thr  Pro Ser Pro Pro Pro  Thr Thr Met
    1715             1720              1725

Thr Thr  Pro Ser Pro Thr Thr  Thr Pro Ser Pro Pro  Thr Thr Thr
```

-continued

```
         1730              1735              1740

Met Thr  Thr Leu Pro Pro Thr  Thr Thr Ser Ser Pro  Leu Thr Thr
    1745              1750              1755

Thr Pro  Leu Pro Pro Ser Ile  Thr Pro Pro Thr Phe  Ser Pro Phe
    1760              1765              1770

Ser Thr  Thr Thr Pro Thr Thr  Pro Cys Val Pro Leu  Cys Asn Trp
    1775              1780              1785

Thr Gly  Trp Leu Asp Ser Gly  Lys Pro Asn Phe His  Lys Pro Gly
    1790              1795              1800

Gly Asp  Thr Glu Leu Ile Gly  Asp Val Cys Gly Pro  Gly Trp Ala
    1805              1810              1815

Ala Asn  Ile Ser Cys Arg Ala  Thr Met Tyr Pro Asp  Val Pro Ile
    1820              1825              1830

Gly Gln  Leu Gly Gln Thr Val  Val Cys Asp Val Ser  Val Gly Leu
    1835              1840              1845

Ile Cys  Lys Asn Glu Asp Gln  Lys Pro Gly Gly Val  Ile Pro Met
    1850              1855              1860

Ala Phe  Cys Leu Asn Tyr Glu  Ile Asn Val Gln Cys  Cys Glu Cys
    1865              1870              1875

Val Thr  Gln Pro Thr Thr Met  Thr Thr Thr Thr Thr  Glu Asn Pro
    1880              1885              1890

Thr Pro  Pro Thr Thr Thr Pro  Ile Thr Thr Thr Thr  Thr Val Thr
    1895              1900              1905

Pro Thr  Pro Thr Pro Thr Gly  Thr Gln Thr Pro Thr  Thr Thr Pro
    1910              1915              1920

Ile Thr  Thr Thr Thr Thr Val  Thr Pro Thr Pro Thr  Pro Thr Gly
    1925              1930              1935

Thr Gln  Thr Pro Thr Thr Thr  Pro Ile Thr Thr Thr  Thr Thr Val
    1940              1945              1950

Thr Pro  Thr Pro Thr Pro Thr  Gly Thr Gln Thr Pro  Thr Thr Thr
    1955              1960              1965

Pro Ile  Thr Thr Thr Thr Thr  Val Thr Pro Thr Pro  Thr Pro Thr
    1970              1975              1980

Gly Thr  Gln Thr Pro Thr Thr  Thr Pro Ile Thr Thr  Thr Thr Thr
    1985              1990              1995

Val Thr  Pro Thr Pro Thr Pro  Thr Gly Thr Gln Thr  Pro Thr Thr
    2000              2005              2010

Thr Pro  Ile Thr Thr Thr Thr  Thr Val Thr Pro Thr  Pro Thr Pro
    2015              2020              2025

Thr Gly  Thr Gln Thr Pro Thr  Thr Thr Pro Ile Thr  Thr Thr Thr
    2030              2035              2040

Thr Val  Thr Pro Thr Pro Thr  Pro Thr Gly Thr Gln  Thr Pro Thr
    2045              2050              2055

Thr Thr  Pro Ile Thr Thr Thr  Thr Thr Val Thr Pro  Thr Pro Thr
    2060              2065              2070

Pro Thr  Gly Thr Gln Thr Pro  Thr Thr Thr Pro Ile  Thr Thr Thr
    2075              2080              2085

Thr Thr  Val Thr Pro Thr Pro  Thr Pro Thr Gly Thr  Gln Thr Pro
    2090              2095              2100

Thr Thr  Thr Pro Ile Thr Thr  Thr Thr Thr Val Thr  Pro Thr Pro
    2105              2110              2115

Thr Pro  Thr Gly Thr Gln Thr  Pro Thr Thr Thr Pro  Ile Thr Thr
    2120              2125              2130
```

-continued

```
Thr Thr  Thr Val Thr Pro Thr  Pro Thr Pro Thr Gly  Thr Gln Thr
    2135             2140             2145

Pro Thr  Thr Thr Pro Ile Thr  Thr Thr Thr Thr Val  Thr Pro Thr
    2150             2155             2160

Pro Thr  Pro Thr Gly Thr Gln  Thr Pro Thr Thr Thr  Pro Ile Thr
    2165             2170             2175

Thr Thr  Thr Thr Val Thr Pro  Thr Pro Thr Pro Thr  Gly Thr Gln
    2180             2185             2190

Thr Pro  Thr Thr Thr Pro Ile  Thr Thr Thr Thr Thr  Val Thr Pro
    2195             2200             2205

Thr Pro  Thr Pro Thr Gly Thr  Gln Thr Pro Thr Thr  Thr Pro Ile
    2210             2215             2220

Thr Thr  Thr Thr Thr Val Thr  Pro Thr Pro Thr Pro  Thr Gly Thr
    2225             2230             2235

Gln Thr  Pro Thr Thr Thr Pro  Ile Thr Thr Thr Thr  Thr Val Thr
    2240             2245             2250

Pro Thr  Pro Thr Pro Thr Gly  Thr Gln Thr Pro Thr  Thr Thr Pro
    2255             2260             2265

Ile Thr  Thr Thr Thr Thr Val  Thr Pro Thr Pro Thr  Pro Thr Gly
    2270             2275             2280

Thr Gln  Thr Pro Thr Thr Thr  Pro Ile Thr Thr Thr  Thr Thr Val
    2285             2290             2295

Thr Pro  Thr Pro Thr Pro Thr  Gly Thr Gln Thr Pro  Thr Thr Thr
    2300             2305             2310

Pro Ile  Thr Thr Thr Thr Thr  Val Thr Pro Thr Pro  Thr Pro Thr
    2315             2320             2325

Gly Thr  Gln Thr Pro Thr Thr  Thr Pro Ile Thr Thr  Thr Thr Thr
    2330             2335             2340

Val Thr  Pro Thr Pro Thr Pro  Thr Gly Thr Gln Thr  Pro Thr Thr
    2345             2350             2355

Thr Pro  Ile Thr Thr Thr Thr  Thr Val Thr Pro Thr  Pro Thr Pro
    2360             2365             2370

Thr Gly  Thr Gln Thr Pro Thr  Thr Thr Pro Ile Thr  Thr Thr Thr
    2375             2380             2385

Thr Val  Thr Pro Thr Pro Thr  Pro Thr Gly Thr Gln  Thr Pro Thr
    2390             2395             2400

Thr Thr  Pro Ile Thr Thr Thr  Thr Thr Val Thr Pro  Thr Pro Thr
    2405             2410             2415

Pro Thr  Gly Thr Gln Thr Pro  Thr Thr Thr Pro Ile  Thr Thr Thr
    2420             2425             2430

Thr Thr  Val Thr Pro Thr Pro  Thr Pro Thr Gly Thr  Gln Thr Pro
    2435             2440             2445

Thr Thr  Thr Pro Ile Thr Thr  Thr Thr Thr Val Thr  Pro Thr Pro
    2450             2455             2460

Thr Pro  Thr Gly Thr Gln Thr  Pro Thr Thr Thr Pro  Ile Thr Thr
    2465             2470             2475

Thr Thr  Thr Val Thr Pro Thr  Pro Thr Pro Thr Gly  Thr Gln Thr
    2480             2485             2490

Pro Thr  Thr Thr Pro Ile Thr  Thr Thr Thr Thr Val  Thr Pro Thr
    2495             2500             2505

Pro Thr  Pro Thr Gly Thr Gln  Thr Pro Thr Thr Thr  Pro Ile Thr
    2510             2515             2520
```

-continued

```
Thr Thr  Thr Thr Val Thr Pro  Thr Pro Thr Pro  Thr Gly Thr Gln
2525             2530            2535

Thr Pro  Thr Thr Thr Pro Ile  Thr Thr Thr Thr  Thr Val Thr Pro
2540             2545            2550

Thr Pro  Thr Pro Thr Gly Thr  Gln Thr Pro Thr  Thr Thr Pro Ile
2555             2560            2565

Thr Thr  Thr Thr Thr Val Thr  Pro Thr Pro Thr  Pro Thr Gly Thr
2570             2575            2580

Gln Thr  Pro Thr Thr Thr Pro  Ile Thr Thr Thr  Thr Thr Val Thr
2585             2590            2595

Pro Thr  Pro Thr Pro Thr Gly  Thr Gln Thr Pro  Thr Thr Thr Pro
2600             2605            2610

Ile Thr  Thr Thr Thr Thr Val  Thr Pro Thr Pro  Thr Pro Thr Gly
2615             2620            2625

Thr Gln  Thr Pro Thr Thr Thr  Pro Ile Thr Thr  Thr Thr Thr Val
2630             2635            2640

Thr Pro  Thr Pro Thr Pro Thr  Gly Thr Gln Thr  Pro Thr Thr Thr
2645             2650            2655

Pro Ile  Thr Thr Thr Thr Thr  Val Thr Pro Thr  Pro Thr Pro Thr
2660             2665            2670

Gly Thr  Gln Thr Pro Thr Thr  Thr Pro Ile Thr  Thr Thr Thr Thr
2675             2680            2685

Val Thr  Pro Thr Pro Thr Pro  Thr Gly Thr Gln  Thr Pro Thr Thr
2690             2695            2700

Thr Pro  Ile Thr Thr Thr Thr  Thr Val Thr Pro  Thr Pro Thr Pro
2705             2710            2715

Thr Gly  Thr Gln Thr Pro Thr  Thr Thr Pro Ile  Thr Thr Thr Thr
2720             2725            2730

Thr Val  Thr Pro Thr Pro Thr  Pro Thr Gly Thr  Gln Thr Pro Thr
2735             2740            2745

Thr Thr  Pro Ile Thr Thr Thr  Thr Thr Val Thr  Pro Thr Pro Thr
2750             2755            2760

Pro Thr  Gly Thr Gln Thr Pro  Thr Thr Thr Pro  Ile Thr Thr Thr
2765             2770            2775

Thr Thr  Val Thr Pro Thr Pro  Thr Pro Thr Gly  Thr Gln Thr Pro
2780             2785            2790

Thr Thr  Thr Pro Ile Thr Thr  Thr Thr Thr Val  Thr Pro Thr Pro
2795             2800            2805

Thr Pro  Thr Gly Thr Gln Thr  Pro Thr Thr Thr  Pro Ile Thr Thr
2810             2815            2820

Thr Thr  Thr Val Thr Pro Thr  Pro Thr Pro Thr  Gly Thr Gln Thr
2825             2830            2835

Pro Thr  Thr Thr Pro Ile Thr  Thr Thr Thr Val  Thr Pro Thr
2840             2845            2850

Pro Thr  Pro Thr Gly Thr Gln  Thr Pro Thr Thr  Thr Pro Ile Thr
2855             2860            2865

Thr Thr  Thr Thr Val Thr Pro  Thr Pro Thr Pro  Thr Gly Thr Gln
2870             2875            2880

Thr Pro  Thr Thr Thr Pro Ile  Thr Thr Thr Thr  Val Thr Pro
2885             2890            2895

Thr Pro  Thr Pro Thr Gly Thr  Gln Thr Pro Thr  Thr Thr Pro Ile
2900             2905            2910

Thr Thr  Thr Thr Thr Val Thr  Pro Thr Pro Thr Pro  Thr Gly Thr
```

-continued

```
         2915              2920              2925

Gln Thr  Pro Thr Thr Thr Pro  Ile Thr Thr Thr Thr  Thr Val Thr
         2930              2935              2940

Pro Thr  Pro Thr Pro Thr Gly  Thr Gln Thr Pro Thr  Thr Thr Pro
         2945              2950              2955

Ile Thr  Thr Thr Thr Thr Val  Thr Pro Thr Pro Thr  Pro Thr Gly
         2960              2965              2970

Thr Gln  Thr Pro Thr Thr Thr  Pro Ile Thr Thr Thr  Thr Thr Val
         2975              2980              2985

Thr Pro  Thr Pro Thr Pro Thr  Gly Thr Gln Thr Pro  Thr Thr Thr
         2990              2995              3000

Pro Ile  Thr Thr Thr Thr Thr  Val Thr Pro Thr Pro  Thr Pro Thr
         3005              3010              3015

Gly Thr  Gln Thr Pro Thr Thr  Thr Pro Ile Thr Thr  Thr Thr Thr
         3020              3025              3030

Val Thr  Pro Thr Pro Thr Pro  Thr Gly Thr Gln Thr  Pro Thr Thr
         3035              3040              3045

Thr Pro  Ile Thr Thr Thr Thr  Thr Val Thr Pro Thr  Pro Thr Pro
         3050              3055              3060

Thr Gly  Thr Gln Thr Pro Thr  Thr Thr Pro Ile Thr  Thr Thr Thr
         3065              3070              3075

Thr Val  Thr Pro Thr Pro Thr  Pro Thr Gly Thr Gln  Thr Pro Thr
         3080              3085              3090

Thr Thr  Pro Ile Thr Thr Thr  Thr Thr Val Thr Pro  Thr Pro Thr
         3095              3100              3105

Pro Thr  Gly Thr Gln Thr Pro  Thr Thr Thr Pro Ile  Thr Thr Thr
         3110              3115              3120

Thr Thr  Val Thr Pro Thr Pro  Thr Pro Thr Gly Thr  Gln Thr Pro
         3125              3130              3135

Thr Thr  Thr Pro Ile Thr Thr  Thr Thr Thr Val Thr  Pro Thr Pro
         3140              3145              3150

Thr Pro  Thr Gly Thr Gln Thr  Pro Thr Thr Thr Pro  Ile Thr Thr
         3155              3160              3165

Thr Thr  Thr Val Thr Pro Thr  Pro Thr Pro Thr Gly  Thr Gln Thr
         3170              3175              3180

Pro Thr  Thr Thr Pro Ile Thr  Thr Thr Thr Thr Val  Thr Pro Thr
         3185              3190              3195

Pro Thr  Pro Thr Gly Thr Gln  Thr Pro Thr Thr Thr  Pro Ile Thr
         3200              3205              3210

Thr Thr  Thr Thr Val Thr Pro  Thr Pro Thr Pro Thr  Gly Thr Gln
         3215              3220              3225

Thr Pro  Thr Thr Thr Pro Ile  Thr Thr Thr Thr Thr  Val Thr Pro
         3230              3235              3240

Thr Pro  Thr Pro Thr Gly Thr  Gln Thr Pro Thr Thr  Thr Pro Ile
         3245              3250              3255

Thr Thr  Thr Thr Thr Val Thr  Pro Thr Pro Thr Pro  Thr Gly Thr
         3260              3265              3270

Gln Thr  Pro Thr Thr Thr Pro  Ile Thr Thr Thr Thr  Thr Val Thr
         3275              3280              3285

Pro Thr  Pro Thr Pro Thr Gly  Thr Gln Thr Pro Thr  Thr Thr Pro
         3290              3295              3300

Ile Thr  Thr Thr Thr Thr Val  Thr Pro Thr Pro Thr  Pro Thr Gly
         3305              3310              3315
```

-continued

```
Thr Gln  Thr Pro Thr Thr Thr  Pro Ile Thr Thr Thr  Thr Thr Val
    3320                3325                3330

Thr Pro  Thr Pro Thr Pro Thr  Gly Thr Gln Thr Pro  Thr Thr Thr
    3335                3340                3345

Pro Ile  Thr Thr Thr Thr Thr  Val Thr Pro Thr Pro  Thr Pro Thr
    3350                3355                3360

Gly Thr  Gln Thr Pro Thr Thr  Thr Pro Ile Thr Thr  Thr Thr Thr
    3365                3370                3375

Val Thr  Pro Thr Pro Thr Pro  Thr Gly Thr Gln Thr  Pro Thr Thr
    3380                3385                3390

Thr Pro  Ile Thr Thr Thr Thr  Thr Val Thr Pro Thr  Pro Thr Pro
    3395                3400                3405

Thr Gly  Thr Gln Thr Pro Thr  Thr Thr Pro Ile Thr  Thr Thr Thr
    3410                3415                3420

Thr Val  Thr Pro Thr Pro Thr  Pro Thr Gly Thr Gln  Thr Pro Thr
    3425                3430                3435

Thr Thr  Pro Ile Thr Thr Thr  Thr Thr Val Thr Pro  Thr Pro Thr
    3440                3445                3450

Pro Thr  Gly Thr Gln Thr Pro  Thr Thr Thr Pro Ile  Thr Thr Thr
    3455                3460                3465

Thr Thr  Val Thr Pro Thr Pro  Thr Pro Thr Gly Thr  Gln Thr Pro
    3470                3475                3480

Thr Thr  Thr Pro Ile Thr Thr  Thr Thr Thr Val Thr  Pro Thr Pro
    3485                3490                3495

Thr Pro  Thr Gly Thr Gln Thr  Pro Thr Thr Thr Pro  Ile Thr Thr
    3500                3505                3510

Thr Thr  Thr Val Thr Pro Thr  Pro Thr Pro Thr Gly  Thr Gln Thr
    3515                3520                3525

Pro Thr  Thr Thr Pro Ile Thr  Thr Thr Thr Val  Thr Pro Thr
    3530                3535                3540

Pro Thr  Pro Thr Gly Thr Gln  Thr Pro Thr Thr Thr  Pro Ile Thr
    3545                3550                3555

Thr Thr  Thr Thr Val Thr Pro  Thr Pro Thr Pro Thr  Gly Thr Gln
    3560                3565                3570

Thr Pro  Thr Thr Thr Pro Ile  Thr Thr Thr Thr Thr  Val Thr Pro
    3575                3580                3585

Thr Pro  Thr Pro Thr Gly Thr  Gln Thr Pro Thr Thr  Thr Pro Ile
    3590                3595                3600

Thr Thr  Thr Thr Thr Val Thr  Pro Thr Pro Thr Pro  Thr Gly Thr
    3605                3610                3615

Gln Thr  Pro Thr Thr Thr Pro  Ile Thr Thr Thr Thr  Thr Val Thr
    3620                3625                3630

Pro Thr  Pro Thr Pro Thr Gly  Thr Gln Thr Pro Thr  Thr Thr Pro
    3635                3640                3645

Ile Thr  Thr Thr Thr Thr Val  Thr Pro Thr Pro Thr  Pro Thr Gly
    3650                3655                3660

Thr Gln  Thr Pro Thr Thr Thr  Pro Ile Thr Thr Thr  Thr Thr Val
    3665                3670                3675

Thr Pro  Thr Pro Thr Pro Thr  Gly Thr Gln Thr Pro  Thr Thr Thr
    3680                3685                3690

Pro Ile  Thr Thr Thr Thr Thr  Val Thr Pro Thr Pro  Thr Pro Thr
    3695                3700                3705
```

-continued

```
Gly Thr  Gln Thr Pro Thr Thr  Thr Pro Ile Thr Thr  Thr Thr Thr
    3710                 3715                 3720

Val Thr  Pro Thr Pro Thr Pro  Thr Gly Thr Gln Thr  Pro Thr Thr
    3725                 3730                 3735

Thr Pro  Ile Thr Thr Thr Thr  Thr Val Thr Pro Thr  Pro Thr Pro
    3740                 3745                 3750

Thr Gly  Thr Gln Thr Pro Thr  Thr Thr Pro Ile Thr  Thr Thr Thr
    3755                 3760                 3765

Thr Val  Thr Pro Thr Pro Thr  Pro Thr Gly Thr Gln  Thr Pro Thr
    3770                 3775                 3780

Thr Thr  Pro Ile Thr Thr Thr  Thr Thr Val Thr Pro  Thr Pro Thr
    3785                 3790                 3795

Pro Thr  Gly Thr Gln Thr Pro  Thr Thr Thr Pro Ile  Thr Thr Thr
    3800                 3805                 3810

Thr Thr  Val Thr Pro Thr Pro  Thr Pro Thr Gly Thr  Gln Thr Pro
    3815                 3820                 3825

Thr Thr  Thr Pro Ile Thr Thr  Thr Thr Thr Val Thr  Pro Thr Pro
    3830                 3835                 3840

Thr Pro  Thr Gly Thr Gln Thr  Pro Thr Thr Thr Pro  Ile Thr Thr
    3845                 3850                 3855

Thr Thr  Thr Val Thr Pro Thr  Pro Thr Pro Thr Gly  Thr Gln Thr
    3860                 3865                 3870

Pro Thr  Thr Thr Pro Ile Thr  Thr Thr Thr Thr Val  Thr Pro Thr
    3875                 3880                 3885

Pro Thr  Pro Thr Gly Thr Gln  Thr Pro Thr Thr Thr  Pro Ile Thr
    3890                 3895                 3900

Thr Thr  Thr Thr Val Thr Pro  Thr Pro Thr Pro Thr  Gly Thr Gln
    3905                 3910                 3915

Thr Pro  Thr Thr Thr Pro Ile  Thr Thr Thr Thr Thr  Val Thr Pro
    3920                 3925                 3930

Thr Pro  Thr Pro Thr Gly Thr  Gln Thr Pro Thr Thr  Thr Pro Ile
    3935                 3940                 3945

Thr Thr  Thr Thr Thr Val Thr  Pro Thr Pro Thr Pro  Thr Gly Thr
    3950                 3955                 3960

Gln Thr  Pro Thr Thr Thr Pro  Ile Thr Thr Thr Thr  Thr Val Thr
    3965                 3970                 3975

Pro Thr  Pro Thr Pro Thr Gly  Thr Gln Thr Pro Thr  Thr Thr Pro
    3980                 3985                 3990

Ile Thr  Thr Thr Thr Thr Val  Thr Pro Thr Pro Thr  Pro Thr Gly
    3995                 4000                 4005

Thr Gln  Thr Pro Thr Thr Thr  Pro Ile Thr Thr Thr  Thr Thr Val
    4010                 4015                 4020

Thr Pro  Thr Pro Thr Pro Thr  Gly Thr Gln Thr Pro  Thr Thr Thr
    4025                 4030                 4035

Pro Ile  Thr Thr Thr Thr Thr  Val Thr Pro Thr Pro  Thr Pro Thr
    4040                 4045                 4050

Gly Thr  Gln Thr Pro Thr Thr  Thr Pro Ile Thr Thr  Thr Thr Thr
    4055                 4060                 4065

Val Thr  Pro Thr Pro Thr Pro  Thr Gly Thr Gln Thr  Pro Thr Thr
    4070                 4075                 4080

Thr Pro  Ile Thr Thr Thr Thr  Thr Val Thr Pro Thr  Pro Thr Pro
    4085                 4090                 4095

Thr Gly  Thr Gln Thr Pro Thr  Thr Thr Pro Ile Thr  Thr Thr Thr
```

```
            4100              4105              4110

Thr Val Thr Pro Thr Pro Thr  Pro Thr Gly Thr Gln  Thr Pro Thr
    4115              4120              4125

Thr Thr  Pro Ile Thr Thr Thr  Thr Thr Val Thr Pro  Thr Pro Thr
    4130              4135              4140

Pro Thr  Gly Thr Gln Thr Pro  Thr Thr Thr Pro Ile  Thr Thr Thr
    4145              4150              4155

Thr Thr  Val Thr Pro Thr Pro  Thr Pro Thr Gly Thr  Gln Thr Pro
    4160              4165              4170

Thr Thr  Thr Pro Ile Thr Thr  Thr Thr Thr Val Thr  Pro Thr Pro
    4175              4180              4185

Thr Pro  Thr Gly Thr Gln Thr  Gly Pro Pro Thr His  Thr Ser Thr
    4190              4195              4200

Ala Pro  Ile Ala Glu Leu Thr  Thr Ser Asn Pro Pro  Pro Glu Ser
    4205              4210              4215

Ser Thr  Pro Gln Thr Ser Arg  Ser Thr Ser Ser Pro  Leu Thr Glu
    4220              4225              4230

Ser Thr  Thr Leu Leu Ser Thr  Leu Pro Pro Ala Ile  Glu Met Thr
    4235              4240              4245

Ser Thr  Ala Pro Pro Ser Thr  Pro Thr Ala Pro Thr  Thr Thr Ser
    4250              4255              4260

Gly Gly  His Thr Leu Ser Pro  Pro Pro Ser Thr Thr  Thr Ser Pro
    4265              4270              4275

Pro Gly  Thr Pro Thr Arg Gly  Thr Thr Thr Gly Ser  Ser Ser Ala
    4280              4285              4290

Pro Thr  Pro Ser Thr Val Gln  Thr Thr Thr Thr Ser  Ala Trp Thr
    4295              4300              4305

Pro Thr  Pro Thr Pro Leu Ser  Thr Pro Ser Ile Ile  Arg Thr Thr
    4310              4315              4320

Gly Leu  Arg Pro Tyr Pro Ser  Ser Val Leu Ile Cys  Cys Val Leu
    4325              4330              4335

Asn Asp  Thr Tyr Tyr Ala Pro  Gly Glu Glu Val Tyr  Asn Gly Thr
    4340              4345              4350

Tyr Gly  Asp Thr Cys Tyr Phe  Val Asn Cys Ser Leu  Ser Cys Thr
    4355              4360              4365

Leu Glu  Phe Tyr Asn Trp Ser  Cys Pro Ser Thr Pro  Ser Pro Thr
    4370              4375              4380

Pro Thr  Pro Ser Lys Ser Thr  Pro Thr Pro Ser Lys  Pro Ser Ser
    4385              4390              4395

Thr Pro  Ser Lys Pro Thr Pro  Gly Thr Lys Pro Pro  Glu Cys Pro
    4400              4405              4410

Asp Phe  Asp Pro Pro Arg Gln  Glu Asn Glu Thr Trp  Trp Leu Cys
    4415              4420              4425

Asp Cys  Phe Met Ala Thr Cys  Lys Tyr Asn Asn Thr  Val Glu Ile
    4430              4435              4440

Val Lys  Val Glu Cys Glu Pro  Pro Pro Met Pro Thr  Cys Ser Asn
    4445              4450              4455

Gly Leu  Gln Pro Val Arg Val  Glu Asp Pro Asp Gly  Cys Cys Trp
    4460              4465              4470

His Trp  Glu Cys Asp Cys Tyr  Cys Thr Gly Trp Gly  Asp Pro His
    4475              4480              4485

Tyr Val  Thr Phe Asp Gly Leu  Tyr Tyr Ser Tyr Gln  Gly Asn Cys
    4490              4495              4500
```

-continued

```
Thr Tyr Val Leu Val Glu Glu  Ile Ser Pro Ser Val  Asp Asn Phe
4505                4510               4515

Gly Val Tyr Ile Asp Asn Tyr  His Cys Asp Pro Asn  Asp Lys Val
4520                4525               4530

Ser Cys Pro Arg Thr Leu Ile  Val Arg His Glu Thr  Gln Glu Val
4535                4540               4545

Leu Ile Lys Thr Val His Met  Met Pro Met Gln Val  Gln Val Gln
4550                4555               4560

Val Asn Arg Gln Ala Val Ala  Leu Pro Tyr Lys Lys  Tyr Gly Leu
4565                4570               4575

Glu Val Tyr Gln Ser Gly Ile  Asn Tyr Val Val Asp  Ile Pro Glu
4580                4585               4590

Leu Gly Val Leu Val Ser Tyr  Asn Gly Leu Ser Phe  Ser Val Arg
4595                4600               4605

Leu Pro Tyr His Arg Phe Gly  Asn Asn Thr Lys Gly  Gln Cys Gly
4610                4615               4620

Thr Cys Thr Asn Thr Thr Ser  Asp Asp Cys Ile Leu  Pro Ser Gly
4625                4630               4635

Glu Ile Val Ser Asn Cys Glu  Ala Ala Ala Asp Gln  Trp Leu Val
4640                4645               4650

Asn Asp Pro Ser Lys Pro His  Cys Pro His Ser Ser  Ser Thr Thr
4655                4660               4665

Lys Arg Pro Ala Val Thr Val  Pro Gly Gly Gly Lys  Thr Thr Pro
4670                4675               4680

His Lys Asp Cys Thr Pro Ser  Pro Leu Cys Gln Leu  Ile Lys Asp
4685                4690               4695

Ser Leu Phe Ala Gln Cys His  Ala Leu Val Pro Pro  Gln His Tyr
4700                4705               4710

Tyr Asp Ala Cys Val Phe Asp  Ser Cys Phe Met Pro  Gly Ser Ser
4715                4720               4725

Leu Glu Cys Ala Ser Leu Gln  Ala Tyr Ala Ala Leu  Cys Ala Gln
4730                4735               4740

Gln Asn Ile Cys Leu Asp Trp  Arg Asn His Thr His  Gly Ala Cys
4745                4750               4755

Leu Val Glu Cys Pro Ser His  Arg Glu Tyr Gln Ala  Cys Gly Pro
4760                4765               4770

Ala Glu Glu Pro Thr Cys Lys  Ser Ser Ser Gln Gln  Asn Asn
4775                4780               4785

Thr Val Leu Val Glu Gly Cys  Phe Cys Pro Glu Gly  Thr Met Asn
4790                4795               4800

Tyr Ala Pro Gly Phe Asp Val  Cys Val Lys Thr Cys  Gly Cys Val
4805                4810               4815

Gly Pro Asp Asn Val Pro Arg  Glu Phe Gly Glu His  Phe Glu Phe
4820                4825               4830

Asp Cys Lys Asn Cys Val Cys  Leu Glu Gly Gly Ser  Gly Ile Ile
4835                4840               4845

Cys Gln Pro Lys Arg Cys Ser  Gln Lys Pro Val Thr  His Cys Val
4850                4855               4860

Glu Asp Gly Thr Tyr Leu Ala  Thr Glu Val Asn Pro  Ala Asp Thr
4865                4870               4875

Cys Cys Asn Ile Thr Val Cys  Lys Cys Asn Thr Ser  Leu Cys Lys
4880                4885               4890
```

```
Glu Lys Pro Ser Val Cys Pro  Leu Gly Phe Glu Val  Lys Ser Lys
    4895             4900                  4905

Met Val Pro Gly Arg Cys Cys  Pro Phe Tyr Trp Cys  Glu Ser Lys
    4910             4915                  4920

Gly Val Cys Val His Gly Asn  Ala Glu Tyr Gln Pro  Gly Ser Pro
    4925             4930                  4935

Val Tyr Ser Ser Lys Cys Gln  Asp Cys Val Cys Thr  Asp Lys Val
    4940             4945                  4950

Asp Asn Asn Thr Leu Leu Asn  Val Ile Ala Cys Thr  His Val Pro
    4955             4960                  4965

Cys Asn Thr Ser Cys Ser Pro  Gly Phe Glu Leu Met  Glu Ala Pro
    4970             4975                  4980

Gly Glu Cys Cys Lys Lys Cys  Glu Gln Thr His Cys  Ile Ile Lys
    4985             4990                  4995

Arg Pro Asp Asn Gln His Val  Ile Leu Lys Pro Gly  Asp Phe Lys
    5000             5005                  5010

Ser Asp Pro Lys Asn Asn Cys  Thr Phe Phe Ser Cys  Val Lys Ile
    5015             5020                  5025

His Asn Gln Leu Ile Ser Ser  Val Ser Asn Ile Thr  Cys Pro Asn
    5030             5035                  5040

Phe Asp Ala Ser Ile Cys Ile  Pro Gly Ser Ile Thr  Phe Met Pro
    5045             5050                  5055

Asn Gly Cys Cys Lys Thr Cys  Thr Pro Arg Asn Glu  Thr Arg Val
    5060             5065                  5070

Pro Cys Ser Thr Val Pro Val  Thr Thr Glu Val Ser  Tyr Ala Gly
    5075             5080                  5085

Cys Thr Lys Thr Val Leu Met  Asn His Cys Ser Gly  Ser Cys Gly
    5090             5095                  5100

Thr Phe Val Met Tyr Ser Ala  Lys Ala Gln Ala Leu  Asp His Ser
    5105             5110                  5115

Cys Ser Cys Cys Lys Glu Glu  Lys Thr Ser Gln Arg  Glu Val Val
    5120             5125                  5130

Leu Ser Cys Pro Asn Gly Gly  Ser Leu Thr His Thr  Tyr Thr His
    5135             5140                  5145

Ile Glu Ser Cys Gln Cys Gln  Asp Thr Val Cys Gly  Leu Pro Thr
    5150             5155                  5160

Gly Thr Ser Arg Arg Ala Arg  Arg Ser Pro Arg His  Leu Gly Ser
    5165             5170                  5175

Gly
```

```
<210> SEQ ID NO 30
<211> LENGTH: 15720
<212> TYPE: DNA
<213> ORGANISM: Homo sapiens

<400> SEQUENCE: 30
caacccacac cgcccctgcc agccaccatg gggctgccac tagcccgcct ggcggctgtg      60
tgcctggccc tgtctttggc aggggggctcg gagctccaga cagagggcag aacccgaaac     120
cacggccaca acgtctgcag cacctggggc aacttccact acaagacctt cgacggggac     180
gtcttccgct tccccggccc ctgcgactac aacttcgcct ccgactgccg aggctcctac     240
aaggaatttg ctgtgcacct gaagcggggt ccgggccagg ctgaggcccc cgccggggtg     300
gagtccatcc tgctgaccat caaggatgac accatctacc tcacccgcca cctggctgtg     360
```

```
cttaacgggg ccgtggtcag caccccgcac tacagccccg ggctgctcat tgagaagagc   420
gatgcctaca ccaaagtcta ctcccgcgcc ggcctcaccc tcatgtggaa ccgggaggat   480
gcactcatgc tggagctgga cactaagttc cggaaccaca cctgtggcct ctgcggggac   540
tacaacggcc tgcagagcta ttcagaattc ctctctgacg gcgtgctctt cagtcccctg   600
gagtttggga acatgcagaa gatcaaccag cccgatgtgg tgtgtgagga tcccgaggag   660
gaggtggccc ccgcatcctg ctccgagcac cgcgccgagt gtgagaggct gctgaccgcc   720
gaggccttcg cggactgtca ggacctggtg ccgctggagc cgtatctgcg cgcctgccag   780
caggaccgct gccggtgccc gggcggtgac acctgcgtct gcagcaccgt ggccgagttc   840
tcccgccagt gctcccacgc cggcggccgg cccgggaact ggaggaccgc cacgctctgc   900
cccaagacct gccccgggaa cctggtgtac ctggagagcg gctcgccctg catggacacc   960
tgctcacacc tggaggtgag cagcctgtgc gaggagcacc gcatggacgg ctgtttctgc  1020
ccagaaggca ccgtatatga cgacatcggg gacagtggct gcgttcctgt gagccagtgc  1080
cactgcaggc tgcacggaca cctgtacaca ccgggccagg agatcaccaa tgactgcgag  1140
cagtgtgtct gtaacgctgg ccgctgggtg tgcaaagacc tgccctgccc cggcacctgt  1200
gccctggaag gcggctccca catcaccacc ttcgatggga gacgtacac cttccacggg  1260 gactgctact atgtcctggc caagggtgac cacaacgatt cctacgctct cctgggcgag  1320
ctggcccccc t gtggctccac agacaagcag acctgcctga gacggtggt gctgctggct  1380 gacaagaaga agaatgtggt ggtcttcaag tccgatggca gtgtactgct caacgagctg  1440
caggtgaacc tgccccacgt gaccgcgagc ttctctgtct tccgcccgtc ttcctaccac  1500
atcatggtga gcatggccat tggcgtccgg ctgcaggtgc agctggcccc agtcatgcaa  1560
ctctttgtga cactggacca ggcctcccag gggcaggtgc agggcctctg cgggaacttc  1620
aacggcctgg aaggtgacga cttcaagacg gccagcgggc tggtggaggc cacgggggcc  1680
ggctttgcca cacctggaa ggcacagtca acctgccatg acaagctgga ctggttggac  1740
gatccctgct ccctgaacat cgagagcgcc aactacgccg agcactggtg ctccctcctg  1800
aagaagacag agacccccctt tggcaggtgc cactcggctg tggaccctgc tgagtattac  1860
aagaggtgca aatatgacac gtgtaactgt cagaacaatg aggactgcct gtgcgccgcc  1920
ctgtcctcct acgcgcgcgc ctgcaccgcc aagggcgtca tgctgtgggg ctggcgggag  1980
catgtctgca acaaggatgt gggctcctgc cccaactcgc aggtcttcct gtacaacctg  2040
accacctgcc agcagacctg ccgctccctc tccgaggccg acagccactg tctcgagggc  2100
tttgcgcctg tggacggctg cggctgccct gaccacacct tcctggacga gaagggccgc  2160
tgcgtacccc tggccaagtg ctcctgttac caccgcggtc tctacctgga ggcggggggac  2220 gtggtcgtca ggcaggaaga acgatgtgtg tgccgggatg ggcggctgca ctgtaggcag  2280
atccggctga tcggccagag ctgcacggcc ccaaagatcc acatggactg cagcaacctg  2340
actgcactgg ccacctcgaa gccccgagcc ctcagctgcc agacgctggc cgccggctat  2400
taccacacag agtgtgtcag tggctgtgtg tgccccgacg ggctgatgga tgacggccgg  2460
ggtggctgcg tggtggagaa ggaatgccct tgcgtccata caacgacct gtattcttcc  2520 ggcgccaaga tcaaggtgga ctgcaatacc tgcacctgca gagaggacg ctgggtgtgc  2580 acccaggctg tgtgccatgg cacctgctcc atttacggga gtggccacta catcaccttt  2640
gacgggaagt actacgactt tgacggacac tgctcctacg tggctgttca ggactactgc  2700
ggccagaact cctcactggg ctcattcagc atcatcaccg agaacgtccc ctgtggcact  2760
```

-continued

```
acgggcgtca cctgctccaa ggccatcaag atcttcatgg ggaggacgga gctgaagttg    2820
gaagacaagc accgtgtggt gatccagcgt gatgagggtc accacgtggc ctacaccacg    2880
cgggaggtgg gccagtacct ggtggtggag tccagcacgg gcatcatcgt catctgggac    2940
aagaggacca ccgtgttcat caagctggct ccctcctaca agggcaccgt gtgtggcctg    3000
tgtgggaact ttgaccaccg ctccaacaac gacttcacca cgcgggacca catggtggtg    3060
agcagcgagc tggacttcgg gaacagctgg aaggaggccc ccacctgccc agatgtgagc    3120
accaaccccg agccctgcag cctgaacccg caccgccgct cctgggccga gaagcagtgc    3180
agcatcctca aaagcagcgt gttcagcatc tgccacagca aggtggaccc caagcccttc    3240
tacgaggcct gtgtgcacga ctcgtgctcc tgtgacacgg gtggggactg tgagtgcttc    3300
tgctctgccg tggcctccta cgcccaggag tgtaccaaag aggggggcctg cgtgttctgg    3360 aggacgccgg acctgtgccc catattctgc gactactaca accctccgca tgagtgtgag    3420
tggcactatg agccatgtgg gaaccggagc ttcgagacct gcaggaccat caatggcatc    3480
cactccaaca tctccgtgtc ctacctggag ggctgctacc cccggtgccc caaggacagg    3540
cccatctatg aggaggatct gaagaagtgt gtcactgcag acaagtgtgg ctgctatgtc    3600
gaggacaccc actacccacc tggagcatcg gttcccaccg aggagacctg caagtcctgc    3660
gtgtgtacca actcctccca agtcgtctgc aggccggagg aaggaaagat tcttaaccag    3720
acccaggatg gcgccttctg ctactgggag atctgtggcc ccaacgggac ggtggagaag    3780
cacttcaaca tctgttccat tacgacacgc ccgtccaccc tgaccacctt caccaccatc    3840
accctcccca ccaccccac caccttcacc actaccacca ccaccaccac cccgacctcc    3900
agcacagttt tatcaacaac tccgaagctg tgctgcctct ggtctgactg gatcaatgag    3960
gaccacccca gcagtggcag cgacgacggt gaccgagaaa catttgatgg ggtctgcggg    4020
gcccctgagg acatcgagtg caggtcggtc aaggatcccc acctcagctt ggagcagcta    4080
ggccagaagg tgcagtgtga tgtctctgtt gggttcattt gcaagaatga agaccagttt    4140
ggaaatggac catttggact gtgttacgac tacaagatac gtgtcaattg ttgctggccc    4200
atggataagt gtatcaccac tcccagccct ccaactacca ctcccagccc tccaccaacc    4260
agcacgacca cccttccacc aaccaccacc cccagccctc caaccaccac cacaaccacc    4320
cctccaccaa ccaccacccc cagccctcca ataaccacca cgaccacccc tccaccaacc    4380
accactccca gccctccaat aagcaccaca accacccctc caccaaccac cactcccagc    4440
cctccaacca ccactcccag ccctccaacc accactccca gccctccaac aaccaccaca    4500 accaccctc caccaaccac cactcccagc cctccaacga ctacgcccat cactccacca    4560
gccagcacta ccacccttcc accaaccacc actcccagcc ctccaacaac caccacaacc    4620 accctccac caaccaccac tcccagtcct ccaacgacta cgcccatcac tccaccaacc    4680
agcactacta cccttccacc aaccaccact cccagccctc caccaaccac cacaaccacc    4740
cctccaccaa ccaccactcc cagccctcca acaaccacca ctcccagtcc tccaacaatc    4800
accacaacca cccctccacc aaccaccact cccagccctc caacaacgac cacaaccacc    4860
cctccaccaa ccaccactcc cagccctcca acgactacac catcactcc accaaccagc    4920 actaccaccc ttccaccaac caccactccc agccctccac caaccaccac aaccacccct    4980
ccaccaacca ccactcccag ccctccaaca accaccactc cagccctcc aataaccacc    5040 acaaccaccc ctccaccaac caccactccc agctctccaa taaccaccac tcccagccct    5100
```

-continued

```
ccaacaacca ccatgaccac cccttcacca accaccaccc ccagctctcc aataaccacc    5160
acaaccaccc cttcctcaac taccactccc agccctccac caaccaccat gaccacccct    5220
tcaccaacca ccactcccag ccctccaaca accaccatga ccacccttcc accaaccacc    5280
acttccagcc ctctaacaac tactcctcta cctccatcaa taactcctcc tacattttca    5340
ccattctcaa cgacaacccc tactacccca tgcgtgcctc tctgcaattg gactggctgg    5400
ctggattctg gaaaacccaa ctttcacaaa ccaggtggag acacagaatt gattggagac    5460
gtctgtggac caggctgggc agctaacatc tcttgcagag ccaccatgta tcctgatgtt    5520
cccattggac agcttggaca aacagtggtg tgtgatgtct ctgtggggct gatatgcaaa    5580
aatgaagacc aaaagccagg tggggtcatc cctatggcct tctgcctcaa ctacgagatc    5640
aacgttcagt gctgtgagtg tgtcacccaa cccaccacca tgacaaccac caccacagag    5700
aacccaactc cgccaaccac gacacccatc accaccacca ctacggtgac cccaacccca    5760
acacccaccg gcacacagac cccaaccacg acacccatca ccaccaccac tacggtgacc    5820
ccaaccccaa cacccaccgg cacacagacc ccaaccacga cacccatcac caccaccact    5880
acggtgaccc caaccccaac acccaccggc acacagaccc caaccacgac acccatcacc    5940
accaccacta cggtgacccc aaccccaaca cccaccggca cagacccca aaccacgaca    6000 cccatcacca ccaccactac ggtgaccca acccaacac ccaccggcac acagacccca    6060
accacgacac ccatcaccac caccactacg gtgacccca ccccaacacc caccggcaca    6120
cagaccccaa ccacgacacc catcaccacc accactacgg tgacccaac cccaacaccc    6180 accggcacac agaccccaac cacgacaccc atcaccacca ccactacggt gacccaacc    6240 ccaacaccca ccggcacaca gacccaacc acgacaccca tcaccaccac cactacggtg    6300
accccaaccc caacacccac cggcacacag accccaacca cgacacccat caccaccacc    6360
actacggtga ccccaacccc aacacccacc ggcacacaga ccccaaccac gacacccatc    6420
accaccacca ctacggtgac cccaacccca acacccaccg gcacacagac cccaaccacg    6480
acacccatca ccaccaccac tacggtgacc ccaaccccaa cacccaccgg cacacagacc    6540
ccaaccacga cacccatcac caccaccact acggtgaccc caaccccaac acccaccggc    6600
acacagaccc caaccacgac acccatcacc accaccacta cggtgacccc aaccccaaca    6660
cccaccggca cagaccccaa ccacgacaca ccatcacca ccaccactac ggtgacccca    6720
accccaacac ccaccggcac acagaccca accacgacac ccatcaccac caccactacg    6780 gtgacccca ccccaacacc caccggcaca cagaccccaa ccacgacacc catcaccacc    6840
accactacgg tgacccaac cccaacaccc accggcacac agaccccaac cacgacaccc    6900
atcaccacca ccactacggt gacccaacc ccaacaccca ccggcacaca gacccaacc    6960 acgacaccca tcaccaccac cactacggtg accccaaccc caacacccac cggcacacag    7020
accccaacca cgacacccat caccaccacc actacggtga ccccaacccc aacacccacc    7080
ggcacacaga ccccaaccac gacacccatc accaccacca ctacggtgac cccaaccccca    7140 acacccaccg gcacacagac cccaaccacg acacccatca ccaccaccac tacggtgacc    7200
ccaaccccaa cacccaccgg cacacagacc ccaaccacga cacccatcac caccaccact    7260
acggtgaccc caacccaac acccaccggc acacagaccc caaccacgac acccatcacc    7320
accaccacta cggtgacccc aaccccaaca cccaccggca cagaccccca aaccacgaca    7380
cccatcacca ccaccactac ggtgacccca accccaacac ccaccggcac acagaccca    7440 accacgacac ccatcaccac caccactacg gtgaccccaa ccccaacacc caccggcaca    7500
```

```
cagaccccaa ccacgacacc catcaccacc accactacgg tgaccccaac cccaacaccc      7560
accggcacac agaccccaac cacgacaccc atcaccacca ccactacggt gaccccaacc      7620
ccaacaccca ccggcacaca gaccccaacc acgacaccca tcaccaccac cactacggtg      7680
accccaaccc caacacccac cggcacacag accccaacca cgacacccat caccaccacc      7740
actacggtga ccccaacccc aacacccacc ggcacacaga ccccaaccac gacacccatc      7800
accaccacca ctacggtgac cccaacccca cacccaccg gcacacagac cccaaccacg       7860
acacccatca ccaccaccac tacggtgacc ccaaccccaa cacccaccgg cacacagacc      7920
ccaaccacga cacccatcac caccaccact acggtgaccc caaccccaac acccaccggc      7980
acacagaccc caaccacgac acccatcacc accaccacta cggtgacccc aaccccaaca      8040
cccaccggca cagacccca aaccacgaca cccatcacca ccaccactac ggtgacccca       8100
accccaacac ccaccggcac acagacccca accacgacac ccatcaccac caccactacg      8160
gtgaccccaa ccccaacacc caccggcaca cagaccccaa ccacgacacc catcaccacc      8220
accactacgg tgaccccaac cccaacaccc accggcacac agaccccaac cacgacaccc      8280
atcaccacca ccactacggt gaccccaacc ccaacaccca ccggcacaca gaccccaacc      8340
acgacaccca tcaccaccac cactacggtg accccaaccc caacacccac cggcacacag      8400
accccaacca cgacacccat caccaccacc actacggtga ccccaaccc aacacccacc       8460 ggcacacaga ccccaaccac gacacccatc accaccacca ctacggtgac cccaacccca      8520
acacccaccg gcacacagac cccaaccacg acacccatca ccaccaccac tacggtgacc      8580
ccaaccccaa cacccaccgg cacacagacc ccaaccacga cacccatcac caccaccact      8640
acggtgaccc caaccccaac acccaccggc acacagaccc caaccacgac acccatcacc      8700
accaccacta cggtgacccc aaccccaaca cccaccggca cagacccca aaccacgaca       8760 cccatcacca ccaccactac ggtgaccca accccaacac ccaccggcac acagacccca       8820
accacgacac ccatcaccac caccactacg gtgaccccaa ccccaacacc caccggcaca      8880
cagaccccaa ccacgacacc catcaccacc accactacgg tgaccccaac cccaacaccc      8940
accggcacac agaccccaac cacgacaccc atcaccacca ccactacggt gaccccaacc      9000
ccaacaccca ccggcacaca gaccccaacc acgacaccca tcaccaccac cactacggtg      9060
accccaaccc caacacccac cggcacacag accccaacca cgacacccat caccaccacc      9120
actacggtga ccccaacccc aacacccacc ggcacacaga ccccaaccac gacacccatc      9180
accaccacca ctacggtgac cccaacccca cacccaccg gcacacagac cccaaccacg       9240
acacccatca ccaccaccac tacggtgacc ccaaccccaa cacccaccgg cacacagacc      9300
ccaaccacga cacccatcac caccaccact acggtgaccc caaccccaac acccaccggc      9360
acacagaccc caaccacgac acccatcacc accaccacta cggtgacccc aaccccaaca      9420
cccaccggca cagacccca aaccacgaca cccatcacca ccaccactac ggtgacccca       9480
accccaacac ccaccggcac acagacccca accacgacac ccatcaccac caccactacg      9540
gtgaccccaa ccccaacacc caccggcaca cagaccccaa ccacgacacc catcaccacc      9600
accactacgg tgaccccaac cccaacaccc accggcacac agaccccaac cacgacaccc      9660
atcaccacca ccactacggt gaccccaacc ccaacaccca ccggcacaca gaccccaacc      9720
acgacaccca tcaccaccac cactacggtg accccaaccc caacacccac cggcacacag      9780
accccaacca cgacacccat caccaccacc actacggtga ccccaaccc aacacccacc       9840
```

-continued

```
ggcacacaga ccccaaccac gacacccatc accaccacca ctacggtgac cccaacccca    9900
acacccaccg gcacacagac cccaaccacg acacccatca ccaccaccac tacggtgacc    9960
ccaaccccaa cacccaccgg cacacagacc ccaaccacga cacccatcac caccaccact   10020
acggtgaccc caaccccaac acccaccggc acacagaccc caaccacgac acccatcacc   10080
accaccacta cggtgacccc aaccccaaca cccaccggca cacagacccc aaccacgaca   10140
cccatcacca ccaccactac ggtgacccca accccaacac ccaccggcac acagacccca   10200
accacgacac ccatcaccac caccactacg gtgaccccaa ccccaacacc caccggcaca   10260
cagaccccaa ccacgacacc catcaccacc accactacgg tgaccccaac cccaacaccc   10320
accggcacac agaccccaac cacgacaccc atcaccacca ccactacggt gaccccaacc   10380
ccaacaccca ccggcacaca gaccccaacc acgacaccca tcaccaccac cactacggtg   10440
accccaaccc caacacccac cggcacacag accccaacca cgacacccat caccaccacc   10500
actacggtga ccccaacccc aacacccacc ggcacacaga ccccaaccac gacacccatc   10560
accaccacca ctacggtgac cccaacccca cacccaccg gcacacagac cccaaccacg    10620
acacccatca ccaccaccac tacggtgacc ccaaccccaa cacccaccgg cacacagacc   10680
ccaaccacga cacccatcac caccaccact acggtgaccc caaccccaac acccaccggc   10740
acacagaccc caaccacgac acccatcacc accaccacta cggtgacccc aaccccaaca   10800
cccaccggca cacagacccc aaccacgaca cccatcacca ccaccactac ggtgacccca   10860
accccaacac ccaccggcac acagacccca accacgacac ccatcaccac caccactacg   10920
gtgaccccaa ccccaacacc caccggcaca cagaccccaa ccacgacacc catcaccacc   10980
accactacgg tgaccccaac cccaacaccc accggcacac agaccccaac cacgacaccc   11040
atcaccacca ccactacggt gaccccaacc ccaacaccca ccggcacaca gaccccaacc   11100
acgacaccca tcaccaccac cactacggtg accccaaccc caacacccac cggcacacag   11160
accccaacca cgacacccat caccaccacc actacggtga ccccaacccc aacacccacc   11220
ggcacacaga ccccaaccac gacacccatc accaccacca ctacggtgac cccaacccca   11280
acacccaccg gcacacagac cccaaccacg acacccatca ccaccaccac tacggtgacc   11340
ccaaccccaa cacccaccgg cacacagacc ccaaccacga cacccatcac caccaccact   11400
acggtgaccc caaccccaac acccaccggc acacagaccc caaccacgac acccatcacc   11460
accaccacta cggtgacccc aaccccaaca cccaccggca cacagacccc aaccacgaca   11520
cccatcacca ccaccactac ggtgacccca accccaacac ccaccggcac acagacccca   11580
accacgacac ccatcaccac caccactacg gtgaccccaa ccccaacacc caccggcaca   11640
cagaccccaa ccacgacacc catcaccacc accactacgg tgaccccaac cccaacaccc   11700
accggcacac agaccccaac cacgacaccc atcaccacca ccactacggt gaccccaacc   11760
ccaacaccca ccggcacaca gaccccaacc acgacaccca tcaccaccac cactacggtg   11820
accccaaccc caacacccac cggcacacag accccaacca cgacacccat caccaccacc   11880
actacggtga ccccaacccc aacacccacc ggcacacaga ccccaaccac gacacccatc   11940
accaccacca ctacggtgac cccaacccca cacccaccg gcacacagac cccaaccacg    12000
acacccatca ccaccaccac tacggtgacc ccaaccccaa cacccaccgg cacacagacc   12060
ccaaccacga cacccatcac caccaccact acggtgaccc caaccccaac acccaccggc   12120
acacagaccc caaccacgac acccatcacc accaccacta cggtgacccc aaccccaaca   12180
cccaccggca cacagacccc aaccacgaca cccatcacca ccaccactac ggtgacccca   12240
```

-continued

```
accccaacac ccaccggcac acagacccca accacgacac ccatcaccac caccactacg   12300
gtgaccccaa ccccaacacc caccggcaca cagacccccaa ccacgacacc catcaccacc   12360
accactacgg tgaccccaac cccaacaccc accggcacac agaccccaac cacgacaccc   12420
atcaccacca ccactacggt gaccccaacc ccaacaccca ccggcacaca gaccccaacc   12480
acgacaccca tcaccaccac cactacggtg accccaaccc caacacccac cggcacacag   12540
accccaacca cgacacccat caccaccacc actacggtga ccccaacccc aacacccacc   12600
ggcacacaga ccgggccccc cacccacaca agcacagcac cgattgctga gttgaccaca   12660
tccaatcctc cgcctgagtc ctcaacccct cagacctctc ggtccacctc ttcccctctc   12720
acggagtcaa ccacccttct gagtaccta ccacctgcca ttgagatgac cagcacggcc   12780
ccaccctcca cacccacggc acccacgacc acgagcggag gccacacact gtctccaccg   12840
cccagcacca ccacgtcccc tccaggcacc cccactcgcg gtaccacgac tgggtcatct   12900
tcagccccca ccccccagcac tgtgcagacg accaccacca gtgcctggac ccccacgccg   12960
accccactct ccacacccag catcatcagg accacaggcc tgaggcccta cccttcctct   13020
gtgcttatct gctgtgtcct gaacgacacc tactacgcac caggtgagga ggtgtacaac   13080
ggcacatacg gagacacctg ttatttcgtc aactgctcac tgagctgtac gttggagttc   13140
tataactggt cctgcccatc cacgccctcc ccaacacccca cgccctccaa gtcgacgccc   13200
acgccttcca agccatcgtc cacgccctcc aagccgacgc ccggcaccaa gccccccgag   13260
tgcccagact ttgatcctcc cagacaggag aacgagactt ggtggctgtg cgactgcttc   13320
atggccacgt gcaagtacaa caacacggtg gagatcgtga aggtggagtg tgagccgccg   13380
cccatgccca cctgctccaa cggcctccaa cccgtgcgcg tcgaggaccc cgacggctgc   13440
tgctggcact gggagtgcga ctgctactgc acgggctggg gcgacccgca ctatgtcacc   13500
ttcgacggac tctactacag ctaccagggc aactgcacct acgtgctggt ggaggagatc   13560
agcccctccg tggacaactt cggagtttac atcgacaact accactgcga tcccaacgac   13620
aaggtgtcct gcccccgcac cctcatcgtg cgccacgaga cccaggaggt gctgatcaag   13680
accgtgcata tgatgcccat gcaggtgcag gtgcaggtga acaggcaggc ggtggcactg   13740
ccctacaaga agtacgggct ggaggtgtac cagtctggca tcaactacgt ggtggacatc   13800
cccgagctgg gtgtcctcgt ctcctacaat ggcctgtcct tctccgtcag gctgccctac   13860
caccggtttg gcaacaacac caagggccag tgtggcacct gcaccaacac cacctccgac   13920
gactgcattc tgcccagcgg gggagatcgtc tccaactgtg aggctgcggc tgaccagtgg   13980
ctggtgaacg acccctccaa gccacactgc ccccacagca gctccacgac caagcgcccg   14040
gccgtcactg tgcccggggg cggtaaaacg accccacaca aggactgcac cccatctccc   14100
ctctgccagc tcatcaagga cagcctgttt gcccagtgcc acgcactggt gccccgcag   14160 cactactacg atgcctgcgt gttcgacagc tgcttcatgc cgggctcgag cctggagtgc   14220
gccagtctgc aggcctacgc agccctctgt gcccagcaga acatctgcct cgactggcgg   14280
aaccacacgc atgggccctg cttggtggag tgcccatctc acagggagta ccaggcctgt   14340
ggccctgcag aagagcccac gtgcaaatcc agctcctccc agcagaacaa cacagtcctg   14400
gtggaaggct gcttctgtcc tgagggcacc atgaactacg ctcctggctt tgatgtctgc   14460
gtgaagacct gcggctgtgt gggacctgac aatgtgccca gagagtttgg ggagcacttc   14520
gagttcgact gcaagaactg tgtctgcctg gagggtggaa gtggcatcat ctgccaaccc   14580
```

-continued

```
aagaggtgca gccagaagcc cgttacccac tgcgtggaag acggcaccta cctcgccacg   14640
gaggtcaacc ctgccgacac ctgctgcaac attaccgtct gcaagtgcaa caccagcctg   14700
tgcaaagaga agccctccgt gtgcccgctg ggattcgaag tgaagagcaa gatggtgcct   14760
ggaaggtgct gtcctttcta ctggtgtgag tccaaggggg tgtgtgttca cgggaatgct   14820
gagtaccagc ccggttctcc agtttattcc tccaagtgcc aggactgcgt gtgcacggac   14880
aaggtggaca caacaccct gctcaacgtc atcgcctgca cccacgtgcc ctgcaacacc   14940
tcctgcagcc ctggcttcga actcatggag gcccccgggg agtgctgtaa gaagtgtgaa   15000
cagacgcact gtatcatcaa acggcccgac aaccagcacg tcatcctgaa gcccggggac   15060
ttcaagagcg acccgaagaa caactgcaca ttcttcagct gcgtgaagat ccacaaccag   15120
ctcatctcgt ccgtctccaa catcacctgc cccaactttg atgccagcat ttgcatcccg   15180
ggctccatca cattcatgcc caatggatgc tgcaagacct gcacccctcg caatgagacc   15240
agggtgccct gctccaccgt ccccgtcacc acggaggttt cgtacgccgg ctgcaccaag   15300
accgtcctca tgaatcattg ctccgggtcc tgcgggacat ttgtcatgta ctcggccaag   15360
gcccaggccc tggaccacag ctgctcctgc tgcaaagagg agaaaaccag ccagcgtgag   15420
gtggtcctga gctgccccaa tggcggctcg ctgacacaca cctacaccca catcgagagc   15480
tgccagtgcc aggacaccgt ctgcgggctc cccaccggca cctcccgccg ggcccggcgc   15540
tcccctaggc atctggggag cgggtgagcg gggtgggcac agccccttc actgccctcg   15600 acagctttac ctcccccgga ccctctgagc ctcctaagct cggcttcctc tcttcagata   15660
tttattgtct gagtctttgt tcagtccttg ctttccaata ataaactcag ggggacatgc   15720
```

```
<210> SEQ ID NO 31
<211> LENGTH: 324
<212> TYPE: PRT
<213> ORGANISM: Homo sapiens

<400> SEQUENCE: 31

Met Phe Pro Ser Pro Ala Leu Thr Pro Thr Pro Phe Ser Val Lys Asp
1               5                   10                  15

Ile Leu Asn Leu Glu Gln Gln Gln Arg Ser Leu Ala Ala Ala Gly Glu
            20                  25                  30

Leu Ser Ala Arg Leu Glu Ala Thr Leu Ala Pro Ser Ser Cys Met Leu
        35                  40                  45

Ala Ala Phe Lys Pro Glu Ala Tyr Ala Gly Pro Glu Ala Ala Ala Pro
    50                  55                  60

Gly Leu Pro Glu Leu Arg Ala Glu Leu Gly Arg Ala Pro Ser Pro Ala
65                  70                  75                  80

Lys Cys Ala Ser Ala Phe Pro Ala Ala Pro Ala Phe Tyr Pro Arg Ala
                85                  90                  95

Tyr Ser Asp Pro Asp Pro Ala Lys Asp Pro Arg Ala Glu Lys Lys Glu
            100                 105                 110

Leu Cys Ala Leu Gln Lys Ala Val Glu Leu Glu Lys Thr Glu Ala Asp
        115                 120                 125

Asn Ala Glu Arg Pro Arg Ala Arg Arg Arg Lys Pro Arg Val Leu
        130                 135                 140

Phe Ser Gln Ala Gln Val Tyr Glu Leu Glu Arg Arg Phe Lys Gln Gln
145                 150                 155                 160

Arg Tyr Leu Ser Ala Pro Glu Arg Asp Gln Leu Ala Ser Val Leu Lys
                165                 170                 175
```

```
Leu Thr Ser Thr Gln Val Lys Ile Trp Phe Gln Asn Arg Arg Tyr Lys
            180                 185                 190

Cys Lys Arg Gln Arg Gln Asp Gln Thr Leu Glu Leu Val Gly Leu Pro
            195                 200                 205

Pro Pro Pro Pro Pro Pro Ala Arg Arg Ile Ala Val Pro Val Leu Val
        210                 215                 220

Arg Asp Gly Lys Pro Cys Leu Gly Asp Ser Ala Pro Tyr Ala Pro Ala
225                 230                 235                 240

Tyr Gly Val Gly Leu Asn Pro Tyr Gly Tyr Asn Ala Tyr Pro Ala Tyr
                245                 250                 255

Pro Gly Tyr Gly Gly Ala Ala Cys Ser Pro Gly Tyr Ser Cys Thr Ala
                260                 265                 270

Ala Tyr Pro Ala Gly Pro Ser Pro Ala Gln Pro Ala Thr Ala Ala Ala
            275                 280                 285

Asn Asn Asn Phe Val Asn Phe Gly Val Gly Asp Leu Asn Ala Val Gln
            290                 295                 300

Ser Pro Gly Ile Pro Gln Ser Asn Ser Gly Val Ser Thr Leu His Gly
305                 310                 315                 320

Ile Arg Ala Trp

<210> SEQ ID NO 32
<211> LENGTH: 1669
<212> TYPE: DNA
<213> ORGANISM: Homo sapiens

<400> SEQUENCE: 32
gctcctgtca tcgaggcccc tggcccaatg gcaggctgag tcccctcct ctggcctggt       60 cccgcctctc ctgccccttg tgctcagcgc tacctgctgc ccggacacat ccagagctgg      120
ccgacgggtg cgcgggcggg cggcggcacc atgcaggaa gctgccaggg gccgtgggca       180
gcgccgcttt ctgccgccca cctggcgctg tgagactggc gctgccacca tgttccccag       240
ccctgctctc acgcccacgc ccttctcagt caaagacatc ctaaacctgg aacagcagca       300
gcgcagcctg gctgccgccg gagagctctc tgcccgcctg gaggcgaccc tggcgccctc       360
ctcctgcatg ctggccgcct tcaagccaga ggcctacgct gggcccgagg cggctgcgcc       420
gggcctccca gagctgcgcg cagagctggg ccgcgcgcct tcaccggcca agtgtgcgtc       480
tgcctttccc gccgcccccg ccttctatcc acgtgcctac agcgaccccg acccagccaa       540
ggaccctaga gccgaaaaga aagagctgtg cgcgctgcag aaggcggtgg agctggagaa       600
gacagaggcg gacaacgcgg agcggcrccg ggcgcgacgg cggaggaagc cgcgcgtgct       660
cttctcgcag gcgcaggtct atgagctgga gcggcgcttc aagcagcagc ggtacctgtc       720
ggcccccgaa cgcgaccagc tggccagcgt gctgaaactc acgtccacgc aggtcaagat       780
ctggttccag aaccggcgct acaagtgcaa gcggcagcgg caggaccaga ctctggagct       840 ggtgggctg ccccgccgc cgccgccgcc tgccgcagg atcgcggtgc cagtgctggt       900
gcgcgatggc aagccatgcc tagggactc ggcgccctac gcgcctgcct acggcgtggg       960
cctcaatccc tacggttata cgcctaccc cgcctatccg ggttacggcg gcgcggcctg      1020
cagccctggc tacagctgca ctgccgctta ccccgccggg ccttccccag cgcagccggc      1080
cactgccgcc gccaacaaca acttcgtgaa cttcggcgtc ggggacttga atgcggttca      1140
gagccccggg attccgcaga gcaactcggg agtgtccacg ctgcatggta tccgagcctg      1200
gtagggaagg gaccgcgtg gcgcgaccct gaccgatccc acctcaacag ctccctgact      1260
```

-continued

```
ctcggggga gaaggggctc ccaacatgac cctgagtccc ctggatttttg cattcactcc    1320 tgcggagacc taggaacttt ttctgtccca cgcgcgtttg ttcttgcgca cgggagagtt    1380
tgtggcggcg attatgcagc gtgcaatgag tgatcctgca gcctggtgtc ttagctgtcc    1440
ccccaggagt gccctccgag agtccatggg caccccggt tggaactggg actgagctcg     1500
ggcacgcagg gcctgagatc tggccgccca ttccgcgagc cagggccggg cgcccgggcc    1560
tttgctatct cgccgtcgcc cgcccacgca cccacccgta tttatgtttt tacctattgc    1620
tgtaagaaat gacgatcccc ttcccattaa agagagtgcg ttgaccccg                1669
```

```
<210> SEQ ID NO 33
<211> LENGTH: 356
<212> TYPE: PRT
<213> ORGANISM: Homo sapiens

<400> SEQUENCE: 33

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Asp Leu Glu Ala Met Asn Ala
        35                  40                  45

Glu Glu Asp Ser Leu Arg Asn Gly Gly Glu Glu Glu Asp Glu Asp
        50                  55                  60

Asp Leu Glu Glu Glu Glu Glu Glu Glu Glu Asp Asp Asp Gln Lys
65                  70                  75                  80

Pro Lys Arg Arg Gly Pro Lys Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
        130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Gln Asp Met Pro Pro His Leu Pro
            195                 200                 205

Thr Ala Ser Ala Ser Phe Pro Val His Pro Tyr Ser Tyr Gln Ser Pro
        210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
        290                 295                 300
```

-continued

```
Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
                325                 330                 335

Asp Ser His Ser His His Glu Arg Val Met Ser Ala Gln Leu Asn Ala
            340                 345                 350

Ile Phe His Asp
        355

<210> SEQ ID NO 34
<211> LENGTH: 3002
<212> TYPE: DNA
<213> ORGANISM: Homo sapiens

<400> SEQUENCE: 34
ggggaggagg ggagaacggg gagcgcacag cctggacgcg tgcgcaggcg tcaggcgcat       60
agacctgcta gcccctcagc tagcggcccc gcccgcgctt agcatcacta actgggctat      120
ataacctgag cgcccgcgcg gccacgcacac gaggaattcg cccacgcagg aggcgcggcg      180
tccggaggcc ccagggttat gagactatca ctgctcagga cctactaaca acaaaggaaa      240
tcgaaacatg accaaatcgt acagcgagag tgggctgatg ggcgagcctc agccccaagg      300
tcctccaagc tggacagacg agtgtctcag ttctcaggac gaggagcacg aggcagacaa      360
gaaggaggac gacctcgaag ccatgaacgc agaggaggac tcactgagga acgggggaga      420
ggaggaggac gaagatgagg acctggaaga ggaggaagaa gaggaagagg aggatgacga      480
tcaaaagccc aagagacgcg gccccaaaaa gaagaagatg actaaggctc gcctggagcg      540
ttttaaattg agacgcatga aggctaacgc ccgggagcgg aaccgcatgc acggactgaa      600
cgcggcgcta gacaacctgc gcaaggtggt gccttgctat tctaagacgc agaagctgtc      660
caaaatcgag actctgcgct tggccaagaa ctacatctgg gctctgtcgg agatcctgcg      720
ctcaggcaaa agcccagacc tggtctcctt cgttcagacg cttttgcaagg gcttatccca      780 acccaccacc aacctggttg cgggctgcct gcaactcaat cctcggactt ttctgcctga      840
gcagaaccag gacatgcccc cccacctgcc gacggccagc gcttccttcc ctgtacaccc      900
ctactcctac cagtcgcctg ggctgcccag tccgccttac ggtaccatgg acagctccca      960
tgtcttccac gttaagcctc cgccgcacgc ctacagcgca gcgctggagc ccttctttga     1020
aagccctctg actgattgca ccagcccttc ctttgatgga cccctcagcc cgccgctcag     1080
catcaatggc aacttctctt tcaaacacga accgtccgcc gagtttgaga aaaattatgc     1140
ctttaccatg cactatcctg cagcgacact ggcaggggcc caaagccacg gatcaatctt     1200
ctcaggcacc gctgcccctc gctgcgagat ccccatagac aatattatgt ccttcgatag     1260
ccattcacat catgagcgag tcatgagtgc ccagctcaat gccatatttc atgattagag     1320
gcacgccagt ttcaccattt ccgggaaacg aacccactgt gcttacagtg actgtcgtgt     1380
ttacaaaagg cagcccttttg ggtactactg ctgcaaagtg caaatactcc aagcttcaag     1440
tgatatatgt atttattgtc attactgcct ttggaagaaa cagggggatca aagttcctgt     1500 tcaccttatg tattattttc tatagctctt ctatttaaaa aataaaaaaa tacagtaaag     1560
tttaaaaaat acaccacgaa tttggtgtgg ctgtattcag atcgtattaa ttatctgatc     1620
gggataacaa aatcacaagc aataattagg atctatgcaa ttttttaaact agtaatgggc     1680 caattaaaat atatataaat atatattttt caaccagcat tttactactt gttacctttc     1740
ccatgctgaa ttattttgtt gtgattttgt acagaatttt taatgacttt ttataatgtg     1800
```

-continued

```
gatttcctat tttaaaacca tgcagcttca tcaatttttta tacatatcag aaaagtagaa    1860
ttatatctaa tttatacaaa ataatttaac taatttaaac cagcagaaaa gtgcttagaa    1920
agttattgtg ttgccttagc acttctttcc tctccaattg taaaaaaaaa aaaaaaaaaa    1980
aaaaaaaaaa aaaaattgca caatttgagc aattcatttc actttaaagt ctttccgtct    2040
ccctaaaata aaaaccagaa tcataatttt caagagaaga aaaaattaag agatacattc    2100
cctatcaaaa catatcaatt caacacatta cttgcacaag cttgtatata catattataa    2160
ataaatgcca acatacccctt ctttaaatca aaagctgctt gactatcaca tacaatttgc    2220
actgttactt tttagtcttt tactcctttg cattccatga ttttacagag aatctgaagc    2280
tattgatgtt tccagaaaat ataaatgcat gattttatac atagtcacaa aaatggtggt    2340
ttgtcatata ttcatgtaat aaatctgagc ctaaatctaa tcaggttgtt aatgttggga    2400
tttatatcta tagtagtcaa ttagtacagt agcttaaata aattcaaacc atttaattca    2460
taattagaac aatagctatt gcatgtaaaa tgcagtccag aataagtgct gtttgagatg    2520
tgatgctggt accactggaa tcgatctgta ctgtaatttt gtttgtaatc ctgtatatta    2580
tggtgtaatg cacaatttag aaaacattca tccagttgca ataaaatagt attgaaagtg    2640
agagcaattg ttgcatttct tcttaaaggg attctgtttt tattttttggg gaaagtagtt    2700 gcttttttgc tgagttaaaa aatactaaac actatatgta gaataaaaga aaagaaaaaa    2760
gtttaccttg gcatatgctc ttgtctgttt atcttgcaca gggagtcacc agttctatgt    2820
agataatgaa aagacctaac tgatatttca ttatttggaa tatgggactg gacggcagta    2880
caaacagtgt gttttttttct ttgtttttaag tggcttagcc tttaggtttt ttatttccat    2940
ttttaaaaat gattgttaca tgttttcttc tatttctttt tttaaaaggt ggattttaat    3000
aa                                                                    3002
```

<210> SEQ ID NO 35
<211> LENGTH: 367
<212> TYPE: PRT
<213> ORGANISM: Homo sapiens

<400> SEQUENCE: 35

```
Met Leu Ala Val Gly Ala Met Glu Gly Thr Arg Gln Ser Ala Phe Leu
1               5                   10                  15

Leu Ser Ser Pro Pro Leu Ala Ala Leu His Ser Met Ala Glu Met Lys
            20                  25                  30

Thr Pro Leu Tyr Pro Ala Ala Tyr Pro Pro Leu Pro Ala Gly Pro Pro
        35                  40                  45

Ser Ser Ser Ser Ser Ser Ser Ser Ser Ser Ser Pro Ser Pro Pro Leu
    50                  55                  60

Gly Thr His Asn Pro Gly Gly Leu Lys Pro Pro Ala Thr Gly Gly Leu
65                  70                  75                  80

Ser Ser Leu Gly Ser Pro Pro Gln Gln Leu Ser Ala Ala Thr Pro His
                85                  90                  95

Gly Ile Asn Asp Ile Leu Ser Arg Pro Ser Met Pro Val Ala Ser Gly
            100                 105                 110

Ala Ala Leu Pro Ser Ala Ser Pro Ser Gly Ser Ser Ser Ser Ser Ser
        115                 120                 125

Ser Ser Ala Ser Ala Ser Ser Ala Ser Ala Ala Ala Ala Ala Ala
    130                 135                 140

Ala Ala Ala Ala Ala Ala Ser Ser Pro Ala Gly Leu Leu Ala Gly Leu
```

```
145             150             155             160

Pro Arg Phe Ser Ser Leu Ser Pro Pro Pro Pro Pro Gly Leu Tyr
            165             170             175

Phe Ser Pro Ser Ala Ala Ala Val Ala Ala Val Gly Arg Tyr Pro Lys
            180             185             190

Pro Leu Ala Glu Leu Pro Gly Arg Thr Pro Ile Phe Trp Pro Gly Val
            195             200             205

Met Gln Ser Pro Pro Trp Arg Asp Ala Arg Leu Ala Cys Thr Pro His
            210             215             220

Gln Gly Ser Ile Leu Leu Asp Lys Asp Gly Lys Arg Lys His Thr Arg
225             230             235             240

Pro Thr Phe Ser Gly Gln Gln Ile Phe Ala Leu Glu Lys Thr Phe Glu
            245             250             255

Gln Thr Lys Tyr Leu Ala Gly Pro Glu Arg Ala Arg Leu Ala Tyr Ser
            260             265             270

Leu Gly Met Thr Glu Ser Gln Val Lys Val Trp Phe Gln Asn Arg Arg
            275             280             285

Thr Lys Trp Arg Lys Lys His Ala Ala Glu Met Ala Thr Ala Lys Lys
            290             295             300

Lys Gln Asp Ser Glu Thr Glu Arg Leu Lys Gly Ala Ser Glu Asn Glu
305             310             315             320

Glu Glu Asp Asp Asp Tyr Asn Lys Pro Leu Asp Pro Asn Ser Asp Asp
            325             330             335

Glu Lys Ile Thr Gln Leu Leu Lys Lys His Lys Ser Ser Ser Gly Gly
            340             345             350

Gly Gly Gly Leu Leu Leu His Ala Ser Glu Pro Glu Ser Ser Ser
            355             360             365

<210> SEQ ID NO 36
<211> LENGTH: 1116
<212> TYPE: DNA
<213> ORGANISM: Homo sapiens

<400> SEQUENCE: 36
cgtgggatgt tagcggtggg ggcaatggag ggcacccggc agagcgcatt cctgctcagc        60
agccctcccc tggccgccct gcacagcatg gccgagatga agaccccgct gtaccctgcc       120
gcgtatcccc cgctgcctgc cggcccccccc tcctcctcgt cctcgtcgtc gtcctcctcg       180
tcgccctccc cgcctctggg cacccacaac ccaggcggcc tgaagccccc ggccacgggg       240
gggctctcat ccctcggcag cccccccgcag cagctctcgg ccgccacccc acacggcatc       300
aacgatatcc tgagccggcc ctccatgccc gtggcctcgg gggccgccct gccctccgcc       360
tcgccctccg gttcctcctc ctcctcttcc tcgtccgcct ctgcctcctc cgcctctgcc       420
gccgccgcgg ctgctgccgc ggccgcagcc gccgcctcat ccccggcggg gctgctggcc       480
ggactgccac gctttagcag cctgagcccg ccgccgccgc cgcccgggct ctacttcagc       540
cccagcgccg cggccgtggc cgccgtgggc cggtacccca agccgctggc tgagctgcct       600
ggccggacgc ccatcttctg gcccggagtg atgcagagcc cgccctggag gacgcacgc       660 ctggcctgta cccctcatca aggatccatt ttgttggaca agacgggaa gagaaaacac       720 acgagaccca cttttttccgg acagcagatc ttcgccctgg agaagacttt cgaacaaaca       780
aaatacttgg cgggggcccga gagggctcgt ttggcctatt cgttggggat gacagagagt       840
caggtcaagg tctggttcca gaaccgccgg accaagtgga ggaagaagca cgctgccgag       900
```

-continued

```
atggccacgg ccaagaagaa gcaggactcg gagacagagc gcctcaaggg ggcctcggag     960
aacgaggaag aggacgacga ctacaataag cctctggatc ccaactcgga cgacgagaaa    1020
atcacgcagc tgttgaagaa gcacaagtcc agcagcggcg gcggcggcgg cctcctactg    1080
cacgcgtccg agccggagag ctcatcctga acgccg                              1116
```

```
<210> SEQ ID NO 37
<211> LENGTH: 353
<212> TYPE: PRT
<213> ORGANISM: Homo sapiens

<400> SEQUENCE: 37

Met Ala Ala Glu Leu Ala Met Gly Ala Glu Leu Pro Ser Ser Pro Leu
1               5                   10                  15

Ala Ile Glu Tyr Val Asn Asp Phe Asp Leu Met Lys Phe Glu Val Lys
            20                  25                  30

Lys Glu Pro Pro Glu Ala Glu Arg Phe Cys His Arg Leu Pro Pro Gly
        35                  40                  45

Ser Leu Ser Ser Thr Pro Leu Ser Thr Pro Cys Ser Ser Val Pro Ser
    50                  55                  60

Ser Pro Ser Phe Cys Ala Pro Ser Pro Gly Thr Gly Gly Gly Gly
65                  70                  75                  80

Ala Gly Gly Gly Gly Ser Ser Gln Ala Gly Gly Ala Pro Gly Pro
            85                  90                  95

Pro Ser Gly Gly Pro Gly Ala Val Gly Gly Thr Ser Gly Lys Pro Ala
            100                 105                 110

Leu Glu Asp Leu Tyr Trp Met Ser Gly Tyr Gln His His Leu Asn Pro
            115                 120                 125

Glu Ala Leu Asn Leu Thr Pro Glu Asp Ala Val Glu Ala Leu Ile Gly
        130                 135                 140

Ser Gly His His Gly Ala His His Gly Ala His His Pro Ala Ala Ala
145                 150                 155                 160

Ala Ala Tyr Glu Ala Phe Arg Gly Pro Gly Phe Ala Gly Gly Gly Gly
            165                 170                 175

Ala Asp Asp Met Gly Ala Gly His His His Gly Ala His His Ala Ala
            180                 185                 190

His His His His Ala Ala His His His His His His His His His His
            195                 200                 205

Gly Gly Ala Gly His Gly Gly Ala Gly His His Val Arg Leu Glu
        210                 215                 220

Glu Arg Phe Ser Asp Asp Gln Leu Val Ser Met Ser Val Arg Glu Leu
225                 230                 235                 240

Asn Arg Gln Leu Arg Gly Phe Ser Lys Glu Glu Val Ile Arg Leu Lys
            245                 250                 255

Gln Lys Arg Arg Thr Leu Lys Asn Arg Gly Tyr Ala Gln Ser Cys Arg
            260                 265                 270

Phe Lys Arg Val Gln Gln Arg His Ile Leu Glu Ser Glu Lys Cys Gln
            275                 280                 285

Leu Gln Ser Gln Val Glu Gln Leu Lys Leu Glu Val Gly Arg Leu Ala
        290                 295                 300

Lys Glu Arg Asp Leu Tyr Lys Glu Lys Tyr Glu Lys Leu Ala Gly Arg
305                 310                 315                 320

Gly Gly Pro Gly Ser Ala Gly Gly Ala Gly Phe Pro Arg Glu Pro Ser
            325                 330                 335
```

```
Pro Pro Gln Ala Gly Pro Gly Gly Ala Lys Gly Thr Ala Asp Phe Phe
        340                 345                 350

Leu
```

```
<210> SEQ ID NO 38
<211> LENGTH: 2058
<212> TYPE: DNA
<213> ORGANISM: Homo sapiens

<400> SEQUENCE: 38
gggtccttca ggtaggaggt cctgggtgac tttggaagtc cgtagtgtct cattgcagat      60
aatttttagc ttagggcctg gtggctaggt cggttctctc ctttccagtc ggagacctct     120
gccgcaaaca tgctccgcca gatcatcggt caggccaaga agcatccgag cttgatcccc     180
ctctttgtat ttattggaac tggagctact ggagcaacac tgtatctctt gcgtctggca     240
ttgttcaatc cagatgtttg ttgggacaga aataacccag agccctggaa caaactgggt     300
cccaatgatc aatacaagtt ctactcagtg aatgtggatt acagcaagct gaagaaggaa     360
cgtccagatt tctaaatgaa atgtttcact ataacgctgc tttagaatga aggtcttcca     420
gaagccacat ccgcacaatt ttccacttaa ccaggaaata tttctcctct aaatgcatga     480
aatcatgttg gagatctcta ttgtaatctc tattggagat tacaatgatt aaatcaataa     540
ataactgaaa cttgatatgt gtcacttttt tatgctgaaa gtatgctctg aactttagag     600
tataggaaat taactattag aatttaaaga atttcttgaa tttctgtagt ttgaaaatac     660
gactttaagc tgctttagta aaacacttcc attttgtgta tagactgttg gtaacttcac     720
tagagcatac ataacaactg gaactggaaa ttatacaaaa gtaaattggg aaggatactc     780
cagcatctga cactggcaaa atggaaacct ttgagtttct cttactggct gttgaagtgt     840
gtgcagtttt taacaatggt ttttacttgg catctctttg ttgtgatttt caaggttata     900
agttgctttg gtcctaggat tgaagttgaa atctgagttt atcagtgcta accatggtgc     960
tagtagtcaa gagatcttga gaattttggc tgctgagtct tggtgcaggg tgcaggtttt    1020 ctttttctttt ttctttttttt ttttttttgag atagtctctg tcacccaggc tggagtgcag    1080
tggtacaaac atggatcact gcagcctcta cctcccgggc ttaagtgatc ctcctgcctc    1140
agcccctaag tagccgggac tacaggtatg tgccaccatg cccagttaat ttttgtaatt    1200
ttttttagac acagggtttt gccatgttgc ccaggctggt ctcaaactct tgagctcaag    1260
cgatccattc tcctcagcct cccagggtgc tgggattaca ggcgtgagcc attgcgctta    1320
gccatggtgc aggttttcaa aggccaggaa gtatattcat aattttaaga tggggaatat    1380
agcaagtttt cacataggtg tgtgtaagtc atcacatcat agaaacttga ggaattcagt    1440
gacattaatt ttggattttc atacgtaagt atacaattaa atgtttacag ggtagtagaa    1500
gcacatttta aatgtcagga actgaactaa gtatttgaat tacgtggatt atctcaaaaa    1560
ttttgaaatt gttaaacgag ttgaattact tgaattcatt ctgttagtca aatggtggat    1620
atttacaccc atgtagtttt gaatttagag tgtgtagagt gttttcagtt accagactcc    1680
atgcttttac ctcctatgtg tcaggtataa tttgaacctc taagaacagg gtttctcaac    1740
cttgccactg ttgactattt ctgaaagaca gtttggttta gcagaccatc ccatgcgctt    1800
tagcttgttt agtagctaac ttgggctctg ccactacaga caaaaagcac tctttccctc    1860
caattcccac aggctatgag aagaatggag acattaccaa atgtccattg gtgggcaaaa    1920
ttgcttcatt cctacctctg ttgagaatta ctctagatcc tttggcacaa attacctcaa    1980
```
agtttaaaat tgtgtaaaca aacagtgtgt catgtaattg aaaaacatta agcaactcca    2040
aataaatgct acattaag                                                  2058

<210> SEQ ID NO 39
<211> LENGTH: 290
<212> TYPE: PRT
<213> ORGANISM: Homo sapiens

<400> SEQUENCE: 39

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
        130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
        210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 40
<211> LENGTH: 531
<212> TYPE: DNA
<213> ORGANISM: Homo sapiens

<400> SEQUENCE: 40
atgaggatat ttgctgtctt tatattcatg acctactggc atttgctgaa cgccccatac    60

```
aacaaaatca accaaagaat tttggttgtg gatccagtca cctctgaaca tgaactgaca        120
tgtcaggctg agggctaccc caaggccgaa gtcatctgga caagcagtga ccatcaagtc        180
ctgagtggta agaccaccac caccaattcc aagagagagg agaagctttt caatgtgacc        240
agcacactga gaatcaacac aacaactaat gagattttct actgcacttt taggagatta        300
gatcctgagg aaaaccatac agctgaattg gtcatcccag aactacctct ggcacatcct        360
ccaaatgaaa ggactcactt ggtaattctg ggagccatct tattatgcct tggtgtagca        420
ctgacattca tcttccgttt aagaaaaggg agaatgatgg atgtgaaaaa atgtggcatc        480
caagatacaa actcaaagaa gcaaagtgat acacatttgg aggagacgta a              531
```

```
<210> SEQ ID NO 41
<211> LENGTH: 343
<212> TYPE: PRT
<213> ORGANISM: Homo sapiens

<400> SEQUENCE: 41

Met Asn Gln Leu Gly Gly Leu Phe Val Asn Gly Arg Pro Leu Pro Leu
1               5                   10                  15

Asp Thr Arg Gln Gln Ile Val Arg Leu Ala Val Ser Gly Met Arg Pro
            20                  25                  30

Cys Asp Ile Ser Arg Ile Leu Lys Val Ser Asn Gly Cys Val Ser Lys
        35                  40                  45

Ile Leu Gly Arg Tyr Tyr Arg Thr Gly Val Leu Glu Pro Lys Gly Ile
    50                  55                  60

Gly Gly Ser Lys Pro Arg Leu Ala Thr Pro Pro Val Val Ala Arg Ile
65                  70                  75                  80

Ala Gln Leu Lys Gly Glu Cys Pro Ala Leu Phe Ala Trp Glu Ile Gln
                85                  90                  95

Arg Gln Leu Cys Ala Glu Gly Leu Cys Thr Gln Asp Lys Thr Pro Ser
            100                 105                 110

Val Ser Ser Ile Asn Arg Val Leu Arg Ala Leu Gln Glu Asp Gln Gly
        115                 120                 125

Leu Pro Cys Thr Arg Leu Arg Ser Pro Ala Val Leu Ala Pro Ala Val
    130                 135                 140

Leu Thr Pro His Ser Gly Ser Glu Thr Pro Arg Gly Thr His Pro Gly
145                 150                 155                 160

Thr Gly His Arg Asn Arg Thr Ile Phe Ser Pro Ser Gln Ala Glu Ala
                165                 170                 175

Leu Glu Lys Glu Phe Gln Arg Gly Gln Tyr Pro Asp Ser Val Ala Arg
            180                 185                 190

Gly Lys Leu Ala Thr Ala Thr Ser Leu Pro Glu Asp Thr Val Arg Val
        195                 200                 205

Trp Phe Ser Asn Arg Arg Ala Lys Trp Arg Arg Gln Glu Lys Leu Lys
    210                 215                 220

Trp Glu Met Gln Leu Pro Gly Ala Ser Gln Gly Leu Thr Val Pro Arg
225                 230                 235                 240

Val Ala Pro Gly Ile Ile Ser Ala Gln Gln Ser Pro Gly Ser Val Pro
                245                 250                 255

Thr Ala Ala Leu Pro Ala Leu Glu Pro Leu Gly Pro Ser Cys Tyr Gln
            260                 265                 270

Leu Cys Trp Ala Thr Ala Pro Glu Arg Cys Leu Ser Asp Thr Pro Pro
        275                 280                 285

Lys Ala Cys Leu Lys Pro Cys Trp Gly His Leu Pro Pro Gln Pro Asn
```

-continued

```
        290              295              300

Ser Leu Asp Ser Gly Leu Leu Cys Leu Pro Cys Pro Ser Ser His Cys
305              310              315              320

His Leu Ala Ser Leu Ser Gly Ser Gln Ala Leu Leu Trp Pro Gly Cys
                325              330              335

Pro Leu Leu Tyr Gly Leu Glu
        340

<210> SEQ ID NO 42
<211> LENGTH: 2010
<212> TYPE: DNA
<213> ORGANISM: Homo sapiens

<400> SEQUENCE: 42
caaagactca cccgtgagcc agctctcaaa gaaagcagct tgcgttgaca gcctgggggc      60
agcaaggatg cagtctccca ggagaggatg cactcggtgg tgggaagcca ggctggaggg     120
gcctgagtga ccctctccac aggcgggcag ggcagtggga gaggtggtgt gtggatacct     180
ctgtctcacg cccagggatc agcagcatga accagcttgg ggggctcttt gtgaatggcc     240
ggcccctgcc tctggatacc cggcagcaga ttgtgcggct agcagtcagt ggaatgcggc     300
cctgtgacat ctcacggatc cttaaggtat ctaatggctg tgtgagcaag atcctagggc     360
gttactaccg cacaggtgtc ttggagccaa agggcattgg gggaagcaag ccacggctgg     420 ctacacccc tgtggtggct cgaattgccc agctgaaggg tgagtgtcca gccctctttg     480
cctgggaaat ccaacgccag ctttgtgctg aagggctttg cacccaggac aagactccca     540
gtgtctcctc catcaaccga gtcctgcggg cattacagga ggaccaggga ctaccgtgca     600
cacggctcag gtcaccagct gttttggctc cagctgtcct cactccccat agtggctctg     660
agactccccg gggtacccac ccagggaccg gccaccggaa tcggactatc ttctccccaa     720
gccaagcaga ggcactggag aaagagttcc agcgtgggca gtatcctgat tcagtggccc     780
gtggaaagct ggctactgcc acctctctgc ctgaggacac ggtgagggtc tggtttttcca     840 acagaagagc caaatggcgt cggcaagaga agctcaagtg ggaaatgcag ctgccaggtg     900
cttcccaggg gctgactgta ccaagggttg ccccaggaat catctctgca cagcagtccc     960
ctggcagtgt gcccacagca gccctgcctg ccctggaacc actgggtccc tcctgctatc    1020
agctgtgctg ggcaacagca ccagaaaggt gtctgagtga cacccacct aaagcctgtc    1080 tcaagccctg ctggggccac ttgccccac agccgaattc cctggactca ggactgcttt    1140
gccttccttg cccttcctcc cactgtcacc tggccagtct tagtggctct caggccctgc    1200
tctggcctgg ctgcccacta ctgtatggct tggaatgagg caggagtggg aaggagatgg    1260
catagagaag atctaatacc atcctgccca ttgtccttac cgtcctgccc atacagactg    1320
tggctccttc ctccttcctg tgattgctcc ctcctgtgtg gacgttgcct ggccctgcct    1380
cgatgcctct ctggcgcatc acctgattgg aggggctggt aaagcaacac ccacccactt    1440
ctcacactag ccttaagagg cctccactca gcagtaataa aagctgtttt tattagcagt    1500
agttctgttg tccatcatgt tttccctatg agcaccccta tgcccactct aatattcaac    1560
aattatagac aatttgccct atcatttatt tacatctatg tatctaccat ctaatctatg    1620
catgtatgta ggcaatacat gtatctaaac aatgtatttg tcaatgcatc aatttaccta    1680
ctctatgtat gcatctatat gtgtattatg tatgcgtgca tgcgtgcgcg cacacacaca    1740
cacacacaca cacactgaca ttatatcatg gcattttatt cctaaatctt ccagcatgca    1800
```

```
tccccaaaaa acaagaaact tgtcttacat aatcacaata atatatccac atctaagaaa    1860
atttactgta acttcttaat ctaagaaaat tatgtatttt tgtcatatgt attttgtcat    1920
atgtattttg tatttgcata tgtattttgt atttgcatat gtattttgt catagcagca     1980 aacagagtga aatgccattt ttcatattct                                     2010
```

```
<210> SEQ ID NO 43
<211> LENGTH: 286
<212> TYPE: PRT
<213> ORGANISM: Homo sapiens

<400> SEQUENCE: 43

Met Gly Ala Asp Gly Met Tyr Asp Lys Leu Arg Met Leu Asn Gly Gln
1               5                   10                  15

Thr Gly Ser Trp Gly Thr Arg Pro Gly Trp Tyr Pro Gly Thr Ser Val
            20                  25                  30

Pro Gly Gln Pro Thr Gln Asp Gly Cys Gln Gln Gln Glu Gly Gly Gly
        35                  40                  45

Glu Asn Thr Asn Ser Ile Ser Ser Asn Gly Glu Asp Ser Asp Glu Ala
    50                  55                  60

Gln Met Arg Leu Gln Leu Lys Arg Lys Leu Gln Arg Asn Arg Thr Ser
65                  70                  75                  80

Phe Thr Gln Glu Gln Ile Glu Ala Leu Glu Lys Glu Phe Glu Arg Thr
                85                  90                  95

His Tyr Pro Asp Val Phe Ala Arg Glu Arg Leu Ala Ala Lys Ile Asp
            100                 105                 110

Leu Pro Glu Ala Arg Ile Gln Val Trp Phe Ser Asn Arg Arg Ala Lys
            115                 120                 125

Trp Arg Arg Glu Glu Lys Leu Arg Asn Gln Arg Arg Gln Ala Ser Asn
        130                 135                 140

Thr Pro Ser His Ile Pro Ile Ser Ser Ser Phe Ser Thr Ser Val Tyr
145                 150                 155                 160

Gln Pro Ile Pro Gln Pro Thr Thr Pro Val Ser Ser Phe Thr Ser Gly
                165                 170                 175

Ser Met Leu Gly Arg Thr Asp Thr Ala Leu Thr Asn Thr Tyr Ser Ala
            180                 185                 190

Leu Pro Pro Met Pro Ser Phe Thr Met Ala Asn Asn Leu Pro Met Gln
            195                 200                 205

Pro Pro Val Pro Ser Gln Thr Ser Ser Tyr Ser Cys Met Leu Pro Thr
        210                 215                 220

Ser Pro Ser Val Asn Gly Arg Ser Tyr Asp Thr Tyr Thr Pro Pro His
225                 230                 235                 240

Met Gln Thr His Met Asn Ser Gln Pro Met Gly Thr Ser Gly Thr Thr
                245                 250                 255

Ser Thr Gly Leu Ile Ser Pro Gly Val Ser Val Pro Val Gln Val Pro
            260                 265                 270

Gly Ser Glu Pro Asp Met Ser Gln Tyr Trp Pro Arg Leu Gln
            275                 280                 285
```

```
<210> SEQ ID NO 44
<211> LENGTH: 6732
<212> TYPE: DNA
<213> ORGANISM: Homo sapiens

<400> SEQUENCE: 44
cttttcaatt agccttccat gcatgatccg gagcgacttc cgcctatttc cagaaattaa      60
```

```
gctcaaactt gacgtgcagc tagtttttatt ttaaagacaa atgtcagaga ggctcatcat    120 attttcccccc ctcttctata tttggagctt atttattgct aagaagctca ggctcctggc    180
gtcaatttat cagtaggctc caaggagaag agaggagagg agaggagagc tgaacaggga    240
gccacgtctt ttcctgggag ggctgctatc taagtcgggg ctgcaggtca cagcggagtg    300
aatcagctcg gtggtgtctt tgtcaacggg cggccactgc cggactccac ccggcagaag    360
attgtagagc tagctcacag cggggcccgg ccgtgcgaca tttcccgaat tctgcagacc    420
catgcagatg caaaagtcca agtgctggac aatcaaaacg tgtccaacgg atgtgtgagt    480
aaaattctgg gcaggtatta cgagactggc tccatcagac ccagggcaat cggtggtagt    540
aaaccgagag tagcgactcc agaagttgta agcaaaatag cccagtataa gcgggagtgc    600
ccgtccatct ttgcttggga aatccgagac agattactgt ccgaggggt ctgtaccaac    660 gataacatac caagcgtgtc atcaataaac agagttcttc gcaacctggc tagcgaaaag    720
caacagatgg gcgcagacgg catgtatgat aaactaagga tgttgaacgg gcagaccgga    780
agctggggca cccgccctgg ttggtatccg gggacttcgg tgccagggca acctacgcaa    840
gatggctgcc agcaacagga aggaggggga gagaatacca actccatcag ttccaacgga    900
gaagattcag atgaggctca aatgcgactt cagctgaagc ggaagctgca aagaaataga    960
acatccttta cccaagagca aattgaggcc ctggagaaag agtttgagag aacccattat   1020
ccagatgtgt ttgcccgaga aagactagca gccaaaatag atctacctga agcaagaata   1080
caggtatggt tttctaatcg aagggccaaa tggagaagag aagaaaaact gaggaatcag   1140
agaagacagg ccagcaacac acctagtcat attcctatca gcagtagttt cagcaccagt   1200
gtctaccaac caattccaca acccaccaca ccggtttcct ccttcacatc tggctccatg   1260
ttgggccgaa cagacacagc cctcacaaac acctacagcg ctctgccgcc tatgcccagc   1320
ttcaccatgg caaataacct gcctatgcaa cccccagtcc ccagccagac ctcctcatac   1380
tcctgcatgc tgcccaccag cccttcggtg aatgggcgga gttatgatac ctacacccccc   1440 ccacatatgc agacacacat gaacagtcag ccaatgggca cctcgggcac cacttcaaca   1500
ggactcattt cccctggtgt gtcagttcca gttcaagttc ccggaagtga acctgatatg   1560
tctcaatact ggccaagatt acagtaaaaa aaaaaaaaa aaaaaaaagg aaaggaaata   1620
ttgtgttaat tcagtcagtg actatgggga cacaacagtt gagctttcag gaaagaaaga   1680
aaaatggctg ttagagccgc ttcagttcta caattgtgtc ctgtattgta ccactgggga   1740
aggaatggac ttgaaacaag gacctttgta tacagaaggc acgatatcag ttggaacaaa   1800
tcttcatttt ggtatccaaa cttttattca ttttggtgta ttatttgtaa atgggcattt   1860
gtatgttata atgaaaaaaa gaacaatgta gactggatgg atgtttgatc tgtgttggtc   1920
atgaagttgt ttttttttt tttaaaaga aaaccatgat caacaagctt tgccacgaat   1980
ttaagagttt tatcaagata tatcgaatac ttctacccat ctgttcatag tttatggact   2040
gatgttccaa gtttgtatca ttcctttgca tataattaaa cctggaacaa catgcactag   2100
atttatgtca gaaatatctg ttggtttttcc aaaggttgtt aacagatgaa gtttatgtgc   2160
aaaaaagggt aagatataaa ttcaaggaag aaaaaaagtt gatagctaaa aggtagagtg   2220
tgtcttcgat ataatccaat ttgtttttatg tcaaaatgta agtatttgtc ttccctagaa   2280
atcctcagaa tgatttctat aataaagtta atttcattta tatttgacaa gaatatagat   2340
gttttataca cattttcatg caatcatacg tttcttttt ggccagcaaa agttaattgt   2400
```

-continued

```
tcttagatat agttgtatta ctgttcacgg tccaatcatt ttgtgcatct agagttcatt      2460
cctaatcaat taaaagtgct tgcaagagtt ttaaacttaa gtgttttgaa gttgttcaca      2520
actacatatc aaaattaacc attgttgatt gtaaaaaacc atgccaaagc ctttgtattt      2580
cctttattat acagttttct ttttaacctt atagtgtggt gttacaaatt ttatttccat      2640
gttagatcaa cattctaaac caatggttac tttcacacac actctgtttt acatcctgat      2700
gatccttaaa aaataatcct tatagatacc ataaatcaaa aacgtgttag aaaaaaattc      2760
cacttacagc agggtgtaga tctgtgccca tttataccca caacatatat acaaaatggt      2820
aacatttccc agttagccat ttaattctaa agctcaaagt ctagaaataa tttaaaaatg      2880
caacaagcga ttagctagga attgtttttt gaattaggac tggcatttttc aatctgggca      2940 gatttccatt gtcagcctat ttcaacaatg atttcactga agtatattca aaagtagatt      3000
tcttaaagga gactttctga aagctgttgc cttttttcaaa taggccctct ccctttttctg      3060 tctccctccc ctttgcacaa gaggcatcat ttcccattga accactacag ctgttcccat      3120
ttgaatcttg ctttctgtgc ggttgtggat ggttggaggg tggaggggggg atgttgcatg      3180 tcaaggaata atgagcacag acacatcaac agacaacaac aaagcagact gtgactggcc      3240
ggtgggaatt aaaggccttc agtcattggc agcttaagcc aaacattccc aaatctatga      3300
agcagggccc attgttggtc agttgttatt tgcaatgaag cacagttctg atcatgttta      3360
aagtggaggc acgcagggca ggagtgcttg agcccaagca aaggatggaa aaaaataagc      3420
ctttgttggg taaaaaagga ctgtctgaga ctttcatttg ttctgtgcaa catataagtc      3480
aatacagata agtcttcctc tgcaaacttc actaaaaagc ctgggggttc tggcagtcta      3540
gattaaaatg cttgcacatg cagaaacctc tggggacaaa gacacacttc cactgaatta      3600
tactctgctt taaaaaaatc cccaaaagca aatgatcaga aatgtagaaa ttaatggaag      3660
gatttaaaca tgaccttctc gttcaatatc tactgttttt tagttaagga attacttgtg      3720
aacagataat tgagattcat tgctccggca tgaaatatac taataatttt attccaccag      3780
agttgctgca catttggaga caccttccta agttgcagtt tttgtatgtg tgcatgtagt      3840
tttgttcagt gtcagcctgc actgcacagc agcacatttc tgcaggggag tgagcacaca      3900
tacgcactgt tggtacaatt gccggtgcag acatttctac ctcctgacat tttgcagcct      3960
acattccctg agggctgtgt gctgagggaa ctgtcagaga agggctatgt gggagtgcat      4020
gccacagctg ctggctggct tacttcttcc ttctcgctgg ctgtaatttc caccacggtc      4080
aggcagccag ttccggccca cggttctgtt gtgtagacag cagagacttt ggagacccgg      4140
atgtcgcacg ccaggtgcaa gaggtgggaa tgggagaaaa ggagtgacgt gggagcggag      4200
ggtctgtatg tgtgcacttg ggcacgtata tgtgtgctct gaaggtcagg attgccaggg      4260
caaagtagca cagtctggta tagtctgaag aagcggctgc tcagctgcag aagccctctg      4320
gtccggcagg atgggaacgg ctgccttgcc ttctgcccac accctaggga catgagctgt      4380
ccttccaaac agagctccag gcactctctt ggggacagca tggcaggctc tgtgtggtag      4440
cagtgcctgg gagttggcct tttactcatt gttgaaataa ttttttgttta ttatttattt      4500 aacgatacat atatttatat atttatcaat ggggtatctg cagggatgtt ttgacaccat      4560
cttccaggat ggagattatt tgtgaagact tcagtagaat cccaggacta aacgtctaaa      4620
ttttttctcc aaacttgact gacttgggaa aaccaggtga atagaataag agctgaatgt      4680
tttaagtaat aaacgttcaa actgctctaa gtaaaaaaat gcattttact gcaatgaatt      4740
tctagaatat ttttcccca aagctatgcc tcctaaccct taaatggtga acaactggtt      4800
```

```
tcttgctaca gctcactgcc atttcttctt actatcatca ctaggtttcc taagattcac    4860
tcatacagta ttatttgaag attcagcttt gttctgtgaa tgtcatctta ggattgtgtc    4920
tatattcttt tgcttatttc tttttactct gggcctctca tactagtaag attttaaaaa    4980
gccttttctt ctctgtatgt ttggctcacc aaggcgaaat atatattctt ctcttttca    5040 tttctcaaga ataaacctca tctgcttttt tgtttttctg tgttttggct tggtactgaa    5100
tgactcaact gctcggtttt aaagttcaaa gtgtaagtac ttagggttag tactgcttat    5160
ttcaataatg ttgacggtga ctatctttgg aaagcagtaa catgctgtct tagaaatgac    5220
attaataatg ggcttaaaca aatgaatagg ggggtccccc cactctcctt ttgtatgcct    5280
atgtgtgtct gatttgttaa aagatggaca gggaattgat tgcagagtgt cgcttccttc    5340
taaagtagtt ttattttgtc tactgttagt atttaaagat cctggaggtg gacataagga    5400
ataaatggaa gagaaaagta gatattgtat ggtggctact aaaaggaaat tcaaaaagtc    5460
ttagaacccg agcacctgag caaactgcag tagtcaaaat atttatctca tgttaaagaa    5520
aggcaaatct agtgtaagaa atgagtacca tatagggttt tgaagttcat atactagaaa    5580
cacttaaaag atatcatttc agatattacg tttggcattg ttcttaagta tttatatctt    5640
tgagtcaagc tgataattaa aaaaaatctg ttaatggagt gtatatttca taatgtatca    5700
aaatggtgtc tatacctaag gtagcattat tgaagagaga tatgtttatg tagtaagtta    5760
ttaacataat gagtaacaaa taatgtttcc agaagaaagg aaaacacatt ttcagagtgc    5820
gtttttatca gaggaagaca aaaatacaca cccctctcca gtagcttatt tttacaaagc    5880
cggcccagtg aattagaaaa acaaagcact tggatatgat ttttggaaag cccaggtaca    5940
cttattattc aaaatgcact tttactgagt ttgaaaagtt tcttttatat ttaaaataag    6000
ggttcaaata tgcatattca attttttatag tagttatcta tttgcaaagc atatattaac    6060
tagtaattgg ctgttaattt tatagacatg gtagccaggg aagtatatca atgacctatt    6120
aagtattttg acaagcaatt tacatatctg atgacctcgt atctctttt cagcaagtca     6180 aatgctatgt aattgttcca ttgtgtgttg tataaaatga atcaacacgg taagaaaaag    6240
gttagagtta ttaaaataat aaactgacta aaatactcat ttgaatttat tcagaatgtt    6300
cataatgctt tcaaaggaca tagcagagct tttgtggagt atccgcacaa cattatttat    6360
tatctatgga ctaaatcaat tttttgaagt tgctttaaaa tttaaaagca cctttgctta    6420
atataaagcc ctttaatttt aactgacaga tcaattctga aactttattt tgaaaagaaa    6480
atggggaaga atctgtgtct ttagaattaa aagaaatgaa aaaaataaac ccgacattct    6540
aaaaaaatag aataagaaac ctgattttta gtactaatga aatagcgggt gacaaaatag    6600
ttgtcttttt gattttgatc acaaaaaata aactggtagt gacaggatat gatggagaga    6660
tttgacatcc tggcaaatca ctgtcattga ttcaattatt ctaattctga ataaaagctg    6720
tatacagtaa aa                                                        6732
```

<210> SEQ ID NO 45
<211> LENGTH: 283
<212> TYPE: PRT
<213> ORGANISM: Homo sapiens

<400> SEQUENCE: 45

```
Met Asn Gly Glu Glu Gln Tyr Tyr Ala Ala Thr Gln Leu Tyr Lys Asp
1               5                   10                  15

Pro Cys Ala Phe Gln Arg Gly Pro Ala Pro Glu Phe Ser Ala Ser Pro
```

-continued

```
                20              25              30

Pro Ala Cys Leu Tyr Met Gly Arg Gln Pro Pro Pro Pro Pro His
         35              40              45

Pro Phe Pro Gly Ala Leu Gly Ala Leu Glu Gln Gly Ser Pro Pro Asp
      50              55              60

Ile Ser Pro Tyr Glu Val Pro Pro Leu Ala Asp Asp Pro Ala Val Ala
65              70              75              80

His Leu His His His Leu Pro Ala Gln Leu Ala Leu Pro His Pro Pro
              85              90              95

Ala Gly Pro Phe Pro Glu Gly Ala Glu Pro Gly Val Leu Glu Glu Pro
           100             105             110

Asn Arg Val Gln Leu Pro Phe Pro Trp Met Lys Ser Thr Lys Ala His
         115             120             125

Ala Trp Lys Gly Gln Trp Ala Gly Gly Ala Tyr Ala Ala Glu Pro Glu
      130             135             140

Glu Asn Lys Arg Thr Arg Thr Ala Tyr Thr Arg Ala Gln Leu Leu Glu
145             150             155             160

Leu Glu Lys Glu Phe Leu Phe Asn Lys Tyr Ile Ser Arg Pro Arg Arg
              165             170             175

Val Glu Leu Ala Val Met Leu Asn Leu Thr Glu Arg His Ile Lys Ile
           180             185             190

Trp Phe Gln Asn Arg Arg Met Lys Trp Lys Lys Glu Glu Asp Lys Lys
         195             200             205

Arg Gly Gly Gly Thr Ala Val Gly Gly Gly Val Ala Glu Pro Glu
      210             215             220

Gln Asp Cys Ala Val Thr Ser Gly Glu Glu Leu Leu Ala Leu Pro Pro
225             230             235             240

Pro Pro Pro Pro Gly Gly Ala Val Pro Pro Ala Ala Pro Val Ala Ala
              245             250             255

Arg Glu Gly Arg Leu Pro Pro Gly Leu Ser Ala Ser Pro Gln Pro Ser
           260             265             270

Ser Val Ala Pro Arg Arg Pro Gln Glu Pro Arg
         275             280
```

<210> SEQ ID NO 46
<211> LENGTH: 2573
<212> TYPE: DNA
<213> ORGANISM: Homo sapiens

<400> SEQUENCE: 46

```
gggtggcgcc gggagtggga acgccacaca gtgccaaatc cccggctcca gctcccgact      60
cccggctccc ggctcccggc tcccggtgcc caatcccggg ccgcagccat gaacggcgag     120
gagcagtact acgcggccac gcagctttac aaggacccat gcgcgttcca gcgaggcccg     180
gcgccggagt tcagcgccag cccccctgcg tgcctgtaca tgggccgcca gcccccgccg     240
ccgccgccgc accgttccc tggcgccctg ggcgcgctgg agcagggcag cccccccggac     300 atctccccgt acgaggtgcc ccccctcgcc gacgacccc cggtggcgca ccttcaccac     360
cacctcccgg ctcagctcgc gctcccccac ccgcccgccg ggcccttccc ggagggagcc     420
gagccgggcg tcctggagga gcccaaccgc gtccagctgc ctttcccatg gatgaagtct     480
accaaagctc acgcgtggaa aggccagtgg gcaggcggcg cctacgctgc ggagccggag     540
gagaacaagc ggacgcgcac ggcctacacg cgcgcacagc tgctagagct ggagaaggag     600
ttcctattca acaagtacat ctcacggccg cgccgggtgg agctggctgt catgttgaac     660
```

```
ttgaccgaga gacacatcaa gatctggttc caaaaccgcc gcatgaagtg gaaaaaggag       720
gaggacaaga agcgcggcgg cgggacagct gtcgggggtg gcggggtcgc ggagcctgag       780
caggactgcg ccgtgacctc cggcgaggag cttctggcgc tgccgccgcc gccgcccccc       840
ggaggtgctg tgccgcccgc tgcccccgtt gccgcccgag agggccgcct gccgcctggc       900
cttagcgcgt cgccacagcc ctccagcgtc gcgcctcggc ggccgcagga accacgatga       960
gaggcaggag ctgctcctgg ctgaggggct tcaaccactc gccgaggagg agcagagggc      1020
ctaggaggac cccgggcgtg gaccacccgc cctggcagtt gaatggggcg gcaattgcgg      1080
ggcccacctt agaccgaagg ggaaaacccg ctctctcagg cgcatgtgcc agttggggcc      1140
ccgcgggtag atgccggcag gccttccgga agaaaaagag ccattggttt ttgtagtatt      1200 ggggcccct tttagtgata ctggattggc gttgtttgtg gctgttgcgc acatccctgc      1260
cctcctacag cactccacct tgggacctgt ttagagaagc cggctcttca aagacaatgg      1320
aaactgtacc atacacattg gaaggctccc taacacacac agcggggaag ctgggccgag      1380
taccttaatc tgccataaag ccattcttac tcgggcgacc cctttaagtt tagaaataat      1440
tgaaaggaaa tgtttgagtt ttcaaagatc ccgtgaaatt gatgccagtg gaatacagtg      1500
agtcctcctc ttcctcctcc tcctcttccc cctcccttc ctcctcctcc tcttctttc      1560 cctcctcttc ctcttcctcc tgctctcctt tcctcccct cctcttttcc ctcctcttcc      1620
tcttcctcct gctctccttt cctcccctc ctctttctcc tcctcctcct cttcttcccc      1680
ctcctctccc tcctcctctt cttcccccct ctctccctcc tcctcttctt ctccctcctc      1740
ttcctcttcc tcctcttcca cgtgctctcc tttcctcccc ctcctcttgc tccccttctt      1800
ccccgtcctc ttcctcctcc tcctcttctt ctccctcctc ttcctcctcc tctttcttcc      1860
tgacctcttt ctttctcctc ctcctccttc tacctcccct tctcatccct cctcttcctc      1920
ttctctagct gcacacttca ctactgcaca tcttataact tgcaccccctt tcttctgagg      1980 aagagaacat cttgcaaggc agggcgagca gcggcagggc tggcttagga gcagtgcaag      2040
agtccctgtg ctccagttcc acactgctgg cagggaaggc aagggggac gggcctggat      2100 ctgggggtga gggagaaaga tggacccctg ggtgaccact aaaccaaaga tattcggaac      2160 tttctatta ggatgtggac gtaattcctg ttccgaggta gaggctgtgc tgaagacaag      2220
cacagtggcc tggtgcgcct tggaaaccaa caactattca cgagccagta tgaccttcac      2280
atctttagaa attatgaaaa cgtatgtgat tggagggttt ggaaaaccag ttatcttatt      2340
taacatttta aaaattacct aacagttatt tacaaacagg tctgtgcatc ccaggtctgt      2400 cttctttca aggtctgggc cttgtgctcg ggttatgttt gtgggaaatg cttaataaat      2460
actgataata tgggaagaga tgaaaactga ttctcctcac tttgtttcaa acctttctgg      2520
cagtgggatg attcgaattc acttttaaaa ttaaattagc gtgttttgtt ttg          2573
```

<210> SEQ ID NO 47
<211> LENGTH: 328
<212> TYPE: PRT
<213> ORGANISM: Homo sapiens

<400> SEQUENCE: 47

```
Met Asp Ala Val Leu Leu Glu His Phe Pro Gly Gly Leu Asp Ala Phe
1               5                   10                  15

Pro Ser Ser Tyr Phe Asp Glu Asp Asp Phe Phe Thr Asp Gln Ser Ser
            20                  25                  30
```

Arg Asp Pro Leu Glu Asp Gly Asp Glu Leu Leu Ala Asp Glu Gln Ala
        35                  40                  45

Glu Val Glu Phe Leu Ser His Gln Leu His Glu Tyr Cys Tyr Arg Asp
    50                  55                  60

Gly Ala Cys Leu Leu Leu Gln Pro Ala Pro Pro Ala Ala Pro Leu Ala
65                  70                  75                  80

Leu Ala Pro Pro Ser Ser Gly Gly Leu Gly Glu Pro Asp Asp Gly Gly
                85                  90                  95

Gly Gly Gly Tyr Cys Cys Glu Thr Gly Ala Pro Pro Gly Gly Phe Pro
                100                 105                 110

Tyr Ser Pro Gly Ser Pro Pro Ser Cys Leu Ala Tyr Pro Cys Ala Gly
        115                 120                 125

Ala Ala Val Leu Ser Pro Gly Ala Arg Leu Arg Gly Leu Ser Gly Ala
        130                 135                 140

Ala Ala Ala Ala Ala Arg Arg Arg Arg Arg Val Arg Ser Glu Ala Glu
145                 150                 155                 160

Leu Gln Gln Leu Arg Gln Ala Ala Asn Val Arg Glu Arg Arg Arg Met
                165                 170                 175

Gln Ser Ile Asn Asp Ala Phe Glu Gly Leu Arg Ser His Ile Pro Thr
                180                 185                 190

Leu Pro Tyr Glu Lys Arg Leu Ser Lys Val Asp Thr Leu Arg Leu Ala
        195                 200                 205

Ile Gly Tyr Ile Asn Phe Leu Ser Glu Leu Val Gln Ala Asp Leu Pro
        210                 215                 220

Leu Arg Gly Gly Gly Ala Gly Gly Cys Gly Gly Pro Gly Gly Gly Gly
225                 230                 235                 240

Arg Leu Gly Gly Asp Ser Pro Gly Ser Gln Ala Gln Lys Val Ile Ile
                245                 250                 255

Cys His Arg Gly Thr Arg Ser Pro Ser Pro Ser Asp Pro Asp Tyr Gly
                260                 265                 270

Leu Pro Pro Leu Ala Gly His Ser Leu Ser Trp Thr Asp Glu Lys Gln
        275                 280                 285

Leu Lys Glu Gln Asn Ile Ile Arg Thr Ala Lys Val Trp Thr Pro Glu
        290                 295                 300

Asp Pro Arg Lys Leu Asn Ser Lys Ser Ser Phe Asn Asn Ile Glu Asn
305                 310                 315                 320

Glu Pro Pro Phe Glu Phe Val Ser
                325

<210> SEQ ID NO 48
<211> LENGTH: 1339
<212> TYPE: DNA
<213> ORGANISM: Homo sapiens

<400> SEQUENCE: 48
atggacgcgg tgttgctgga gcacttcccc gggggcctag acgcctttcc ttcttcgtac      60
ttcgacgagg acgacttctt caccgaccag tcttcacggg accccctgga ggacggcgat     120
gagctgctgg cggacgagca ggccgaggtg gagttcctta gccaccagct ccacgagtac     180
tgctaccgcg acgggcgtg cctgctgctg cagcccgcgc cccgcgccgc cccgctagcg     240
ctcgccccgc cgtcctcggg gggcctcggt gagccagacg acggcggcgg cggcggctac     300
tgctgcgaga cggggcgcc cccaggcggc ttccccctact cgcccggctc gccgcccctcg     360 tgcctggcct accgtgcgc cggggcggca gtactgtctc ccggggcgcg gctgcgcggc     420

-continued

```
ctgagcggag cggcggctgc ggcggcgcgg cgccggcggc gggtgcgctc cgaggcggag      480
ctgcagcagc tgcggcaggc ggccaacgtg cgcgagcggc ggcgcatgca gtccatcaac      540
gacgccttcg aggggctgcg ctcgcacatc cccacgctgc cctacgagaa gcgcctctcc      600
aaggtggaca cgctgcgcct ggccatcggc tacatcaact tcctcagcga gctcgtgcag      660
gccgacctgc ccttgcgcgg cggtggcgcg ggcggctgcg ggggccgggg cggcggcggg      720
cgcctgggcg gggacagccc gggcagccag gcccagaagg tcatcatctg ccatcggggc      780
acccggtccc cctcccccag cgaccctgat tatggcctcc ctcccctagc aggacactct      840
ctctcatgga ctgatgaaaa acaactcaag gaacaaaata ttatccgaac agccaaagtc      900
tggaccccag aggaccccag aaaactcaac agcaaatctt ccttcaacaa catagaaaac      960
gaaccaccat ttgagtttgt gtcctgagaa gtcccagact cggctgaaga tctgattatg      1020
tctctgtgca tattgtacat gtaaatatct ataatgtaaa tgtaatttaa gaatcaaatt      1080
tttcgaatgg caatcaactg tttattattt atctatttat tatcctgttg agttgatgaa      1140
atagatgatt tctttttaaa tatataattt atataactta tcctgatttt ctgaaaatat      1200
gcaatagcct atgattttcc tgaactctgt gttgttggga gaactctggc cagaaaacgt      1260
cctgcttatt tattgccaga tatggtttat ttctaagcgt tgtcaataaa tgctatttac      1320
accttttcct gaaaaaaaa                                                   1339
```

<210> SEQ ID NO 49
<211> LENGTH: 1555
<212> TYPE: DNA
<213> ORGANISM: Homo sapiens

<400> SEQUENCE: 49

```
cggcgatggc cccactcgga tacttcttac tcctctgcag cctgaagcag gctctgggca       60
gctacccgat ctggtggtcg ctggctgttg ggccacagta ttcctccctg ggctcgcagc      120
ccatcctgtg tgccagcatc ccgggcctgg tccccaagca gctccgcttc tgcaggaact      180
acgtggagat catgcccagc gtggccgagg gcatcaagat tggcatccag gagtgccagc      240
accagttccg cggccgccgg tggaactgca ccaccgtcca cgacagcctg gccatcttcg      300
ggcccgtgct ggacaaagct accagggagt cggcctttgt ccacgccatt gcctcagccg      360
gtgtggcctt tgcagtgaca cgctcatgtg cagaaggcac ggccgccatc tgtggctgca      420
gcagccgcca ccagggctca ccaggcaagg gctggaagtg gggtggctgt agcgaggaca      480
tcgagtttgg tgggatggtg tctcgggagt tcgccgacgc ccgggagaac cggccagatg      540
cccgctcagc catgaaccgc cacaacaacg aggctgggcg ccaggccatc gccagccaca      600
tgcacctcaa gtgcaagtgc cacgggctgt cgggcagctg cgaggtgaag acatgctggt      660
ggtcgcaacc cgacttccgc gccatcggtg acttcctcaa ggacaagtac gacagcgcct      720
cggagatggt ggtggagaag caccgggagt cccgcggctg ggtggagacc ctgcggccgc      780 gctacacctta cttcaaggtg cccacggagc gcgacctggt ctactacgag gcctcgccca      840
acttctgcga gcccaaccct gagacgggct ccttcggcac gcgcgaccgc acctgcaacg      900
tcagctcgca cggcatcgac ggctgcgacc tgctgtgctg cggccgcggc cacaacgcgc      960
gagcggagcg gcgccgggag aagtgccgct gcgtgttcca ctggtgctgc tacgtcagct      1020
gccaggagtg cacgcgcgtc tacgacgtgc acacctgcaa gtaggcaccg gccgcggctc      1080
cccctggacg gggcgggccc tgcctgaggg tgggcttttc cctgggtgga gcaggactcc      1140
cacctaaacg gggcagtact cctccctggg ggcgggactc ctccctgggg gtggggctcc      1200
```

-continued

```
tacctgggggg cagaactcct acctgaaggc agggctcctc cctggagcta gtgtctcctc    1260
tctggtggct gggctgctcc tgaatgaggc ggagctccag gatgggggagg ggctctgcgt    1320 tggcttctcc ctggggacgg ggctcccctg gacagaggcg gggctacaga ttgggcgggg    1380
cttctcttgg gtgggacagg gcttctcctg cgggggcgag gccctcccca gtaaggggcgt    1440 ggctctgggt gggcgggggca ctaggtaggc ttctacctgc aggcgggggct cctcctgaag    1500 gaggcgggggc tctaggatgg ggcacggctc tggggtaggc tgctccctga gggcg    1555
```

<210> SEQ ID NO 50
<211> LENGTH: 385
<212> TYPE: PRT
<213> ORGANISM: Homo sapiens

<400> SEQUENCE: 50

```
Met Ala Pro Leu Gly Tyr Phe Leu Leu Leu Cys Ser Leu Lys Gln Ala
1               5                   10                  15

Leu Gly Ser Tyr Pro Ile Trp Trp Ser Leu Ala Val Gly Pro Gln Tyr
                20                  25                  30

Ser Ser Leu Gly Ser Gln Pro Ile Leu Cys Ala Ser Ile Pro Gly Leu
            35                  40                  45

Val Pro Lys Gln Leu Arg Phe Cys Arg Asn Tyr Val Glu Ile Met Pro
        50                  55                  60

Ser Val Ala Glu Gly Ile Lys Ile Gly Ile Gln Glu Cys Gln His Gln
65                  70                  75                  80

Phe Arg Gly Arg Arg Trp Asn Cys Thr Thr Val His Asp Ser Leu Ala
                85                  90                  95

Ile Phe Gly Pro Val Leu Asp Lys Ala Thr Arg Glu Ser Ala Phe Val
                100                 105                 110

His Ala Ile Ala Ser Ala Gly Val Ala Phe Ala Val Thr Arg Ser Cys
            115                 120                 125

Ala Glu Gly Thr Ala Ala Ile Cys Gly Cys Ser Ser Arg His Gln Gly
        130                 135                 140

Ser Pro Gly Lys Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                165                 170                 175

Pro Asp Ala Arg Ser Ala Met Asn Arg His Asn Asn Glu Ala Gly Arg
                180                 185                 190

Gln Ala Ile Ala Ser His Met His Leu Lys Cys Lys Cys His Gly Leu
            195                 200                 205

Ser Gly Ser Cys Glu Val Lys Thr Cys Trp Trp Ser Gln Pro Asp Phe
        210                 215                 220

Arg Ala Ile Gly Asp Phe Leu Lys Asp Lys Tyr Asp Ser Ala Ser Glu
225                 230                 235                 240

Met Val Val Glu Lys His Arg Glu Ser Arg Gly Trp Val Glu Thr Leu
                245                 250                 255

Arg Pro Arg Tyr Thr Tyr Phe Lys Val Pro Thr Glu Arg Asp Leu Val
                260                 265                 270

Tyr Tyr Glu Ala Ser Pro Asn Phe Cys Glu Pro Asn Pro Glu Thr Gly
            275                 280                 285

Ser Phe Gly Thr Arg Asp Arg Thr Cys Asn Val Ser Ser His Gly Ile
        290                 295                 300

Asp Gly Cys Asp Leu Leu Cys Cys Gly Arg Gly His Asn Ala Arg Ala
```

-continued

```
305              310              315              320

Glu Arg Arg Arg Glu Lys Cys Arg Cys Val Phe His Trp Cys Cys Tyr
                325              330              335

Val Ser Cys Gln Glu Cys Thr Arg Val Tyr Asp Val His Thr Cys Lys
            340              345              350

Asn Pro Gly Ser Arg Ala Gly Asn Ser Ala His Gln Pro Pro His Pro
        355              360              365

Gln Pro Pro Val Arg Phe His Pro Pro Leu Arg Arg Ala Gly Lys Val
    370              375              380

Pro
385
```

```
<210> SEQ ID NO 51
<211> LENGTH: 1056
<212> TYPE: DNA
<213> ORGANISM: Homo sapiens

<400> SEQUENCE: 51
atgagtcccc gctcgtgcct gcgttcgctg cgcctcctcg tcttcgccgt cttctcagcc      60
gccgcgagca actggctgta cctggccaag ctgtcgtcgg tggggagcat ctcagaggag    120
gagacgtgcg agaaactcaa gggcctgatc cagaggcagg tgcagatgtg caagcggaac    180
ctggaagtca tggactcggt gcgccgcggt gcccagctgg ccattgagga gtgccagtac    240
cagttccgga accggcgctg gaactgctcc acactcgact ccttgcccgt cttcggcaag    300
gtggtgacgc aagggattcg ggaggcggcc ttggtgtacg ccatctcttc ggcaggtgtg    360
gcctttgcag tgacgcgggc gtgcagcagt ggggagctgg agaagtgcgg ctgtgacagg    420
acagtgcatg gggtcagccc acagggcttc cagtggtcag gatgctctga caacatcgcc    480
tacggtgtgg ccttctcaca gtcgtttgtg gatgtgcggg agagaagcaa gggggcctcg    540
tccagcagag ccctcatgaa cctccacaac aatgaggccg gcaggaaggc catcctgaca    600
cacatgcggg tggaatgcaa gtgccacggg gtgtcaggct cctgtgaggt aaagacgtgc    660
tggcgagccg tgccgccctt ccgccaggtg ggtcacgcac tgaaggagaa gtttgatggt    720
gccactgagg tggagccacg ccgcgtgggc tcctccaggg cactggtgcc acgcaacgca    780
cagttcaagc cgcacacaga tgaggacttg gtgtacttgg agcctagccc cgacttctgt    840
gagcaggaca tgcgcagcgg cgtgctgggc acgagggggcc gcacatgcaa caagacgtcc    900
aaggccatcg acggctgtga gctgctgtgc tgtggccgcg gcttccacac ggcgcaggtg    960
gagctggctg aacgctgcag ctgcaaattc cactggtgct gcttcgtcaa gtgccggcag   1020
tgccagcggc tcgtggagtt gcacacgtgc cgatga                             1056
```

```
<210> SEQ ID NO 52
<211> LENGTH: 351
<212> TYPE: PRT
<213> ORGANISM: Homo sapiens

<400> SEQUENCE: 52

Met Ser Pro Arg Ser Cys Leu Arg Ser Leu Arg Leu Leu Val Phe Ala
1               5                  10                  15

Val Phe Ser Ala Ala Ala Ser Asn Trp Leu Tyr Leu Ala Lys Leu Ser
            20                  25                  30

Ser Val Gly Ser Ile Ser Glu Glu Thr Cys Glu Lys Leu Lys Gly
        35                  40                  45

Leu Ile Gln Arg Gln Val Gln Met Cys Lys Arg Asn Leu Glu Val Met
```

```
        50                  55                  60

Asp Ser Val Arg Arg Gly Ala Gln Leu Ala Ile Glu Glu Cys Gln Tyr
65                  70                  75                  80

Gln Phe Arg Asn Arg Arg Trp Asn Cys Ser Thr Leu Asp Ser Leu Pro
                85                  90                  95

Val Phe Gly Lys Val Val Thr Gln Gly Ile Arg Glu Ala Ala Leu Val
                100                 105                 110

Tyr Ala Ile Ser Ser Ala Gly Val Ala Phe Ala Val Thr Arg Ala Cys
            115                 120                 125

Ser Ser Gly Glu Leu Glu Lys Cys Gly Cys Asp Arg Thr Val His Gly
            130                 135                 140

Val Ser Pro Gln Gly Phe Gln Trp Ser Gly Cys Ser Asp Asn Ile Ala
145                 150                 155                 160

Tyr Gly Val Ala Phe Ser Gln Ser Phe Val Asp Val Arg Glu Arg Ser
                165                 170                 175

Lys Gly Ala Ser Ser Ser Arg Ala Leu Met Asn Leu His Asn Asn Glu
                180                 185                 190

Ala Gly Arg Lys Ala Ile Leu Thr His Met Arg Val Glu Cys Lys Cys
            195                 200                 205

His Gly Val Ser Gly Ser Cys Glu Val Lys Thr Cys Trp Arg Ala Val
        210                 215                 220

Pro Pro Phe Arg Gln Val Gly His Ala Leu Lys Glu Lys Phe Asp Gly
225                 230                 235                 240

Ala Thr Glu Val Glu Pro Arg Arg Val Gly Ser Ser Arg Ala Leu Val
                245                 250                 255

Pro Arg Asn Ala Gln Phe Lys Pro His Thr Asp Glu Asp Leu Val Tyr
                260                 265                 270

Leu Glu Pro Ser Pro Asp Phe Cys Glu Gln Asp Met Arg Ser Gly Val
                275                 280                 285

Leu Gly Thr Arg Gly Arg Thr Cys Asn Lys Thr Ser Lys Ala Ile Asp
            290                 295                 300

Gly Cys Glu Leu Leu Cys Cys Gly Arg Gly Phe His Thr Ala Gln Val
305                 310                 315                 320

Glu Leu Ala Glu Arg Cys Ser Cys Lys Phe His Trp Cys Cys Phe Val
                325                 330                 335

Lys Cys Arg Gln Cys Gln Arg Leu Val Glu Leu His Thr Cys Arg
                340                 345                 350
```

```
<210> SEQ ID NO 53
<211> LENGTH: 1143
<212> TYPE: DNA
<213> ORGANISM: Homo sapiens

<400> SEQUENCE: 53
atgaagaagt ccattggaat attaagccca ggagttgctt tggggatggc tggaagtgca      60
atgtcttcca agttcttcct agtggctttg gccatatttt tctccttcgc ccaggttgta     120
attgaagcca attcttggtg gtcgctaggt atgaataacc ctgttcagat gtcagaagta     180
tatattatag gagcacagcc tctctgcagc caactggcag gactttctca aggacagaag     240
aaactgtgcc acttgtatca ggaccacatg cagtacatcg agaaggcgc gaagacaggc      300 atcaaagaat gccagtatca attccgacat cgaaggtgga actgcagcac tgtggataac     360
acctctgttt ttggcagggt gatgcagata ggcagccgcg agacggcctt cacatacgcg     420
gtgagcgcag caggggtggt gaacgccatg agccgggcgt ccgcgagggg cgagctgtcc     480
```

```
acctgcggct gcagccgcgc cgcgcgcccc aaggacctgc cgcgggactg gctctggggc     540
ggctgcggcg acaacatcga ctatggctac cgctttgcca aggagttcgt ggacgcccgc     600
gagcgggagc gcatccacgc caagggctcc tacgagagtg ctcgcatcct catgaacctg     660
cacaacaacg aggccggccg caggacggtg tacaacctgg ctgatgtggc ctgcaagtgc     720 catgggtgt ccggctcatg tagcctgaag acatgctggc tgcagctggc agacttccgc      780
aaggtgggtg atgccctgaa ggagaagtac gacagcgcgg cggccatgcg gctcaacagc     840
cggggcaagt tggtacaggt caacagccgc ttcaactcgc ccaccacaca agacctggtc     900
tacatcgacc ccagccctga ctactgcgtg cgcaatgaga gcaccggctc gctgggcacg     960
cagggccgcc tgtgcaacaa gacgtcggag ggcatggatg gctgcgagct catgtgctgc    1020
ggccgtggct acgaccagtt caagaccgtg cagacggagc gctgccactg caagttccac    1080
tggtgctgct acgtcaagtg caagaagtgc acggagatcg tggaccagtt tgtgtgcaag    1140
tag                                                                 1143
```

```
<210> SEQ ID NO 54
<211> LENGTH: 380
<212> TYPE: PRT
<213> ORGANISM: Homo sapiens

<400> SEQUENCE: 54

Met Lys Lys Ser Ile Gly Ile Leu Ser Pro Gly Val Ala Leu Gly Met
1               5                   10                  15

Ala Gly Ser Ala Met Ser Ser Lys Phe Phe Leu Val Ala Leu Ala Ile
            20                  25                  30

Phe Phe Ser Phe Ala Gln Val Val Ile Glu Ala Asn Ser Trp Trp Ser
        35                  40                  45

Leu Gly Met Asn Asn Pro Val Gln Met Ser Glu Val Tyr Ile Ile Gly
    50                  55                  60

Ala Gln Pro Leu Cys Ser Gln Leu Ala Gly Leu Ser Gln Gly Gln Lys
65                  70                  75                  80

Lys Leu Cys His Leu Tyr Gln Asp His Met Gln Tyr Ile Gly Glu Gly
                85                  90                  95

Ala Lys Thr Gly Ile Lys Glu Cys Gln Tyr Gln Phe Arg His Arg Arg
            100                 105                 110

Trp Asn Cys Ser Thr Val Asp Asn Thr Ser Val Phe Gly Arg Val Met
            115                 120                 125

Gln Ile Gly Ser Arg Glu Thr Ala Phe Thr Tyr Ala Val Ser Ala Ala
        130                 135                 140

Gly Val Val Asn Ala Met Ser Arg Ala Cys Arg Glu Gly Glu Leu Ser
145                 150                 155                 160

Thr Cys Gly Cys Ser Arg Ala Ala Arg Pro Lys Asp Leu Pro Arg Asp
                165                 170                 175

Trp Leu Trp Gly Gly Cys Gly Asp Asn Ile Asp Tyr Gly Tyr Arg Phe
            180                 185                 190

Ala Lys Glu Phe Val Asp Ala Arg Glu Arg Glu Arg Ile His Ala Lys
            195                 200                 205

Gly Ser Tyr Glu Ser Ala Arg Ile Leu Met Asn Leu His Asn Asn Glu
        210                 215                 220

Ala Gly Arg Arg Thr Val Tyr Asn Leu Ala Asp Val Ala Cys Lys Cys
225                 230                 235                 240

His Gly Val Ser Gly Ser Cys Ser Leu Lys Thr Cys Trp Leu Gln Leu
```

-continued

```
                    245                 250                 255

Ala Asp Phe Arg Lys Val Gly Asp Ala Leu Lys Glu Lys Tyr Asp Ser
            260                 265                 270

Ala Ala Ala Met Arg Leu Asn Ser Arg Gly Lys Leu Val Gln Val Asn
            275                 280                 285

Ser Arg Phe Asn Ser Pro Thr Thr Gln Asp Leu Val Tyr Ile Asp Pro
    290                 295                 300

Ser Pro Asp Tyr Cys Val Arg Asn Glu Ser Thr Gly Ser Leu Gly Thr
305                 310                 315                 320

Gln Gly Arg Leu Cys Asn Lys Thr Ser Glu Gly Met Asp Gly Cys Glu
            325                 330                 335

Leu Met Cys Cys Gly Arg Gly Tyr Asp Gln Phe Lys Thr Val Gln Thr
            340                 345                 350

Glu Arg Cys His Cys Lys Phe His Trp Cys Cys Tyr Val Lys Cys Lys
            355                 360                 365

Lys Cys Thr Glu Ile Val Asp Gln Phe Val Cys Lys
    370                 375                 380
```

```
<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gctaacactg tcgcagtttg a                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cgaacagctg gaatcaatgt g                                              21

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tgcagctacg ctaccagga                                                 19

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ggaggctgag ttcgcttgg                                                 19
```

```
<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ctcggaggta gttccggttc                                                          20

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tctgcccaat ctgacgaaga g                                                        21

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
atgctccgcc agatcatcg                                                           19

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tgccagacgc aagagataca g                                                        21

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ggccttcagt actccctgca                                                          20

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gggacttgga gcttgagtcc t                                                        21

<210> SEQ ID NO 65
```

-continued

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gcggagtgta atcagtattt gga                                              23

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gcatttgatc ccgtacaacc t                                                21

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gcctgcgcta attgtaggag                                                  20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cgcacttgaa agttgcaaaa                                                  20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ttcaggacgg ggtgagttac                                                  20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tttggcatgg tacaggttca                                                  20

<210> SEQ ID NO 71
<211> LENGTH: 20
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gctggaatca atttcccaga                                                    20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ctccccacac aggatgagtt                                                    20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
agcctttgtg aaccaacacc                                                    20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gctggtagag ggagcagatg                                                    20

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
aggcagaccc actcagtga                                                     19

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
aacaatggcg acctcttctg                                                    20

<210> SEQ ID NO 77
<211> LENGTH: 22
<212> TYPE: DNA

-continued

<213> ORGANISM: Artificial Sequence
<220> FEATURE:
<223> OTHER INFORMATION: Description of Artificial Sequence: Synthetic
      primer

<400> SEQUENCE: 77
gtacttcttg gcagagctgc tg                                                      22

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cagaagaaat tcttgcagcc ag                                                      22

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ggatgaagtc taccaaagct cacgc                                                   25

<210> SEQ ID NO 80
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ccagatcttg atgtgtctct cggtc                                                   25

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
cttcagcaag gaggaggtca tc                                                      22

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ctcgtatttc tccttgtaca ggtcc                                                   25

<210> SEQ ID NO 83
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 83
attcgttggg gatgacagag                                                20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tcaacagctg cgtgattttc                                                20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gatgggcttg gctttgtaga                                                20

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ggagggaagt ccactctgc                                                 19

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gttctcagga cgaggagcac                                                20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
cttgggcttt tgatcgtcat                                                20

<210> SEQ ID NO 89
<211> LENGTH: 20
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 89
tatggtggtg ccgactacaa                                                20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
tgcttgtcca gatgacttcg                                                20

<210> SEQ ID NO 91
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gtgctgatgg gcaagaac                                                  18

<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
aggtcctcct tggtgaac                                                  18

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
tgctgcataa tcagctacgg                                                20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gctggtcaca ttgagaagca                                                20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued

```
      primer

<400> SEQUENCE: 95
gcaaggcatt cttcaagagg                                    20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ggctgggcag ctgtactcta                                    20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ctctcgactg ggtgaaggag                                    20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
gaagagccag cacaaaggtc                                    20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
gaagccctga aagacgacag                                    20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
tcgacacgaa ctctccctct                                    20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 101
gatccgagtg ctctttggag                                              20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
atgtcatcca gaagcccaag                                              20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gtggttgacg ctgtccgtca                                              20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
ctgttcgtcc ttcatcaaga                                              20

<210> SEQ ID NO 105
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
ataagacaca gttatgctta tggaagcgtg ctgacaaaca gtaattacag agctgaggat    60
catctgttca gtcttgaaaa taaaagtttt attctgctca taataaatg attgcagcat    120 cagaatgagg aaggaaaggt agaatgagga taaatacaat tttagaaatg gtatagactt    180
tgcaaatcac cacctcttcc attgataaat ttagaatcta gagttgagtt agatattgac    240
actggttctc caagagaaag gtaaaataaa agcaatcgga ctctttagag cttttgttta    300
tggcctgtct gggccctttg ttgtaaccct gtcatgccct tatgctgatt accttcttgt    360
agaacaagaa gtattgacta gagaatgaat gatgtgtagt ccctagccct taggaaactc    420
tctcaaagag caatgtcttt aacatatgaa ttctgttttt ttcctccttt tacctttccc    480 tttcccttc tctatttttc accatctctt ttgtttctac ctcttttggt ctctgtgctt    540
gacactctct cctctttctg tctctctttg tatctcctca atctcaggct tctctgcaga    600

<210> SEQ ID NO 106
<211> LENGTH: 600
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 106
ctggtggctc ttcagacgcc agtgggagct acagttcaac catgaatggc catcagaacg      60
gacttgactc gccacctctc taccctctg ctcctatcct gggaggtagt gggcctgtca      120
ggaaactgta tgatgactgc tccagcacca ttgttgaaga tccccagacc aagtgtgaat      180
acatgctcaa ctcgatgccc aagagactgt gtttagtgtg tggtgacatc gcttctgggt      240
accactatgg ggtagcatca tgtgaagcct gcaaggcatt cttcaagagg acaattcaag      300
gttagtgtcg gacctgggaa tactctcccc acttccaacc tcacatgatg ggttttgtt      360 tttccttatt cttattctca taagtcaagt atcatagttt taattctctc ttgagtagaa      420
aatggaaata gattacaatt gatagtggaa gatttataga ataaaatccc cccagatata      480
ctccatatct attaatttc ctcttactgt taagctttaa tggtgcaagg ataataaact      540
ttgggtagag tttacaagag catagttatt attagagcaa tgtgggtcta tatagcaact      600

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gtccatgctg atccatcctt                                                  20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
tgcttctccg gtattgttcc                                                  20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gtccatgctg atccatcctt                                                  20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
tgcttctccg gtattgttcc                                                  20